(12) United States Patent
Sade-Feldman et al.

(10) Patent No.: US 12,226,479 B2
(45) Date of Patent: Feb. 18, 2025

(54) METHODS AND COMPOSITIONS OF USE OF CD8+ TUMOR INFILTRATING LYMPHOCYTE SUBTYPES AND GENE SIGNATURES THEREOF

(71) Applicants: THE GENERAL HOSPITAL CORPORATION, Boston, MA (US); THE BROAD INSTITUTE, INC., Cambridge, MA (US)

(72) Inventors: Moshe Sade-Feldman, Boston, MA (US); Keren Yizhak, Cambridge, MA (US); Gad Getz, Boston, MA (US); Nir Hacohen, Boston, MA (US)

(73) Assignees: The General Hospital Corporation, Boston, MA (US); The Broad Institute, Inc., Cambridge, MA (US)

( * ) Notice: Subject to any disclaimer, the term of this patent is extended or adjusted under 35 U.S.C. 154(b) by 0 days.

(21) Appl. No.: 16/612,485

(22) PCT Filed: May 11, 2018

(86) PCT No.: PCT/US2018/032466
§ 371 (c)(1),
(2) Date: Nov. 11, 2019

(87) PCT Pub. No.: WO2018/209324
PCT Pub. Date: Nov. 15, 2018

(65) Prior Publication Data
US 2020/0147210 A1 May 14, 2020

Related U.S. Application Data

(60) Provisional application No. 62/574,878, filed on Oct. 20, 2017, provisional application No. 62/505,101, filed on May 11, 2017.

(51) Int. Cl.
| | |
|---|---|
| *A61K 39/395* | (2006.01) |
| *A61K 38/45* | (2006.01) |
| *A61K 39/00* | (2006.01) |
| *A61P 35/00* | (2006.01) |
| *C12N 5/0783* | (2010.01) |
| *C12N 15/10* | (2006.01) |
| *C12Q 1/6886* | (2018.01) |

(52) U.S. Cl.
CPC .......... *A61K 39/3955* (2013.01); *A61K 38/45* (2013.01); *A61K 39/4611* (2023.05); *A61K 39/4631* (2023.05); *A61K 39/46449* (2023.05); *A61P 35/00* (2018.01); *C12N 5/0636* (2013.01); *C12N 15/10* (2013.01); *C12Q 1/6886* (2013.01); *A61K 2239/57* (2023.05); *C12Q 2600/106* (2013.01); *C12Q 2600/118* (2013.01); *C12Q 2600/158* (2013.01); *G01N 2800/52* (2013.01)

(58) Field of Classification Search
CPC .... A61K 39/3955; A61K 35/17; A61K 38/45; C12N 15/10; C12N 5/0636; A61P 35/00; C12Q 1/6886; C12Q 2600/158; C12Q 2600/118; C12Q 2600/106; G01N 2800/52; G01N 33/574
See application file for complete search history.

(56) References Cited

U.S. PATENT DOCUMENTS

| | | | |
|---|---|---|---|
| 4,816,567 A | 3/1989 | Cabilly et al. | |
| 5,270,163 A | 12/1993 | Gold et al. | |
| 5,686,281 A | 11/1997 | Roberts | |
| 5,811,097 A | 9/1998 | Allison et al. | |
| 5,843,728 A | 12/1998 | Seed et al. | |
| 5,851,828 A | 12/1998 | Seed et al. | |
| 5,858,358 A | 1/1999 | June et al. | |
| 5,869,326 A | 2/1999 | Hofmann | |
| 5,883,223 A | 3/1999 | Gray | |
| 5,906,936 A | 5/1999 | Eshhar et al. | |
| 5,912,170 A | 6/1999 | Seed et al. | |
| 5,912,172 A | 6/1999 | Eshhar et al. | |
| 6,004,811 A | 12/1999 | Seed et al. | |

(Continued)

FOREIGN PATENT DOCUMENTS

| | | | |
|---|---|---|---|
| EP | 2 771 468 B1 | 2/2015 | |
| EP | 2 784 162 B1 | 4/2015 | |

(Continued)

OTHER PUBLICATIONS

Utzschneider, et al., "T cell Factor 1-Expressing Memory-like CD8+ T cells Sustain the Immune Response to Chronic Viral Infections", Immunity, vol. 45, No. 2, Aug. 16, 2016, pp. 415-427.*

(Continued)

*Primary Examiner* — Alana Harris Dent
(74) *Attorney, Agent, or Firm* — Wenderoth, Lind & Ponack, L.L.P.

(57) ABSTRACT

The subject matter disclosed herein is generally directed to CD8+ tumor infiltrating lymphocytes comprising gene signatures associated with response to immunotherapy treatment. Moreover, the subject matter disclosed herein is generally directed to methods and compositions for use of the gene signatures. Specifically, disclosed herein are gene signatures associated with response to checkpoint blockade therapy and immune cell subtypes characterized by said gene signatures. Further disclosed are methods of using said gene signatures and immune cell subtypes. Further disclosed are pharmaceutical compositions comprising populations of CD8+ TILs enriched for a specific subtype.

5 Claims, 87 Drawing Sheets
Specification includes a Sequence Listing.

(56) References Cited

U.S. PATENT DOCUMENTS

| | | | |
|---|---|---|---|
| 6,040,177 A | 3/2000 | Riddell et al. |
| 6,284,240 B1 | 9/2001 | Seed et al. |
| 6,352,694 B1 | 3/2002 | June et al. |
| 6,392,013 B1 | 5/2002 | Seed et al. |
| 6,410,014 B1 | 6/2002 | Seed et al. |
| 6,479,626 B1 | 11/2002 | Kim et al. |
| 6,489,458 B2 | 12/2002 | Hackett et al. |
| 6,534,055 B1 | 3/2003 | June et al. |
| 6,534,261 B1 | 3/2003 | Cox et al. |
| 6,607,882 B1 | 8/2003 | Cox et al. |
| 6,617,439 B1 | 9/2003 | Beaudoin et al. |
| 6,746,838 B1 | 6/2004 | Choo et al. |
| 6,753,162 B1 | 6/2004 | Seed et al. |
| 6,794,136 B1 | 9/2004 | Eisenberg et al. |
| 6,797,514 B2 | 9/2004 | Berenson et al. |
| 6,824,978 B1 | 11/2004 | Cox et al. |
| 6,866,997 B1 | 3/2005 | Choo et al. |
| 6,867,041 B2 | 3/2005 | Berenson et al. |
| 6,887,466 B2 | 5/2005 | June et al. |
| 6,903,185 B2 | 6/2005 | Kim et al. |
| 6,905,680 B2 | 6/2005 | June et al. |
| 6,905,681 B1 | 6/2005 | June et al. |
| 6,905,874 B2 | 6/2005 | Berenson et al. |
| 6,933,113 B2 | 8/2005 | Case et al. |
| 6,979,539 B2 | 12/2005 | Cox et al. |
| 7,013,219 B2 | 3/2006 | Case et al. |
| 7,030,215 B2 | 4/2006 | Liu et al. |
| 7,144,575 B2 | 12/2006 | June et al. |
| 7,148,203 B2 | 12/2006 | Hackett et al. |
| 7,160,682 B2 | 1/2007 | Hackett et al. |
| 7,175,843 B2 | 2/2007 | June et al. |
| 7,220,719 B2 | 5/2007 | Case et al. |
| 7,232,566 B2 | 6/2007 | June et al. |
| 7,241,573 B2 | 7/2007 | Choo et al. |
| 7,241,574 B2 | 7/2007 | Choo et al. |
| 7,446,190 B2 | 11/2008 | Sadelain et al. |
| 7,572,631 B2 | 8/2009 | Berenson et al. |
| 7,585,849 B2 | 9/2009 | Liu et al. |
| 7,595,376 B2 | 9/2009 | Kim et al. |
| 7,741,465 B1 | 6/2010 | Eshhar et al. |
| 7,985,739 B2 | 7/2011 | Kay et al. |
| 8,021,867 B2 | 9/2011 | Smith et al. |
| 8,034,334 B2 | 10/2011 | Dudley et al. |
| 8,088,379 B2 | 1/2012 | Robbins et al. |
| 8,119,361 B2 | 2/2012 | Smith et al. |
| 8,119,381 B2 | 2/2012 | Smith et al. |
| 8,124,369 B2 | 2/2012 | Smith et al. |
| 8,129,134 B2 | 3/2012 | Smith et al. |
| 8,133,697 B2 | 3/2012 | Smith et al. |
| 8,163,514 B2 | 4/2012 | Smith et al. |
| 8,211,422 B2 | 7/2012 | Eshhar et al. |
| 8,227,432 B2 | 7/2012 | Hackett et al. |
| 8,399,645 B2 | 3/2013 | Campana et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,637,307 B2 | 1/2014 | June et al. |
| 8,697,359 B1 | 4/2014 | Zhang |
| 8,697,854 B2 | 4/2014 | Schendel et al. |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,906,682 B2 | 12/2014 | June et al. |
| 8,911,993 B2 | 12/2014 | June et al. |
| 8,916,381 B1 | 12/2014 | June et al. |
| 8,932,814 B2 | 1/2015 | Cong et al. |
| 8,945,839 B2 | 2/2015 | Zhang |
| 8,975,071 B1 | 3/2015 | June et al. |
| 8,993,233 B2 | 3/2015 | Zhang et al. |
| 8,999,641 B2 | 4/2015 | Zhang et al. |
| 9,101,584 B2 | 8/2015 | June et al. |
| 9,102,760 B2 | 8/2015 | June et al. |
| 9,102,761 B2 | 8/2015 | June et al. |
| 9,115,402 B2 | 8/2015 | Hacohen et al. |
| 9,181,527 B2 | 11/2015 | Sentman |
| 9,233,125 B2 | 1/2016 | Davila et al. |
| 2004/0171156 A1 | 9/2004 | Hartley et al. |
| 2004/0224402 A1 | 11/2004 | Bonyhadi et al. |
| 2010/0104509 A1 | 4/2010 | King et al. |
| 2010/0204182 A1 | 8/2010 | Muller et al. |
| 2011/0265198 A1 | 10/2011 | Gregory et al. |
| 2012/0017290 A1 | 1/2012 | Cui et al. |
| 2012/0244133 A1 | 9/2012 | Rosenberg et al. |
| 2013/0071414 A1 | 3/2013 | Dotti et al. |
| 2013/0123345 A1 | 5/2013 | Davis |
| 2013/0236946 A1 | 9/2013 | Gouble |
| 2013/0273062 A1 | 10/2013 | Bensussan et al. |
| 2013/0330325 A1 | 12/2013 | Grabe |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0310830 A1 | 10/2014 | Zhang et al. |
| 2015/0184139 A1 | 7/2015 | Zhang et al. |
| 2015/0368342 A1 | 12/2015 | Wu et al. |
| 2015/0368360 A1 | 12/2015 | Liang et al. |
| 2016/0046724 A1 | 2/2016 | Brogdon et al. |
| 2016/0129109 A1 | 5/2016 | Davila et al. |
| 2016/0145350 A1 | 5/2016 | Lonberg |
| 2016/0166613 A1 | 6/2016 | Spencer et al. |
| 2016/0175359 A1 | 6/2016 | Spencer et al. |
| 2016/0208243 A1 | 7/2016 | Zhang et al. |
| 2017/0119807 A1 | 5/2017 | Lee |
| 2017/0175144 A1 | 6/2017 | Zhang et al. |
| 2017/0211142 A1 | 7/2017 | Smargon et al. |
| 2017/0283504 A1 | 10/2017 | Wiltzius et al. |
| 2017/0306335 A1 | 10/2017 | Zhang et al. |
| 2017/0321198 A1 | 11/2017 | Severinov et al. |
| 2017/0349914 A1 | 12/2017 | Cox et al. |
| 2018/0010134 A1 | 1/2018 | Sharp et al. |
| 2018/0044662 A1 | 2/2018 | Platt et al. |
| 2018/0057810 A1 | 3/2018 | Zhang et al. |
| 2018/0072742 A1* | 3/2018 | Chen .................. A61P 9/00 |
| 2018/0085444 A1 | 3/2018 | Morgan et al. |
| 2018/0112255 A1 | 4/2018 | Chen et al. |
| 2018/0163265 A1 | 6/2018 | Zhang et al. |
| 2018/0207273 A1* | 7/2018 | Dranoff .................. A61P 35/00 |
| 2018/0312824 A1 | 11/2018 | Zhang et al. |
| 2018/0320163 A1 | 11/2018 | Koonin et al. |
| 2019/0359971 A1 | 11/2019 | Zhang et al. |
| 2020/0131488 A1 | 4/2020 | Cox et al. |
| 2020/0308560 A1 | 10/2020 | Zhang et al. |

FOREIGN PATENT DOCUMENTS

| | | |
|---|---|---|
| EP | 2 764 103 B1 | 8/2015 |
| EP | 3 009 511 A2 | 4/2016 |
| WO | 92/15322 A1 | 9/1992 |
| WO | 96/40281 A2 | 12/1996 |
| WO | 97/49450 A1 | 12/1997 |
| WO | 98/52609 A1 | 11/1998 |
| WO | 03/020763 A2 | 3/2003 |
| WO | 03/057171 A2 | 7/2003 |
| WO | 2004/033685 A1 | 4/2004 |
| WO | 2004/044004 A2 | 5/2004 |
| WO | 2004/074322 A1 | 9/2004 |

(56) References Cited

FOREIGN PATENT DOCUMENTS

| | | |
|---|---|---|
| WO | 2005/113595 A2 | 12/2005 |
| WO | 2005/114215 A2 | 12/2005 |
| WO | 2006/000830 A2 | 1/2006 |
| WO | 2006/125962 A2 | 11/2006 |
| WO | 2008/038002 A2 | 4/2008 |
| WO | 2008/039818 A2 | 4/2008 |
| WO | 2011/146862 A1 | 11/2011 |
| WO | 2012/058460 A2 | 5/2012 |
| WO | 2012/079000 A1 | 6/2012 |
| WO | 2013/039889 A1 | 3/2013 |
| WO | 2013/040371 A2 | 3/2013 |
| WO | 2013/044225 A1 | 3/2013 |
| WO | 2013/154760 A1 | 10/2013 |
| WO | 2013/166321 A1 | 11/2013 |
| WO | 2013/176915 A1 | 11/2013 |
| WO | 2014/011987 A1 | 1/2014 |
| WO | 2014/018863 A1 | 1/2014 |
| WO | 2014/018423 A3 | 4/2014 |
| WO | 2014/059173 A2 | 4/2014 |
| WO | 2014/083173 A1 | 6/2014 |
| WO | 2014/093595 A1 | 6/2014 |
| WO | 2014/093622 A2 | 6/2014 |
| WO | 2014/093635 A1 | 6/2014 |
| WO | 2014/093655 A2 | 6/2014 |
| WO | 2014/093661 A2 | 6/2014 |
| WO | 2014/093694 A1 | 6/2014 |
| WO | 2014/093701 A1 | 6/2014 |
| WO | 2014/093709 A1 | 6/2014 |
| WO | 2014/093712 A1 | 6/2014 |
| WO | 2014/093718 A1 | 6/2014 |
| WO | 2014/133567 A1 | 9/2014 |
| WO | 2014/133568 A1 | 9/2014 |
| WO | 2014/134165 A1 | 9/2014 |
| WO | 2014/168874 A2 | 10/2014 |
| WO | 2014/172606 A1 | 10/2014 |
| WO | 2014/184744 A1 | 11/2014 |
| WO | 2014/191128 A1 | 12/2014 |
| WO | 2014/204723 A1 | 12/2014 |
| WO | 2014/204724 A1 | 12/2014 |
| WO | 2014/204725 A1 | 12/2014 |
| WO | 2014/204726 A1 | 12/2014 |
| WO | 2014/204727 A1 | 12/2014 |
| WO | 2014/204728 A1 | 12/2014 |
| WO | 2014/204729 A1 | 12/2014 |
| WO | 2014/210353 A2 | 12/2014 |
| WO | 2015/057834 A1 | 4/2015 |
| WO | 2015/057852 A1 | 4/2015 |
| WO | 2015/058052 A1 | 4/2015 |
| WO | 2015/070083 A1 | 5/2015 |
| WO | 2015/085233 A1 | 6/2015 |
| WO | 2015/089351 A1 | 6/2015 |
| WO | 2015/089354 A1 | 6/2015 |
| WO | 2015/089364 A1 | 6/2015 |
| WO | 2015/089419 A2 | 6/2015 |
| WO | 2015/089427 A1 | 6/2015 |
| WO | 2015/089462 A1 | 6/2015 |
| WO | 2015/089465 A1 | 6/2015 |
| WO | 2015/089473 A1 | 6/2015 |
| WO | 2015/089486 A2 | 6/2015 |
| WO | 2015/095811 A2 | 6/2015 |
| WO | 2015/120096 A2 | 8/2015 |
| WO | 2015/142675 A2 | 9/2015 |
| WO | 2015/158671 A1 | 10/2015 |
| WO | 2015/187528 A1 | 12/2015 |
| WO | 2016/000304 A1 | 1/2016 |
| WO | 2016/011210 A2 | 1/2016 |
| WO | 2016/014789 A2 | 1/2016 |
| WO | 2016/040476 A1 | 3/2016 |
| WO | 2016/049258 A2 | 3/2016 |
| WO | 2016034718 A1 | 3/2016 |
| WO | WO-2016061456 A2 * | 4/2016 ........... C12Q 1/6883 |
| WO | 2016/070061 A1 | 5/2016 |
| WO | 2016073845 A1 | 5/2016 |
| WO | 2016/094867 A1 | 6/2016 |
| WO | 2016/094872 A1 | 6/2016 |
| WO | 2016/094874 A1 | 6/2016 |
| WO | 2016/100977 A1 | 6/2016 |
| WO | 2016/106244 A1 | 6/2016 |
| WO | 2016100975 A1 | 6/2016 |
| WO | 2016/161516 A1 | 10/2016 |
| WO | 2016/168584 A1 | 10/2016 |
| WO | 2016/187508 A2 | 11/2016 |
| WO | 2016/191756 A1 | 12/2016 |
| WO | 2016/196388 A1 | 12/2016 |
| WO | 2017/004916 A1 | 1/2017 |
| WO | 2017/011804 A1 | 1/2017 |
| WO | 2017/070395 A1 | 4/2017 |
| WO | 2017/070605 A1 | 4/2017 |
| WO | WO-2017069958 A2 * | 4/2017 ........... C07K 14/705 |
| WO | 2017089334 A1 | 6/2017 |
| WO | 2017/164936 A1 | 9/2017 |
| WO | 2017165412 A2 | 9/2017 |
| WO | 2017/211900 A1 | 12/2017 |
| WO | 2018/028647 A1 | 2/2018 |
| WO | 2018/035250 A1 | 2/2018 |
| WO | 2018065622 A1 | 4/2018 |
| WO | 2018067991 A1 | 4/2018 |
| WO | 2018/209324 A2 | 11/2018 |
| WO | 2019096900 A1 | 5/2019 |
| WO | 2019178269 A2 | 9/2019 |

OTHER PUBLICATIONS

AdooQ®Bioscience Catalog, 3 sheets, printed Feb. 26, 2021.*
Muller et al. Polyoxometalates—a new class of potent ecto-nucleosidetriphosphate diphosphohydrolase (NTPDase) inhibitors. Biorganic & Medicinal Chemistry Letters 16: 5943-5947, 2006.*
Anderson (Cancer Immunology Research 2(5): 393-398, May 2014).*
Canale et al., CD39 expression defines cell exhaustion in tumor-infiltrating CD8+ T cells. Cancer Res. 78(1): 115-28, published online Oct. 24, 2017.*
Bu et al. Ovarian carcinoma-infiltrating regulatory T cells were more potent suppressors of CD8+ T cell inflammation than their peripheral counterparts, a function dependent on TIM3 expression. Tumor Biol. 37: 3949-3956, published online Oct. 19, 2015.*
Sun, et al., "CD39/ENTPD1 expression by CD4+Foxp3+ regulatory T cells promotes hepatic metastatic tumor growth in mice", Gastroenterology, vol. 139, No. 3, Jun. 25, 2010, pp. 1030-1040.
Zhou, et al., "Differentiation and Persistence of Memory CD8+ T cells Depend on T cell Factor 1", Immunity, vol. 33, No. 2, Aug. 27, 2010, pp. 229-240.
International Search Report and Written Opinion issued by the United States Patent Office, as International Searching Authority for PCT/US2018/032466 on Oct. 30, 2018.
Allard, et al., "The ectonucleotidases CD39 and CD73: novel checkpoint inhibitor targets", Immunology Reviews, vol. 276, No. 1, Mar. 4, 2017, pp. 121-144.
Bastid, et al., "ENTPD1/CD39 is a promising therapeutic target in oncology", Oncogene, vol. 32, No. 14, Jul. 2, 2012, pp. 1743-1751.
Jamieson, et al., "Gene expression profiling to predict responsiveness to immunotherapy", Cancer Gene Therapy, vol. 24, No. 3,, Nov. 11, 2016, 134-140.
Jing, et al., "Combined immune checkpoint protein blockade and low dose whole body irradiation as immunotherapy for myeloma", Journal for Immuno Therapy of Cancer, vol. 3, No. 2, Jan. 20, 2015, pp. 1-15.
Kim, et al., "Combination Therapy with Anti-PD-1, Anti-TIM-3, and Focal Radiation Results in Regression of Murine Gliomas", Clinical Cancer Research, vol. 23, No. 1, Jan. 1, 2017, pp. 124-136.
"Communication pursuant to Rule 164(1) EPC", Partial Supplementary European Search Report issued by the European Patent Office (EPO) for counterpart European Application No. 18798914.0 on Jan. 15, 2021.
"Extended European Search Report", issued by the European Patent Office on May 26, 2021 for EP Application No. 18798914.0.
Perrot, et al., "Preclinical development of humanized CD39 (IPH52) and CD73 (IPH53) blocking antibodies targeting the ATP/Adenosine immune checkpoint pathway for cancer immunotherapy", XP055533457, Apr. 14, 2018.

(56) References Cited

OTHER PUBLICATIONS

Wolchok, et al., "Overall Survival with Combined Nivolumab and Ipilimumab in Advanced Melanoma," The New England Journal of Medicine, vol. 377, No. 14, pp. 1345-1356, Oct. 5, 2017.
Boshuizen et al., "Rational Cancer Treatment Combinations: An Urgent Clinical Need", Molecular Cell 78, pp. 1002-1018, 2020.
Wolf et al., "TIM3 comes of age as an inhibitory receptor", Nature Reviews, vol. 20, pp. 173-185, 2020.
The Broad Institute, Inc., Communication pursuant to Article 94(3) EPC for European Patent Application No. 18798914.0, Feb. 24, 2023, 4 pages.
The Broad Institute Inc., International Preliminary Report on Patentability Chapter I received for International PCT Application Serial No. PCT/US2018/032466 mailed on Nov. 21, 2019, 12 pages.
Allard, et al., "Targeting Cd73 Enhances the Antitumor Activity of Anti-PD-1 and Anti-CTLA-4 mAbs", Clinical Cancer Research, vol. 19, Aug. 27, 2013, 12 pages.
Anderson, et al., "Lag-3, Tim-3, and TIGIT: Co-inhibitory Receptors with Specialized Functions in Immune Regulation", Immunity, vol. 44, No. 5, May 17, 2016, 989-1004.
Baitsch, et al., "Exhaustion of Tumor-Specific CD8+ T cells in Metastases from Melanoma Patients", Journal of Clinical Investigation, vol. 121, No. 6, May 2011, 12 pages.
Carpenter, et al., "CellProfiler: Image Analysis Software for Identifying and Quantifying Cell Phenotypes", Genome Biology, vol. 7, No. 10, 2006, 11 pages.
Gupta, et al., "CD39 Expression Identifies Terminally Exhausted CD8+ T Cells", PLOS Pathogens, vol. 11, No. 10, Oct. 20, 2015, 1-21 pp.
Hurton, et al., "Tethered IL-15 Augments Antitumor Activity and Promotes a Stem-cell Memory Subset in Tumor-Specific T Cells", Proceedings of the National Academy of Sciences United States of America, vol. 113, No. 48, Nov. 14, 2016, e7788-e7797.
Im, et al., "Defining CD8+ T Cells that Provide the Proliferative Burst After PD-1 Therapy", Nature, vol. 537, No. 7620, Sep. 15, 2016, 30 pages.
Kamentsky, et al., "Improved Structure Function and Compatibility for Cell Profiler: Modular High-Throughput Image Analysis Software", Bioinformatics, vol. 27, No. 8, Apr. 2011, 1179-1180.
Marraco, et al., "Inhibitory Receptors Beyond T Cell Exhaustion", Frontiers in Immunology, vol. 6, Article 310, Jun. 26, 2015, 14 pages.
Mckinney, et al., "A Cd8 T Cell Transcription Signature Predicts Prognosis in Autoimmune Disease", Nature Medicine, vol. 16, No. 5, May 2010, 13 pages.
Philip, et al., "Chromatin States Define Tumour-Specific T Cell Dysfunction and Reprogramming", Nature, vol. 545, No. 7655, May 25, 2017, 35 pages.
Shum, et al., "Constitutive Signaling from an Engineered IL7 Receptor Promotes Durable Tumor Elimination by Tumor-Redirected T Cells", Cancer Discovery, vol. 7, No. 11, Nov. 2017, 21 pages.
Tirosh, et al., "Dissecting The Multicellular Ecosystem of Metastatic Melanoma by Single-Cell RNA-Seq", Science, vol. 352, No. 6282, Apr. 8, 2016, 23 pages.
Waugh, et al., "Molecular Profile of Tumor-Specific CD8+ T Cell Hypofunction in a Transplantable Murine Cancer Model", Journal of Immunology, vol. 4, No. 197, Aug. 15, 2016, 29 pages.
Wherry, et al., "Molecular Signature of CD8+ T Cell Exhaustion During Chronic Viral Infection", Immunity, vol. 27, No. 4, Oct. 1, 2007, 670-684.
Young, et al., "Targeting Cancer-derived Adenosine: New Therapeutic Approaches", Cancer Discovery, vol. 4, Jul. 17, 2014, 12 pages.

* cited by examiner

SEQUENCE LISTING

```
<160> NUMBER OF SEQ ID NOS: 21

<210> SEQ ID NO 1
<211> LENGTH: 107
<212> TYPE: PRT
<213> ORGANISM: Homo sapiens

<400> SEQUENCE: 1

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser
            100                 105

<210> SEQ ID NO 2
<211> LENGTH: 9
<212> TYPE: PRT
<213> ORGANISM: Homo sapiens

<400> SEQUENCE: 2

Ile Glu Val Met Tyr Pro Pro Pro Tyr
1               5

<210> SEQ ID NO 3
<211> LENGTH: 107
<212> TYPE: PRT
<213> ORGANISM: Homo sapiens

<400> SEQUENCE: 3

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser
            100                 105
```

```
<210> SEQ ID NO 4
<211> LENGTH: 7
<212> TYPE: PRT
<213> ORGANISM: Simian virus 40

<400> SEQUENCE: 4

Pro Lys Lys Lys Arg Lys Val
1               5

<210> SEQ ID NO 5
<211> LENGTH: 16
<212> TYPE: PRT
<213> ORGANISM: Unknown
<220> FEATURE:
<223> OTHER INFORMATION: nucleoplasmin bipartite NLS

<400> SEQUENCE: 5

Lys Arg Pro Ala Ala Thr Lys Lys Ala Gly Gln Ala Lys Lys Lys Lys
1               5                   10                  15

<210> SEQ ID NO 6
<211> LENGTH: 9
<212> TYPE: PRT
<213> ORGANISM: Unknown
<220> FEATURE:
<223> OTHER INFORMATION: c-myc NLS

<400> SEQUENCE: 6

Pro Ala Ala Lys Arg Val Lys Leu Asp
1               5

<210> SEQ ID NO 7
<211> LENGTH: 11
<212> TYPE: PRT
<213> ORGANISM: Unknown
<220> FEATURE:
<223> OTHER INFORMATION: c-myc NLS

<400> SEQUENCE: 7

Arg Gln Arg Arg Asn Glu Leu Lys Arg Ser Pro
1               5                   10

<210> SEQ ID NO 8
<211> LENGTH: 38
<212> TYPE: PRT
<213> ORGANISM: Unknown
<220> FEATURE:
<223> OTHER INFORMATION: hRNPA1 M9 NLS

<400> SEQUENCE: 8

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 9
<211> LENGTH: 42
<212> TYPE: PRT
<213> ORGANISM: Unknown
<220> FEATURE:
<223> OTHER INFORMATION: IBB domain from importin-alpha

<400> SEQUENCE: 9
```

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
                20                  25                  30

Asp Glu Gln Ile Leu Lys Arg Arg Asn Val
            35                  40

<210> SEQ ID NO 10
<211> LENGTH: 8
<212> TYPE: PRT
<213> ORGANISM: Unknown
<220> FEATURE:
<223> OTHER INFORMATION: myoma T protein

<400> SEQUENCE: 10

Val Ser Arg Lys Arg Pro Arg Pro
1               5

<210> SEQ ID NO 11
<211> LENGTH: 8
<212> TYPE: PRT
<213> ORGANISM: Unknown
<220> FEATURE:
<223> OTHER INFORMATION: myoma Tprotein

<400> SEQUENCE: 11

Pro Pro Lys Lys Ala Arg Glu Asp
1               5

<210> SEQ ID NO 12
<211> LENGTH: 8
<212> TYPE: PRT
<213> ORGANISM: Homo sapiens

<400> SEQUENCE: 12

Pro Gln Pro Lys Lys Lys Pro Leu
1               5

<210> SEQ ID NO 13
<211> LENGTH: 12
<212> TYPE: PRT
<213> ORGANISM: Mus

<400> SEQUENCE: 13

Ser Ala Leu Ile Lys Lys Lys Lys Lys Met Ala Pro
1               5                   10

<210> SEQ ID NO 14
<211> LENGTH: 5
<212> TYPE: PRT
<213> ORGANISM: Influenze virus NS1

<400> SEQUENCE: 14

Asp Arg Leu Arg Arg
1               5

<210> SEQ ID NO 15
<211> LENGTH: 7
<212> TYPE: PRT
<213> ORGANISM: infulenza virus

<400> SEQUENCE: 15

Pro Lys Gln Lys Lys Arg Lys
1               5

<210> SEQ ID NO 16
<211> LENGTH: 10
<212> TYPE: PRT
<213> ORGANISM: Hepatittis virus delta antigen

<400> SEQUENCE: 16

```
Arg Lys Leu Lys Lys Lys Ile Lys Lys Leu
1               5                   10
```

<210> SEQ ID NO 17
<211> LENGTH: 10
<212> TYPE: PRT
<213> ORGANISM: Mus sp.

<400> SEQUENCE: 17

```
Arg Glu Lys Lys Lys Phe Leu Lys Arg Arg
1               5                   10
```

<210> SEQ ID NO 18
<211> LENGTH: 20
<212> TYPE: PRT
<213> ORGANISM: Homo sapiens

<400> SEQUENCE: 18

```
Lys Arg Lys Gly Asp Glu Val Asp Gly Val Asp Glu Val Ala Lys Lys
1               5                   10                  15

Lys Ser Lys Lys
            20
```

<210> SEQ ID NO 19
<211> LENGTH: 17
<212> TYPE: PRT
<213> ORGANISM: Homo sapiens

<400> SEQUENCE: 19

```
Arg Lys Cys Leu Gln Ala Gly Met Asn Leu Glu Ala Arg Lys Thr Lys
1               5                   10                  15

Lys
```

<210> SEQ ID NO 20
<211> LENGTH: 288
<212> TYPE: PRT
<213> ORGANISM: Artificial Sequence
<220> FEATURE:
<223> OTHER INFORMATION: Synthetic

<400> SEQUENCE: 20

```
Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Ala Pro Ser Pro Ala Phe
    50                  55                  60

Ser Ala Asp Ser Phe Ser Asp Leu Leu Arg Gln Phe Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
```

```
            100                 105                 110
Ala Ala Asp Ala Pro Pro Thr Met Arg Val Ala Val Thr Ala Ala
            115                 120                 125

Arg Pro Pro Arg Ala Lys Pro Ala Pro Arg Arg Ala Ala Gln Pro
130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                    165                 170                 175

Ala Gln His His Glu Ala Leu Val Gly His Gly Phe Thr His Ala His
                180                 185                 190

Ile Val Ala Leu Ser Gln His Pro Ala Ala Leu Gly Thr Val Ala Val
                195                 200                 205

Lys Tyr Gln Asp Met Ile Ala Ala Leu Pro Glu Ala Thr His Glu Ala
            210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
                245                 250                 255

Thr Gly Gln Leu Leu Lys Ile Ala Lys Arg Gly Gly Val Thr Ala Val
            260                 265                 270

Glu Ala Val His Ala Trp Arg Asn Ala Leu Thr Gly Ala Pro Leu Asn
                275                 280                 285

<210> SEQ ID NO 21
<211> LENGTH: 183
<212> TYPE: PRT
<213> ORGANISM: Artificial Sequence
<220> FEATURE:
<223> OTHER INFORMATION: Synthetic

<400> SEQUENCE: 21

Arg Pro Ala Leu Glu Ser Ile Val Ala Gln Leu Ser Arg Pro Asp Pro
1               5                   10                  15

Ala Leu Ala Ala Leu Thr Asn Asp His Leu Val Ala Leu Ala Cys Leu
                20                  25                  30

Gly Gly Arg Pro Ala Leu Asp Ala Val Lys Lys Gly Leu Pro His Ala
            35                  40                  45

Pro Ala Leu Ile Lys Arg Thr Asn Arg Arg Ile Pro Glu Arg Thr Ser
50                  55                  60

His Arg Val Ala Asp His Ala Gln Val Val Arg Val Leu Gly Phe Phe
65                  70                  75                  80

Gln Cys His Ser His Pro Ala Gln Ala Phe Asp Asp Ala Met Thr Gln
                85                  90                  95

Phe Gly Met Ser Arg His Gly Leu Leu Gln Leu Phe Arg Arg Val Gly
            100                 105                 110

Val Thr Glu Leu Glu Ala Arg Ser Gly Thr Leu Pro Pro Ala Ser Gln
        115                 120                 125

Arg Trp Asp Arg Ile Leu Gln Ala Ser Gly Met Lys Arg Ala Lys Pro
        130                 135                 140

Ser Pro Thr Ser Thr Gln Thr Pro Asp Gln Ala Ser Leu His Ala Phe
145                 150                 155                 160
```

```
Ala Asp Ser Leu Glu Arg Asp Leu Asp Ala Pro Ser Pro Met His Glu
            165                 170                 175

Gly Asp Gln Thr Arg Ala Ser
            180
```

METHODS AND COMPOSITIONS OF USE OF CD8+ TUMOR INFILTRATING LYMPHOCYTE SUBTYPES AND GENE SIGNATURES THEREOF

CROSS-REFERENCE TO RELATED APPLICATIONS

This application claims the benefit of U.S. Provisional Application Nos. 62/505,101, filed May 11, 2017 and 62/574,878, filed Oct. 20, 2017. The entire contents of the above-identified applications are hereby fully incorporated herein by reference.

STATEMENT REGARDING FEDERALLY SPONSORED RESEARCH

This invention was made with government support under Grant No. CA208756 awarded by the National Institutes of Health. The government has certain rights in the invention.

TECHNICAL FIELD

The subject matter disclosed herein is generally directed to CD8+ tumor infiltrating lymphocytes comprising gene signatures associated with response to immunotherapy treatment and overall survival. Moreover, the subject matter disclosed herein is generally directed to methods and compositions for use of the signature genes.

BACKGROUND

The development of antibodies that effectively block the activities of immune checkpoint proteins, including CTLA4, PD-1 or its ligand, PD-L1[1], has led to their approval by the FDA for treating a wide variety of cancers, including melanoma, non-small-cell lung carcinoma (NSCLC), renal cell carcinoma (RCC), urothelial bladder cancer (UBC), head and neck squamous cell carcinoma (HNSCC), refractory Hodgkin's lymphoma (HL), and most recently hepatocellular carcinoma (HCC) and gastric cancer[2]. In melanoma, despite the high response rate (~20% for anti-CTLA4, ~45% for anti-PD-1, ~60% for anti-PD-1+ anti-CTLA4)[3,4], most patients are refractory to therapy or acquire resistance, and eventually succumb to disease. Thus, identification of the key components that drive or prevent effective responses to checkpoint therapy remains an urgent need for accelerating progress in the fields of cancer immunotherapy, and perhaps, medical oncology.

Checkpoint therapies are designed to overcome the inhibition of antigen-specific, effector T lymphocytes (T-cells) by the tumor or the immune microenvironment. Thus, the state and number of these cells, especially CD8+ cytotoxic T-cells are likely to determine the clinical outcome. Indeed, the number of infiltrating CD8+ T-cells detected before[5] or during early treatment[6] have been shown to be associated with clinical outcome. The ability of these CD8+ T-cells to target the malignant cells is dampened by persistent exposure to stimulation and co-inhibition by checkpoint proteins, resulting in a state of exhaustion[7,8], characterized by the expression of multiple co-inhibitory receptors on the T-cell surface (e.g. PD1, CTLA4, TIM3, TIGIT), unique regulators of gene expression (BATF, PRDM1), and most importantly, dysfunctional effector activity. Additionally, the efficiency of checkpoint therapy depends on CD8+ T-cell recognition of neoantigens presented on human leukocyte antigen (HLA) class I by tumor cells[9,10]. Hence, a deeper understanding of the cellular and molecular determinants of response are needed.

To date, several factors have been analyzed for their association with tumor growth and clinical outcome in patients. These include levels of PD-L1 protein[4,11], load of tumor-derived neoantigens 1, defects in antigen presentation and IFNg pathways[13-16], abundance of partially exhausted CD8+ T-cells in the tumor[17], proportion of suppressive myeloid cells in the blood[18], and the magnitude of T-cell reinvigoration in relation to pretreatment tumor burden[19]. While these studies have collectively contributed to the model explaining the efficacy of checkpoint therapy, their major limitations include low predictive power and the use of pre-defined immune markers, limiting their ability to identify optimal and novel components that explain or predict clinical outcomes. Thus, there is a need to more systematically identify markers and mechanisms associated with response to therapy.

Citation or identification of any document in this application is not an admission that such document is available as prior art to the present invention.

SUMMARY

In one aspect, the present invention provides for a method of detecting a checkpoint blockade (CPB) therapy responder gene signature comprising, detecting in CD45+ cells obtained from a biological sample the expression of a gene signature comprising one or more genes or polypeptides selected from the group consisting of: TCF7; or TCF7, PLAC8, LTB, and CCR7; or TCF7, LEF1, S1PR1, PLAC8, LTB, CCR7, IGHD, PAX5, FCRL1, FCER2, CD19, CD22, BANK1, MS4A1, BLK, RALGPS2 and FAM129C; or TCF7, PLAC8, LTB, LY9, SELL, IGKC and CCR7.

In another aspect, the present invention provides for a method of detecting a checkpoint blockade (CPB) therapy responder gene signature comprising, detecting in CD8+T cells obtained from a biological sample the expression of a gene signature comprising one or more genes or polypeptides selected from the group consisting of: TCF7; or TCF7 and IL7R; or TCF7, IL7R, FOSL2, REL, FOXP1, and STAT4; or TCF7, PLAC8, LTB, and CCR7; or TCF7, LEF1, S1PR1, PLAC8, LTB, and CCR7; or TCF7, IL7R, GPR183, and MGAT4A; or TCF7, IL7R, GPR183, LMNA, NR4A3, CD55, AIM1, MGAT4A, PER1, FOSL2, TSPYL2, REL, FAM177A1, YPEL5, TC2N and CSRNP1; or TCF7, IL7R, GPR183, LMNA, NR4A3, CD55, AIM1, MGAT4A, PER1, FOSL2, TSPYL2, REL, FAM177A1, YPEL5, TC2N, CSRNP1, FAM65B, PIK3R1, RGPD6, SKIL, TSC22D2, USP36, FOXP1, EGR1, MYADM, ZFP36L2, FAM102A, RGCC, PDE4B, PFKFB3, FOSB, DCTN6 and BTG2; or CD8_G genes listed in Table 6.

In certain embodiments, the CD8 T cells having a responder signature does not express ENTPD1 (CD39) and HAVCR2.

In another aspect, the present invention provides for a method of detecting a checkpoint blockade (CPB) therapy non-responder gene signature comprising, detecting in CD45+ cells obtained from a biological sample the expression of a gene signature comprising one or more genes or polypeptides selected from the group consisting of: ENTPD1 and HAVCR2; or CCL3, CD38 and HAVCR2; or CD38, PDCD1, CCL3, SNAP47, VCAM1, HAVCR2, FASLG, ENTPD1, SIRPG, MYO7A, FABP5, NDUFB3, UBE2F, CLTA and SNRPD1; or FASLG, VCAM1, CCL3, LAG3, CXCR6, IFNG, PDCD1, KLRD1, HAVCR2, SIRPG, SNAP47, DTHD1, PRF1, GZMH, F2R, CD38, CXCL13, TNFRSF4, TNFRSF18, MAF, ETV7, CD4, CTLA4, FCRL6, SPON2, KLRG1, TRGC1, A2M, FCGR3A, GZMA, HOPX, NKG7, PXN, TNFRSF9, GEM, NAB1, DFNB31, CADM1, CRTAM, GPR56, MYO7A, DUSP4, METRNL and PHLDA1; or LAYN, GEM, VCAM1, RDH10, TNFRSF18, FAM3C, AFAP1L2, KIR2DL4, MTSS1, ETV1, CTLA4, MYO7A, ENTPD1, TNFRSF9, CADM1, DFNB31, CXCL13, HAVCR2, GPR56, GOLIM4, NAB1, PHLDA1, TGIF1, SEC14L1, IGFLR1, NAMPTL, PAM, HSPB1, TNIP3, BPGM, TP53INP1, TRPS1, UBE2F, NDFIP2, PON2, PELI1, METRNL, SNAP47 and APLP2; or CCL3, LGALS1, CD38, EPSTI1, WARS, PLEK, HAVCR2, LGALS3, FABP5, MT2A, GBP1, PLSCR1, CCR5, GSTO1, ANXA5, GLUL, PYCARD, TYMP, IFI6, VAMP5, OASL, GZMB, TXN, SQRDL, RHOC, AP2S1, GZMH, CCL4L2, SNAP47, LAP3, ATP6V1B2, CCL4L1, LAMP2, PSMA4, SERPINB1, HIGD1A, UBE2F, TALDO1, CD63, CLTA, S100A11, PHPT1, GBP4, PRDX3, PSMB2, BST2, GBP5, CTSC, NDUFB3, NPC2, GALM, GLIPR2, CCL4, PRF1, IFNG, IFI30, CHST12, ISG15, MYD88, IDH2, MTHFD2, CHMP2A, NDUFA9, CHMP5, CALM3, ANXA2, PPT1, GTF3C6, NDUFAB1, CXCR6, RNF181, LGALS9, COX5A, OAS2, PDCD1, SNRPC, BHLHE40, TWF2, SLAMF7, TXN2, CARD16, ANAPC11, MRPL51, LIMS1, NDUFA12, RANBP1, GBP2, PSMC1, ACTR1A, CD2BP2, VDAC1, EMC7, MX1, GPS1, ATP5J2, USMG5, SHFM1, ATP5I, FAM96A, CASP1, PARP9, NOP10, GNG5, CYC1, RAB11A, PGAM1, ENTPD1, PDIA6, PSMC3, TMBIM1, UBE2L6, PSMA6, EIF6, DCTN3, SEC11A, CSTB, ETFB, DBI, GRN, ELOVL1, UBE2L3, PSMB3, NDUFB7, DOK2, SEC61G, IGFLR1, ATP5H, COPZ1, ATP6V1F, BNIP3L, NUTF2, AKR1A1, MDH2, VAMP8, ROMO1, CXCR3, SAMHD1, NUCB1, ACTN4, ZYX, FLOT1, BLOC1S1, STAT1, VIMP, PAM, NUDT21, MYO1G, C17orf49, GTF2A2, HIST2H2AA4, C19orf10, ABI3, TRAPPC5, PSMC4, NDUFC2, HN1, SNRPD3, CMC1, RAB27A, NDUFA6, POMP, PFKP, ATP5G3, TMEM179B, PSMD9, IRF7, CNIH1, DYNLRB1, APOL2, TKT, DCTN2, GSDMD, STOM, CTSD, KDELR2, ATP5J, RPS27L, PSME2, DRAP1, NDUFB10, DECR1, GSTP1, TMED9, MGAT1, HSPB1, COX8A, ZEB2, ILK, PSMB6, HK1, CD58, TMX1, GZMA, SRI, PSMG2, ARL8B, NKG7, GPX1, ACP5, CHP1, GPR171, ATP6V0B, KLRD1, H2AFY, PPM1G, PRDX5, PSMA5, FBXW5, ATP6AP1, CD4, SNRPD1, XAF1, LY6E, DYNLT1, AK2, PSMA2, YIPF3, S100A10, SCP2, MRPS34, PSMD4, CDC123, BTG3, TMEM258, TSPO, SDHB, TCEB1, WDR83OS, HCST, NAA10, CTSB, YARS, GLRX, RBCK1, RBX1, LAMTOR1, UQCRFS1, NDUFB4, CAPZA2, BRK1, ADRM1, NDUFB2, ETFA, VDAC3, NUDT5, IFITM3, BANF1, ZNHIT1, CAPG, NHP2, LASP1, TOMM5, MVP, CTSW, AURKAIP1, RARRES3, PSMB10, TMEM173, SLX1A, APOBEC3G, GIMAP4, EIF4E, CTLA4, NDUFS8, CYB5B, PIK3R5, HEXB, STXBP2, PSMD8, SEC61B, RGS10, PHB, ATP5C1, ARF5, SUMO3, PRDX6, RNH1, ATP5F1, UQCRC1, SARNP, PLIN2, PIN1, SDHC, SF3B14, CAPRIN1, POLR2G, COX7B, UQCR10, FBXO7, NDUFB6, S100A4, PRELID1, TRPV2, SF3B5, MYO1F, SCAMP2, RNF7, CXCL13, RAB1B, SHKBP1, PET100, HM13, VTI1B, S100A6, ARPC5, FDPS, MINOS1, RAB10, NEDD8, BATF, PHB2, ERH, NCOA4, PDIA4, PSMB9, C11orf48, TMEM50A, TIGIT, NDUFA11, NELFE, COX6C, SLA2, PSMB8, NDUFS7, RER1, RAB8A, CAPN1, MRPL20, COX5B, SEC13, FKBP1A, PRDM1, RAB1A, RHOG, CYB5R3, AIP, ABRACL, PSMB7, COX6B1, PSMD7, PPA1, PCMT1, SURF4, ENY2, TCEB2, MAP2K3, AL353354.2, AKIRIN2, MAPRE1, GRSF1, DUSP4, ATG3, SRGAP2, ATP6V0D1, NELFCD, LRPAP1, C14orf166, SNRPB2, CHMP4A, SFT2D1, CASP4, NME1-NME2, FAM96B, FDFT1, SLC25A39, LMAN2, MDH1, RHBDD2, ARPC5L, TBCA, EBP, SEC14L1, EIF2S2, CST7, STARD7, SOD2, SPN, FAM32A, SEC11C, TNFRSF1B, POLR2E, NDUFA13, OSTC, UFC1, C18orf32, SRP19, C14orf2, UQCR11, PDCD6, AP2M1, PPP1CA, ATP6AP2, SSR3, UNC13D, FERMT3, ARHGAP1, EIF3I, CECR1, MRPS6, DNPH1, DCXR, PSMF1, SNRPG, CNDP2, ANXA11, SLMO2, C16orf13, CAPN2, BSG, LAMTOR5, SIVA1, TRAPPC1, TMCO1, PSMD13, PSMB1, RSU1, NDUFA1, TUBB, DCTN1, SH3GLB1, BCAP31, RTFDC1, UFD1L, GPI, DNAJB11, SNX17, SH2D2A, C1orf43, BUD31, PSTPIP1, CTSA, TPST2, MPV17, APMAP, CMC2, UQCRQ, TBCB, C9orf16, PARK7, ATP5EP2, SHISA5, SMC4, TAP1, SCAND1, SIRPG, HDLBP, EMC4, FIS1, TPI1, GOLGA7, POLR2J, EIF2S1, UBA3, P4HB, UQCRH, CSNK2B, SZRD1, NDUFA3, ATP5O, DERL2, COPS6, COPE, SNX6, FLII and ERGIC3.

In another aspect, the present invention provides for a method of detecting a checkpoint blockade (CPB) therapy non-responder gene signature comprising, detecting in CD8+ T cells obtained from a biological sample the expression of a gene signature comprising one or more genes or polypeptides selected from the group consisting of: ENTPD1 and HAVCR2; or CCL3, CD38 and HAVCR2; or CD38, CCL3, VCAM1, GOLIM4, HAVCR2, PRDX3, ENTPD1, PTTG1, CCR5, TRAFD1, PDCD1, CXCR6, BATF, PTPN6, LAG3 and CTLA4; or LAYN, GEM, VCAM1, RDH10, TNFRSF18, FAM3C, AFAP1L2, KIR2DL4, MTSS1, ETV1, CTLA4, MYO7A, ENTPD1, TNFRSF9, CADM1, DFNB31, CXCL13, HAVCR2, GPR56, GOLIM4, NAB1, PHLDA1, TGIF1, SEC14L1, IGFLR1, NAMPTL, PAM, HSPB1, TNIP3, BPGM, TP53INP1, TRPS1, UBE2F, NDFIP2, PON2, PELI1, METRNL, SNAP47 and APLP2; or CD38, EPSTI1, GOLIM4, WARS, PDCD1, CCL3, SNAP47, VCAM1, SKA2, HAVCR2, LGALS9, PRDX3, FASLG, ENTPD1, FABP5, SIRPG, LSM2, NDUFB3, TRAFD1, UBE2F, NMI, IFI35, CLTA, MTHFD1, MYO7A, IFI27L2, MCM5, STMN1, ID3, RGS3, SNRPD1, PTTG1 and FIBP; or CD8_B genes listed in Table 6.

In certain embodiments, the biological sample is a tumor sample obtained from a subject in need thereof. In certain embodiments, the gene signature is detected in tumor infiltrating lymphocytes (TILs). In certain embodiments, the biological sample comprises ex vivo or in vitro immune cells, preferably CD8+ T cells. In certain embodiments, the gene signature is detected by deconvolution of bulk expression data such that gene expression in immune cells is detected.

In certain embodiments, detecting a higher proportion immune cells expressing a responder signature as compared to a non-responder signature indicates sensitivity to checkpoint blockade (CPB) therapy and an increased overall survival, and wherein detecting a higher proportion immune cells expressing a non-responder signature indicates resistance to checkpoint blockade (CPB) therapy and a decreased overall survival. In certain embodiments, detecting a higher proportion of TCF7+CD8+ as compared to TCF7−CD8+ T cells indicates sensitivity to checkpoint blockade (CPB) therapy and an increased overall survival, and wherein detecting a higher proportion TCF7−CD8+ as compared to TCF7+CD8+ T cells indicates resistance to checkpoint blockade (CPB) therapy and a decreased overall survival. In certain embodiments, TCF7+CD8+ and TCF7−CD8+ T cells are detected by immunofluorescence. In certain embodiments, the checkpoint blockade (CPB) therapy comprises anti-CTLA4, anti-PD-L1, anti-PD1 therapy or combinations thereof.

In another aspect, the present invention provides for a method of predicting cancer clinical outcome in a subject in need thereof comprising detecting in a sample obtained from the subject the ratio of immune cells enriched for expression of a gene signature according to any of claims 1 to 3 as compared to immune cells enriched for expression of a gene signature according to claim 4 or 5, wherein a ratio greater than one indicates sensitivity to an immunotherapy and an increased overall survival, and wherein a ratio less than one indicates resistance to an immunotherapy and a decreased overall survival.

In another aspect, the present invention provides for a method of predicting cancer clinical outcome in a subject in need thereof comprising detecting in a sample obtained from the subject the ratio of TCF7+CD8+ to TCF7−CD8+ T cells, wherein a ratio greater than one indicates sensitivity to an immunotherapy and an increased overall survival and wherein a ratio less than one indicates resistance to an immunotherapy and a decreased overall survival. In certain embodiments, TCF7+CD8+ and TCF7−CD8+ T cells are detected by immunofluorescence.

In certain embodiments, the method further comprises detecting mutations associated with loss of antigen presentation in tumor cells obtained from the subject, wherein detecting a mutation associated with loss of antigen presentation indicates resistance to an immunotherapy and a decreased overall survival. In certain embodiments, the mutations result in the loss of one or more genes or polypeptides selected from the group consisting of B2M, HLA-A, HLA-B, and HLA-C. In certain embodiments, predicting cancer clinical outcome is performed before, after or during treatment with a checkpoint blockade (CPB) therapy.

In another aspect, the present invention provides for a method of enriching for memory/effector CD8+ T cells comprising sorting for CD8+ T cells lacking expression of ENTPD1 and HAVCR2 and/or lacking expression of CD38.

In another aspect, the present invention provides for a method of enriching for exhausted CD8+ T cells comprising sorting for CD8+ T cells that express ENTPD1 and HAVCR2 and/or express CD38.

In certain embodiments, the cells are sorted using antibodies specific to ENTPD1 and HAVCR2 and/or CD38.

In another aspect, the present invention provides for a population of CD8+ T cells, wherein the population of cells comprises CD8+ T cells that lack expression of ENTPD1 and HAVCR2 and/or CD38. The population of cells may be depleted for CD8+ T cells that express ENTPD1 and HAVCR2 and/or CD38. The population of cells may be enriched for CD8+ T cells that lack expression of ENTPD1 and HAVCR2 and/or CD38.

In another aspect, the present invention provides for a population of CD8+ T cells, wherein the population of cells comprises cells having a responder gene signature according to any of claims 1 to 3. The population of cells may be depleted for cells having a non-responder gene signature according to claim 4 or 5. The population of cells may be enriched for cells having a responder gene signature according to any of claims 1 to 3. The population of cells may express a chimeric antigen receptor (CAR) or an endogenous T cell receptor (TCR). The population of cells may comprise CD8+ T cells obtained from a subject suffering from cancer.

In certain embodiments, the population of CD8+ T cells are modulated to decrease activity or expression of one or more genes or polypeptides selected from the group consisting of: ENTPD1 and HAVCR2; or CCL3, CD38 and HAVCR2; or CD38, CCL3, VCAM1, GOLIM4, HAVCR2, PRDX3, ENTPD1, PTTG1, CCR5, TRAFD1, PDCD1, CXCR6, BATF, PTPN6, LAG3 and CTLA4; or CD38, EPSTI1, GOLIM4, WARS, PDCD1, CCL3, SNAP47, VCAM1, SKA2, HAVCR2, LGALS9, PRDX3, FASLG, ENTPD1, FABP5, SIRPG, LSM2, NDUFB3, TRAFD1, UBE2F, NMI, IFI35, CLTA, MTHFD1, MYO7A, IFI27L2, MCM5, STMN1, ID3, RGS3, SNRPD1, PTTG1 and FIBP; or CD8_B genes listed in Table 6.

In certain embodiments, the population of CD8+ T cells are modulated to increase activity or expression one or more genes or polypeptides selected from the group consisting of: TCF7; or TCF7 and IL7R; or TCF7, IL7R, FOSL2, REL, FOXP1, and STAT4; or TCF7, PLAC8, LTB, and CCR7; or TCF7, LEF1, S1PR1, PLAC8, LTB, and CCR7; or TCF7, IL7R, GPR183, and MGAT4A; or TCF7, IL7R, GPR183, LMNA, NR4A3, CD55, AIM1, MGAT4A, PER1, FOSL2, TSPYL2, REL, FAM177A1, YPEL5, TC2N and CSRNP1; or TCF7, IL7R, GPR183, LMNA, NR4A3, CD55, AIM1, MGAT4A, PER1, FOSL2, TSPYL2, REL, FAM177A1, YPEL5, TC2N, CSRNP1, FAM65B, PIK3R1, RGPD6, SKIL, TSC22D2, USP36, FOXP1, EGR1, MYADM, ZFP36L2, FAM102A, RGCC, PDE4B, PFKFB3, FOSB, DCTN6 and BTG2; or CD8_G genes listed in Table 6.

In certain embodiments, the one or more genes are modulated with a genetic modifying agent. In certain embodiments, the population of cells comprises activated T cells. In certain embodiments, the population of cells comprises T cells activated with tumor specific antigens. In certain embodiments, the tumor specific antigens are subject specific antigens.

In another aspect, the present invention provides for a pharmaceutical composition comprising the population of cells according to any embodiment herein.

In another aspect, the present invention provides for a method of treating cancer in a subject in need thereof comprising administering an inhibitor of CD39 and an inhibitor of TIM3 or an inhibitor of CD39 and an inhibitor of PD1. The inhibitor of TIM3 may comprise anti-TIM3 antibodies or the inhibitor of PD1 may comprise anti-PD1 antibodies. The inhibitor of CD39 may comprise POM-1.

In another aspect, the present invention provides for a method of treating cancer in a subject in need thereof comprising: predicting cancer clinical outcome in the subject according to any of claims 14 to 19; and treating the subject, wherein responders are treated with an immunotherapy comprising checkpoint blockade (CPB) therapy, wherein non-responders are treated with: adoptive cell transfer and optionally checkpoint blockade (CPB) therapy; or an inhibitor of CD39 and an inhibitor of TIM3; or an inhibitor of CD39 and an inhibitor of PD1; or an agent capable of targeting, inhibiting or depleting CD8+ TILs having said non-responder signature and optionally checkpoint blockade (CPB) therapy; or an agent capable of activating, maintaining or increasing CD8+ TILs having said responder signature and optionally checkpoint blockade (CPB) therapy, or wherein non-responders comprising tumors not capable of presenting antigens are treated with a therapy other than checkpoint blockade (CPB) therapy.

In certain embodiments, the adoptive cell transfer comprises: autologous T cells having the responder signature; or autologous T cells specific against tumor antigens, having the responder signature; or autologous T cells transduced with T cell receptors targeting tumor antigens, having the responder signature; or autologous CAR T cells having the responder gene signature; or allogenic T cells having the responder signature; or allogenic T cells specific against tumor antigens, having the responder signature; or allogenic T cells transduced with T cell receptors targeting tumor antigens, having the responder signature; or allogenic CAR T cells having the responder gene signature. In certain embodiments, the autologous T cells are obtained from the subject and cells having the non-responder signature are depleted and/or cells having the responder signature are expanded. In certain embodiments, CAR T cells are enriched for cells having a responder signature or depleted for cells having a non-responder signature. In certain embodiments, the agent capable of targeting, inhibiting or depleting CD8+ TILs having a non-responder signature comprises: an agent capable of binding to a cell surface or secreted CD8+ T cell non-responder signature gene; or an agent capable of reducing the expression or activity of the non-responder signature. In certain embodiments, the agent capable of activating, maintaining or increasing CD8+ TILs having a responder signature comprises an agent capable of increasing or activating the expression of the responder signature. In certain embodiments, checkpoint blockade (CPB) therapy comprises anti-CTLA4, anti-PD-L1, anti-PD1 therapy or combinations thereof.

In another aspect, the present invention provides for a method of treating cancer in a subject in need thereof comprising administering an agent capable of increasing the expression or activity of one or more genes or polypeptides selected from the group consisting of TCF7, IL7R, GPR183, LMNA, NR4A3, CD55, AIM1, MGAT4A, PER1, FOSL2, TSPYL2, REL, FAM177A1, YPEL5, TC2N, CSRNP1, FAM65B, PIK3R1, RGPD6, SKIL, TSC22D2, USP36, FOXP1, STAT4, PLAC8, LTB LEF1, S1PR1, EGR1, MYADM, ZFP36L2, FAM102A, RGCC, PDE4B, PFKFB3, FOSB, DCTN6 and BTG2 in combination with checkpoint blockade therapy.

In another aspect, the present invention provides for a method of treating cancer in a subject in need thereof comprising administering an agent capable of reducing the expression or activity of one or more genes or polypeptides selected from the group consisting of CD38, CCL3, VCAM1, GOLIM4, HAVCR2, PRDX3, ENTPD1, PTTG1, CCR5, TRAFD1, PDCD1, CXCR6, BATF, PTPN6, LAG3 and CTLA4 in combination with checkpoint blockade therapy.

In another aspect, the present invention provides for a method of treating cancer in a subject in need thereof comprising administering CD8+ T cells expressing a gene signature comprising of one or more genes selected from the group consisting of TCF7, IL7R, GPR183, LMNA, NR4A3, CD55, AIM1, MGAT4A, PER1, FOSL2, TSPYL2, REL, FAM177A1, YPEL5, TC2N, CSRNP1, FAM65B, PIK3R1, RGPD6, SKIL, TSC22D2, USP36, FOXP1, STAT4, PLAC8, LTB LEF1, S1PR1, EGR1, MYADM, ZFP36L2, FAM102A, RGCC, PDE4B, PFKFB3, FOSB, DCTN6 and BTG2 in combination with checkpoint blockade therapy.

In certain embodiments, agent comprises a therapeutic antibody, antibody fragment, antibody-like protein scaffold, aptamer, protein, genetic modifying agent or small molecule.

In another aspect, the present invention provides for a method of monitoring a subject in need thereof undergoing treatment with checkpoint blockade (CPB) therapy, said method comprising detecting in a tumor sample obtained from the subject the expression or activity of a gene signature comprising one or more genes or polypeptides selected from the group consisting of: ENTPD1 and HAVCR2; or CCL3, CD38 and HAVCR2; or CD38, CCL3, VCAM1, GOLIM4, HAVCR2, PRDX3, ENTPD1, PTTG1, CCR5, TRAFD1, PDCD1, CXCR6, BATF, PTPN6, LAG3 and CTLA4; or CD38, EPSTI1, GOLIM4, WARS, PDCD1, CCL3, SNAP47, VCAM1, SKA2, HAVCR2, LGALS9, PRDX3, FASLG, ENTPD1, FABP5, SIRPG, LSM2, NDUFB3, TRAFD1, UBE2F, NMI, IFI35, CLTA, MTHFD1, MYO7A, IFI27L2, MCM5, STMN1, ID3, RGS3, SNRPD1, PTTG1 and FIBP; or CD8_B genes listed in Table 6, wherein the treatment is adjusted if the signature is increased in CD8+ TILs after treatment.

In another aspect, the present invention provides for a method of monitoring a subject in need thereof undergoing treatment with checkpoint blockade (CPB) therapy, said method comprising detecting in a tumor sample obtained from the subject the expression or activity of a gene signature comprising one or more genes or polypeptides selected from the group consisting of: TCF7; or TCF7 and IL7R; or TCF7, IL7R, FOSL2, REL, FOXP1, and STAT4; or TCF7, PLAC8, LTB, and CCR7; or TCF7, LEF1, S1PR1, PLAC8, LTB, and CCR7; or TCF7, IL7R, GPR183, and MGAT4A; or TCF7, IL7R, GPR183, LMNA, NR4A3, CD55, AIM1, MGAT4A, PER1, FOSL2, TSPYL2, REL, FAM177A1, YPEL5, TC2N and CSRNP1; or TCF7, IL7R, GPR183, LMNA, NR4A3, CD55, AIM1, MGAT4A, PER1, FOSL2, TSPYL2, REL, FAM177A1, YPEL5, TC2N, CSRNP1, FAM65B, PIK3R1, RGPD6, SKIL, TSC22D2, USP36, FOXP1, EGR1, MYADM, ZFP36L2, FAM102A, RGCC, PDE4B, PFKFB3, FOSB, DCTN6 and BTG2; or CD8_G genes listed in Table 6, wherein the treatment is adjusted if the signature is decreased in CD8+ TILs after treatment.

In another aspect, the present invention provides for a method of manufacturing cells for use in adoptive cell transfer comprising: obtaining CD8+ T cells; and depleting cells having a non-responder signature as defined in claim 4 or 5 or selecting for cells having a responder signature as defined in any of claims 1 to 3. The method may further comprise expanding cells having a responder signature. The method may further comprise activating the cells. The method may further comprise expressing a chimeric antigen receptor (CAR) or an endogenous T cell receptor (TCR) in the cells.

In another aspect, the present invention provides for a kit comprising reagents to detect at least one gene or polypeptide according to a gene signature as defined in claim 1 or 5. The kit may comprise at least one antibody, antibody fragment, or aptamer. The kit may comprise primers and/or probes or fluorescently bar-coded oligonucleotide probes for hybridization to RNA.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

FIG. 21A illustrates a tSNE analysis showing that tumor infiltrating CD8 T cells cluster into G1 or G2. FIG. 21B illustrates a heat map showing expression of G1 and G2 genes in responders and non-responders. FIG. 21C illustrates the ratio of G2/G1 expression in responders and non-responders. Patients positive for antigen presentation and the IFN gamma pathway and patients defective for antigen presentation and the IFN gamma pathway are distinguished. FIG. 21D illustrates a graph showing overall survival of patients with low or high expression of G1. FIG. 21E illustrates immunofluorescence images stained for CD8 and TCF7 in a responder and non-responder patient. The percentage of CD8+ cells and the ratio of TCF+/TCF−CD8+ cells are calculated for the responder and non-responder patient.

FIG. 22A-22C—illustrate immunofluorescence imaging and calculation of TCF7 positive CD8 cells using CellProfiler (cellprofiler.org) and a novel pipeline.

FIG. 23—The immune landscape of melanoma patients treated with checkpoint therapy.

FIG. 24—Identification of CD8$^+$ T-cell states associated with clinical outcome.

FIG. 26—Discriminating exhausted from memory cells using TIM3 and ENTPD1/CD39.

FIG. 27—Distinctive chromatin accessibility in $CD39^+TIM3^+$ and $CD39^-TIM3^-$ cells.

FIG. 28—TCR analysis and its relationship with cell state and clinical outcome.

*P=0.03 for CD8_3; *P=0.02 for CD8_5.

FIG. 29—Association of the 11 CD45$^+$ clusters with clinical outcome during the course of checkpoint therapy.

FIG. 30—Supervised analysis of T cell states.

FIG. 31—Comparing the composition of known cell types with clinical outcome and checkpoint therapy.

FIG. 32—Supervised analysis of CD4$^+$ and CD8$^+$ T-cells expressing effector, memory and regulatory genes.

FIG. 34—Detection of cluster-specific genes differentially expressed between responder and non-responder samples.

FIG. 37—Quantification of two CD8$^+$ T cell states associated with clinical response.

FIG. 38—Detection of defects in antigen presentation increases response prediction.

FIG. 39—Detection and quantitation of TCF7$^+$CD8$^+$ and TCF7$^-$CD8$^+$ cells in a cohort of patients treated with anti-PD1.

FIG. 40—Quantification of CD8$^+$TCF7$^+$ and CD8$^+$TCF7$^-$ protein levels in responder and non-responder lesions.

FIG. 41—High frequencies of CD8$^+$TCF7$^+$ T cells are associated with and predict clinical response.

FIG. 42—TCF7 kinetics between baseline and post-treatment samples.

FIG. 43—Proportion of exhaustion and memory markers across the six clusters.

FIG. 44—Hierarchical and trajectory analysis of CD8+ T-cell clusters.

FIG. 45—Characterization of CD39$^+$CD8$^+$ cells in melanoma patients.

FIG. 46—Dual inhibition of PD1 and CD39 synergistically reduces tumor growth and improves survival.

FIG. 47—CD39$^+$TIM3$^+$ and CD39$^-$TIM3-cells have a distinctive epigenetic landscape.

FIG. 48—Coupling TCR clonality with T-cell states.

FIG. 52—Hierarchical structure of splitting clusters. Clustering of CD8_B and CD8_G, separately, into two (upper panel) or three (lower panel) clusters.

DETAILED DESCRIPTION

Figure 1:
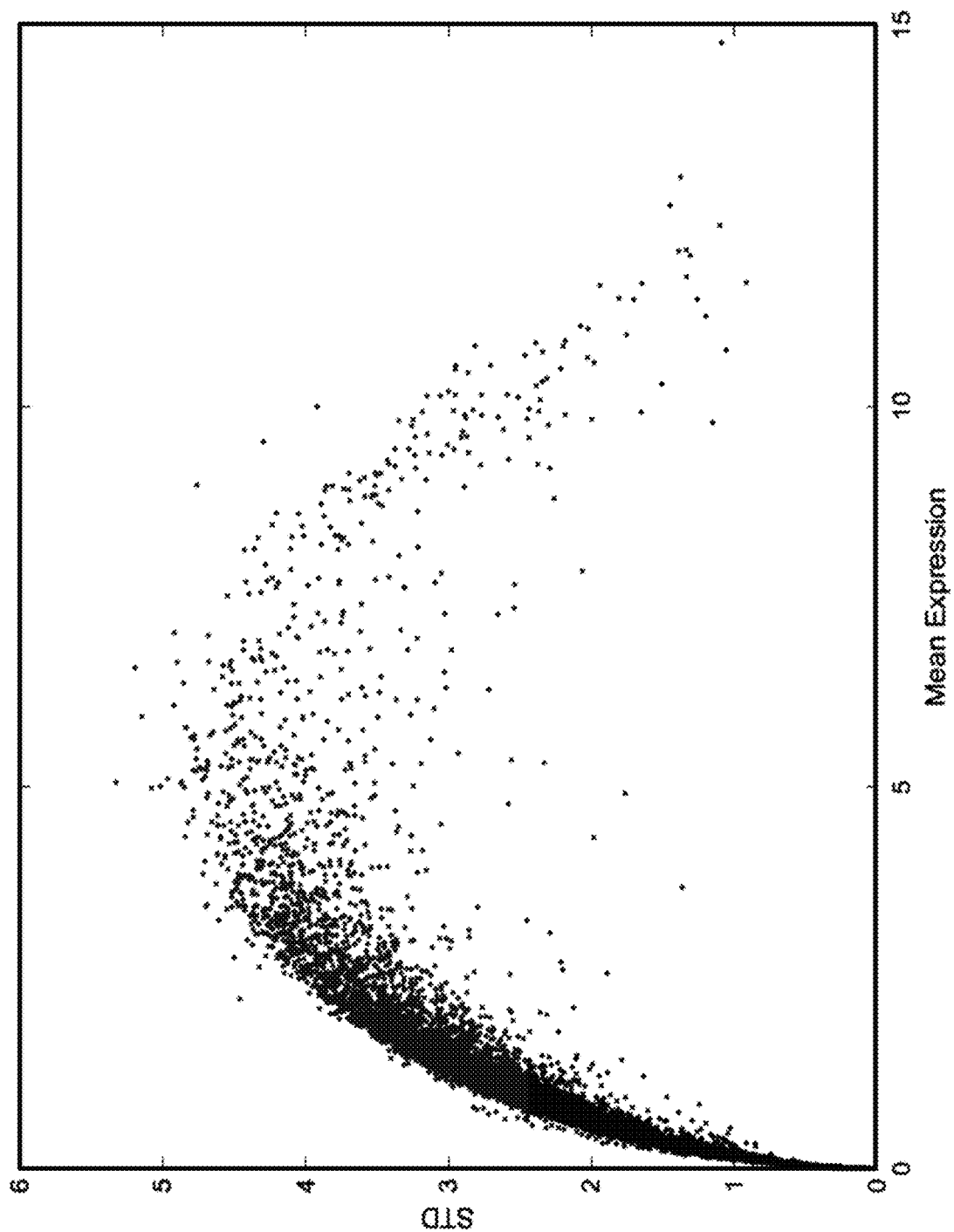
FIG. 1—illustrates the mean expression of genes in CD8+ T cells and the variability in expression. The most variable genes are selected for tSNE analysis based on genes with a var>6 and that are expressed in at least 5% of the cells (~4000 genes).

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011

As used herein, the singular forms "a" "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

The terms "subject", "individual" or "patient" are used interchangeably throughout this specification, and typically and preferably denote humans, but may also encompass reference to non-human animals, preferably warm-blooded animals, even more preferably mammals, such as, e.g., non-human primates, rodents, canines, felines, equines, ovines, porcines, and the like. The term "non-human animals" includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is a non-human mammal. In another embodiment, the subject is human. In another embodiment, the subject is an experimental animal or animal substitute as a disease model. The term does not denote a particular age or sex. Thus, adult and newborn subjects, as well as fetuses, whether male or female, are intended to be covered. Examples of subjects include humans, dogs, cats, cows, goats, and mice. The term subject is further intended to include transgenic species.

All publications, published patent documents, and patent applications cited in this application are indicative of the level of skill in the art(s) to which the application pertains. All publications, published patent documents, and patent applications cited herein are hereby incorporated by reference to the same extent as though each individual publication, published patent document, or patent application was specifically and individually indicated as being incorporated by reference.

Overview

Embodiments disclosed herein relate to cell products, substances, compositions, markers, marker signatures, molecular targets, kits of parts and methods useful in characterizing, evaluating and modulating the immune system and immune responses. Applicants used single-cell RNA sequencing (scRNA-seq) to gain a deeper understanding of the cellular and molecular components orchestrating immunity in melanoma patients treated with checkpoint therapy. Through this unbiased approach, Applicants defined the immune cell composition of melanoma tumors, identified unique cell states coupled with response, and developed a simple assay that can accurately predict clinical outcome in an independent cohort. Moreover, Applicants assessed the identity and function of some of the newly identified cell states, delineated their epigenetic landscape, and tested a new therapeutic combination that enhanced immunity in a mouse melanoma model. The analysis demonstrates the utility of applying unbiased single-cell methods to uncover the principles that underlie the success or failure of immunotherapy.

Thus, it is an objective of the present invention to determine whether a patient should be treated with a checkpoint blockade (CPB) therapy. Applicants have identified that the ratio of CD8+ TILs expressing a non-responder signature and CD8+ TILs expressing a responder signature can predict sensitivity or resistance to CPB therapy as well as predicting overall survival. Applicants have further identified that detecting the quantity of CD8+ T cells expressing a single transcription factor that is part of the responder signature can be used to distinguish between CPB therapy responders and non-responders. It is another objective of the present invention to modulate the ratio of CD8+ TILs expressing a non-responder signature to CD8+ TILs expressing a responder signature. It is another objective of the present invention to provide for adoptive cell transfer methods for treatment of a cancer patient, wherein the cells are enriched for CD8+ TILs expressing a responder signature. It is another objective of the present invention to select patients for treatment with an immunotherapy. It is another object of the invention to target non-responder CD8+ T cells for cancer therapy.

The biomarkers of the present invention were discovered by analysis of expression profiles of single immune cells within populations of cells from freshly isolated tumors, thus allowing the discovery of novel gene signatures and immune cell subtypes that were previously unrecognized. Treatment of solid tumors has been revolutionized by immune checkpoint blockade therapies; yet even in melanoma, for which high response rates are observed, the majority of patients do not respond. Specifically, to identify key immunological components associated with success or failure of immunotherapy, Applicants profiled 16,291 immune cells from 48 tumor samples of melanoma patients treated with checkpoint inhibitors, using single-cell transcriptomics. Applicants obtained samples from melanoma patients receiving checkpoint blockade therapy both before they received treatment and after they received treatment with a checkpoint inhibitor. Applicants have identified a non-responder signature and a responder signature in the CD8+ TILs. Applicants have identified that the ratio of CD8+ TILs expressing a non-responder signature and CD8+ TILs expressing a responder signature can predict sensitivity or resistance to CPB therapy, as well as predicting overall survival. Applicants identified unique exhaustion and memory/effector states of $CD8^+$ T-cells associated with tumor regression, and found that the expression of a single transcription factor, TCF7, in $CD8^+$ T-cells was sufficient to predict clinical outcome in an independent cohort. Specifically, Applicants show using immunofluorescence that responders have more CD8+TCF7+ T cells than CD8+ $TCF7^-$ T cells and vice versa. Thus, detection of CD8+ TCF7+ T cells may be used to predict overall survival in cancer patients. Applicants delineated the epigenetic landscape and clonality of these T-cell states, and demonstrated enhanced anti-tumor immunity by targeting a novel combination of factors identified in exhausted cells. Applicants, show using a melanoma cancer model that targeting CD39 and TIM3 on non-responder cells results in a significant increase in survival. This study provides extensive unbiased data in human tumors for discovery of predictors, therapeutic targets and combination therapies for enhancing checkpoint immunotherapy.

The presence of CD8+ T cell subtypes may be determined by subtype specific signature biomarkers. It is generally recognized within the art, that tumors are a conglomeration of many cells that make up a tumor microenvironment, whereby the cells communicate and affect each other in specific ways. As such, specific immune cell types within this microenvironment may express certain gene products for this microenvironment.

In further aspects, the invention relates to a signature or set of biomarkers (e.g., responder and/or non-responder signature) that may be detected in combination with other signatures or set of biomarkers (e.g., malignant cell signatures). The signatures may be a gene signature, protein signature, and/or other genetic or epigenetic signature of particular tumor cell subpopulations, as defined herein (e.g., tumor cells with mutations in genes associated with antigen presentation or the IFN gamma pathway).

The invention hereto also further relates to particular immune cell subpopulations, which may be identified based on the methods according to the invention as discussed herein; as well as methods to obtain such cell subpopulations; use of such subpopulations in therapeutics; controlling therapeutic responses by targeting biomarkers relevant to the cell subpopulation; and screening methods to identify agents capable of inducing or suppressing particular immune cell (sub)populations.

In certain example embodiments, the immune cells comprise two sub-populations. A first subpopulation characterized by the expression of a number of inhibitory receptors (non-responder), and a second subpopulation characterized by the expression of a number of memory and/or differentiation genes (responder). In certain example embodiments, these subpopulations may be used to determine responsiveness to various therapeutics. Particular advantageous uses include methods for identifying agents capable of inducing or suppressing particular immune cell (sub)populations based on the gene signatures, protein signature, and/or other genetic or epigenetic signature as defined herein.

The invention further relates to agents capable of inducing or suppressing particular immune cell (sub)populations based on the gene signatures, protein signature, and/or other genetic or epigenetic signature as defined herein, as well as their use for modulating, such as inducing or repressing, a particular gene signature, protein signature, and/or other genetic or epigenetic signature. In one embodiment, genes in one population of cells may be activated or suppressed in order to affect the cells of another population. In related aspects, modulating, such as inducing or repressing, a particular a particular gene signature, protein signature, and/or other genetic or epigenetic signature may modify overall immune cell composition, such as immune cell composition, such as immune cell subpopulation composition or distribution, or functionality.

Biomarkers and Signatures

The invention further relates to various biomarkers for detecting immune cell (e.g., CD8+ T cell) subpopulations. In certain example embodiments, these CD8+ T cell populations are tumor infiltrating lymphocytes (TIL). The methods may comprise detecting a first population of CD8+ T cells as described further below, a second population of CD8+ T cells as described further below, or both. The first and second CD8+ T cell populations may be detected by detecting one or more biomarkers in a sample.

The term "biomarker" is widespread in the art and commonly broadly denotes a biological molecule, more particularly an endogenous biological molecule, and/or a detectable portion thereof, whose qualitative and/or quantitative evaluation in a tested object (e.g., in or on a cell, cell population, tissue, organ, or organism, e.g., in a biological sample of a subject) is predictive or informative with respect to one or more aspects of the tested object's phenotype and/or genotype. The terms "marker" and "biomarker" may be used interchangeably throughout this specification. Biomarkers as intended herein may be nucleic acid-based or peptide-, polypeptide- and/or protein-based. For example, a marker may be comprised of peptide(s), polypeptide(s) and/or protein(s) encoded by a given gene, or of detectable portions thereof. Further, whereas the term "nucleic acid" generally encompasses DNA, RNA and DNA/RNA hybrid molecules, in the context of markers the term may typically refer to heterogeneous nuclear RNA (hnRNA), pre-mRNA, messenger RNA (mRNA), or complementary DNA (cDNA), or detectable portions thereof. Such nucleic acid species are particularly useful as markers, since they contain qualitative and/or quantitative information about the expression of the gene. Particularly preferably, a nucleic acid-based marker may encompass mRNA of a given gene, or cDNA made of the mRNA, or detectable portions thereof. Any such nucleic acid(s), peptide(s), polypeptide(s) and/or protein(s) encoded by or produced from a given gene are encompassed by the term "gene product(s)".

Preferably, markers as intended herein may be extracellular or cell surface markers, as methods to measure extracellular or cell surface marker(s) need not disturb the integrity of the cell membrane and may not require fixation/permeabilization of the cells.

Unless otherwise apparent from the context, reference herein to any marker, such as a peptide, polypeptide, protein, or nucleic acid, may generally also encompass modified forms of said marker, such as bearing post-expression modifications including, for example, phosphorylation, glycosylation, lipidation, methylation, cysteinylation, sulphonation, glutathionylation, acetylation, oxidation of methionine to methionine sulphoxide or methionine sulphone, and the like.

The term "peptide" as used throughout this specification preferably refers to a polypeptide as used herein consisting essentially of 50 amino acids or less, e.g., 45 amino acids or less, preferably 40 amino acids or less, e.g., 35 amino acids or less, more preferably 30 amino acids or less, e.g., 25 or less, 20 or less, 15 or less, 10 or less or 5 or less amino acids.

The term "polypeptide" as used throughout this specification generally encompasses polymeric chains of amino acid residues linked by peptide bonds. Hence, insofar a protein is only composed of a single polypeptide chain, the terms "protein" and "polypeptide" may be used interchangeably herein to denote such a protein. The term is not limited to any minimum length of the polypeptide chain. The term may encompass naturally, recombinantly, semi-synthetically or synthetically produced polypeptides. The term also encompasses polypeptides that carry one or more co- or post-expression-type modifications of the polypeptide chain, such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes polypeptide variants or mutants which carry amino acid sequence variations vis-à-vis a corresponding native polypeptide, such as, e.g., amino acid deletions, additions and/or substitutions. The term contemplates both full-length polypeptides and polypeptide parts or fragments, e.g., naturally-occurring polypeptide parts that ensue from processing of such full-length polypeptides.

The term "protein" as used throughout this specification generally encompasses macromolecules comprising one or more polypeptide chains, i.e., polymeric chains of amino acid residues linked by peptide bonds. The term may encompass naturally, recombinantly, semi-synthetically or synthetically produced proteins. The term also encompasses proteins that carry one or more co- or post-expression-type modifications of the polypeptide chain(s), such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes protein variants or mutants which carry amino acid sequence variations vis-à-vis a corresponding native proteins, such as, e.g., amino acid deletions, additions and/or substitutions. The term contemplates both full-length proteins and protein parts or fragments, e.g., naturally-occurring protein parts that ensue from processing of such full-length proteins.

The reference to any marker, including any peptide, polypeptide, protein, or nucleic acid, corresponds to the marker commonly known under the respective designations in the art. The terms encompass such markers of any organism where found, and particularly of animals, preferably warm-blooded animals, more preferably vertebrates, yet more preferably mammals, including humans and non-human mammals, still more preferably of humans. All gene name symbols refer to the gene as commonly known in the art. The examples described herein that refer to the human gene names are to be understood to also encompasses genes in any other organism (e.g., homologous, orthologous genes). The term, homolog, may apply to the relationship between genes separated by the event of speciation (e.g., ortholog). Orthologs are genes in different species that evolved from a common ancestral gene by speciation. Normally, orthologs retain the same function in the course of evolution. Gene symbols may be those referred to by the HUGO Gene Nomenclature Committee (HGNC) or National Center for Biotechnology Information (NCBI). Any reference to the gene symbol is a reference made to the entire gene or variants of the gene. The signature as described herein may encompass any of the genes described herein.

The terms particularly encompass such markers, including any peptides, polypeptides, proteins, or nucleic acids, with a native sequence, i.e., ones of which the primary sequence is the same as that of the markers found in or derived from nature. A skilled person understands that native sequences may differ between different species due to genetic divergence between such species. Moreover, native sequences may differ between or within different individuals of the same species due to normal genetic diversity (variation) within a given species. Also, native sequences may differ between or even within different individuals of the same species due to somatic mutations, or post-transcriptional or post-translational modifications. Any such variants or isoforms of markers are intended herein. Accordingly, all sequences of markers found in or derived from nature are considered "native". The terms encompass the markers when forming a part of a living organism, organ, tissue or cell, when forming a part of a biological sample, as well as when at least partly isolated from such sources. The terms also encompass markers when produced by recombinant or synthetic means.

In certain embodiments, markers, including any peptides, polypeptides, proteins, or nucleic acids, may be human, i.e., their primary sequence may be the same as a corresponding primary sequence of or present in a naturally occurring human markers. Hence, the qualifier "human" in this connection relates to the primary sequence of the respective markers, rather than to their origin or source. For example, such markers may be present in or isolated from samples of human subjects or may be obtained by other means (e.g., by recombinant expression, cell-free transcription or translation, or non-biological nucleic acid or peptide synthesis).

The reference herein to any marker, including any peptide, polypeptide, protein, or nucleic acid, also encompasses fragments thereof. Hence, the reference herein to measuring (or measuring the quantity of) any one marker may encompass measuring the marker and/or measuring one or more fragments thereof.

For example, any marker and/or one or more fragments thereof may be measured collectively, such that the measured quantity corresponds to the sum amounts of the collectively measured species. In another example, any marker and/or one or more fragments thereof may be measured each individually. The terms encompass fragments arising by any mechanism, in vivo and/or in vitro, such as, without limitation, by alternative transcription or translation, exo- and/or endo-proteolysis, exo- and/or endo-nucleolysis, or degradation of the peptide, polypeptide, protein, or nucleic acid, such as, for example, by physical, chemical and/or enzymatic proteolysis or nucleolysis.

The term "fragment" as used throughout this specification with reference to a peptide, polypeptide, or protein generally denotes a portion of the peptide, polypeptide, or protein, such as typically an N- and/or C-terminally truncated form of the peptide, polypeptide, or protein. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the amino acid sequence length of said peptide, polypeptide, or protein. For example, insofar not exceeding the length of the full-length peptide, polypeptide, or protein, a fragment may include a sequence of ≥5 consecutive amino acids, or ≥10 consecutive amino acids, or ≥20 consecutive amino acids, or ≥30 consecutive amino acids, e.g., ≥40 consecutive amino acids, such as for example ≥50 consecutive amino acids, e.g., ≥60, ≥70, ≥80, ≥90, ≥100, ≥200, ≥300, ≥400, ≥500 or ≥600 consecutive amino acids of the corresponding full-length peptide, polypeptide, or protein.

The term "fragment" as used throughout this specification with reference to a nucleic acid (polynucleotide) generally denotes a 5'- and/or 3'-truncated form of a nucleic acid. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the nucleic acid sequence length of said nucleic acid. For example, insofar not exceeding the length of the full-length nucleic acid, a fragment may include a sequence of ≥5 consecutive nucleotides, or ≥10 consecutive nucleotides, or ≥20 consecutive nucleotides, or ≥30 consecutive nucleotides, e.g., ≥40 consecutive nucleotides, such as for example ≥50 consecutive nucleotides, e.g., ≥60, ≥70, ≥80, ≥90, ≥100, ≥200, ≥300, ≥400, ≥500 or ≥600 consecutive nucleotides of the corresponding full-length nucleic acid.

Cells such as immune cells as disclosed herein may in the context of the present specification be said to "comprise the expression" or conversely to "not express" one or more markers, such as one or more genes or gene products; or be described as "positive" or conversely as "negative" for one or more markers, such as one or more genes or gene products; or be said to "comprise" a defined "gene or gene product signature".

Such terms are commonplace and well-understood by the skilled person when characterizing cell phenotypes. By means of additional guidance, when a cell is said to be positive for or to express or comprise expression of a given marker, such as a given gene or gene product, a skilled person would conclude the presence or evidence of a distinct signal for the marker when carrying out a measurement capable of detecting or quantifying the marker in or on the cell. Suitably, the presence or evidence of the distinct signal for the marker would be concluded based on a comparison of the measurement result obtained for the cell to a result of the same measurement carried out for a negative control (for example, a cell known to not express the marker) and/or a positive control (for example, a cell known to express the marker). Where the measurement method allows for a quantitative assessment of the marker, a positive cell may generate a signal for the marker that is at least 1.5-fold higher than a signal generated for the marker by a negative control cell or than an average signal generated for the marker by a population of negative control cells, e.g., at least 2-fold, at least 4-fold, at least 10-fold, at least 20-fold, at least 30-fold, at least 40-fold, at least 50-fold higher or even higher. Further, a positive cell may generate a signal for the marker that is 3.0 or more standard deviations, e.g., 3.5 or more, 4.0 or more, 4.5 or more, or 5.0 or more standard deviations, higher than an average signal generated for the marker by a population of negative control cells.

Use of Signature Genes

The present invention is also directed to signatures and uses thereof. As used herein a "signature" may encompass any gene or genes, protein or proteins, or epigenetic element(s) whose expression profile or whose occurrence is associated with a specific cell type, subtype, or cell state of a specific cell type or subtype within a population of cells (e.g., tumor infiltrating lymphocytes). In certain embodiments, the expression of the CD8+ TIL signatures are dependent on epigenetic modification of the genes or regulatory elements associated with the genes. Thus, in certain embodiments, use of signature genes includes epigenetic modifications that may be detected or modulated. For ease of discussion, when discussing gene expression, any of gene or genes, protein or proteins, or epigenetic element(s) may be substituted. As used herein, the terms "signature", "expression profile", or "expression program" may be used interchangeably. It is to be understood that also when referring to proteins (e.g. differentially expressed proteins), such may fall within the definition of "gene" signature. Levels of expression or activity or prevalence may be compared between different cells in order to characterize or identify for instance signatures specific for cell (sub)populations. Increased or decreased expression or activity of signature genes may be compared between different cells in order to characterize or identify for instance specific cell (sub)populations. The detection of a signature in single cells may be used to identify and quantitate for instance specific cell (sub)populations. A signature may include a gene or genes, protein or proteins, or epigenetic element(s) whose expression or occurrence is specific to a cell (sub)population, such that expression or occurrence is exclusive to the cell (sub)population. A gene signature as used herein, may thus refer to any set of up- and down-regulated genes that are representative of a cell type or subtype. A gene signature as used herein, may also refer to any set of up- and down-regulated genes between different cells or cell (sub)populations derived from a gene-expression profile. For example, a gene signature may comprise a list of genes differentially expressed in a distinction of interest.

The signature as defined herein (being it a gene signature, protein signature or other genetic or epigenetic signature) can be used to indicate the presence of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest for instance particular therapies, or to follow up treatment, or to suggest ways to modulate immune systems. The signatures of the present invention may be discovered by analysis of expression profiles of single-cells within a population of cells from isolated samples (e.g. tumor samples), thus allowing the discovery of novel cell subtypes or cell states that were previously invisible or unrecognized. The presence of subtypes or cell states may be determined by subtype specific or cell state specific signatures. The presence of these specific cell (sub)types or cell states may be determined by applying the signature genes to bulk sequencing data in a sample. Not being bound by a theory the signatures of the present invention may be microenvironment specific, such as their expression in a particular spatio-temporal context. Not being bound by a theory, signatures as discussed herein are specific to a particular pathological context. Not being bound by a theory, a combination of cell subtypes having a particular signature may indicate an outcome. Not being bound by a theory, the signatures can be used to deconvolute the network of cells present in a particular pathological condition. Not being bound by a theory the presence of specific cells and cell subtypes are indicative of a particular response to treatment, such as including increased or decreased susceptibility to treatment. The signature may indicate the presence of one particular cell type.

The signature according to certain embodiments of the present invention may comprise or consist of one or more genes, proteins and/or epigenetic elements, such as for instance 1, 2, 3, 4, 5, 6, 7, 8, 9, 10 or more. In certain embodiments, the signature may comprise or consist of two or more genes, proteins and/or epigenetic elements, such as for instance 2, 3, 4, 5, 6, 7, 8, 9, 10 or more. In certain embodiments, the signature may comprise or consist of three or more genes, proteins and/or epigenetic elements, such as for instance 3, 4, 5, 6, 7, 8, 9, 10 or more. In certain embodiments, the signature may comprise or consist of four or more genes, proteins and/or epigenetic elements, such as for instance 4, 5, 6, 7, 8, 9, 10 or more. In certain embodiments, the signature may comprise or consist of five or more genes, proteins and/or epigenetic elements, such as for instance 5, 6, 7, 8, 9, 10 or more. In certain embodiments, the signature may comprise or consist of six or more genes, proteins and/or epigenetic elements, such as for instance 6, 7, 8, 9, 10 or more. In certain embodiments, the signature may comprise or consist of seven or more genes, proteins and/or epigenetic elements, such as for instance 7, 8, 9, 10 or more. In certain embodiments, the signature may comprise or consist of eight or more genes, proteins and/or epigenetic elements, such as for instance 8, 9, 10 or more. In certain embodiments, the signature may comprise or consist of nine or more genes, proteins and/or epigenetic elements, such as for instance 9, 10 or more. In certain embodiments, the signature may comprise or consist of ten or more genes, proteins and/or epigenetic elements, such as for instance 10, 11, 12, 13, 14, 15, or more. It is to be understood that a signature according to the invention may for instance also include genes or proteins as well as epigenetic elements combined.

In certain embodiments, a signature is characterized as being specific for a particular immune cell or immune cell (sub)population if it is upregulated or only present, detected or detectable in that particular immune cell or immune cell (sub)population, or alternatively is downregulated or only absent, or undetectable in that particular immune cell or immune cell (sub)population. In this context, a signature consists of one or more differentially expressed genes/proteins or differential epigenetic elements when comparing different cells or cell (sub)populations, including comparing different immune cell or immune cell (sub)populations, as well as comparing immune cell or immune cell (sub)populations with non-immune cell or non-immune cell (sub) populations. It is to be understood that "differentially expressed" genes/proteins include genes/proteins which are up- or down-regulated as well as genes/proteins which are turned on or off. When referring to up- or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

As discussed herein, differentially expressed genes/proteins, or differential epigenetic elements may be differentially expressed on a single cell level, or may be differentially expressed on a cell population level. Preferably, the differentially expressed genes/proteins or epigenetic elements as discussed herein, such as constituting the gene signatures as discussed herein, when as to the cell population or subpopulation level, refer to genes that are differentially expressed in all or substantially all cells of the population or subpopulation (such as at least 80%, preferably at least 90%, such as at least 95% of the individual cells). This allows one to define a particular subpopulation of immune cells. As referred to herein, a "subpopulation" of cells preferably refers to a particular subset of cells of a particular cell type which can be distinguished or are uniquely identifiable and set apart from other cells of this cell type. The cell subpopulation may be phenotypically characterized, and is preferably characterized by the signature as discussed herein. A cell (sub)population as referred to herein may constitute of a (sub)population of cells of a particular cell type characterized by a specific cell state.

When referring to induction, or alternatively suppression of a particular signature, preferable is meant induction or alternatively suppression (or upregulation or downregulation) of at least one gene/protein and/or epigenetic element of the signature, such as for instance at least to, at least three, at least four, at least five, at least six, or all genes/proteins and/or epigenetic elements of the signature.

Signatures may be functionally validated as being uniquely associated with a particular immune responder phenotype. Induction or suppression of a particular signature may consequentially be associated with or causally drive a particular immune responder phenotype.

Various aspects and embodiments of the invention may involve analyzing gene signatures, protein signature, and/or other genetic or epigenetic signature based on single cell analyses (e.g. single cell RNA sequencing) or alternatively based on cell population analyses, as is defined herein elsewhere.

In certain example embodiments, the signature genes may be used to deconvolute the network of cells present in a tumor based on comparing them to data from bulk analysis of a tumor sample. In certain example embodiments, the presence of specific immune cells and immune cell subtypes may be indicative of tumor growth, invasiveness and/or resistance to treatment. In one example embodiment, detection or one or more signature genes may indicate the presence of a particular cell type or cell types. In certain example embodiments, the presence of immune cell types within a tumor may indicate that the tumor will be resistant to a treatment. In one embodiment, the signature genes of the present invention are applied to bulk sequencing data from a tumor sample obtained from a subject, such that information relating to disease outcome and personalized treatments is determined.

In certain embodiments, cell type markers for immune cells present in a tumor (i.e., tumor microenvironment) may be used to deconvolute bulk expression data (see, e.g, Venteicher, A. S., Tirosh, I., Hebert, C., Yizhak, K., C., N., Filbin, M. G., Hoverstadt, V., Escalante, L. E., Saw, M. L., Rodman, C., et al. (2017). Decoupling genetics, lineages and tumor micro-environment in gliomas by single-cell RNA-seq. Science 355; Tirosh, I., Izar, B., Prakadan, S. M., Wadsworth, M. H., 2nd, Treacy, D., Trombetta, J. J., Rotem, A., Rodman, C., Lian, C., Murphy, G., et al. (2016a). Dissecting the multicellular ecosystem of metastatic melanoma by single-cell RNA-seq. Science 352, 189-196; and Tirosh, I., Venteicher, A. S., Hebert, C., Escalante, L. E., Patel, A. P., Yizhak, K., Fisher, J. M., Rodman, C., Mount, C., Filbin, M. G., et al. (2016b). Single-cell RNA-seq supports a developmental hierarchy in human oligodendroglioma. Nature 539, 309-313).

In certain embodiments, mutations occur in individual cancers that may be used to detect cancer progression. These mutations may be used in conjunction with the responder and non-responder phenotypes described herein. Mutations related to T cell cytolytic activity against tumors have been characterized and may be detected as part of the present invention (see e.g., Rooney et al., Molecular and genetic properties of tumors associated with local immune cytolytic activity, Cell. 2015 Jan. 15; 160(1-2): 48-61). In certain example embodiments, a patient may be selected for a check point blockade therapy based on detection of a gene signature as described herein in combination with mutations related to T cell cytolytic activity (see e.g., WO2016100975A1). In certain embodiments, cancer specific mutations associated with cytolytic activity may be a mutation in a gene selected from the group consisting of CASP8, B2M, PIK3CA, SMC1A, ARID5B, TET2, ALPK2, COL5A1, TP53, DNER, NCOR1, MORC4, CIC, IRF6, MYOCD, ANKLE1, CNKSR1, NF1, SOS1, ARID2, CUL4B, DDX3X, FUBP1, TCP11L2, HLA-A, B or C, CSNK2A1, MET, ASXL1, PD-L1, PD-L2, IDO1, IDO2, ALOX12B and ALOX15B, or copy number gain, excluding whole-chromosome events, impacting any of the following chromosomal bands: 6q16.1-q21, 6q22.31-q24.1, 6q25.1-q26, 7p11.2-q11.1, 8p23.1, 8p11.23-p11.21 (containing IDO1, ID02), 9p24.2-p23 (containing PDL1, PDL2), 10p15.3, 10p15.1-p13, 11p14.1, 12p13.32-p13.2, 17p13.1 (containing ALOX12B, ALOX15B), and 22q11.1-q11.21. In certain embodiments, the mutation is further associated with antigen presentation. Mutations associated with antigen presentation may comprises mutations in B2M and HLA-A, B or C. Detection of "Non-Responder" Sub-Populations In one embodiment, the method comprises detecting a first population of immune cells from a biological sample of a subject. Immune cells can be detected by sorting for CD45+ cells. CD45 is a pan-leukocyte protein. In one embodiment, the method comprises detecting a first population of CD8+ TIL from a biological sample of a subject. In certain example embodiments, detection of the first population in the biological sample indicates a likelihood that a subject will be non-responsive to a particular therapy. In certain example embodiments, detection of the first population indicates a likelihood the subject will be non-responsive to a checkpoint blockade therapy. The first population may generally be characterized by increased expression of inhibitory receptors.

A marker, for example a gene or gene product, for example a peptide, polypeptide, protein, or nucleic acid, or a group of two or more markers, is "detected" or "measured" in a tested object (e.g., in or on a cell, cell population, tissue, organ, or organism, e.g., in a biological sample of a subject) when the presence or absence and/or quantity of said marker or said group of markers is detected or determined in the tested object, preferably substantially to the exclusion of other molecules and analytes, e.g., other genes or gene products.

The terms "sample" or "biological sample" as used throughout this specification include any biological specimen obtained from a subject. Particularly useful samples are those known to comprise, or expected or predicted to comprise immune cells as taught herein. Preferably, a sample may be readily obtainable by minimally invasive methods, such as blood collection or tissue biopsy, allowing the removal/isolation/provision of the sample from the subject. Examples of particularly useful samples include without limitation whole blood or a cell-containing fraction of whole blood, such as serum, white blood cells, or peripheral blood mononuclear cells (PBMC), lymph, lymphatic tissue, inflammation fluid, tissue specimens, or tissue biopsies. The term "tissue" as used throughout this specification refers to any animal tissue types including, but not limited to, bone, bone marrow, neural tissue, fibrous connective tissue, cartilage, muscle, vasculature, skin, adipose tissue, blood and glandular tissue or other non-bone tissue. The tissue may be healthy or affected by pathological alterations, e.g., tumor tissue or tissue affected by a disease comprising an immune component. The tissue may be from a living subject or may be cadaveric tissue. The tissue may be autologous tissue or syngeneic tissue or may be allograft or xenograft tissue. A biological sample may also include cells grown in tissue culture, such as cells used for screening drugs or primary cells grown in culture for expansion.

The term "immune cell" as used throughout this specification generally encompasses any cell derived from a hematopoietic stem cell that plays a role in the immune response. The term is intended to encompass immune cells both of the innate or adaptive immune system. The immune cell as referred to herein may be a leukocyte, at any stage of differentiation (e.g., a stem cell, a progenitor cell, a mature cell) or any activation stage. Immune cells include lymphocytes (such as natural killer cells, T-cells (including, e.g., thymocytes, Th or Tc; Th1, Th2, Th17, Th$\alpha\beta$, CD4+, CD8+, effector Th, memory Th, regulatory Th, CD4+/CD8+ thymocytes, CD4−/CD8− thymocytes, $\gamma\delta$ T cells, etc.) or B-cells (including, e.g., pro-B cells, early pro-B cells, late pro-B cells, pre-B cells, large pre-B cells, small pre-B cells, immature or mature B-cells, producing antibodies of any isotype, T1 B-cells, T2, B-cells, naïve B-cells, GC B-cells, plasmablasts, memory B-cells, plasma cells, follicular B-cells, marginal zone B-cells, B-1 cells, B-2 cells, regulatory B cells, etc.), such as for instance, monocytes (including, e.g., classical, non-classical, or intermediate monocytes), (segmented or banded) neutrophils, eosinophils, basophils, mast cells, histiocytes, microglia, including various subtypes, maturation, differentiation, or activation stages, such as for instance hematopoietic stem cells, myeloid progenitors, lymphoid progenitors, myeloblasts, promyelocytes, myelocytes, metamyelocytes, monoblasts, promonocytes, lymphoblasts, prolymphocytes, small lymphocytes, macrophages (including, e.g., Kupffer cells, stellate macrophages, M1 or M2 macrophages), (myeloid or lymphoid) dendritic cells (including, e.g., Langerhans cells, conventional or myeloid dendritic cells, plasmacytoid dendritic cells, mDC-1, mDC-2, Mo-DC, HP-DC, veiled cells), granulocytes, polymorphonuclear cells, antigen-presenting cells (APC), etc.

The terms "quantity", "amount" and "level" are synonymous and generally well-understood in the art. The terms as used throughout this specification may particularly refer to an absolute quantification of a marker in a tested object (e.g., in or on a cell, cell population, tissue, organ, or organism, e.g., in a biological sample of a subject), or to a relative quantification of a marker in a tested object, i.e., relative to another value such as relative to a reference value, or to a range of values indicating a base-line of the marker. Such values or ranges may be obtained as conventionally known.

An absolute quantity of a marker may be advantageously expressed as weight or as molar amount, or more commonly as a concentration, e.g., weight per volume or mol per volume. A relative quantity of a marker may be advantageously expressed as an increase or decrease or as a fold-increase or fold-decrease relative to said another value, such as relative to a reference value. Performing a relative comparison between first and second variables (e.g., first and second quantities) may but need not require determining first the absolute values of said first and second variables. For example, a measurement method may produce quantifiable readouts (such as, e.g., signal intensities) for said first and second variables, wherein said readouts are a function of the value of said variables, and wherein said readouts may be directly compared to produce a relative value for the first variable vs. the second variable, without the actual need to first convert the readouts to absolute values of the respective variables.

The terms "diagnosis" and "monitoring" are commonplace and well-understood in medical practice. By means of further explanation and without limitation the term "diagnosis" generally refers to the process or act of recognising, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition).

The term "monitoring" generally refers to the follow-up of a disease or a condition in a subject for any changes which may occur over time.

The terms "prognosing" or "prognosis" generally refer to an anticipation on the progression of a disease or condition and the prospect (e.g., the probability, duration, and/or extent) of recovery. A good prognosis of the diseases or conditions taught herein may generally encompass anticipation of a satisfactory partial or complete recovery from the diseases or conditions, preferably within an acceptable time period. A good prognosis of such may more commonly encompass anticipation of not further worsening or aggravating of such, preferably within a given time period. A poor prognosis of the diseases or conditions as taught herein may generally encompass anticipation of a substandard recovery and/or unsatisfactorily slow recovery, or to substantially no recovery or even further worsening of such.

The terms also encompass prediction of a disease. The terms "predicting" or "prediction" generally refer to an advance declaration, indication or foretelling of a disease or condition in a subject not (yet) having said disease or condition. For example, a prediction of a disease or condition in a subject may indicate a probability, chance or risk that the subject will develop said disease or condition, for example within a certain time period or by a certain age. Said probability, chance or risk may be indicated inter alia as an absolute value, range or statistics, or may be indicated relative to a suitable control subject or subject population (such as, e.g., relative to a general, normal or healthy subject or subject population). Hence, the probability, chance or risk that a subject will develop a disease or condition may be advantageously indicated as increased or decreased, or as fold-increased or fold-decreased relative to a suitable control subject or subject population. As used herein, the term "prediction" of the conditions or diseases as taught herein in a subject may also particularly mean that the subject has a 'positive' prediction of such, i.e., that the subject is at risk of having such (e.g., the risk is significantly increased vis-à-vis a control subject or subject population). The term "prediction of no" diseases or conditions as taught herein as described herein in a subject may particularly mean that the subject has a 'negative' prediction of such, i.e., that the subject's risk of having such is not significantly increased vis-à-vis a control subject or subject population.

Reference values may be established according to known procedures previously employed for other cell populations, biomarkers and gene or gene product signatures. For example, a reference value may be established in an individual or a population of individuals characterized by a particular diagnosis, prediction and/or prognosis of said disease or condition (i.e., for whom said diagnosis, prediction and/or prognosis of the disease or condition holds true). Such population may comprise without limitation 2 or more, 10 or more, 100 or more, or even several hundred or more individuals.

A "deviation" of a first value from a second value may generally encompass any direction (e.g., increase: first value>second value; or decrease: first value<second value) and any extent of alteration.

For example, a deviation may encompass a decrease in a first value by, without limitation, at least about 10% (about 0.9-fold or less), or by at least about 20% (about 0.8-fold or less), or by at least about 30% (about 0.7-fold or less), or by at least about 40% (about 0.6-fold or less), or by at least about 50% (about 0.5-fold or less), or by at least about 60% (about 0.4-fold or less), or by at least about 70% (about 0.3-fold or less), or by at least about 80% (about 0.2-fold or less), or by at least about 90% (about 0.1-fold or less), relative to a second value with which a comparison is being made.

For example, a deviation may encompass an increase of a first value by, without limitation, at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 700% (about 8-fold or more), or like, relative to a second value with which a comparison is being made.

Preferably, a deviation may refer to a statistically significant observed alteration. For example, a deviation may refer to an observed alteration which falls outside of error margins of reference values in a given population (as expressed, for example, by standard deviation or standard error, or by a predetermined multiple thereof, e.g., ±1×SD or ±2×SD or ±3×SD, or ±1×SE or ±2×SE or ±3×SE). Deviation may also refer to a value falling outside of a reference range defined by values in a given population (for example, outside of a range which comprises ≥40%, ≥50%, ≥60%, ≥70%, ≥75% or ≥80% or ≥85% or ≥90% or ≥95% or even ≥100% of values in said population).

In a further embodiment, a deviation may be concluded if an observed alteration is beyond a given threshold or cut-off. Such threshold or cut-off may be selected as generally known in the art to provide for a chosen sensitivity and/or specificity of the prediction methods, e.g., sensitivity and/or specificity of at least 50%, or at least 60%, or at least 70%, or at least 80%, or at least 85%, or at least 90%, or at least 95%.

For example, receiver-operating characteristic (ROC) curve analysis can be used to select an optimal cut-off value of the quantity of a given immune cell population, biomarker or gene or gene product signatures, for clinical use of the present diagnostic tests, based on acceptable sensitivity and specificity, or related performance measures which are well-known per se, such as positive predictive value (PPV), negative predictive value (NPV), positive likelihood ratio (LR+), negative likelihood ratio (LR−), Youden index, or similar.

In certain embodiments, subjects comprising CD8+ TILs having a non-responder gene signature as described herein are treated with a non-immunotherapy treatment. A non-immunotherapy treatment may involve a non-immunotherapy standard of care. Aspects of the invention involve modifying the therapy within a standard of care based on the detection of a gene signature as described herein. The term "standard of care" as used herein refers to the current treatment that is accepted by medical experts as a proper treatment for a certain type of disease and that is widely used by healthcare professionals. Standard of care is also called best practice, standard medical care, and standard therapy. Standards of care for cancer generally include surgery, lymph node removal, radiation, chemotherapy, targeted therapies, antibodies targeting the tumor, and immunotherapy. The standards of care for the most common cancers can be found on the website of National Cancer Institute (cancer.gov/cancertopics). A treatment clinical trial is a research study meant to help improve current treatments or obtain information on new treatments for patients with cancer. When clinical trials show that a new treatment is better than the standard treatment, the new treatment may be considered the new standard treatment.

In certain example embodiments, a method for detecting the first CD8+ tumor infiltrating lymphocyte (TIL) subpopulation comprises detecting increased expression of one or more biomarkers in a sample, wherein the one or more biomarkers are selected from a first group consisting of CD38, CCL3, VCAM1, GOLIM4, HAVCR2, PRDX3, ENTPD1, PTTG1, CCR5, TRAFD1, PDCD1, CXCR6, BATF, PTPN6, LAG3 and CTLA4 or any CD8_B gene listed in Table 6.

The terms "increased" or "increase" or "upregulated" or "upregulate" as used herein generally mean an increase by a statically significant amount. For avoidance of doubt, "increased" means a statistically significant increase of at least 10% as compared to a reference level, including an increase of at least 20%, at least 30%, at least 40%, at least 50%, at least 60%, at least 70%, at least 80%, at least 90%, at least 100% or more, including, for example at least 2-fold, at least 3-fold, at least 4-fold, at least 5-fold, at least 10-fold increase or greater as compared to a reference level, as that term is defined herein.

In one example embodiment, the method comprises detecting CD83 and at least N additional biomarkers selected from the first group, wherein N equals 2, 3, 4, 5, 6, 7, 8, 9, 10, 11, 12, 13, 14, or 15.

In another example embodiment, the method comprises detecting CCL3 and at least N additional biomarkers selected from the first group, wherein N equals 2, 3, 4, 5, 6, 7, 8, 9, 10, 11, 12, 13, 14, or 15.

In another example embodiment, the method comprises detecting VCAM1 and at least N additional biomarkers selected from the first group, wherein N equals 2, 3, 4, 5, 6, 7, 8, 9, 10, 11, 12, 13, 14, or 15.

In another example embodiment, the method comprises detecting GOLIM4 and at least N additional biomarkers selected from the first group, wherein N equals 2, 3, 4, 5, 6, 7, 8, 9, 10, 11, 12, 13, 14, or 15.

In another example embodiment, the method comprises detecting HAVCR2 and at least N additional biomarkers selected from the first group, wherein N equals 2, 3, 4, 5, 6, 7, 8, 9, 10, 11, 12, 13, 14, or 15.

In another example embodiment, the method comprises detecting PRDX3 and at least N additional biomarkers selected from the first group, wherein N equals 2, 3, 4, 5, 6, 7, 8, 9, 10, 11, 12, 13, 14, or 15.

In another example embodiment, the method comprises detecting ENTPD1 and at least N additional biomarkers selected from the first group, wherein N equals 2, 3, 4, 5, 6, 7, 8, 9, 10, 11, 12, 13, 14, or 15.

In another example embodiment, the method comprises detecting PTTG1 and at least N additional biomarkers selected from the first group, wherein N equals 2, 3, 4, 5, 6, 7, 8, 9, 10, 11, 12, 13, 14, or 15.

In another example embodiments, the method may comprise detecting CCR5 and at least N additional biomarkers selected from the first group, wherein N equals 2, 3, 4, 5, 6, 7, 8, 9, 10, 11, 12, 13, 14, or 15.

In another example embodiment, the method may comprise detecting TRAFD1 and at least N additional biomarkers selected from the first group, wherein N equals 2, 3, 4, 5, 6, 7, 8, 9, 10, 11, 12, 13, 14, or 15.

In another example embodiment, the method may comprise detecting PDCD1 and at least N additional biomarkers selected from the first group, wherein N equals 2, 3, 4, 5, 6, 7, 8, 9, 10, 11, 12, 13, 14, or 15.

In another example embodiments, the method may comprise detecting CXCR6, and at least N additional biomarkers selected from the first group, wherein N equals 2, 3, 4, 5, 6, 7, 8, 9, 10, 11, 12, 13, 14, or 15.

In another example embodiment, the method may comprise detecting BATF and at least N additional biomarkers selected from the first group, wherein N equals 2, 3, 4, 5, 6, 7, 8, 9, 10, 11, 12, 13, 14, or 15.

In another example embodiment, the method may comprise detecting PTPN6 and at least N additional biomarkers selected from the first group, wherein N equals 2, 3, 4, 5, 6, 7, 8, 9, 10, 11, 12, 13, 14, or 15.

In another example embodiment, the method may comprise detecting LAG3 and at least N additional biomarkers selected from the first group, wherein N equals 2, 3, 4, 5, 6, 7, 8, 9, 10, 11, 12, 13, 14, or 15.

In another example embodiment, the method may comprise detecting CTLA4 and at least N additional biomarkers selected from the first group, wherein N equals 2, 3, 4, 5, 6, 7, 8, 9, 10, 11, 12, 13, 14, or 15.

In certain example embodiments, the method comprises detecting a first population of CD45+ cells obtained from a biological sample. In certain example embodiments, detection of the population in the biological sample indicates a likelihood that a subject will be responsive to a particular therapy. In certain example embodiments, detection of the population indicates a likelihood the subject will be responsive to a checkpoint blockade therapy. The population may generally be characterized by increased expression of memory and differentiation genes.

In certain embodiments, the population is characterized by expression of a gene signature comprising one or more genes or polypeptides selected from the group consisting of: TCF7; TCF7, PLAC8, LTB, and CCR7; or TCF7, LEF1, S1PR1, PLAC8, LTB, CCR7, IGHD, PAX5, FCRL1, FCER2, CD19, CD22, BANK1, MS4A1, BLK, RALGPS2 and FAM129C; or TCF7, PLAC8, LTB, LY9, SELL, IGKC and CCR7 (Tables 4 and 5).

Detection of "Responder" Sub-Populations

In another embodiment, the method comprises detecting a population of CD8+ TIL from a biological sample of a subject. In certain example embodiments, detection of the population in the biological sample indicates a likelihood that a subject will be responsive to a particular therapy. In certain example embodiments, detection of the population indicates a likelihood the subject will be responsive to a checkpoint blockade therapy. The second population may generally be characterized by increased expression of memory and differentiation genes.

In certain example embodiments, a method for detecting the second CD8+ tumor infiltrating lymphocyte (TIL) subpopulation comprises detecting increased expression of one or more biomarkers selected from a second group consisting of L7R, GPR183, TCF7, LMNA, NR4A3, CD55, AIM1, MGAT4A, PER1, FOSL2, TSPYL2, REL, FAM177A1, YPEL5, TC2N, CSRNP1, FAM65B, PIK3R1, RGPD6, SKIL, TSC22D2, USP36, FOXP1, EGR1, MYADM, ZFP36L2, FAM102A, RGCC, PDE4B, PFKFB3, FOSB, DCTN6 and BTG2. In certain embodiments, the method comprises detecting increased expression of one or more biomarkers selected from a second group consisting of IL7R, GPR183, TCF7, LMNA, NR4A3, CD55, AIM1, MGAT4A, PER1, FOSL2, TSPYL2, REL, FAM177A1, YPEL5, TC2N and CSRNP1. In certain embodiments, the method comprises detecting increased expression of TCF7. In certain embodiments, the method comprises detecting increased expression or any CD8_G gene listed in Table 6.

In one example embodiment, the method of detecting the second population may comprise detecting IL7R and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32

In another example embodiment, the method of detecting the second population may comprise GPR183 and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32

In another example embodiment, the method of detecting the second population may comprise TCF7 and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In another example embodiment, the method of detecting the second population may comprise LMNA and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In another example embodiment, the method of detecting the second population may comprise NR4A3 and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In another example embodiment, the method of detecting the second population may comprise CD55 and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In another example embodiment, the method of detecting the second population may comprise AIM1 and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In another example embodiment, the method of detecting the second population may comprise MGAT4A and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In another example embodiment, the method of detecting the second population may comprise PER1 and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In another example embodiment, the method of detecting the second population may comprise FOSL2 and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In another example embodiment, the method of detecting the second population may comprise TSPYL2 and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In another example embodiment, the method of detecting the second population may comprise REL and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In another example embodiment, the method of detecting the second population may comprise FAM177A1 and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In another example embodiment, the method of detecting the second population may comprise YPEL5 and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In another example embodiment, the method of detecting the second population may comprise TC2N and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In another example embodiment, the method of detecting the second population may comprise CSRNP1 and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In another example embodiment, the method of detecting the second population may comprise FAM65B and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In another example embodiment, the method of detecting the second population may comprise PIK3R1 and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In another example embodiment, the method of detecting the second population may comprise RGPD6 and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In another example embodiment, the method of detecting the second population may comprise SKIL and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In another example embodiment, the method of detecting the second population may comprise TSC22D2 and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In another example embodiment, the method of detecting the second population may comprise USP36 and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In another example embodiment, the method of detecting the second population may comprise FOXP1 and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In another example embodiment, the method of detecting the second population may comprise EGR1 and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In another example embodiment, the method of detecting the second population may comprise MYADM and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In another example embodiment, the method of detecting the second population may comprise ZP36L2 and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In another example embodiment, the method of detecting the second population may comprise FAM102A and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In another example embodiment, the method of detecting the second population may comprise RGCC and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In another example embodiment, the method of detecting the second population may comprise PDE4B and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In another example embodiment, the method of detecting the second population may comprise PFKFB3 and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In another example embodiment, the method of detecting the second population may comprise FOSB and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In another example embodiment, the method of detecting the second population may comprise DCTN6 and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In another example embodiment, the method of detecting the second population may comprise BTG2 and at least N additional biomarkers selected from the first group, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32.

In certain example embodiments, the method comprises detecting a second population of CD45+ cells obtained from a biological sample. In certain example embodiments, detection of the population in the biological sample indicates a likelihood that a subject will be nonresponsive to a particular therapy. In certain example embodiments, detection of the population indicates a likelihood the subject will be nonresponsive to a checkpoint blockade therapy.

In certain embodiments, the population is characterized by expression of a gene signature comprising one or more genes or polypeptides selected from the group consisting of: ENTPD1 and HAVCR2; or CCL3, CD38 and HAVCR2; or CD38, PDCD1, CCL3, SNAP47, VCAM1, HAVCR2, FASLG, ENTPD1, SIRPG, MYO7A, FABP5, NDUFB3, UBE2F, CLTA and SNRPD1; or FASLG, VCAM1, CCL3, LAG3, CXCR6, IFNG, PDCD1, KLRD1, HAVCR2, SIRPG, SNAP47, DTHD1, PRF1, GZMH, F2R, CD38, CXCL13, TNFRSF4, TNFRSF18, MAF, ETV7, CD4, CTLA4, FCRL6, SPON2, KLRG1, TRGC1, A2M, FCGR3A, GZMA, HOPX, NKG7, PXN, TNFRSF9, GEM, NAB1, DFNB31, CADM1, CRTAM, GPR56, MYO7A, DUSP4, METRNL and PHLDA1; or CCL3, LGALS1, CD38, EPSTI1, WARS, PLEK, HAVCR2, LGALS3, FABP5, MT2A, GBP1, PLSCR1, CCR5, GSTO1, ANXA5, GLUL, PYCARD, TYMP, IFI6, VAMP5, OASL, GZMB, TXN, SQRDL, RHOC, AP2S1, GZMH, CCL4L2, SNAP47, LAP3, ATP6V1B2, CCL4L1, LAMP2, PSMA4, SERPINB1, HIGD1A, UBE2F, TALDO1, CD63, CLTA, S100A11, PHPT1, GBP4, PRDX3, PSMB2, BST2, GBP5, CTSC, NDUFB3, NPC2, GALM, GLIPR2, CCL4, PRF1, IFNG, IFI30, CHST12, ISG15, MYD88, IDH2, MTHFD2, CHMP2A, NDUFA9, CHMP5, CALM3, ANXA2, PPT1, GTF3C6, NDUFAB1, CXCR6, RNF181, LGALS9, COX5A, OAS2, PDCD1, SNRPC, BHLHE40, TWF2, SLAMF7, TXN2, CARD16, ANAPC11, MRPL51, LIMS1, NDUFA12, RANBP1, GBP2, PSMC1, ACTRIA, CD2BP2, VDAC1, EMC7, MX1, GPS1, ATP5J2, USMG5, SHFM1, ATP5I, FAM96A, CASP1, PARP9, NOP10, GNG5, CYC1, RAB11A, PGAM1, ENTPD1, PDIA6, PSMC3, TMBIM1, UBE2L6, PSMA6, EIF6, DCTN3, SEC11A, CSTB, ETFB, DBI, GRN, ELOVL1, UBE2L3, PSMB3, NDUFB7, DOK2, SEC61G, IGFLR1, ATP5H, COPZ1, ATP6V1F, BNIP3L, NUTF2, AKR1A1, MDH2, VAMP8, ROMO1, CXCR3, SAMHD1, NUCB1, ACTN4, ZYX, FLOT1, BLOC1S1, STAT1, VIMP, PAM, NUDT21, MYO1G, C17orf49, GTF2A2, HIST2H2AA4, C19orf10, ABI3, TRAPPC5, PSMC4, NDUFC2, HN1, SNRPD3, CMC1, RAB27A, NDUFA6, POMP, PFKP, ATP5G3, TMEM179B, PSMD9, IRF7, CNIH1, DYNLRB1, APOL2, TKT, DCTN2, GSDMD, STOM, CTSD, KDELR2, ATP5J, RPS27L, PSME2, DRAP1, NDUFB10, DECR1, GSTP1, TMED9, MGAT1, HSPB1, COX8A, ZEB2, ILK, PSMB6, HK1, CD58, TMX1, GZMA, SRI, PSMG2, ARL8B, NKG7, GPX1, ACP5, CHP1, GPR171, ATP6V0B, KLRD1, H2AFY, PPM1G, PRDX5, PSMA5, FBXW5, ATP6AP1, CD4, SNRPD1, XAF1, LY6E, DYNLT1, AK2, PSMA2, YIPF3, S100A10, SCP2, MRPS34, PSMD4, CDC123, BTG3, TMEM258, TSPO, SDHB, TCEB1, WDR83OS, HCST, NAA10, CTSB, YARS, GLRX, RBCK1, RBX1, LAMTOR1, UQCRFS1, NDUFB4, CAPZA2, BRK1, ADRM1, NDUFB2, ETFA, VDAC3, NUDT5, IFITM3, BANF1, ZNHIT1, CAPG, NHP2, LASP1, TOMM5, MVP, CTSW, AURKAIP1, RARRES3, PSMB10, TMEM173, SLX1A, APOBEC3G, GIMAP4, EIF4E, CTLA4, NDUFS8, CYB5B, PIK3R5, HEXB, STXBP2, PSMD8, SEC61B, RGS10, PHB, ATP5C1, ARF5, SUMO3, PRDX6, RNH1, ATP5F1, UQCRC1, SARNP, PLIN2, PIN1, SDHC, SF3B14, CAPRIN1, POLR2G, COX7B, UQCR10, FBXO7, NDUFB6, S100A4, PRELID1, TRPV2, SF3B5, MYO1F, SCAMP2, RNF7, CXCL13, RAB1B, SHKBP1, PET100, HM13, VTI1B, S100A6, ARPC5, FDPS, MINOS1, RAB10, NEDD8, BATF, PHB2, ERH, NCOA4, PDIA4, PSMB9, C11 orf48, TMEM50A, TIGIT, NDUFA11, NELFE, COX6C, SLA2, PSMB8, NDUFS7, RER1, RAB8A, CAPN1, MRPL20, COX5B, SEC13, FKBP1A, PRDM1, RAB1A, RHOG, CYB5R3, AIP, ABRACL, PSMB7, COX6B1, PSMD7, PPA1, PCMT1, SURF4, ENY2, TCEB2, MAP2K3, AL353354.2, AKIRIN2, MAPRE1, GRSF1, DUSP4, ATG3, SRGAP2, ATP6V0D1, NELFCD, LRPAP1, C14orf166, SNRPB2, CHMP4A, SFT2D1, CASP4, NME1-NME2, FAM96B, FDFT1, SLC25A39, LMAN2, MDH1, RHBDD2, ARPC5L, TBCA, EBP, SEC14L1, EIF2S2, CST7, STARD7, SOD2, SPN, FAM32A, SEC11C, TNFRSF1B, POLR2E, NDUFA13, OSTC, UFC1, C18orf32, SRP19, C14orf2, UQCR11, PDCD6, AP2M1, PPP1CA, ATP6AP2, SSR3, UNC13D, FERMT3, ARHGAP1, EIF3I, CECR1, MRPS6, DNPH1, DCXR, PSMF1, SNRPG, CNDP2, ANXA11, SLMO2, C16orf13, CAPN2, BSG, LAMTOR5, SIVA1, TRAPPC1, TMCO1, PSMD13, PSMB1, RSU1, NDUFA1, TUBB, DCTN1, SH3GLB1, BCAP31, RTFDC1, UFD1L, GPI, DNAJB11, SNX17, SH2D2A, C1orf43, BUD31, PSTPIP1, CTSA, TPST2, MPV17, APMAP, CMC2, UQCRQ, TBCB, C9orf16, PARK7, ATP5EP2, SHISA5, SMC4, TAP1, SCANDI, SIRPG, HDLBP, EMC4, FIS1, TPI1, GOLGA7, POLR2J, EIF2S1, UBA3, P4HB, UQCRH, CSNK2B, SZRD1, NDUFA3, ATP5O, DERL2, COPS6, COPE, SNX6, FLII and ERGIC3. (Tables 4 and 5).

Treatment Selection

In another aspect, the invention comprises determining a subject's responsiveness to a particular therapeutic, including a checkpoint blockade therapeutic, by determining a ratio of the first cell population to the second cell population, wherein if the ratio of the second population in a sample is lower relative to the first population the subject is classified as non-responsive to the therapeutic, and wherein if the ratio of the second cell population is higher in a sample relative to the first population the patient is classified as responsive to the therapeutic.

Thus, in certain example embodiments a method of treating a subject in need thereof may comprise detecting a first CD8+ cell population from a sample from the subject using any of the biomarkers or combination of biomarkers discussed above, detecting a second CD8+ cell population from a same or different sample from the subject using any of the biomarkers or combination of biomarkers discussed above, and determining a ratio of the first CD8+ population to the second CD8+ population, wherein the subject is treated with a first therapeutic or therapeutic combination if the ratio of the first population is higher relative to the second population, and wherein the subject is treated with a second therapeutic or therapeutic combination if the ratio of the second population is higher relative to the first population. In certain example embodiment, the first therapeutic or therapeutic combination is a non-checkpoint blockade therapeutic, and the second therapeutic or therapeutic combination is a checkpoint blockade therapeutic.

Thus, in certain example embodiments a method of treating a subject in need thereof may comprise detecting a first CD45+ cell population from a sample from the subject using any of the biomarkers or combination of biomarkers discussed above, detecting a second CD45+ cell population from a same or different sample from the subject using any of the biomarkers or combination of biomarkers discussed above, and determining a ratio of the first CD45+ population to the second CD45+ population, wherein the subject is treated with a first therapeutic or therapeutic combination if the ratio of the first population is higher relative to the second population, and wherein the subject is treated with a second therapeutic or therapeutic combination if the ratio of the second population is higher relative to the first population. In certain example embodiment, the first therapeutic or therapeutic combination is a non-checkpoint blockade therapeutic, and the second therapeutic or therapeutic combination is a checkpoint blockade therapeutic.

Detection of Biomarkers

Depending on factors that can be evaluated and decided on by a skilled person, such as, inter alia, the type of a marker (e.g., peptide, polypeptide, protein, or nucleic acid), the type of the tested object (e.g., a cell, cell population, tissue, organ, or organism, e.g., the type of biological sample of a subject, e.g., whole blood, plasma, serum, tissue biopsy), the expected abundance of the marker in the tested object, the type, robustness, sensitivity and/or specificity of the detection method used to detect the marker, etc., the marker may be measured directly in the tested object, or the tested object may be subjected to one or more processing steps aimed at achieving an adequate measurement of the marker.

In one embodiment, the biomarkers are detected by immunofluorescence, immunohistochemistry, fluorescence activated cell sorting (FACS), mass cytometry (CyTOF), Drop-seq, RNA-seq, scRNA-seq, InDrop, single cell qPCR, MERFISH (multiplex (in situ) RNA FISH) and/or by in situ hybridization. Other methods including absorbance assays and colorimetric assays are known in the art and may be used herein. In certain embodiments, primers and/or probes or fluorescently bar-coded oligonucleotide probes for hybridization to RNA are used to detect biomarkers (see e.g., Geiss G K, et al., Direct multiplexed measurement of gene expression with color-coded probe pairs. Nat Biotechnol. 2008 March; 26(3):317-25).

In other example embodiments, detection of a mark may include immunological assay methods, wherein the ability of an assay to separate, detect and/or quantify a marker (such as, preferably, peptide, polypeptide, or protein) is conferred by specific binding between a separable, detectable and/or quantifiable immunological binding agent (antibody) and the marker. Immunological assay methods include without limitation immunohistochemistry, immunocytochemistry, flow cytometry, mass cytometry, fluorescence activated cell sorting (FACS), fluorescence microscopy, fluorescence based cell sorting using microfluidic systems, immunoaffinity adsorption based techniques such as affinity chromatography, magnetic particle separation, magnetic activated cell sorting or bead based cell sorting using microfluidic systems, enzyme-linked immunosorbent assay (ELISA) and ELISPOT based techniques, radioimmunoassay (RIA), Western blot, etc.

In certain example embodiments, detection of a marker or signature may include biochemical assay methods, including inter alia assays of enzymatic activity, membrane channel activity, substance-binding activity, gene regulatory activity, or cell signalling activity of a marker, e.g., peptide, polypeptide, protein, or nucleic acid.

In other example embodiments, detection of a mark may include mass spectrometry analysis methods. Generally, any mass spectrometric (MS) techniques that are capable of obtaining precise information on the mass of peptides, and preferably also on fragmentation and/or (partial) amino acid sequence of selected peptides (e.g., in tandem mass spectrometry, MS/MS; or in post source decay, TOF MS), may be useful herein for separation, detection and/or quantification of markers (such as, preferably, peptides, polypeptides, or proteins). Suitable peptide MS and MS/MS techniques and systems are well-known per se (see, e.g., Methods in Molecular Biology, vol. 146: "Mass Spectrometry of Proteins and Peptides", by Chapman, ed., Humana Press 2000, ISBN 089603609x; Biemann 1990. Methods Enzymol 193: 455-79; or Methods in Enzymology, vol. 402: "Biological Mass Spectrometry", by Burlingame, ed., Academic Press 2005, ISBN 9780121828073) and may be used herein. MS arrangements, instruments and systems suitable for biomarker peptide analysis may include, without limitation, matrix-assisted laser desorption/ionisation time-of-flight (MALDI-TOF) MS; MALDI-TOF post-source-decay (PSD); MALDI-TOF/TOF; surface-enhanced laser desorption/ionization time-of-flight mass spectrometry (SELDI-TOF) MS; electrospray ionization mass spectrometry (ESI-MS); ESI-MS/MS; ESI-MS/(MS)n (n is an integer greater than zero); ESI 3D or linear (2D) ion trap MS; ESI triple quadrupole MS; ESI quadrupole orthogonal TOF (Q-TOF); ESI Fourier transform MS systems; desorption/ionization on silicon (DIOS); secondary ion mass spectrometry (SIMS); atmospheric pressure chemical ionization mass spectrometry (APCI-MS); APCI-MS/MS; APCI-(MS)n; atmospheric pressure photoionization mass spectrometry (APPI-MS); APPI-MS/MS; and APPI-(MS)n. Peptide ion fragmentation in tandem MS (MS/MS) arrangements may be achieved using manners established in the art, such as, e.g., collision induced dissociation (CID). Detection and quantification of markers by mass spectrometry may involve multiple reaction monitoring (MRM), such as described among others by Kuhn et al. 2004 (Proteomics 4: 1175-86). MS peptide analysis methods may be advantageously combined with upstream peptide or protein separation or fractionation methods, such as for example with the chromatographic and other methods.

In other example embodiments, detection of a marker may include chromatography methods. In a one example embodiment, chromatography refers to a process in which a mixture of substances (analytes) carried by a moving stream of liquid or gas ("mobile phase") is separated into components as a result of differential distribution of the analytes, as they flow around or over a stationary liquid or solid phase ("stationary phase"), between said mobile phase and said stationary phase. The stationary phase may be usually a finely divided solid, a sheet of filter material, or a thin film of a liquid on the surface of a solid, or the like. Chromatography may be columnar. While particulars of chromatography are well known in the art, for further guidance see, e.g., Meyer M., 1998, ISBN: 047198373X, and "Practical HPLC Methodology and Applications", Bidlingmeyer, B. A., John Wiley & Sons Inc., 1993. Exemplary types of chromatography include, without limitation, high-performance liquid chromatography (HPLC), normal phase HPLC (NP-HPLC), reversed phase HPLC (RP-HPLC), ion exchange chromatography (IEC), such as cation or anion exchange chromatography, hydrophilic interaction chromatography (HILIC), hydrophobic interaction chromatography (HIC), size exclusion chromatography (SEC) including gel filtration chromatography or gel permeation chromatography, chromatofocusing, affinity chromatography such as immunoaffinity, immobilised metal affinity chromatography, and the like.

In certain embodiments, further techniques for separating, detecting and/or quantifying markers may be used in conjunction with any of the above described detection methods.

Such methods include, without limitation, chemical extraction partitioning, isoelectric focusing (IEF) including capillary isoelectric focusing (CIEF), capillary isotachophoresis (CITP), capillary electrochromatography (CEC), and the like, one-dimensional polyacrylamide gel electrophoresis (PAGE), two-dimensional polyacrylamide gel electrophoresis (2D-PAGE), capillary gel electrophoresis (CGE), capillary zone electrophoresis (CZE), micellar electrokinetic chromatography (MEKC), free flow electrophoresis (FFE), etc.

In certain examples, such methods may include separating, detecting and/or quantifying markers at the nucleic acid level, more particularly RNA level, e.g., at the level of hnRNA, pre-mRNA, mRNA, or cDNA. Standard quantitative RNA or cDNA measurement tools known in the art may be used. Non-limiting examples include hybridization-based analysis, microarray expression analysis, digital gene expression profiling (DGE), RNA-in-situ hybridization (RISH), Northern-blot analysis and the like; PCR, RT-PCR, RT-qPCR, end-point PCR, digital PCR or the like; supported oligonucleotide detection, pyrosequencing, polony cyclic sequencing by synthesis, simultaneous bi-directional sequencing, single-molecule sequencing, single molecule real time sequencing, true single molecule sequencing, hybridization-assisted nanopore sequencing, sequencing by synthesis, single-cell RNA sequencing (scRNA seq), or the like.

In certain embodiments, the invention involves plate based single cell RNA sequencing (see, e.g., Picelli, S. et al., 2014, "Full-length RNA-seq from single cells using Smart-seq2" Nature protocols 9, 171-181, doi:10.1038/nprot.2014.006).

In certain embodiments, the invention involves high-throughput single-cell RNA-seq and/or targeted nucleic acid profiling (for example, sequencing, quantitative reverse transcription polymerase chain reaction, and the like) where the RNAs from different cells are tagged individually, allowing a single library to be created while retaining the cell identity of each read. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352):661-667, 2017; and Gierahn et al., "Seq-Well: portable, low-cost RNA sequencing of single cells at high throughput" Nature Methods 14, 395-398 (2017), all the contents and disclosure of each of which are herein incorporated by reference in their entirety.

In certain embodiments, the invention involves single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October; 14(10):955-958; and International patent application number PCT/US2016/059239, published as WO2017164936 on Sep. 28, 2017, which are herein incorporated by reference in their entirety.

In one embodiment, immune cells are stained for immune cell subtype specific signature genes. In one embodiment, the cells are fixed. In another embodiment, the cells are formalin fixed and paraffin embedded. In another example embodiment, the immune cell subtypes may be quantitated in a section of a tumor.

The method may allow to detect or conclude the presence or absence of the specified immune cells in a tested object (e.g., in a cell population, tissue, organ, organism, or in a biological sample of a subject). The method may also allow to quantify the specified immune cells in a tested object (e.g., in a cell population, tissue, organ, organism, or in a biological sample of a subject). The quantity of the specified immune cells in the tested object such as the biological sample may be suitably expressed for example as the number (count) of the specified immune cells per standard unit of volume (e.g., ml, µl or nl) or weight (e.g., g or mg or ng) of the tested object such as the biological sample. The quantity of the specified immune cells in the tested object such as the biological sample may also be suitably expressed as a percentage or fraction (by number) of all cells comprised in the tested object such as the biological sample, or as a percentage or fraction (by number) of a select subset of the cells comprised in the tested object such as the biological sample, e.g., as a percentage or fraction (by number) of white blood cells, peripheral blood mononuclear cells, immune cells, antigen presenting cells, or dendritic cells comprised in the tested object such as the biological sample. The quantity of the specified immune cells in the tested object such as the biological sample may also be suitably represented by an absolute or relative quantity of a suitable surrogate analyte, such as a peptide, polypeptide, protein, or nucleic acid expressed or comprised by the specified immune cells.

Where a marker is detected in or on a cell, the cell may be conventionally denoted as positive (+) or negative (−) for the marker. Semi-quantitative denotations of marker expression in cells are also commonplace in the art, such as particularly in flow cytometry quantifications, for example, "dim" vs. "bright", or "low" vs. "medium"/"intermediate" vs. "high", or "−" vs. "+" vs. "++", commonly controlled in flow cytometry quantifications by setting of the gates. Where a marker is quantified in or on a cell, absolute quantity of the marker may also be expressed for example as the number of molecules of the marker comprised by the cell.

Where a marker is detected and/or quantified on a single cell level in a cell population, the quantity of the marker may also be expressed as a percentage or fraction (by number) of cells comprised in said population that are positive for said marker, or as percentages or fractions (by number) of cells comprised in said population that are "dim" or "bright", or that are "low" or "medium"/"intermediate" or "high", or that are "−" or "+" or "++". By means of an example, a sizeable proportion of the tested cells of the cell population may be positive for the marker, e.g., at least about 20%, at least about 40%, at least about 50%, at least about 60%, at least about 70%, at least about 80%, at least about 90%, at least about 95%, or up to 100%.

Isolated Cells

In one aspect, the invention is directed to isolated cell populations having the phenotypes described herein and/or as identified by the signatures defined herein. Accordingly, methods for detecting, quantifying or isolating the specified immune cells may be marker-based or gene or gene product signature-based, i.e., may involve isolation of cells expressing or not expressing marker(s) or combination(s) of markers the expression or lack of expression of which is taught herein as typifying or characterizing the specified immune cells, or may involve detection, quantification or isolation of cells comprising gene or gene product signature(s) taught herein as typifying or characterizing the specified immune cells.

The terms "isolating" or "purifying" as used throughout this specification with reference to a particular component of a composition or mixture (e.g., the tested object such as the biological sample) encompass processes or techniques whereby such component is separated from one or more or (substantially) all other components of the composition or mixture (e.g., the tested object such as the biological sample). The terms do not require absolute purity. Instead, isolating or purifying the component will produce a discrete environment in which the abundance of the component relative to one or more or all other components is greater than in the starting composition or mixture (e.g., the tested object such as the biological sample). A discrete environment may denote a single medium, such as for example a single solution, dispersion, gel, precipitate, etc. Isolating or purifying the specified immune cells from the tested object such as the biological sample may increase the abundance of the specified immune cells relative to all other cells comprised in the tested object such as the biological sample, or relative to other cells of a select subset of the cells comprised in the tested object such as the biological sample, e.g., relative to other white blood cells, peripheral blood mononuclear cells, immune cells, antigen presenting cells, or dendritic cells comprised in the tested object such as the biological sample. By means of example, isolating or purifying the specified immune cells from the tested object such as the biological sample may yield a cell population, in which the specified immune cells constitute at least 40% (by number) of all cells of said cell population, for example, at least 45%, preferably at least 50%, at least 55%, more preferably at least 60%, at least 65%, still more preferably at least 70%, at least 75%, even more preferably at least 80%, at least 85%, and yet more preferably at least 90%, at least 95%, at least 96%, at least 97%, at least 98%, at least 99%, or even 100% of all cells of said cell population.

Any existing, available or conventional separation, detection and/or quantification methods may be used to measure the presence or absence (e.g., readout being present vs. absent; or detectable amount vs. undetectable amount) and/or quantity (e.g., readout being an absolute or relative quantity) of the specified immune cells in, or to isolate the specified immune cells from, a tested object (e.g., a cell population, tissue, organ, organism, or a biological sample of a subject). Such methods allow to detect, quantify or isolate the specified immune cells in or from the tested object (e.g., a cell population, tissue, organ, organism, or a biological sample of a subject) substantially to the exclusion of other cells comprised in the tested object. Such methods may allow to detect, quantify or isolate the specified immune cells with sensitivity of at least 50%, at least 55%, at least 60%, at least 65%, preferably at least 70%, at least 75%, more preferably at least 80%, at least 85%, even more preferably at least 90%, at least 95%, at least 96%, at least 97%, at least 98%, at least 99%, or even 100%, and/or with specificity of at least 50%, at least 55%, at least 60%, at least 65%, preferably at least 70%, at least 75%, more preferably at least 80%, at least 85%, even more preferably at least 90%, at least 95%, at least 96%, at least 97%, at least 98%, at least 99%, or even 100%. By means of example, at least 40% (by number), for example at least 45%, preferably at least 50%, at least 55%, more preferably at least 60%, at least 65%, still more preferably at least 70%, at least 75%, even more preferably at least 80%, at least 85%, and yet more preferably at least 90%, at least 95%, at least 96%, at least 97%, at least 98%, at least 99%, or even 100% of all cells detected, quantified or isolated by such methods may correspond to the specified immune cells.

The isolated immune cells or immune cell populations as disclosed throughout this specification may be suitably cultured or cultivated in vitro. The terms "culturing" or "cell culture" are common in the art and broadly refer to maintenance of cells and potentially expansion (proliferation, propagation) of cells in vitro. Typically, animal cells, such as mammalian cells, such as human cells, are cultured by exposing them to (i.e., contacting them with) a suitable cell culture medium in a vessel or container adequate for the purpose (e.g., a 96-, 24-, or 6-well plate, a T-25, T-75, T-150 or T-225 flask, or a cell factory), at art-known conditions conducive to in vitro cell culture, such as temperature of 37° C., 5% v/v CO2 and >95% humidity.

The term "medium" as used herein broadly encompasses any cell culture medium conducive to maintenance of cells, preferably conducive to proliferation of cells. Typically, the medium will be a liquid culture medium, which facilitates easy manipulation (e.g., decantation, pipetting, centrifugation, filtration, and such) thereof.

Typically, the medium will comprise a basal medium formulation as known in the art. Many basal media formulations (available, e.g., from the American Type Culture Collection, ATCC; or from Invitrogen, Carlsbad, California) can be used, including but not limited to Eagle's Minimum Essential Medium (MEM), Dulbecco's Modified Eagle's Medium (DMEM), alpha modified Minimum Essential Medium (alpha-MEM), Basal Medium Essential (BME), Iscove's Modified Dulbecco's Medium (IMDM), BGJb medium, F-12 Nutrient Mixture (Ham), Liebovitz L-15, DMEM/F-12, Essential Modified Eagle's Medium (EMEM), RPMI-1640, Medium 199, Waymouth's MB 752/1 or Williams Medium E, and modifications and/or combinations thereof. Compositions of basal media are generally known in the art and it is within the skill of one in the art to modify or modulate concentrations of media and/or media supplements as necessary for the cells cultured.

Such basal media formulations contain ingredients necessary for mammalian cell development, which are known per se. By means of illustration and not limitation, these ingredients may include inorganic salts (in particular salts containing Na, K, Mg, Ca, Cl, P and possibly Cu, Fe, Se and Zn), physiological buffers (e.g., HEPES, bicarbonate), nucleotides, nucleosides and/or nucleic acid bases, ribose, deoxyribose, amino acids, vitamins, antioxidants (e.g., glutathione) and sources of carbon (e.g., glucose, sodium pyruvate, sodium acetate), etc.

For use in culture, basal media can be supplied with one or more further components. For example, additional supplements can be used to supply the cells with the necessary trace elements and substances for optimal growth and expansion. Furthermore, antioxidant supplements may be added, e.g., β-mercaptoethanol. While many basal media already contain amino acids, some amino acids may be supplemented later, e.g., L-glutamine, which is known to be less stable when in solution. A medium may be further supplied with antibiotic and/or antimycotic compounds, such as, typically, mixtures of penicillin and streptomycin, and/or other compounds, exemplified but not limited to, amphotericin, ampicillin, gentamicin, bleomycin, hygromycin, kanamycin, mitomycin, mycophenolic acid, nalidixic acid, neomycin, nystatin, paromomycin, polymyxin, puromycin, rifampicin, spectinomycin, tetracycline, tylosin, and zeocin.

Lipids and lipid carriers can also be used to supplement cell culture media. Such lipids and carriers can include, but are not limited to cyclodextrin, cholesterol, linoleic acid conjugated to albumin, linoleic acid and oleic acid conjugated to albumin, unconjugated linoleic acid, linoleic-oleic-arachidonic acid conjugated to albumin, oleic acid unconjugated and conjugated to albumin, among others. Albumin can similarly be used in fatty-acid free formulations.

Also contemplated is supplementation of cell culture media with mammalian plasma or sera. Plasma or sera often contain cellular factors and components that facilitate cell viability and expansion. Optionally, plasma or serum may be heat inactivated. Heat inactivation is used in the art mainly to remove the complement. Heat inactivation typically involves incubating the plasma or serum at 56° C. for 30 to 60 min, e.g., 30 min, with steady mixing, after which the plasma or serum is allowed to gradually cool to ambient temperature. A skilled person will be aware of any common modifications and requirements of the above procedure. Optionally, plasma or serum may be sterilised prior to storage or use. Usual means of sterilisation may involve, e.g., filtration through one or more filters with pore size smaller than 1 µm, preferably smaller than 0.5 µm, e.g., smaller than 0.45 µm, 0.40 µm, 0.35 µm, 0.30 µm or 0.25 µm, more preferably 0.2 µm or smaller, e.g., 0.15 µm or smaller, 0.10 µm or smaller. Suitable sera or plasmas for use in media as taught herein may include human serum or plasma, or serum or plasma from non-human animals, preferably non-human mammals, such as, e.g., non-human primates (e.g., lemurs, monkeys, apes), foetal or adult bovine, horse, porcine, lamb, goat, dog, rabbit, mouse or rat serum or plasma, etc., or any combination of such. In certain preferred embodiments, a medium as taught herein may comprise bovine serum or plasma, preferably foetal bovine (calf) serum or plasma, more preferably foetal bovine (calf) serum (FCS or FBS). When culturing human cells, media may preferably comprise human serum or plasma, such as autologous or allogeneic human serum or plasma, preferably human serum, such as autologous or allogeneic human serum, more preferably autologous human serum or plasma, even more preferably autologous human serum.

In certain preferred embodiments, serum or plasma can be substituted in media by serum replacements, such as to provide for serum-free media (i.e., chemically defined media). The provision of serum-free media may be advantageous particularly with view to administration of the media or fraction(s) thereof to subjects, especially to human subjects (e.g., improved bio-safety). By the term "serum replacement" it is broadly meant any a composition that may be used to replace the functions (e.g., cell maintenance and growth supportive function) of animal serum in a cell culture medium. A conventional serum replacement may typically comprise vitamins, albumin, lipids, amino acids, transferrin, antioxidants, insulin and trace elements. Many commercialized serum replacement additives, such as KnockOut Serum Replacement (KOSR), N2, B27, Insulin-Transferrin-Selenium Supplement (ITS), and G5 are well known and are readily available to those skilled in the art.

Plasma or serum or serum replacement may be comprised in media as taught herein at a proportion (volume of plasma or serum or serum replacement/volume of medium) between about 0.5% v/v and about 40.0% v/v, preferably between about 5.0% v/v and about 20.0% v/v, e.g., between about 5.0% v/v and about 15.0% v/v, more preferably between about 8.0% v/v and about 12.0% v/v, e.g., about 10.0% v/v.

In certain embodiments, methods for detecting, quantifying or isolating the specified immune cells may be single-cell-based, i.e., may allow to discretely detect, quantify or isolate the specified immune cells as individual cells. In other embodiments, methods for detecting, quantifying or isolating the specified immune cells may be cell population-based, i.e., may only allow to detect, quantify or isolate the specified immune cells as a group or collection of cells, without providing information on or allowing to isolate individual cells.

Methods for detecting, quantifying or isolating the specified immune cells may employ any of the above-described techniques for measuring markers, insofar the separation or the qualitative and/or quantitative measurement of the marker(s) can be correlated with or translated into detection, quantification or isolation of the specified immune cells. For example, any of the above-described biochemical assay methods, immunological assay methods, mass spectrometry analysis methods, chromatography methods, or nucleic acid analysis method, or combinations thereof for measuring markers, may be employed for detecting, quantifying or isolating the specified immune cells.

In certain embodiments, the cells are detected, quantified or isolated using a technique selected from the group consisting of flow cytometry, fluorescence activated cell sorting, mass cytometry, fluorescence microscopy, affinity separation, magnetic cell separation, microfluidic separation, and combinations thereof.

Flow cytometry encompasses methods by which individual cells of a cell population are analyzed by their optical properties (e.g., light absorbance, light scattering and fluorescence properties, etc.) as they pass in a narrow stream in single file through a laser beam. Flow cytometry methods include fluorescence activated cell sorting (FACS) methods by which a population of cells having particular optical properties are separated from other cells.

Elemental mass spectrometry-based flow cytometry, or mass cytometry, offers an approach to analyze cells by replacing fluorochrome-labelled binding reagents with mass tagged binding reagents, i.e., tagged with an element or isotope having a defined mass. In these methods, labeled particles are introduced into a mass cytometer, where they are individually atomized and ionized. The individual particles are then subjected to elemental analysis, which identifies and measures the abundance of the mass tags used. The identities and the amounts of the isotopic elements associated with each particle are then stored and analyzed. Due to the resolution of elemental analysis and the number of elemental isotopes that can be used, it is possible to simultaneously measure up to 100 or more parameters on a single particle.

Fluorescence microscopy broadly encompasses methods by which individual cells of a cell population are microscopically analyzed by their fluorescence properties. Fluorescence microscopy approaches may be manual or preferably automated.

Affinity separation also referred to as affinity chromatography broadly encompasses techniques involving specific interactions of cells present in a mobile phase, such as a suitable liquid phase (e.g., cell population in an aqueous suspension) with, and thereby adsorption of the cells to, a stationary phase, such as a suitable solid phase; followed by separation of the stationary phase from the remainder of the mobile phase; and recovery (e.g., elution) of the adsorbed cells from the stationary phase. Affinity separation may be columnar, or alternatively, may entail batch treatment, wherein the stationary phase is collected/separated from the liquid phases by suitable techniques, such as centrifugation or application of magnetic field (e.g., where the stationary phase comprises magnetic substrate, such as magnetic particles or beads). Accordingly, magnetic cell separation is also envisaged herein.

Microfluidic systems allow for accurate and high throughput cell detection, quantification and/or sorting, exploiting a variety of physical principles. Cell sorting on microchips provides numerous advantages by reducing the size of necessary equipment, eliminating potentially biohazardous aerosols, and simplifying the complex protocols commonly associated with cell sorting. The term "microfluidic system" as used throughout this specification broadly refers to systems having one or more fluid microchannels. Microchannels denote fluid channels having cross-sectional dimensions the largest of which are typically less than 1 mm, preferably less than 500 m, more preferably less than 400 m, more preferably less than 300 m, more preferably less than 200 m, e.g., 100 m or smaller. Such microfluidic systems can be used for manipulating fluid and/or objects such as droplets, bubbles, capsules, particles, cells and the like. Microfluidic systems may allow for example for fluorescent label-based (e.g., employing fluorophore-conjugated binding agent(s), such as fluorophore-conjugated antibody(ies)), bead-based (e.g., bead-conjugated binding agent(s), such as bead-conjugated antibody(ies)), or label-free cell sorting (reviewed in Shields et al., Lab Chip. 2015, vol. 15: 1230-1249).

Use of Specific Binding Agents

In certain embodiments, the aforementioned methods and techniques may employ agent(s) capable of specifically binding to one or more gene products, e.g., peptides, polypeptides, proteins, or nucleic acids, expressed or not expressed by the immune cells as taught herein. In certain preferred embodiments, such one or more gene products, e.g., peptides, polypeptides, or proteins, may be expressed on the cell surface of the immune cells (i.e., cell surface markers, e.g., transmembrane peptides, polypeptides or proteins, or secreted peptides, polypeptides or proteins which remain associated with the cell surface). Hence, further disclosed are binding agents capable of specifically binding to markers, such as genes or gene products, e.g., peptides, polypeptides, proteins, or nucleic acids as taught herein. Binding agents as intended throughout this specification may include inter alia antibodies, aptamers, spiegelmers (L-aptamers), photoaptamers, protein, peptides, peptidomimetics, nucleic acids such as oligonucleotides (e.g., hybridization probes or amplification or sequencing primers and primer pairs), small molecules, or combinations thereof.

The term "aptamer" refers to single-stranded or double-stranded oligo-DNA, oligo-RNA or oligo-DNA/RNA or any analogue thereof that specifically binds to a target molecule such as a peptide. Advantageously, aptamers display fairly high specificity and affinity (e.g., KA in the order 1×109 M-1) for their targets. Aptamer production is described inter alia in U.S. Pat. No. 5,270,163; Ellington & Szostak 1990 (Nature 346: 818-822); Tuerk & Gold 1990 (Science 249: 505-510); or "The Aptamer Handbook: Functional Oligonucleotides and Their Applications", by Klussmann, ed., Wiley-VCH 2006, ISBN 3527310592, incorporated by reference herein. The term "photoaptamer" refers to an aptamer that contains one or more photoreactive functional groups that can covalently bind to or crosslink with a target molecule. The term "spiegelmer" refers to an aptamer which includes L-DNA, L-RNA, or other left-handed nucleotide derivatives or nucleotide-like molecules. Aptamers containing left-handed nucleotides are resistant to degradation by naturally occurring enzymes, which normally act on substrates containing right-handed nucleotides. The term "peptidomimetic" refers to a non-peptide agent that is a topological analogue of a corresponding peptide. Methods of rationally designing peptidomimetics of peptides are known in the art. For example, the rational design of three peptidomimetics based on the sulphated 8-mer peptide CCK26-33, and of two peptidomimetics based on the 11-mer peptide Substance P, and related peptidomimetic design principles, are described in Horwell 1995 (Trends Biotechnol 13: 132-134).

Binding agents may be in various forms, e.g., lyophilised, free in solution, or immobilised on a solid phase. They may be, e.g., provided in a multi-well plate or as an array or microarray, or they may be packaged separately, individually, or in combination.

The term "specifically bind" as used throughout this specification means that an agent (denoted herein also as "specific-binding agent") binds to one or more desired molecules or analytes (e.g., peptides, polypeptides, proteins, or nucleic acids) substantially to the exclusion of other molecules which are random or unrelated, and optionally substantially to the exclusion of other molecules that are structurally related. The term "specifically bind" does not necessarily require that an agent binds exclusively to its intended target(s). For example, an agent may be said to specifically bind to target(s) of interest if its affinity for such intended target(s) under the conditions of binding is at least about 2-fold greater, preferably at least about 5-fold greater, more preferably at least about 10-fold greater, yet more preferably at least about 25-fold greater, still more preferably at least about 50-fold greater, and even more preferably at least about 100-fold, or at least about 1000-fold, or at least about $10^4$-fold, or at least about $10^5$-fold, or at least about $10^6$-fold or more greater, than its affinity for a non-target molecule, such as for a suitable control molecule (e.g., bovine serum albumin, casein).

Preferably, the specific binding agent may bind to its intended target(s) with affinity constant (KA) of such binding KA≥1×$10^6$ M$^{-1}$, more preferably KA≥1×$10^7$ M$^{-1}$, yet more preferably KA≥1×$10^8$ M$^{-1}$, even more preferably KA≥1×$10^9$ M$^{-1}$, and still more preferably KA≥1×$10^{10}$ M$^{-1}$ or KA≥1×$10^{11}$ M$^{-1}$ or KA≥1×$10^{12}$ M$^{-1}$, wherein KA=[SBA_T]/[SBA][T], SBA denotes the specific-binding agent, T denotes the intended target. Determination of KA can be carried out by methods known in the art, such as for example, using equilibrium dialysis and Scatchard plot analysis.

In certain embodiments, the one or more binding agents may be one or more antibodies. As used herein, the term "antibody" is used in its broadest sense and generally refers to any immunologic binding agent. The term specifically encompasses intact monoclonal antibodies, polyclonal antibodies, multivalent (e.g., 2-, 3- or more-valent) and/or multi-specific antibodies (e.g., bi- or more-specific antibodies) formed from at least two intact antibodies, and antibody fragments insofar they exhibit the desired biological activity (particularly, ability to specifically bind an antigen of interest, i.e., antigen-binding fragments), as well as multivalent and/or multi-specific composites of such fragments. The term "antibody" is not only inclusive of antibodies generated by methods comprising immunization, but also includes any polypeptide, e.g., a recombinantly expressed polypeptide, which is made to encompass at least one complementarity-determining region (CDR) capable of specifically binding to an epitope on an antigen of interest. Hence, the term applies to such molecules regardless whether they are produced in vitro or in vivo. Antibodies also encompasses chimeric, humanized and fully humanized antibodies.

An antibody may be any of IgA, IgD, IgE, IgG and IgM classes, and preferably IgG class antibody. An antibody may be a polyclonal antibody, e.g., an antiserum or immunoglobulins purified there from (e.g., affinity-purified). An antibody may be a monoclonal antibody or a mixture of monoclonal antibodies. Monoclonal antibodies can target a particular antigen or a particular epitope within an antigen with greater selectivity and reproducibility. By means of example and not limitation, monoclonal antibodies may be made by the hybridoma method first described by Kohler et al. 1975 (Nature 256: 495), or may be made by recombinant DNA methods (e.g., as in U.S. Pat. No. 4,816,567). Monoclonal antibodies may also be isolated from phage antibody libraries using techniques as described by Clackson et al. 1991 (Nature 352: 624-628) and Marks et al. 1991 (J Mol Biol 222: 581-597), for example.

Antibody binding agents may be antibody fragments. "Antibody fragments" comprise a portion of an intact antibody, comprising the antigen-binding or variable region thereof. Examples of antibody fragments include Fab, Fab', F(ab')2, Fv and scFv fragments, single domain (sd) Fv, such as VH domains, VL domains and VHH domains; diabodies; linear antibodies; single-chain antibody molecules, in particular heavy-chain antibodies; and multivalent and/or multispecific antibodies formed from antibody fragment(s), e.g., diabodies, tribodies, and multibodies. The above designations Fab, Fab', F(ab')2, Fv, scFv etc. are intended to have their art-established meaning.

The term antibody includes antibodies originating from or comprising one or more portions derived from any animal species, preferably vertebrate species, including, e.g., birds and mammals. Without limitation, the antibodies may be chicken, turkey, goose, duck, guinea fowl, quail or pheasant. Also without limitation, the antibodies may be human, murine (e.g., mouse, rat, etc.), donkey, rabbit, goat, sheep, guinea pig, camel (e.g., *Camelus bactrianus* and *Camelus dromedarius*), llama (e.g., *Lama pacos, Lama glama* or *Lama vicugna*) or horse.

A skilled person will understand that an antibody can include one or more amino acid deletions, additions and/or substitutions (e.g., conservative substitutions), insofar such alterations preserve its binding of the respective antigen. An antibody may also include one or more native or artificial modifications of its constituent amino acid residues (e.g., glycosylation, etc.).

Methods of producing polyclonal and monoclonal antibodies as well as fragments thereof are well known in the art, as are methods to produce recombinant antibodies or fragments thereof (see for example, Harlow and Lane, "Antibodies: A Laboratory Manual", Cold Spring Harbour Laboratory, New York, 1988; Harlow and Lane, "Using Antibodies: A Laboratory Manual", Cold Spring Harbour Laboratory, New York, 1999, ISBN 0879695447; "Monoclonal Antibodies: A Manual of Techniques", by Zola, ed., CRC Press 1987, ISBN 0849364760; "Monoclonal Antibodies: A Practical Approach", by Dean & Shepherd, eds., Oxford University Press 2000, ISBN 0199637229; Methods in Molecular Biology, vol. 248: "Antibody Engineering: Methods and Protocols", Lo, ed., Humana Press 2004, ISBN 1588290921).

As used herein, a "blocking" antibody or an antibody "antagonist" is one which inhibits or reduces biological activity of the antigen(s) it binds. In certain embodiments, the blocking antibodies or antagonist antibodies or portions thereof described herein completely inhibit the biological activity of the antigen(s).

Antibodies may act as agonists or antagonists of the recognized polypeptides. For example, the present invention includes antibodies which disrupt receptor/ligand interactions either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or of one of its down-stream substrates by immunoprecipitation followed by western blot analysis. In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex. Likewise, encompassed by the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides disclosed herein. The antibody agonists and antagonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16): 3668-3678 (1998); Harrop et al., J. Immunol. 161(4):1786-1794 (1998); Zhu et al., Cancer Res. 58(15):3209-3214 (1998); Yoon et al., J. Immunol. 160(7):3170-3179 (1998); Prat et al., J. Cell. Sci. III (Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167 (1998); Bartunek et al., Cytokine 8(1):14-20 (1996).

The antibodies as defined for the present invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Simple binding assays can be used to screen for or detect agents that bind to a target protein, or disrupt the interaction between proteins (e.g., a receptor and a ligand). Because certain targets of the present invention are transmembrane proteins, assays that use the soluble forms of these proteins rather than full-length protein can be used, in some embodiments. Soluble forms include, for example, those lacking the transmembrane domain and/or those comprising the IgV domain or fragments thereof which retain their ability to bind their cognate binding partners. Further, agents that inhibit or enhance protein interactions for use in the compositions and methods described herein, can include recombinant peptidomimetics.

Detection methods useful in screening assays include antibody-based methods, detection of a reporter moiety, detection of cytokines as described herein, and detection of a gene signature as described herein.

Another variation of assays to determine binding of a receptor protein to a ligand protein is through the use of affinity biosensor methods. Such methods may be based on the piezoelectric effect, electrochemistry, or optical methods, such as ellipsometry, optical wave guidance, and surface plasmon resonance (SPR).

The term "antibody-like protein scaffolds" or "engineered protein scaffolds" broadly encompasses proteinaceous non-immunoglobulin specific-binding agents, typically obtained by combinatorial engineering (such as site-directed random mutagenesis in combination with phage display or other molecular selection techniques). Usually, such scaffolds are derived from robust and small soluble monomeric proteins (such as Kunitz inhibitors or lipocalins) or from a stably folded extra-membrane domain of a cell surface receptor (such as protein A, fibronectin or the ankyrin repeat).

Such scaffolds have been extensively reviewed in Binz et al. (Engineering novel binding proteins from nonimmunoglobulin domains. Nat Biotechnol 2005, 23:1257-1268), Gebauer and Skerra (Engineered protein scaffolds as next-generation antibody therapeutics. Curr Opin Chem Biol. 2009, 13:245-55), Gill and Damle (Biopharmaceutical drug discovery using novel protein scaffolds. Curr Opin Biotechnol 2006, 17:653-658), Skerra (Engineered protein scaffolds for molecular recognition. J Mol Recognit 2000, 13:167-187), and Skerra (Alternative non-antibody scaffolds for molecular recognition. Curr Opin Biotechnol 2007, 18:295-304), and include without limitation affibodies, based on the Z-domain of staphylococcal protein A, a three-helix bundle of 58 residues providing an interface on two of its alpha-helices (Nygren, Alternative binding proteins: Affibody binding proteins developed from a small three-helix bundle scaffold. FEBS J 2008, 275:2668-2676); engineered Kunitz domains based on a small (ca. 58 residues) and robust, disulphide-crosslinked serine protease inhibitor, typically of human origin (e.g. LACI-D1), which can be engineered for different protease specificities (Nixon and Wood, Engineered protein inhibitors of proteases. Curr Opin Drug Discov Dev 2006, 9:261-268); monobodies or adnectins based on the 10th extracellular domain of human fibronectin III (10fn3), which adopts an Ig-like beta-sandwich fold (94 residues) with 2-3 exposed loops, but lacks the central disulphide bridge (Koide and Koide, Monobodies: antibody mimics based on the scaffold of the fibronectin type III domain. Methods Mol Biol 2007, 352:95-109); anticalins derived from the lipocalins, a diverse family of eight-stranded beta-barrel proteins (ca. 180 residues) that naturally form binding sites for small ligands by means of four structurally variable loops at the open end, which are abundant in humans, insects, and many other organisms (Skerra, Alternative binding proteins: Anticalins-harnessing the structural plasticity of the lipocalin ligand pocket to engineer novel binding activities. FEBS J 2008, 275:2677-2683); DARPins, designed ankyrin repeat domains (166 residues), which provide a rigid interface arising from typically three repeated beta-turns (Stumpp et al., DARPins: a new generation of protein therapeutics. Drug Discov Today 2008, 13:695-701); avimers (multimerized LDLR-A module) (Silverman et al., Multivalent avimer proteins evolved by exon shuffling of a family of human receptor domains. Nat Biotechnol 2005, 23:1556-1561); and cysteine-rich knottin peptides (Kolmar, Alternative binding proteins: biological activity and therapeutic potential of cystine-knot miniproteins. FEBS J 2008, 275:2684-2690).

Nucleic acid binding agents, such as oligonucleotide binding agents, are typically at least partly antisense to a target nucleic acid of interest. The term "antisense" generally refers to an agent (e.g., an oligonucleotide) configured to specifically anneal with (hybridize to) a given sequence in a target nucleic acid, such as for example in a target DNA, hnRNA, pre-mRNA or mRNA, and typically comprises, consist essentially of or consist of a nucleic acid sequence that is complementary or substantially complementary to said target nucleic acid sequence. Antisense agents suitable for use herein, such as hybridization probes or amplification or sequencing primers and primer pairs) may typically be capable of annealing with (hybridizing to) the respective target nucleic acid sequences at high stringency conditions, and capable of hybridizing specifically to the target under physiological conditions. The terms "complementary" or "complementarity" as used throughout this specification with reference to nucleic acids, refer to the normal binding of single-stranded nucleic acids under permissive salt (ionic strength) and temperature conditions by base pairing, preferably Watson-Crick base pairing. By means of example, complementary Watson-Crick base pairing occurs between the bases A and T, A and U or G and C. For example, the sequence 5'-A-G-U-3' is complementary to sequence 5'-A-C-U-3'.

The reference to oligonucleotides may in particular but without limitation include hybridization probes and/or amplification primers and/or sequencing primers, etc., as commonly used in nucleic acid detection technologies.

Binding agents as discussed herein may suitably comprise a detectable label. The term "label" refers to any atom, molecule, moiety or biomolecule that may be used to provide a detectable and preferably quantifiable read-out or property, and that may be attached to or made part of an entity of interest, such as a binding agent. Labels may be suitably detectable by for example mass spectrometric, spectroscopic, optical, colourimetric, magnetic, photochemical, biochemical, immunochemical or chemical means. Labels include without limitation dyes; radiolabels such as $^{32}$P, $^{33}$P, $^{35}$S, $^{125}$I, $^{131}$I; electron-dense reagents; enzymes (e.g., horse-radish peroxidase or alkaline phosphatase as commonly used in immunoassays); binding moieties such as biotin-streptavidin; haptens such as digoxigenin; luminogenic, phosphorescent or fluorogenic moieties; mass tags; and fluorescent dyes alone or in combination with moieties that may suppress or shift emission spectra by fluorescence resonance energy transfer (FRET).

In some embodiments, binding agents may be provided with a tag that permits detection with another agent (e.g., with a probe binding partner). Such tags may be, for example, biotin, streptavidin, his-tag, myc tag, maltose, maltose binding protein or any other kind of tag known in the art that has a binding partner. Example of associations which may be utilised in the probe:binding partner arrangement may be any, and includes, for example biotin:streptavidin, his-tag:metal ion (e.g., Ni2+), maltose:maltose binding protein, etc.

The marker-binding agent conjugate may be associated with or attached to a detection agent to facilitate detection. Examples of detection agents include, but are not limited to, luminescent labels; colourimetric labels, such as dyes; fluorescent labels; or chemical labels, such as electroactive agents (e.g., ferrocyanide); enzymes; radioactive labels; or radiofrequency labels. The detection agent may be a particle. Examples of such particles include, but are not limited to, colloidal gold particles; colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles; colloidal lead selenide particles; colloidal cadmium selenide particles; colloidal metal phosphate particles; colloidal metal ferrite particles; any of the above-mentioned colloidal particles coated with organic or inorganic layers; protein or peptide molecules; liposomes; or organic polymer latex particles, such as polystyrene latex beads. Preferable particles may be colloidal gold particles.

In certain embodiments, the one or more binding agents are configured for use in a technique selected from the group consisting of flow cytometry, fluorescence activated cell sorting, mass cytometry, fluorescence microscopy, affinity separation, magnetic cell separation, microfluidic separation, and combinations thereof.

Therapeutic Uses of Isolated Cells

In certain embodiments, the method may comprise: a) isolating from a biological sample of the subject an immune cell or immune cell population as disclosed herein; b) in vitro expanding the immune cell or immune cell population of a); and c) administering the in vitro expanded immune cell or immune cell population of b) to the subject.

In certain embodiments, the method may further comprise formulating the in vitro expanded immune cell or immune cell population of b) into a pharmaceutical composition.

A "pharmaceutical composition" refers to a composition that usually contains an excipient, such as a pharmaceutically acceptable carrier that is conventional in the art and that is suitable for administration to cells or to a subject.

The term "pharmaceutically acceptable" as used throughout this specification is consistent with the art and means compatible with the other ingredients of a pharmaceutical composition and not deleterious to the recipient thereof.

As used herein, "carrier" or "excipient" includes any and all solvents, diluents, buffers (such as, e.g., neutral buffered saline or phosphate buffered saline), solubilisers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavourings, aromatisers, thickeners, agents for achieving a depot effect, coatings, antifungal agents, preservatives, stabilisers, antioxidants, tonicity controlling agents, absorption delaying agents, and the like. The use of such media and agents for pharmaceutical active components is well known in the art. Such materials should be non-toxic and should not interfere with the activity of the cells or active components.

The precise nature of the carrier or excipient or other material will depend on the route of administration. For example, the composition may be in the form of a parenterally acceptable aqueous solution, which is pyrogen-free and has suitable pH, isotonicity and stability. For general principles in medicinal formulation, the reader is referred to Cell Therapy: Stem Cell Transplantation, Gene Therapy, and Cellular Immunotherapy, by G. Morstyn & W. Sheridan eds., Cambridge University Press, 1996; and Hematopoietic Stem Cell Therapy, E. D. Ball, J. Lister & P. Law, Churchill Livingstone, 2000.

The pharmaceutical composition can be applied parenterally, rectally, orally or topically. Preferably, the pharmaceutical composition may be used for intravenous, intramuscular, subcutaneous, peritoneal, peridural, rectal, nasal, pulmonary, mucosal, or oral application. In a preferred embodiment, the pharmaceutical composition according to the invention is intended to be used as an infuse. The skilled person will understand that compositions which are to be administered orally or topically will usually not comprise cells, although it may be envisioned for oral compositions to also comprise cells, for example when gastro-intestinal tract indications are treated. Each of the cells or active components (e.g., immunomodulants) as discussed herein may be administered by the same route or may be administered by a different route. By means of example, and without limitation, cells may be administered parenterally and other active components may be administered orally.

Liquid pharmaceutical compositions may generally include a liquid carrier such as water or a pharmaceutically acceptable aqueous solution. For example, physiological saline solution, tissue or cell culture media, dextrose or other saccharide solution or glycols such as ethylene glycol, propylene glycol or polyethylene glycol may be included.

The composition may include one or more cell protective molecules, cell regenerative molecules, growth factors, anti-apoptotic factors or factors that regulate gene expression in the cells. Such substances may render the cells independent of their environment.

Such pharmaceutical compositions may contain further components ensuring the viability of the cells therein. For example, the compositions may comprise a suitable buffer system (e.g., phosphate or carbonate buffer system) to achieve desirable pH, more usually near neutral pH, and may comprise sufficient salt to ensure isoosmotic conditions for the cells to prevent osmotic stress. For example, suitable solution for these purposes may be phosphate-buffered saline (PBS), sodium chloride solution, Ringer's Injection or Lactated Ringer's Injection, as known in the art. Further, the composition may comprise a carrier protein, e.g., albumin (e.g., bovine or human albumin), which may increase the viability of the cells.

Further suitably pharmaceutically acceptable carriers or additives are well known to those skilled in the art and for instance may be selected from proteins such as collagen or gelatine, carbohydrates such as starch, polysaccharides, sugars (dextrose, glucose and sucrose), cellulose derivatives like sodium or calcium carboxymethylcellulose, hydroxypropyl cellulose or hydroxypropylmethyl cellulose, pregelatinized starches, pectin agar, carrageenan, clays, hydrophilic gums (acacia gum, guar gum, arabic gum and xanthan gum), alginic acid, alginates, hyaluronic acid, polyglycolic and polylactic acid, dextran, pectins, synthetic polymers such as water-soluble acrylic polymer or polyvinylpyrrolidone, proteoglycans, calcium phosphate and the like.

In certain embodiments, a pharmaceutical cell preparation as taught herein may be administered in a form of liquid composition. In embodiments, the cells or pharmaceutical composition comprising such can be administered systemically, topically, within an organ or at a site of organ dysfunction or lesion.

Preferably, the pharmaceutical compositions may comprise a therapeutically effective amount of the specified immune cells and/or other active components (e.g., immunomodulants). The term "therapeutically effective amount" refers to an amount which can elicit a biological or medicinal response in a tissue, system, animal or human that is being sought by a researcher, veterinarian, medical doctor or other clinician, and in particular can prevent or alleviate one or more of the local or systemic symptoms or features of a disease or condition being treated.

In certain embodiments, a treatment or pharmaceutical composition that reduces a non-responder signature, increases a responder signature, modulates the ratio of responder to non-responder CD8+ TILs, depletes non-responder CD8+ TILs, or increases responder CD8+ TILs is co-administered with a check point blockade therapy or is administered before administration of a check point blockade therapy. The check point blockade therapy may be an inhibitor of any check point protein described herein. The checkpoint blockade therapy may comprise anti-TIM3, anti-CTLA4, anti-PD-L1, anti-PD1, anti-TIGIT, anti-LAG3, or combinations thereof. Specific check point inhibitors include, but are not limited to anti-CTLA4 antibodies (e.g., Ipilimumab), anti-PD-1 antibodies (e.g., Nivolumab, Pembrolizumab), and anti-PD-L1 antibodies (e.g., Atezolizumab).

In certain embodiments, a marker of non-responder cells is targeted as described herein. In certain embodiments, CD39 is targeted. In certain embodiments, CD39 is targeted in combination with one or more checkpoint inhibitors. In certain embodiments, CD39 is inhibited in combination with one or more checkpoint inhibitors. In certain embodiments, CD39 is inhibited in combination with anti-TIM3. In certain embodiments, CD39 is inhibited in combination with anti-PD1. In certain embodiments, CD39 is inhibited in combination with anti-CTLA4. In certain embodiments, CD39 is inhibited in combination with anti-PD-L1. In certain embodiments, CD39 is inhibited in combination with anti-TIM3 and anti-CTLA4. In certain embodiments, CD39 is inhibited in combination with anti-TIM3 and anti-PD-1. In certain embodiments, CD39 is inhibited in combination of any one or more of anti-TIM3, anti-CTLA4, anti-PD-L1, anti-PD1, anti-TIGIT, or anti-LAG3.

As used herein, the term "CD39" has its general meaning in the art and refers to the CD39 protein also named as ectonucleoside triphosphate diphosphohydrolase-1 (EN-TPD1). CD39 is an ectoenzyme that hydrolases ATP/UTP and ADP/UDP to the respective nucleosides such as AMP.

Accordingly, the term "CD39 inhibitor" refers to a compound that inhibits the activity or expression of CD39. In some embodiments, the CD39 inhibitor is an antibody having specificity for CD39. In certain embodiments, the CD39 inhibitor is a small molecule. CD39 activity modulators are well known in the art. For example, 6-N,N-Diethyl-d-β-γ-dibromomethylene adenosine triphosphate (ARL 67156) (Levesque et al (2007) Br, J. Pharmacol, 152: 141-150; Crack et al. (1959) Br. J. Pharmacol. 114: 475-481; Kennedy et al. (1996) Semtn. Neurosci. 8: 195-199) and 8-thiobutyladenosine 5'-triphosphate (8-Bu-S-ATP) are small molecule CD39 inhibitors (Gendron et al. (2000) J Med Chem. 43:2239-2247). Other small molecule CD39 inhibitors, such as polyoxometalate-1 (POM-1) and α,β-methylene ADP (APCP), are also well known in the art (see, U.S. 2010/204182 and US2013/0123345; U.S. Pat. No. 6,617,439). In addition, nucleic acid and antibody inhibitors of CD39 are also well known in the art (see, e.g., US20130273062A1).

As used throughout this specification, "immune response" refers to a response by a cell of the immune system, such as a B cell, T cell (CD4+ or CD8+), regulatory T cell, antigen-presenting cell, dendritic cell, monocyte, macrophage, NKT cell, NK cell, basophil, eosinophil, or neutrophil, to a stimulus. In some embodiments, the response is specific for a particular antigen (an "antigen-specific response"), and refers to a response by a CD4 T cell, CD8 T cell, or B cell via their antigen-specific receptor. In some embodiments, an immune response is a T cell response, such as a CD4+ response or a CD8+ response. Such responses by these cells can include, for example, cytotoxicity, proliferation, cytokine or chemokine production, trafficking, or phagocytosis, and can be dependent on the nature of the immune cell undergoing the response.

T cell response refers more specifically to an immune response in which T cells directly or indirectly mediate or otherwise contribute to an immune response in a subject. T cell-mediated response may be associated with cell mediated effects, cytokine mediated effects, and even effects associated with B cells if the B cells are stimulated, for example, by cytokines secreted by T cells. By means of an example but without limitation, effector functions of MHC class I restricted Cytotoxic T lymphocytes (CTLs), may include cytokine and/or cytolytic capabilities, such as lysis of target cells presenting an antigen peptide recognised by the T cell receptor (naturally-occurring TCR or genetically engineered TCR, e.g., chimeric antigen receptor, CAR), secretion of cytokines, preferably IFN gamma, TNF alpha and/or or more immunostimulatory cytokines, such as IL-2, and/or antigen peptide-induced secretion of cytotoxic effector molecules, such as granzymes, perforins or granulysin. By means of example but without limitation, for MHC class II restricted T helper (Th) cells, effector functions may be antigen peptide-induced secretion of cytokines, preferably, IFN gamma, TNF alpha, IL-4, IL5, IL-10, and/or IL-2. By means of example but without limitation, for T regulatory (Treg) cells, effector functions may be antigen peptide-induced secretion of cytokines, preferably, IL-10, IL-35, and/or TGF-beta. B cell response refers more specifically to an immune response in which B cells directly or indirectly mediate or otherwise contribute to an immune response in a subject. Effector functions of B cells may include in particular production and secretion of antigen-specific antibodies by B cells (e.g., polyclonal B cell response to a plurality of the epitopes of an antigen (antigen-specific antibody response)), antigen presentation, and/or cytokine secretion.

The term "immune tolerance" as used throughout this specification refers to any mechanism by which a potentially injurious immune response is prevented, suppressed, delayed in the onset or progression, reduced in the risk of the onset or progression, or shifted to a non-injurious immune response. Specific immune tolerance occurs when immune tolerance is preferentially invoked against certain antigen(s) in comparison with others.

The term "antigen" as used throughout this specification refers to a molecule or a portion of a molecule capable of being bound by an antibody, or by a T cell receptor (TCR) when presented by MHC molecules. At the molecular level, an antigen is characterized by its ability to be bound at the antigen-binding site of an antibody. The specific binding denotes that the antigen will be bound in a highly selective manner by its cognate antibody and not by the multitude of other antibodies which may be evoked by other antigens. An antigen is additionally capable of being recognized by the immune system. In some instances, an antigen is capable of eliciting a humoral immune response in a subject. In some instances, an antigen is capable of eliciting a cellular immune response in a subject, leading to the activation of B—and/or T-lymphocytes. In some instances, an antigen is capable of eliciting a humoral and cellular immune response in a subject. Hence, an antigen may be preferably antigenic and immunogenic. Alternatively, an antigen may be antigenic and not immunogenic. Typically, an antigen may be a peptide, polypeptide, protein, nucleic acid, an oligo- or polysaccharide, or a lipid, or any combination thereof, a glycoprotein, proteoglycan, glycolipid, etc. In certain embodiments, an antigen may be a peptide, polypeptide, or protein. An antigen may have one or more than one epitope. The terms "antigenic determinant" or "epitope" generally refer to the region or part of an antigen that specifically reacts with or is recognized by the immune system, specifically by antibodies, B cells, or T cells.

An antigen as contemplated throughout this specification may be obtained by any means available to a skilled person, e.g., may be isolated from a naturally-occurring material comprising the antigen, or may be produced recombinantly by a suitable host or host cell expression system and optionally isolated therefrom (e.g., a suitable bacterial, yeast, fungal, plant or animal host or host cell expression system), or may be produced recombinantly by cell-free transcription or translation, or non-biological nucleic acid or peptide synthesis.

The term "tumor antigen" as used throughout this specification refers to an antigen that is uniquely or differentially expressed by a tumor cell, whether intracellular or on the tumor cell surface (preferably on the tumor cell surface), compared to a normal or non-neoplastic cell. By means of example, a tumor antigen may be present in or on a tumor cell and not typically in or on normal cells or non-neoplastic cells (e.g., only expressed by a restricted number of normal tissues, such as testis and/or placenta), or a tumor antigen may be present in or on a tumor cell in greater amounts than in or on normal or non-neoplastic cells, or a tumor antigen may be present in or on tumor cells in a different form than that found in or on normal or non-neoplastic cells. The term thus includes tumor-specific antigens (TSA), including tumor-specific membrane antigens, tumor-associated antigens (TAA), including tumor-associated membrane antigens, embryonic antigens on tumors, growth factor receptors, growth factor ligands, etc. The term further includes cancer/testis (CT) antigens. Examples of tumor antigens include, without limitation, 3-human chorionic gonadotropin (PHCG), glycoprotein 100 (gp100/Pme117), carcinoembryonic antigen (CEA), tyrosinase, tyrosinase-related protein 1 (gp75/TRP1), tyrosinase-related protein 2 (TRP-2), NY-BR-1, NY-CO-58, NY-ESO-1, MN/gp250, idiotypes, telomerase, synovial sarcoma X breakpoint 2 (SSX2), mucin 1 (MUC-1), antigens of the melanoma-associated antigen (MAGE) family, high molecular weight-melanoma associated antigen (HMW-MAA), melanoma antigen recognized by T cells 1 (MART1), Wilms' tumor gene 1 (WT1), HER2/neu, mesothelin (MSLN), alphafetoprotein (AFP), cancer antigen 125 (CA-125), and abnormal forms of ras or p53 (see also, WO2016187508A2). Tumor antigens may also be subject specific (e.g., subject specific neoantigens; see, e.g., U.S. Pat. No. 9,115,402; and international patent application publication numbers WO2016100977A1, WO2014168874A2, WO2015085233A1, and WO2015095811A2).

The term "in vitro" generally denotes outside, or external to, a body, e.g., an animal or human body. The term encompasses "ex vivo".

In certain embodiments, the immune cell or immune cell population is autologous to said subject, i.e., the immune cell or immune cell population is isolated from the same subject as the subject to which/whom the immune cell or immune cell population is to be administered. In certain further embodiments, the immune cell or immune cell population is syngeneic to said subject, i.e., the immune cell or immune cell population is isolated from an identical twin of the subject to which/whom the immune cell or immune cell population is to be administered. In certain further embodiments, the immune cell or immune cell population is allogeneic to said subject, i.e., the immune cell or immune cell population is isolated from a different subject of the same species as the subject to which/whom the immune cell or immune cell population is to be administered. In certain embodiments, the immune cell or immune cell population may even be xenogeneic to said subject, i.e., the immune cell or immune cell population may be isolated from a subject of a different species than the subject to which/whom the immune cell or immune cell population is to be administered.

Preferably, non-autologous, such as allogeneic cells may be selected such as to maximize the tissue compatibility between the subject and the administered cells, thereby reducing the chance of rejection of the administered cells by patient's immune system or graft-vs.-host reaction. For example, advantageously the cells may be typically selected which have either identical HLA haplotypes (including one or preferably more HLA-A, HLA-B, HLA-C, HLA-D, HLA-DR, HLA-DP and HLA-DQ) to the subject, or which have the most HLA antigen alleles common to the subject and none or the least of HLA antigens to which the subject contains pre-existing anti-HLA antibodies.

Activated T Cell Compositions

A further aspect of the invention relates to a method for preparing a composition comprising activated T cells, the method comprising isolating T cells from a biological sample of a subject and contacting said T cells in vitro with an immune cell or immune cell population, wherein the immune cell or immune cell population has been loaded with an antigen.

"Activation" generally refers to the state of a cell, such as preferably T cell, following sufficient cell surface moiety ligation (e.g., interaction between the T cell receptor on the surface of a T cell (such as naturally-occurring TCR or genetically engineered TCR, e.g., chimeric antigen receptor, CAR) and MIC-bound antigen peptide presented on the surface of an antigen presenting cell (e.g., dendritic cell) to induce a noticeable biochemical or morphological change of the cell, such as preferably T cell. In particular, "activation" may refer to the state of a T cell that has been sufficiently stimulated to induce detectable cellular proliferation of the T cell. Activation can also encompass induced cytokine production, and detectable T cell effector functions, e.g., regulatory or cytolytic effector functions. The T cells and antigen presenting cells may be suitably contacted by admixing the T cells and antigen presenting cells in an aqueous composition, e.g., in a culture medium, in sufficient numbers and for a sufficient duration of time to produce the desired T cell activation.

A further aspect of the invention relates to a method for adoptive immunotherapy in a subject in need thereof comprising administering to said subject a composition comprising activated T cells prepared with the method as taught above.

In certain embodiments, said T cells are CD8+ T cells, i.e., T cells expressing the CD8+ cell surface marker. More preferably, said T cells may be CD8+ T cells and said subject is suffering from proliferative disease.

In certain embodiments, the T cell, preferably a CD8+ T cell, may display specificity to a desired antigen, such as specificity to a tumor antigen (tumor antigen specificity). By means of an example, the T cell, preferably a CD8+ T cell, may have been isolated from a tumor of a subject. More preferably, the immune cell may be a tumor infiltrating lymphocyte (TIL). Generally, "tumor infiltrating lymphocytes" or "TILs" refer to white blood cells that have left the bloodstream and migrated into a tumor. Such T cells typically endogenously express a T cell receptor having specificity to an antigen expressed by the tumor cells (tumor antigen specificity).

In alternative embodiments, a T cell, preferably a CD8+ T cell, may be engineered to express a T cell receptor having specificity to a desired antigen, such as specificity to a tumor antigen (tumor antigen specificity). For example, the T cell, preferably a CD8+ T cell, may comprise a chimeric antigen receptor (CAR) having specificity to a desired antigen, such as a tumor-specific chimeric antigen receptor (CAR).

Adoptive Cell Therapy

In certain embodiments, the immune cells or immune cell populations as taught herein may be used for adoptive cell transfer (ACT). In certain embodiments, responder T cells are used for adoptive transfer. The cells may be further modified as discussed herein. The cells may express an endogenous T cell receptor (TCR) or a chimeric antigen receptor (CAR). As used herein, "ACT", "adoptive cell therapy" and "adoptive cell transfer" may be used interchangeably. In certain embodiments, Adoptive cell therapy (ACT) can refer to the transfer of cells to a patient with the goal of transferring the functionality and characteristics into the new host by engraftment of the cells (see, e.g., Mettananda et al., Editing an α-globin enhancer in primary human hematopoietic stem cells as a treatment for β-thalassemia, Nat Commun. 2017 Sep. 4; 8(1):424). As used herein, the term "engraft" or "engraftment" refers to the process of cell incorporation into a tissue of interest in vivo through contact with existing cells of the tissue. Adoptive cell therapy (ACT) can refer to the transfer of cells, most commonly immune-derived cells, back into the same patient or into a new recipient host with the goal of transferring the immunologic functionality and characteristics into the new host. If possible, use of autologous cells helps the recipient by minimizing GVHD issues. The adoptive transfer of autologous tumor infiltrating lymphocytes (TIL) (Besser et al., (2010) Clin. Cancer Res 16 (9) 2646-55; Dudley et al., (2002) Science 298 (5594): 850-4; and Dudley et al., (2005) Journal of Clinical Oncology 23 (10): 2346-57.) or genetically re-directed peripheral blood mononuclear cells (Johnson et al., (2009) Blood 114 (3): 535-46; and Morgan et al., (2006) Science 314(5796) 126-9) has been used to successfully treat patients with advanced solid tumors, including melanoma and colorectal carcinoma, as well as patients with CD19-expressing hematologic malignancies (Kalos et al., (2011) Science Translational Medicine 3 (95): 95ra73). In certain embodiments, allogenic cells immune cells are transferred (see, e.g., Ren et al., (2017) Clin Cancer Res 23 (9) 2255-2266). As described further herein, allogenic cells can be edited to reduce alloreactivity and prevent graft-versus-host disease. Thus, use of allogenic cells allows for cells to be obtained from healthy donors and prepared for use in patients as opposed to preparing autologous cells from a patient after diagnosis.

Aspects of the invention involve the adoptive transfer of immune system cells, such as T cells, specific for selected antigens, such as tumor associated antigens or tumor specific neoantigens (see, e.g., Maus et al., 2014, Adoptive Immunotherapy for Cancer or Viruses, Annual Review of Immunology, Vol. 32: 189-225; Rosenberg and Restifo, 2015, Adoptive cell transfer as personalized immunotherapy for human cancer, Science Vol. 348 no. 6230 pp. 62-68; Restifo et al., 2015, Adoptive immunotherapy for cancer: harnessing the T cell response. Nat. Rev. Immunol. 12(4): 269-281; and Jenson and Riddell, 2014, Design and implementation of adoptive therapy with chimeric antigen receptor-modified T cells. Immunol Rev. 257(1): 127-144; and Rajasagi et al., 2014, Systematic identification of personal tumor-specific neoantigens in chronic lymphocytic leukemia. Blood. 2014 Jul. 17; 124(3):453-62).

In certain embodiments, an antigen (such as a tumor antigen) to be targeted in adoptive cell therapy (such as particularly CAR or TCR T-cell therapy) of a disease (such as particularly of tumor or cancer) may be selected from a group consisting of: B cell maturation antigen (BCMA) (see, e.g., Friedman et al., Effective Targeting of Multiple BCMA-Expressing Hematological Malignancies by Anti-BCMA CAR T Cells, Hum Gene Ther. 2018 Mar. 8; Berdeja J G, et al. Durable clinical responses in heavily pretreated patients with relapsed/refractory multiple myeloma: updated results from a multicenter study of bb2121 anti-Bcma CAR T cell therapy. Blood. 2017; 130:740; and Mouhieddine and Ghobrial, Immunotherapy in Multiple Myeloma: The Era of CAR T Cell Therapy, Hematologist, May-June 2018, Volume 15, issue 3); PSA (prostate-specific antigen); prostate-specific membrane antigen (PSMA); PSCA (Prostate stem cell antigen); Tyrosine-protein kinase transmembrane receptor ROR1; fibroblast activation protein (FAP); Tumor-associated glycoprotein 72 (TAG72); Carcinoembryonic antigen (CEA); Epithelial cell adhesion molecule (EPCAM); Mesothelin; Human Epidermal growth factor Receptor 2 (ERBB2 (Her2/neu)); Prostase; Prostatic acid phosphatase (PAP); elongation factor 2 mutant (ELF2M); Insulin-like growth factor 1 receptor (IGF-1R); gp1OO; BCR-ABL (breakpoint cluster region-Abelson); tyrosinase; New York esophageal squamous cell carcinoma 1 (NY-ESO-1); κ-light chain, LAGE (L antigen); MAGE (melanoma antigen); Melanoma-associated antigen 1 (MAGE-A1); MAGE A3; MAGE A6; legumain; Human papillomavirus (HPV) E6; HPV E7; prostein; survivin; PCTA1 (Galectin 8); Melan-A/MART-1; Ras mutant; TRP-1 (tyrosinase related protein 1, or gp75); Tyrosinase-related Protein 2 (TRP2); TRP-2/INT2 (TRP-2/intron 2); RAGE (renal antigen); receptor for advanced glycation end products 1 (RAGE1); Renal ubiquitous 1, 2

(RU1, RU2); intestinal carboxyl esterase (iCE); Heat shock protein 70-2 (HSP70-2) mutant; thyroid stimulating hormone receptor (TSHR); CD123; CD171; CD19; CD20; CD22; CD26; CD30; CD33; CD44v7/8 (cluster of differentiation 44, exons 7/8); CD53; CD92; CD100; CD148; CD150; CD200; CD261; CD262; CD362; CS-1 (CD2 subset 1, CRACC, SLAMF7, CD319, and 19A24); C-type lectin-like molecule-1 (CLL-1); ganglioside GD3 (aNeu5Ac (2-8)aNeu5Ac(2-3)bDGalp(1-4)bDGlcp(1-1)Cer); Tn antigen (Tn Ag); Fms-Like Tyrosine Kinase 3 (FLT3); CD38; CD138; CD44v6; B7H3 (CD276); KIT (CD117); Interleukin-13 receptor subunit alpha-2 (IL-13Ra2); Interleukin 11 receptor alpha (IL-11Ra); prostate stem cell antigen (PSCA); Protease Serine 21 (PRSS21); vascular endothelial growth factor receptor 2 (VEGFR2); Lewis(Y) antigen; CD24; Platelet-derived growth factor receptor beta (PDGFR-beta); stage-specific embryonic antigen-4 (SSEA-4); Mucin 1, cell surface associated (MUC1); mucin 16 (MUC16); epidermal growth factor receptor (EGFR); epidermal growth factor receptor variant III (EGFRvIII); neural cell adhesion molecule (NCAM); carbonic anhydrase IX (CAIX); Proteasome (Prosome, Macropain) Subunit, Beta Type, 9 (LMP2); ephrin type-A receptor 2 (EphA2); Ephrin B2; Fucosyl GM1; sialyl Lewis adhesion molecule (sLe); ganglioside GM3 (aNeu5Ac(2-3)bDGalp(1-4)bDGlcp(1-1) Cer); TGS5; high molecular weight-melanoma-associated antigen (HMWMAA); o-acetyl-GD2 ganglioside (OAcGD2); Folate receptor alpha; Folate receptor beta; tumor endothelial marker 1 (TEM1/CD248); tumor endothelial marker 7-related (TEM7R); claudin 6 (CLDN6); G protein-coupled receptor class C group 5, member D (GPRC5D); chromosome X open reading frame 61 (CX-ORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); CT (cancer/testis (antigen)); melanoma cancer testis antigen-1 (MAD-CT-1); melanoma cancer testis antigen-2 (MAD-CT-2); Fos-related antigen 1; p53; p53 mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; Cyclin D1; v-myc avian myelocytomatosis viral oncogene neuroblastoma derived homolog (MYCN); Ras Homolog Family Member C (RhoC); Cytochrome P450 1B1 (CYP1B1); CCCTC-Binding Factor (Zinc Finger Protein)-Like (BORIS); Squamous Cell Carcinoma Antigen Recognized By T Cells-1 or 3 (SART1, SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint-1, -2, -3 or -4 (SSX1, SSX2, SSX3, SSX4); CD79a; CD79b; CD72; Leukocyte-associated immunoglobulin-like receptor 1 (LAIR1); Fc fragment of IgA receptor (FCAR); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); mouse double minute 2 homolog (MDM2); livin; alphafetoprotein (AFP); transmembrane activator and CAML Interactor (TACI); B-cell activating factor receptor (BAFF-R); V-Ki-ras2 Kirsten rat sarcoma viral oncogene homolog (KRAS); immunoglobulin lambda-like polypeptide 1 (IGLL1); 707-AP (707 alanine proline); ART-4 (adenocarcinoma antigen recognized by T4 cells); BAGE (B antigen; b-catenin/m, b-catenin/mutated); CAMEL (CTL-recognized antigen on melanoma); CAP1 (carcinoembryonic antigen peptide 1); CASP-8 (caspase-8); CDC27m (cell-division cycle 27 mutated); CDK4/m (cycline-dependent kinase 4 mutated); Cyp-B (cyclophilin B); DAM (differentiation antigen melanoma); EGP-2 (epithelial glycoprotein 2); EGP-40 (epithelial glycoprotein 40); Erbb2, 3, 4 (erythroblastic leukemia viral oncogene homolog-2, -3, 4); FBP (folate binding protein); fAchR (Fetal acetylcholine receptor); G250 (glycoprotein 250); GAGE (G antigen); GnT-V (N-acetylglucosaminyltransferase V); HAGE (helicase antigen); ULA-A (human leukocyte antigen-A); HST2 (human signet ring tumor 2); KIAA0205; KDR (kinase insert domain receptor); LDLR/FUT (low density lipid receptor/GDP L-fucose: b-D-galactosidase 2-a-L fucosyl-transferase); L1CAM (L1 cell adhesion molecule); MC1R (melanocortin 1 receptor); Myosin/m (myosin mutated); MUM-1, -2, -3 (melanoma ubiquitous mutated 1, 2, 3); NA88-A (NA cDNA clone of patient M88); KG2D (Natural killer group 2, member D) ligands; oncofetal antigen (h5T4); p190 minor bcr-abl (protein of 190KD bcr-abl); Pml/RARa (promyelocytic leukaemia/retinoic acid receptor a); PRAME (preferentially expressed antigen of melanoma); SAGE (sarcoma antigen); TEL/AML1 (translocation Ets-family leukemia/acute myeloid leukemia 1); TPI/m (triose-phosphate isomerase mutated); CD70; and any combination thereof.

In certain embodiments, an antigen to be targeted in adoptive cell therapy (such as particularly CAR or TCR T-cell therapy) of a disease (such as particularly of tumor or cancer) is a tumor-specific antigen (TSA).

In certain embodiments, an antigen to be targeted in adoptive cell therapy (such as particularly CAR or TCR T-cell therapy) of a disease (such as particularly of tumor or cancer) is a neoantigen.

In certain embodiments, an antigen to be targeted in adoptive cell therapy (such as particularly CAR or TCR T-cell therapy) of a disease (such as particularly of tumor or cancer) is a tumor-associated antigen (TAA).

In certain embodiments, an antigen to be targeted in adoptive cell therapy (such as particularly CAR or TCR T-cell therapy) of a disease (such as particularly of tumor or cancer) is a universal tumor antigen. In certain preferred embodiments, the universal tumor antigen is selected from the group consisting of: a human telomerase reverse transcriptase (hTERT), survivin, mouse double minute 2 homolog (MDM2), cytochrome P450 1B 1 (CYP1B), HER2/neu, Wilms' tumor gene 1 (WT1), livin, alphafeto-protein (AFP), carcinoembryonic antigen (CEA), mucin 16 (MUC16), MUC1, prostate-specific membrane antigen (PSMA), p53, cyclin (Dl), and any combinations thereof.

In certain embodiments, an antigen (such as a tumor antigen) to be targeted in adoptive cell therapy (such as particularly CAR or TCR T-cell therapy) of a disease (such as particularly of tumor or cancer) may be selected from a group consisting of: CD19, BCMA, CD70, CLL-1, MAGE A3, MAGE A6, HPV E6, HPV E7, WT1, CD22, CD171, ROR1, MUC16, and SSX2. In certain preferred embodiments, the antigen may be CD19. For example, CD19 may be targeted in hematologic malignancies, such as in lymphomas, more particularly in B-cell lymphomas, such as without limitation in diffuse large B-cell lymphoma, primary mediastinal b-cell lymphoma, transformed follicular lymphoma, marginal zone lymphoma, mantle cell lymphoma, acute lymphoblastic leukemia including adult and pediatric ALL, non-Hodgkin lymphoma, indolent non-Hodgkin lymphoma, or chronic lymphocytic leukemia. For example, BCMA may be targeted in multiple myeloma or plasma cell leukemia (see, e.g., 2018 American Association for Cancer Research (AACR) Annual meeting Poster: Allogeneic Chimeric Antigen Receptor T Cells Targeting B Cell Maturation Antigen). For example, CLL1 may be targeted in acute myeloid leukemia. For example, MAGE A3, MAGE A6, SSX2, and/or KRAS may be targeted in solid tumors. For example, HPV E6 and/or HPV E7 may be targeted in cervical cancer or head and neck cancer. For example, WT1 may be targeted in acute myeloid leukemia (AML), myelodysplastic syndromes (MDS), chronic myeloid leukemia (CML), non-small cell lung cancer, breast, pancreatic, ovarian or colorectal cancers, or mesothelioma. For example, CD22 may be targeted in B cell malignancies, including non-Hodgkin lymphoma, diffuse large B-cell lymphoma, or acute lymphoblastic leukemia. For example, CD171 may be targeted in neuroblastoma, glioblastoma, or lung, pancreatic, or ovarian cancers. For example, ROR1 may be targeted in ROR1+ malignancies, including non-small cell lung cancer, triple negative breast cancer, pancreatic cancer, prostate cancer, ALL, chronic lymphocytic leukemia, or mantle cell lymphoma. For example, MUC16 may be targeted in MUC16ecto+ epithelial ovarian, fallopian tube or primary peritoneal cancer. For example, CD70 may be targeted in both hematologic malignancies as well as in solid cancers such as renal cell carcinoma (RCC), gliomas (e.g., GBM), and head and neck cancers (HNSCC). CD70 is expressed in both hematologic malignancies as well as in solid cancers, while its expression in normal tissues is restricted to a subset of lymphoid cell types (see, e.g., 2018 American Association for Cancer Research (AACR) Annual meeting Poster: Allogeneic CRISPR Engineered Anti-CD70 CAR-T Cells Demonstrate Potent Preclinical Activity Against Both Solid and Hematological Cancer Cells).

Various strategies may for example be employed to genetically modify T cells by altering the specificity of the T cell receptor (TCR) for example by introducing new TCR a and R chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088, 379).

As an alternative to, or addition to, TCR modifications, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004, 811; 6,284,240; 6,392,013; 6,410,014; 6,753,162; 8,211, 422; and, PCT Publication WO9215322).

In general, CARs are comprised of an extracellular domain, a transmembrane domain, and an intracellular domain, wherein the extracellular domain comprises an antigen-binding domain that is specific for a predetermined target. While the antigen-binding domain of a CAR is often an antibody or antibody fragment (e.g., a single chain variable fragment, scFv), the binding domain is not particularly limited so long as it results in specific recognition of a target. For example, in some embodiments, the antigen-binding domain may comprise a receptor, such that the CAR is capable of binding to the ligand of the receptor. Alternatively, the antigen-binding domain may comprise a ligand, such that the CAR is capable of binding the endogenous receptor of that ligand.

The antigen-binding domain of a CAR is generally separated from the transmembrane domain by a hinge or spacer. The spacer is also not particularly limited, and it is designed to provide the CAR with flexibility. For example, a spacer domain may comprise a portion of a human Fc domain, including a portion of the CH3 domain, or the hinge region of any immunoglobulin, such as IgA, IgD, IgE, IgG, or IgM, or variants thereof. Furthermore, the hinge region may be modified so as to prevent off-target binding by FcRs or other potential interfering objects. For example, the hinge may comprise an IgG4 Fc domain with or without a S228P, L235E, and/or N297Q mutation (according to Kabat numbering) in order to decrease binding to FcRs. Additional spacers/hinges include, but are not limited to, CD4, CD8, and CD28 hinge regions.

The transmembrane domain of a CAR may be derived either from a natural or from a synthetic source. Where the source is natural, the domain may be derived from any membrane bound or transmembrane protein. Transmembrane regions of particular use in this disclosure may be derived from CD8, CD28, CD3, CD45, CD4, CD5, CDS, CD9, CD16, CD22, CD33, CD37, CD64, CD80, CD86, CD134, CD137, CD154, TCR. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Alternative CAR constructs may be characterized as belonging to successive generations. First-generation CARs typically consist of a single-chain variable fragment of an antibody specific for an antigen, for example comprising a VL linked to a VH of a specific antibody, linked by a flexible linker, for example by a CD8α hinge domain and a CD8α transmembrane domain, to the transmembrane and intracellular signaling domains of either CD3ζ or FcRγ (scFv-CD3ζ or scFv-FcRγ; see U.S. Pat. Nos. 7,741,465; 5,912,172; 5,906,936). Second-generation CARs incorporate the intracellular domains of one or more costimulatory molecules, such as CD28, OX40 (CD134), or 4-1BB (CD137) within the endodomain (for example scFv-CD28/OX40/4-1BB-CD3ζ; see U.S. Pat. Nos. 8,911,993; 8,916,381; 8,975,071; 9,101,584; 9,102,760; 9,102,761). Third-generation CARs include a combination of costimulatory endodomains, such a CD3ζ-chain, CD97, GDI la-CD18, CD2, ICOS, CD27, CD154, CDS, OX40, 4-1BB, CD2, CD7, LIGHT, LFA-1, NKG2C, B7-H3, CD30, CD40, PD-1, or CD28 signaling domains (for example scFv-CD28-4-1BB-CD3ζ or scFv-CD28-OX40-CD3ζ; see U.S. Pat. Nos. 8,906,682; 8,399, 645; 5,686,281; PCT Publication No. WO2014134165; PCT Publication No. WO2012079000). In certain embodiments, the primary signaling domain comprises a functional signaling domain of a protein selected from the group consisting of: CD3 zeta, CD3 gamma, CD3 delta, CD3 epsilon, common FcR gamma (FCERIG), FcR beta (Fc Epsilon R1b), CD79a, CD79b, Fc gamma RIIa, DAP10, and DAP12. In certain preferred embodiments, the primary signaling domain comprises a functional signaling domain of CD3ζ or FcRγ. In certain embodiments, the one or more costimulatory signaling domains comprise a functional signaling domain of a protein selected, each independently, from the group consisting of: CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8 alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD1 Id, ITGAE, CD103, ITGAL, CD11a, LFA-1, ITGAM, CD11b, ITGAX, CD11c, ITGB1, CD29, ITGB2, CD18, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D. In certain embodiments, the one or more costimulatory signaling domains comprise a functional signaling domain of a protein selected, each independently, from the group consisting of: 4-1BB, CD27, and CD28. In certain embodiments, a chimeric antigen receptor may have the design as described in U.S. Pat. No. 7,446,190, comprising an intracellular domain of CD3ζ chain (such as amino acid residues 52-163 of the human CD3 zeta chain, as shown in SEQ ID NO: 14 of U.S. Pat. No. 7,446,190), a signaling region from CD28 and an antigen-binding element (or portion or domain; such as scFv). The CD28 portion, when between the zeta chain portion and the antigen-binding element, may suitably include the transmembrane and signaling domains of CD28 (such as amino acid residues 114-220 of SEQ ID NO: 10, full sequence shown in SEQ ID NO: 6 of U.S. Pat. No. 7,446,190; these can include the following portion of CD28 as set forth in Genbank identifier NM_006139 (sequence version 1, 2 or 3): IEVMYPPPYLD-NEKSNGTIIHVKGKHLCPSPLFPGPSKPFWVLVVVGG-VLACYSLLVT VAFIIFWVRSKRSRLLHSDYMNMT-PRRPGPTRKHYQPYAPPRDFAAYRS)(SEQ ID No. 1). Alternatively, when the zeta sequence lies between the CD28 sequence and the antigen-binding element, intracellular domain of CD28 can be used alone (such as amino sequence set forth in SEQ ID NO: 9 of U.S. Pat. No. 7,446,190). Hence, certain embodiments employ a CAR comprising (a) a zeta chain portion comprising the intracellular domain of human CD3ζ chain, (b) a costimulatory signaling region, and (c) an antigen-binding element (or portion or domain), wherein the costimulatory signaling region comprises the amino acid sequence encoded by SEQ ID NO: 6 of U.S. Pat. No. 7,446,190.

Alternatively, costimulation may be orchestrated by expressing CARs in antigen-specific T cells, chosen so as to be activated and expanded following engagement of their native αβTCR, for example by antigen on professional antigen-presenting cells, with attendant costimulation. In addition, additional engineered receptors may be provided on the immunoresponsive cells, for example to improve targeting of a T-cell attack and/or minimize side effects By means of an example and without limitation, Kochenderfer et al., (2009) J Immunother. 32 (7): 689-702 described anti-CD19 chimeric antigen receptors (CAR). FMC63-28Z CAR contained a single chain variable region moiety (scFv) recognizing CD19 derived from the FMC63 mouse hybridoma (described in Nicholson et al., (1997) Molecular Immunology 34: 1157-1165), a portion of the human CD28 molecule, and the intracellular component of the human TCR-ζ molecule. FMC63-CD828BBZ CAR contained the FMC63 scFv, the hinge and transmembrane regions of the CD8 molecule, the cytoplasmic portions of CD28 and 4-1BB, and the cytoplasmic component of the TCR-ζ molecule. The exact sequence of the CD28 molecule included in the FMC63-28Z CAR corresponded to Genbank identifier NM_006139; the sequence included all amino acids starting with the amino acid sequence IEVMYPPPY and continuing all the way to the carboxy-terminus of the protein. To encode the anti-CD19 scFv component of the vector, the authors designed a DNA sequence which was based on a portion of a previously published CAR (Cooper et al., (2003) Blood 101: 1637-1644). This sequence encoded the following components in frame from the 5' end to the 3' end: an XhoI site, the human granulocyte-macrophage colony-stimulating factor (GM-CSF) receptor α-chain signal sequence, the FMC63 light chain variable region (as in Nicholson et al., supra), a linker peptide (as in Cooper et al., supra), the FMC63 heavy chain variable region (as in Nicholson et al., supra), and a NotI site. A plasmid encoding this sequence was digested with XhoI and NotI. To form the MSGV-FMC63-28Z retroviral vector, the XhoI and NotI-digested fragment encoding the FMC63 scFv was ligated into a second XhoI and NotI-digested fragment that encoded the MSGV retroviral backbone (as in Hughes et al., (2005) Human Gene Therapy 16: 457-472) as well as part of the extracellular portion of human CD28, the entire transmembrane and cytoplasmic portion of human CD28, and the cytoplasmic portion of the human TCR-ζ molecule (as in Maher et al., 2002) Nature Biotechnology 20: 70-75). The FMC63-28Z CAR is included in the KTE-C19 (axicabtagene ciloleucel) anti-CD19 CAR-T therapy product in development by Kite Pharma, Inc. for the treatment of inter alia patients with relapsed/refractory aggressive B-cell non-Hodgkin lymphoma (NHL). Accordingly, in certain embodiments, cells intended for adoptive cell therapies, more particularly immunoresponsive cells such as T cells, may express the FMC63-28Z CAR as described by Kochenderfer et al. (supra). Hence, in certain embodiments, cells intended for adoptive cell therapies, more particularly immunoresponsive cells such as T cells, may comprise a CAR comprising an extracellular antigen-binding element (or portion or domain; such as scFv) that specifically binds to an antigen, an intracellular signaling domain comprising an intracellular domain of a CD3ζ chain, and a costimulatory signaling region comprising a signaling domain of CD28. Preferably, the CD28 amino acid sequence is as set forth in Genbank identifier NM_006139 (sequence version 1, 2 or 3) starting with the amino acid sequence IEVMYPPPY (SEQ. ID. No. 2) and continuing all the way to the carboxy-terminus of the protein. The sequence is reproduced herein: IEVMYPPPYLD-NEKSNGTIIHVKGKHLCPSPLFPGPSKPFWVLVVVG-GVLACYSLLVT VAFIIFWVRSKRSRLLHSDYMNMT-PRRPGPTRKHYQPYAPPRDFAAYRS (SEQ. ID. No. 3). Preferably, the antigen is CD19, more preferably the antigen-binding element is an anti-CD19 scFv, even more preferably the anti-CD19 scFv as described by Kochenderfer et al. (supra).

Additional anti-CD19 CARs are further described in WO2015187528. More particularly Example 1 and Table 1 of WO2015187528, incorporated by reference herein, demonstrate the generation of anti-CD19 CARs based on a fully human anti-CD19 monoclonal antibody (47G4, as described in US20100104509) and murine anti-CD19 monoclonal antibody (as described in Nicholson et al. and explained above). Various combinations of a signal sequence (human CD8-alpha or GM-CSF receptor), extracellular and transmembrane regions (human CD8-alpha) and intracellular T-cell signalling domains (CD28-CD3ζ; 4-1BB-CD3ζ; CD27-CD3ζ; CD28-CD27-CD3ζ; 4-1BB-CD27-CD3ζ; CD27-4-1BB-CD3ζ; CD28-CD27-FcεRI gamma chain; or CD28-FcεRI gamma chain) were disclosed. Hence, in certain embodiments, cells intended for adoptive cell therapies, more particularly immunoresponsive cells such as T cells, may comprise a CAR comprising an extracellular antigen-binding element that specifically binds to an antigen, an extracellular and transmembrane region as set forth in Table 1 of WO2015187528 and an intracellular T-cell signalling domain as set forth in Table 1 of WO2015187528. Preferably, the antigen is CD19, more preferably the antigen-binding element is an anti-CD19 scFv, even more preferably the mouse or human anti-CD19 scFv as described in Example 1 of WO2015187528. In certain embodiments, the CAR comprises, consists essentially of or consists of an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13 as set forth in Table 1 of WO2015187528.

By means of an example and without limitation, chimeric antigen receptor that recognizes the CD70 antigen is described in WO2012058460A2 (see also, Park et al., CD70 as a target for chimeric antigen receptor T cells in head and neck squamous cell carcinoma, Oral Oncol. 2018 March; 78:145-150; and Jin et al., CD70, a novel target of CAR T-cell therapy for gliomas, Neuro Oncol. 2018 Jan. 10; 20(1):55-65). CD70 is expressed by diffuse large B—cell and follicular lymphoma and also by the malignant cells of Hodgkins lymphoma, Waldenstrom's macroglobulinemia and multiple myeloma, and by HTLV-1- and EBV-associated malignancies. (Agathanggelou et al. Am. J. Pathol. 1995; 147: 1152-1160; Hunter et al., Blood 2004; 104:4881. 26; Lens et al., J Immunol. 2005; 174:6212-6219; Baba et al., J Virol. 2008; 82:3843-3852.) In addition, CD70 is expressed by non-hematological malignancies such as renal cell carcinoma and glioblastoma. (Junker et al., J Urol. 2005; 173:2150-2153; Chahlavi et al., Cancer Res 2005; 65:5428-5438) Physiologically, CD70 expression is transient and restricted to a subset of highly activated T, B, and dendritic cells.

By means of an example and without limitation, chimeric antigen receptor that recognizes BCMA has been described (see, e.g., US20160046724A1; WO2016014789A2; WO2017211900A1; WO2015158671A1; US20180085444A1; WO2018028647A1; US20170283504A1; and WO2013154760A1).

In certain embodiments, the immune cell may, in addition to a CAR or exogenous TCR as described herein, further comprise a chimeric inhibitory receptor (inhibitory CAR) that specifically binds to a second target antigen and is capable of inducing an inhibitory or immunosuppressive or repressive signal to the cell upon recognition of the second target antigen. In certain embodiments, the chimeric inhibitory receptor comprises an extracellular antigen-binding element (or portion or domain) configured to specifically bind to a target antigen, a transmembrane domain, and an intracellular immunosuppressive or repressive signaling domain. In certain embodiments, the second target antigen is an antigen that is not expressed on the surface of a cancer cell or infected cell or the expression of which is downregulated on a cancer cell or an infected cell. In certain embodiments, the second target antigen is an MHC-class I molecule. In certain embodiments, the intracellular signaling domain comprises a functional signaling portion of an immune checkpoint molecule, such as for example PD-1 or CTLA4. Advantageously, the inclusion of such inhibitory CAR reduces the chance of the engineered immune cells attacking non-target (e.g., non-cancer) tissues.

Alternatively, T-cells expressing CARs may be further modified to reduce or eliminate expression of endogenous TCRs in order to reduce off-target effects. Reduction or elimination of endogenous TCRs can reduce off-target effects and increase the effectiveness of the T cells (U.S. Pat. No. 9,181,527). T cells stably lacking expression of a functional TCR may be produced using a variety of approaches. T cells internalize, sort, and degrade the entire T cell receptor as a complex, with a half-life of about 10 hours in resting T cells and 3 hours in stimulated T cells (von Essen, M. et al. 2004. J. Immunol. 173:384-393). Proper functioning of the TCR complex requires the proper stoichiometric ratio of the proteins that compose the TCR complex. TCR function also requires two functioning TCR zeta proteins with ITAM motifs. The activation of the TCR upon engagement of its MHC-peptide ligand requires the engagement of several TCRs on the same T cell, which all must signal properly. Thus, if a TCR complex is destabilized with proteins that do not associate properly or cannot signal optimally, the T cell will not become activated sufficiently to begin a cellular response.

Accordingly, in some embodiments, TCR expression may eliminated using RNA interference (e.g., shRNA, siRNA, miRNA, etc.), CRISPR, or other methods that target the nucleic acids encoding specific TCRs (e.g., TCRα and TCRβ) and/or CD3 chains in primary T cells. By blocking expression of one or more of these proteins, the T cell will no longer produce one or more of the key components of the TCR complex, thereby destabilizing the TCR complex and preventing cell surface expression of a functional TCR.

In some instances, CAR may also comprise a switch mechanism for controlling expression and/or activation of the CAR. For example, a CAR may comprise an extracellular, transmembrane, and intracellular domain, in which the extracellular domain comprises a target-specific binding element that comprises a label, binding domain, or tag that is specific for a molecule other than the target antigen that is expressed on or by a target cell. In such embodiments, the specificity of the CAR is provided by a second construct that comprises a target antigen binding domain (e.g., an scFv or a bispecific antibody that is specific for both the target antigen and the label or tag on the CAR) and a domain that is recognized by or binds to the label, binding domain, or tag on the CAR. See, e.g., WO 2013/044225, WO 2016/000304, WO 2015/057834, WO 2015/057852, WO 2016/070061, U.S. Pat. No. 9,233,125, US 2016/0129109. In this way, a T-cell that expresses the CAR can be administered to a subject, but the CAR cannot bind its target antigen until the second composition comprising an antigen-specific binding domain is administered.

Alternative switch mechanisms include CARs that require multimerization in order to activate their signaling function (see, e.g., US 2015/0368342, US 2016/0175359, US 2015/0368360) and/or an exogenous signal, such as a small molecule drug (US 2016/0166613, Yung et al., Science, 2015), in order to elicit a T-cell response. Some CARs may also comprise a "suicide switch" to induce cell death of the CAR T-cells following treatment (Buddee et al., PLoS One, 2013) or to downregulate expression of the CAR following binding to the target antigen (WO 2016/011210).

Alternative techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARs, for example using 2nd generation antigen-specific CARs signaling through CD3ζ and either CD28 or CD137. Viral vectors may for example include vectors based on HIV, SV40, EBV, HSV or BPV.

Cells that are targeted for transformation may for example include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells may be differentiated. T cells expressing a desired CAR may for example be selected through co-culture with γ-irradiated activating and propagating cells (AaPC), which co-express the cancer antigen and co-stimulatory molecules. The engineered CAR T-cells may be expanded, for example by co-culture on AaPC in presence of soluble factors, such as IL-2 and IL-21. This expansion may for example be carried out so as to provide memory CAR+ T cells (which may for example be assayed by non-enzymatic digital array and/or multi-panel flow cytometry). In this way, CAR T cells may be provided that have specific cytotoxic activity against antigen-bearing tumors (optionally in conjunction with production of desired chemokines such as interferon-γ). CAR T cells of this kind may for example be used in animal models, for example to treat tumor xenografts.

In certain embodiments, ACT includes co-transferring CD4+Th1 cells and CD8+ CTLs to induce a synergistic antitumour response (see, e.g., Li et al., Adoptive cell therapy with CD4+T helper 1 cells and CD8+ cytotoxic T cells enhances complete rejection of an established tumour, leading to generation of endogenous memory responses to non-targeted tumour epitopes. Clin Transl Immunology. 2017 October; 6(10): e160).

In certain embodiments, Th17 cells are transferred to a subject in need thereof. Th17 cells have been reported to directly eradicate melanoma tumors in mice to a greater extent than Th1 cells (Muranski P, et al., Tumor-specific Th17-polarized cells eradicate large established melanoma. Blood. 2008 Jul. 15; 112(2):362-73; and Martin-Orozco N, et al., T helper 17 cells promote cytotoxic T cell activation in tumor immunity. Immunity. 2009 Nov. 20; 31(5):787-98). Those studies involved an adoptive T cell transfer (ACT) therapy approach, which takes advantage of CD4+ T cells that express a TCR recognizing tyrosinase tumor antigen. Exploitation of the TCR leads to rapid expansion of Th17 populations to large numbers ex vivo for reinfusion into the autologous tumor-bearing hosts.

In certain embodiments, ACT may include autologous iPSC-based vaccines, such as irradiated iPSCs in autologous anti-tumor vaccines (see e.g., Kooreman, Nigel G. et al., Autologous iPSC-Based Vaccines Elicit Anti-tumor Responses In Vivo, Cell Stem Cell 22, 1-13, 2018, doi.org/10.1016/j.stem.2018.01.016).

Unlike T-cell receptors (TCRs) that are MHC restricted, CARs can potentially bind any cell surface-expressed antigen and can thus be more universally used to treat patients (see Irving et al., Engineering Chimeric Antigen Receptor T-Cells for Racing in Solid Tumors: Don't Forget the Fuel, Front. Immunol., 3 Apr. 2017, doi.org/10.3389/fimmu.2017.00267). In certain embodiments, in the absence of endogenous T-cell infiltrate (e.g., due to aberrant antigen processing and presentation), which precludes the use of TIL therapy and immune checkpoint blockade, the transfer of CAR T-cells may be used to treat patients (see, e.g., Hinrichs C S, Rosenberg S A. Exploiting the curative potential of adoptive T-cell therapy for cancer. Immunol Rev (2014) 257(1):56-71. doi:10.1111/imr.12132).

Approaches such as the foregoing may be adapted to provide methods of treating and/or increasing survival of a subject having a disease, such as a neoplasia, for example by administering an effective amount of an immunoresponsive cell comprising an antigen recognizing receptor that binds a selected antigen, wherein the binding activates the immunoresponsive cell, thereby treating or preventing the disease (such as a neoplasia, a pathogen infection, an autoimmune disorder, or an allogeneic transplant reaction).

In certain embodiments, the treatment can be administered after lymphodepleting pretreatment in the form of chemotherapy (typically a combination of cyclophosphamide and fludarabine) or radiation therapy. Initial studies in ACT had short lived responses and the transferred cells did not persist in vivo for very long (Houot et al., T-cell-based immunotherapy: adoptive cell transfer and checkpoint inhibition. Cancer Immunol Res (2015) 3(10):1115-22; and Kamta et al., Advancing Cancer Therapy with Present and Emerging Immuno-Oncology Approaches. Front. Oncol. (2017) 7:64). Immune suppressor cells like Tregs and MDSCs may attenuate the activity of transferred cells by outcompeting them for the necessary cytokines. Not being bound by a theory lymphodepleting pretreatment may eliminate the suppressor cells allowing the TILs to persist.

In one embodiment, the treatment can be administrated into patients undergoing an immunosuppressive treatment (e.g., glucocorticoid treatment). The cells or population of cells, may be made resistant to at least one immunosuppressive agent due to the inactivation of a gene encoding a receptor for such immunosuppressive agent. In certain embodiments, the immunosuppressive treatment provides for the selection and expansion of the immunoresponsive T cells within the patient.

In certain embodiments, the treatment can be administered before primary treatment (e.g., surgery or radiation therapy) to shrink a tumor before the primary treatment. In another embodiment, the treatment can be administered after primary treatment to remove any remaining cancer cells.

In certain embodiments, immunometabolic barriers can be targeted therapeutically prior to and/or during ACT to enhance responses to ACT or CAR T-cell therapy and to support endogenous immunity (see, e.g., Irving et al., Engineering Chimeric Antigen Receptor T-Cells for Racing in Solid Tumors: Don't Forget the Fuel, Front. Immunol., 3 Apr. 2017, doi.org/10.3389/fimmu.2017.00267).

The administration of cells or population of cells, such as immune system cells or cell populations, such as more particularly immunoresponsive cells or cell populations, as disclosed herein may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, intrathecally, by intravenous or intralymphatic injection, or intraperitoneally. In some embodiments, the disclosed CARs may be delivered or administered into a cavity formed by the resection of tumor tissue (i.e. intracavity delivery) or directly into a tumor prior to resection (i.e. intratumoral delivery). In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. Dosing in CAR T cell therapies may for example involve administration of from $10^6$ to $10^9$ cells/kg, with or without a course of lymphodepletion, for example with cyclophosphamide. The cells or population of cells can be administrated in one or more doses. In another embodiment, the effective amount of cells are administrated as a single dose. In another embodiment, the effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells are administrated parenterally. The administration can be an intravenous administration. The administration can be directly done by injection within a tumor.

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6: 95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6):1107-15 (2010)).

In a further refinement of adoptive therapies, genome editing may be used to tailor immunoresponsive cells to alternative implementations, for example providing edited CAR T cells (see Poirot et al., 2015, Multiplex genome edited T-cell manufacturing platform for "off-the-shelf" adoptive T-cell immunotherapies, Cancer Res 75 (18): 3853; Ren et al., 2017, Multiplex genome editing to generate universal CAR T cells resistant to PD1 inhibition, Clin Cancer Res. 2017 May 1; 23(9):2255-2266. doi: 10.1158/1078-0432.CCR-16-1300. Epub 2016 Nov. 4; Qasim et al., 2017, Molecular remission of infant B-ALL after infusion of universal TALEN gene-edited CAR T cells, Sci Transl Med. 2017 Jan. 25; 9(374); Legut, et al., 2018, CRISPR-mediated TCR replacement generates superior anticancer transgenic T cells. Blood, 131(3), 311-322; and Georgiadis et al., Long Terminal Repeat CRISPR-CAR-Coupled "Universal" T Cells Mediate Potent Anti-leukemic Effects, Molecular Therapy, In Press, Corrected Proof, Available online 6 Mar. 2018). Cells may be edited using any CRISPR system and method of use thereof as described herein. CRISPR systems may be delivered to an immune cell by any method described herein. In preferred embodiments, cells are edited ex vivo and transferred to a subject in need thereof. Immunoresponsive cells, CAR T cells or any cells used for adoptive cell transfer may be edited. Editing may be performed for example to insert or knock-in an exogenous gene, such as an exogenous gene encoding a CAR or a TCR, at a preselected locus in a cell (e.g. TRAC locus); to eliminate potential alloreactive T-cell receptors (TCR) or to prevent inappropriate pairing between endogenous and exogenous TCR chains, such as to knock-out or knock-down expression of an endogenous TCR in a cell; to disrupt the target of a chemotherapeutic agent in a cell; to block an immune checkpoint, such as to knock-out or knock-down expression of an immune checkpoint protein or receptor in a cell; to knock-out or knock-down expression of other gene or genes in a cell, the reduced expression or lack of expression of which can enhance the efficacy of adoptive therapies using the cell; to knock-out or knock-down expression of an endogenous gene in a cell, said endogenous gene encoding an antigen targeted by an exogenous CAR or TCR; to knock-out or knock-down expression of one or more MHC constituent proteins in a cell; to activate a T cell; to modulate cells such that the cells are resistant to exhaustion or dysfunction; and/or increase the differentiation and/or proliferation of functionally exhausted or dysfunctional $CD8^+$ T-cells (see PCT Patent Publications: WO2013176915, WO2014059173, WO2014172606, WO2014184744, and WO2014191128).

In certain embodiments, editing may result in inactivation of a gene. By inactivating a gene, it is intended that the gene of interest is not expressed in a functional protein form. In a particular embodiment, the CRISPR system specifically catalyzes cleavage in one targeted gene thereby inactivating said targeted gene. The nucleic acid strand breaks caused are commonly repaired through the distinct mechanisms of homologous recombination or non-homologous end joining (NHEJ). However, NHEJ is an imperfect repair process that often results in changes to the DNA sequence at the site of the cleavage. Repair via non-homologous end joining (NHEJ) often results in small insertions or deletions (Indel) and can be used for the creation of specific gene knockouts. Cells in which a cleavage induced mutagenesis event has occurred can be identified and/or selected by well-known methods in the art. In certain embodiments, homology directed repair (HDR) is used to concurrently inactivate a gene (e.g., TRAC) and insert an endogenous TCR or CAR into the inactivated locus.

Hence, in certain embodiments, editing of cells (such as by CRISPR/Cas), particularly cells intended for adoptive cell therapies, more particularly immunoresponsive cells such as T cells, may be performed to insert or knock-in an exogenous gene, such as an exogenous gene encoding a CAR or a TCR, at a preselected locus in a cell. Conventionally, nucleic acid molecules encoding CARs or TCRs are transfected or transduced to cells using randomly integrating vectors, which, depending on the site of integration, may lead to clonal expansion, oncogenic transformation, variegated transgene expression and/or transcriptional silencing of the transgene. Directing of transgene(s) to a specific locus in a cell can minimize or avoid such risks and advantageously provide for uniform expression of the transgene(s) by the cells. Without limitation, suitable 'safe harbor' loci for directed transgene integration include CCR5 or AAVS1. Homology-directed repair (HDR) strategies are known and described elsewhere in this specification allowing to insert transgenes into desired loci (e.g., TRAC locus).

Further suitable loci for insertion of transgenes, in particular CAR or exogenous TCR transgenes, include without limitation loci comprising genes coding for constituents of endogenous T-cell receptor, such as T-cell receptor alpha locus (TRA) or T-cell receptor beta locus (TRB), for example T-cell receptor alpha constant (TRAC) locus, T-cell receptor beta constant 1 (TRBC1) locus or T-cell receptor beta constant 2 (TRBC1) locus. Advantageously, insertion of a transgene into such locus can simultaneously achieve expression of the transgene, potentially controlled by the endogenous promoter, and knock-out expression of the endogenous TCR. This approach has been exemplified in Eyquem et al., (2017) Nature 543: 113-117, wherein the authors used CRISPR/Cas9 gene editing to knock-in a DNA molecule encoding a CD19-specific CAR into the TRAC locus downstream of the endogenous promoter; the CAR-T cells obtained by CRISPR were significantly superior in terms of reduced tonic CAR signaling and exhaustion.

T cell receptors (TCR) are cell surface receptors that participate in the activation of T cells in response to the presentation of antigen. The TCR is generally made from two chains, α and β, which assemble to form a heterodimer and associates with the CD3-transducing subunits to form the T cell receptor complex present on the cell surface. Each α and β chain of the TCR consists of an immunoglobulin-like N-terminal variable (V) and constant (C) region, a hydrophobic transmembrane domain, and a short cytoplasmic region. As for immunoglobulin molecules, the variable region of the α and β chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of graft versus host disease (GVHD). The inactivation of TCRα or TCRβ can result in the elimination of the TCR from the surface of T cells preventing recognition of alloantigen and thus GVHD. However, TCR disruption generally results in the elimination of the CD3 signaling component and alters the means of further T cell expansion.

Hence, in certain embodiments, editing of cells (such as by CRISPR/Cas), particularly cells intended for adoptive cell therapies, more particularly immunoresponsive cells such as T cells, may be performed to knock-out or knock-down expression of an endogenous TCR in a cell. For example, NHEJ-based or HDR-based gene editing approaches can be employed to disrupt the endogenous TCR alpha and/or beta chain genes. For example, gene editing system or systems, such as CRISPR/Cas system or systems, can be designed to target a sequence found within the TCR beta chain conserved between the beta 1 and beta 2 constant region genes (TRBC1 and TRBC2) and/or to target the constant region of the TCR alpha chain (TRAC) gene.

Allogeneic cells are rapidly rejected by the host immune system. It has been demonstrated that, allogeneic leukocytes present in non-irradiated blood products will persist for no more than 5 to 6 days (Boni, Muranski et al. 2008 Blood 1; 112(12):4746-54). Thus, to prevent rejection of allogeneic cells, the host's immune system usually has to be suppressed to some extent. However, in the case of adoptive cell transfer the use of immunosuppressive drugs also have a detrimental effect on the introduced therapeutic T cells. Therefore, to effectively use an adoptive immunotherapy approach in these conditions, the introduced cells would need to be resistant to the immunosuppressive treatment. Thus, in a particular embodiment, the present invention further comprises a step of modifying T cells to make them resistant to an immunosuppressive agent, preferably by inactivating at least one gene encoding a target for an immunosuppressive agent. An immunosuppressive agent is an agent that suppresses immune function by one of several mechanisms of action. An immunosuppressive agent can be, but is not limited to a calcineurin inhibitor, a target of rapamycin, an interleukin-2 receptor α-chain blocker, an inhibitor of inosine monophosphate dehydrogenase, an inhibitor of dihydrofolic acid reductase, a corticosteroid or an immunosuppressive antimetabolite. The present invention allows conferring immunosuppressive resistance to T cells for immunotherapy by inactivating the target of the immunosuppressive agent in T cells. As non-limiting examples, targets for an immunosuppressive agent can be a receptor for an immunosuppressive agent such as: CD52, glucocorticoid receptor (GR), a FKBP family gene member and a cyclophilin family gene member.

In certain embodiments, editing of cells (such as by CRISPR/Cas), particularly cells intended for adoptive cell therapies, more particularly immunoresponsive cells such as T cells, may be performed to block an immune checkpoint, such as to knock-out or knock-down expression of an immune checkpoint protein or receptor in a cell. Immune checkpoints are inhibitory pathways that slow down or stop immune reactions and prevent excessive tissue damage from uncontrolled activity of immune cells. In certain embodiments, the immune checkpoint targeted is the programmed death-1 (PD-1 or CD279) gene (PDCD1). In other embodiments, the immune checkpoint targeted is cytotoxic T-lymphocyte-associated antigen (CTLA-4). In additional embodiments, the immune checkpoint targeted is another member of the CD28 and CTLA4 Ig superfamily such as BTLA, LAG3, ICOS, PDL1 or KIR. In further additional embodiments, the immune checkpoint targeted is a member of the TNFR superfamily such as CD40, OX40, CD137, GITR, CD27 or TIM-3.

Additional immune checkpoints include Src homology 2 domain-containing protein tyrosine phosphatase 1 (SHP-1) (Watson H A, et al., SHP-1: the next checkpoint target for cancer immunotherapy? Biochem Soc Trans. 2016 Apr. 15; 44(2):356-62). SHP-1 is a widely expressed inhibitory protein tyrosine phosphatase (PTP). In T-cells, it is a negative regulator of antigen-dependent activation and proliferation. It is a cytosolic protein, and therefore not amenable to antibody-mediated therapies, but its role in activation and proliferation makes it an attractive target for genetic manipulation in adoptive transfer strategies, such as chimeric antigen receptor (CAR) T cells. Immune checkpoints may also include T cell immunoreceptor with Ig and ITIM domains (TIGIT/Vstm3/WUCAM/VSIG9) and VISTA (Le Mercier I, et al., (2015) Beyond CTLA-4 and PD-1, the generation Z of negative checkpoint regulators. Front. Immunol. 6:418).

WO2014172606 relates to the use of MT1 and/or MT2 inhibitors to increase proliferation and/or activity of exhausted CD8+ T-cells and to decrease CD8+ T-cell exhaustion (e.g., decrease functionally exhausted or unresponsive CD8+ immune cells). In certain embodiments, metallothioneins are targeted by gene editing in adoptively transferred T cells.

In certain embodiments, targets of gene editing may be at least one targeted locus involved in the expression of an immune checkpoint protein. Such targets may include, but are not limited to CTLA4, PPP2CA, PPP2CB, PTPN6, PTPN22, PDCD1, ICOS (CD278), PDL1, KIR, LAG3, HAVCR2, BTLA, CD160, TIGIT, CD96, CRTAM, LAIR1, SIGLEC7, SIGLEC9, CD244 (2B4), TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, VISTA, GUCY1A2, GUCY1A3, GUCY1B2, GUCY1B3, MT1, MT2, CD40, OX40, CD137, GITR, CD27, SHP-1, TIM-3, CEACAM-1, CEACAM-3, or CEACAM-5. In preferred embodiments, the gene locus involved in the expression of PD-1 or CTLA-4 genes is targeted. In other preferred embodiments, combinations of genes are targeted, such as but not limited to PD-1 and TIGIT.

By means of an example and without limitation, WO2016196388 concerns an engineered T cell comprising (a) a genetically engineered antigen receptor that specifically binds to an antigen, which receptor may be a CAR; and (b) a disrupted gene encoding a PD-L1, an agent for disruption of a gene encoding a PD-L1, and/or disruption of a gene encoding PD-L1, wherein the disruption of the gene may be mediated by a gene editing nuclease, a zinc finger nuclease (ZFN), CRISPR/Cas9 and/or TALEN. WO2015142675 relates to immune effector cells comprising a CAR in combination with an agent (such as CRISPR, TALEN or ZFN) that increases the efficacy of the immune effector cells in the treatment of cancer, wherein the agent may inhibit an immune inhibitory molecule, such as PD1, PD-L1, CTLA-4, TIM-3, LAG-3, VISTA, BTLA, TIGIT, LAIR1, CD160, 2B4, TGFR beta, CEACAM-1, CEACAM-3, or CEACAM-5. Ren et al., (2017) Clin Cancer Res 23 (9) 2255-2266 performed lentiviral delivery of CAR and electro-transfer of Cas9 mRNA and gRNAs targeting endogenous TCR, 3-2 microglobulin (B2M) and PD1 simultaneously, to generate gene-disrupted allogeneic CAR T cells deficient of TCR, HLA class I molecule and PD1.

In certain embodiments, cells may be engineered to express a CAR, wherein expression and/or function of methylcytosine dioxygenase genes (TET1, TET2 and/or TET3) in the cells has been reduced or eliminated, such as by CRISPR, ZNF or TALEN (for example, as described in WO201704916).

In certain embodiments, editing of cells (such as by CRISPR/Cas), particularly cells intended for adoptive cell therapies, more particularly immunoresponsive cells such as T cells, may be performed to knock-out or knock-down expression of an endogenous gene in a cell, said endogenous gene encoding an antigen targeted by an exogenous CAR or TCR, thereby reducing the likelihood of targeting of the engineered cells. In certain embodiments, the targeted antigen may be one or more antigen selected from the group consisting of CD38, CD138, CS-1, CD33, CD26, CD30, CD53, CD92, CD100, CD148, CD150, CD200, CD261, CD262, CD362, human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53, cyclin (D1), B cell maturation antigen (BCMA), transmembrane activator and CAML Interactor (TACI), and B-cell activating factor receptor (BAFF-R) (for example, as described in WO2016011210 and WO2017011804).

In certain embodiments, editing of cells (such as by CRISPR/Cas), particularly cells intended for adoptive cell therapies, more particularly immunoresponsive cells such as T cells, may be performed to knock-out or knock-down expression of one or more MHC constituent proteins, such as one or more HLA proteins and/or beta-2 microglobulin (B2M), in a cell, whereby rejection of non-autologous (e.g., allogeneic) cells by the recipient's immune system can be reduced or avoided. In preferred embodiments, one or more HLA class I proteins, such as HLA-A, B and/or C, and/or B2M may be knocked-out or knocked-down. Preferably, B2M may be knocked-out or knocked-down. By means of an example, Ren et al., (2017) Clin Cancer Res 23 (9) 2255-2266 performed lentiviral delivery of CAR and electro-transfer of Cas9 mRNA and gRNAs targeting endogenous TCR, β-2 microglobulin (B2M) and PD1 simultaneously, to generate gene-disrupted allogeneic CAR T cells deficient of TCR, HLA class I molecule and PD1.

In other embodiments, at least two genes are edited. Pairs of genes may include, but are not limited to PD1 and TCRα, PD1 and TCRβ, CTLA-4 and TCRα, CTLA-4 and TCRβ, LAG3 and TCRα, LAG3 and TCRβ, Tim3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ, B2M and TCRα, B2M and TCRβ.

In certain embodiments, a cell may be multiply edited (multiplex genome editing) as taught herein to (1) knock-out or knock-down expression of an endogenous TCR (for example, TRBC1, TRBC2 and/or TRAC), (2) knock-out or knock-down expression of an immune checkpoint protein or receptor (for example PD1, PD-L1 and/or CTLA4); and (3) knock-out or knock-down expression of one or more MHC constituent proteins (for example, HLA-A, B and/or C, and/or B2M, preferably B2M).

Whether prior to or after genetic modification of the T cells, the T cells can be activated and expanded generally using methods as described, for example, in U.S. Pat. Nos. 6,352,694; 6,534,055; 6,905,680; 5,858,358; 6,887,466; 6,905,681; 7,144,575; 7,232,566; 7,175,843; 5,883,223; 6,905,874; 6,797,514; 6,867,041; and 7,572,631. T cells can be expanded in vitro or in vivo.

Immune cells may be obtained using any method known in the art. In one embodiment, allogenic T cells may be obtained from healthy subjects. In one embodiment T cells that have infiltrated a tumor are isolated. T cells may be removed during surgery. T cells may be isolated after removal of tumor tissue by biopsy. T cells may be isolated by any means known in the art. In one embodiment, T cells are obtained by apheresis. In one embodiment, the method may comprise obtaining a bulk population of T cells from a tumor sample by any suitable method known in the art. For example, a bulk population of T cells can be obtained from a tumor sample by dissociating the tumor sample into a cell suspension from which specific cell populations can be selected. Suitable methods of obtaining a bulk population of T cells may include, but are not limited to, any one or more of mechanically dissociating (e.g., mincing) the tumor, enzymatically dissociating (e.g., digesting) the tumor, and aspiration (e.g., as with a needle).

The bulk population of T cells obtained from a tumor sample may comprise any suitable type of T cell. Preferably, the bulk population of T cells obtained from a tumor sample comprises tumor infiltrating lymphocytes (TILs).

The tumor sample may be obtained from any mammal. Unless stated otherwise, as used herein, the term "mammal" refers to any mammal including, but not limited to, mammals of the order Lagomorpha, such as rabbits; the order Carnivora, including Felines (cats) and Canines (dogs); the order Artiodactyla, including Bovines (cows) and Swines (pigs); or of the order Perissodactyla, including Equines (horses). The mammals may be non-human primates, e.g., of the order Primates, Ceboids, or Simoids (monkeys) or of the order Anthropoids (humans and apes). In some embodiments, the mammal may be a mammal of the order Rodentia, such as mice and hamsters. Preferably, the mammal is a non-human primate or a human. An especially preferred mammal is the human.

T cells can be obtained from a number of sources, including peripheral blood mononuclear cells, bone marrow, lymph node tissue, spleen tissue, and tumors. In certain embodiments of the present invention, T cells can be obtained from a unit of blood collected from a subject using any number of techniques known to the skilled artisan, such as Ficoll separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient. A specific subpopulation of T cells, such as CD28+, CD4+, CDC, CD45RA+, and CD45RO+ T cells, can be further isolated by positive or negative selection techniques. For example, in one preferred embodiment, T cells are isolated by incubation with anti-CD3/anti-CD28 (i.e., 3×28)-conjugated beads, such as DYNABEADS® M-450 CD3/CD28 T, or XCYTE DYNABEADS™ for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells.

Enrichment of a T cell population by negative selection can be accomplished with a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

Further, monocyte populations (i.e., CD14+ cells) may be depleted from blood preparations by a variety of methodologies, including anti-CD14 coated beads or columns, or utilization of the phagocytotic activity of these cells to facilitate removal. Accordingly, in one embodiment, the invention uses paramagnetic particles of a size sufficient to be engulfed by phagocytotic monocytes. In certain embodiments, the paramagnetic particles are commercially available beads, for example, those produced by Life Technologies under the trade name Dynabeads™. In one embodiment, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be isolated. In certain embodiments, the irrelevant beads include beads coated with sheep anti-mouse antibodies, goat anti-mouse antibodies, and human serum albumin.

In brief, such depletion of monocytes is performed by preincubating T cells isolated from whole blood, apheresed peripheral blood, or tumors with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology may be used including a variety of which are commercially available, (e.g., DYNAL® Magnetic Particle Concentrator (DYNAL MPC®)). Assurance of requisite depletion can be monitored by a variety of methodologies known to those of ordinary skill in the art, including flow cytometric analysis of CD14 positive cells, before and after depletion.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

T cells can also be frozen. Wishing not to be bound by theory, the freeze and subsequent thaw step provides a more uniform product by removing granulocytes and to some extent monocytes in the cell population. After a washing step to remove plasma and platelets, the cells may be suspended in a freezing solution. While many freezing solutions and parameters are known in the art and will be useful in this context, one method involves using PBS containing 20% DMSO and 8% human serum albumin, or other suitable cell freezing media, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

T cells for use in the present invention may also be antigen-specific T cells. For example, tumor-specific T cells can be used. In certain embodiments, antigen-specific T cells can be isolated from a patient of interest, such as a patient afflicted with a cancer or an infectious disease. In one embodiment, neoepitopes are determined for a subject and T cells specific to these antigens are isolated. Antigen-specific cells for use in expansion may also be generated in vitro using any number of methods known in the art, for example, as described in U.S. Patent Publication No. US 20040224402 entitled, Generation and Isolation of Antigen-Specific T Cells, or in U.S. Pat. No. 6,040,177. Antigen-specific cells for use in the present invention may also be generated using any number of methods known in the art, for example, as described in Current Protocols in Immunology, or Current Protocols in Cell Biology, both published by John Wiley & Sons, Inc., Boston, Mass.

In a related embodiment, it may be desirable to sort or otherwise positively select (e.g. via magnetic selection) the antigen specific cells prior to or following one or two rounds of expansion. Sorting or positively selecting antigen-specific cells can be carried out using peptide-MHC tetramers (Altman, et al., Science. 1996 Oct. 4; 274(5284):94-6). In another embodiment, the adaptable tetramer technology approach is used (Andersen et al., 2012 Nat Protoc. 7:891-902). Tetramers are limited by the need to utilize predicted binding peptides based on prior hypotheses, and the restriction to specific HLAs. Peptide-MHC tetramers can be generated using techniques known in the art and can be made with any MHC molecule of interest and any antigen of interest as described herein. Specific epitopes to be used in this context can be identified using numerous assays known in the art. For example, the ability of a polypeptide to bind to MHC class I may be evaluated indirectly by monitoring the ability to promote incorporation of $^{125}$I labeled β2-microglobulin (β2m) into MHC class I/β2m/peptide heterotrimeric complexes (see Parker et al., J. Immunol. 152:163, 1994).

In one embodiment cells are directly labeled with an epitope-specific reagent for isolation by flow cytometry followed by characterization of phenotype and TCRs. In one embodiment, T cells are isolated by contacting with T cell specific antibodies. Sorting of antigen-specific T cells, or generally any cells of the present invention, can be carried out using any of a variety of commercially available cell sorters, including, but not limited to, MoFlo sorter (Dako-Cytomation, Fort Collins, Colo.), FACSAria™, FACSArray™, FACSVantage™ BD™ LSR II, and FACSCalibur™ (BD Biosciences, San Jose, Calif.).

In a preferred embodiment, the method comprises selecting cells that also express CD3. The method may comprise specifically selecting the cells in any suitable manner. Preferably, the selecting is carried out using flow cytometry. The flow cytometry may be carried out using any suitable method known in the art. The flow cytometry may employ any suitable antibodies and stains. Preferably, the antibody is chosen such that it specifically recognizes and binds to the particular biomarker being selected. For example, the specific selection of CD3, CD8, TIM-3, LAG-3, 4-1BB, or PD-1 may be carried out using anti-CD3, anti-CD8, anti-TIM-3, anti-LAG-3, anti-4-1BB, or anti-PD-1 antibodies, respectively. The antibody or antibodies may be conjugated to a bead (e.g., a magnetic bead) or to a fluorochrome. Preferably, the flow cytometry is fluorescence-activated cell sorting (FACS). TCRs expressed on T cells can be selected based on reactivity to autologous tumors. Additionally, T cells that are reactive to tumors can be selected for based on markers using the methods described in patent publication Nos. WO2014133567 and WO2014133568, herein incorporated by reference in their entirety. Additionally, activated T cells can be selected for based on surface expression of CD107a.

In one embodiment of the invention, the method further comprises expanding the numbers of T cells in the enriched cell population. Such methods are described in U.S. Pat. No. 8,637,307 and is herein incorporated by reference in its entirety. The numbers of T cells may be increased at least about 3-fold (or 4-, 5-, 6-, 7-, 8-, or 9-fold), more preferably at least about 10-fold (or 20-, 30-, 40-, 50-, 60-, 70-, 80-, or 90-fold), more preferably at least about 100-fold, more preferably at least about 1,000 fold, or most preferably at least about 100,000-fold. The numbers of T cells may be expanded using any suitable method known in the art. Exemplary methods of expanding the numbers of cells are described in patent publication No. WO 2003057171, U.S. Pat. No. 8,034,334, and U.S. Patent Application Publication No. 2012/0244133, each of which is incorporated herein by reference.

In one embodiment, ex vivo T cell expansion can be performed by isolation of T cells and subsequent stimulation or activation followed by further expansion. In one embodiment of the invention, the T cells may be stimulated or activated by a single agent. In another embodiment, T cells are stimulated or activated with two agents, one that induces a primary signal and a second that is a co-stimulatory signal. Ligands useful for stimulating a single signal or stimulating a primary signal and an accessory molecule that stimulates a second signal may be used in soluble form. Ligands may be attached to the surface of a cell, to an Engineered Multivalent Signaling Platform (EMSP), or immobilized on a surface. In a preferred embodiment both primary and secondary agents are co-immobilized on a surface, for example a bead or a cell. In one embodiment, the molecule providing the primary activation signal may be a CD3 ligand, and the co-stimulatory molecule may be a CD28 ligand or 4-1BB ligand.

In certain embodiments, T cells comprising a CAR or an exogenous TCR, may be manufactured as described in WO2015120096, by a method comprising: enriching a population of lymphocytes obtained from a donor subject; stimulating the population of lymphocytes with one or more T-cell stimulating agents to produce a population of activated T cells, wherein the stimulation is performed in a closed system using serum-free culture medium; transducing the population of activated T cells with a viral vector comprising a nucleic acid molecule which encodes the CAR or TCR, using a single cycle transduction to produce a population of transduced T cells, wherein the transduction is performed in a closed system using serum-free culture medium; and expanding the population of transduced T cells for a predetermined time to produce a population of engineered T cells, wherein the expansion is performed in a closed system using serum-free culture medium. In certain embodiments, T cells comprising a CAR or an exogenous TCR, may be manufactured as described in WO2015120096, by a method comprising: obtaining a population of lymphocytes; stimulating the population of lymphocytes with one or more stimulating agents to produce a population of activated T cells, wherein the stimulation is performed in a closed system using serum-free culture medium; transducing the population of activated T cells with a viral vector comprising a nucleic acid molecule which encodes the CAR or TCR, using at least one cycle transduction to produce a population of transduced T cells, wherein the transduction is performed in a closed system using serum-free culture medium; and expanding the population of transduced T cells to produce a population of engineered T cells, wherein the expansion is performed in a closed system using serum-free culture medium. The predetermined time for expanding the population of transduced T cells may be 3 days. The time from enriching the population of lymphocytes to producing the engineered T cells may be 6 days. The closed system may be a closed bag system. Further provided is population of T cells comprising a CAR or an exogenous TCR obtainable or obtained by said method, and a pharmaceutical composition comprising such cells.

In certain embodiments, T cell maturation or differentiation in vitro may be delayed or inhibited by the method as described in WO2017070395, comprising contacting one or more T cells from a subject in need of a T cell therapy with an AKT inhibitor (such as, e.g., one or a combination of two or more AKT inhibitors disclosed in claim 8 of WO2017070395) and at least one of exogenous Interleukin-7 (IL-7) and exogenous Interleukin-15 (IL-15), wherein the resulting T cells exhibit delayed maturation or differentiation, and/or wherein the resulting T cells exhibit improved T cell function (such as, e.g., increased T cell proliferation; increased cytokine production; and/or increased cytolytic activity) relative to a T cell function of a T cell cultured in the absence of an AKT inhibitor.

In certain embodiments, a patient in need of a T cell therapy may be conditioned by a method as described in WO2016191756 comprising administering to the patient a dose of cyclophosphamide between 200 mg/m2/day and 2000 mg/m2/day and a dose of fludarabine between 20 mg/m2/day and 900 mg/m$^2$/day.

In one embodiment, adoptive cell transfer may comprise: isolating from a biological sample of the subject a CD8$^+$ T cell population; depleting from the CD8$^+$ T cell population CD8$^+$ T cells having a non-responder signature as described herein; in vitro expanding the depleted CD8$^+$ T cell population; and administering the in vitro expanded CD8$^+$ T cell population to the subject. In one embodiment, adoptive cell transfer may comprise: isolating from a biological sample of the subject a CD8$^+$ T cell or CD8$^+$ T cell population having a responder signature as described herein; in vitro expanding the CD8$^+$ T cell or CD8$^+$ T cell population; and administering the in vitro expanded CD8$^+$ T cell or CD8$^+$ T cell population to the subject. The method may further comprise enriching the expanded cells for CD8$^+$ T cells having a responder signature as described herein. The method may further comprise depleting the expanded cells for CD8$^+$ T cells having a non-responder signature as described herein. In certain embodiments, the method may further comprise formulating the in vitro expanded immune cell or immune cell population into a pharmaceutical composition.

Cancer

In certain example embodiments, the pharmaceutical compositions and adoptive cell transfer strategies may be used to treat various forms of cancer. Examples of cancer include but are not limited to carcinoma, lymphoma, blastoma, sarcoma, and leukemia or lymphoid malignancies. More particular examples of such cancers include without limitation: squamous cell cancer (e.g., epithelial squamous cell cancer), lung cancer including small-cell lung cancer, non-small cell lung cancer, adenocarcinoma of the lung, squamous carcinoma of the lung and large cell carcinoma of the lung, cancer of the peritoneum, hepatocellular cancer, gastric or stomach cancer including gastrointestinal cancer, pancreatic cancer, glioma, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulvar cancer, thyroid cancer, hepatic carcinoma, anal carcinoma, penile carcinoma, as well as CNS cancer, melanoma, head and neck cancer, bone cancer, bone marrow cancer, duodenum cancer, oesophageal cancer, thyroid cancer, or hematological cancer.

Other non-limiting examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumours, Breast Cancer, Cancer of the Renal Pelvis and Urethra, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Glioblastoma, Childhood Cerebellar Astrocytoma, Childhood Cerebral Astrocytoma, Childhood Extracranial Germ Cell Tumours, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumours, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumours, Exocrine Pancreatic Cancer, Extracranial Germ Cell Tumour, Extragonadal Germ Cell Tumour, Extrahepatic Bile Duct Cancer, Eye Cancer, Female Breast Cancer, Gaucher's Disease, Gallbladder Cancer, Gastric Cancer, Gastrointestinal Carcinoid Tumour, Gastrointestinal Tumours, Germ Cell Tumours, Gestational Trophoblastic Tumour, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumour, Ovarian Low Malignant Potential Tumour, Pancreatic Cancer, Paraproteinemias, Purpura, Parathyroid Cancer, Penile Cancer, Pheochromocytoma, Pituitary Tumour, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Urethra Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumours, T-Cell Lymphoma, Testicular Cancer, Thymoma, Thyroid Cancer, Transitional Cell Cancer of the Renal Pelvis and Urethra, Transitional Renal Pelvis and Urethra Cancer, Trophoblastic Tumours, Urethra and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, or Wilms' Tumour.

In further examples, any combinations of methods such as discussed herein may be employed.

Identifying Immunomodulators

A further aspect of the invention relates to a method for identifying an immunomodulant capable of modulating one or more phenotypic aspects of an immune cell or immune cell population as disclosed herein, comprising: a) applying a candidate immunomodulant to the immune cell or immune cell population; b) detecting modulation of one or more phenotypic aspects of the immune cell or immune cell population by the candidate immunomodulant, thereby identifying the immunomodulant.

The term "modulate" broadly denotes a qualitative and/or quantitative alteration, change or variation in that which is being modulated. Where modulation can be assessed quantitatively—for example, where modulation comprises or consists of a change in a quantifiable variable such as a quantifiable property of a cell or where a quantifiable variable provides a suitable surrogate for the modulation—modulation specifically encompasses both increase (e.g., activation) or decrease (e.g., inhibition) in the measured variable. The term encompasses any extent of such modulation, e.g., any extent of such increase or decrease, and may more particularly refer to statistically significant increase or decrease in the measured variable. By means of example, modulation may encompass an increase in the value of the measured variable by at least about 10%, e.g., by at least about 20%, preferably by at least about 30%, e.g., by at least about 40%, more preferably by at least about 50%, e.g., by at least about 75%, even more preferably by at least about 100%, e.g., by at least about 150%, 200%, 250%, 300%, 400% or by at least about 500%, compared to a reference situation without said modulation; or modulation may encompass a decrease or reduction in the value of the measured variable by at least about 10%, e.g., by at least about 20%, by at least about 30%, e.g., by at least about 40%, by at least about 50%, e.g., by at least about 60%, by at least about 70%, e.g., by at least about 80%, by at least about 90%, e.g., by at least about 95%, such as by at least about 96%, 97%, 98%, 99% or even by 100%, compared to a reference situation without said modulation. Preferably, modulation may be specific or selective, hence, one or more desired phenotypic aspects of an immune cell or immune cell population may be modulated without substantially altering other (unintended, undesired) phenotypic aspect(s).

The term "immunomodulant" broadly encompasses any condition, substance or agent capable of modulating one or more phenotypic aspects of an immune cell or immune cell population as disclosed herein. Such conditions, substances or agents may be of physical, chemical, biochemical and/or biological nature. The term "candidate immunomodulant" refers to any condition, substance or agent that is being examined for the ability to modulate one or more phenotypic aspects of an immune cell or immune cell population as disclosed herein in a method comprising applying the candidate immunomodulant to the immune cell or immune cell population (e.g., exposing the immune cell or immune cell population to the candidate immunomodulant or contacting the immune cell or immune cell population with the candidate immunomodulant) and observing whether the desired modulation takes place.

Immunomodulants may include any potential class of biologically active conditions, substances or agents, such as for instance antibodies, proteins, peptides, nucleic acids, oligonucleotides, small molecules, or combinations thereof.

By means of example but without limitation, immunomodulants can include low molecular weight compounds, but may also be larger compounds, or any organic or inorganic molecule effective in the given situation, including modified and unmodified nucleic acids such as antisense nucleic acids, RNAi, such as siRNA or shRNA, CRISPR/Cas systems, peptides, peptidomimetics, receptors, ligands, and antibodies, aptamers, polypeptides, nucleic acid analogues or variants thereof. Examples include an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof. Agents can be selected from a group comprising: chemicals; small molecules; nucleic acid sequences; nucleic acid analogues; proteins; peptides; aptamers; antibodies; or fragments thereof. A nucleic acid sequence can be RNA or DNA, and can be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), locked nucleic acid (LNA), modified RNA (mod-RNA), single guide RNA etc. Such nucleic acid sequences include, for example, but are not limited to, nucleic acid sequence encoding proteins, for example that act as transcriptional repressors, antisense molecules, ribozymes, small inhibitory nucleic acid sequences, for example but are not limited to RNAi, shRNAi, siRNA, micro RNAi (mRNAi), antisense oligonucleotides, CRISPR guide RNA, for example that target a CRISPR enzyme to a specific DNA target sequence etc. A protein and/or peptide or fragment thereof can be any protein of interest, for example, but are not limited to: mutated proteins; therapeutic proteins and truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, minibodies, triabodies, humanized proteins, humanized antibodies, chimeric antibodies, modified proteins and fragments thereof. Alternatively, the agent can be intracellular within the cell as a result of introduction of a nucleic acid sequence into the cell and its transcription resulting in the production of the nucleic acid and/or protein modulator of a gene within the cell. In some embodiments, the agent is any chemical, entity or moiety, including without limitation synthetic and naturally-occurring non-proteinaceous entities. In certain embodiments, the agent is a small molecule having a chemical moiety. Agents can be known to have a desired activity and/or property, or can be selected from a library of diverse compounds.

In certain embodiments, an immunomodulant may be a hormone, a cytokine, a lymphokine, a growth factor, a chemokine, a cell surface receptor ligand such as a cell surface receptor agonist or antagonist, or a mitogen.

Non-limiting examples of hormones include growth hormone (GH), adrenocorticotropic hormone (ACTH), dehydroepiandrosterone (DHEA), cortisol, epinephrine, thyroid hormone, estrogen, progesterone, testosterone, or combinations thereof.

Non-limiting examples of cytokines include lymphokines (e.g., interferon-$\gamma$, IL-2, IL-3, IL-4, IL-6, granulocyte-macrophage colony-stimulating factor (GM-CSF), interferon-$\gamma$, leukocyte migration inhibitory factors (T-LIF, B-LIF), lymphotoxin-alpha, macrophage-activating factor (MAF), macrophage migration-inhibitory factor (MIF), neuroleukin, immunologic suppressor factors, transfer factors, or combinations thereof), monokines (e.g., IL-1, TNF-alpha, interferon-$\alpha$, interferon-$\beta$, colony stimulating factors, e.g., CSF2, CSF3, macrophage CSF or GM-CSF, or combinations thereof), chemokines (e.g., beta-thromboglobulin, C chemokines, CC chemokines, CXC chemokines, CX3C chemokines, macrophage inflammatory protein (MIP), or combinations thereof), interleukins (e.g., IL-1, IL-2, IL-3, IL-4, IL-5, IL-6, IL-7, IL-8, IL-9, IL-10, IL-11, IL-12, IL-13, IL-14, IL-15, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, or combinations thereof), and several related signalling molecules, such as tumour necrosis factor (TNF) and interferons (e.g., interferon-$\alpha$, interferon-$\beta$, interferon-$\gamma$, interferon-$\lambda$, or combinations thereof).

Non-limiting examples of growth factors include those of fibroblast growth factor (FGF) family, bone morphogenic protein (BMP) family, platelet derived growth factor (PDGF) family, transforming growth factor beta (TGFbeta) family, nerve growth factor (NGF) family, epidermal growth factor (EGF) family, insulin related growth factor (IGF) family, hepatocyte growth factor (HGF) family, hematopoietic growth factors (HeGFs), platelet-derived endothelial cell growth factor (PD-ECGF), angiopoietin, vascular endothelial growth factor (VEGF) family, glucocorticoids, or combinations thereof.

Non-limiting examples of mitogens include phytohaemagglutinin (PHA), concanavalin A (conA), lipopolysaccharide (LPS), pokeweed mitogen (PWM), phorbol ester such as phorbol myristate acetate (PMA) with or without ionomycin, or combinations thereof.

Non-limiting examples of cell surface receptors the ligands of which may act as immunomodulants include Toll-like receptors (TLRs) (e.g., TLR1, TLR2, TLR3, TLR4, TLR5, TLR6, TLR7, TLR8, TLR9, TLR10, TLR11, TLR12 or TLR13), CD80, CD86, CD40, CCR7, or C-type lectin receptors.

Altering Expression Using Immunomodulants

In certain embodiments, an immunomodulant may comprise altering expression and/or activity of one or more endogenous genes of the immune cell. The term "altered expression" denotes that the modification of the immune cell alters, i.e., changes or modulates, the expression of the recited gene(s) or polypeptides(s). The term "altered expression" encompasses any direction and any extent of said alteration. Hence, "altered expression" may reflect qualitative and/or quantitative change(s) of expression, and specifically encompasses both increase (e.g., activation or stimulation) or decrease (e.g., inhibition) of expression.

In certain embodiments, the present invention provides for gene signature screening. The concept of signature screening was introduced by Stegmaier et al. (Gene expression-based high-throughput screening (GE-HTS) and application to leukemia differentiation. Nature Genet. 36, 257-263 (2004)), who realized that if a gene-expression signature was the proxy for a phenotype of interest, it could be used to find small molecules that effect that phenotype without knowledge of a validated drug target. The signature of the present may be used to screen for drugs that reduce the signature in immune cells as described herein. The signature may be used for GE-HTS. In certain embodiments, pharmacological screens may be used to identify drugs that are selectively toxic to immune cells having a non-responder signature. In certain embodiments, drugs selectively toxic to immune cells having a non-responder signature are used for treatment of a cancer patient.

The Connectivity Map (cmap) is a collection of genome-wide transcriptional expression data from cultured human cells treated with bioactive small molecules and simple pattern-matching algorithms that together enable the discovery of functional connections between drugs, genes and diseases through the transitory feature of common gene-expression changes (see, Lamb et al., The Connectivity Map: Using Gene-Expression Signatures to Connect Small Molecules, Genes, and Disease. Science 29 Sep. 2006: Vol. 313, Issue 5795, pp. 1929-1935, DOI: 10.1126/science.1132939; and Lamb, J., The Connectivity Map: a new tool for biomedical research. Nature Reviews Cancer January 2007: Vol. 7, pp. 54-60). In certain embodiments, Cmap can be used to screen for small molecules capable of modulating a signature of the present invention in silico.

Any one or more of the several successive molecular mechanisms involved in the expression of a given gene or polypeptide may be targeted by the immune cell modification as intended herein. Without limitation, these may include targeting the gene sequence (e.g., targeting the polypeptide-encoding, non-coding and/or regulatory portions of the gene sequence), the transcription of the gene into RNA, the polyadenylation and where applicable splicing and/or other post-transcriptional modifications of the RNA into mRNA, the localization of the mRNA into cell cytoplasm, where applicable other post-transcriptional modifications of the mRNA, the translation of the mRNA into a polypeptide chain, where applicable post-translational modifications of the polypeptide, and/or folding of the polypeptide chain into the mature conformation of the polypeptide. For compartmentalized polypeptides, such as secreted polypeptides and transmembrane polypeptides, this may further include targeting trafficking of the polypeptides, i.e., the cellular mechanism by which polypeptides are transported to the appropriate sub-cellular compartment or organelle, membrane, e.g. the plasma membrane, or outside the cell.

Hence, "altered expression" may particularly denote altered production of the recited gene products by the modified immune cell. As used herein, the term "gene product(s)" includes RNA transcribed from a gene (e.g., mRNA), or a polypeptide encoded by a gene or translated from RNA.

Also, "altered expression" as intended herein may encompass modulating the activity of one or more endogenous gene products. Accordingly, "altered expression", "altering expression", "modulating expression", or "detecting expression" or similar may be used interchangeably with respectively "altered expression or activity", "altering expression or activity", "modulating expression or activity", or "detecting expression or activity" or similar. As used herein, "modulating" or "to modulate" generally means either reducing or inhibiting the activity of a target or antigen, or alternatively increasing the activity of the target or antigen, as measured using a suitable in vitro, cellular or in vivo assay. In particular, "modulating" or "to modulate" can mean either reducing or inhibiting the (relevant or intended) activity of, or alternatively increasing the (relevant or intended) biological activity of the target or antigen, as measured using a suitable in vitro, cellular or in vivo assay (which will usually depend on the target or antigen involved), by at least 5%, at least 10%, at least 25%, at least 50%, at least 60%, at least 70%, at least 80%, or 90% or more, compared to activity of the target or antigen in the same assay under the same conditions but without the presence of the inhibitor/antagonist agents or activator/agonist agents described herein.

As will be clear to the skilled person, "modulating" can also involve effecting a change (which can either be an increase or a decrease) in affinity, avidity, specificity and/or selectivity of a target or antigen, for one or more of its targets compared to the same conditions but without the presence of a modulating agent. Again, this can be determined in any suitable manner and/or using any suitable assay known per se, depending on the target. In particular, an action as an inhibitor/antagonist or activator/agonist can be such that an intended biological or physiological activity is increased or decreased, respectively, by at least 5%, at least 10%, at least 25%, at least 50%, at least 60%, at least 70%, at least 80%, or 90% or more, compared to the biological or physiological activity in the same assay under the same conditions but without the presence of the inhibitor/antagonist agent or activator/agonist agent. Modulating can also involve activating the target or antigen or the mechanism or pathway in which it is involved.

In certain embodiments, an immunomodulant may be or may result in a genetic modification (e.g., mutation, editing, transgenesis, or combinations thereof) of an immune cell, for example, a genetic perturbation, such as a knock-out (i.e., resulting in a complete absence of expression and/or activity) of one or more endogenous genes/gene products, or a knock-down (i.e., resulting in a partial absence of expression and/or activity) of one or more endogenous genes/gene products, or another type of genetic modification modulating the expression and/or activity of one or more endogenous genes/gene products, or for example, introduction of one or more transgenes, such as one or more transgenes encoding one or more gene products. Such transgene may be suitably operably linked to suitable regulatory sequences, e.g., may be comprised in an expression cassette or an expression vector comprising suitable regulatory sequences, or may be configured to become operably linked to suitable regulatory sequences once inserted into the genetic material (e.g., genome) of the immune cell.

Any types of mutations achieving the intended effects are contemplated herein. For example, suitable mutations may include deletions, insertions, and/or substitutions. The term "deletion" refers to a mutation wherein one or more nucleotides, typically consecutive nucleotides, of a nucleic acid are removed, i.e., deleted, from the nucleic acid. The term "insertion" refers to a mutation wherein one or more nucleotides, typically consecutive nucleotides, are added, i.e., inserted, into a nucleic acid. The term "substitution" refers to a mutation wherein one or more nucleotides of a nucleic acid are each independently replaced, i.e., substituted, by another nucleotide.

In certain embodiments, a mutation may introduce a premature in-frame stop codon into the open reading frame (ORF) encoding a gene product. Such premature stop codon may lead to production of a C-terminally truncated form of said polypeptide (this may preferably affect, such as diminish or abolish, some or all biological function(s) of the polypeptide) or, especially when the stop codon is introduced close to (e.g., about 20 or less, or about 10 or less amino acids downstream of) the translation initiation codon of the ORF, the stop codon may effectively abolish the production of the polypeptide. Various ways of introducing a premature in-frame stop codon are apparent to a skilled person. For example but without limitation, a suitable insertion, deletion or substitution of one or more nucleotides in the ORF may introduce the premature in-frame stop codon.

In other embodiments, a mutation may introduce a frame shift (e.g., +1 or +2 frame shift) in the ORF encoding a gene product. Typically, such frame shift may lead to a previously out-of-frame stop codon downstream of the mutation becoming an in-frame stop codon. Hence, such frame shift may lead to production of a form of the polypeptide having an alternative C-terminal portion and/or a C-terminally truncated form of said polypeptide (this may preferably affect, such as diminish or abolish, some or all biological function(s) of the polypeptide) or, especially when the mutation is introduced close to (e.g., about 20 or less, or about 10 or less amino acids downstream of) the translation initiation codon of the ORF, the frame shift may effectively abolish the production of the polypeptide. Various ways of introducing a frame shift are apparent to a skilled person. For example but without limitation, a suitable insertion or deletion of one or more (not multiple of 3) nucleotides in the ORF may lead to a frame shift.

In further embodiments, a mutation may delete at least a portion of the ORF encoding a gene product. Such deletion may lead to production of an N-terminally truncated form, a C-terminally truncated form and/or an internally deleted form of said polypeptide (this may preferably affect, such as diminish or abolish, some or all biological function(s) of the polypeptide). Preferably, the deletion may remove about 20% or more, or about 50% or more of the ORF's nucleotides. Especially when the deletion removes a sizeable portion of the ORF (e.g., about 50% or more, preferably about 60% or more, more preferably about 70% or more, even more preferably about 80% or more, still more preferably about 90% or more of the ORF's nucleotides) or when the deletion removes the entire ORF, the deletion may effectively abolish the production of the polypeptide. The skilled person can readily introduce such deletions.

In further embodiments, a mutation may delete at least a portion of a gene promoter, leading to impaired transcription of the gene product.

In certain other embodiments, a mutation may be a substitution of one or more nucleotides in the ORF encoding a gene product resulting in substitution of one or more amino acids of the polypeptide. Such mutation may typically preserve the production of the polypeptide, and may preferably affect, such as diminish or abolish, some or all biological function(s) of the polypeptide. The skilled person can readily introduce such substitutions.

In certain preferred embodiments, a mutation may abolish native splicing of a pre-mRNA encoding a gene product. In the absence of native splicing, the pre-mRNA may be degraded, or the pre-mRNA may be alternatively spliced, or the pre-mRNA may be spliced improperly employing latent splice site(s) if available. Hence, such mutation may typically effectively abolish the production of the polypeptide's mRNA and thus the production of the polypeptide. Various ways of interfering with proper splicing are available to a skilled person, such as for example but without limitation, mutations which alter the sequence of one or more sequence elements required for splicing to render them inoperable, or mutations which comprise or consist of a deletion of one or more sequence elements required for splicing. The terms "splicing", "splicing of a gene", "splicing of a pre-mRNA" and similar as used herein are synonymous and have their art-established meaning. By means of additional explanation, splicing denotes the process and means of removing intervening sequences (introns) from pre-mRNA in the process of producing mature mRNA. The reference to splicing particularly aims at native splicing such as occurs under normal physiological conditions. The terms "pre-mRNA" and "transcript" are used herein to denote RNA species that precede mature mRNA, such as in particular a primary RNA transcript and any partially processed forms thereof. Sequence elements required for splicing refer particularly to cis elements in the sequence of pre-mRNA which direct the cellular splicing machinery (spliceosome) towards correct and precise removal of introns from the pre-mRNA. Sequence elements involved in splicing are generally known per se and can be further determined by known techniques including inter alia mutation or deletion analysis. By means of further explanation, "splice donor site" or "5' splice site" generally refer to a conserved sequence immediately adjacent to an exon-intron boundary at the 5' end of an intron. Commonly, a splice donor site may contain a dinucleotide GU, and may involve a consensus sequence of about 8 bases at about positions +2 to −6. "Splice acceptor site" or "3' splice site" generally refers to a conserved sequence immediately adjacent to an intron-exon boundary at the 3' end of an intron. Commonly, a splice acceptor site may contain a dinucleotide AG, and may involve a consensus sequence of about 16 bases at about positions −14 to +2.

Genetic Modifying Agents

In certain embodiments, the one or more modulating agents may be a genetic modifying agent. The genetic modifying agent may comprise a CRISPR system, a zinc finger nuclease system, a TALEN, or a meganuclease.

In general, a CRISPR-Cas or CRISPR system as used in herein and in documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g, Shmakov et al. (2015) "Discovery and Functional Characterization of Diverse Class 2 CRISPR-Cas Systems", Molecular Cell, DOI: dx.doi.org/10.1016/j.molcel.2015.10.008.

In certain embodiments, a protospacer adjacent motif (PAM) or PAM-like motif directs binding of the effector protein complex as disclosed herein to the target locus of interest. In some embodiments, the PAM may be a 5' PAM (i.e., located upstream of the 5' end of the protospacer). In other embodiments, the PAM may be a 3' PAM (i.e., located downstream of the 5' end of the protospacer). The term "PAM" may be used interchangeably with the term "PFS" or "protospacer flanking site" or "protospacer flanking sequence".

In a preferred embodiment, the CRISPR effector protein may recognize a 3' PAM. In certain embodiments, the CRISPR effector protein may recognize a 3' PAM which is 5'H, wherein H is A, C or U.

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to a RNA polynucleotide being or comprising the target sequence. In other words, the target RNA may be a RNA polynucleotide or a part of a RNA polynucleotide to which a part of the gRNA, i.e. the guide sequence, is designed to have complementarity and to which the effector function mediated by the complex comprising CRISPR effector protein and a gRNA is to be directed. In some embodiments, a target sequence is located in the nucleus or cytoplasm of a cell.

In certain example embodiments, the CRISPR effector protein may be delivered using a nucleic acid molecule encoding the CRISPR effector protein. The nucleic acid molecule encoding a CRISPR effector protein, may advantageously be a codon optimized CRISPR effector protein. An example of a codon optimized sequence, is in this instance a sequence optimized for expression in eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR effector protein is a codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at kazusa.orjp/codon/ and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In certain embodiments, the methods as described herein may comprise providing a Cas transgenic cell in which one or more nucleic acids encoding one or more guide RNAs are provided or introduced operably connected in the cell with a regulatory element comprising a promoter of one or more gene of interest. As used herein, the term "Cas transgenic cell" refers to a cell, such as a eukaryotic cell, in which a Cas gene has been genomically integrated. The nature, type, or origin of the cell are not particularly limiting according to the present invention. Also the way the Cas transgene is introduced in the cell may vary and can be any method as is known in the art. In certain embodiments, the Cas transgenic cell is obtained by introducing the Cas transgene in an isolated cell. In certain other embodiments, the Cas transgenic cell is obtained by isolating cells from a Cas transgenic organism. By means of example, and without limitation, the Cas transgenic cell as referred to herein may be derived from a Cas transgenic eukaryote, such as a Cas knock-in eukaryote. Reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. By means of further example reference is made to Platt et. al. (Cell; 159(2):440-455 (2014)), describing a Cas9 knock-in mouse, which is incorporated herein by reference. The Cas transgene can further comprise a Lox-Stop-polyA-Lox(LSL) cassette thereby rendering Cas expression inducible by Cre recombinase. Alternatively, the Cas transgenic cell may be obtained by introducing the Cas transgene in an isolated cell. Delivery systems for transgenes are well known in the art. By means of example, the Cas transgene may be delivered in for instance eukaryotic cell by means of vector (e.g., AAV, adenovirus, lentivirus) and/or particle and/or nanoparticle delivery, as also described herein elsewhere.

It will be understood by the skilled person that the cell, such as the Cas transgenic cell, as referred to herein may comprise further genomic alterations besides having an integrated Cas gene or the mutations arising from the sequence specific action of Cas when complexed with RNA capable of guiding Cas to a target locus.

In certain aspects the invention involves vectors, e.g. for delivering or introducing in a cell Cas and/or RNA capable of guiding Cas to a target locus (i.e. guide RNA), but also for propagating these components (e.g. in prokaryotic cells). A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety. Thus, the embodiments disclosed herein may also comprise transgenic cells comprising the CRISPR effector system. In certain example embodiments, the transgenic cell may function as an individual discrete volume. In other words samples comprising a masking construct may be delivered to a cell, for example in a suitable delivery vesicle and if the target is present in the delivery vesicle the CRISPR effector is activated and a detectable signal generated.

The vector(s) can include the regulatory element(s), e.g., promoter(s). The vector(s) can comprise Cas encoding sequences, and/or a single, but possibly also can comprise at least 3 or 8 or 16 or 32 or 48 or 50 guide RNA(s) (e.g., sgRNAs) encoding sequences, such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s); and, when a single vector provides for more than 16 RNA(s), one or more promoter(s) can drive expression of more than one of the RNA(s), e.g., when there are 32 RNA(s), each promoter can drive expression of two RNA(s), and when there are 48 RNA(s), each promoter can drive expression of three RNA(s). By simple arithmetic and well established cloning protocols and the teachings in this disclosure one skilled in the art can readily practice the invention as to the RNA(s) for a suitable exemplary vector such as AAV, and a suitable promoter such as the U6 promoter. For example, the packaging limit of AAV is ~4.7 kb. The length of a single U6-gRNA (plus restriction sites for cloning) is 361 bp. Therefore, the skilled person can readily fit about 12-16, e.g., 13 U6-gRNA cassettes in a single vector. This can be assembled by any suitable means, such as a golden gate strategy used for TALE assembly (genome-engineering.org/taleffectors/). The skilled person can also use a tandem guide strategy to increase the number of U6-gRNAs by approximately 1.5 times, e.g., to increase from 12-16, e.g., 13 to approximately 18-24, e.g., about 19 U6-gRNAs. Therefore, one skilled in the art can readily reach approximately 18-24, e.g., about 19 promoter-RNAs, e.g., U6-gRNAs in a single vector, e.g., an AAV vector. A further means for increasing the number of promoters and RNAs in a vector is to use a single promoter (e.g., U6) to express an array of RNAs separated by cleavable sequences. And an even further means for increasing the number of promoter-RNAs in a vector, is to express an array of promoter-RNAs separated by cleavable sequences in the intron of a coding sequence or gene; and, in this instance it is advantageous to use a polymerase II promoter, which can have increased expression and enable the transcription of long RNA in a tissue specific manner. (see, e.g., nar.oxfordjournals. org/content/34/7/e53.short and nature.com/mt/journal/v16/n9/abs/mt2008144a.html). In an advantageous embodiment, AAV may package U6 tandem gRNA targeting up to about 50 genes. Accordingly, from the knowledge in the art and the teachings in this disclosure the skilled person can readily make and use vector(s), e.g., a single vector, expressing multiple RNAs or guides under the control or operatively or functionally linked to one or more promoters-especially as to the numbers of RNAs or guides discussed herein, without any undue experimentation.

The guide RNA(s) encoding sequences and/or Cas encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, Hi, retroviral Rous sarcoma virus (RSV) LTR promoter, the cytomegalovirus (CMV) promoter, the SV40 promoter, the dihydrofolate reductase promoter, the 3-actin promoter, the phosphoglycerol kinase (PGK) promoter, and the EF1α promoter. An advantageous promoter is the promoter is U6.

Additional effectors for use according to the invention can be identified by their proximity to cas1 genes, for example, though not limited to, within the region 20 kb from the start of the cas1 gene and 20 kb from the end of the cas1 gene. In certain embodiments, the effector protein comprises at least one HEPN domain and at least 500 amino acids, and wherein the C2c2 effector protein is naturally present in a prokaryotic genome within 20 kb upstream or downstream of a Cas gene or a CRISPR array. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In certain example embodiments, the C2c2 effector protein is naturally present in a prokaryotic genome within 20 kb upstream or downstream of a Cas 1 gene. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related.

In some embodiments, the Cas sequence is fused to one or more nuclear localization sequences (NLSs), such as about or more than about 1, 2, 3, 4, 5, 6, 7, 8, 9, 10, or more NLSs. In some embodiments, the Cas comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the Cas comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 4); the NLS from nucleoplasmin (e.g. the nucleoplasmin bipartite NLS with the sequence KRPAATKKAGQAKKKK) (SEQ ID NO: 5); the c-myc NLS having the amino acid sequence PAAKRVKLD (SEQ ID NO: 6) or RQRRNELKRSP (SEQ ID NO: 7); the hnRNPA1 M9 NLS having the sequence NQSSNFGPMKGGNFGGRSSGPYGGGGQYFAK-PRNQGGY(SEQ ID NO: 8); the sequence RMRIZFKNKGKDTAELRRRRVEVSVELRKAKKD-EQILKRRNV (SEQ ID NO: 9) of the IBB domain from importin-alpha; the sequences VSRKRPRP (SEQ ID NO: 10) and PPKKARED (SEQ ID NO: 11) of the myoma T protein; the sequence POPKKKPL (SEQ ID NO: 12) of human p53; the sequence SALIKKKKKMAP (SEQ ID NO: 13) of mouse c-abl IV; the sequences DRLRR (SEQ ID NO: 14) and PKQKKRK (SEQ ID NO: 15) of the influenza virus NS1; the sequence RKLKKKIKKL (SEQ ID NO: 16) of the Hepatitis virus delta antigen; the sequence REKKKFLKRR (SEQ ID NO: 17) of the mouse Mx1 protein; the sequence KRKGDEVDGVDEVAKKKSKK (SEQ ID NO: 18) of the human poly(ADP-ribose) polymerase; and the sequence RKCLQAGMNLEARKTKK (SEQ ID NO: 19) of the steroid hormone receptors (human) glucocorticoid. In general, the one or more NLSs are of sufficient strength to drive accumulation of the Cas in a detectable amount in the nucleus of a eukaryotic cell. In general, strength of nuclear localization activity may derive from the number of NLSs in the Cas, the particular NLS(s) used, or a combination of these factors. Detection of accumulation in the nucleus may be performed by any suitable technique. For example, a detectable marker may be fused to the Cas, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or Cas enzyme activity), as compared to a control no exposed to the Cas or complex, or exposed to a Cas lacking the one or more NLSs.

Guide Molecules

The methods described herein may be used to screen inhibition of CRISPR systems employing different types of guide molecules. As used herein, the term "guide sequence" and "guide molecule" in the context of a CRISPR-Cas system, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. The guide sequences made using the methods disclosed herein may be a full-length guide sequence, a truncated guide sequence, a full-length sgRNA sequence, a truncated sgRNA sequence, or an E+F sgRNA sequence. In some embodiments, the degree of complementarity of the guide sequence to a given target sequence, when optimally aligned using a suitable alignment algorithm, is about or more than about 50%, 60%, 75%, 80%, 85%, 90%, 95%, 97.5%, 99%, or more. In certain example embodiments, the guide molecule comprises a guide sequence that may be designed to have at least one mismatch with the target sequence, such that a RNA duplex formed between the guide sequence and the target sequence. Accordingly, the degree of complementarity is preferably less than 99%. For instance, where the guide sequence consists of 24 nucleotides, the degree of complementarity is more particularly about 96% or less. In particular embodiments, the guide sequence is designed to have a stretch of two or more adjacent mismatching nucleotides, such that the degree of complementarity over the entire guide sequence is further reduced. For instance, where the guide sequence consists of 24 nucleotides, the degree of complementarity is more particularly about 96% or less, more particularly, about 92% or less, more particularly about 88% or less, more particularly about 84% or less, more particularly about 80% or less, more particularly about 76% or less, more particularly about 72% or less, depending on whether the stretch of two or more mismatching nucleotides encompasses 2, 3, 4, 5, 6 or 7 nucleotides, etc. In some embodiments, aside from the stretch of one or more mismatching nucleotides, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence (or a sequence in the vicinity thereof) may be evaluated in a test tube by providing the target nucleic acid sequence, components of a nucleic acid-targeting complex, including the guide sequence to be tested and a control guide sequence different from the test guide sequence, and comparing binding or rate of cleavage at or in the vicinity of the target sequence between the test and control guide sequence reactions. Other assays are possible, and will occur to those skilled in the art. A guide sequence, and hence a nucleic acid-targeting guide RNA may be selected to target any target nucleic acid sequence.

In certain embodiments, the guide sequence or spacer length of the guide molecules is from 15 to 50 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer. In certain example embodiment, the guide sequence is 15, 16, 17, 18, 19, 20, 21, 22, 23, 24, 25, 26, 27, 28, 29, 30, 31, 32, 33, 34, 35, 36, 37, 38, 39 40, 41, 42, 43, 44, 45, 46, 47 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nt.

In some embodiments, the guide sequence is an RNA sequence of between 10 to 50 nt in length, but more particularly of about 20-30 nt advantageously about 20 nt, 23-25 nt or 24 nt. The guide sequence is selected so as to ensure that it hybridizes to the target sequence. This is described more in detail below. Selection can encompass further steps which increase efficacy and specificity.

In some embodiments, the guide sequence has a canonical length (e.g., about 15-30 nt) is used to hybridize with the target RNA or DNA. In some embodiments, a guide molecule is longer than the canonical length (e.g., >30 nt) is used to hybridize with the target RNA or DNA, such that a region of the guide sequence hybridizes with a region of the RNA or DNA strand outside of the Cas-guide target complex. This can be of interest where additional modifications, such as deamination of nucleotides is of interest. In alternative embodiments, it is of interest to maintain the limitation of the canonical guide sequence length.

In some embodiments, the sequence of the guide molecule (direct repeat and/or spacer) is selected to reduce the degree secondary structure within the guide molecule. In some embodiments, about or less than about 75%, 50%, 40%, 30%, 25%, 20%, 15%, 10%, 5%, 1%, or fewer of the nucleotides of the nucleic acid-targeting guide RNA participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and PA Carr and GM Church, 2009, Nature Biotechnology 27(12): 1151-62).

In some embodiments, it is of interest to reduce the susceptibility of the guide molecule to RNA cleavage, such as to cleavage by Cas13. Accordingly, in particular embodiments, the guide molecule is adjusted to avoid cleavage by Cas13 or other RNA-cleaving enzymes.

In certain embodiments, the guide molecule comprises non-naturally occurring nucleic acids and/or non-naturally occurring nucleotides and/or nucleotide analogs, and/or chemically modifications. Preferably, these non-naturally occurring nucleic acids and non-naturally occurring nucleotides are located outside the guide sequence. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, a locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, or 2'-fluoro analogs. Further examples of modified bases include, but are not limited to, 2-aminopurine, 5-bromo-uridine, pseudouridine, inosine, 7-methylguanosine. Examples of guide RNA chemical modifications include, without limitation, incorporation of 2'-O-methyl (M), 2'-O-methyl 3' phosphorothioate (MS), S-constrained ethyl(cEt), or 2'-O-methyl 3' thioPACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33(9):985-9, doi:10.1038/nbt.3290, published online 29 Jun. 2015 Ragdarm et al., 0215, *PNAS*, E7110-E7111; Allerson et al., *J. Med. Chem.* 2005, 48:901-904; Bramsen et al., *Front. Genet.*, 2012, 3:154; Deng et al., *PNAS*, 2015, 112:11870-11875; Sharma et al., *Med Chem Comm.*, 2014, 5:1454-1471; Hendel et al., *Nat. Biotechnol.* (2015) 33(9): 985-989; Li et al., *Nature Biomedical Engineering*, 2017, 1, 0066 DOI:10.1038/s41551-017-0066). In some embodiments, the 5' and/or 3' end of a guide RNA is modified by a variety of functional moieties including fluorescent dyes, polyethylene glycol, cholesterol, proteins, or detection tags. (See Kelly et al., 2016, *J. Biotech.* 233:74-83). In certain embodiments, a guide comprises ribonucleotides in a region that binds to a target RNA and one or more deoxyribonucleotides and/or nucleotide analogs in a region that binds to Cas13. In an embodiment of the invention, deoxyribonucleotides and/or nucleotide analogs are incorporated in engineered guide structures, such as, without limitation, stem-loop regions, and the seed region. For Cas13 guide, in certain embodiments, the modification is not in the 5'-handle of the stem-loop regions. Chemical modification in the 5'-handle of the stem-loop region of a guide may abolish its function (see Li, et al., *Nature Biomedical Engineering*, 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either the 3' or the 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at the 5' and/or the 3' end of the guide are chemically modified with 2'-O-methyl (M), 2'-O-methyl 3' phosphorothioate (MS), S-constrained ethyl(cEt), or 2'-O-methyl 3' thioPACE (MSP). Such modification can enhance genome editing efficiency (see Hendel et al., Nat. Biotechnol. (2015) 33(9): 985-989). In certain embodiments, all of the phosphodiester bonds of a guide are substituted with phosphorothioates (PS) for enhancing levels of gene disruption. In certain embodiments, more than five nucleotides at the 5' and/or the 3' end of the guide are chemically modified with 2'-O-Me, 2'-F or S-constrained ethyl(cEt). Such chemically modified guide can mediate enhanced levels of gene disruption (see Ragdarm et al., 0215, PNAS, E7110-E7111). In an embodiment of the invention, a guide is modified to comprise a chemical moiety at its 3' and/or 5' end. Such moieties include, but are not limited to amine, azide, alkyne, thio, dibenzocyclooctyne (DBCO), or Rhodamine. In certain embodiment, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells generically edited by a CRISPR system (see Lee et al., eLife, 2017, 6:e25312, DOI:10.7554).

In some embodiments, the modification to the guide is a chemical modification, an insertion, a deletion or a split. In some embodiments, the chemical modification includes, but is not limited to, incorporation of 2'-O-methyl (M) analogs, 2'-deoxy analogs, 2-thiouridine analogs, N6-methyladenosine analogs, 2'-fluoro analogs, 2-aminopurine, 5-bromo-uridine, pseudouridine (Ψ), N1-methylpseudouridine (me1Ψ), 5-methoxyuridine(5moU), inosine, 7-methylguanosine, 2'-O-methyl 3'phosphorothioate (MS), S-constrained ethyl(cEt), phosphorothioate (PS), or 2'-O-methyl 3'thioPACE (MSP). In some embodiments, the guide comprises one or more of phosphorothioate modifications. In certain embodiments, at least 1, 2, 3, 4, 5, 6, 7, 8, 9, 10, 11, 12, 13, 14, 15, 16, 17, 18, 19, 20, or 25 nucleotides of the guide are chemically modified. In certain embodiments, one or more nucleotides in the seed region are chemically modified. In certain embodiments, one or more nucleotides in the 3'-terminus are chemically modified. In certain embodiments, none of the nucleotides in the 5'-handle is chemically modified. In some embodiments, the chemical modification in the seed region is a minor modification, such as incorporation of a 2'-fluoro analog. In a specific embodiment, one nucleotide of the seed region is replaced with a 2'-fluoro analog. In some embodiments, 5 to 10 nucleotides in the 3'-terminus are chemically modified. Such chemical modifications at the 3'-terminus of the Cas13 CrRNA may improve Cas13 activity. In a specific embodiment, 1, 2, 3, 4, 5, 6, 7, 8, 9 or 10 nucleotides in the 3'-terminus are replaced with 2'-fluoro analogues. In a specific embodiment, 1, 2, 3, 4, 5, 6, 7, 8, 9 or 10 nucleotides in the 3'-terminus are replaced with 2'-O-methyl (M) analogs.

In some embodiments, the loop of the 5'-handle of the guide is modified. In some embodiments, the loop of the 5'-handle of the guide is modified to have a deletion, an insertion, a split, or chemical modifications. In certain embodiments, the modified loop comprises 3, 4, or 5 nucleotides. In certain embodiments, the loop comprises the sequence of UCUU, UUUU, UAUU, or UGUU.

In some embodiments, the guide molecule forms a stem-loop with a separate non-covalently linked sequence, which can be DNA or RNA. In particular embodiments, the sequences forming the guide are first synthesized using the standard phosphoramidite synthetic protocol (Herdewijn, P., ed., Methods in Molecular Biology Col 288, Oligonucleotide Synthesis: Methods and Applications, Humana Press, New Jersey (2012)). In some embodiments, these sequences can be functionalized to contain an appropriate functional group for ligation using the standard protocol known in the art (Hermanson, G. T., Bioconjugate Techniques, Academic Press (2013)). Examples of functional groups include, but are not limited to, hydroxyl, amine, carboxylic acid, carboxylic acid halide, carboxylic acid active ester, aldehyde, carbonyl, chlorocarbonyl, imidazolylcarbonyl, hydrozide, semicarbazide, thio semicarbazide, thiol, maleimide, haloalkyl, sulfonyl, ally, propargyl, diene, alkyne, and azide. Once this sequence is functionalized, a covalent chemical bond or linkage can be formed between this sequence and the direct repeat sequence. Examples of chemical bonds include, but are not limited to, those based on carbamates, ethers, esters, amides, imines, amidines, aminotriazines, hydrozone, disulfides, thioethers, thioesters, phosphorothioates, phosphorodithioates, sulfonamides, sulfonates, fulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, these stem-loop forming sequences can be chemically synthesized. In some embodiments, the chemical synthesis uses automated, solid-phase oligonucleotide synthesis machines with 2'-acetoxyethyl orthoester (2'-ACE) (Scaringe et al., J. Am. Chem. Soc. (1998) 120: 11820-11821; Scaringe, Methods Enzymol. (2000) 317: 3-18) or 2'-thionocarbamate (2'-TC) chemistry (Dellinger et al., J. Am. Chem. Soc. (2011) 133: 11540-11546; Hendel et al., Nat. Biotechnol. (2015) 33:985-989).

In certain embodiments, the guide molecule comprises (1) a guide sequence capable of hybridizing to a target locus and (2) a tracr mate or direct repeat sequence whereby the direct repeat sequence is located upstream (i.e., 5') from the guide sequence. In a particular embodiment the seed sequence (i.e. the sequence essential critical for recognition and/or hybridization to the sequence at the target locus) of th guide sequence is approximately within the first 10 nucleotides of the guide sequence.

In a particular embodiment the guide molecule comprises a guide sequence linked to a direct repeat sequence, wherein the direct repeat sequence comprises one or more stem loops or optimized secondary structures. In particular embodiments, the direct repeat has a minimum length of 16 nts and a single stem loop. In further embodiments the direct repeat has a length longer than 16 nts, preferably more than 17 nts, and has more than one stem loops or optimized secondary structures. In particular embodiments the guide molecule comprises or consists of the guide sequence linked to all or part of the natural direct repeat sequence. A typical Type V or Type VI CRISPR-cas guide molecule comprises (in 3' to 5' direction or in 5' to 3' direction): a guide sequence a first complimentary stretch (the "repeat"), a loop (which is typically 4 or 5 nucleotides long), a second complimentary stretch (the "anti-repeat" being complimentary to the repeat), and a poly A (often poly U in RNA) tail (terminator). In certain embodiments, the direct repeat sequence retains its natural architecture and forms a single stem loop. In particular embodiments, certain aspects of the guide architecture can be modified, for example by addition, subtraction, or substitution of features, whereas certain other aspects of guide architecture are maintained. Preferred locations for engineered guide molecule modifications, including but not limited to insertions, deletions, and substitutions include guide termini and regions of the guide molecule that are exposed when complexed with the CRISPR-Cas protein and/or target, for example the stemloop of the direct repeat sequence.

In particular embodiments, the stem comprises at least about 4 bp comprising complementary X and Y sequences, although stems of more, e.g., 5, 6, 7, 8, 9, 10, 11 or 12 or fewer, e.g., 3, 2, base pairs are also contemplated. Thus, for example X2-10 and Y2-10 (wherein X and Y represent any complementary set of nucleotides) may be contemplated. In one aspect, the stem made of the X and Y nucleotides, together with the loop will form a complete hairpin in the overall secondary structure; and, this may be advantageous and the amount of base pairs can be any amount that forms a complete hairpin. In one aspect, any complementary X:Y basepairing sequence (e.g., as to length) is tolerated, so long as the secondary structure of the entire guide molecule is preserved. In one aspect, the loop that connects the stem made of X:Y basepairs can be any sequence of the same length (e.g., 4 or 5 nucleotides) or longer that does not interrupt the overall secondary structure of the guide molecule. In one aspect, the stemloop can further comprise, e.g. an MS2 aptamer. In one aspect, the stem comprises about 5-7 bp comprising complementary X and Y sequences, although stems of more or fewer basepairs are also contemplated. In one aspect, non-Watson Crick basepairing is contemplated, where such pairing otherwise generally preserves the architecture of the stemloop at that position.

In particular embodiments the natural hairpin or stemloop structure of the guide molecule is extended or replaced by an extended stemloop. It has been demonstrated that extension of the stem can enhance the assembly of the guide molecule with the CRISPR-Cas protein (Chen et al. Cell. (2013); 155(7): 1479-1491). In particular embodiments the stem of the stemloop is extended by at least 1, 2, 3, 4, 5 or more complementary basepairs (i.e. corresponding to the addition of 2, 4, 6, 8, 10 or more nucleotides in the guide molecule). In particular embodiments these are located at the end of the stem, adjacent to the loop of the stemloop.

In particular embodiments, the susceptibility of the guide molecule to RNAses or to decreased expression can be reduced by slight modifications of the sequence of the guide molecule which do not affect its function. For instance, in particular embodiments, premature termination of transcription, such as premature transcription of U6 Pol-III, can be removed by modifying a putative Pol-III terminator (4 consecutive U's) in the guide molecules sequence. Where such sequence modification is required in the stemloop of the guide molecule, it is preferably ensured by a basepair flip.

In a particular embodiment, the direct repeat may be modified to comprise one or more protein-binding RNA aptamers. In a particular embodiment, one or more aptamers may be included such as part of optimized secondary structure. Such aptamers may be capable of binding a bacteriophage coat protein as detailed further herein.

In some embodiments, the guide molecule forms a duplex with a target RNA comprising at least one target cytosine residue to be edited. Upon hybridization of the guide RNA molecule to the target RNA, the cytidine deaminase binds to the single strand RNA in the duplex made accessible by the mismatch in the guide sequence and catalyzes deamination of one or more target cytosine residues comprised within the stretch of mismatching nucleotides.

A guide sequence, and hence a nucleic acid-targeting guide RNA may be selected to target any target nucleic acid sequence. The target sequence may be mRNA.

In certain embodiments, the target sequence should be associated with a PAM (protospacer adjacent motif) or PFS (protospacer flanking sequence or site); that is, a short sequence recognized by the CRISPR complex. Depending on the nature of the CRISPR-Cas protein, the target sequence should be selected such that its complementary sequence in the DNA duplex (also referred to herein as the non-target sequence) is upstream or downstream of the PAM. In the embodiments of the present invention where the CRISPR-Cas protein is a Cas13 protein, the complementary sequence of the target sequence is downstream or 3' of the PAM or upstream or 5' of the PAM. The precise sequence and length requirements for the PAM differ depending on the Cas13 protein used, but PAMs are typically 2-5 base pair sequences adjacent the protospacer (that is, the target sequence). Examples of the natural PAM sequences for different Cas13 orthologues are provided herein below and the skilled person will be able to identify further PAM sequences for use with a given Cas13 protein.

Further, engineering of the PAM Interacting (PI) domain may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23; 523 (7561):481-5. doi:10.1038/nature14592. As further detailed herein, the skilled person will understand that Cas13 proteins may be modified analogously.

In particular embodiment, the guide is an escorted guide. By "escorted" is meant that the CRISPR-Cas system or complex or guide is delivered to a selected time or place within a cell, so that activity of the CRISPR-Cas system or complex or guide is spatially or temporally controlled. For example, the activity and destination of the 3 CRISPR-Cas system or complex or guide may be controlled by an escort RNA aptamer sequence that has binding affinity for an aptamer ligand, such as a cell surface protein or other localized cellular component. Alternatively, the escort aptamer may for example be responsive to an aptamer effector on or in the cell, such as a transient effector, such as an external energy source that is applied to the cell at a particular time.

The escorted CRISPR-Cas systems or complexes have a guide molecule with a functional structure designed to improve guide molecule structure, architecture, stability, genetic expression, or any combination thereof. Such a structure can include an aptamer.

Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and, Hicke B J, Stephens A W. "Escort aptamers: a delivery service for diagnosis and therapy." J Clin Invest 2000, 106:923-928.). Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4).

Accordingly, in particular embodiments, the guide molecule is modified, e.g., by one or more aptamer(s) designed to improve guide molecule delivery, including delivery across the cellular membrane, to intracellular compartments, or into the nucleus. Such a structure can include, either in addition to the one or more aptamer(s) or without such one or more aptamer(s), moiety(ies) so as to render the guide molecule deliverable, inducible or responsive to a selected effector. The invention accordingly comprehends an guide molecule that responds to normal or pathological physiological conditions, including without limitation pH, hypoxia, 02 concentration, temperature, protein concentration, enzymatic concentration, lipid structure, light exposure, mechanical disruption (e.g. ultrasound waves), magnetic fields, electric fields, or electromagnetic radiation.

Light responsiveness of an inducible system may be achieved via the activation and binding of cryptochrome-2 and CIB1. Blue light stimulation induces an activating conformational change in cryptochrome-2, resulting in recruitment of its binding partner CIB1. This binding is fast and reversible, achieving saturation in <15 sec following pulsed stimulation and returning to baseline <15 min after the end of stimulation. These rapid binding kinetics result in a system temporally bound only by the speed of transcription/translation and transcript/protein degradation, rather than uptake and clearance of inducing agents. Cryptochrome-2 activation is also highly sensitive, allowing for the use of low light intensity stimulation and mitigating the risks of phototoxicity. Further, in a context such as the intact mammalian brain, variable light intensity may be used to control the size of a stimulated region, allowing for greater precision than vector delivery alone may offer.

The invention contemplates energy sources such as electromagnetic radiation, sound energy or thermal energy to induce the guide. Advantageously, the electromagnetic radiation is a component of visible light. In a preferred embodiment, the light is a blue light with a wavelength of about 450 to about 495 nm. In an especially preferred embodiment, the wavelength is about 488 nm. In another preferred embodiment, the light stimulation is via pulses. The light power may range from about 0-9 mW/cm$^2$. In a preferred embodiment, a stimulation paradigm of as low as 0.25 sec every 15 sec should result in maximal activation.

The chemical or energy sensitive guide may undergo a conformational change upon induction by the binding of a chemical source or by the energy allowing it act as a guide and have the Cas13 CRISPR-Cas system or complex function. The invention can involve applying the chemical source or energy so as to have the guide function and the Cas13 CRISPR-Cas system or complex function; and optionally further determining that the expression of the genomic locus is altered.

There are several different designs of this chemical inducible system: 1. ABI-PYL based system inducible by Abscisic Acid (ABA) (see, e.g., stke.sciencemag.org/cgi/content/abstract/sigtrans;4/164/rs2), 2. FKBP-FRB based system inducible by rapamycin (or related chemicals based on rapamycin) (see, e.g., nature.com/nmeth/journal/v2/n6/full/nmeth763.html), 3. GID1-GAIbased system inducible by Gibberellin (GA) (see, e.g., nature.com/nchembio/journal/v8/n5/full/nchembio.922.html).

A chemical inducible system can be an estrogen receptor (ER) based system inducible by 4-hydroxytamoxifen (4OHT) (see, e.g., pnas.org/content/104/3/1027.abstract). A mutated ligand-binding domain of the estrogen receptor called ERT2 translocates into the nucleus of cells upon binding of 4-hydroxytamoxifen. In further embodiments of the invention any naturally occurring or engineered derivative of any nuclear receptor, thyroid hormone receptor, retinoic acid receptor, estrogen receptor, estrogen-related receptor, glucocorticoid receptor, progesterone receptor, androgen receptor may be used in inducible systems analogous to the ER based inducible system.

Another inducible system is based on the design using Transient receptor potential (TRP) ion channel based system inducible by energy, heat or radio-wave (see, e.g., sciencemag.org/content/336/6081/604). These TRP family proteins respond to different stimuli, including light and heat. When this protein is activated by light or heat, the ion channel will open and allow the entering of ions such as calcium into the plasma membrane. This influx of ions will bind to intracellular ion interacting partners linked to a polypeptide including the guide and the other components of the Cas13 CRISPR-Cas complex or system, and the binding will induce the change of sub-cellular localization of the polypeptide, leading to the entire polypeptide entering the nucleus of cells. Once inside the nucleus, the guide protein and the other components of the Cas13 CRISPR-Cas complex will be active and modulating target gene expression in cells.

While light activation may be an advantageous embodiment, sometimes it may be disadvantageous especially for in vivo applications in which the light may not penetrate the skin or other organs. In this instance, other methods of energy activation are contemplated, in particular, electric field energy and/or ultrasound which have a similar effect.

Electric field energy is preferably administered substantially as described in the art, using one or more electric pulses of from about 1 Volt/cm to about 10 kVolts/cm under in vivo conditions. Instead of or in addition to the pulses, the electric field may be delivered in a continuous manner. The electric pulse may be applied for between 1 µs and 500 milliseconds, preferably between 1 µs and 100 milliseconds. The electric field may be applied continuously or in a pulsed manner for 5 about minutes.

As used herein, 'electric field energy' is the electrical energy to which a cell is exposed. Preferably the electric field has a strength of from about 1 Volt/cm to about 10 kVolts/cm or more under in vivo conditions (see WO97/49450).

As used herein, the term "electric field" includes one or more pulses at variable capacitance and voltage and including exponential and/or square wave and/or modulated wave and/or modulated square wave forms. References to electric fields and electricity should be taken to include reference the presence of an electric potential difference in the environment of a cell. Such an environment may be set up by way of static electricity, alternating current (AC), direct current (DC), etc, as known in the art. The electric field may be uniform, non-uniform or otherwise, and may vary in strength and/or direction in a time dependent manner.

Single or multiple applications of electric field, as well as single or multiple applications of ultrasound are also possible, in any order and in any combination. The ultrasound and/or the electric field may be delivered as single or multiple continuous applications, or as pulses (pulsatile delivery).

Electroporation has been used in both in vitro and in vivo procedures to introduce foreign material into living cells. With in vitro applications, a sample of live cells is first mixed with the agent of interest and placed between electrodes such as parallel plates. Then, the electrodes apply an electrical field to the cell/implant mixture. Examples of systems that perform in vitro electroporation include the Electro Cell Manipulator ECM600 product, and the Electro Square Porator T820, both made by the BTX Division of Genetronics, Inc (see U.S. Pat. No. 5,869,326).

The known electroporation techniques (both in vitro and in vivo) function by applying a brief high voltage pulse to electrodes positioned around the treatment region. The electric field generated between the electrodes causes the cell membranes to temporarily become porous, whereupon molecules of the agent of interest enter the cells. In known electroporation applications, this electric field comprises a single square wave pulse on the order of 1000 V/cm, of about 100 .mu·s duration. Such a pulse may be generated, for example, in known applications of the Electro Square Porator T820.

Preferably, the electric field has a strength of from about 1 V/cm to about 10 kV/cm under in vitro conditions. Thus, the electric field may have a strength of 1 V/cm, 2 V/cm, 3 V/cm, 4 V/cm, 5 V/cm, 6 V/cm, 7 V/cm, 8 V/cm, 9 V/cm, 10 V/cm, 20 V/cm, 50 V/cm, 100 V/cm, 200 V/cm, 300 V/cm, 400 V/cm, 500 V/cm, 600 V/cm, 700 V/cm, 800 V/cm, 900 V/cm, 1 kV/cm, 2 kV/cm, 5 kV/cm, 10 kV/cm, 20 kV/cm, 50 kV/cm or more. More preferably from about 0.5 kV/cm to about 4.0 kV/cm under in vitro conditions. Preferably the electric field has a strength of from about 1 V/cm to about 10 kV/cm under in vivo conditions. However, the electric field strengths may be lowered where the number of pulses delivered to the target site are increased. Thus, pulsatile delivery of electric fields at lower field strengths is envisaged.

Preferably the application of the electric field is in the form of multiple pulses such as double pulses of the same strength and capacitance or sequential pulses of varying strength and/or capacitance. As used herein, the term "pulse" includes one or more electric pulses at variable capacitance and voltage and including exponential and/or square wave and/or modulated wave/square wave forms.

Preferably the electric pulse is delivered as a waveform selected from an exponential wave form, a square wave form, a modulated wave form and a modulated square wave form.

A preferred embodiment employs direct current at low voltage. Thus, Applicants disclose the use of an electric field which is applied to the cell, tissue or tissue mass at a field strength of between 1V/cm and 20V/cm, for a period of 100 milliseconds or more, preferably 15 minutes or more.

Ultrasound is advantageously administered at a power level of from about 0.05 W/cm2 to about 100 W/cm2. Diagnostic or therapeutic ultrasound may be used, or combinations thereof.

As used herein, the term "ultrasound" refers to a form of energy which consists of mechanical vibrations the frequencies of which are so high they are above the range of human hearing. Lower frequency limit of the ultrasonic spectrum may generally be taken as about 20 kHz. Most diagnostic applications of ultrasound employ frequencies in the range 1 and 15 MHz' (From Ultrasonics in Clinical Diagnosis, P. N. T. Wells, ed., 2nd. Edition, Publ. Churchill Livingstone [Edinburgh, London & NY, 1977]).

Ultrasound has been used in both diagnostic and therapeutic applications. When used as a diagnostic tool ("diagnostic ultrasound"), ultrasound is typically used in an energy density range of up to about 100 mW/cm2 (FDA recommendation), although energy densities of up to 750 mW/cm2 have been used. In physiotherapy, ultrasound is typically used as an energy source in a range up to about 3 to 4 W/cm2 (WHO recommendation). In other therapeutic applications, higher intensities of ultrasound may be employed, for example, HIFU at 100 W/cm up to 1 kW/cm2 (or even higher) for short periods of time. The term "ultrasound" as used in this specification is intended to encompass diagnostic, therapeutic and focused ultrasound.

Focused ultrasound (FUS) allows thermal energy to be delivered without an invasive probe (see Morocz et al 1998 Journal of Magnetic Resonance Imaging Vol. 8, No. 1, pp. 136-142. Another form of focused ultrasound is high intensity focused ultrasound (HIFU) which is reviewed by Moussatov et al in Ultrasonics (1998) Vol. 36, No. 8, pp. 893-900 and TranHuuHue et al in Acustica (1997) Vol. 83, No. 6, pp. 1103-1106.

Preferably, a combination of diagnostic ultrasound and a therapeutic ultrasound is employed. This combination is not intended to be limiting, however, and the skilled reader will appreciate that any variety of combinations of ultrasound may be used. Additionally, the energy density, frequency of ultrasound, and period of exposure may be varied.

Preferably the exposure to an ultrasound energy source is at a power density of from about 0.05 to about 100 Wcm-2. Even more preferably, the exposure to an ultrasound energy source is at a power density of from about 1 to about 15 Wcm-2.

Preferably the exposure to an ultrasound energy source is at a frequency of from about 0.015 to about 10.0 MHz. More preferably the exposure to an ultrasound energy source is at a frequency of from about 0.02 to about 5.0 MHz or about 6.0 MHz. Most preferably, the ultrasound is applied at a frequency of 3 MHz.

Preferably the exposure is for periods of from about 10 milliseconds to about 60 minutes. Preferably the exposure is for periods of from about 1 second to about 5 minutes. More preferably, the ultrasound is applied for about 2 minutes. Depending on the particular target cell to be disrupted, however, the exposure may be for a longer duration, for example, for 15 minutes.

Advantageously, the target tissue is exposed to an ultrasound energy source at an acoustic power density of from about 0.05 Wcm-2 to about 10 Wcm-2 with a frequency ranging from about 0.015 to about 10 MHz (see WO 98/52609). However, alternatives are also possible, for example, exposure to an ultrasound energy source at an acoustic power density of above 100 Wcm-2, but for reduced periods of time, for example, 1000 Wcm-2 for periods in the millisecond range or less.

Preferably the application of the ultrasound is in the form of multiple pulses; thus, both continuous wave and pulsed wave (pulsatile delivery of ultrasound) may be employed in any combination. For example, continuous wave ultrasound may be applied, followed by pulsed wave ultrasound, or vice versa. This may be repeated any number of times, in any order and combination. The pulsed wave ultrasound may be applied against a background of continuous wave ultrasound, and any number of pulses may be used in any number of groups.

Preferably, the ultrasound may comprise pulsed wave ultrasound. In a highly preferred embodiment, the ultrasound is applied at a power density of 0.7 Wcm-2 or 1.25 Wcm-2 as a continuous wave. Higher power densities may be employed if pulsed wave ultrasound is used.

Use of ultrasound is advantageous as, like light, it may be focused accurately on a target. Moreover, ultrasound is advantageous as it may be focused more deeply into tissues unlike light. It is therefore better suited to whole-tissue penetration (such as but not limited to a lobe of the liver) or whole organ (such as but not limited to the entire liver or an entire muscle, such as the heart) therapy. Another important advantage is that ultrasound is a non-invasive stimulus which is used in a wide variety of diagnostic and therapeutic applications. By way of example, ultrasound is well known in medical imaging techniques and, additionally, in orthopedic therapy. Furthermore, instruments suitable for the application of ultrasound to a subject vertebrate are widely available and their use is well known in the art.

In particular embodiments, the guide molecule is modified by a secondary structure to increase the specificity of the CRISPR-Cas system and the secondary structure can protect against exonuclease activity and allow for 5' additions to the guide sequence also referred to herein as a protected guide molecule.

In one aspect, the invention provides for hybridizing a "protector RNA" to a sequence of the guide molecule, wherein the "protector RNA" is an RNA strand complementary to the 3' end of the guide molecule to thereby generate a partially double-stranded guide RNA. In an embodiment of the invention, protecting mismatched bases (i.e. the bases of the guide molecule which do not form part of the guide sequence) with a perfectly complementary protector sequence decreases the likelihood of target RNA binding to the mismatched basepairs at the 3' end. In particular embodiments of the invention, additional sequences comprising an extended length may also be present within the guide molecule such that the guide comprises a protector sequence within the guide molecule. This "protector sequence" ensures that the guide molecule comprises a "protected sequence" in addition to an "exposed sequence" (comprising the part of the guide sequence hybridizing to the target sequence). In particular embodiments, the guide molecule is modified by the presence of the protector guide to comprise a secondary structure such as a hairpin. Advantageously there are three or four to thirty or more, e.g., about 10 or more, contiguous base pairs having complementarity to the protected sequence, the guide sequence or both. It is advantageous that the protected portion does not impede thermodynamics of the CRISPR-Cas system interacting with its target. By providing such an extension including a partially double stranded guide molecule, the guide molecule is considered protected and results in improved specific binding of the CRISPR-Cas complex, while maintaining specific activity.

In particular embodiments, use is made of a truncated guide (tru-guide), i.e. a guide molecule which comprises a guide sequence which is truncated in length with respect to the canonical guide sequence length. As described by Nowak et al. (Nucleic Acids Res (2016) 44 (20): 9555-9564), such guides may allow catalytically active CRISPR-Cas enzyme to bind its target without cleaving the target RNA. In particular embodiments, a truncated guide is used which allows the binding of the target but retains only nickase activity of the CRISPR-Cas enzyme.

CRISPR RNA-Targeting Effector Proteins

In one example embodiment, the CRISPR system effector protein is an RNA-targeting effector protein. In certain embodiments, the CRISPR system effector protein is a Type VI CRISPR system targeting RNA (e.g., Cas13a, Cas13b, Cas13c or Cas13d). Example RNA-targeting effector proteins include Cas13b and C2c2 (now known as Cas13a). It will be understood that the term "C2c2" herein is used interchangeably with "Cas13a". "C2c2" is now referred to as "Cas13a", and the terms are used interchangeably herein unless indicated otherwise. As used herein, the term "Cas13" refers to any Type VI CRISPR system targeting RNA (e.g., Cas13a, Cas13b, Cas13c or Cas13d). When the CRISPR protein is a C2c2 protein, a tracrRNA is not required. C2c2 has been described in Abudayyeh et al. (2016) "C2c2 is a single-component programmable RNA-guided RNA-targeting CRISPR effector"; Science; DOI:10.1126/science.aaf5573; and Shmakov et al. (2015) "Discovery and Functional Characterization of Diverse Class 2 CRISPR-Cas Systems", Molecular Cell, DOI: dx.doi.org/10.1016/j.molcel.2015.10.008; which are incorporated herein in their entirety by reference. Cas13b has been described in Smargon et al. (2017) "Cas13b Is a Type VI-B CRISPR-Associated RNA-Guided RNases Differentially Regulated by Accessory Proteins Csx27 and Csx28," Molecular Cell. 65, 1-13; dx.doi.org/10.1016/j.molcel.2016.12.023., which is incorporated herein in its entirety by reference.

In some embodiments, one or more elements of a nucleic acid-targeting system is derived from a particular organism comprising an endogenous CRISPR RNA-targeting system. In certain example embodiments, the effector protein CRISPR RNA-targeting system comprises at least one HEPN domain, including but not limited to the HEPN domains described herein, HEPN domains known in the art, and domains recognized to be HEPN domains by comparison to consensus sequence motifs. Several such domains are provided herein. In one non-limiting example, a consensus sequence can be derived from the sequences of C2c2 or Cas13b orthologs provided herein. In certain example embodiments, the effector protein comprises a single HEPN domain. In certain other example embodiments, the effector protein comprises two HEPN domains.

In one example embodiment, the effector protein comprise one or more HEPN domains comprising a RxxxxH motif sequence. The RxxxxH motif sequence can be, without limitation, from a HEPN domain described herein or a HEPN domain known in the art. RxxxxH motif sequences further include motif sequences created by combining portions of two or more HEPN domains. As noted, consensus sequences can be derived from the sequences of the orthologs disclosed in U.S. Provisional Patent Application 62/432,240 entitled "Novel CRISPR Enzymes and Systems," U.S. Provisional Patent Application 62/471,710 entitled "Novel Type VI CRISPR Orthologs and Systems" filed on Mar. 15, 2017, and U.S. Provisional Patent Application entitled "Novel Type VI CRISPR Orthologs and Systems," filed on Apr. 12, 2017.

In certain other example embodiments, the CRISPR system effector protein is a C2c2 nuclease. The activity of C2c2 may depend on the presence of two HEPN domains. These have been shown to be RNase domains, i.e. nuclease (in particular an endonuclease) cutting RNA. C2c2 HEPN may also target DNA, or potentially DNA and/or RNA. On the basis that the HEPN domains of C2c2 are at least capable of binding to and, in their wild-type form, cutting RNA, then it is preferred that the C2c2 effector protein has RNase function. Regarding C2c2 CRISPR systems, reference is made to U.S. Provisional 62/351,662 filed on Jun. 17, 2016 and U.S. Provisional 62/376,377 filed on Aug. 17, 2016. Reference is also made to U.S. Provisional 62/351,803 filed on Jun. 17, 2016. Reference is also made to U.S. Provisional entitled "Novel Crispr Enzymes and Systems" filed Dec. 8, 2016 bearing Broad Institute No. 10035.PA4. Reference is further made to East-Seletsky et al. "Two distinct RNase activities of CRISPR-C2c2 enable guide-RNA processing and RNA detection" Nature doi:10/1038/nature19802 and Abudayyeh et al. "C2c2 is a single-component programmable RNA-guided RNA targeting CRISPR effector" bioRxiv doi:10.1101/054742.

In certain embodiments, the C2c2 effector protein is from an organism of a genus selected from the group consisting of: *Leptotrichia, Listeria, Corynebacterium, Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor, Mycoplasma, Campylobacter,* and *Lachnospira*, or the C2c2 effector protein is an organism selected from the group consisting of: *Leptotrichia shahii, Leptotrichia. wadei, Listeria seeligeri, Clostridium aminophilum, Carnobacterium gallinarum, Paludibacter propionicigenes, Listeria weihenstephanensis*, or the C2c2 effector protein is a *L. wadei* F0279 or *L. wadei* F0279 (Lw2) C2C2 effector protein. In another embodiment, the one or more guide RNAs are designed to detect a single nucleotide polymorphism, splice variant of a transcript, or a frameshift mutation in a target RNA or DNA.

In certain example embodiments, the RNA-targeting effector protein is a Type VI-B effector protein, such as Cas13b and Group 29 or Group 30 proteins. In certain example embodiments, the RNA-targeting effector protein comprises one or more HEPN domains. In certain example embodiments, the RNA-targeting effector protein comprises a C-terminal HEPN domain, a N-terminal HEPN domain, or both. Regarding example Type VI-B effector proteins that may be used in the context of this invention, reference is made to U.S. application Ser. No. 15/331,792 entitled "Novel CRISPR Enzymes and Systems" and filed Oct. 21, 2016, International Patent Application No. PCT/US2016/058302 entitled "Novel CRISPR Enzymes and Systems", and filed Oct. 21, 2016, and Smargon et al. "Cas13b is a Type VI-B CRISPR-associated RNA-Guided RNase differentially regulated by accessory proteins Csx27 and Csx28" Molecular Cell, 65, 1-13 (2017); dx.doi.org/10.1016/j.molcel.2016.12.023, and U.S. Provisional Application No. to be assigned, entitled "Novel Cas13b Orthologues CRISPR Enzymes and System" filed Mar. 15, 2017. In particular embodiments, the Cas13b enzyme is derived from *Bergeyella zoohelcum*.

In certain example embodiments, the RNA-targeting effector protein is a Cas13c effector protein as disclosed in U.S. Provisional Patent Application No. 62/525,165 filed Jun. 26, 2017, and PCT Application No. US 2017/047193 filed Aug. 16, 2017.

In some embodiments, one or more elements of a nucleic acid-targeting system is derived from a particular organism comprising an endogenous CRISPR RNA-targeting system. In certain embodiments, the CRISPR RNA-targeting system is found in *Eubacterium* and *Ruminococcus*. In certain embodiments, the effector protein comprises targeted and collateral ssRNA cleavage activity. In certain embodiments, the effector protein comprises dual HEPN domains. In certain embodiments, the effector protein lacks a counterpart to the Helical-1 domain of Cas13a. In certain embodiments, the effector protein is smaller than previously characterized class 2 CRISPR effectors, with a median size of 928 aa. This median size is 190 aa (17%) less than that of Cas13c, more than 200 aa (18%) less than that of Cas13b, and more than 300 aa (26%) less than that of Cas13a. In certain embodiments, the effector protein has no requirement for a flanking sequence (e.g., PFS, PAM).

In certain embodiments, the effector protein locus structures include a WYL domain containing accessory protein (so denoted after three amino acids that were conserved in the originally identified group of these domains; see, e.g., WYL domain IPR026881). In certain embodiments, the WYL domain accessory protein comprises at least one helix-turn-helix (HTH) or ribbon-helix-helix (RHH) DNA-binding domain. In certain embodiments, the WYL domain containing accessory protein increases both the targeted and the collateral ssRNA cleavage activity of the RNA-targeting effector protein. In certain embodiments, the WYL domain containing accessory protein comprises an N-terminal RHH domain, as well as a pattern of primarily hydrophobic conserved residues, including an invariant tyrosine-leucine doublet corresponding to the original WYL motif. In certain embodiments, the WYL domain containing accessory protein is WYL1. WYL1 is a single WYL-domain protein associated primarily with *Ruminococcus*.

In other example embodiments, the Type VI RNA-targeting Cas enzyme is Cas13d. In certain embodiments, Cas13d is *Eubacterium siraeum* DSM 15702 (EsCas13d) or *Ruminococcus* sp. N15.MGS-57 (RspCas13d) (see, e.g., Yan et al., Cas13d Is a Compact RNA-Targeting Type VI CRISPR Effector Positively Modulated by a WYL-Domain-Containing Accessory Protein, Molecular Cell (2018), doi.org/10.1016/j.molcel.2018.02.028). RspCas13d and EsCas13d have no flanking sequence requirements (e.g., PFS, PAM).

Cas13 RNA Editing

In one aspect, the invention provides a method of modifying or editing a target transcript in a eukaryotic cell. In some embodiments, the method comprises allowing a CRISPR-Cas effector module complex to bind to the target polynucleotide to effect RNA base editing, wherein the CRISPR-Cas effector module complex comprises a Cas effector module complexed with a guide sequence hybridized to a target sequence within said target polynucleotide, wherein said guide sequence is linked to a direct repeat sequence. In some embodiments, the Cas effector module comprises a catalytically inactive CRISPR-Cas protein. In some embodiments, the guide sequence is designed to introduce one or more mismatches to the RNA/RNA duplex formed between the target sequence and the guide sequence. In particular embodiments, the mismatch is an A-C mismatch. In some embodiments, the Cas effector may associate with one or more functional domains (e.g. via fusion protein or suitable linkers). In some embodiments, the effector domain comprises one or more cytidine or adenosine deaminases that mediate endogenous editing of via hydrolytic deamination. In particular embodiments, the effector domain comprises the adenosine deaminase acting on RNA (ADAR) family of enzymes. In particular embodiments, the adenosine deaminase protein or catalytic domain thereof capable of deaminating adenosine or cytidine in RNA or is an RNA specific adenosine deaminase and/or is a bacterial, human, cephalopod, or *Drosophila* adenosine deaminase protein or catalytic domain thereof, preferably TadA, more preferably ADAR, optionally huADAR, optionally (hu)ADAR1 or (hu)ADAR2, preferably huADAR2 or catalytic domain thereof.

The present application relates to modifying a target RNA sequence of interest (see, e.g, Cox et al., Science. 2017 Nov. 24; 358(6366):1019-1027). Using RNA-targeting rather than DNA targeting offers several advantages relevant for therapeutic development. First, there are substantial safety benefits to targeting RNA: there will be fewer off-target events because the available sequence space in the transcriptome is significantly smaller than the genome, and if an off-target event does occur, it will be transient and less likely to induce negative side effects. Second, RNA-targeting therapeutics will be more efficient because they are cell-type independent and not have to enter the nucleus, making them easier to deliver.

A further aspect of the invention relates to the method and composition as envisaged herein for use in prophylactic or therapeutic treatment, preferably wherein said target locus of interest is within a human or animal and to methods of modifying an Adenine or Cytidine in a target RNA sequence of interest, comprising delivering to said target RNA, the composition as described herein. In particular embodiments, the CRISPR system and the adenosine deaminase, or catalytic domain thereof, are delivered as one or more polynucleotide molecules, as a ribonucleoprotein complex, optionally via particles, vesicles, or one or more viral vectors. In particular embodiments, the invention thus comprises compositions for use in therapy. This implies that the methods can be performed in vivo, ex vivo or in vitro. In particular embodiments, when the target is a human or animal target, the method is carried out ex vivo or in vitro.

A further aspect of the invention relates to the method as envisaged herein for use in prophylactic or therapeutic treatment, preferably wherein said target of interest is within a human or animal and to methods of modifying an Adenine or Cytidine in a target RNA sequence of interest, comprising delivering to said target RNA, the composition as described herein. In particular embodiments, the CRISPR system and the adenosine deaminase, or catalytic domain thereof, are delivered as one or more polynucleotide molecules, as a ribonucleoprotein complex, optionally via particles, vesicles, or one or more viral vectors.

In one aspect, the invention provides a method of generating a eukaryotic cell comprising a modified or edited gene. In some embodiments, the method comprises (a) introducing one or more vectors into a eukaryotic cell, wherein the one or more vectors drive expression of one or more of: Cas effector module, and a guide sequence linked to a direct repeat sequence, wherein the Cas effector module associate one or more effector domains that mediate base editing, and (b) allowing a CRISPR-Cas effector module complex to bind to a target polynucleotide to effect base editing of the target polynucleotide within said disease gene, wherein the CRISPR-Cas effector module complex comprises a Cas effector module complexed with the guide sequence that is hybridized to the target sequence within the target polynucleotide, wherein the guide sequence may be designed to introduce one or more mismatches between the RNA/RNA duplex formed between the guide sequence and the target sequence. In particular embodiments, the mismatch is an A-C mismatch. In some embodiments, the Cas effector may associate with one or more functional domains (e.g. via fusion protein or suitable linkers). In some embodiments, the effector domain comprises one or more cytidine or adenosine deaminases that mediate endogenous editing of via hydrolytic deamination. In particular embodiments, the effector domain comprises the adenosine deaminase acting on RNA (ADAR) family of enzymes. In particular embodiments, the adenosine deaminase protein or catalytic domain thereof capable of deaminating adenosine or cytidine in RNA or is an RNA specific adenosine deaminase and/or is a bacterial, human, cephalopod, or *Drosophila* adenosine deaminase protein or catalytic domain thereof, preferably TadA, more preferably ADAR, optionally huADAR, optionally (hu)ADAR1 or (hu)ADAR2, preferably huADAR2 or catalytic domain thereof.

A further aspect relates to an isolated cell obtained or obtainable from the methods described herein comprising the composition described herein or progeny of said modified cell, preferably wherein said cell comprises a hypoxanthine or a guanine in replace of said Adenine in said target RNA of interest compared to a corresponding cell not subjected to the method. In particular embodiments, the cell is a eukaryotic cell, preferably a human or non-human animal cell, optionally a therapeutic T cell or an antibody-producing B-cell.

In some embodiments, the modified cell is a therapeutic T cell, such as a T cell suitable for adoptive cell transfer therapies (e.g., CAR-T therapies). The modification may result in one or more desirable traits in the therapeutic T cell, as described further herein.

The invention further relates to a method for cell therapy, comprising administering to a patient in need thereof the modified cell described herein, wherein the presence of the modified cell remedies a disease in the patient.

The present invention may be further illustrated and extended based on aspects of CRISPR-Cas development and use as set forth in the following articles and particularly as relates to delivery of a CRISPR protein complex and uses of an RNA guided endonuclease in cells and organisms:

Multiplex genome engineering using CRISPR-Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR-Cas-Mediated Genome Engineering. Wang H., Yang H., Shivalila C S., Dawlaty M M., Cheng A W., Zhang F., Jaenisch R. Cell May 9; 153(4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463): 472-6. doi:10.1038/Nature12466. Epub 2013 Aug. 23 (2013);

Double Nicking by RNA-Guided CRISPR Cas9 for Enhanced Genome Editing Specificity. Ran, FA., Hsu, PD., Lin, CY., Gootenberg, J S., Konermann, S., Trevino, AE., Scott, DA., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, FA., Konermann, S., Agarwala, V., Li, Y., Fine, E., Wu, X., Shalem, O., Cradick, TJ., Marraffini, LA., Bao, G., & Zhang, F. Nat Biotechnol doi:10.1038/nbt.2647 (2013);

Genome engineering using the CRISPR-Cas9 system. Ran, FA., Hsu, PD., Wright, J., Agarwala, V., Scott, DA., Zhang, F. Nature Protocols November; 8(11):2281-308 (2013-B);

Genome-Scale CRISPR-Cas9 Knockout Screening in Human Cells. Shalem, O., Sanjana, NE., Hartenian, E., Shi, X., Scott, DA., Mikkelson, T., Heckl, D., Ebert, BL., Root, DE., Doench, JG., Zhang, F. Science December 12. (2013);

Crystal structure of cas9 in complex with guide RNA and target DNA. Nishimasu, H., Ran, FA., Hsu, PD., Konermann, S., Shehata, SI., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi:10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure™, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI:10.1016/j.cell.2014.09.014(2014);

Development and Applications of CRISPR-Cas9 for Genome Engineering, Hsu P D, Lander E S, Zhang F., Cell. June 5; 157(6):1262-78 (2014).

Genetic screens in human cells using the CRISPR-Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh 00, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546):186-91 (2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR-Cas9 cleavage of viral DNA efficiently suppresses hepatitis B virus," Scientific Reports 5:10833. doi:10.1038/srep10833 (Jun. 2, 2015)

Nishimasu et al., Crystal Structure of *Staphylococcus aureus* Cas9," Cell 162, 1113-1126 (Aug. 27, 2015)

BCL11A enhancer dissection by Cas9-mediated in situ saturating mutagenesis, Canver et al., Nature 527(7577): 192-7 (Nov. 12, 2015) doi:10.1038/nature15521. Epub 2015 Sep. 16.

*Cpf1 Is a Single RNA-Guided Endonuclease of a Class 2 CRISPR-Cas System*, Zetsche et al., Cell 163, 759-71 (Sep. 25, 2015).

*Discovery and Functional Characterization of Diverse Class 2 CRISPR-Cas Systems*, Shmakov et al., Molecular Cell, 60(3), 385-397 doi:10.1016/j.molcel.2015.10.008 Epub Oct. 22, 2015.

*Rationally engineered Cas9 nucleases with improved specificity*, Slaymaker et al., Science 2016 Jan. 1 351(6268): 84-88 doi: 0.1126/science.aad5227. Epub 2015 Dec. 1.

Gao et al, "Engineered Cpf1 Enzymes with Altered PAM Specificities," bioRxiv 091611; doi: http://dx.doi.org/10.1101/091611 (Dec. 4, 2016).

Cox et al., "RNA editing with CRISPR-Cas13," Science. 2017 Nov. 24; 358(6366):1019-1027. doi:10.1126/science.aaq0180. Epub 2017 Oct. 25.

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA: Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli,* 65% that were recovered contained the mutation.

Wang et al. (2013) used the CRISPR-Cas system for the one-step generation of mice carrying mutations in multiple genes which were traditionally generated in multiple steps by sequential recombination in embryonic stem cells and/or time-consuming intercrossing of mice with a single mutation. The CRISPR-Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and guide RNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR-Cas9 knockout and nucleotide preference at the cleavage site. The authors also found that the sequence preference for CRISPRi/a is substantially different from that for CRISPR-Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Canver et al. (2015) demonstrated a CRISPR-Cas9-based functional investigation of non-coding genomic elements. The authors we developed pooled CRISPR-Cas9 guide RNA libraries to perform in situ saturating mutagenesis of the human and mouse BCL11A enhancers which revealed critical features of the enhancers.

Zetsche et al. (2015) reported characterization of Cpf1, a class 2 CRISPR nuclease from *Francisella novicida* U112 having features distinct from Cas9. Cpf1 is a single RNA-guided endonuclease lacking tracrRNA, utilizes a T-rich protospacer-adjacent motif, and cleaves DNA via a staggered DNA double-stranded break.

Shmakov et al. (2015) reported three distinct Class 2 CRISPR-Cas systems. Two system CRISPR enzymes (C2c1 and C2c3) contain RuvC-like endonuclease domains distantly related to Cpf1. Unlike Cpf1, C2c1 depends on both crRNA and tracrRNA for DNA cleavage. The third enzyme (C2c2) contains two predicted HEPN RNase domains and is tracrRNA independent.

Slaymaker et al (2016) reported the use of structure-guided protein engineering to improve the specificity of *Streptococcus pyogenes* Cas9 (SpCas9). The authors developed "enhanced specificity" SpCas9 (eSpCas9) variants which maintained robust on-target cleavage with reduced off-target effects.

Cox et al., (2017) reported the use of catalytically inactive Cas13 (dCas13) to direct adenosine-to-inosine deaminase activity by ADAR2 (adenosine deaminase acting on RNA type 2) to transcripts in mammalian cells. The system, referred to as RNA Editing for Programmable A to I Replacement (REPAIR), has no strict sequence constraints and can be used to edit full-length transcripts. The authors further engineered the system to create a high-specificity variant and minimized the system to facilitate viral delivery.

The methods and tools provided herein are may be designed for use with or Cas13, a type II nuclease that does not make use of tracrRNA. Orthologs of Cas13 have been identified in different bacterial species as described herein. Further type II nucleases with similar properties can be identified using methods described in the art (Shmakov et al. 2015, 60:385-397; Abudayeh et al. 2016, Science, 5; 353 (6299)). In particular embodiments, such methods for identifying novel CRISPR effector proteins may comprise the steps of selecting sequences from the database encoding a seed which identifies the presence of a CRISPR Cas locus, identifying loci located within 10 kb of the seed comprising Open Reading Frames (ORFs) in the selected sequences, selecting therefrom loci comprising ORFs of which only a single ORF encodes a novel CRISPR effector having greater than 700 amino acids and no more than 90% homology to a known CRISPR effector. In particular embodiments, the seed is a protein that is common to the CRISPR-Cas system, such as Cas1. In further embodiments, the CRISPR array is used as a seed to identify new effector proteins.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

With respect to general information on CRISPR/Cas Systems, components thereof, and delivery of such components, including methods, materials, delivery vehicles, vectors, particles, and making and using thereof, including as to amounts and formulations, as well as CRISPR-Cas-expressing eukaryotic cells, CRISPR-Cas expressing eukaryotes, such as a mouse, reference is made to: U.S. Pat. Nos. 8,999,641, 8,993,233, 8,697,359, 8,771,945, 8,795,965, 8,865,406, 8,871,445, 8,889,356, 8,889,418, 8,895,308, 8,906,616, 8,932,814, and 8,945,839; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); Ser. No. 14/054,414 European Patent Applications EP 2 771 468 (EP13818570.7), EP 2 764 103 (EP13824232.6), and EP 2 784 162 (EP14170383.5); and PCT Patent Publications WO2014/093661 (PCT/US2013/074743), WO2014/093694 (PCT/US2013/074790), WO2014/093595 (PCT/US2013/074611), WO2014/093718 (PCT/US2013/074825), WO2014/093709 (PCT/US2013/074812), WO2014/093622 (PCT/US2013/074667), WO2014/093635 (PCT/US2013/074691), WO2014/093655 (PCT/US2013/074736), WO2014/093712 (PCT/US2013/074819), WO2014/093701 (PCT/US2013/074800), WO2014/018423 (PCT/US2013/051418), WO2014/204723 (PCT/US2014/041790), WO2014/204724 (PCT/US2014/041800), WO2014/204725 (PCT/US2014/041803), WO2014/204726 (PCT/US2014/041804), WO2014/204727 (PCT/US2014/041806), WO2014/204728 (PCT/US2014/041808), WO2014/204729 (PCT/US2014/041809), WO2015/089351 (PCT/US2014/069897), WO2015/089354 (PCT/US2014/069902), WO2015/089364 (PCT/US2014/069925), WO2015/089427 (PCT/US2014/070068), WO2015/089462 (PCT/US2014/070127), WO2015/089419 (PCT/US2014/070057), WO2015/089465 (PCT/US2014/070135), WO2015/089486 (PCT/US2014/070175), WO2015/058052 (PCT/US2014/061077), WO2015/070083 (PCT/US2014/064663), WO2015/089354 (PCT/US2014/069902), WO2015/089351 (PCT/US2014/069897), WO2015/089364 (PCT/US2014/069925), WO2015/089427 (PCT/US2014/070068), WO2015/089473 (PCT/US2014/070152), WO2015/089486 (PCT/US2014/070175), WO2016/049258 (PCT/US2015/051830), WO2016/094867 (PCT/US2015/065385), WO2016/094872 (PCT/US2015/065393), WO2016/094874 (PCT/US2015/065396), WO2016/106244 (PCT/US2015/067177).

Mention is also made of U.S. application 62/180,709, 17 Jun. 15, PROTECTED GUIDE RNAS (PGRNAS); U.S. application 62/091,455, filed, 12 Dec. 14, PROTECTED GUIDE RNAS (PGRNAS); U.S. application 62/096,708, 24 Dec. 14, PROTECTED GUIDE RNAS (PGRNAS); U.S. applications 62/091,462, 12 Dec. 14, 62/096,324, 23 Dec. 14, 62/180,681, 17 Jun. 2015, and 62/237,496, 5 Oct. 2015, DEAD GUIDES FOR CRISPR TRANSCRIPTION FACTORS; U.S. application 62/091,456, 12 Dec. 14 and 62/180,692, 17 Jun. 2015, ESCORTED AND FUNCTIONALIZED GUIDES FOR CRISPR-CAS SYSTEMS; U.S. application 62/091,461, 12 Dec. 14, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. application 62/094,903, 19 Dec. 14, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 14, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 14, 62/181,641, 18 Jun. 2015, and 62/181,667, 18 Jun. 2015, RNA-TARGETING SYSTEM; U.S. application 62/096,656, 24 Dec. 14 and 62/181,151, 17 Jun. 2015, CRISPR HAVING OR ASSOCIATED WITH DESTABILIZATION DOMAINS; U.S. application 62/096,697, 24 Dec. 14, CRISPR HAVING OR ASSOCIATED WITH AAV; U.S. application 62/098,158, 30 Dec. 14, ENGINEERED CRISPR COMPLEX INSERTIONAL TARGETING SYSTEMS; U.S. application 62/151,052, 22 Apr. 15, CELLULAR TARGETING FOR EXTRACELLULAR EXOSOMAL REPORTING; U.S. application 62/054,490, 24 Sep. 14, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 61/939,154, 12 Feb. 14, SYSTEMS, METHODS AND COMPOSITIONS FOR SEQUENCE MANIPULATION WITH OPTIMIZED FUNCTIONAL CRISPR-CAS SYSTEMS; U.S. application 62/055,484, 25 Sep. 14, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 14, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. applications 62/054,675, 24 Sep. 14 and 62/181,002, 17 Jun. 2015, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 14, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 14, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 14, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 14 and 62/181,690, 18 Jun. 2015, FUNCTIONAL SCREENING WITH OPTIMIZED FUNCTIONAL CRISPR-CAS SYSTEMS; U.S. application 62/055,487, 25 Sep. 14, FUNCTIONAL SCREENING WITH OPTIMIZED FUNCTIONAL CRISPR-CAS SYSTEMS; U.S. application 62/087,546, 4 Dec. 14 and 62/181,687, 18 Jun. 2015, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 14, CRISPR MEDIATED IN VIVO MODELING AND GENETIC SCREENING OF TUMOR GROWTH AND METASTASIS.

Mention is made of U.S. applications 62/181,659, 18 Jun. 2015 and 62/207,318, 19 Aug. 2015, ENGINEERING AND OPTIMIZATION OF SYSTEMS, METHODS, ENZYME AND GUIDE SCAFFOLDS OF CAS9 ORTHOLOGS AND VARIANTS FOR SEQUENCE MANIPULATION. Mention is made of U.S. applications 62/181,663, 18 Jun. 2015 and 62/245,264, 22 Oct. 2015, NOVEL CRISPR ENZYMES AND SYSTEMS, U.S. applications 62/181,675, 18 Jun. 2015, 62/285,349, 22 Oct. 2015, 62/296,522, 17 Feb. 2016, and 62/320,231, 8 Apr. 2016, NOVEL CRISPR ENZYMES AND SYSTEMS, U.S. application 62/232,067, 24 Sep. 2015, U.S. application Ser. No. 14/975,085, 18 Dec. 2015, European application No. 16150428.7, U.S. application 62/205,733, 16 Aug. 2015, U.S. application 62/201,542, 5 Aug. 2015, U.S. application 62/193,507, 16 Jul. 2015, and U.S. application 62/181,739, 18 Jun. 2015, each entitled NOVEL CRISPR ENZYMES AND SYSTEMS and of U.S. application 62/245,270, 22 Oct. 2015, NOVEL CRISPR ENZYMES AND SYSTEMS. Mention is also made of U.S. application 61/939,256, 12 Feb. 2014, and WO 2015/089473 (PCT/US2014/070152), 12 Dec. 2014, each entitled ENGINEERING OF SYSTEMS, METHODS AND OPTIMIZED GUIDE COMPOSITIONS WITH NEW ARCHITECTURES FOR SEQUENCE MANIPULATION. Mention is also made of PCT/US2015/045504, 15 Aug. 2015, U.S. application 62/180,699, 17 Jun. 2015, and U.S. application 62/038,358, 17 Aug. 2014, each entitled GENOME EDITING USING CAS9 NICKASES.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

In particular embodiments, pre-complexed guide RNA and CRISPR effector protein, (optionally, adenosine deaminase fused to a CRISPR protein or an adaptor) are delivered as a ribonucleoprotein (RNP). RNPs have the advantage that they lead to rapid editing effects even more so than the RNA method because this process avoids the need for transcription. An important advantage is that both RNP delivery is transient, reducing off-target effects and toxicity issues. Efficient genome editing in different cell types has been observed by Kim et al. (2014, Genome Res. 24(6):1012-9), Paix et al. (2015, Genetics 204(1):47-54), Chu et al. (2016, BMC Biotechnol. 16:4), and Wang et al. (2013, Cell. 9; 153(4):910-8).

In particular embodiments, the ribonucleoprotein is delivered by way of a polypeptide-based shuttle agent as described in WO2016161516. WO2016161516 describes efficient transduction of polypeptide cargos using synthetic peptides comprising an endosome leakage domain (ELD) operably linked to a cell penetrating domain (CPD), to a histidine-rich domain and a CPD. Similarly these polypeptides can be used for the delivery of CRISPR-effector based RNPs in eukaryotic cells.

ZN-Finger Nucleases

Other preferred tools for genome editing for use in the context of this invention include zinc finger systems and TALE systems. One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms. Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference.

Tale Systems

As disclosed herein editing can be made by way of the transcription activator-like effector nucleases (TALENs) system. Transcription activator-like effectors (TALEs) can be engineered to bind practically any desired DNA sequence. Exemplary methods of genome editing using the TALEN system can be found for example in Cermak T. Doyle E L. Christian M. Wang L. Zhang Y. Schmidt C, et al. Efficient design and assembly of custom TALEN and other TAL effector-based constructs for DNA targeting. Nucleic Acids Res. 2011; 39:e82; Zhang F. Cong L. Lodato S. Kosuri S. Church G M. Arlotta P Efficient construction of sequence-specific TAL effectors for modulating mammalian transcription. Nat Biotechnol. 2011; 29:149-153 and U.S. Pat. Nos. 8,450,471, 8,440,431 and 8,440,432, all of which are specifically incorporated by reference.

In advantageous embodiments of the invention, the methods provided herein use isolated, non-naturally occurring, recombinant or engineered DNA binding proteins that comprise TALE monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", or "TALE monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is X1-11-(X12X13)-X14-33 or 34 or 35, where the subscript indicates the amino acid position and X represents any amino acid. X12X13 indicate the RVDs. In some polypeptide monomers, the variable amino acid at position 13 is missing or absent and in such polypeptide monomers, the RVD consists of a single amino acid. In such cases the RVD may be alternatively represented as X*, where X represents X12 and (*) indicates that X13 is absent. The DNA binding domain comprises several repeats of TALE monomers and this may be represented as (X1-11-(X12X13)-X14-33 or 34 or 35)z, where in an advantageous embodiment, z is at least 5 to 40. In a further advantageous embodiment, z is at least 10 to 26.

The TALE monomers have a nucleotide binding affinity that is determined by the identity of the amino acids in its RVD. For example, polypeptide monomers with an RVD of NI preferentially bind to adenine (A), polypeptide monomers with an RVD of NG preferentially bind to thymine (T), polypeptide monomers with an RVD of HD preferentially bind to cytosine (C) and polypeptide monomers with an RVD of NN preferentially bind to both adenine (A) and guanine (G). In yet another embodiment of the invention, polypeptide monomers with an RVD of IG preferentially bind to T. Thus, the number and order of the polypeptide monomer repeats in the nucleic acid binding domain of a TALE determines its nucleic acid target specificity. In still further embodiments of the invention, polypeptide monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety.

The TALE polypeptides used in methods of the invention are isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In a preferred embodiment of the invention, polypeptide monomers having RVDs RN, NN, NK, SN, NH, KN, HN, NQ, HH, RG, KH, RH and SS preferentially bind to guanine. In a much more advantageous embodiment of the invention, polypeptide monomers having RVDs RN, NK, NQ, HH, KH, RH, SS and SN preferentially bind to guanine and thereby allow the generation of TALE polypeptides with high binding specificity for guanine containing target nucleic acid sequences. In an even more advantageous embodiment of the invention, polypeptide monomers having RVDs HH, KH, NH, NK, NQ, RH, RN and SS preferentially bind to guanine and thereby allow the generation of TALE polypeptides with high binding specificity for guanine containing target nucleic acid sequences. In a further advantageous embodiment, the RVDs that have high binding specificity for guanine are RN, NH RH and KH. Furthermore, polypeptide monomers having an RVD of NV preferentially bind to adenine and guanine. In more preferred embodiments of the invention, polypeptide monomers having RVDs of H*, HA, KA, N*, NA, NC, NS, RA, and S* bind to adenine, guanine, cytosine and thymine with comparable affinity.

The predetermined N-terminal to C-terminal order of the one or more polypeptide monomers of the nucleic acid or DNA binding domain determines the corresponding predetermined target nucleic acid sequence to which the TALE polypeptides will bind. As used herein the polypeptide monomers and at least one or more half polypeptide monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases this region may be referred to as repeat 0. In animal genomes, TALE binding sites do not necessarily have to begin with a thymine (T) and TALE polypeptides may target DNA sequences that begin with T, A, G or C. The tandem repeat of TALE monomers always ends with a half-length repeat or a stretch of sequence that may share identity with only the first 20 amino acids of a repetitive full length TALE monomer and this half repeat may be referred to as a half-monomer (FIG. 8), which is included in the term "TALE monomer". Therefore, it follows that the length of the nucleic acid or DNA being targeted is equal to the number of full polypeptide monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

An exemplary amino acid sequence of a N-terminal capping region is:

```
                                            (SEQ ID NO: 20)
M D P I R S R T P S P A R E L L S G P Q P D G V Q P

T A D R G V S P P A G G P L D G L P A R R T M S R T

R L P S P P A P S P A F S A D S F S D L L R Q F D P

S L F N T S L F D S L P P F G A H H T E A A T G E W

D E V Q S G L R A A D A P P P T M R V A V T A A R P

P R A K P A P R R R A A Q P S D A S P A A Q V D L R

T L G Y S Q Q Q Q E K I K P K V R S T V A Q H H E A

L V G H G F T H A H I V A L S Q H P A A L G T V A V

K Y Q D M I A A L P E A T H E A I V G V G K Q W S G

A R A L E A L L T V A G E L R G P P L Q L D T G Q L
```

-continued

```
L K I A K R G G V T A V E A V H A W R N A L T G A P
L N
```

An exemplary amino acid sequence of a C-terminal capping region is:

```
                                              (SEQ ID NO: 21)
R P A L E S I V A Q L S R P D P A L A A L T N D H L
V A L A C L G G R P A L D A V K K G L P H A P A L I
K R T N R R I P E R T S H R V A D H A Q V V R V L G
F F Q C H S H P A Q A F D D A M T Q F G M S R H G L
L Q L F R R V G V T E L E A R S G T L P P A S Q R W
D R I L Q A S G M K R A K P S P T S T Q T P D Q A S
L H A F A D S L E R D L D A P S P M H E G D Q T R A
S
```

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full length capping region, while fragments that include the C-terminal 20 amino acids retain greater than 50% of the efficacy of the full length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies may be generated by any of a number of computer programs known in the art, which include but are not limited to BLAST or FASTA. Suitable computer program for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In advantageous embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an mSin interaction domain (SID). SID4X domain or a Kruppel-associated box (KRAB) or fragments of the KRAB domain. In some embodiments the effector domain is an enhancer of transcription (i.e. an activation domain), such as the VP16, VP64 or p65 activation domain. In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination the activities described herein.

Meganucleases

As disclosed herein editing can be made by way of meganucleases, which are endodeoxyribonucleases characterized by a large recognition site (double-stranded DNA sequences of 12 to 40 base pairs). Exemplary method for using meganucleases can be found in U.S. Pat. Nos. 8,163,514; 8,133,697; 8,021,867; 8,119,361; 8,119,381; 8,124,369; and 8,129,134, which are specifically incorporated by reference.

Transcriptional Activation/Repression

In certain embodiments, an immunomodulant may comprise (i) a DNA-binding portion configured to specifically bind to the endogenous gene and (ii) an effector domain mediating a biological activity.

In certain embodiments, the DNA-binding portion may comprises a zinc finger protein or DNA-binding domain thereof, a transcription activator-like effector (TALE) protein or DNA-binding domain thereof, or an RNA-guided protein or DNA-binding domain thereof.

In certain embodiments, the DNA-binding portion may comprise (i) Cas9 or Cpf1 or any Cas protein described herein modified to eliminate its nuclease activity, or (ii) DNA-binding domain of Cas9 or Cpf1 or any Cas protein described herein.

In some embodiments, the effector domain may be a transcriptional inhibitor (i.e., a repressor domain), such as an mSin interaction domain (SID). SID4X domain or a Kruppel-associated box (KRAB) or fragments of the KRAB domain. In some embodiments the effector domain may be an enhancer of transcription (i.e. an activation domain), such as the VP16, VP64 or p65 activation domain. In some embodiments, the nucleic acid binding portion may be linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal. In some embodiments, the effector domain may be a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination the activities described herein.

In certain embodiments, the agent capable of specifically binding to a gene product expressed on the cell surface of the immune cell is an antibody.

By means of an example, an agent, such as an antibody, capable of specifically binding to a gene product expressed on the cell surface of the immune cells may be conjugated with a therapeutic or effector agent for targeted delivery of the therapeutic or effector agent to the immune cells.

Examples of such therapeutic or effector agents include immunomodulatory classes as discussed herein, such as without limitation a toxin, drug, radionuclide, cytokine, lymphokine, chemokine, growth factor, tumor necrosis factor, hormone, hormone antagonist, enzyme, oligonucleotide, siRNA, RNAi, photoactive therapeutic agent, anti-angiogenic agent and pro-apoptotic agent.

Example toxins include ricin, abrin, alpha toxin, saporin, ribonuclease (RNase), DNase I, Staphylococcal enterotoxin-A, pokeweed antiviral protein, gelonin, diphtheria toxin, *Pseudomonas* exotoxin, or *Pseudomonas* endotoxin.

Example radionuclides include $^{103m}$Rh, $^{103}$Ru, $^{105}$Rh, $^{105}$Ru, $^{107}$Hg, $^{109}$Pd, $^{109}$Pt, $^{111}$Ag, $^{111}$In, $^{113m}$In $^{119}$Sb, $^{11}$C, $^{121m}$Te, $^{122m}$Te, $^{125}$I, $^{125m}$Te, $^{126}$I, $^{131}$I, $^{133}$I, $^{13}$N, $^{142}$Pr, $^{143}$Pr, $^{149}$Pm, $^{152}$Dy, $^{153}$Sm, $^{15}$O, $^{161}$Ho, $^{161}$Tb, $^{165}$Tm, $^{166}$Dy, $^{166}$Ho, $^{167}$Tm, $^{168}$Tm, $^{169}$Er, $^{169}$Yb, $^{177}$Lu, $^{186}$Re, $^{188}$Re, $^{189m}$OS, $^{189}$Re, $^{192}$Ir, $^{194}$Ir, $^{197}$Pt, $^{198}$Au, $^{199}$Au, $^{201}$Tl, $^{203}$Hg, $^{211}$At, $^{211}$Bi, $^{211}$Pb, $^{212}$Bi, $^{212}$Pb, $^{213}$Bi, $^{215}$Po, $^{217}$At, $^{219}$Rn, $^{221}$Fr, $^{223}$Ra, $^{224}$Ac, $^{225}$Ac, $^{225}$Fm, $^{32}$P, $^{33}$P, $^{47}$Sc, $^{51}$Cr, $^{57}$Co, $^{58}$Co, $^{59}$Fe, $^{62}$Cu, $^{67}$Cu, $^{67}$Ga, $^{75}$Br, $^{75}$Se, $^{76}$Br, $^{77}$As, $^{77}$Br, $^{80m}$Br, $^{89}$Sr, $^{90}$Y, $^{95}$Ru, $^{97}$Ru, $^{99}$Mo or $^{99m}$Tc. Preferably, the radionuclide may be an alpha-particle-emitting radionuclide.

Example enzymes include malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase or acetylcholinesterase. Such enzymes may be used, for example, in combination with prodrugs that are administered in relatively non-toxic form and converted at the target site by the enzyme into a cytotoxic agent. In other alternatives, a drug may be converted into less toxic form by endogenous enzymes in the subject but may be reconverted into a cytotoxic form by the therapeutic enzyme.

Kits

In another aspect, the invention is directed to kit and kit of parts. The terms "kit of parts" and "kit" as used throughout this specification refer to a product containing components necessary for carrying out the specified methods (e.g., methods for detecting, quantifying or isolating immune cells as taught herein), packed so as to allow their transport and storage. Materials suitable for packing the components comprised in a kit include crystal, plastic (e.g., polyethylene, polypropylene, polycarbonate), bottles, flasks, vials, ampules, paper, envelopes, or other types of containers, carriers or supports. Where a kit comprises a plurality of components, at least a subset of the components (e.g., two or more of the plurality of components) or all of the components may be physically separated, e.g., comprised in or on separate containers, carriers or supports. The components comprised in a kit may be sufficient or may not be sufficient for carrying out the specified methods, such that external reagents or substances may not be necessary or may be necessary for performing the methods, respectively. Typically, kits are employed in conjunction with standard laboratory equipment, such as liquid handling equipment, environment (e.g., temperature) controlling equipment, analytical instruments, etc. In addition to the recited binding agents(s) as taught herein, such as for example, antibodies, hybridization probes, amplification and/or sequencing primers, optionally provided on arrays or microarrays, the present kits may also include some or all of solvents, buffers (such as for example but without limitation histidine-buffers, citrate-buffers, succinate-buffers, acetate-buffers, phosphate-buffers, formate buffers, benzoate buffers, TRIS (Tris (hydroxymethyl)-aminomethane) buffers or maleate buffers, or mixtures thereof), enzymes (such as for example but without limitation thermostable DNA polymerase), detectable labels, detection reagents, and control formulations (positive and/or negative), useful in the specified methods. Typically, the kits may also include instructions for use thereof, such as on a printed insert or on a computer readable medium. The terms may be used interchangeably with the term "article of manufacture", which broadly encompasses any man-made tangible structural product, when used in the present context.

The invention is further described in the following examples, which do not limit the scope of the invention described in the claims.

EXAMPLES

Example 1—Identification of CD8+ TIL Sub-Types in Melanoma Patients Treated with Checkpoint Blockade Therapy Applicants obtained samples from melanoma patients receiving checkpoint blockade therapy both before they received treatment and after they received treatment with a checkpoint inhibitor (3 patients were treated with anti-CTLA4, 2 were treated with a combination of anti-CTLA4+ anti-PD1 and the rest were treated with anti-PD1).

Figure 2:
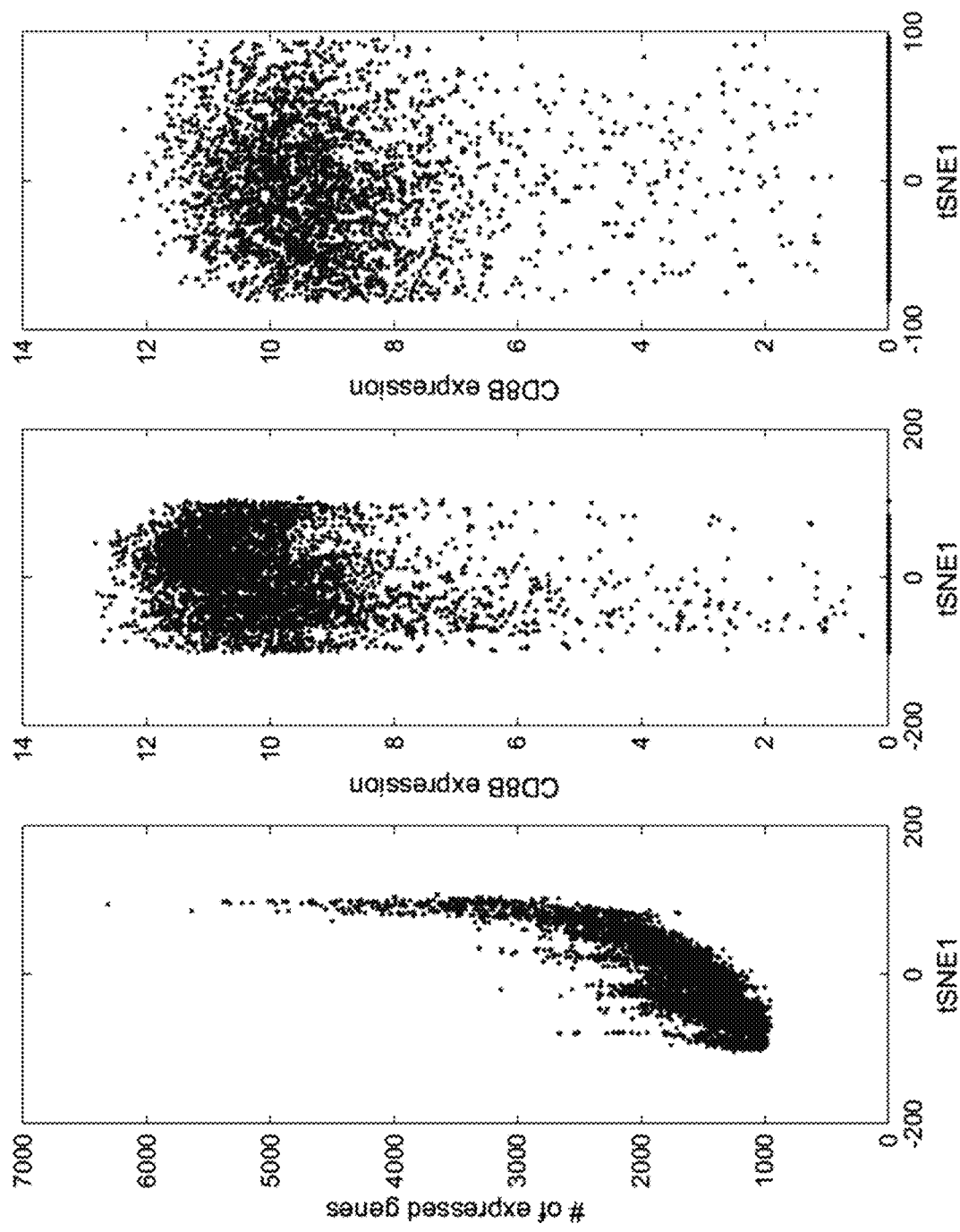
FIG. 2—illustrates tSNE analysis based on most variable genes in CD8 cells. tSNE1 is correlated with the number of expressed genes. As a control, expression of CD8A\CD8B is not correlated with tSNE score FIG. 3—illustrates clustering by tSNE analysis of single cells and association with response to check point blockade therapy.

Single immune cells from these patient samples were each sequenced by RNA-seq and computational analysis was performed on each immune cell type to determine whether there was a correlation between immune cells and how well or not well the patient responded to the treatment. FIG. 1 shows the mean expression of genes in the single cells and shows the variability of gene expression between single cells. A threshold was established, such that genes with (var\mean)>6 and genes that were expressed in at least 5% of the cells were selected. About 4000 genes were selected and the results were robust to this threshold. Dimension reduction is performed such that the genes with the most variance are used to further cluster the cells (e.g., tSNE analysis). Applicants performed tSNE analysis using tSNE1 based on the most variable genes in CD8+ cells (FIG. 2). tSNE1 is correlated with the number of expressed genes (FIG. 2, left). As a control, expression of CD8A\CD8B is not correlated with tSNE score (FIG. 2, middle and right). In other words, the level of expression of the genes in tSNE1 did not correlate to expression of CD8A\CD8B.

Figure 3:
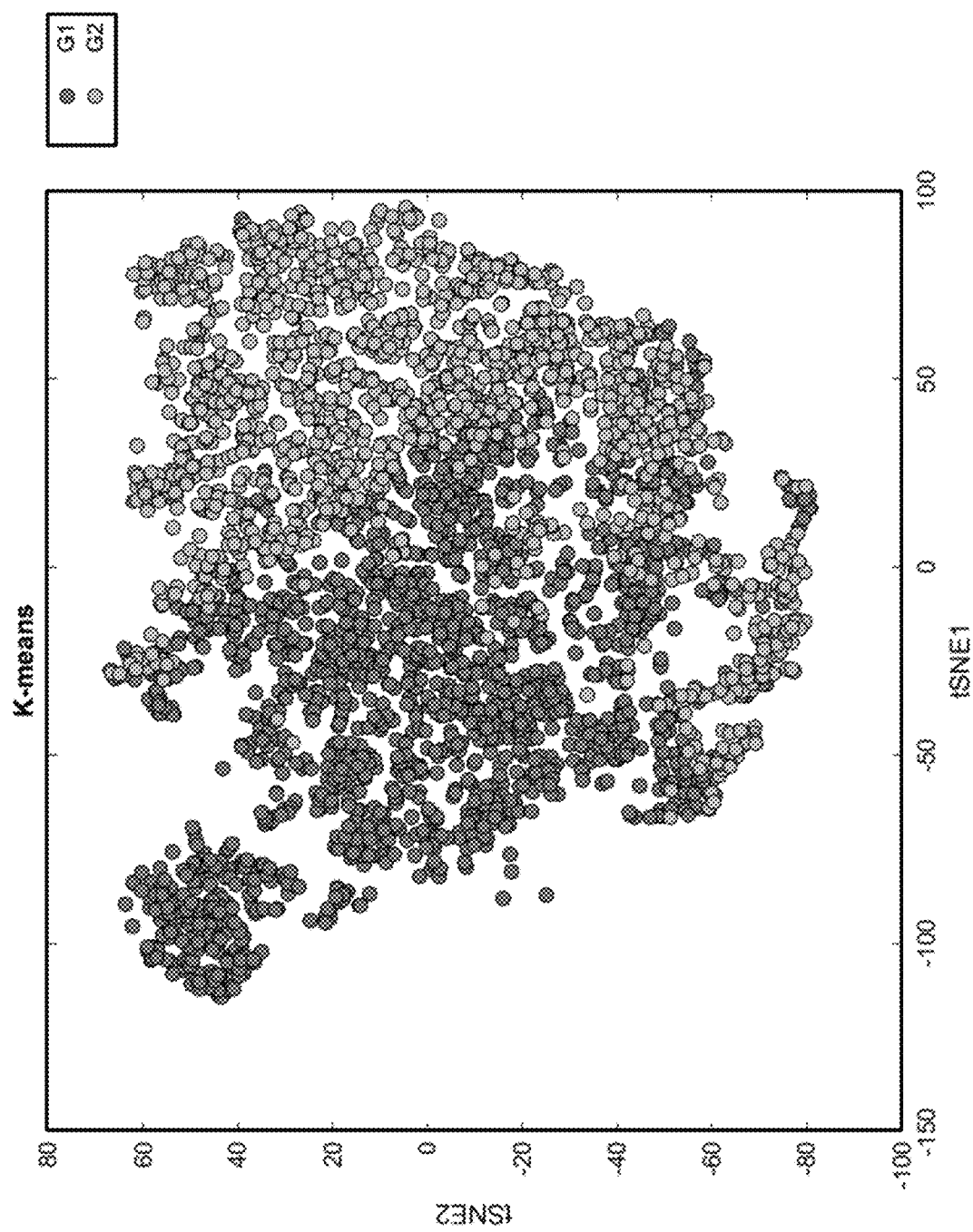
Figure 4:
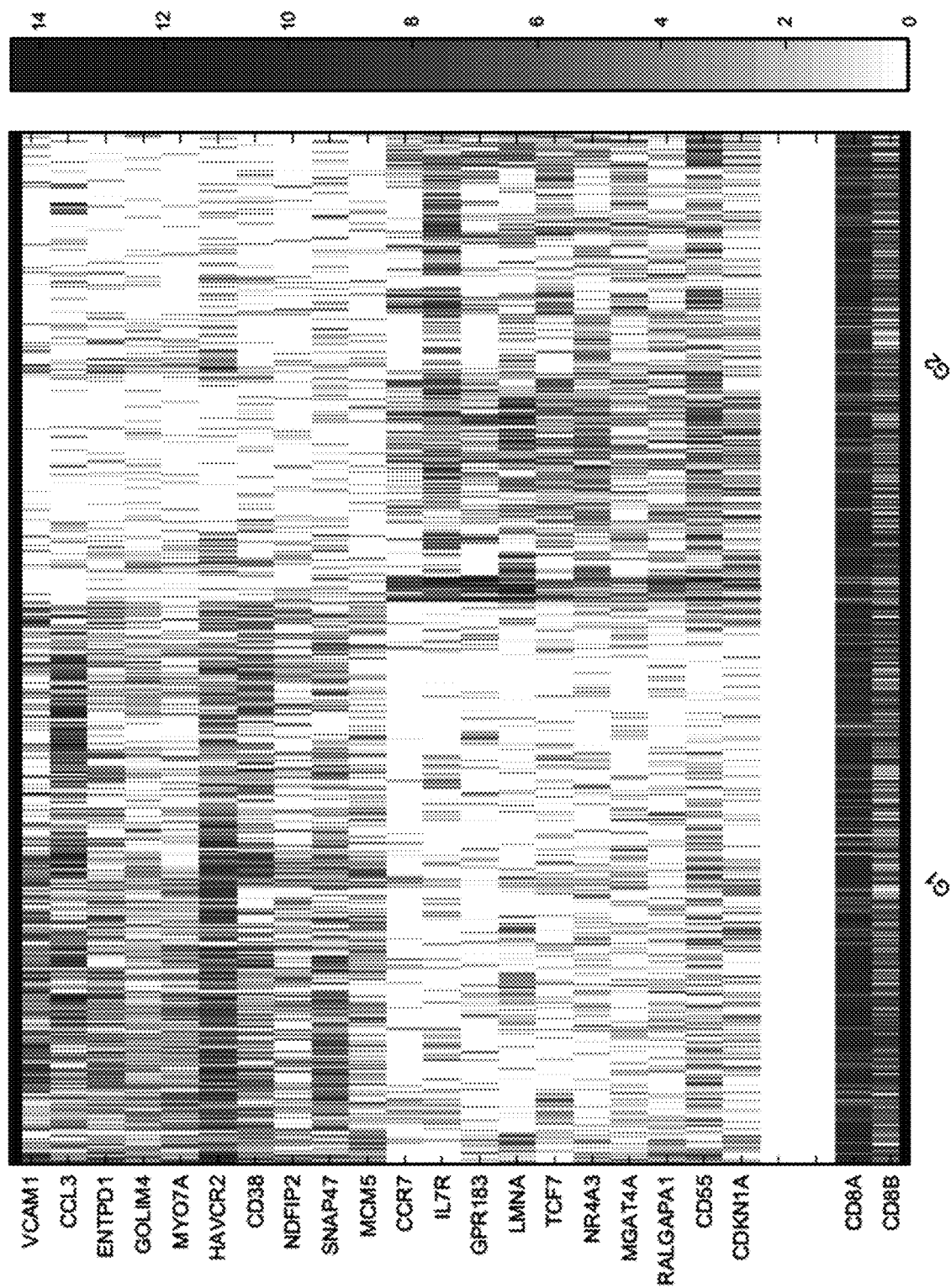
FIG. 4—illustrates a heatmap of genes in the clusters from FIG. 3.

CD8+ TILs were clustered into two groups (dark—G1; light—G2) according to tSNE1 and tSNE2 (FIG. 3). Starting with two clusters, applicants clearly see one cluster (G1) enriched with inhibitory receptors and the other one (G2) enriched with memory and differentiation genes (FIG. 4). Group 2 CD8+ TILs are not functional.

Figure 5:
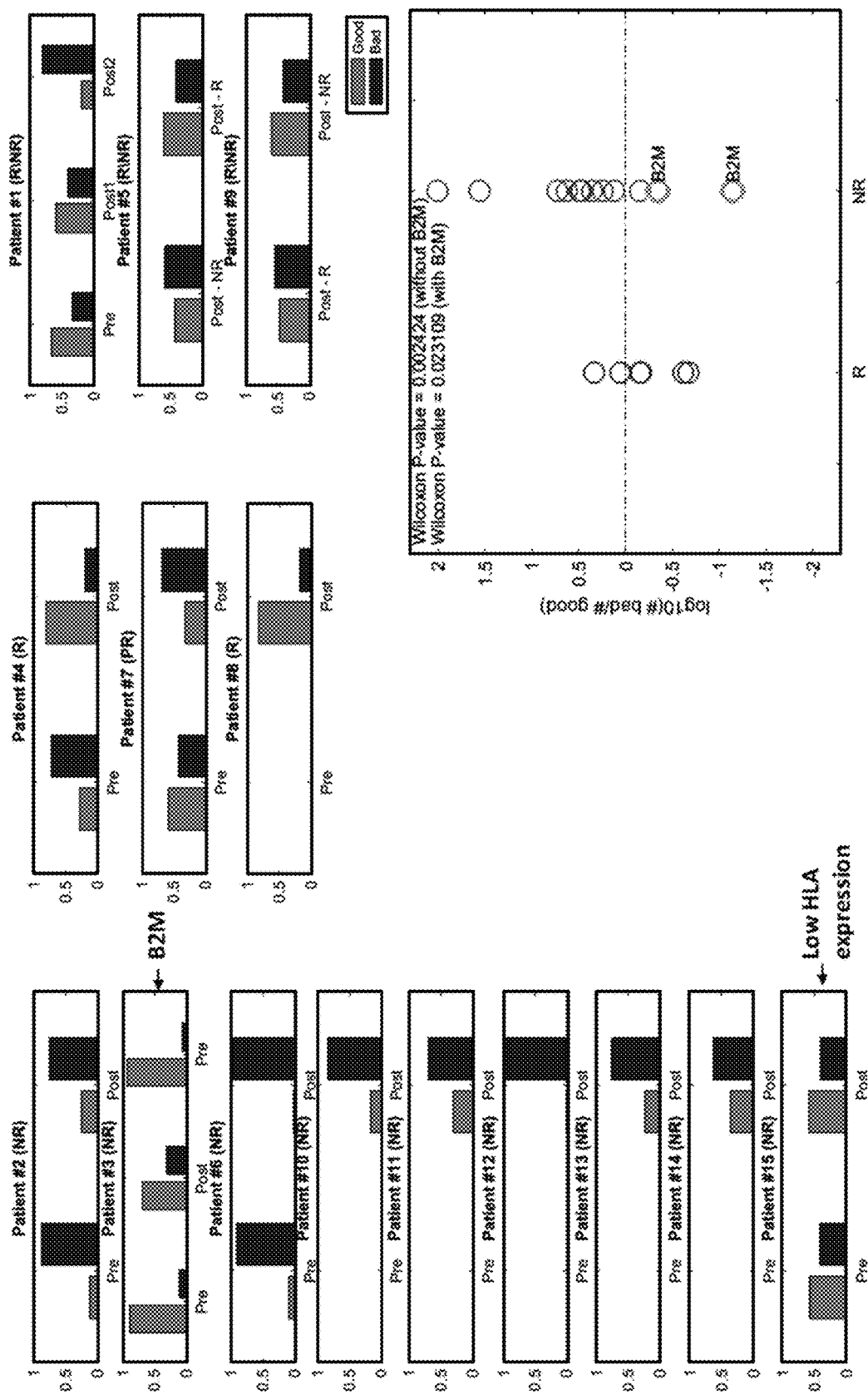
FIG. 5—illustrates the percentage of cells having a non-responder (Bad) and responder (Good) signature in patients that responded (R) or did not respond (NR) to checkpoint blockade therapy.

Example 2—the Ratio of CD8+ TIL Subtypes Correlates to Response to Checkpoint Blockade Therapy Applicants discovered a correlation in the CD8+ T cell context in that group 1 was enriched in non-responders to checkpoint blockade therapy and group 2 was enriched in responders to checkpoint blockade therapy (FIG. 5). There are some intermediate cells between the two clusters, but in this analysis Applicants divided the cells only into two clusters. For each patient Applicants measured the ratio between responder and non-responder cells. Overall there are more responder cells in responders and vice versa. Outliers in the non-responder group were deficient in expression of genes associated with antigen presentation (e.g., B2M and HLA).

Applicants determined combinations of genes corresponding to the non-responder gene signature, such that the combinations of genes detected in the "non-responder" subpopulation can be used to distinguish "non-responder" from "responder" CD8+ T Cells. One combination comprises LAYN, GEM, VCAM1, RDH10, TNFRSF18, FAM3C, AFAP1L2, KIR2DL4, MTSS1, ETV1, CTLA4, MYO7A, ENTPD1, TNFRSF9, CADM1, DFNB31, CXCL13, HAVCR2, GPR56, GOLIM4, NAB1, PHLDA1, TGIF1, SEC14L1, IGFLR1, NAMPTL, PAM, HSPB1, TNIP3, BPGM, TP53INP1, TRPS1, UBE2F, NDFIP2, PON2, PELI1, METRNL, SNAP47, APLP2 and/or PDCD1. Another combination comprises the genes in ranked order CD38, CCL3, VCAM1, MYO7A, GOLIM4, HAVCR2, MCM5, NDFIP2, WARS, STMN1, LSM2, PRDX3, MTHFD1, SKA2, ENTPD1, SNAP47, FASLG, IFI35, PTTG1, DNPH1, EPSTI1, UBE2F, NMI, ACP5, CCR5, TRAFD1 and PDCD1. In preferred embodiments, the combination of non-responder signature comprises the genes in ranked order CD38, CCL3, VCAM1, GOLIM4, HAVCR2, PRDX3, ENTPD1, PTTG1, CCR5, TRAFD1, PDCD1, CXCR6, BATF, PTPN6, LAG3 and CTLA4. In certain embodiments, the non-responder signature comprises one or more genes, starting at the first gene and ending at the last gene, according to the ranked order.

Applicants determined that the ratio of CD8+ TILs having a non-responder signature and responder signature could be used to predict the response to checkpoint blockade therapy. Applicants measured CD8+ TIL populations in pre-treatment and post treatment samples (FIG. 5). The responder subpopulation was enriched in samples from patients who responded to checkpoint blockade therapy and the non-responder subpopulation was enriched in samples from patients who did not respond. More than one or two known inhibitory receptors are expressed on the non-responder cells. In the non-responder signature, there are receptors that could be used as potential targets (e.g., KIR2DL4 and ENTPD1). Targeting more than one receptor can be more effective than a single checkpoint blockade therapy.

Example 3—Further Cluster Analysis of CD8+ TIL Sub-Types

Figure 6:
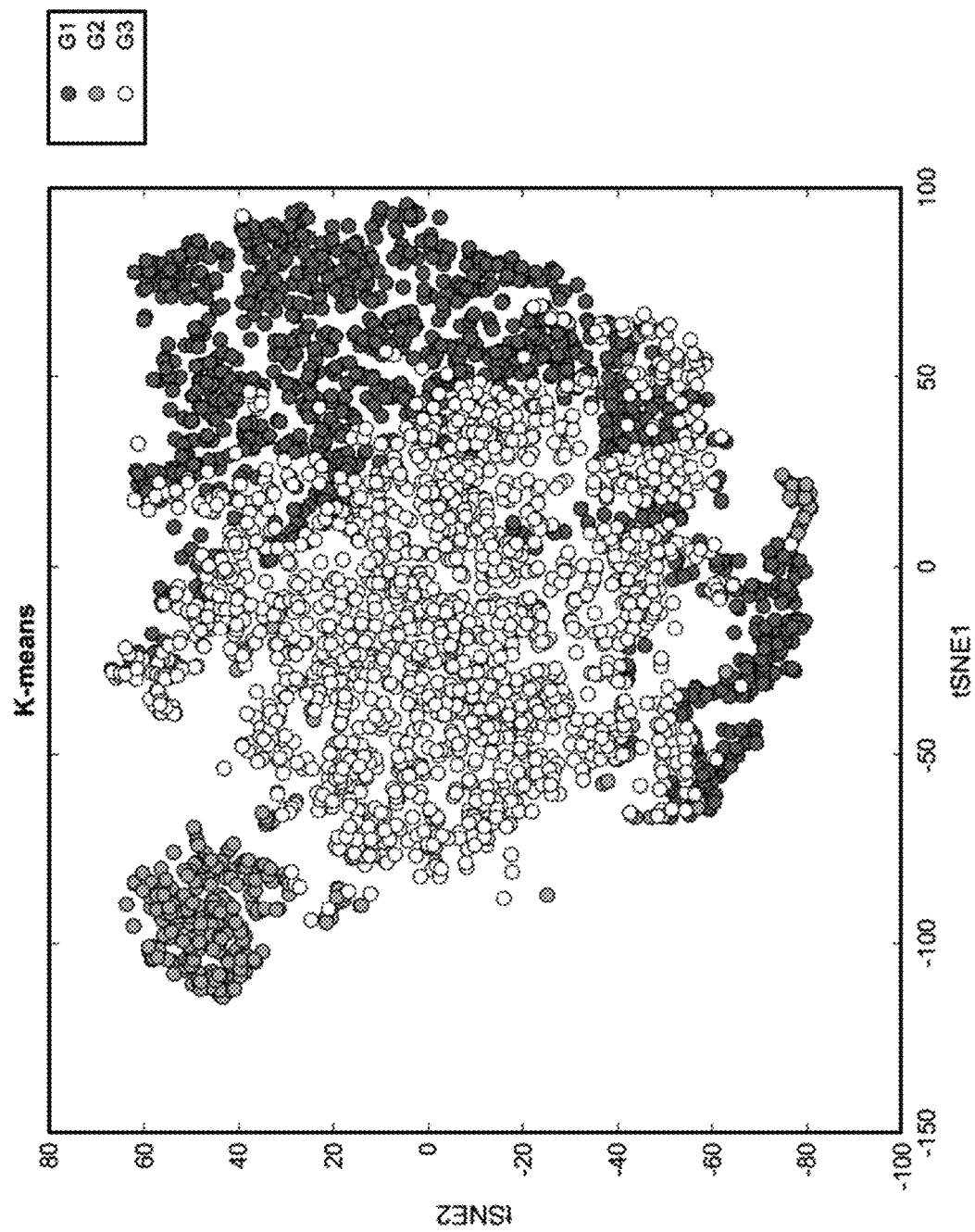
FIG. 6—illustrates further cluster analysis showing the non-responder cluster can be split into two clusters.
Figure 7:
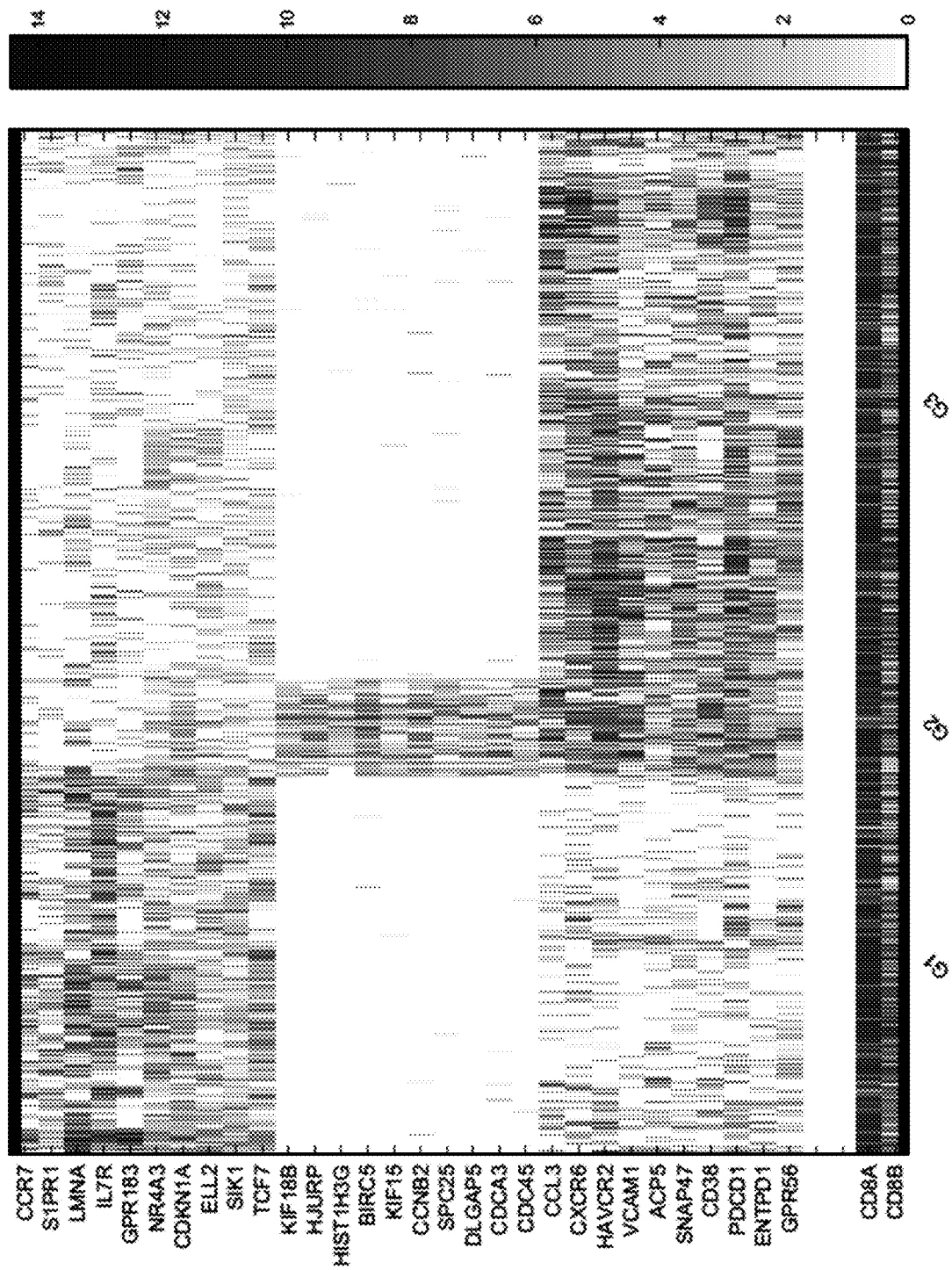
FIG. 7—illustrates a heatmap of genes in the clusters from FIG. 6.

Applicants performed further clustering analysis and determined that the "non-responder" cluster can be split into two clusters (G2 & G3) (FIG. 6). Both clusters express co-inhibitory receptors, but a subset of the cells (G2) also have a high expression of cell cycle genes (FIG. 7).

Figure 8:
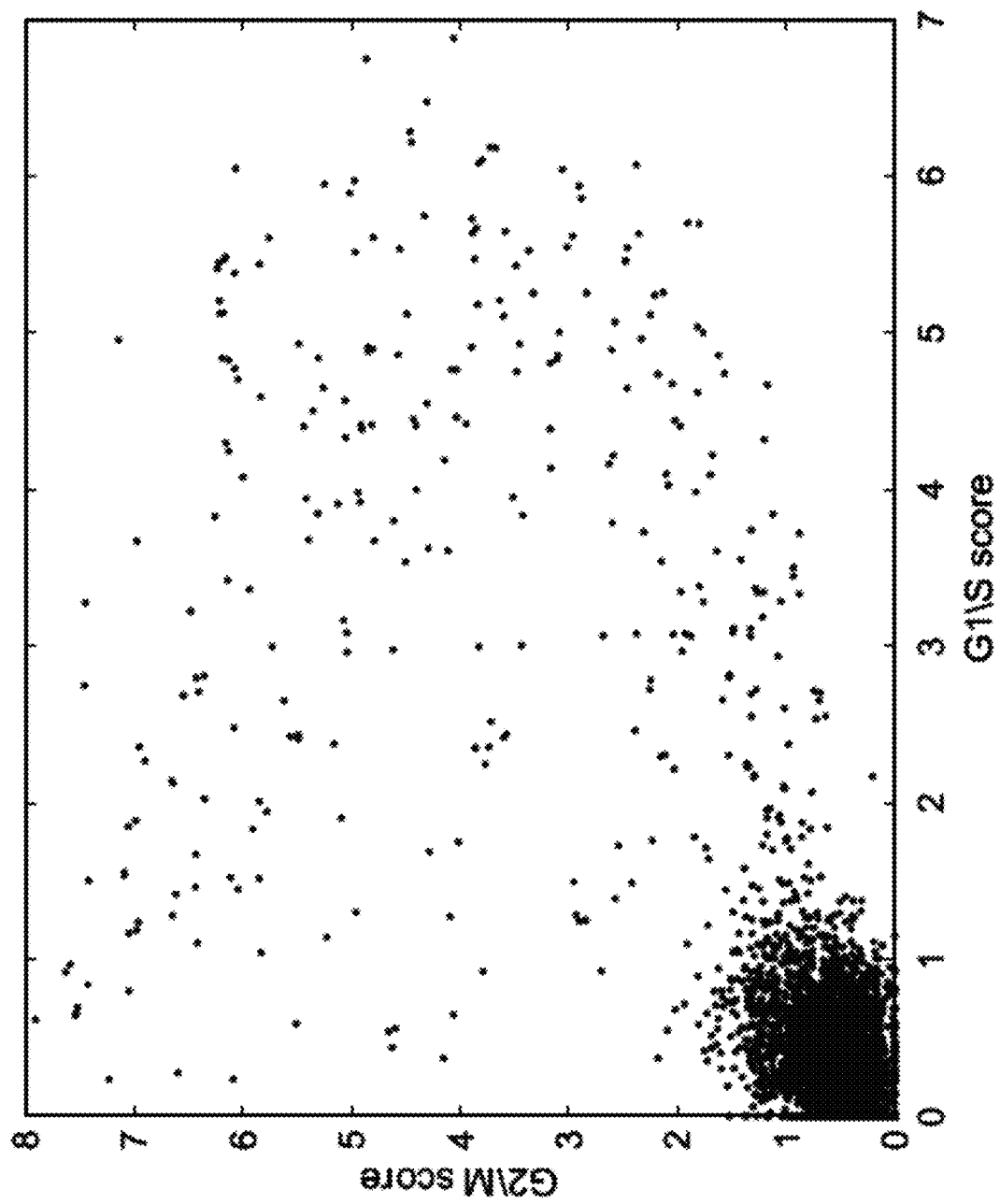
FIG. 8—illustrates cell cycle analysis of the single cells.
Figure 9:
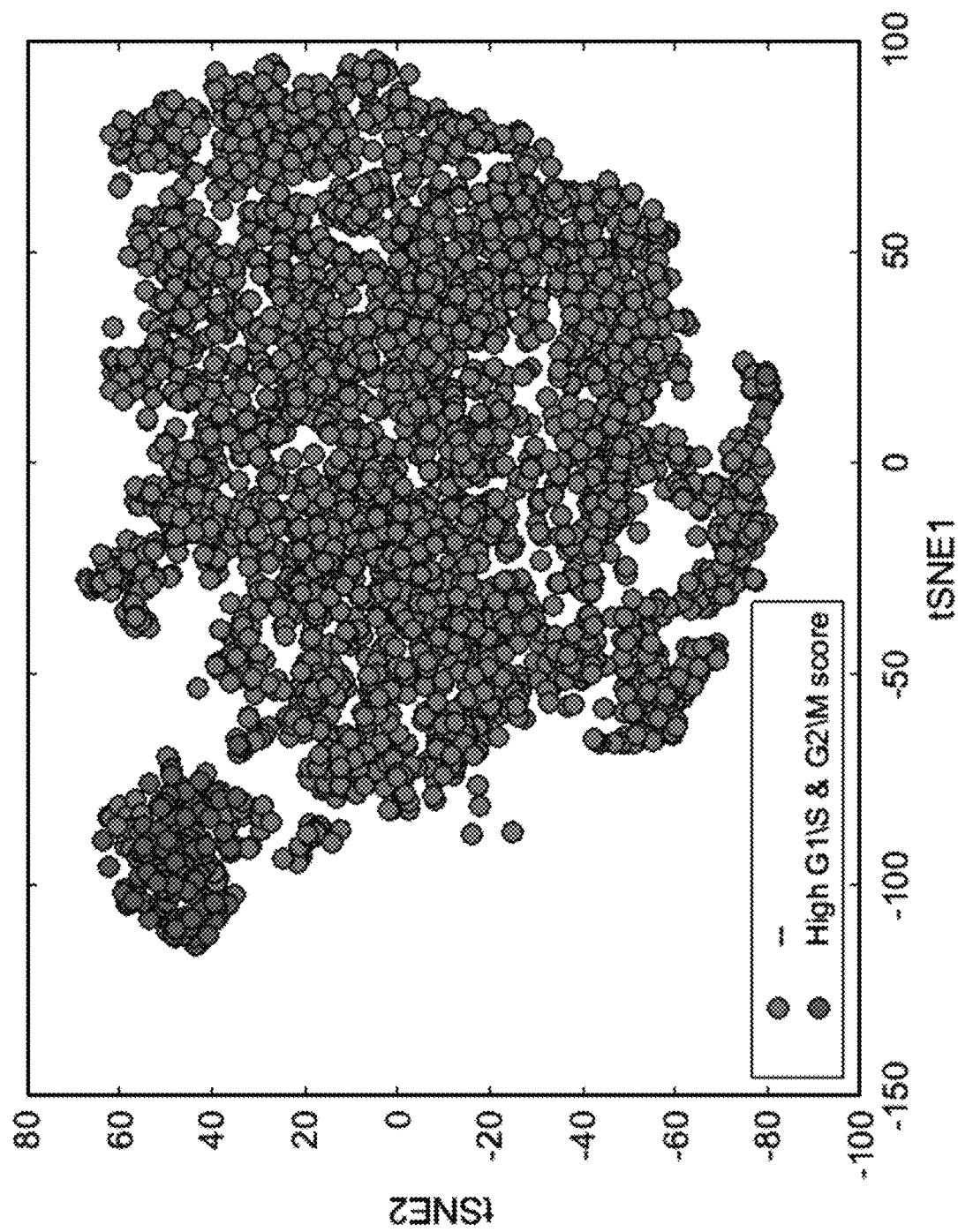
FIG. 9—illustrates a cell cycle cluster based on FIG. 8.

Applicants performed cell cycle analysis of CD8+ TILs (FIG. 8, 9). G1\S and G2\M scores are based on the average expression of genes from Tirosh, I., et al. (2016, Dissecting the multicellular ecosystem of metastatic melanoma by single-cell RNA-seq. Science 352, 189-196). Cells with a high G1\S and G2\M score correspond to the cell cycle cluster.

Figure 10:
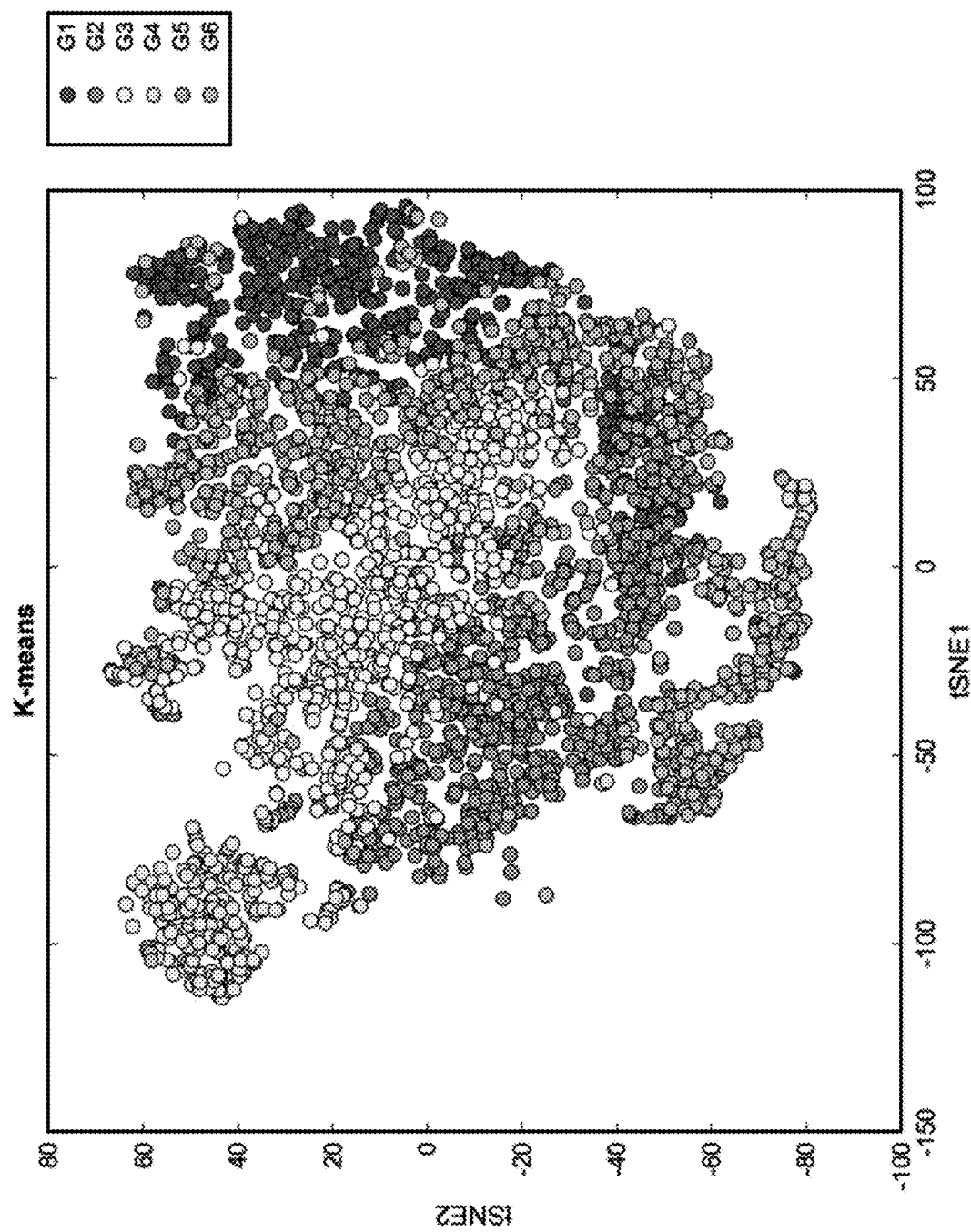
FIG. 10—illustrates further cluster analysis showing the T cells can be separated into 6 clusters.
Figure 11:
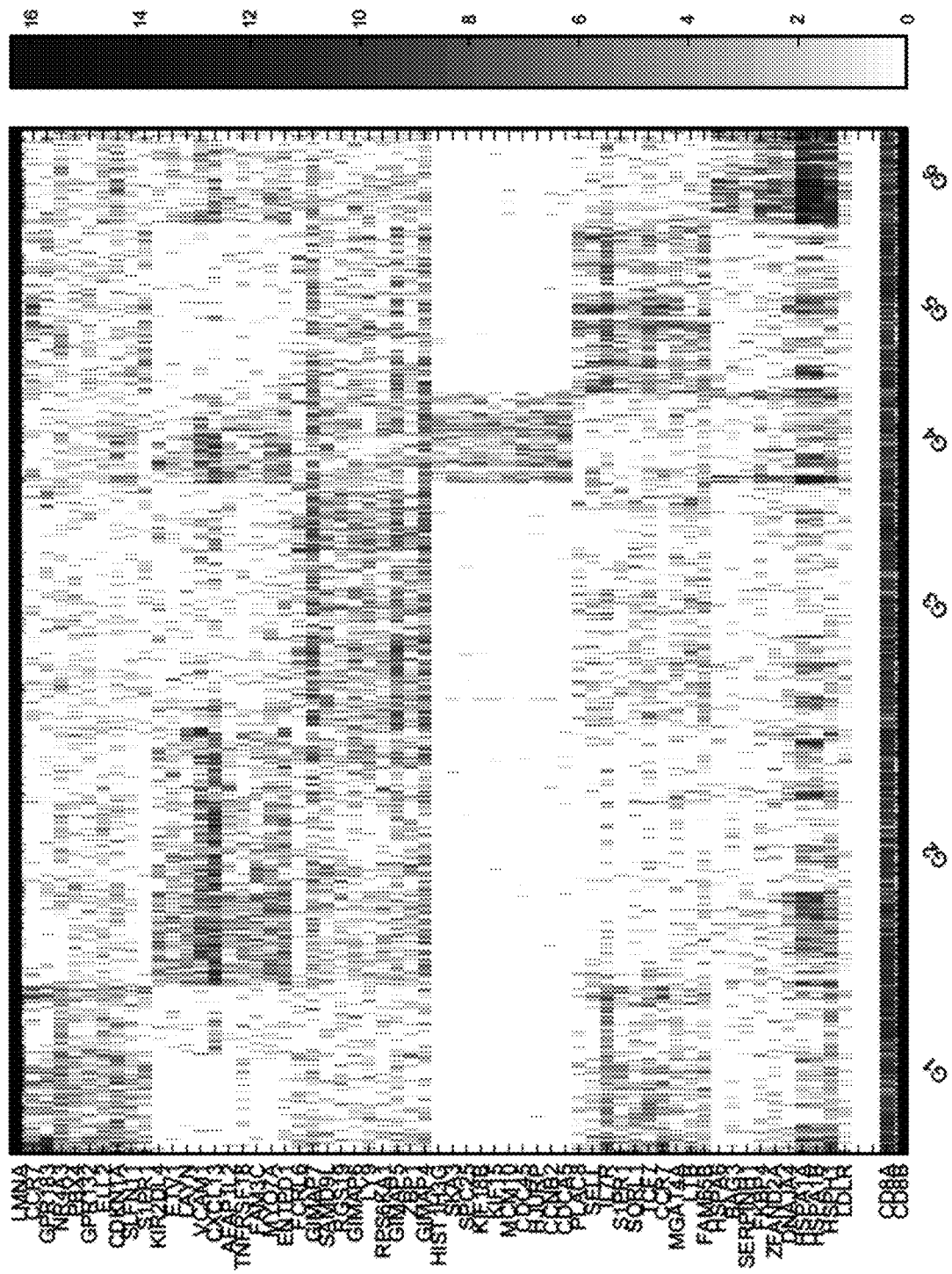
FIG. 11—illustrates a heatmap of genes in the clusters from FIG. 10.

Further clustering analysis indicated that the CD8+ TILs can be divided into 6 clusters (FIG. 10). Expression of genes in each cluster is shown in a heatmap (FIG. 11). Expression of genes in G1 related to activation (response to stimulation), G2 related to exhaustion genes, G4 related to cell cycle genes, G5 related to memory\differentiation genes, and G6 related to heat shock\stress response genes.

Exemplary gene lists include "JCI" related to exhaustion in CD8 cells melanoma patients (Baitsch, et al., J Clin Invest. 2011; 121(6):2350-2360. doi:10.1172/JCI46102), "Smith" related to autoimmunity (McKinney et al., Nat Med. 2010 May; 16(5):586-91, 1p following 591. doi:

10.1038/nm.2130) and "Held" related to TCF7 and memory (Utzschneider et al., Immunity. 2016 Aug. 16; 45(2):415-27. doi:10.1016/j.immuni.2016.07.021). Focusing on the gene lists: the JCI list is enriched with cluster #2 (P=4.3e-11) and the Smith list is enriched with cluster #4 (P=1.7e-9). The MSigDB includes 4872 gene sets associated with immunity. Dozens to hundreds of them correspond with the clusters described herein.

Figure 12:
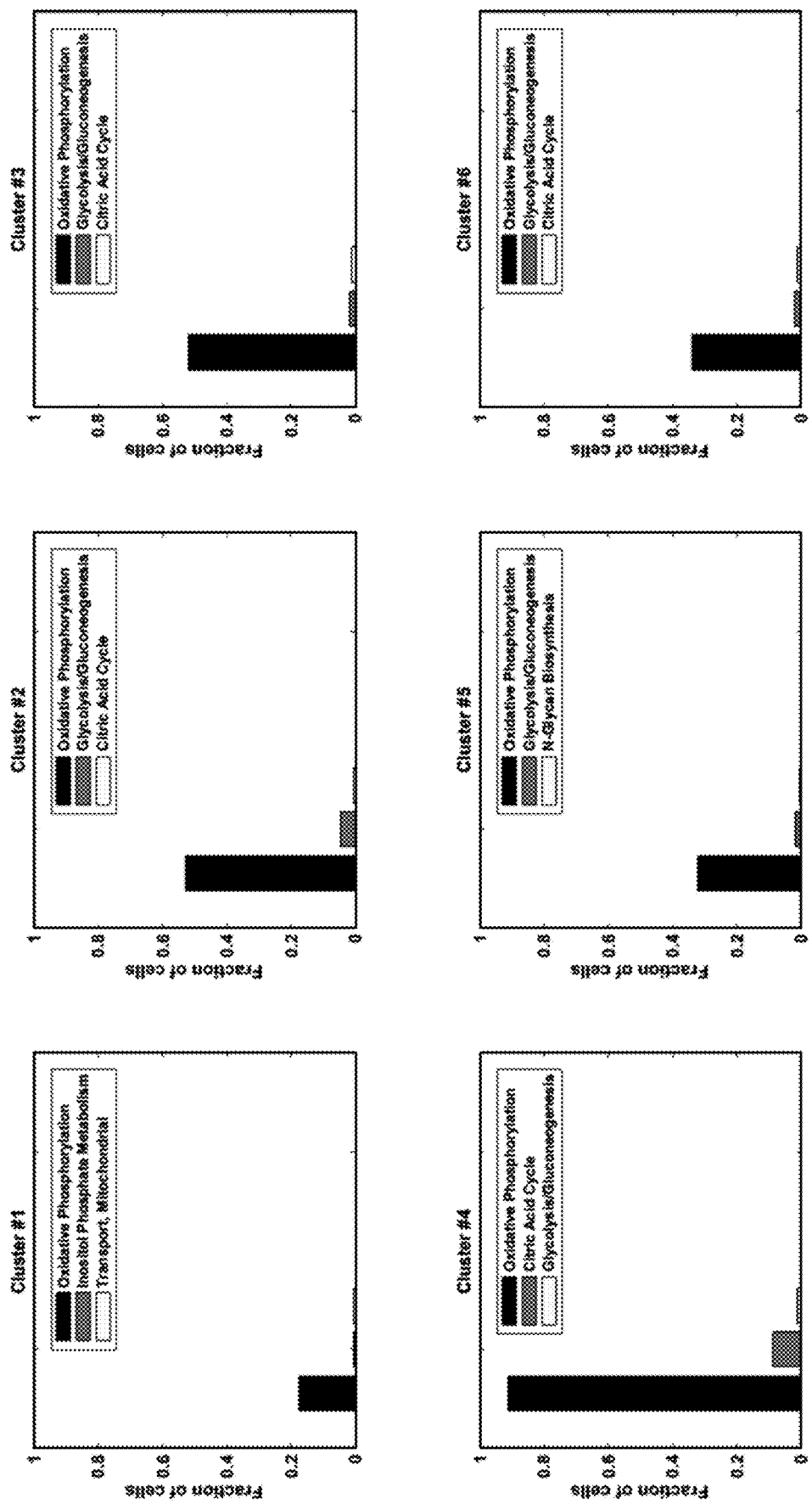
FIG. 12—illustrates the enrichment for metabolic functions in the 6 clusters from FIG. 10.
Figure 13:
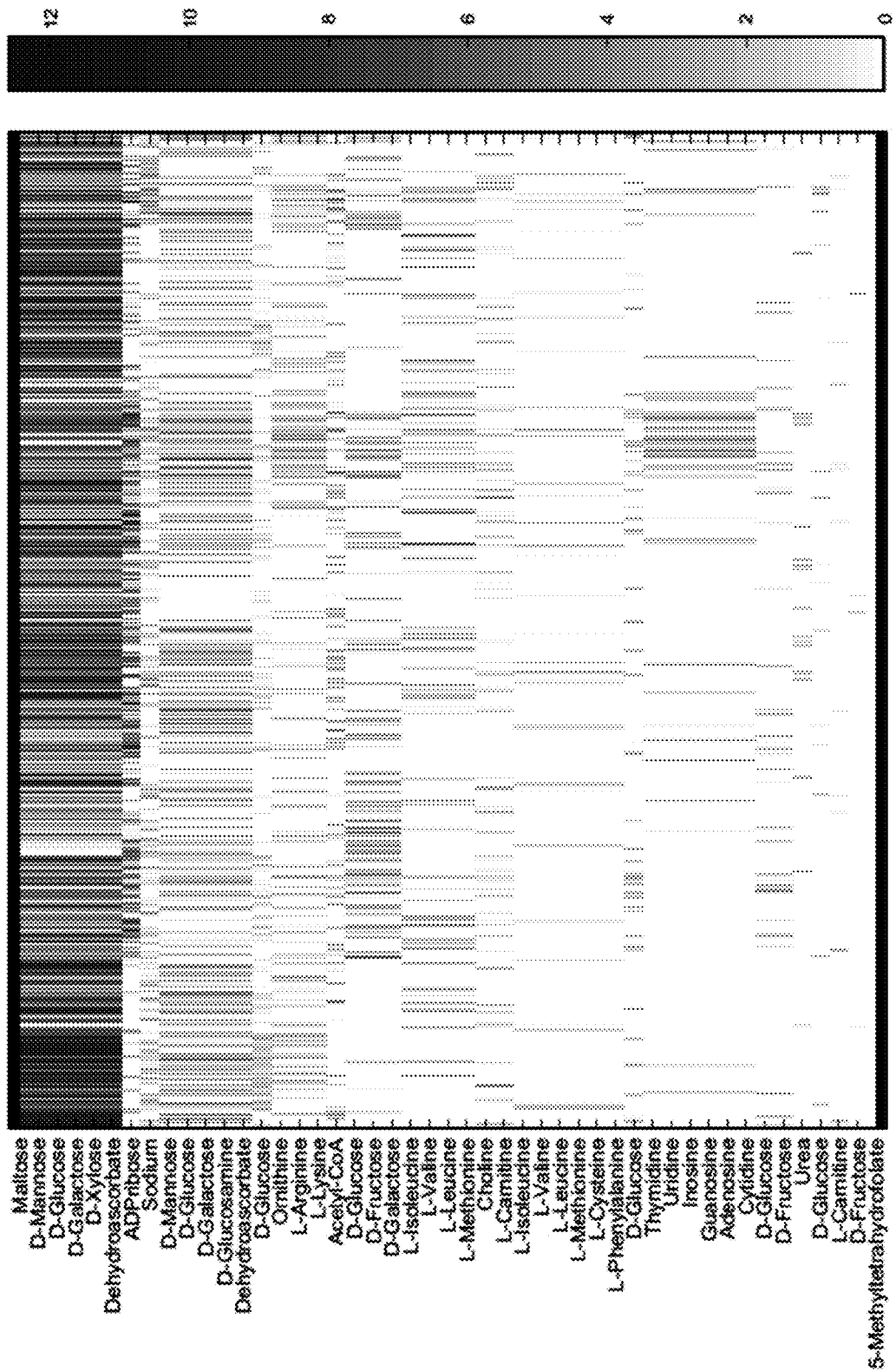
FIG. 13—illustrates transport reaction activity across the 6 clusters from FIG. 10. Heatmap shows metabolites associated with the transporter genes.
Figure 14:
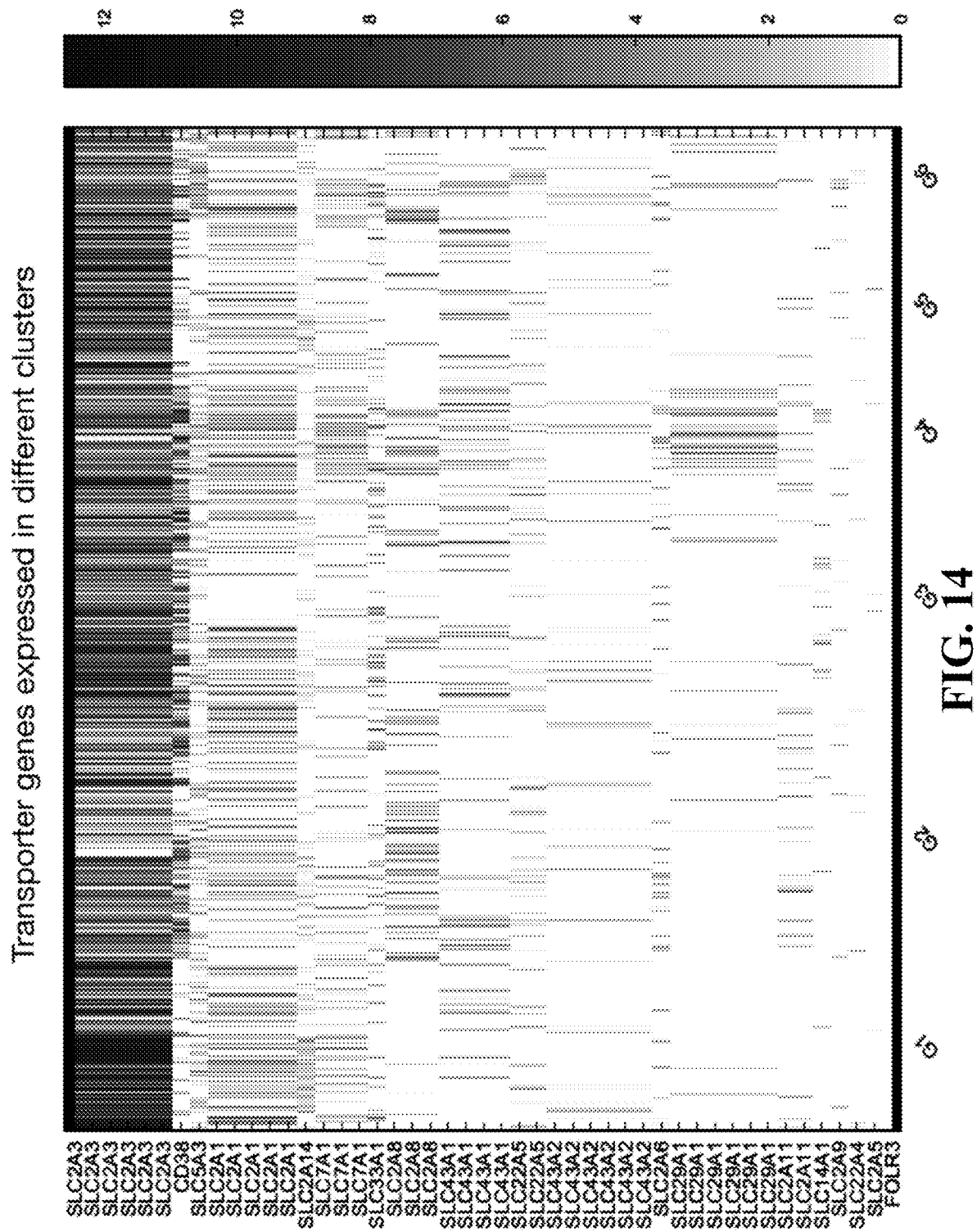
FIG. 14—illustrates transport reaction activity across the 6 clusters from FIG. 10. Heatmap shows transporter genes expressed in the different clusters.

Applicants analyzed the enrichment for metabolic functions. Applicants analyzed the fraction of cells in each cluster that were significantly enriched with a metabolic pathway (FIG. 12). The exhaustion (#2) and cell cycle (#4) clusters had the highest degree of metabolic activity with many oxphos expressed genes. Applicants analyzed transport reaction activity across the clusters. FIG. 13 shows levels of metabolites associated with the transporter genes. FIG. 14 shows expression of transporter genes expressed in the different clusters.

Example 4—Isolation, Depletion and Enrichment of CD8+ TIL Sub-Types from Melanoma Samples Modulation of the ratio of responder to non-responder CD8+ TILs may be used in the treatment of cancer patients (e.g., adoptive cell therapy, CAR T cells). Applicants isolated the non-responder and responder CD8+ TIL populations from melanoma tumors. The isolation may be used to enrich responder populations or deplete non-responder populations, preferably in adoptive T cell transfer and CAR-T cells therapies. Isolation may be performed using population specific surface markers.

Figure 19:
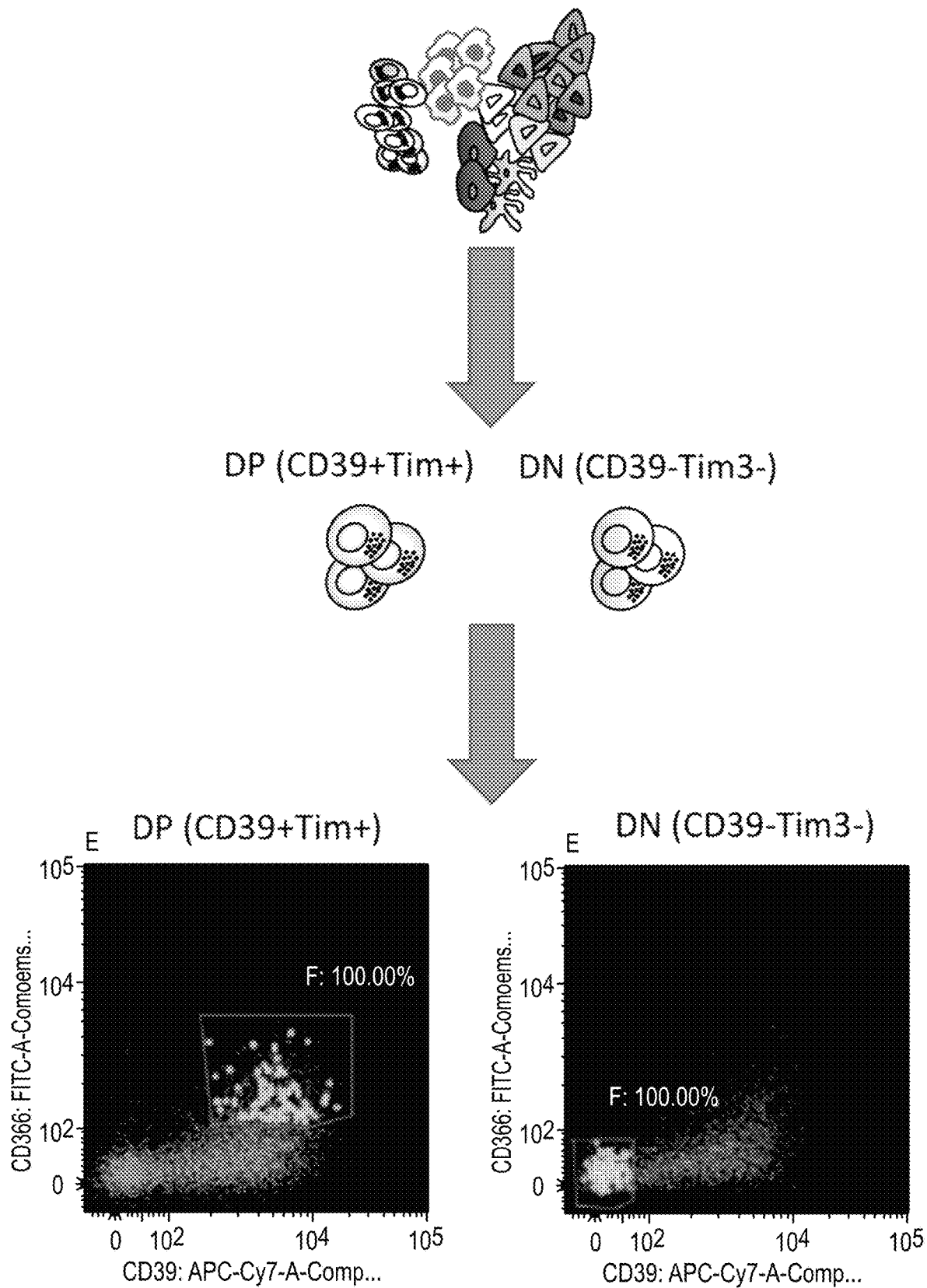
FIG. 19—illustrates FACS analysis of CD39+Tim3+ (DP) cells and CD39−Tim3− (DN) cells sorted from patient samples using cluster specific markers.
Figure 20:
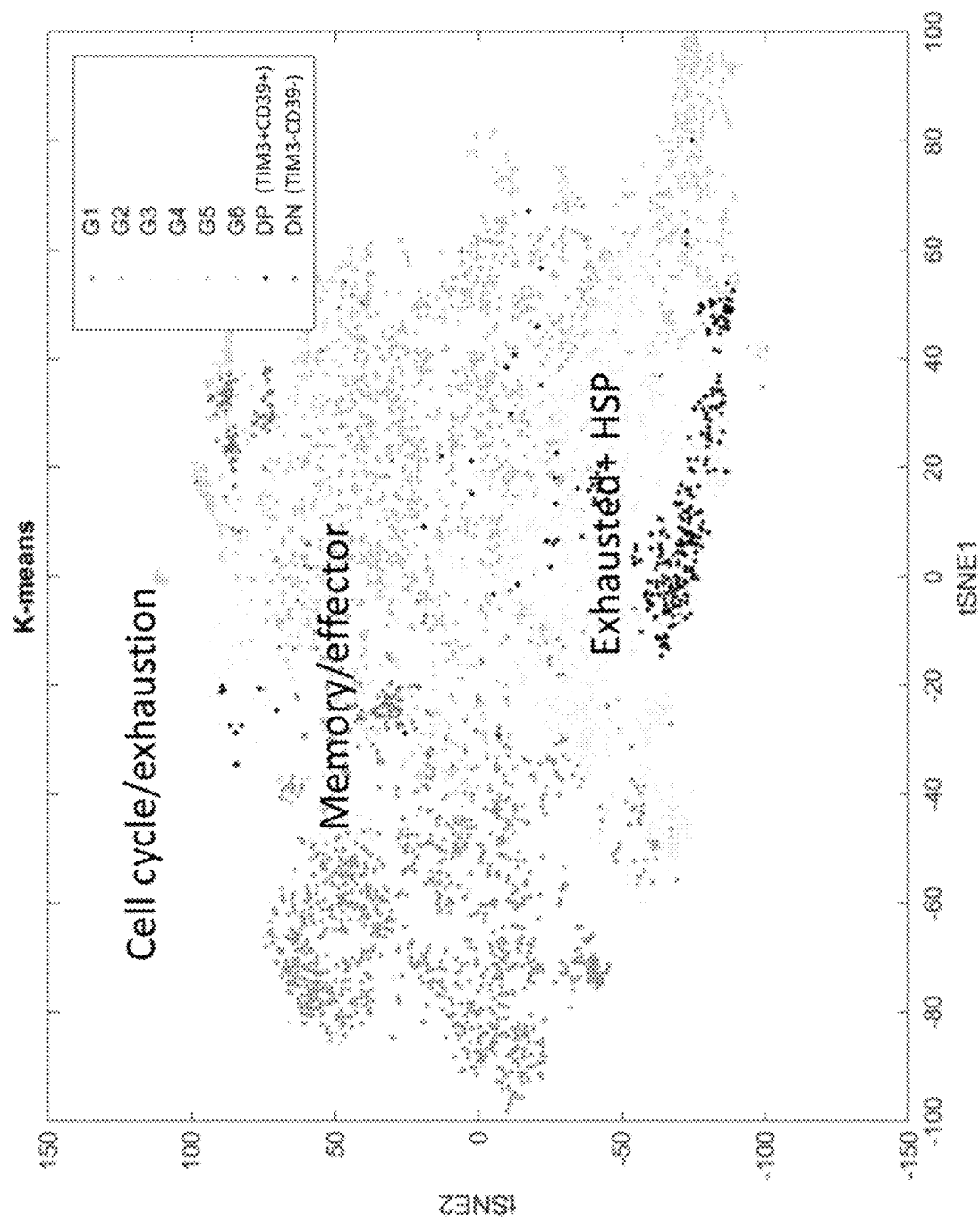
FIG. 20—illustrates tSNE analysis of cells sorted in FIG. 19 using cluster specific markers.

Specifically, Applicants isolated the different populations of cells from patient samples, performed scRNAseq and mapped them back to the clusters originally found using tSNE analysis (FIGS. 19 and 20). For isolation of cells from cluster G2 Applicants used CD45+CD3+CD8+CD39+Tim3+ antibodies and for cluster G5 Applicants used CD45+CD3+CD8+PD1+Tim3+ antibodies. In this tSNE plot G2 and G5 represent cells from the two exhaustion clusters. Applicants sorted for cells using CD45+CD3+CD8+CD39−Tim3− markers and CD45+CD3+CD8+PD1−Tim3− markers and obtained cells from cluster G1 in this tSNE plot. G1 in this tSNE analysis represents effector/memory cells (e.g., responder). Thus, cells from the exhaustion cluster (non-responder gene signature) and effector/memory cluster (responder gene signature) can be isolated and enriched. These results were validated in 3 different patients. In other words, Applicants sorted cells that should be in clusters G2, G5 and G1 based on discriminative markers identified in the original scRNAseq. Applicants then used scRNA-seq to show that the sorted cells map back to the original G2, G5 and G1 clusters, demonstrating that the markers work and that the clusters are reproducible.

Example 5—Identifying Marker Genes

In an exemplary embodiment, Applicants perform the following steps for identifying marker genes:
1. Given a cluster i and a gene j, Applicants apply a fisher test using the number of cells expressing gene j in cluster i vs. the number of cells expressing gene j in cells that do not belong to cluster i.
2. Removing genes that have a low expression in both groups.
3. Considering only genes that pass Bonferroni correction and log(FC)>0.5.
4. Sorting by log Fold-change (genes that are highly expressed in cluster i are ranked the highest).

Example 6—T Cell Receptor (TCR) Analysis

Figure 15:
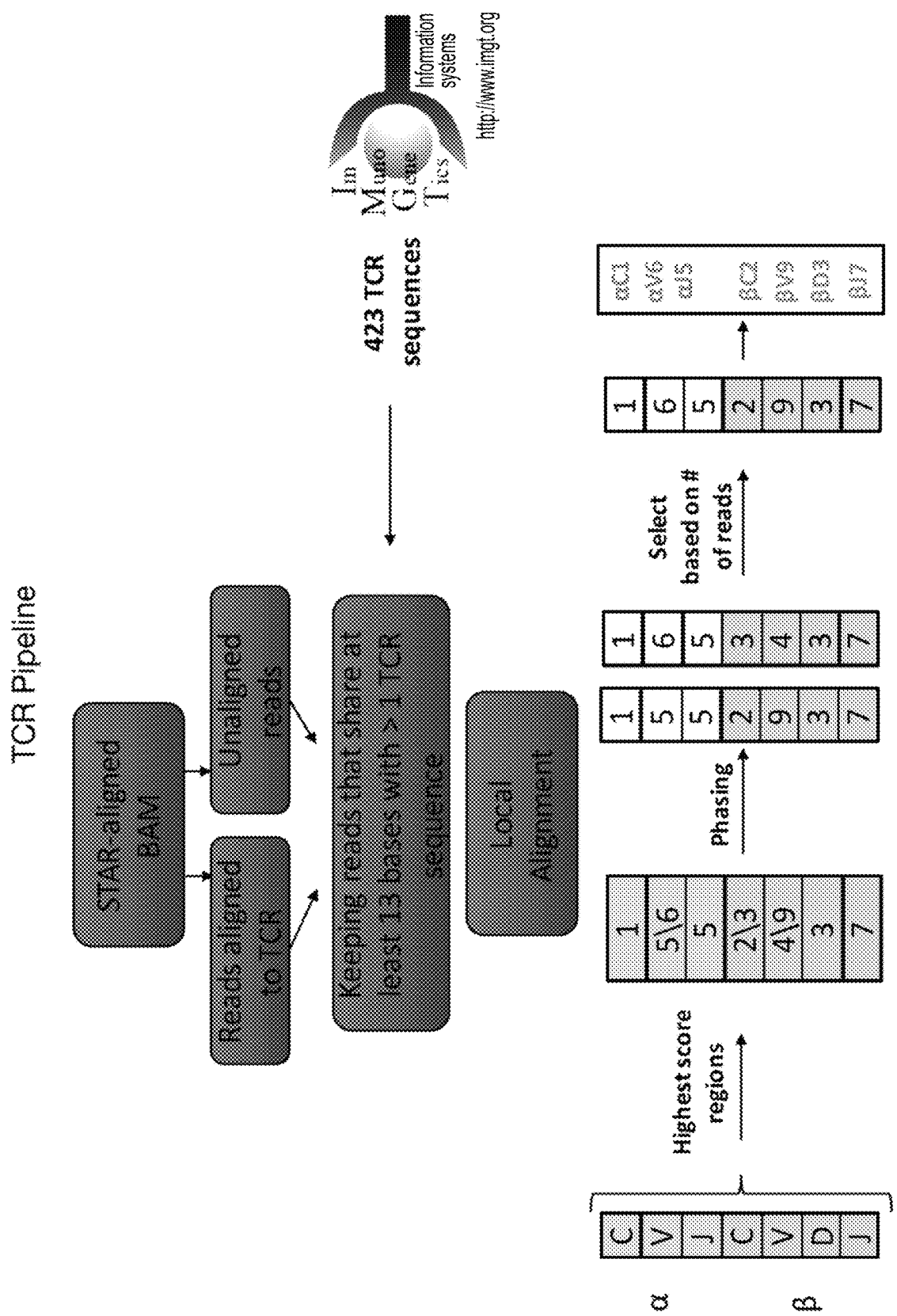
FIG. 15—illustrates a pipeline for determining T cell receptors (TCR).
Figure 16:
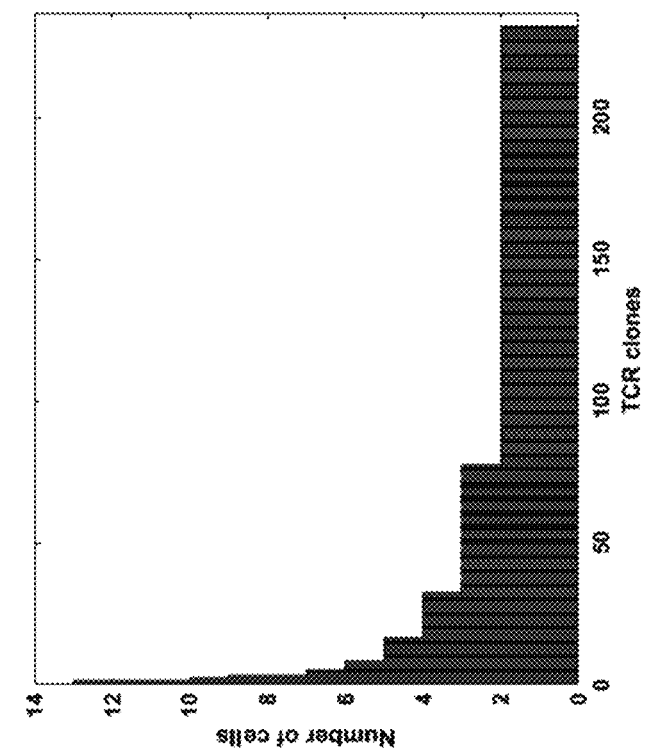
FIG. 16—illustrates TCR analysis in the single T cells. Left panel shows clonal expansion as determined by the same TCR being detected in the same patient in different time points. Right panel shows clonal enrichment as determined by the same TCR being detected in the same patient in single time points.
Figure 16:
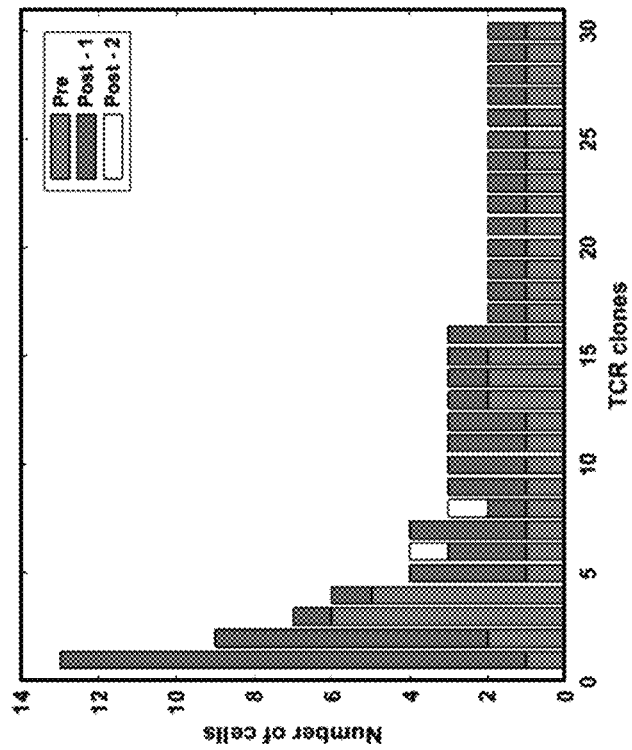

FIG. 15 shows a TCR pipeline for identifying TCRs. FIG. 16 shows clonal expansion of TCRs pre- and post-treatment with checkpoint blockade therapy (left) and clonal enrichment of TCRs detected in the same patient at single time points (right).

Example 7—δγ T-Cell Analysis

Figure 17:
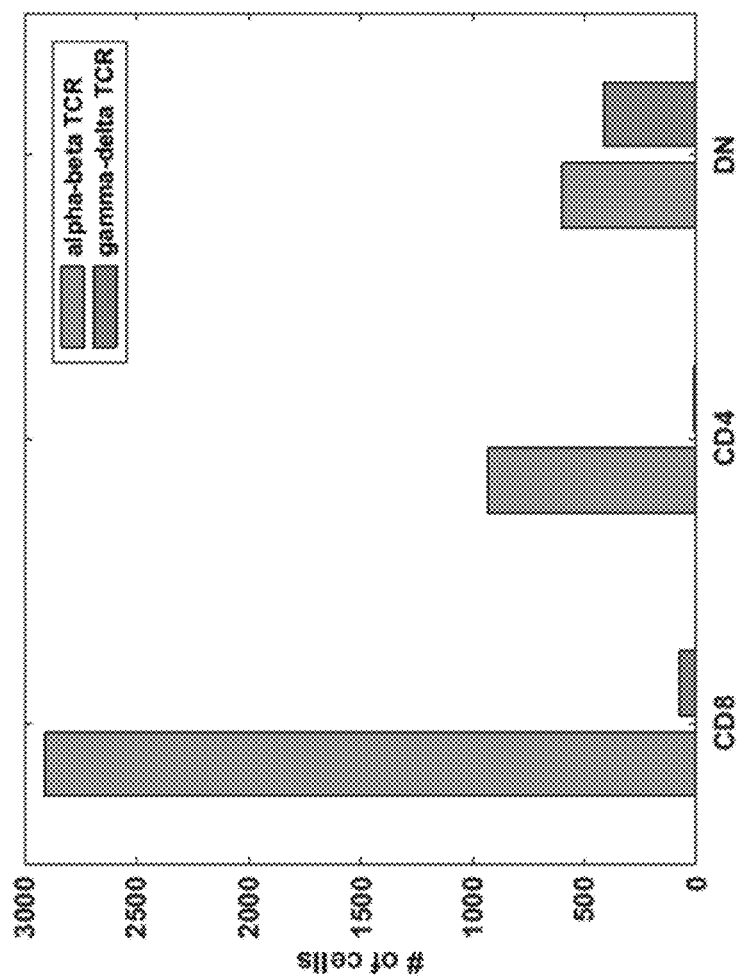
FIG. 17—illustrates that δγ T-cells are enriched in CD4/CD8 double negative T cells (DN).
Figure 18:
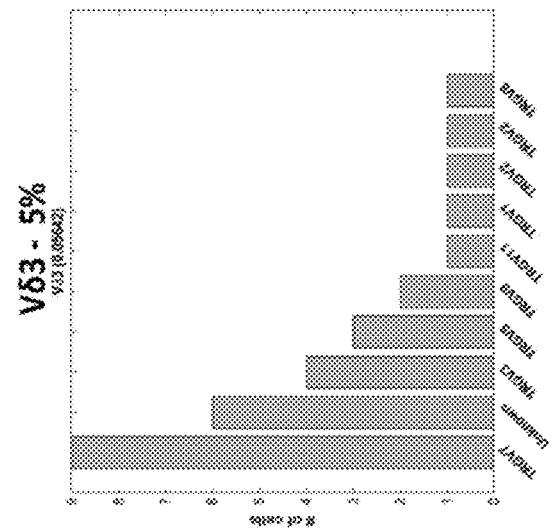
FIG. 18—illustrates analysis of Vδ1, Vδ2 and Vδ3 T-cells.
Figure 18:
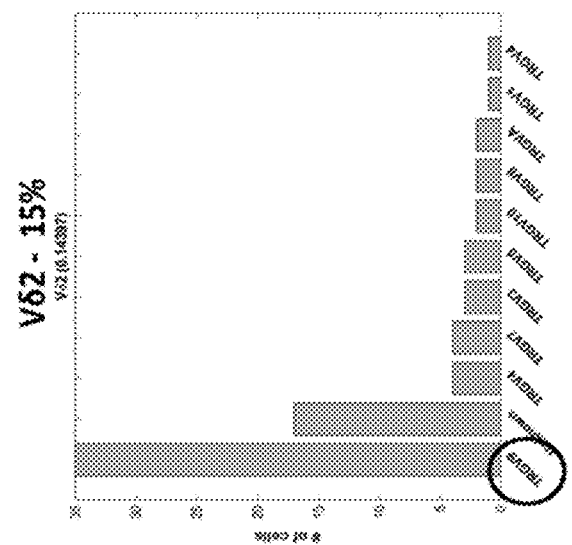
Figure 18:
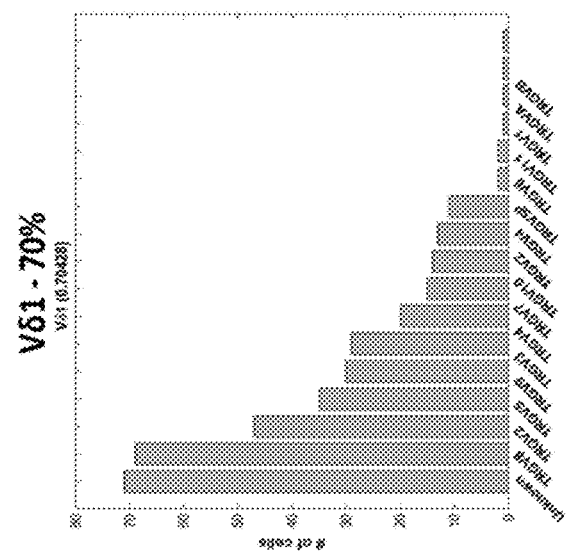

Applicants determined that δγ T-cells are Enriched in CD4/CD8 double negative (DN) T cells (FIG. 17). Applicants observed no difference between responders and non-responders in terms of V1 and V2 (FIG. 18). Vδ1 T-cells have a high expression of inhibitory receptors and Vδ2 T-cells have a higher expression of KLRB1 and other genes.

Example 8—TCF7 Expression Distinguishes Between Responder and Non-Responder Patients Tcf7 is also known as TCF-1 (encoded by Tcf7), and as used herein Tcf7 refers to the human gene, mouse gene and all other orthologues. Tcf7 may refer to the genes identified by the accession numbers NM_009331.4, NM_001313981.1, NM 003202.4, NM_213648.4, NM_201634.4, NM_001134851.3, NM_201632.4, NM_001346425.1, and NM_001346450.1. TCF-1 is known as a signal-dependent transducer of environmental signals from the Wnt pathway via β-catenin (Rothenberg, Curr Opin Immunol. 2012 April; 24(2):132-8).

Figure 21A:
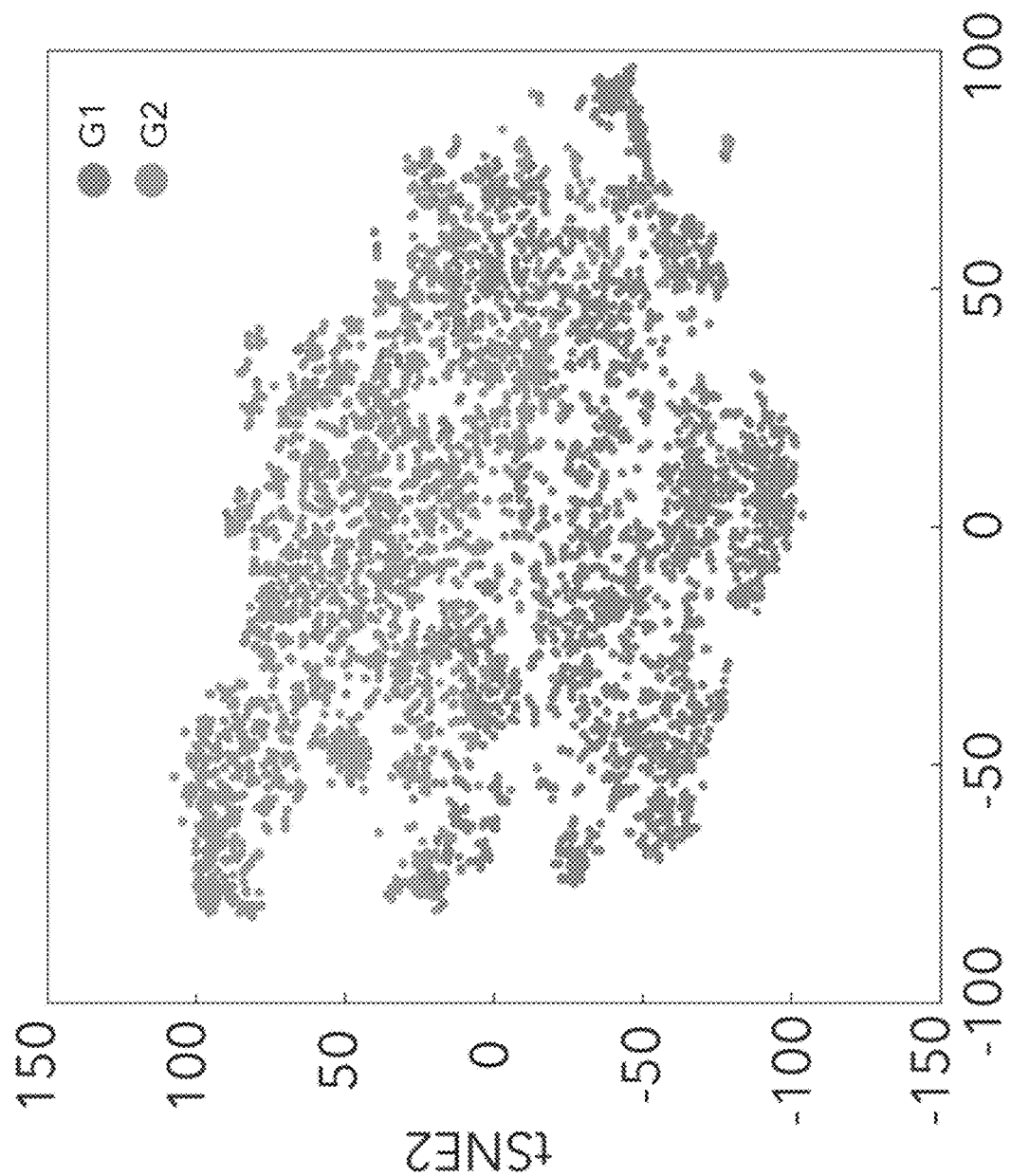
FIG. 21A-21E—illustrates characterization of tumor infiltrating CD8 T cells. G1 refers to group 1, responder signature and G2 refers to group 2, non-responder signature in this figure.
Figure 21B:
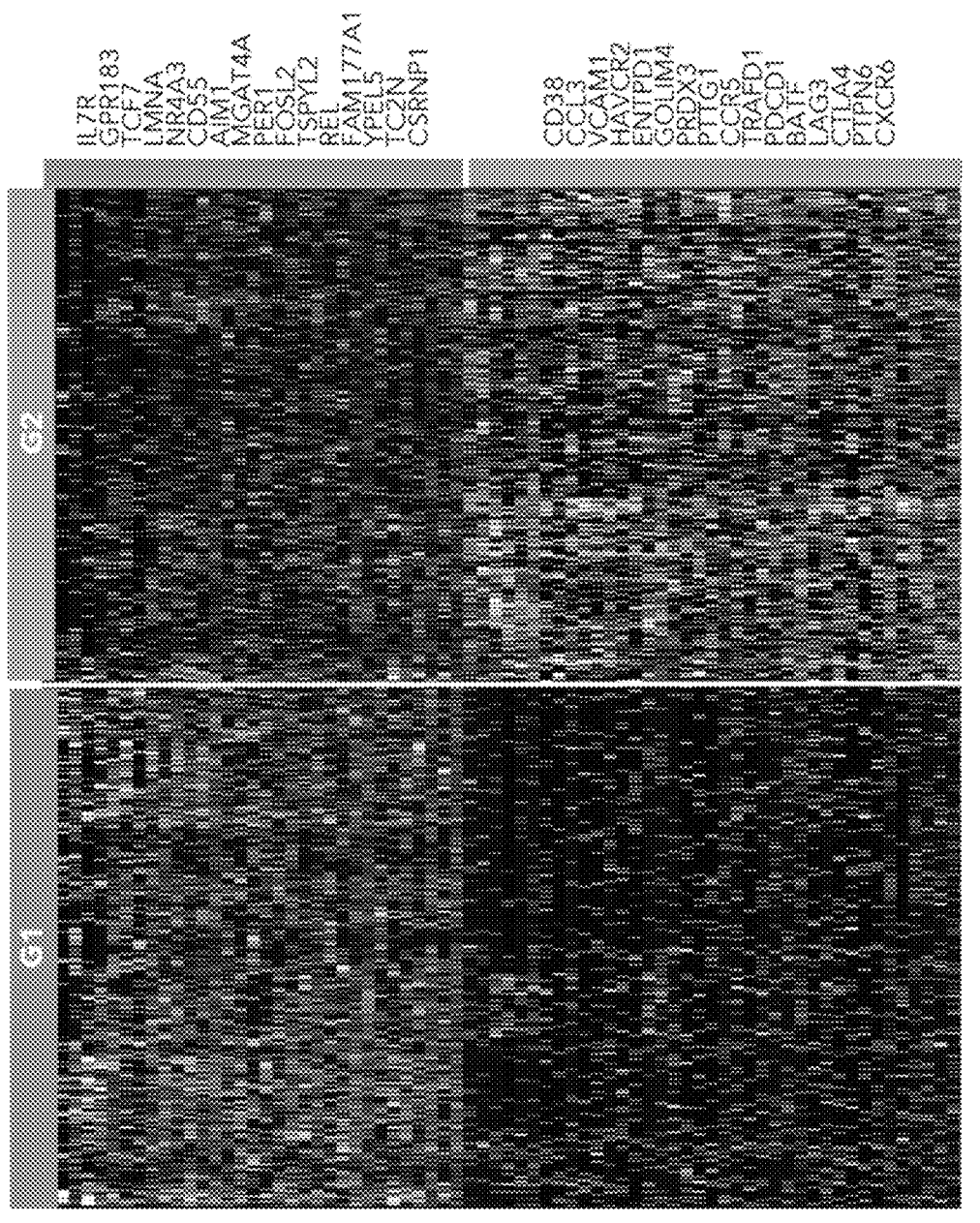
Figure 21C:
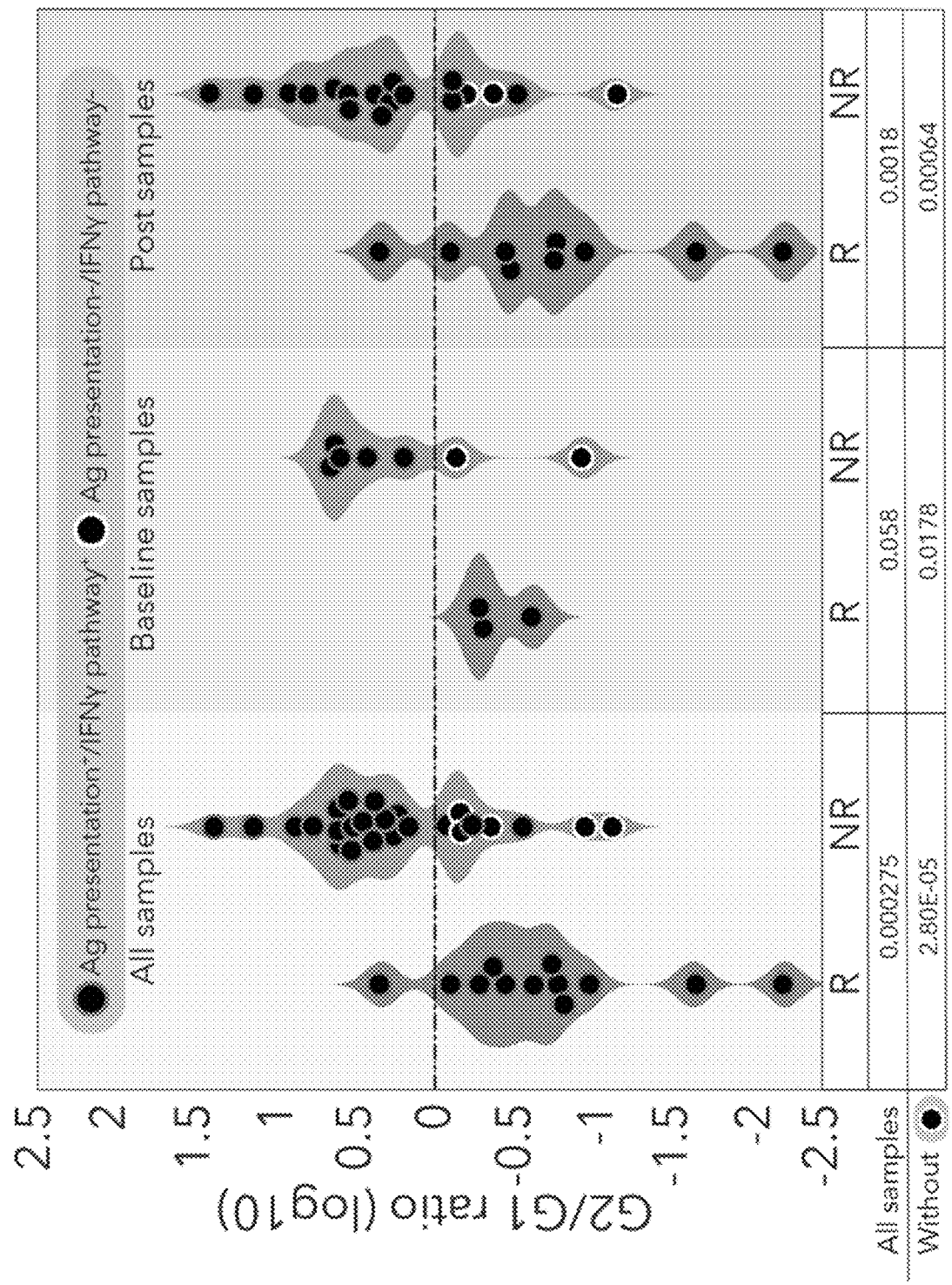
Figure 21D:
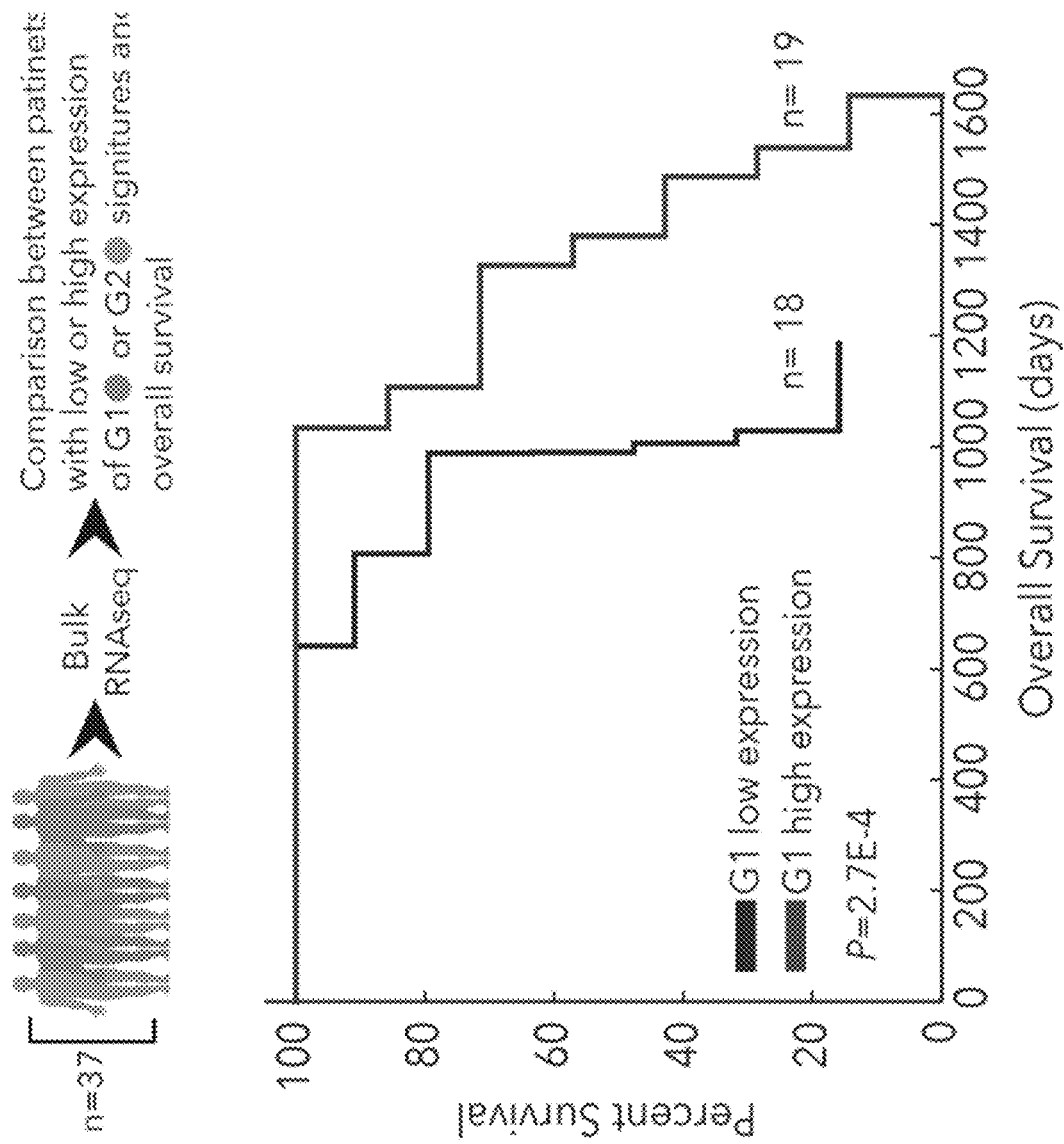
Figure 21E:
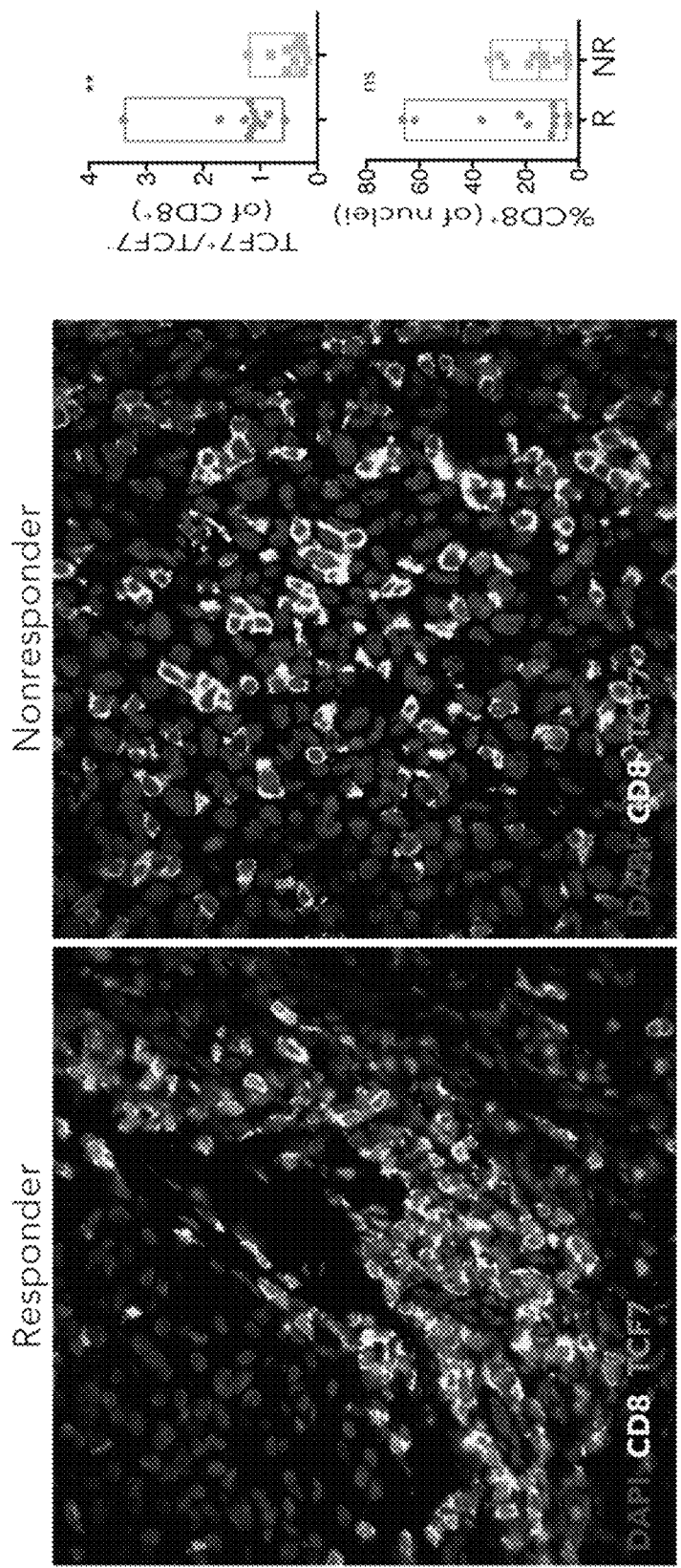

Applicants show that tumor infiltrating CD8 T cells corresponding to CPB therapy responders and non-responders cluster into two distinct groups (G1 or G2 in this plot) (FIG. 21a). Applicants identified a responder gene signature (G1 in this figure) and a non-responder gene signature (G2 in this figure). The expression of G1 and G2 genes in CD8 T cells are mutually exclusive, such that high expression of G1 is associated with low expression of G2, while high expression of G2 is associated with low expression of G1 (FIG. 21b). The ratio of G2/G1 expression on CD8 T cells can distinguish responders and non-responders before and after treatment (FIG. 21c). All of the responder patients had functional antigen presentation and the IFN gamma pathway, thus showing that these pathways are required to have a response to CPB therapy. The non-responders in the base line samples with a G2/G1 below 1 (i.e., G1 expression is higher than G2) both had defective antigen presentation and IFN gamma pathways. All of the patients with defective antigen presentation and IFN gamma pathways were non-responders and had G2/G1 ratios below 1. The responder and non-responder signatures can predict overall survival in cancer. Patients with low or high expression of G1 (responder signature) have shorter or longer overall survival (FIG. 21d). TCF7 is a transcription factor expressed in G1 and can be used alone to predict outcomes in melanoma. Immunofluorescence images stained for CD8 and TCF7 show more TCF7+ cells in a responder patient than in a non-responder patient (FIG. 21e). The percentage of CD8+ cells and the ratio of TCF+/TCF− CD8+ cells are calculated for the responder and non-responder patient.

Figure 22A:
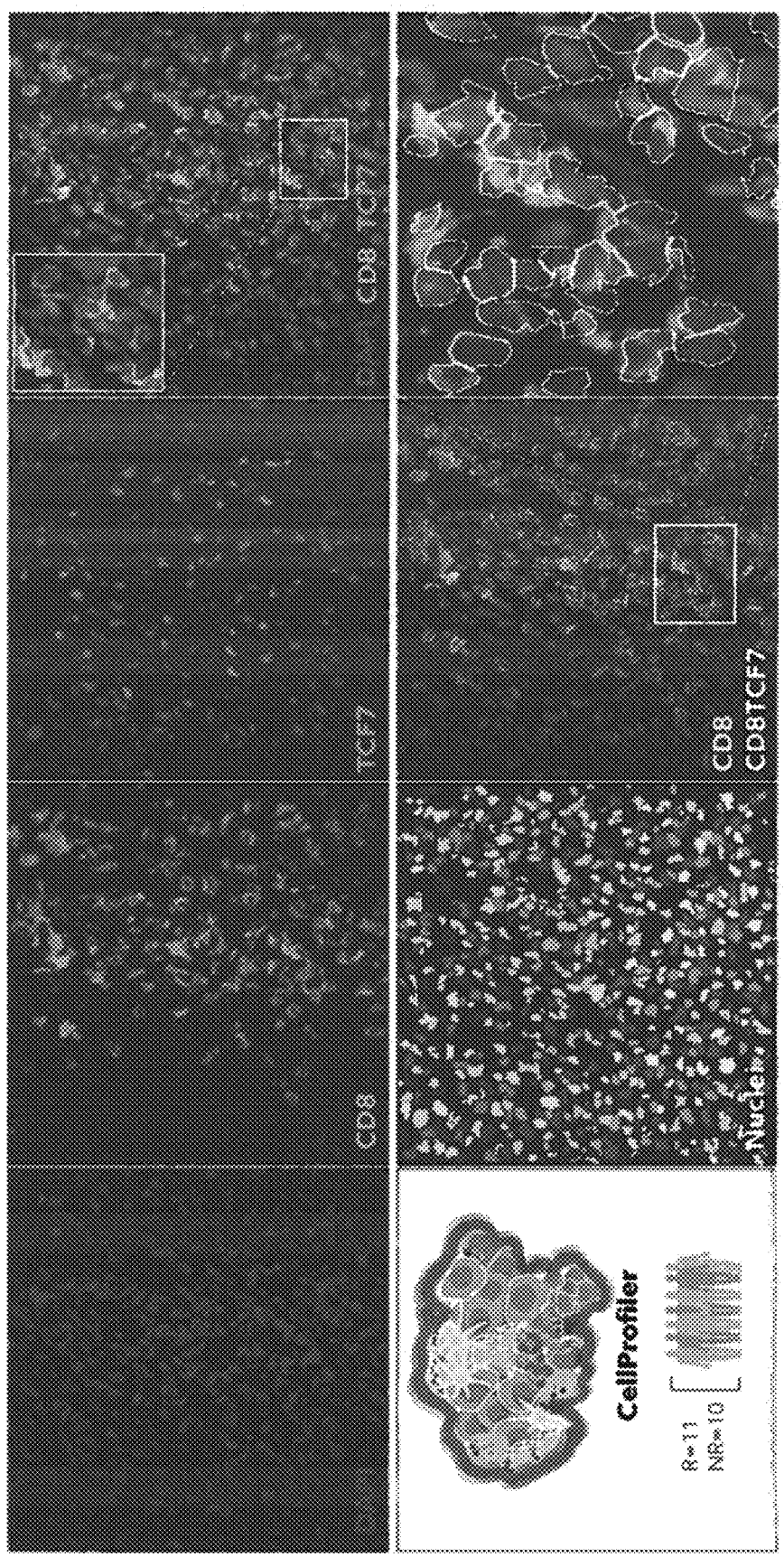
Figure 22B:
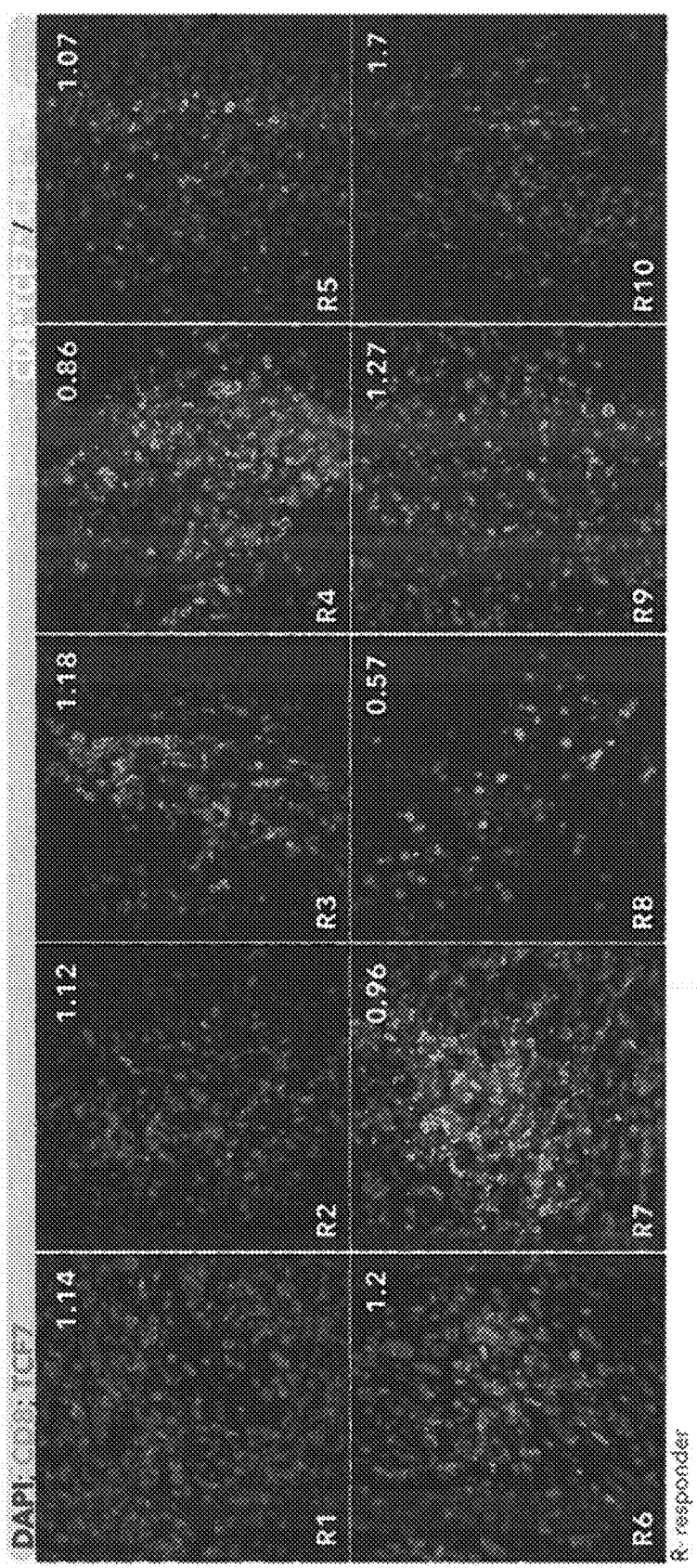
Figure 22C:
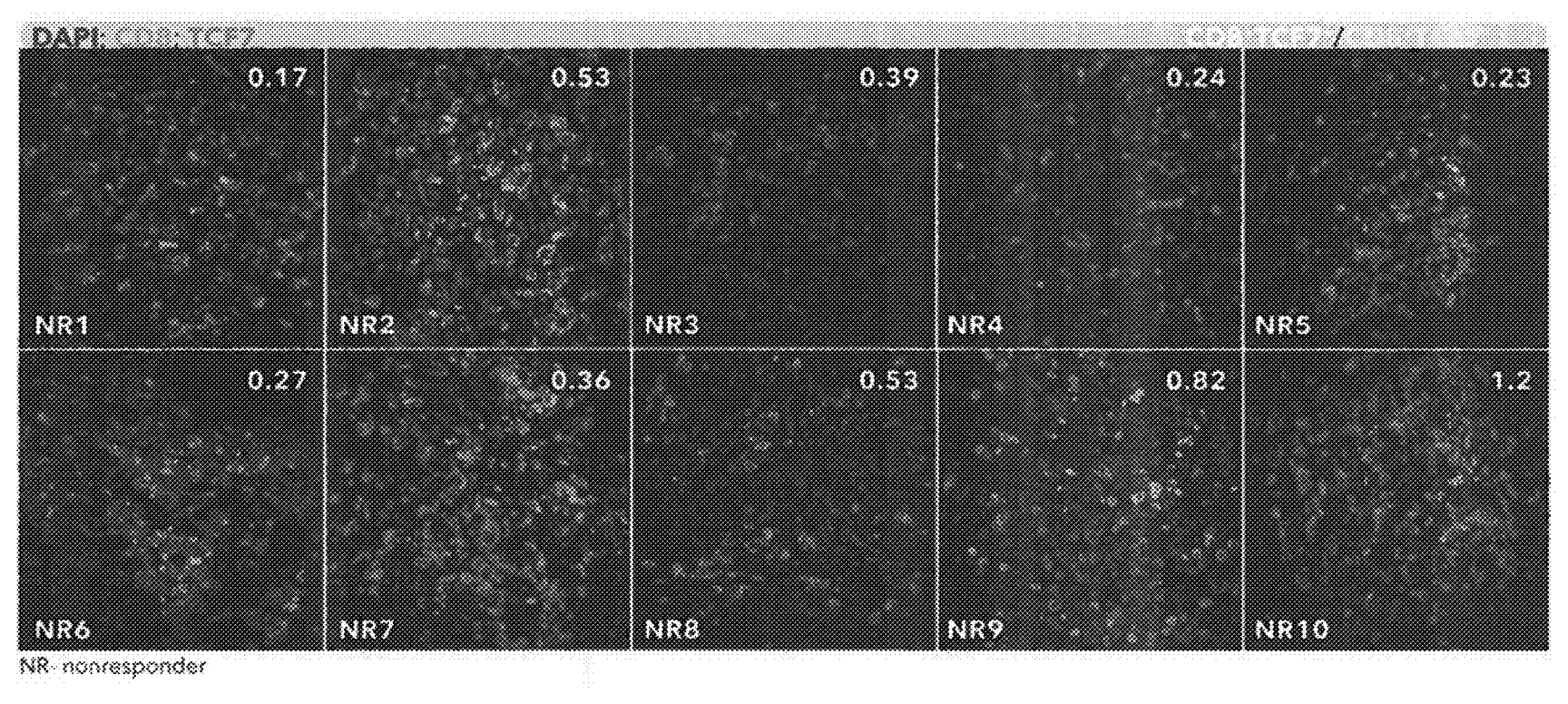

FIG. 22 shows immunofluorescence imaging and calculation of TCF7 positive CD8 cells using CellProfiler and a novel pipeline (see, e.g., Carpenter et al., (2006) CellProfiler: image analysis software for identifying and quantifying cell phenotypes. Genome Biology 7:R100. PMID: 17076895; and Kamentsky et al., (2011) Improved structure, function, and compatibility for CellProfiler: modular high-throughput image analysis software. Bioinformatics 2011/ doi. PMID: 21349861 PMCID: PMC3072555). Responders (FIG. 22b) and non-responders (FIG. 22c) were assayed. The responders had consistently more TCF7+ cells as indicated by the CellProfiler scores.

Immunofluorescence assay and analysis. Multiplex staining was performed on 4 μm formalin-fixed paraffin-embedded sections using the Opal multiplex IHC system (PerkinElmer; NEL800001KT) according to the manufacturer's instructions. Briefly, slides were baked for 1 hour at 65° C. followed by deparaffinization with xylene and a graded series of ethanol dilutions (100%, 95% and 70%), fixation with 10% neutral buffered formalin for 30 minutes, microwave antigen retrieval using the AR9 buffer (PerkinElmer; AR900250ML), and blocking. Primary antibodies used for staining were: CD8α (Biolegend; C8/144B; 372902; 1:100) detected with OPAL520 (1:100; Cy2); TCF7 (Cell Signaling; #2203; 1:100) detected with OPAL690 (1:100; Cy5.5). Counterstain was done using DAPI (1:1000) and subsequently mounted using Vectashield (Vectra; H-1000) fluorescence media. Slides were imaged using the Olympus IX83 confocal microscope by scanning 10 random fields on each sample at 40× magnification, and analyzed with CellProfiler 2.2.0 (ref-PMID: 17076895) to detect the total number of nuclei, CD8$^+$, TCF7$^+$, and CD8$^+$TCF7$^+$ cells. Due to cellular heterogeneity between different slides/patients, in each sample the percentage of CD8$^+$TCF7$^-$ or CD8$^+$TCF7$^+$ was calculated out of the total nuclei detected. For the analysis, a new pipeline was made for detection of cells positive for CD8 and TCF7 (see below).

Figure 23A:
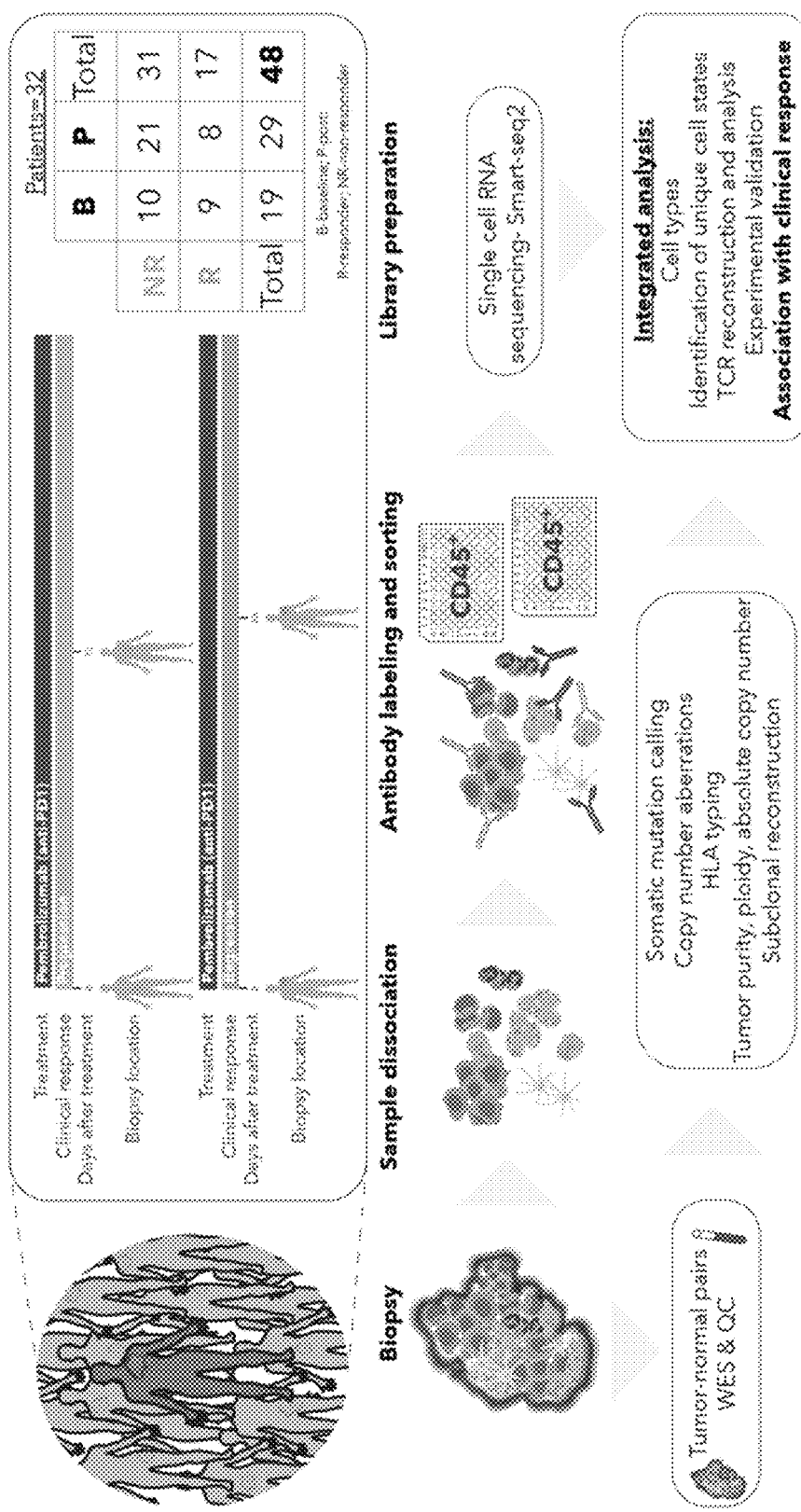
FIG. 23A. Schematic of the studied cohort. Top panel describes the 32 patient cohort, number of samples taken relevant to treatment initiation (baseline-B, on/post treatment-P) along with the clinical status (responder-R, nonresponder-NR). Lower panel delineates the workflow used. WES—whole exome sequencing, QC—quality control, TCR—T cell receptor.

Example 9—Single Cell Profiling of Immune Cells in Patients Treated with Checkpoint Inhibitors To analyze the properties of immune cells associated with successful or failed checkpoint therapies, Applicants performed scRNA-seq on 48 tumor biopsies from 32 metastatic melanoma patients treated with checkpoint therapy (with 37 anti-PD1; and 11 anti-CTLA4+PD1 samples). This cohort included 11 patients with longitudinal biopsies taken at baseline and during treatment, 1 patient with 2 biopsies taken at one time point, and 20 patients with 1 sample each, taken at baseline or during treatment (FIG. 23A and Table 1). Applicants used the following patient response categories defined by RECIST criteria: complete response (CR) and partial response (PR) for responders, or stable disease (SD) and progressive disease (PD) for non-responders[20]. However, to relate molecular and cellular variables with responses of the 48 lesions to therapy, Applicants focused on individual samples and classified them based on radiologic tumor assessments into two categories: progression/non-responder (NR, n=31, including SD/PD samples) or regression/responder (R, n=17, including CR/PR samples), which enabled us to associate response with molecular signatures at the single sample level (Table 1). Profiling was performed on 19,392 sorted CD45$^+$ cells using an optimized version of the full length Smart-seq2 protocol[21], with a median of ~1.4 million paired-end reads per cell. A total of 16,291 sequenced cells passed quality control with a median of 2,588 genes detected per cell, and were used for downstream analysis (Methods). Whole exome sequencing (WES) was available for 20 patients, with 4 that had mutations in B2M, JAK1, STAT1 and IFNGR1 (Table 1), recently reported as mechanisms for primary or acquired resistance to checkpoint therapy in melanoma[13-15].

Figure 23B:
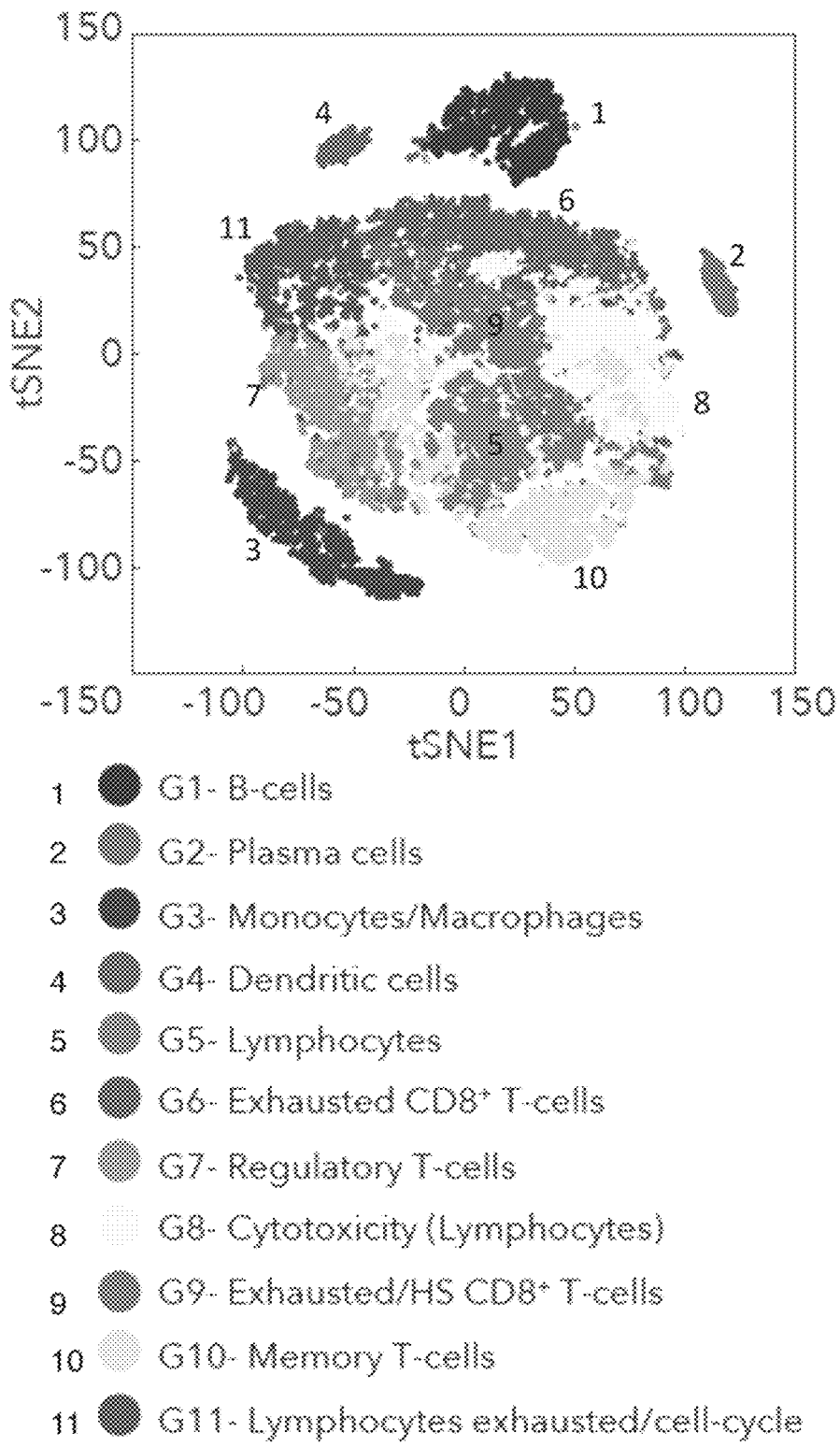
FIG. 23B. tSNE plot of all CD45+ cells collected in this study. Cells are shaded based on 11 clusters identified by k-means clustering analysis (Methods).
Figure 23C:
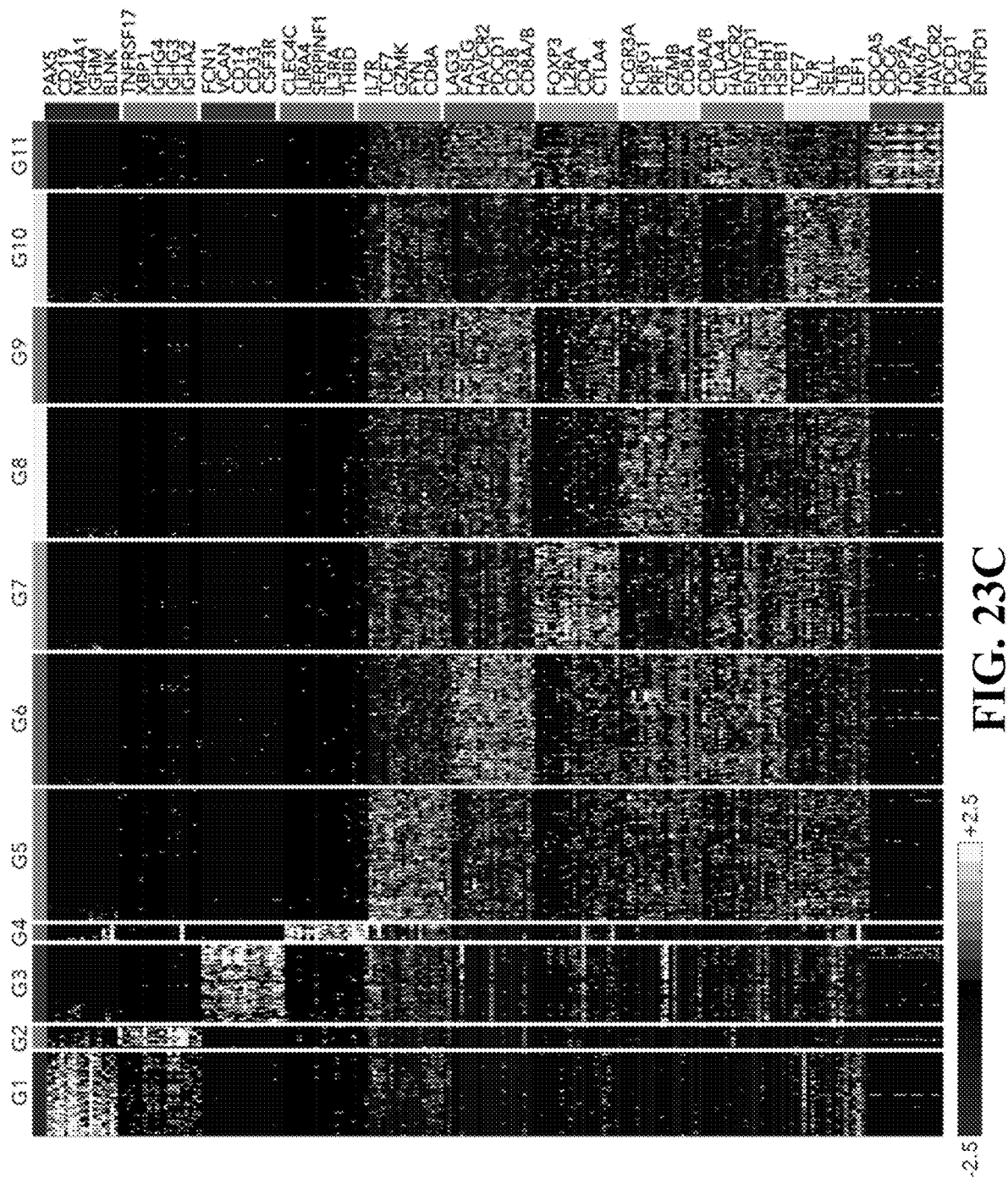
FIG. 23C. Heatmap describing scaled expression values ($\log_2$(TPM+1)) of discriminative gene sets for each cluster defined in (B). A list of representative genes is shown for each cluster next to the right margin bars. Shading scheme is based on z-score distribution from −2.5 to 2.5.
Figures 23D, 23E, 23F, 23G:
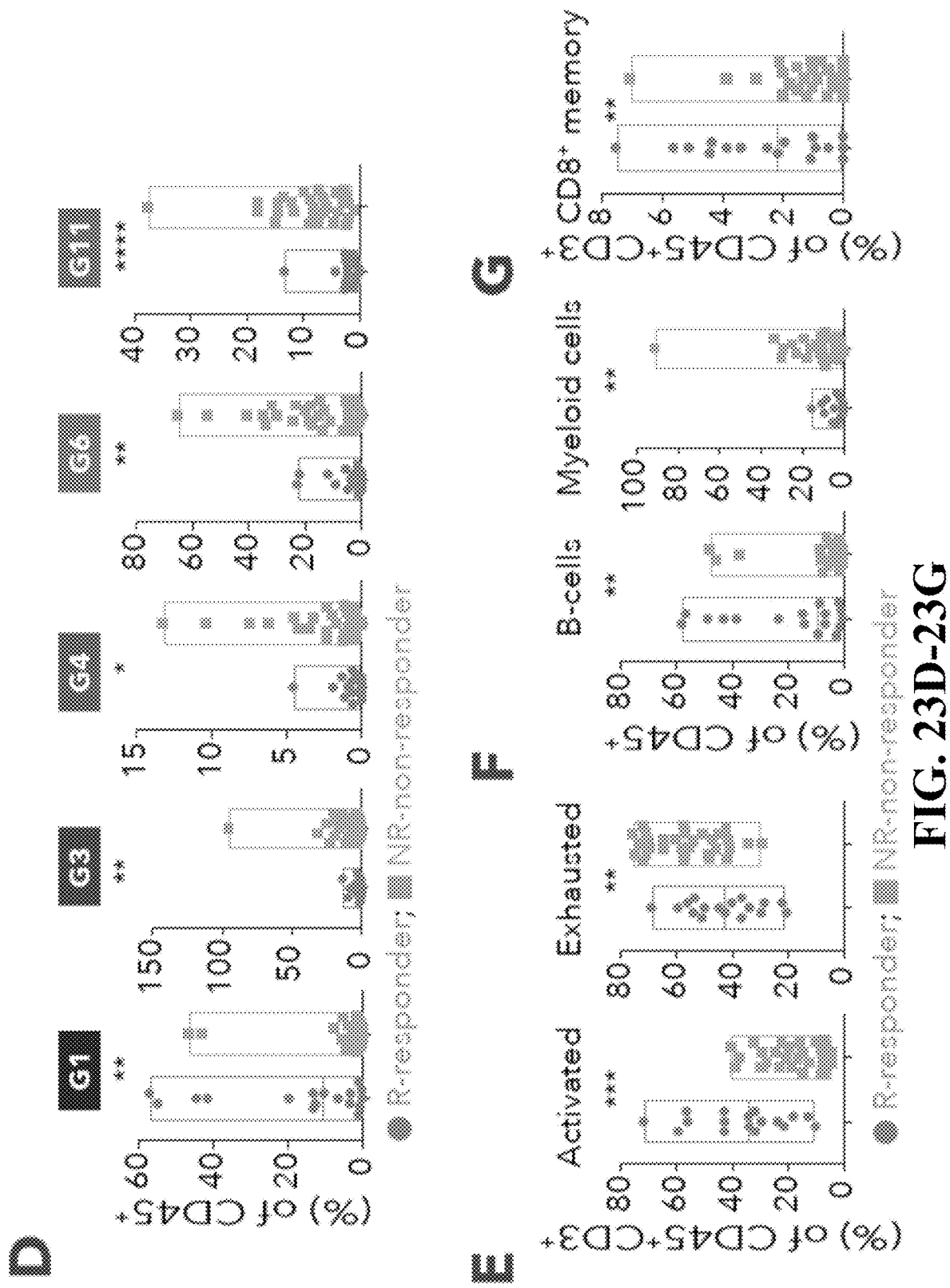
FIG. 23D. Box plots comparing the percentage of cells (out of CD45$^+$) in G1, G3, G4, G6 and G11 clusters as defined in (B), between responder and non-responder lesions. Each symbol represents an individual sample. Two-sided Wilcoxon rank-sum P-value is shown P=0.003; P 0.003; *P=0.01; P=0.005; P=1.3×10$^{-5}$.
FIG. 23E. Box plots comparing the percentage of exhausted and activated CD45+CD3+ cells on the basis of a pre-defined list of known marker genes (table 3), between responder and non-responder lesions. Each symbol represents an individual sample. Two-sided Wilcoxon rank-sum P-value is shown *P=2×10$^{-4}$; P=0.002.
FIG. 23F. Box plots comparing the percentage of B-cells and Myeloid cells on the basis of a pre-defined list of known marker genes (table 3) between responder and non-responder lesions. Each symbol represents an individual sample. Two-sided Wilcoxon rank-sum P-value is shown P=0.004; P=0.002.
FIG. 23G. Box plots comparing the percentage of Memory CD8$^+$ T-cells on the basis of a pre-defined list of known marker genes (table 3) between responder and non-responder lesions. Each symbol represents an individual sample. Two-sided Wilcoxon rank-sum P-value is shown P=0.001.
Figures 29A, 29B:
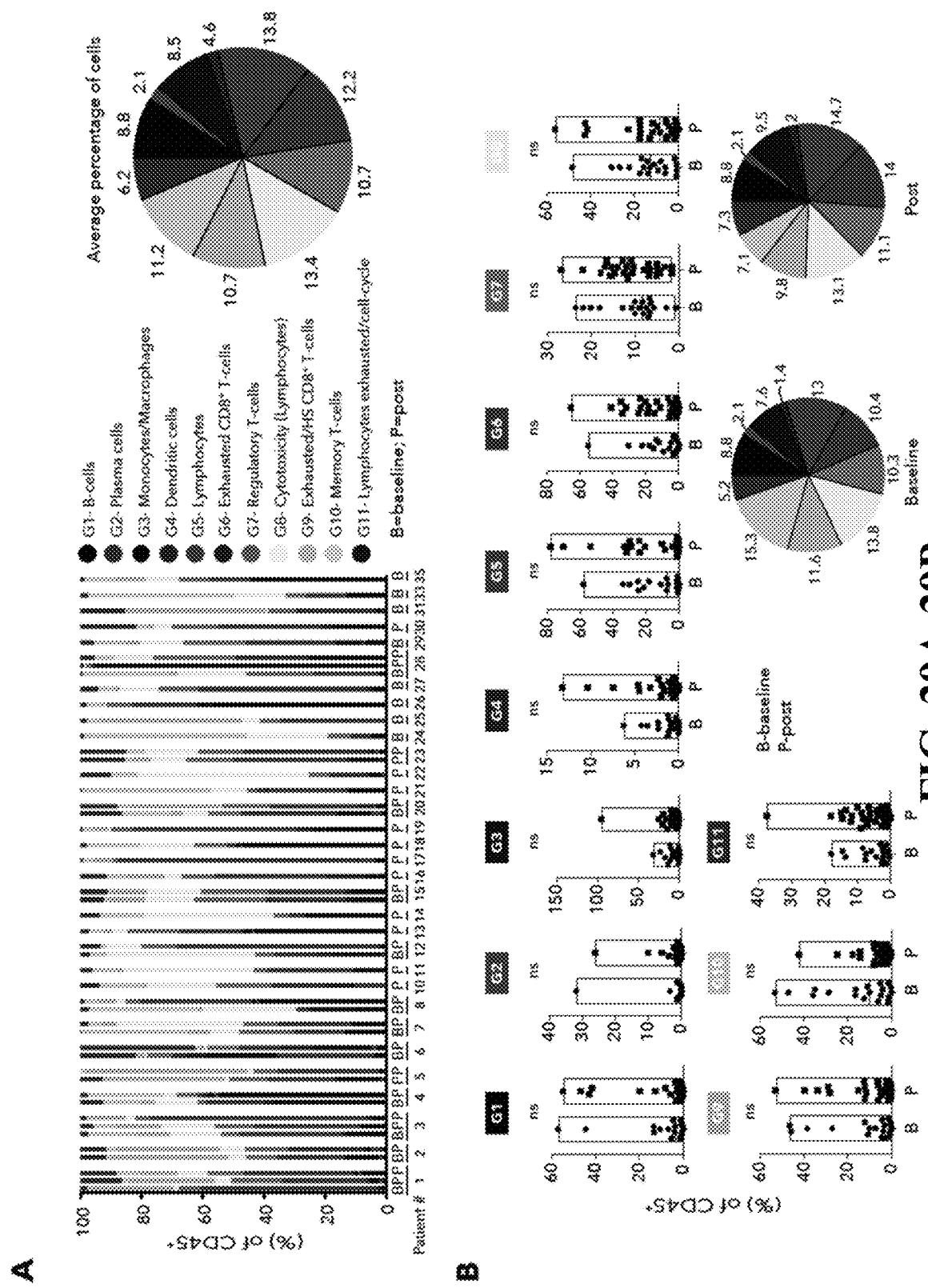
FIG. 29A. For each patient, the percentage of cells (out of CD45$^+$ cells) classified to one of the 11 clusters identified by k-means clustering is shown. Pie chart on the right, summarizes the corresponding percentages across all cells collected in this study.
FIG. 29B-C. Box plots comparing the abundance of cells in the corresponding clusters between all baseline and post-treatment samples (B) and only in patients with matched longitudinal samples (C). Pie charts on the right, summarizes the corresponding percentages for each analysis.
Figures 29C, 29D:
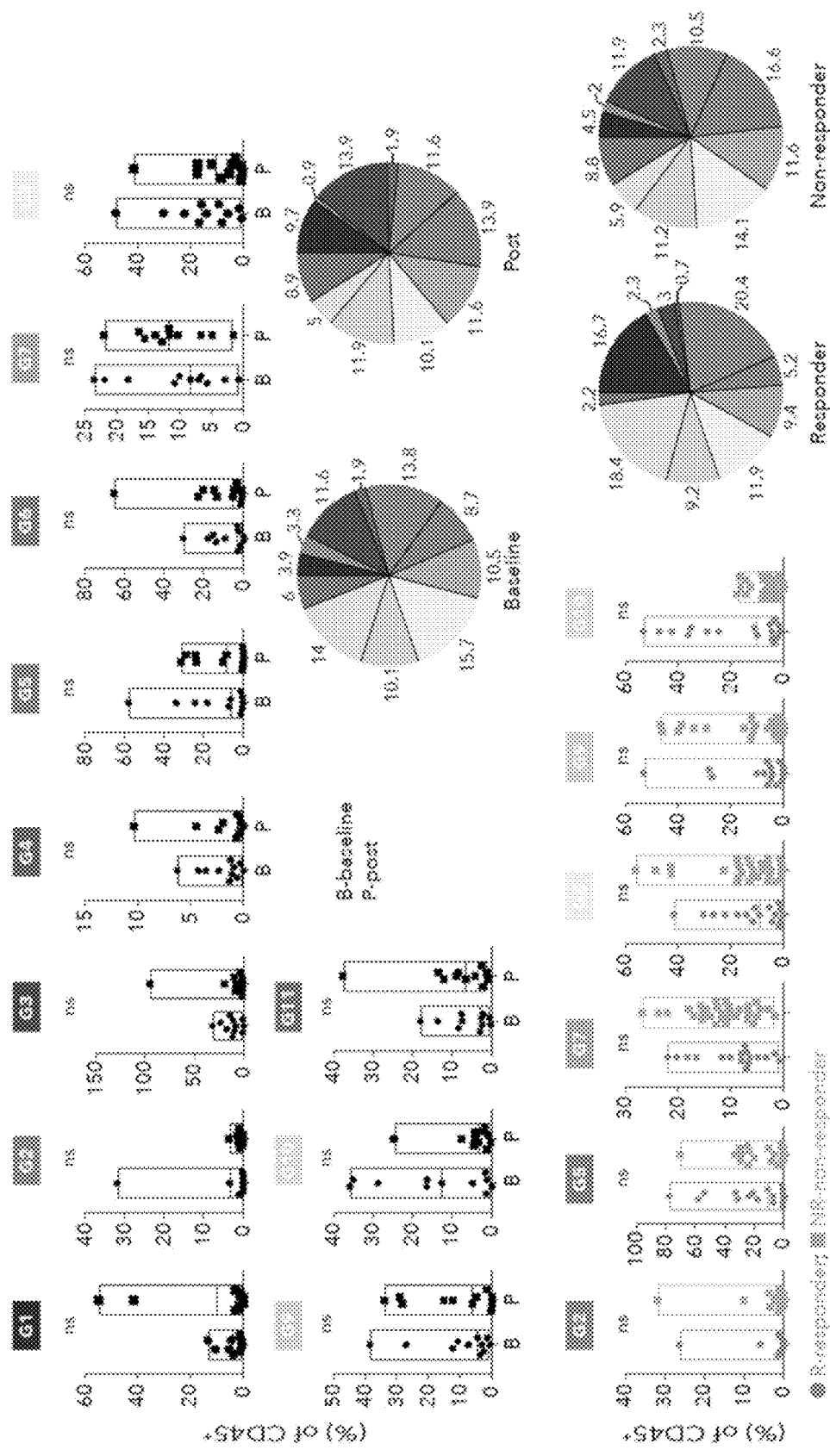
FIG. 29D. Box plots comparing the abundance of cells in the corresponding clusters between responder and non-responder lesions. Pie chart on the right, summarizes the corresponding percentages for each cluster. B—baseline, P—post, R—responder, NR—non-responder, n.s—not significant.
Figure 30A:
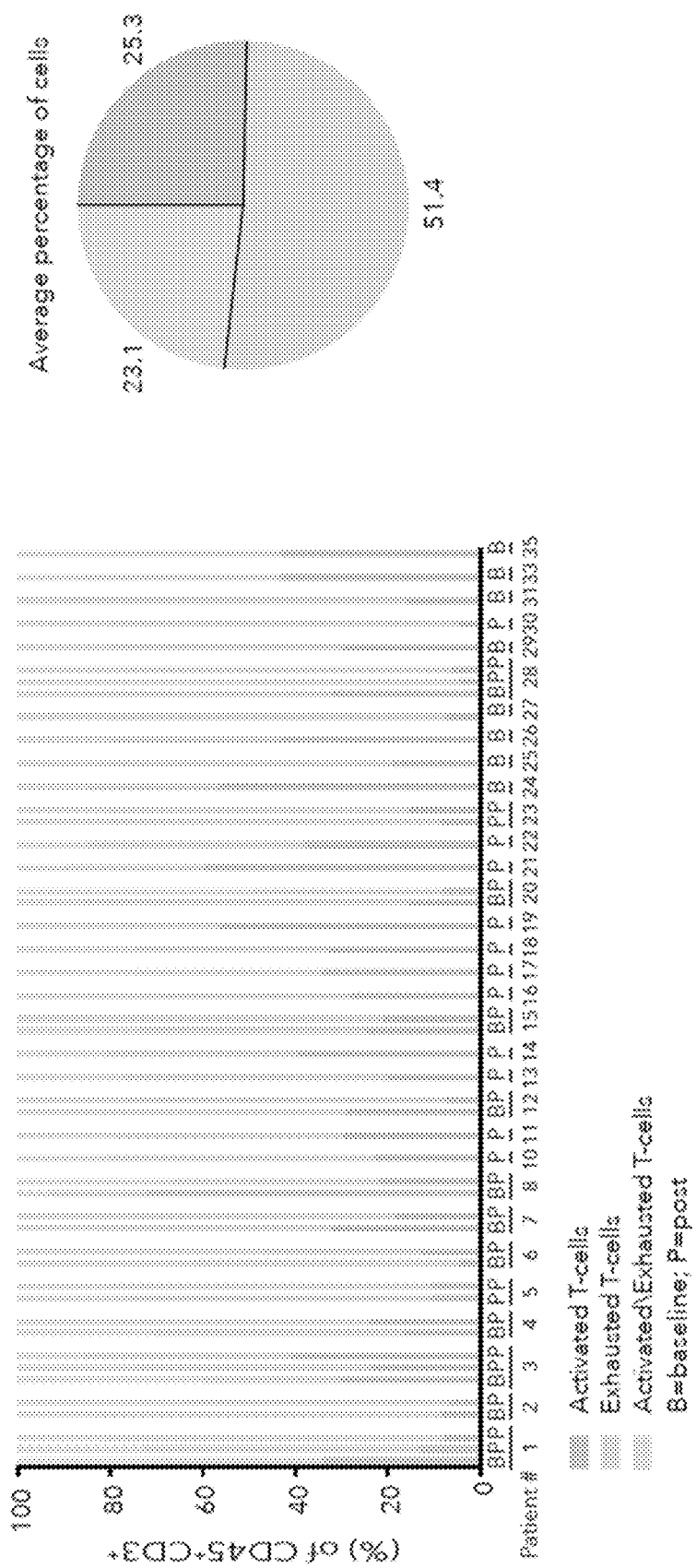
FIG. 30A. The percentage of exhausted, activated or activated/exhausted CD45$^+$CD3$^+$ cells in each patient, on the basis of a pre-defined list of known marker genes is shown. Pie chart on the right summarizes the corresponding percentage across all CD45$^+$CD3$^+$ T-cells collected in this study FIG. 30B. Comparison of the abundance of all three cell states as in (A) between baseline and post-treatment samples (left) and responder and non-responder lesions (right), on the basis of the pre-defined list of known genes as in (A).
Figures 30B, 30C, 30D:
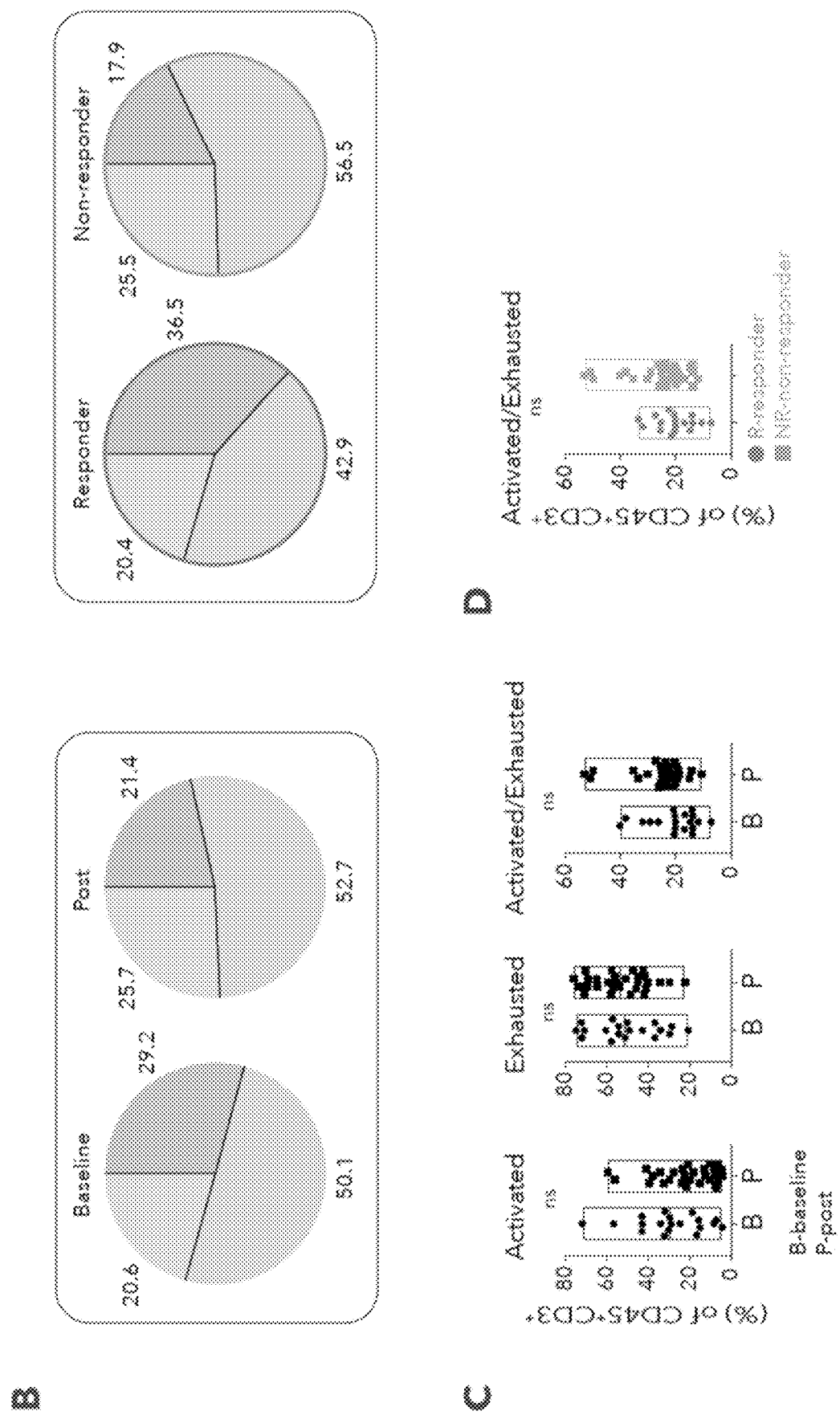
FIG. 30C-D. Box plots comparing the abundance of cells in all three cell states between baseline and post-treatment samples (C) and for the activated/exhausted state between responder and non-responder lesions (D). B—baseline, P—post, R—responder, NR—non-responder, ns—not significant.

Example 10—the Immune Cell Composition of Melanoma Tumors and their Association with Clinical Outcome To define the immune landscape in an unbiased manner, Applicants initially performed unsupervised clustering of cells (on 16,291 cells that passed quality control, based on the ~4,000 most variable genes across all cells) using k-means clustering with a correlation distance metric (Methods). After testing for the robustness of this clustering solution and relationships to previously known cell types, Applicants identified 11 clusters that included, 2 B-cell clusters (G1—B-cells; G2—plasma cells), 2 myeloid clusters (G3—monocytes/macrophages; G4—dendritic cells) and 7 clusters enriched for T/NK/NKT cells (G5-11), accounting for most of the immune infiltrate detected within the cohort (FIG. 23B—C and Table 2). Applicants then tested whether these clusters change between baseline and post-therapy samples, or between responder and non-responder tumors. While differences in cluster frequencies were detected when looking at the single patient level between baseline and post-treatment samples (FIG. 29A), no statistically significant changes in cluster frequencies were seen when Applicants compared all aggregated baseline to all aggregated on-treatment samples, or when only looking at patients with matched longitudinal samples (FIG. 29B-C). However, when analyzing by clinical outcome, Applicants found that one cluster is significantly enriched in responder lesions while 4 clusters are enriched in non-responder lesions. Specifically, those include G1 (B-cells; Two-sided Wilcoxon P-value P=0.003), G3 (monocytes/macrophages, P-value=0.003), G4 (dendritic cells, P-value=0.015) G6 (Exhausted CD8$^+$ T-cells, P-value=0.005) and G11 (Lymphocytes exhausted/cell cycle, P-value=1.33×10$^{-5}$; FIG. 23D and FIG. 29D). While both G6 and G11 clusters were enriched for genes linked to T-cell exhaustion, with differentially higher expression of co-inhibitory receptors (LAG3, PDCD1, CD38, HAVCR2, TIGIT and ENTPD1); G11 was also enriched for cell cycle genes (negative regulators: CASP3, CDK2, BRCA2, RBI and TP53; positive regulators: CDK1, CCNB1, MKI67, CDK4, CDCA5 and TOP2A) (Table 2). Consistent with these results, when using previously defined signatures for T-cell exhaustion[7,22] (Table 3), Applicants observed a significant enrichment of T-cells with an exhausted signature in non-responder lesions (two-sided Wilcoxon P-value=0.002) and with an activated signature in responder lesions (P-value=2×10$^{-4}$), but not when these signatures were compared between baseline and post-therapy samples (FIG. 23E and FIG. 30).

Figure 23H:
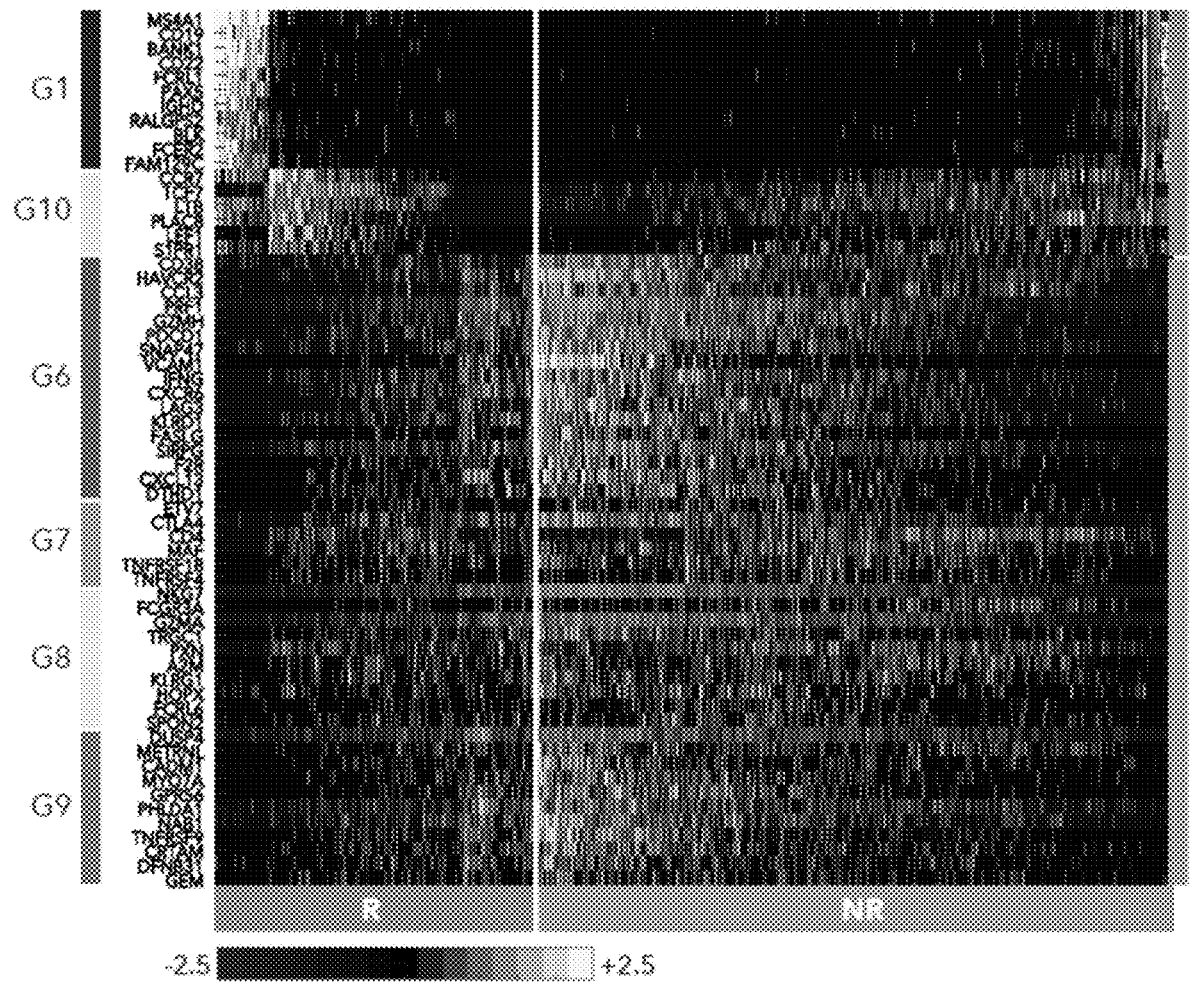
FIG. 23H. Heatmap describing scaled expression values ($\log_2$(TPM+1)) of discriminative gene sets between responder and non-responder lesions. Marker genes are shown per cluster. Shading scheme is based on z-score distribution from −2.5 to 2.5.
Figures 31A, 31B, 31C, 31D:
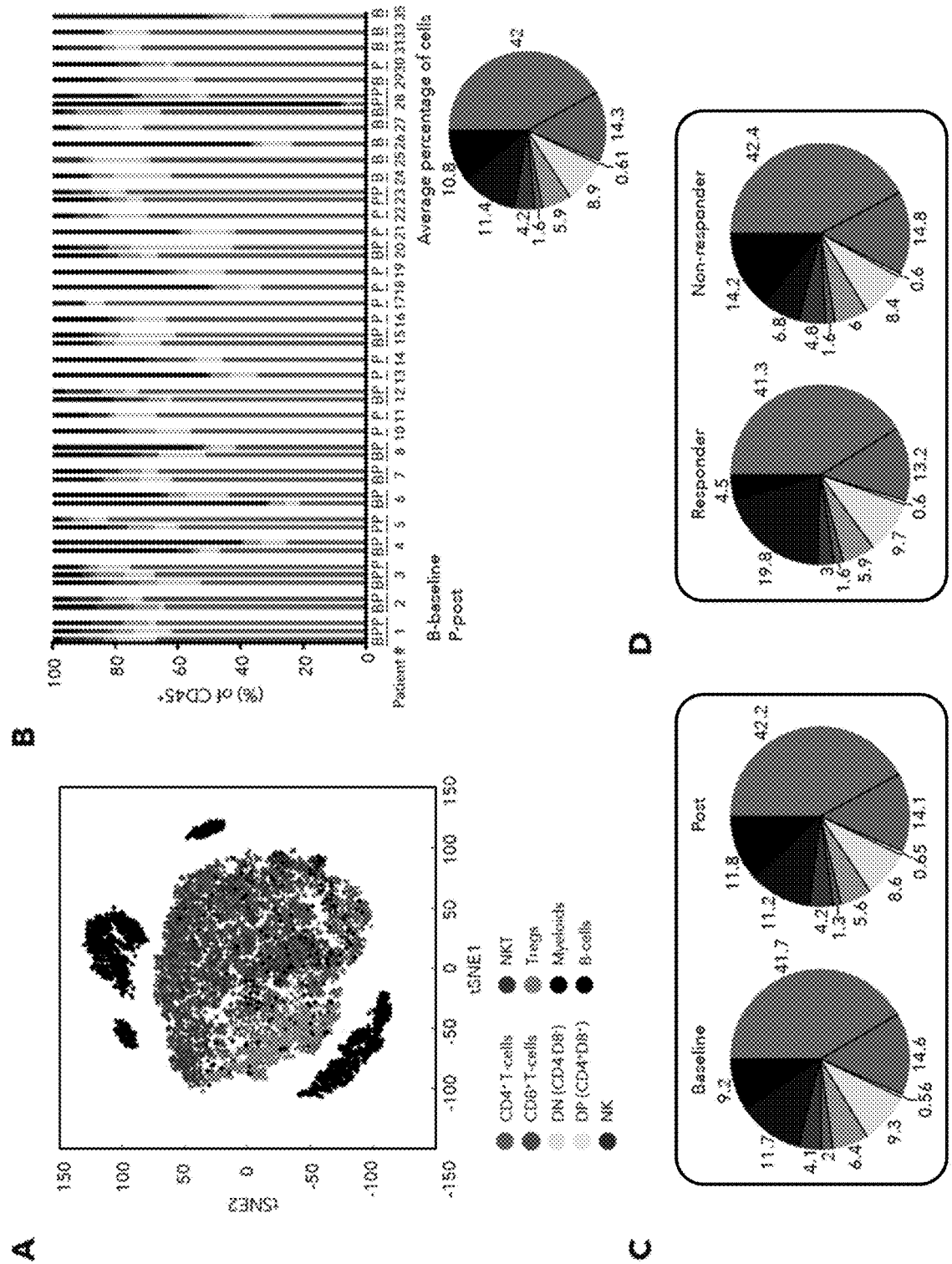
FIG. 31A. tSNE plot of all CD45+ cells collected in this study. Cells are shaded by cell type on the basis of pre-defined markers (table 3).
FIG. 31B. The percentage of known immune cell types in each patient, on the basis of a pre-defined list of known marker genes. Pie chart (below bar graph) summarizes the corresponding percentage of known cell types across all CD45+ cells collected in this cohort.
FIG. 31C-D. A comparison of the abundance of known cell types as in (B) between baseline and post-treatment samples (C) and responder and non-responder lesions (D).
Figures 31E, 31F:
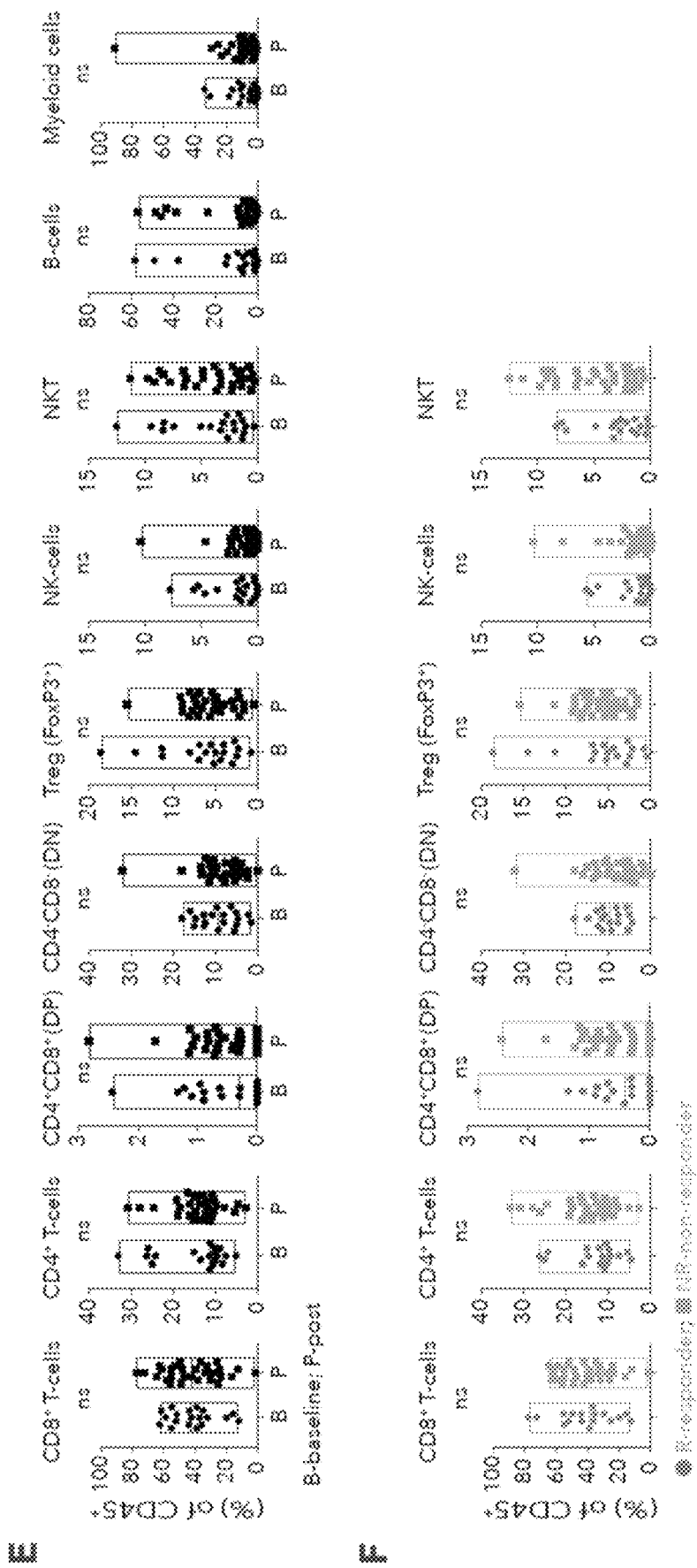
FIG. 31E-F. Box plots comparing the abundance of known cell types between baseline and post-treatment samples (E) and between responder and non-responder lesions (F). B—baseline, P—post, R—responder, NR—non-responder, ns—not significant.
Figure 32A:
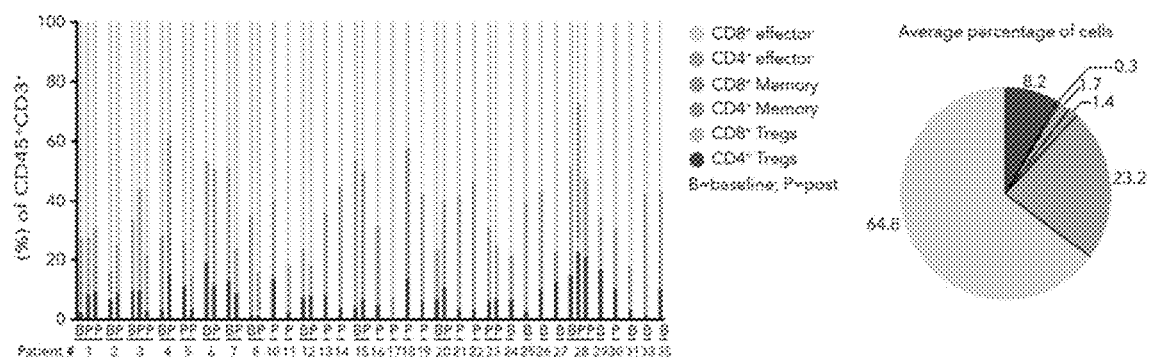
FIG. 32A. The percentage of effector, memory and regulatory CD45$^+$CD3$^+$ cells in each patient, on the basis of pre-defined list of known marker genes is shown. Pie chart on the right summarizes the corresponding percentage across all CD45$^+$CD3$^+$ T-cells collected in this study.
Figure 32B:
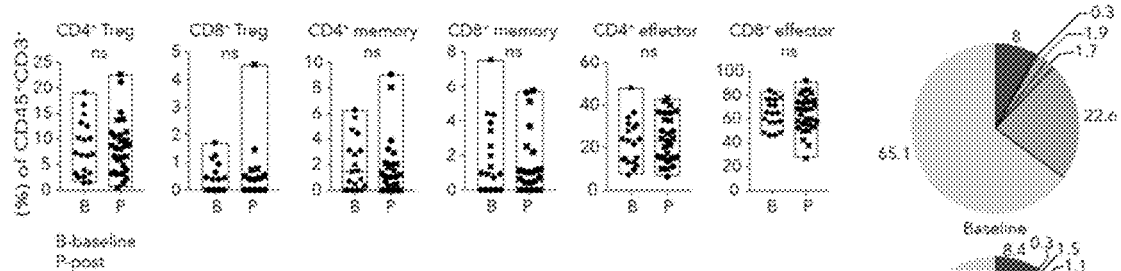
FIG. 32B-C. Box plots and pie charts comparing the abundance of different T-cell types between baseline and post-treatment samples (B) and between responder and non-responder lesions (C). B—baseline, P—post, R—responder, NR—non-responder, ns—not significant.
Figure 32C:
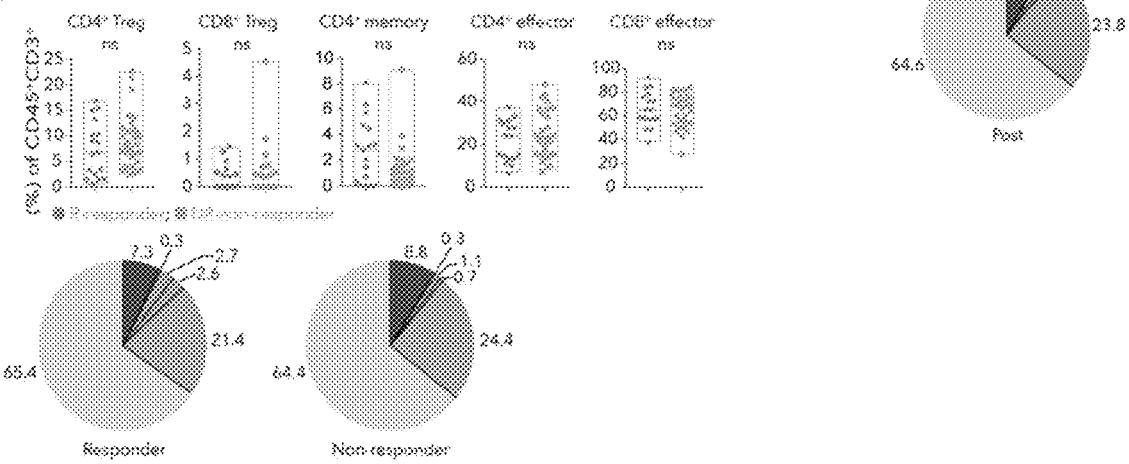
Figure 33:
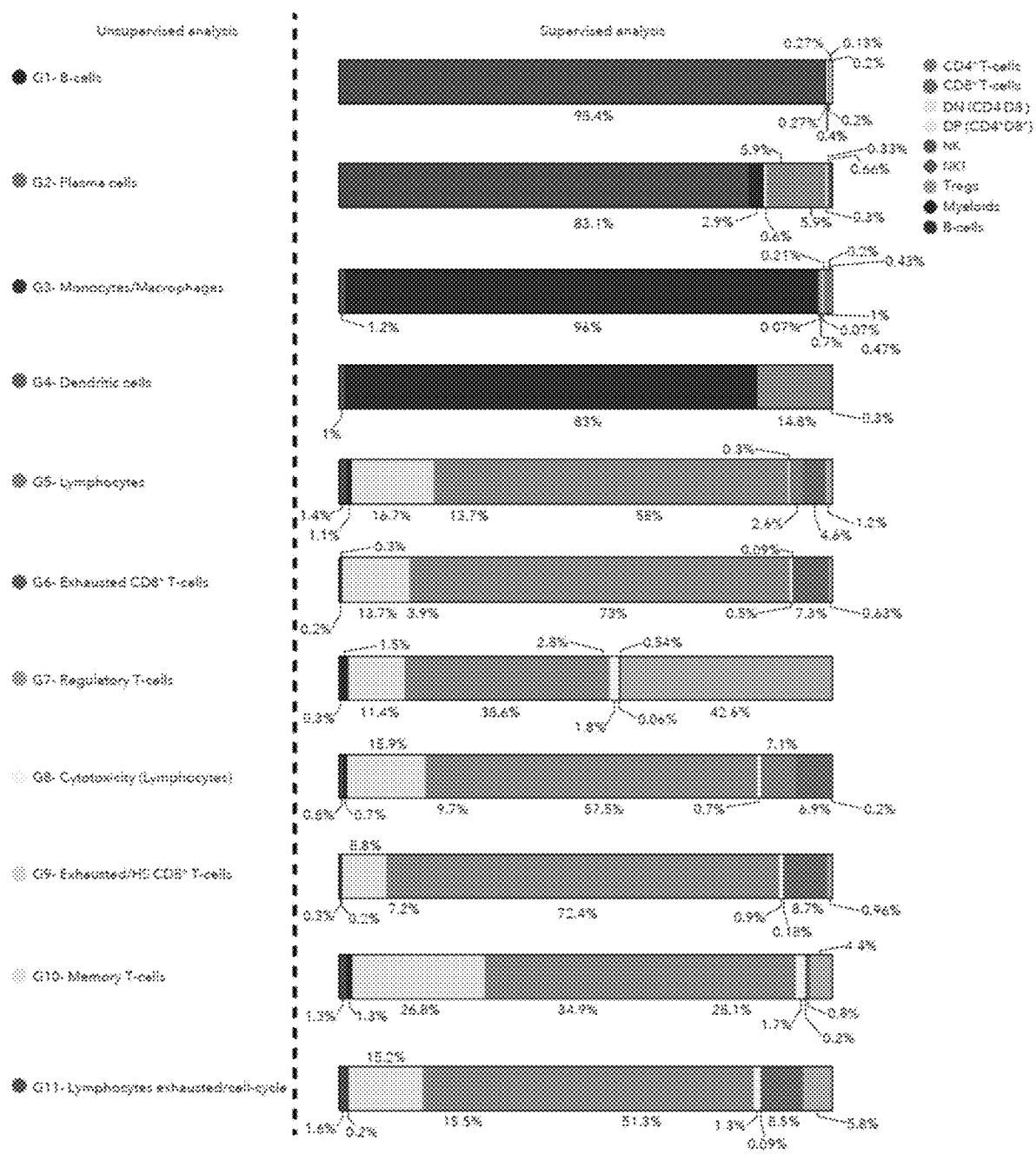
FIG. 33—Comparing the supervised cell type classification to the unsupervised clustering of immune cells. A comparison between the supervised classification of single cells to cell types (right) to the unsupervised clustering of immune cells identified by k-means clustering (left). For each one of the 11 unsupervised clusters identified, the percentage of cell types as defined by the supervised analysis is shown.
Figure 34A:
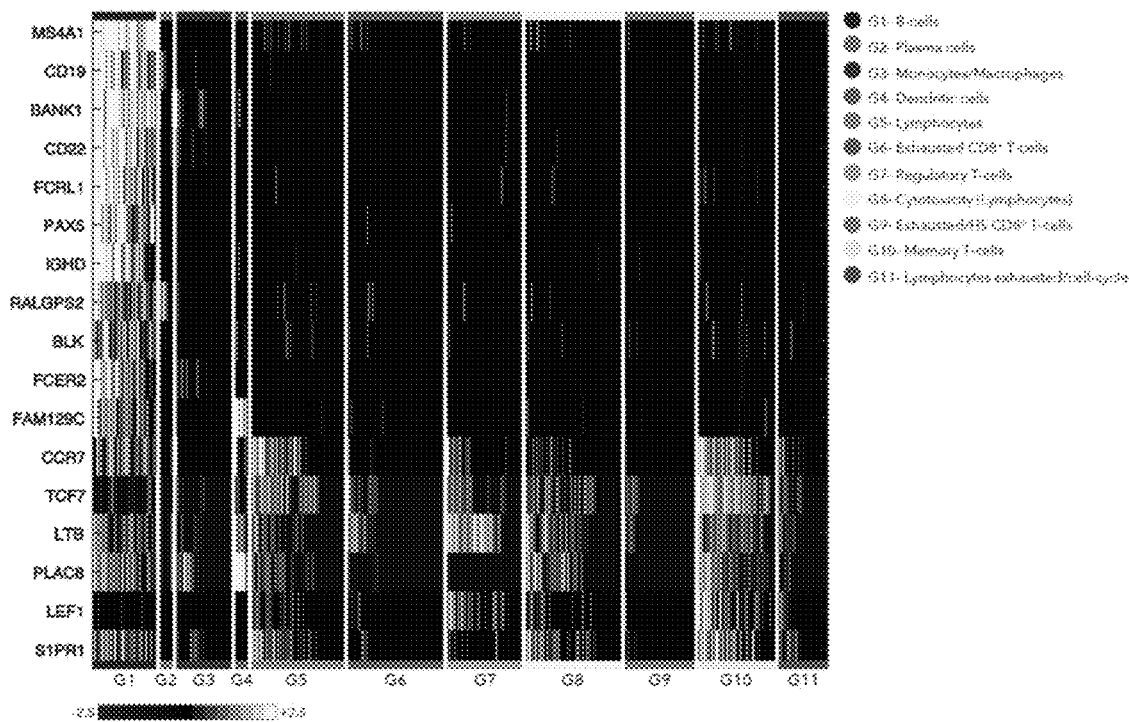
FIG. 34A-B. Heatmap showing scaled expression values (log 2(TPM+1)) of genes that are significantly more expressed in responder (A) and non-responder (B) samples. The analysis was done on a specific set of genes (top 20 cluster-specific marker genes, Table 2). A list of all significant genes is shown for each cluster next to the left margin. Shading scheme is based on z-score distribution from −2.5 to 2.5.
Figure 34B:
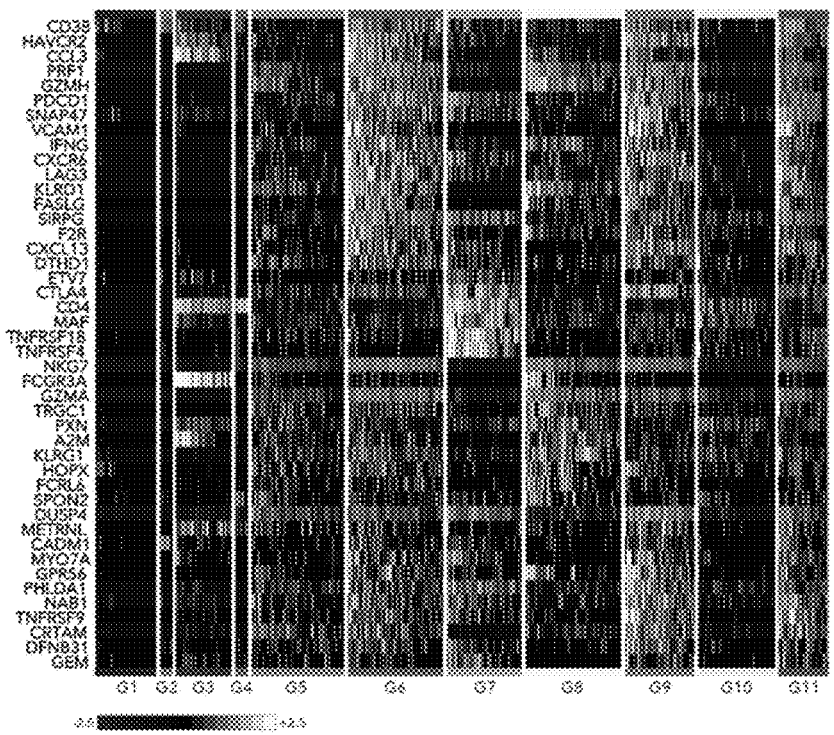

Since the clusters (G5-G11) from the unsupervised analysis did not separate specific cell types, but mostly cell states, likely due to the shared transcriptional programs between T, NK and NKT cells[23,24], Applicants also determined the composition of known cell types using pre-defined markers (Table 3 and FIGS. 31 and 32). In agreement with the unsupervised analysis, Applicants found a significant enrichment of B-cells in responder lesions (P-value=0.004) and of myeloid cells in non-responder lesions (P-value=0.002; FIG. 23F). Moreover, Applicants observed a significant enrichment of CD8$^+$ memory T-cells in responder lesions (P-value=0.001, FIG. 23G). No significant differences in the composition of known cell types were detected between baseline and post-treatment samples when samples were aggregated together. However, changes were observed when looking at the single patient level (FIGS. 31 and 32). Next, when comparing all 11 clusters identified in the unsupervised analysis to the pre-defined markers, Applicants found very high correspondence between clusters G1-G4 and the pre-defined B/myeloid cell markers. In contrast, clusters G5-G11 did not show strong correspondence to a specific cell type, suggesting that different lymphocytes (e.g. T, NK and NKT cells) share similar cell states of exhaustion, activation, cytotoxicity and memory (FIG. 33). Finally, Applicants wanted to leverage the unbiased approach to identify not only clusters but also specific markers associated with response. To that end, Applicants used two different strategies. (1). focusing on cluster discriminating genes, and examining whether they are differentially expressed between responder and non-responder samples (Table 4; FIG. 23H and FIG. 34); and (2). examining all genes in an unbiased manner and searching for differentially expressed genes (from all cells) between responder and non-responder samples (Table 5 and FIG. 35). sing these two different approaches (cluster specific and non-specific) Applicants identified an overlap for markers significantly enriched in responders (PLAC8, LTB, TCF7 and CCR7) and non-responder (CCL3, CD38 and HAVCR2) samples. Applicants conclude that the methods used here, reveal novel cell states and markers that associate with the clinical outcome of individual tumors to therapy, demonstrating the power of unbiased approaches to find molecular correlates of response.

Figure 24A:
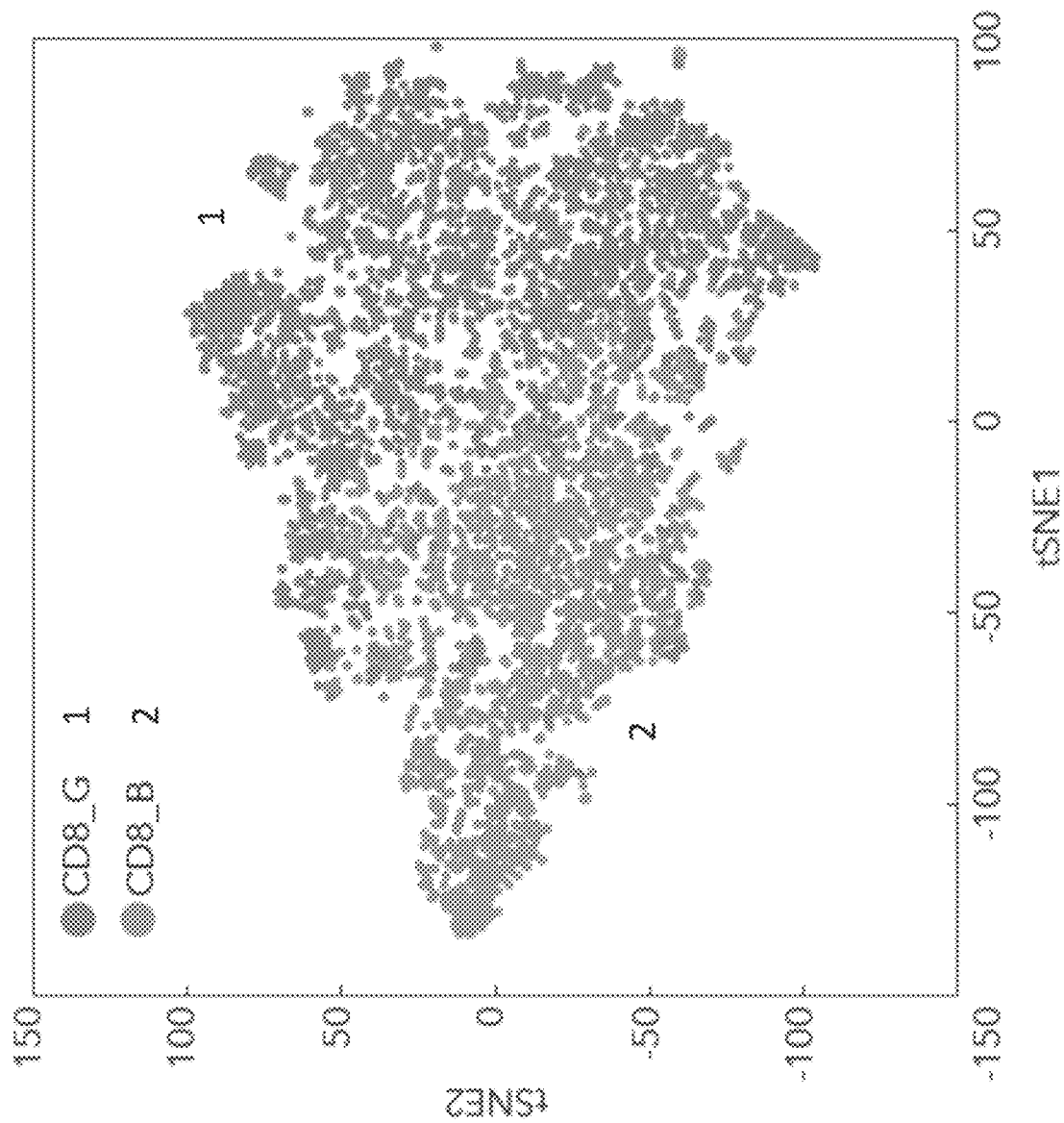
FIG. 24A. tSNE plot of all CD8$^+$ T cells collected in this study. Cells are shaded based on 2 clusters identified by k-means clustering (Methods).
Figure 24B:
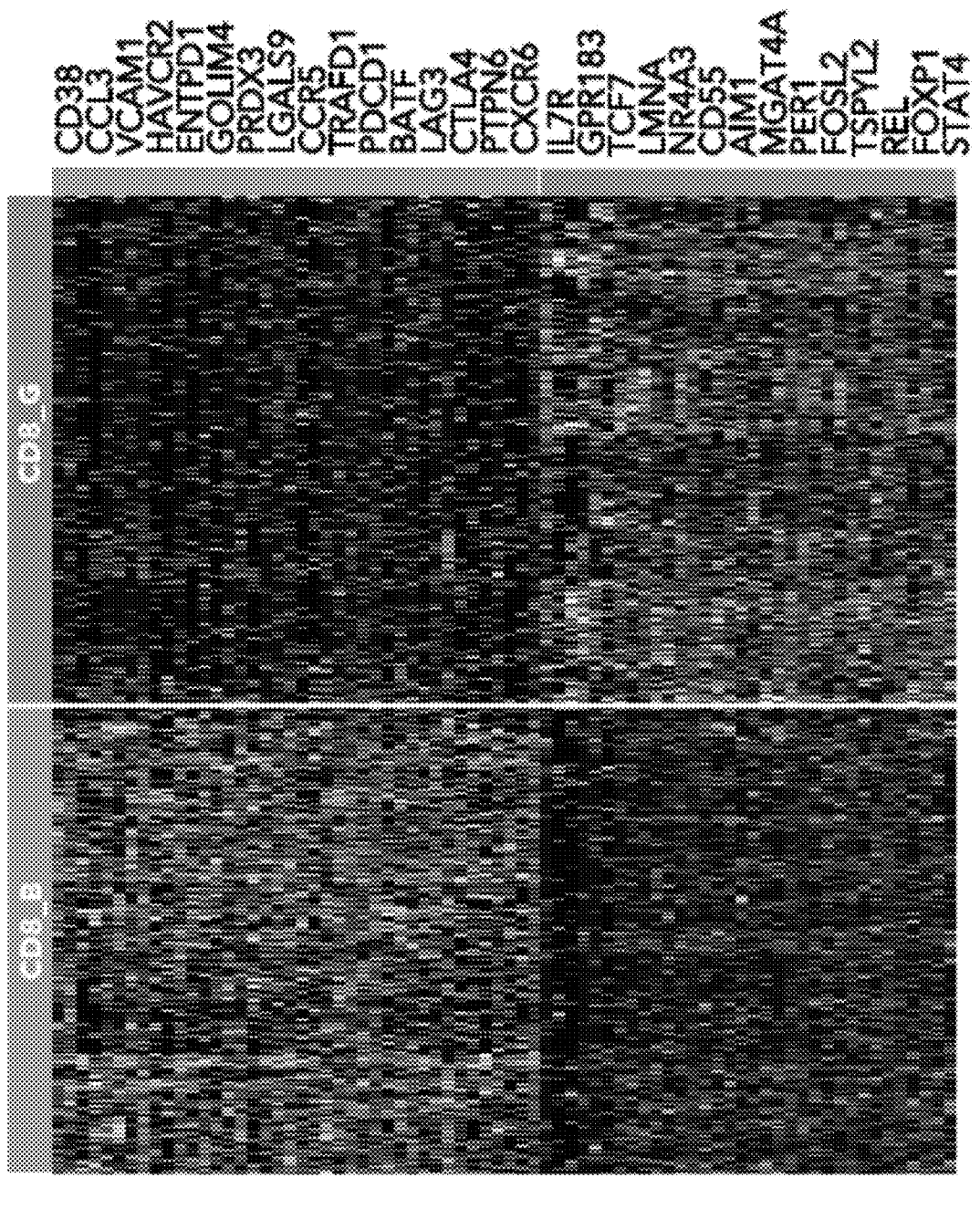
FIG. 24B. Heatmap showing scaled expression values ($\log_2$(TPM+1)) of discriminating genes for the clusters defined in (A). A list of representative genes are shown for each cluster next to the right margin bars. Shading scheme is based on z-score distribution from −2.5 to 2.5.
Figure 24C:
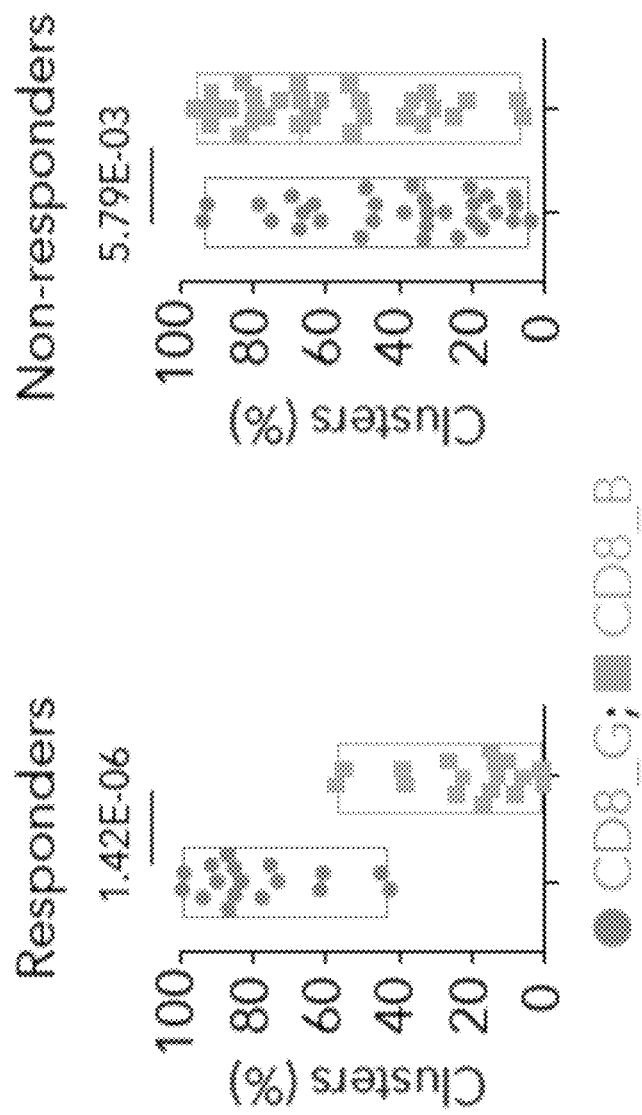
FIG. 24C. Box plots comparing the percentage of CD8_G and CD8_B (out of CD8+ cells) clusters in responder and non-responder lesions. Each symbol represents an individual sample. Two-sided Wilcoxon rank-sum P-value is shown P=1.4×10$^{-6}$ responders; P=0.005 non-responders.
Figure 24D:
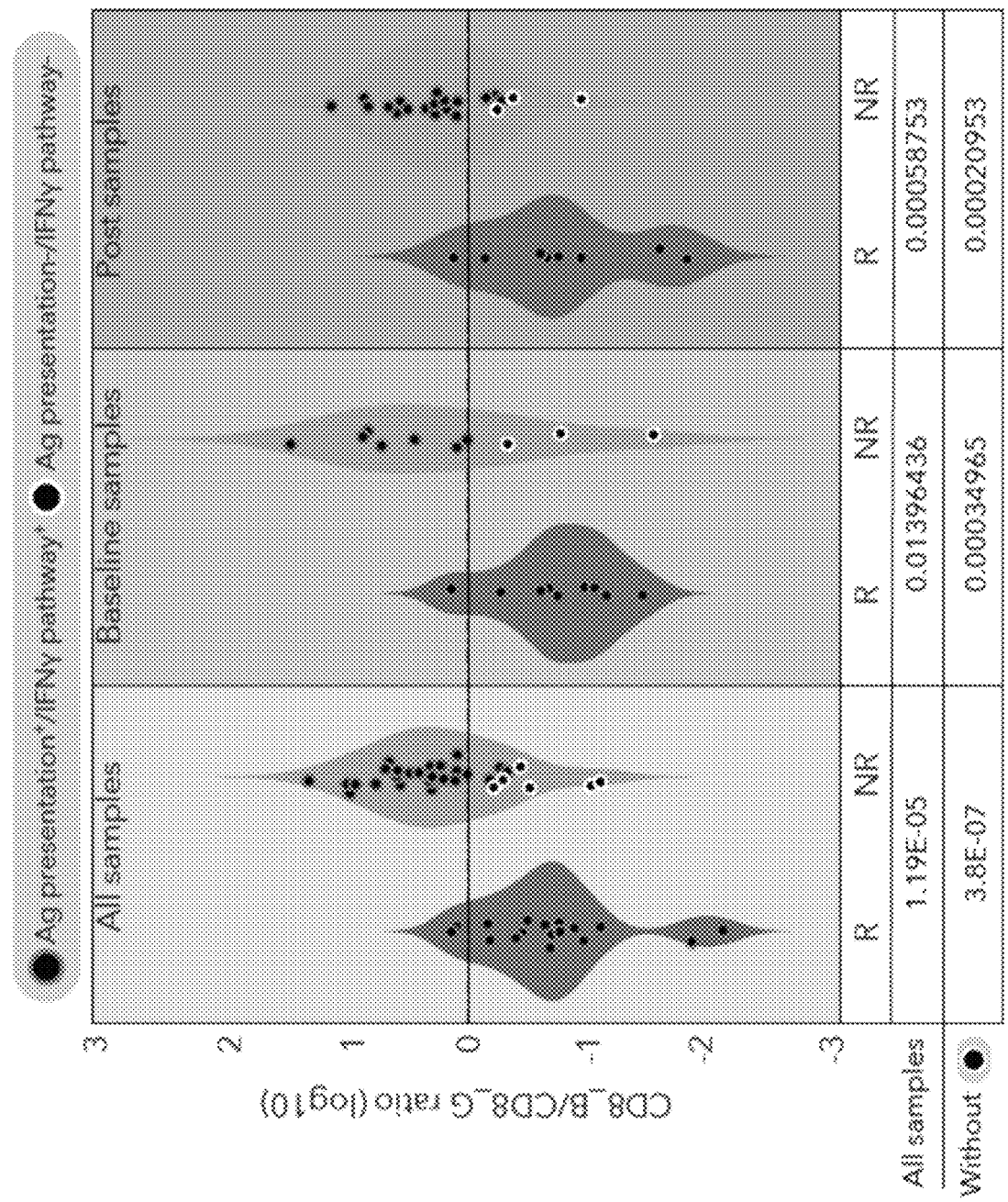
FIG. 24D. The $\log_{10}$ ratio between the number of cells in CD8_B/CD8_G per sample is computed. A comparison of this measurement between responder and non-responder lesions is shown for all samples, baseline and post-treatment samples separately. Circles marked in white represents samples with defects in antigen presentation and the IFNγ pathway (Ag presentation-/IFNγ pathway-) as inferred by WES, IHC and flow-cytometry analysis. Marked Circles represent samples without defects in those pathways. The significance score (one-sided Wilcoxon P-value) for each comparison is shown below.
Figure 36:
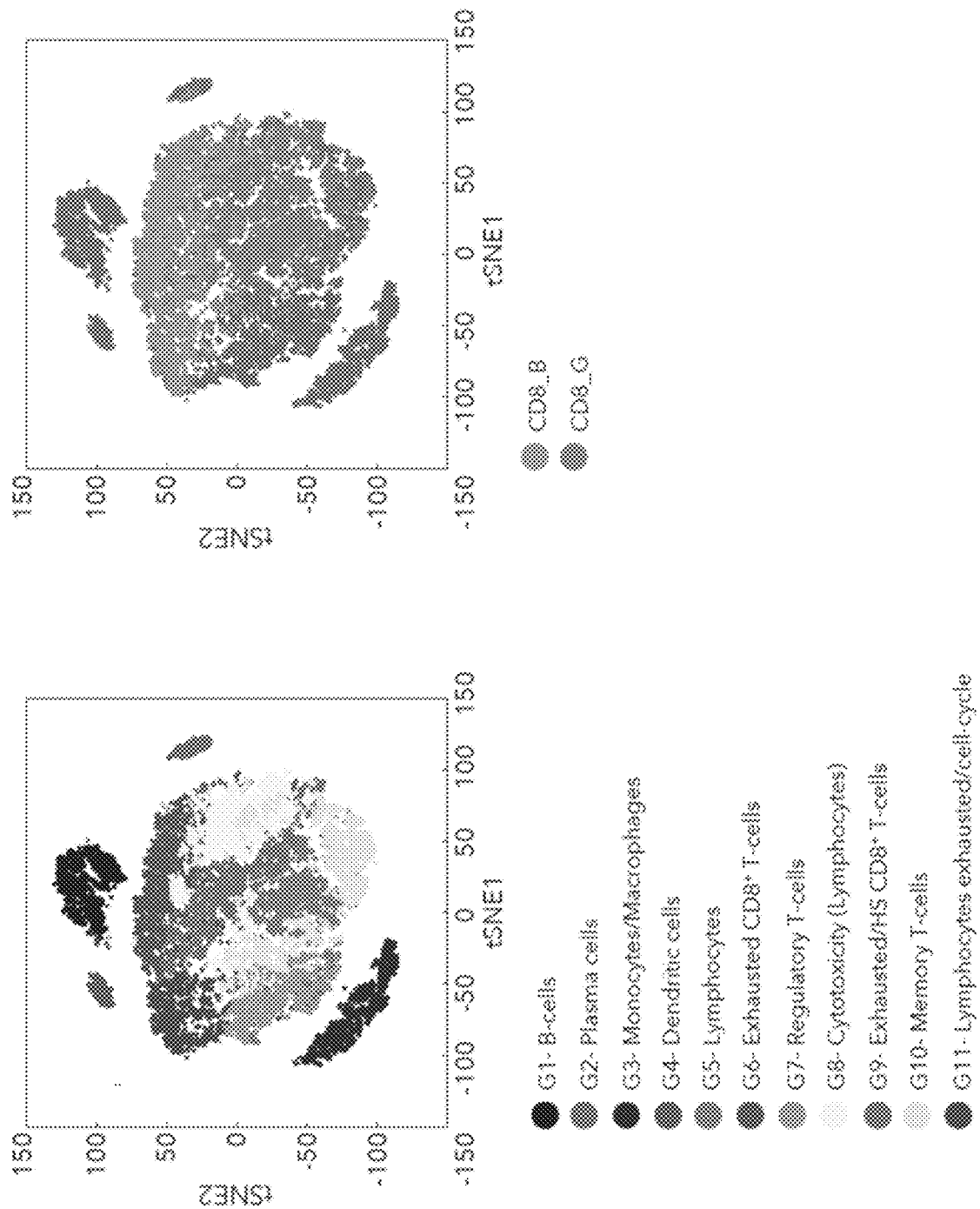
FIG. 36—Annotating CD8_G and CD8_B clusters to the whole immune cell population clusters. tSNE plot of all CD45$^+$ clusters (n=11) collected in this study (left) is shown. Cells are shaded based on 11 clusters identified by k-means clustering analysis (Methods). Right tSNE plot shows the distribution of CD8_G and CD8_B in relation to all immune cells analyzed in this study.
Figure 37A:
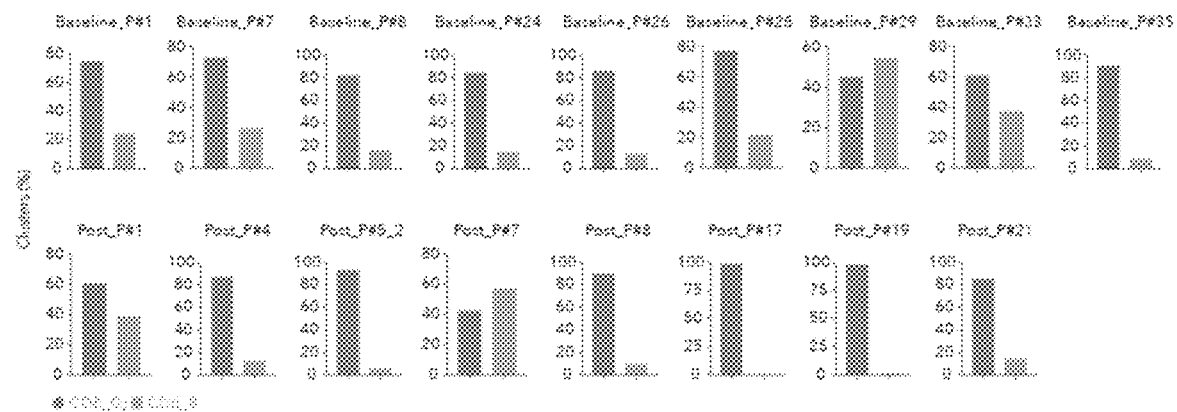
FIG. 37A-B. For each sample, the percentage of cells found in CD8_G and CD8_B (out of all CD8$^+$ T cells) in responder lesions (A) and non-responder lesions (B) is shown. * symbol marks samples with defects in antigen presentation and the IFNγ pathway as inferred from WES, IHC and flow-cytometry analysis. P # indicates patient number as described in table 1.
Figure 37B:
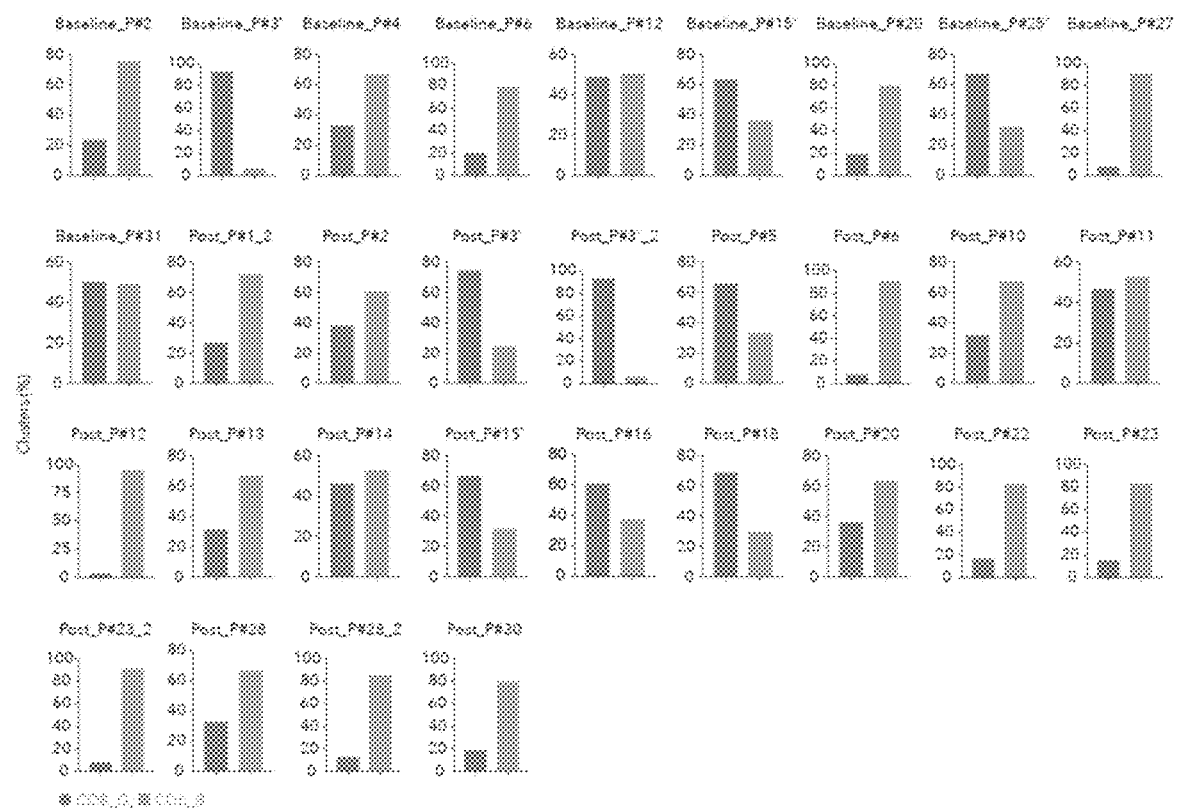
Figure 37C:
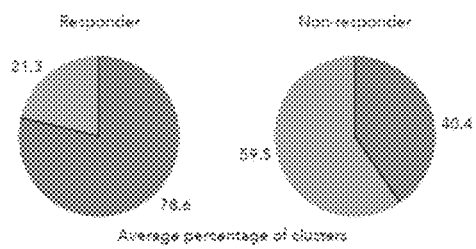
FIG. 37C. Pie charts summarize the average percentage of the 2 clusters in the responders and non-responders groups.
Figures 38A, 38B, 38C, 38D:
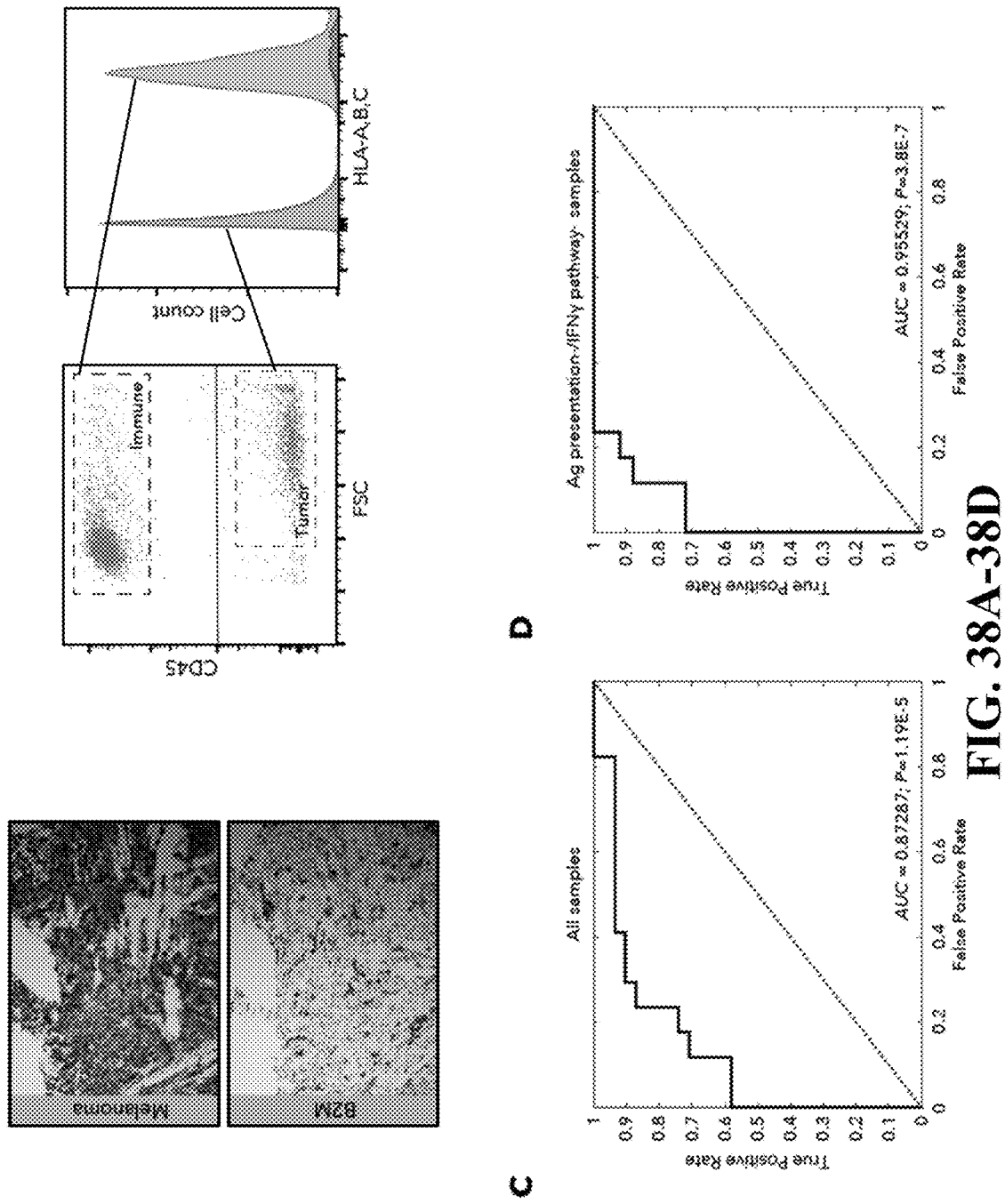
FIG. 38A. Representative immunohistochemistry staining (1 out of 3) of sections from patient #3 with homozygote mutations in B2M (as inferred from WES). Sections were stained with an antibody cocktail for melanoma cells (mel.cocktail) using anti-melanosome (HMB45), anti-MART-1/melan A and anti-Tyrosinase, to discern melanoma cells from normal cells; or with an antibody specific for B2M. Original Magnification ×100.
FIG. 38B. Flow-cytometry plot (left) and histogram (right), showing the expression of HLA-A,B,C in immune and tumor cells in patient #15.
FIG. 38C-D. Receiver operating characteristic (ROC) analysis was constructed to evaluate the prognostic power of the ratio between CD8_B/CD8_G as shown in FIG. 24D between responder and non-responder lesions. The area under the ROC curve (AUC) was used to quantify response prediction, and one-sided Wilcoxon test was used to assess significance of the AUC results. The AUC value for all samples (C) was 0.87 (P=1.1×10$^{-5}$) and (D) 0.95 (P=3.8×10$^{-7}$) when excluding the 6 samples with defects in antigen presentation and the IFNγ pathway as inferred by WES, IHC and flow-cytometry analysis.

Example 11—Unbiased Definition of CD8+ T-Cell States and their Association with Response to Therapy Based on the significant association of T-cell states and markers with clinical response using either unsupervised or supervised analyses, their highest abundance within the cohort, and due to the dependency of checkpoint therapies on CD8+ T-cell recognition of tumor antigens presented by human leukocyte antigen (HLA) class-I complexes[5,25], Applicants next focused the analysis on CD8+ T-cells. Clustering of all CD8+ T-cells (n=6,350) by k-means clustering revealed 2 cell states:CD8_G with increased expression of genes linked to memory, activation and cell survival (IL7R, TCF7, REL, FOXP1, FOSL2 and STAT4)[26] and reduced expression of co-inhibitory molecules; and CD8_B enriched for genes linked to cell exhaustion (CD38, HAVCR2, ENTPD1, PDCD1, BATF, LAG3, CTLA4 and PTPN6) (FIG. 24A-B and Table 6). When annotating these two clusters to the 11 clusters identified by the unsupervised analysis (FIG. 23B), CD8_G cells were distributed primarily in G10 (memory T-cells), G5 (lymphocytes) and G8 (cytotoxicity) clusters, and CD8_B cells were localized mainly in clusters G11 (lymphocytes exhausted/cell-cycle), G6 (exhausted CD8+ T-cells) and G9 (exhausted/HS CD8+ T-cells; FIG. 36). A central question is whether these states are associated with clinical outcome and what is their predictive power to distinguish responding from non-responding tumors. When comparing between these two cell states, Applicants found a significant enrichment for CD8_G in responding lesions (two-sided Wilcoxon P-value=$1.4 \times 10^{-6}$) and CD8_B in non-responding lesions (P-value=0.0058; FIG. 24C). While cells with both states coexist in each of the responder and non-responder lesions, an overall higher proportion of CD8_G cells is found in responders, and CD8_B cells in non-responders (FIG. 37). Thus, Applicants decided to calculate the ratio between the number of cells in these 2 clusters and observed a significant separation between responders (CD8_B/CD8_G<1) and non-responders (CD8_B/CD8_G>1) when looking at all samples, as well as baseline or post-treatment samples separately (FIG. 24D). However, 9 non-responding lesions had unexpected ratios (CD8_B/CD8_G<1), and were more enriched for CD8_G. Applicants hypothesized that although these patients might have productive immunity, they had developed de novo resistance to checkpoint therapy. To dissect the genetic alterations associated with resistance, Applicants performed WES followed by immunohistochemistry and flow cytometry, and observed that 6 out of 9 samples (no DNA or slides were available for the 3 remaining lesions) showed complete loss of B2M or HLA-A,B,C (class-I), recently reported as a mechanism of resistance to checkpoint inhibition therapy in melanoma[14,15] (Table 1 and FIG. 38A-B). An analysis of predictive performance for the identified signatures demonstrated excellent predictive power when considering all samples (AUC of ROC=0.87; one-sided Wilcoxon P-value=$1.1 \times 10^{-5}$). However, when excluding the 6 samples deficient for B2M or HLA-A,B,C, the predictive power was increased significantly (AUC of ROC=0.96; P-value=$3.8 \times 10^{-7}$, FIG. 38C-D).

Figure 24E:
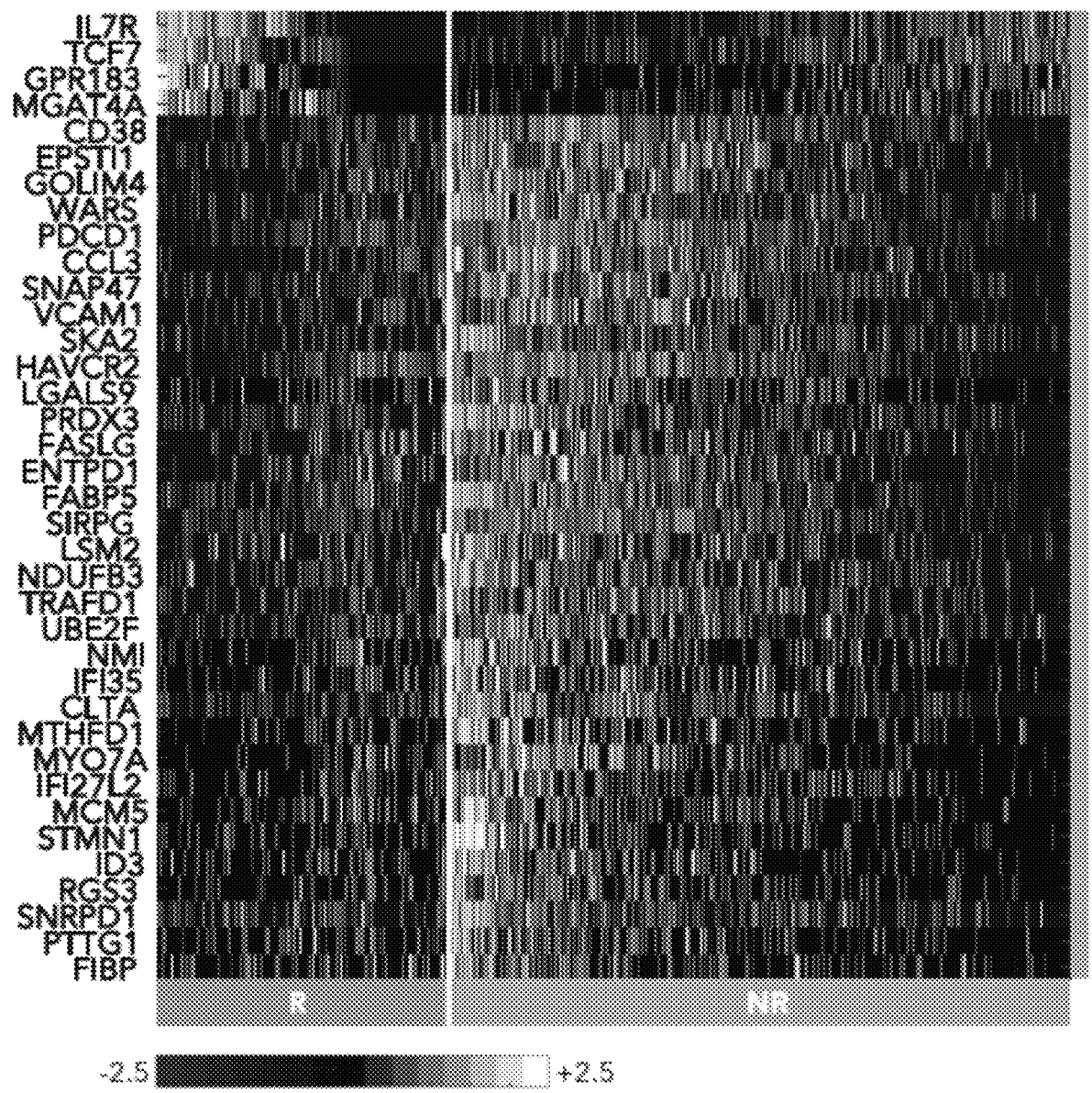
FIG. 24E. Heatmap describing scaled expression values ($\log_2(TPM+1)$) of discriminative gene sets from CD8_G and CD8_B clusters between responder and non-responder lesions. Marker genes are shown per cluster. Shading scheme is based on z-score distribution from −2.5 to 2.5.
Figure 24F:
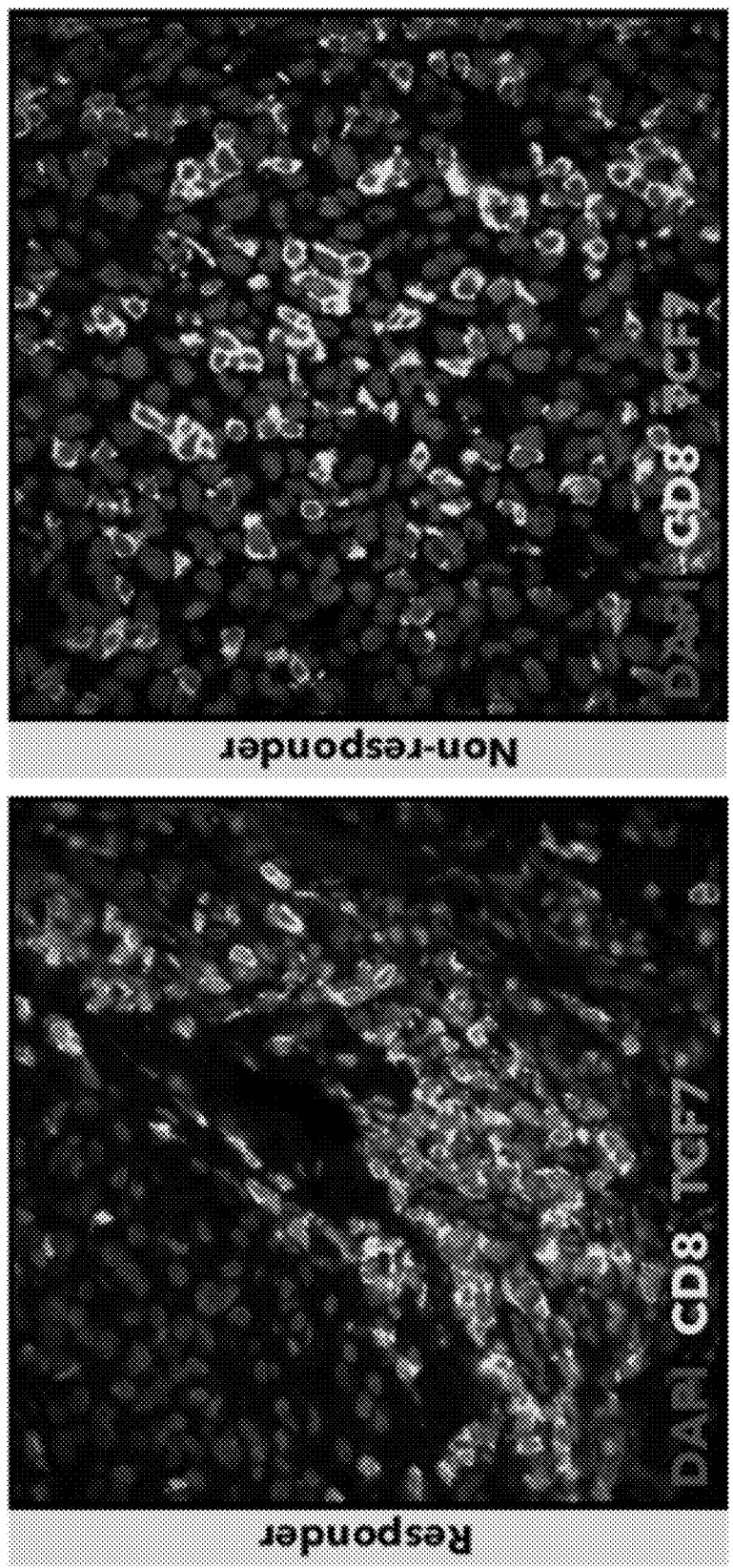
FIG. 24F. Representative images from the multiplex immunofluorescence staining of tissue nuclei stained with DAPI, CD8 and TCF7 from a responder and non-responder patient prior to therapy with anti-PD1. Original Magnification ×400. G. Box plots comparing the percentage of $CD8^+TCF7^+$ and $CD8^+TCF7^-$ cells as inferred by immunofluorescence staining, between responder and non-responder patients. Each symbol represents an individual sample. Two-sided Wilcoxon rank-sum P-value is shown, $P=3.9\times10^{-6}$ responders; $P=1.1\times10^{-8}$ non-responders.

Similarly to the analysis performed on all immune cells, Applicants sought to identify specific CD8+ markers associated with clinical outcome. To that end Applicants focused on CD8_G and CD8_B top discriminating genes and examined whether they are differentially expressed between responder and non-responder samples. Applicants identified TCF7 and IL7R as the top two CD8+ markers to be significantly associated with response, the first being also significant in the initial marker analysis when looking at all CD45+ cells. Moreover, Applicants found a ~45% overlap between markers associated with non-responder lesions in CD8+ T-cells and all immune cells (CD38, PDCD1, CCL3, SNAP47, VCAM1, HAVCR2, FASLG, ENTPD1, SIRPG, MYO7A, FABP5, NDUFB3, UBE2F, CLTA and SNRPD1; FIG. 24E and Table 7). Overall, the results suggest that the abundance of CD8_G and CD8_B cellular states could be critical to the success of checkpoint therapy.

Figure 35:
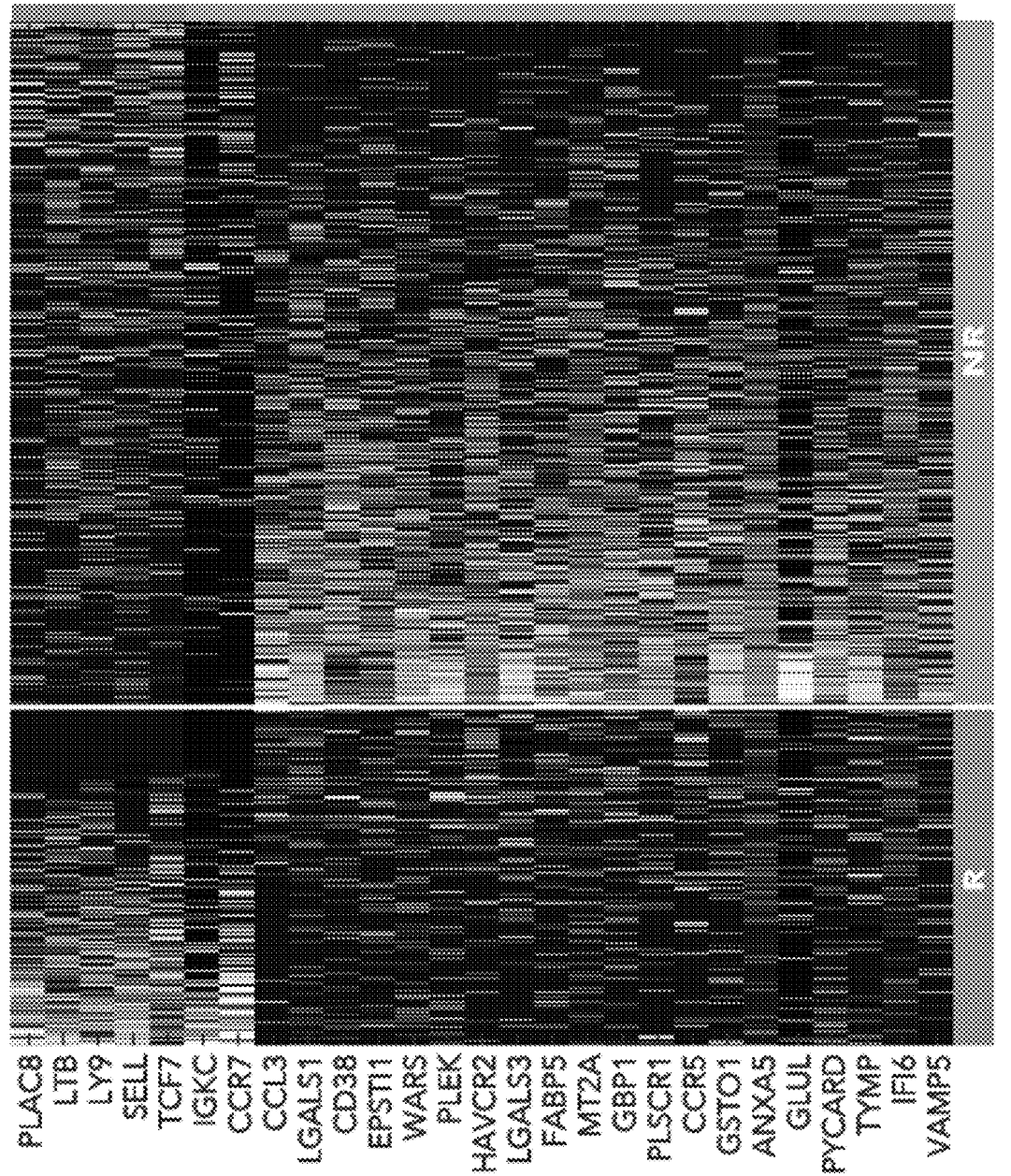
FIG. 35—Detection of genes differentially expressed between responder and non-responder samples. Heatmap showing scaled expression values (log 2(TPM+1)) of genes that are differentially expressed between responder and non-responder samples. A list of representative genes is shown for each cluster next to the left margin. Shading scheme is based on z-score distribution from −2.5 to 2.5.

Example 12—Elevated Frequencies of CD8+TCF7+ T-Cells are Associated with Outcome in a Second Independent Anti-PD1-Treated Cohort Since the ratio between CD8_G and CD8_B was significantly associated with response, Applicants considered whether any of the specific markers identified in these clusters could be used to predict response to treatment in a second cohort, using a different approach that could easily be applied in the clinic. Applicants selected the proteins CD8α and transcription factor 7 (TCF7) for this analysis, because TCF7 was the only top marker linked to response when analyzing all immune or only CD8+ T-cells (FIG. 23H; FIG. 35 and FIG. 24E), differentially expressed in CD8_G (4-fold higher expression than in CD8_B), and since all lymphocytes related clusters that were associated with response were either enriched for or completely composed of CD8+ T-cells (FIGS. 23 and 24 and FIG. 33). TCF7 is part of the Wnt/β-catenin signaling pathway[27] and has been shown to be crucial for differentiation, self-renewal and persistence of memory CD8+ T-cells[28], as well as reinvigoration and effective immunity of CD8+ T-cells against chronic LCMV infection upon anti-PD1 treatment[29,30]. Thus, Applicants considered its association with response in a second cohort of 33 patients (n=43 samples) treated with anti-PD1 (Table 8). Using immunofluorescence staining followed by automated image analysis with CellProfiler[31]

Figures 24G, 24H, 24I, 24J:
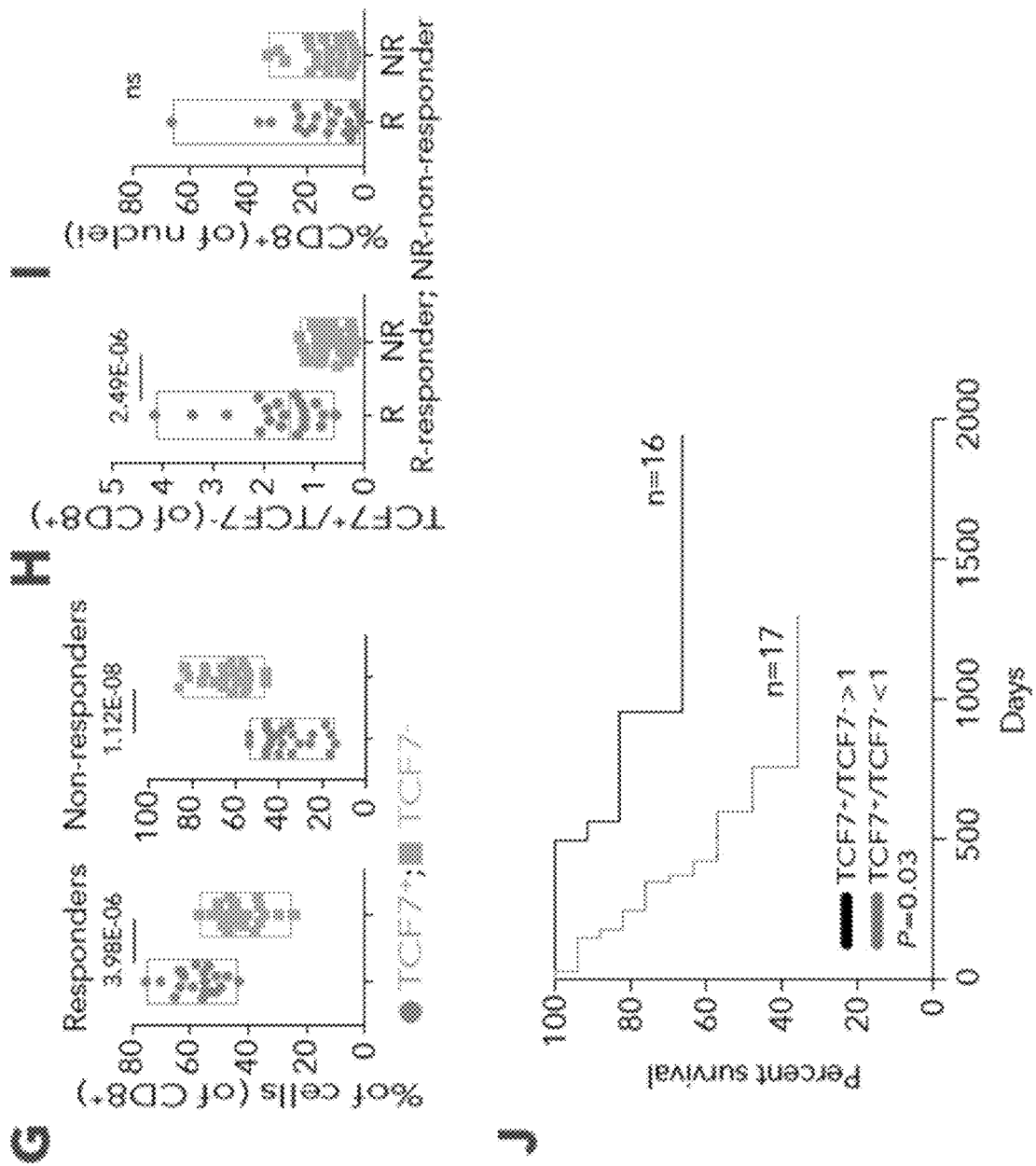
FIG. 24H-I. Box plots showing a quantitative analysis (Methods) of $TCF7^+CD8^+/TCF7^-CD8^+$ ratio out of $CD8^+$ cells (H) and of $CD8^+$ cells out of all nuclei (I) between responder (n=20) and non-responder patients (n=23). n.s—not significant. One-sided Wilcoxon P-value is shown $P=2.4\times10^{-6}$. J. Kaplan-Meier survival curve, composed of data from 33 patients treated with anti-PD1 therapy. Patients were divided into two groups based on $TCF7^+CD8^+/TCF7^-CD8^+$ ratio (n=16>1; n=17<1) as inferred by immunofluorescence staining. A ratio of $TCF7^+CD8^+/TCF7^-CD8^+>1$ was associated with better overall survival (log-rank P=0.03) when compared to patients with $TCF7^+CD8^+/TCF7^-CD8^+<1$.
Figure 39A:
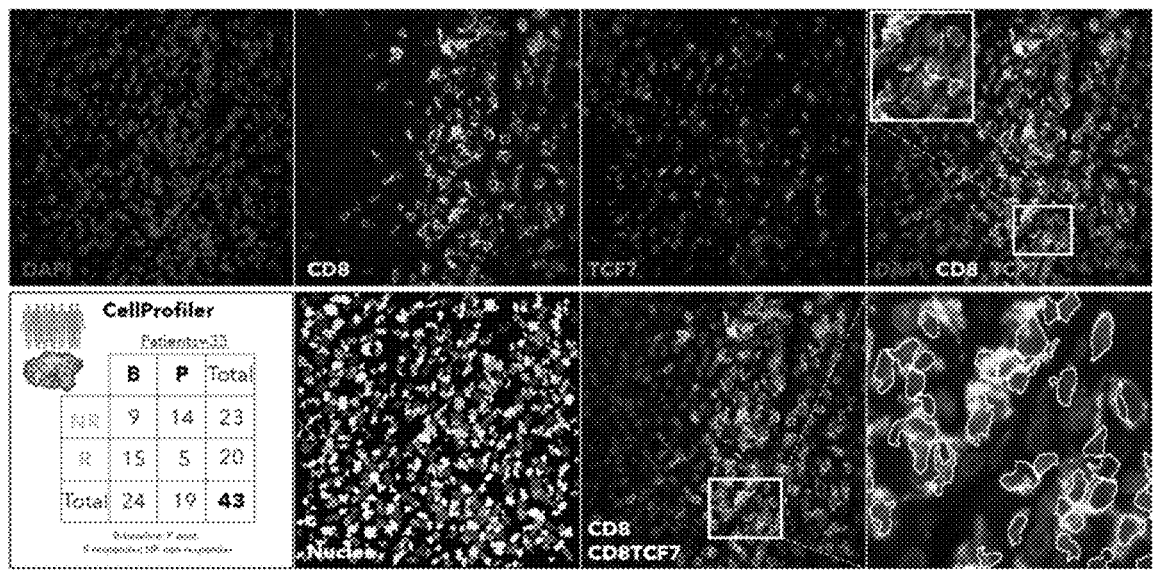
FIG. 39A. Schematic illustration for the immunofluorescence pipeline. Sections from an independent cohort of 33 patients (n=43 samples; responders=20, non-responders=23) treated with anti-PD1 were stained with DAPI, CD8 and TCF7 and analyzed with CellProfiler (Methods). For each sample the percentage of CD8$^+$TCF7$^-$ (line) or CD8$^+$TCF7$^+$ (white line) was calculated out of the total nuclei detected.
Figure 39B:
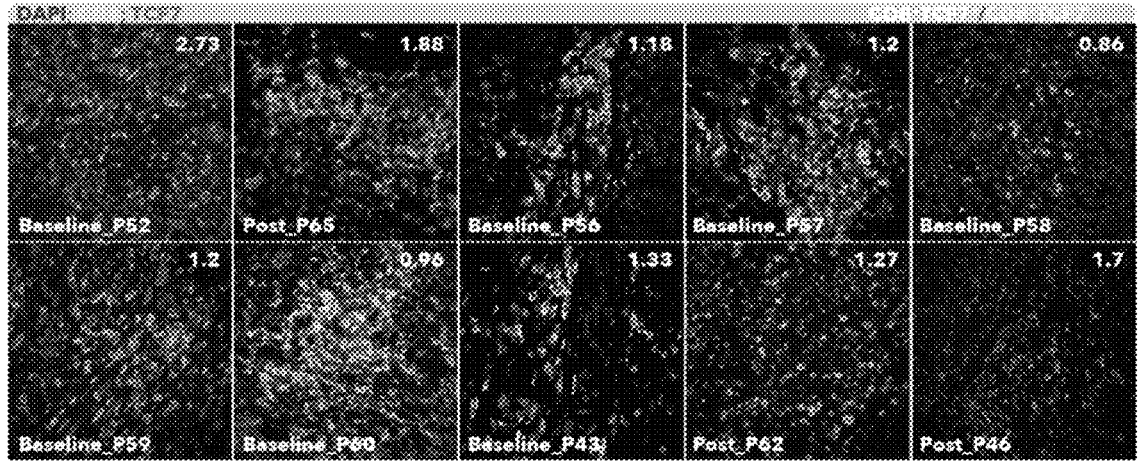
FIG. 39B-C. Representative overlayed images from melanomas of 10 responder (B) and 10 non-responder patients (C) stained with DAPI, CD8 and TCF7. For each patient, 10 random fields were scanned and analyzed. The ratio of CD8$^+$TCF7$^+$/CD8$^+$TCF7$^-$ detected in each patient is shown on the upper right corner of the imaged sections. Original Magnification ×400. TCF7—transcription factor 7.
Figure 39C:
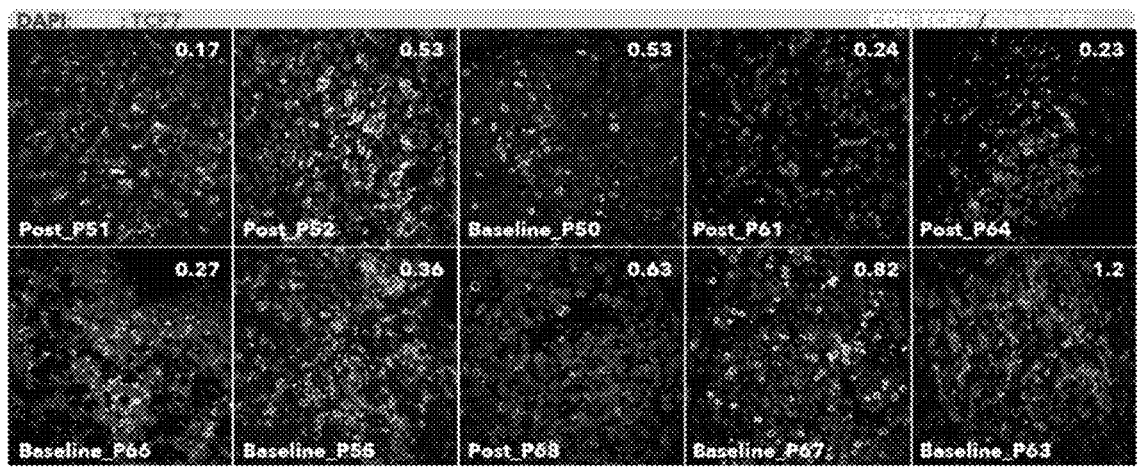
Figure 40A:
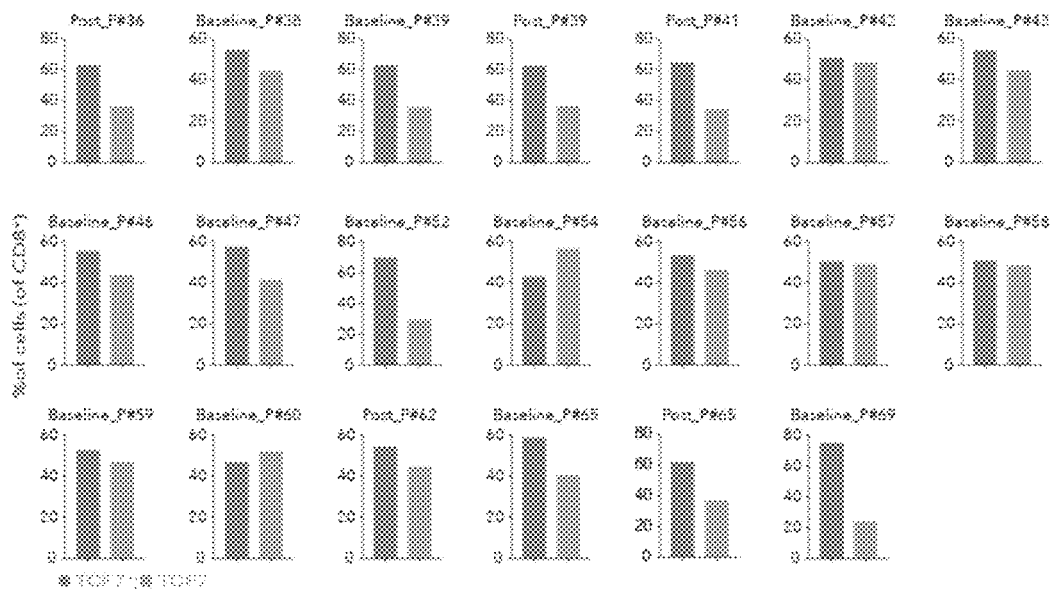
FIG. 40A-B. For each sample, the percentage of CD8+TCF7+ and CD8+TCF7− cells (out of all CD8$^+$ T cells) found in responder (n=20) lesions (A) and non-responder (n=23) lesions (B) is shown. P # indicates patient number as described in table 8.
Figure 40B:
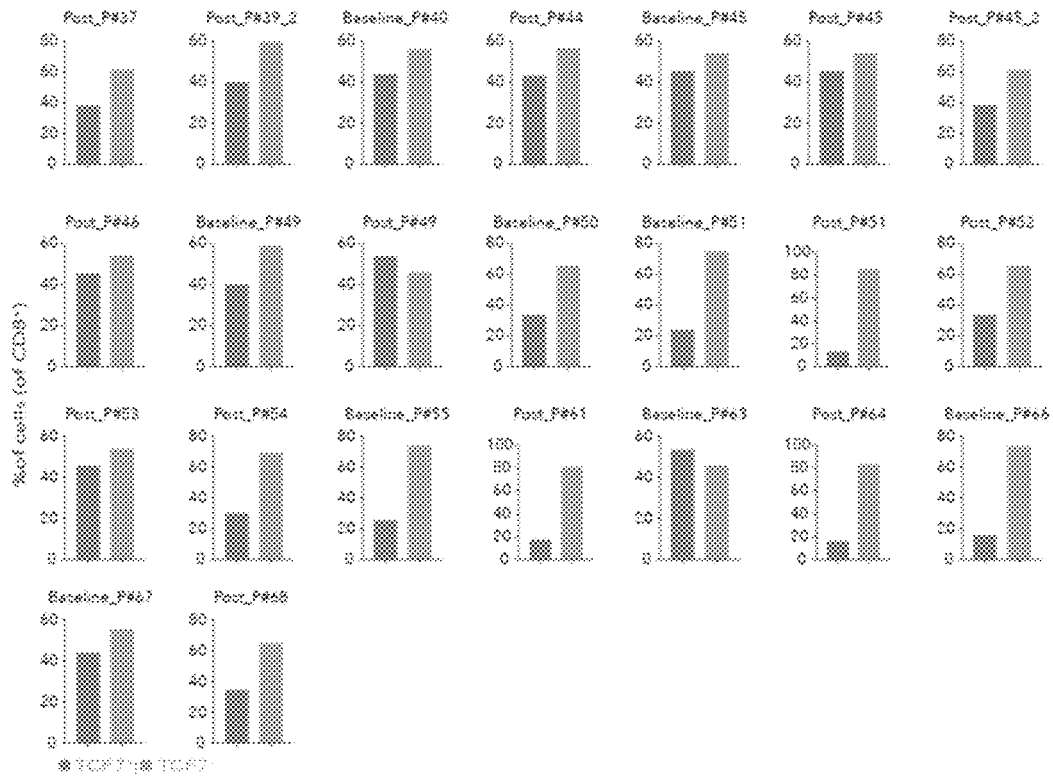
Figure 40C:
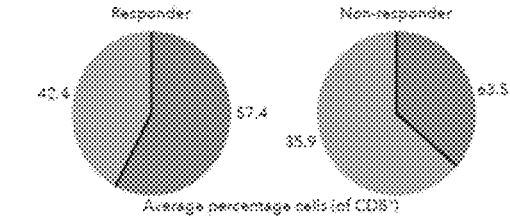
FIG. 40C. Pie charts summarize the average percentage of the 2 cell phenotypes in the responders and non-responders groups.
Figures 41A, 41B, 41C, 41D:
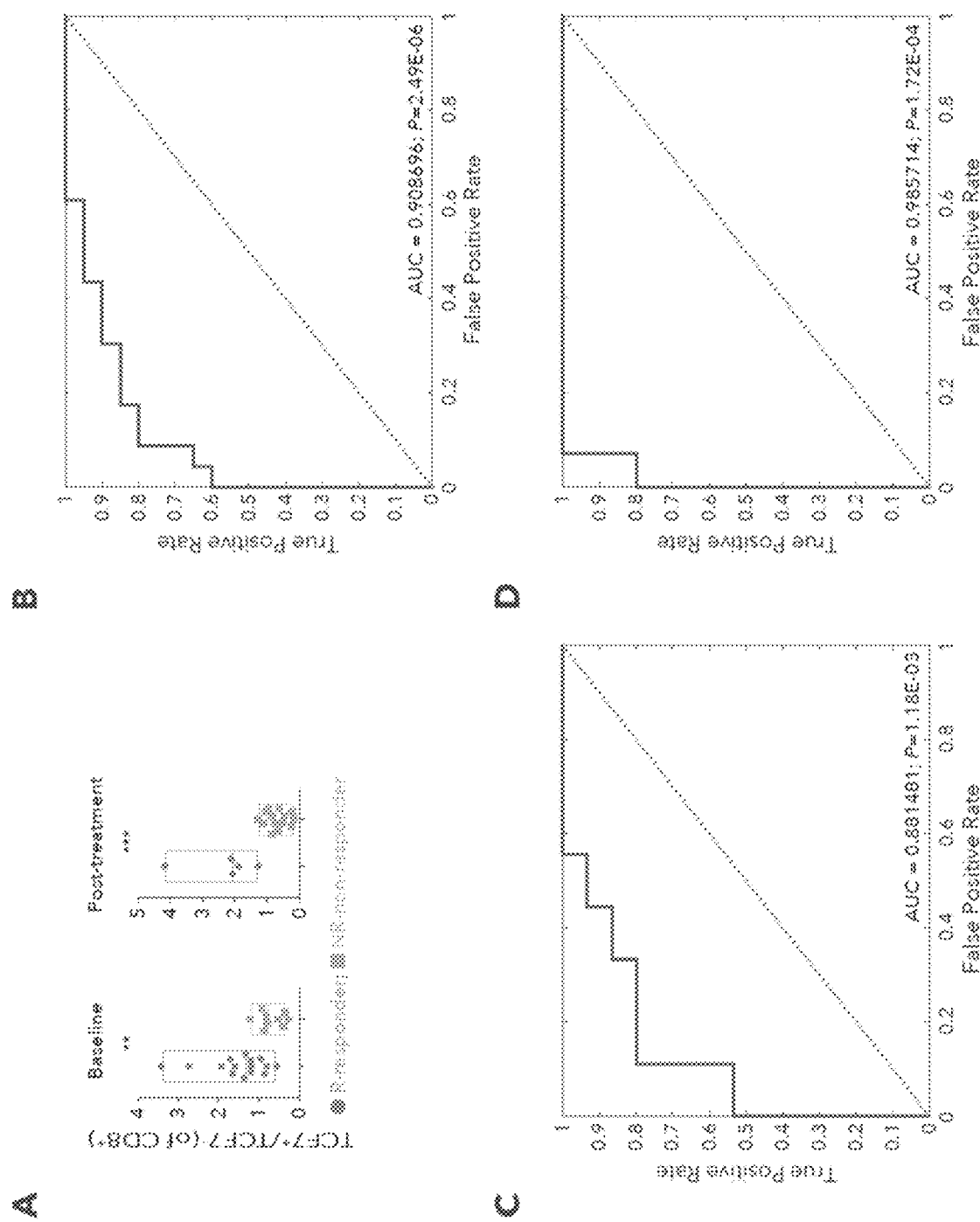
FIG. 41A. Box plots showing the quantitative analysis of TCF7$^+$CD8$^+$/TCF7$^-$CD8$^+$ ratio in baseline and post-treatment samples, between responder (n=20) and non-responder patients (n=23). One-sided Wilcoxon P-value is shown, P=0.0011, *P=0.00017.
FIG. 41B-D. Receiver operating characteristic (ROC) analysis was constructed to evaluate the prognostic power of the ratio between TCF7$^+$CD8$^+$/TCF7$^-$CD8$^+$ between responder and non-responder lesions. The area under the ROC curve (AUC) was used to quantify response prediction, and one-sided Wilcoxon test was used to assess significance of the AUC results. The AUC value was 0.9 (P=2.4×10$^{-6}$) for all samples (B), 0.88 (P=1.1×10$^{-3}$) for post-treatment samples (C) and 0.98 (P=1.7×10$^{-4}$) for baseline samples (D).

(FIG. 24F, FIG. 39 and pipeline), Applicants calculated the ratio of TCF7$^+$CD8$^+$ to TCF7$^-$ CD8$^+$ cells and its association with response. When comparing between these two cell phenotypes Applicants found a significant enrichment for TCF7$^+$CD8$^+$ in responding patients (two-sided Wilcoxon P-value=3.9×10$^{-6}$) and TCF7$^-$CD8$^+$ in non-responder patients (P-value=1.1×10$^{-8}$; FIG. 24G), and saw that cells with both states coexist in each of the responder and non-responder lesions (FIG. 40). Analogous to the CD8$^+$ single-cell RNA-seq analysis Applicants performed (FIG. 24D), Applicants found that a ratio >1 of TCF7$^+$CD8$^+$ to TCF7$^-$CD8$^+$ is typically associated with clinical response and a ratio <1 with lack of response when looking at all (n=43; one-sided Wilcoxon P-value=2.4×10$^{-6}$; FIG. 24H), baseline (n=24; P-value=0.001) or post-treatment (n=19; P-value=1.7×10$^{-4}$; FIG. 41A) samples. In contrast, no significant difference was observed when looking only at the percentage of tumor-associated CD8$^+$ T-cells between responding and non-responding patients (FIG. 24I). Consistent with the ability to predict lesion-level responses using the single-cell RNA-seq-derived signatures in the first cohort, the power to predict response was similar in this independent cohort for all (AUC=0.91; FIG. 41B), baseline (AUC=0.88; FIG. 41C) or post-treatment samples (AUC=0.98; FIG. 41D). Additionally, when performing a Kaplan-Meier survival analysis Applicants found that patients with a ratio >1 have a significantly higher survival rate as compared to those with a ratio <1 (logrank P-value=0.03, FIG. 24J).

Figures 42A, 42B:
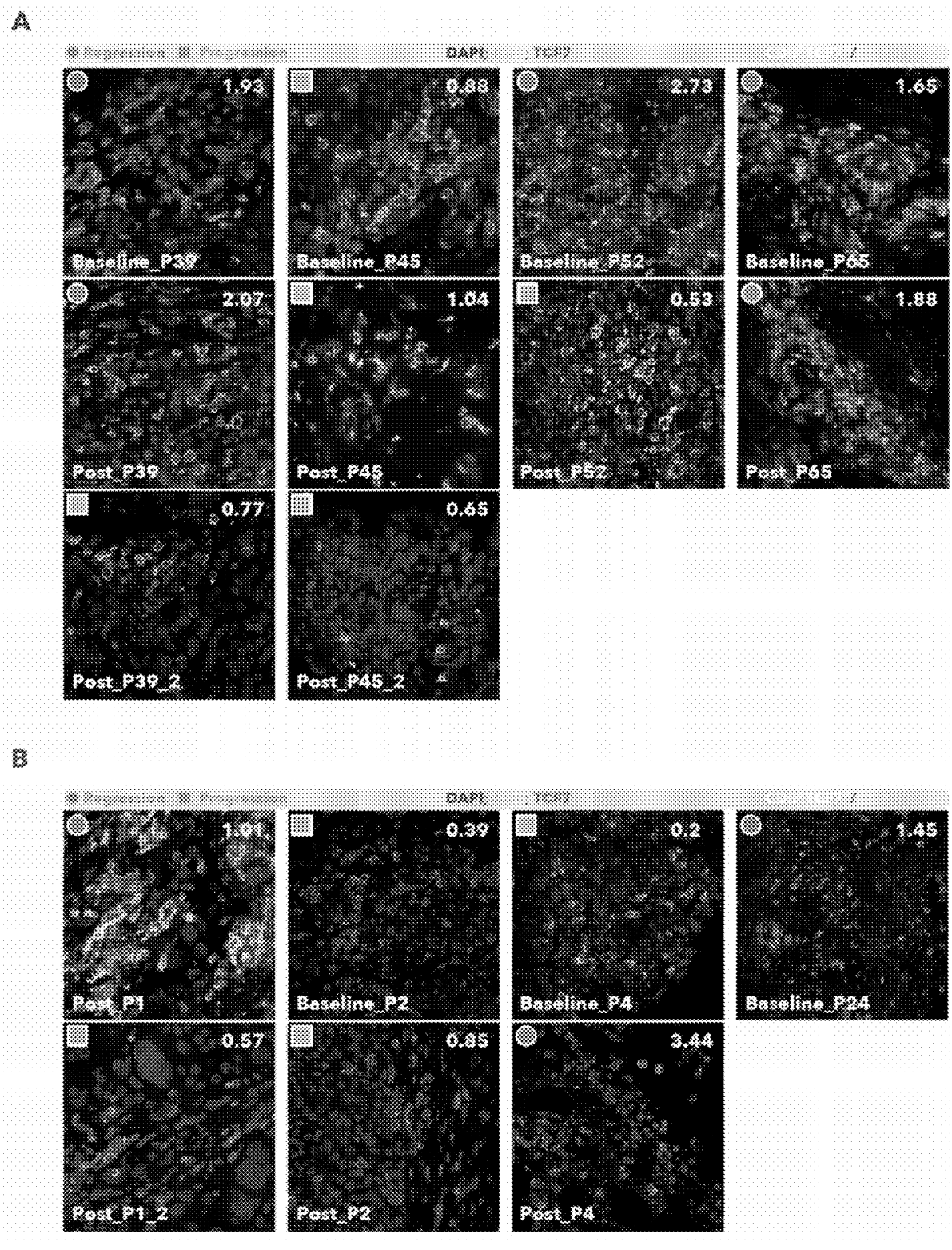
FIG. 42A-B. Representative overlayed images from patients with matched baseline and post-treatment samples from the second PD1 cohort (A) and from the initial single-cell RNA-seq cohort (B) stained with DAPI, CD8 and TCF7. For each patient, 10 random fields were scanned and analyzed. The ratio of CD8$^+$TCF7$^+$/CD8$^+$TCF7$^-$ detected in each patient is shown on the upper right corner of the imaged sections, left upper corner shows lesion status: regression (circles), progression (squares). Original Magnification ×400. TCF7—transcription factor 7.

Finally, Applicants asked if TCF7 protein levels changes overtime between matched baseline and post-treatment samples in the same patient. 8 patients out of 33 in the second cohort had matched baseline and post-treatment samples (Table 8). Although minor differences were detected in TCF7$^+$CD8$^+$ levels between baseline and post-treatment samples, the main change was observed when classifying samples by their response or lack of response to therapy, regardless of the fact if the sample was taken at baseline or during/after treatment (FIG. 40 and FIG. 42A). Moreover, immunofluorescence staining of additional 7 samples (n=4 patients), initially analyzed in the single-cell RNA-seq cohort revealed similar pattern between the TCF7$^+$CD8$^+$/TCF7$^-$CD8$^+$ ratio detected when performing the immunofluorescence staining pipeline to the CD8_B/CD8_G ratio Applicants identified when analyzing the single-cell RNA-seq data (FIG. 37, FIG. 42B and Table 8). Collectively, the results suggest that the ratio between CD8$^+$ T-cell subsets with distinctive phenotypes is a predictor of clinical outcome and survival.

Figure 25A:
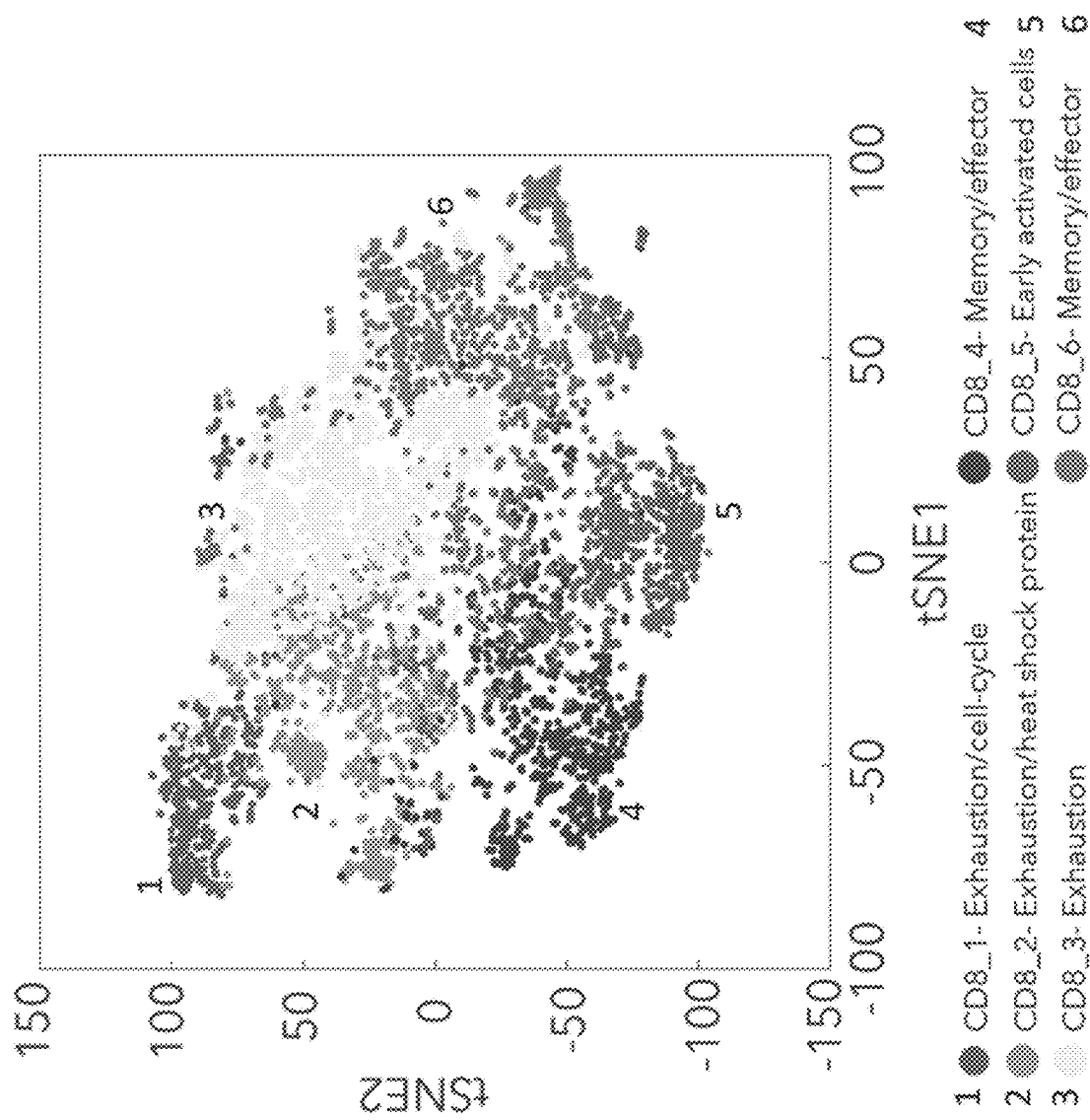
FIG. 25A. tSNE plot of all $CD8^+$ T-cells collected in this study. Cells are shaded based on 6 clusters identified by k-means clustering (Methods).
Figure 25B:
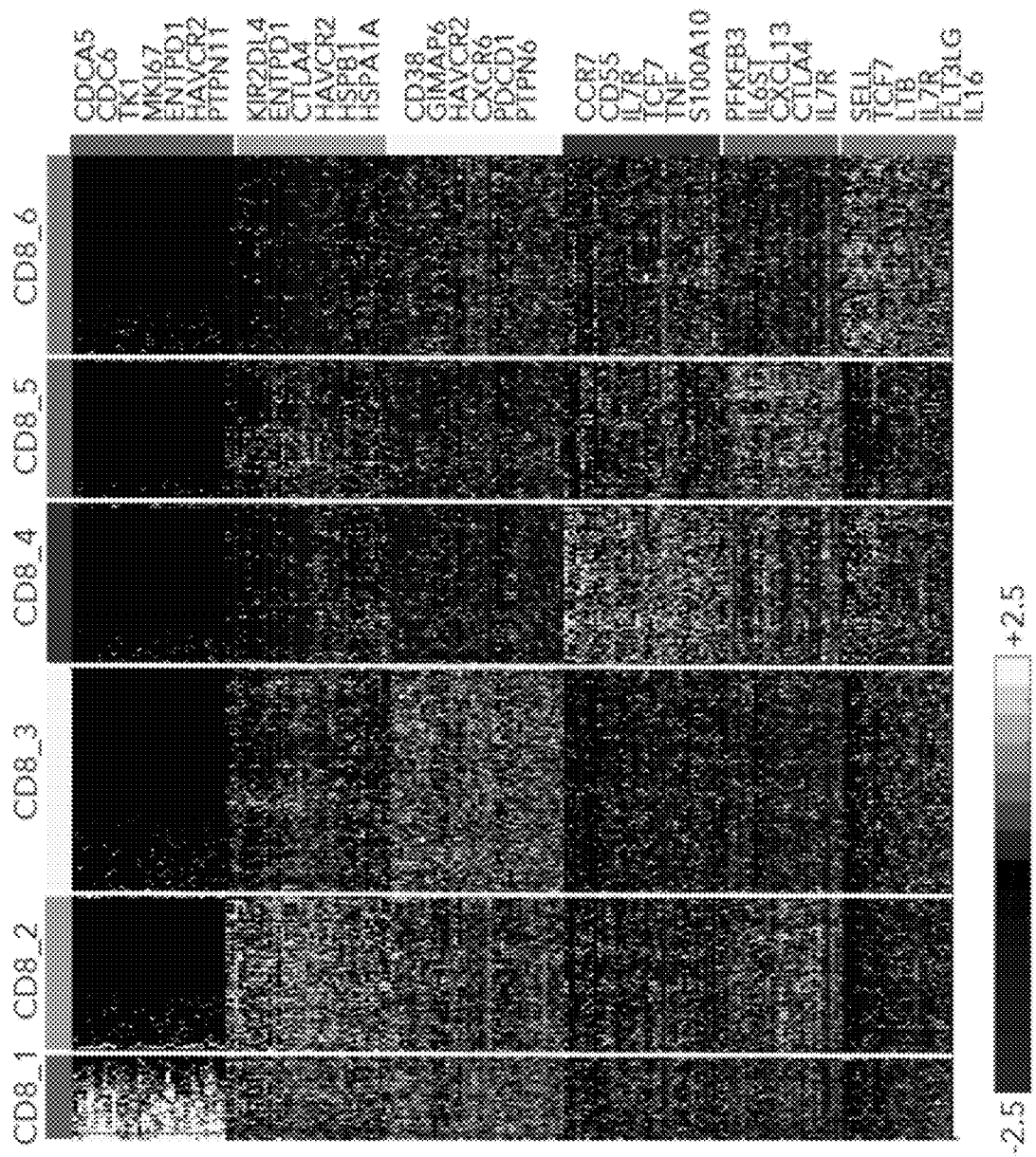
FIG. 25B. Heatmap showing scaled expression values (log 2(TPM+1)) of discriminative gene sets for each cluster defined in (A). A list of representative genes is shown for each cluster next to the right margin bars. Shading scheme is based on z-score distribution from −2.5 to 2.5.
Figure 25C:
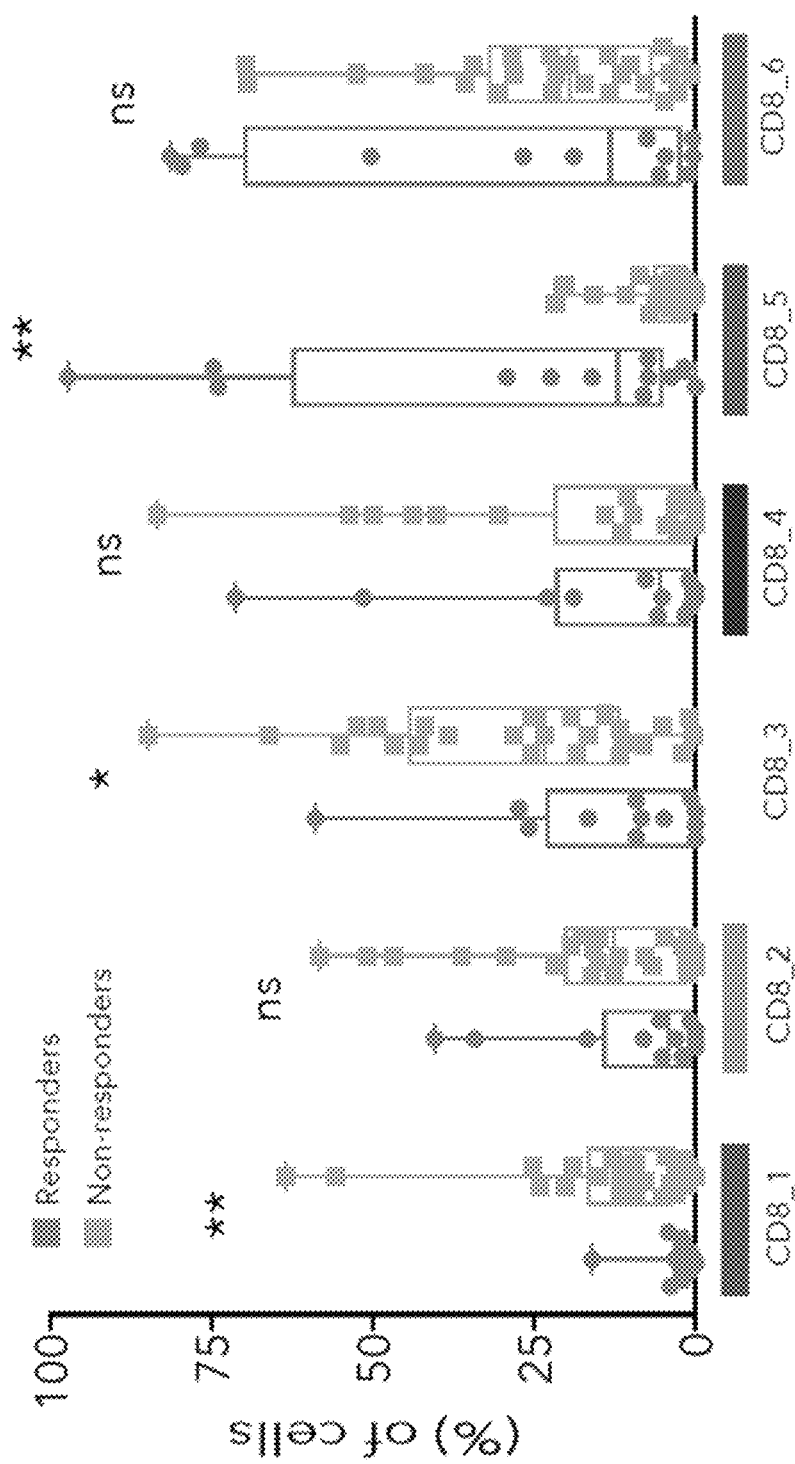
FIG. 25C. Box plots comparing the percentage of CD8_1 to 6 (out of CD8+ cells) clusters between responders and non-responders. Each symbol represents an individual sample. One-sided Wilcoxon P-values are shown, **P-value=0.001 for CD8_1, *P-value=0.013 for CD8_3, **P-value=0.003, and ns—not significant. D. Trajectory analysis for the 6 $CD8^+$ T-cells clusters identified in (A). Cell expression profiles in a two dimensional independent space. Solid black line indicates the main diameter path of the minimum spanning tree (MST) and provides the backbone of Monocle's pseudotime ordering of the cells. Each dot represents an individual cell shaded by cluster (upper plot) or by pseudotime (lower plot).
Figures 43A, 43B, 43C, 43D, 43E, 43F, 43G, 43H, 43I:
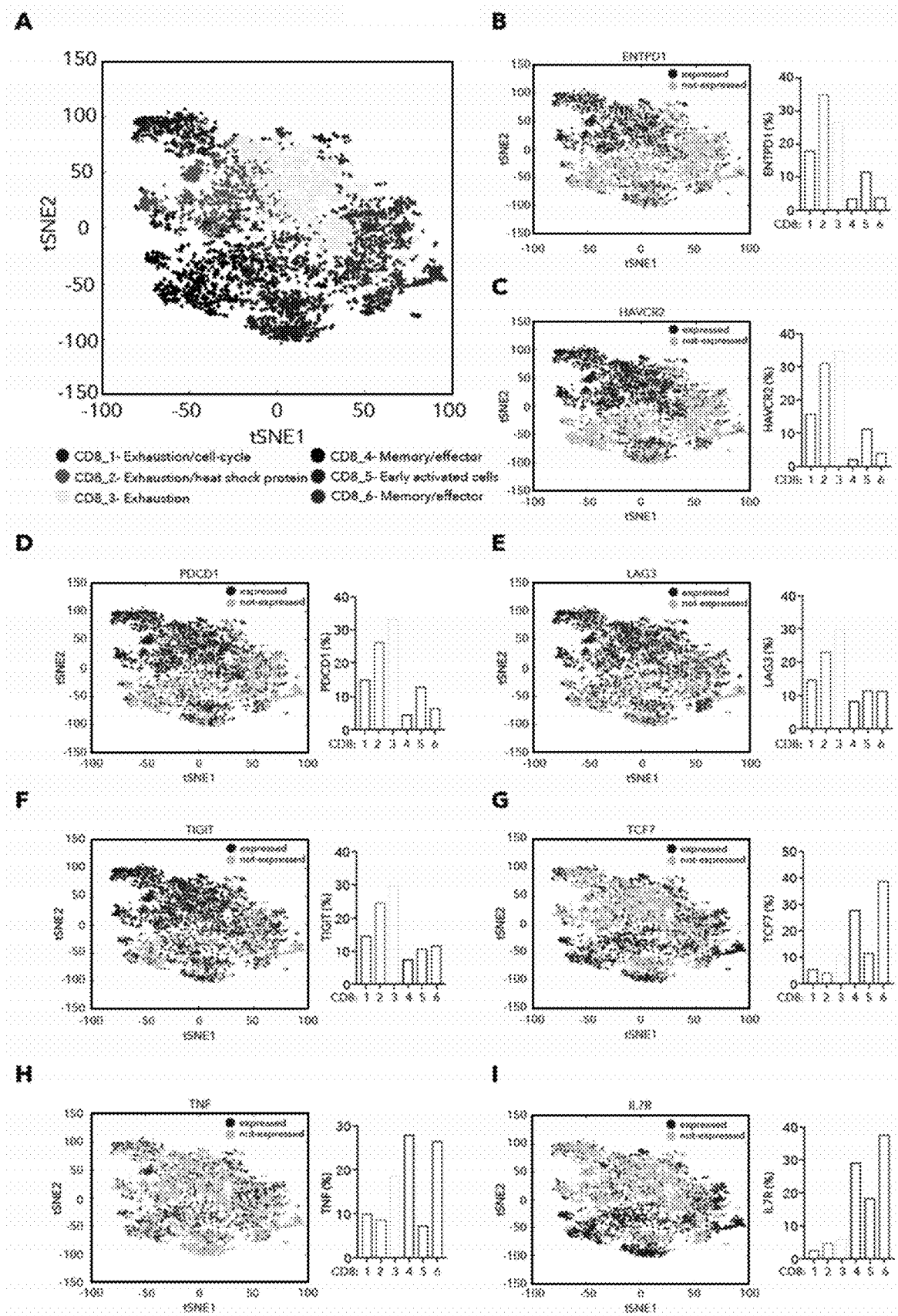
FIG. 43A. tSNE plot of all CD8$^+$ T-cells profiled in the first cohort. Cells are shaded based on 6 clusters identified by k-means clustering as shown in FIG. 25A. B-I. tSNE plot shaded such that single-cells with a high expression level ($\log_2$(TPM+1)>2) of ENTPD1(B), HAVCR2(C), PDCD1(D), LAG3(E), TIGIT(F) TCF7(G), TNF(H), and IL7R(I) are shaded, and those with a low expression level ($\log_2$(TPM+1)2) are shaded in gray. Bar plots (to the right) summarize the corresponding percentages of each gene in the 6 identified.
Figures 44A, 44B, 44C:
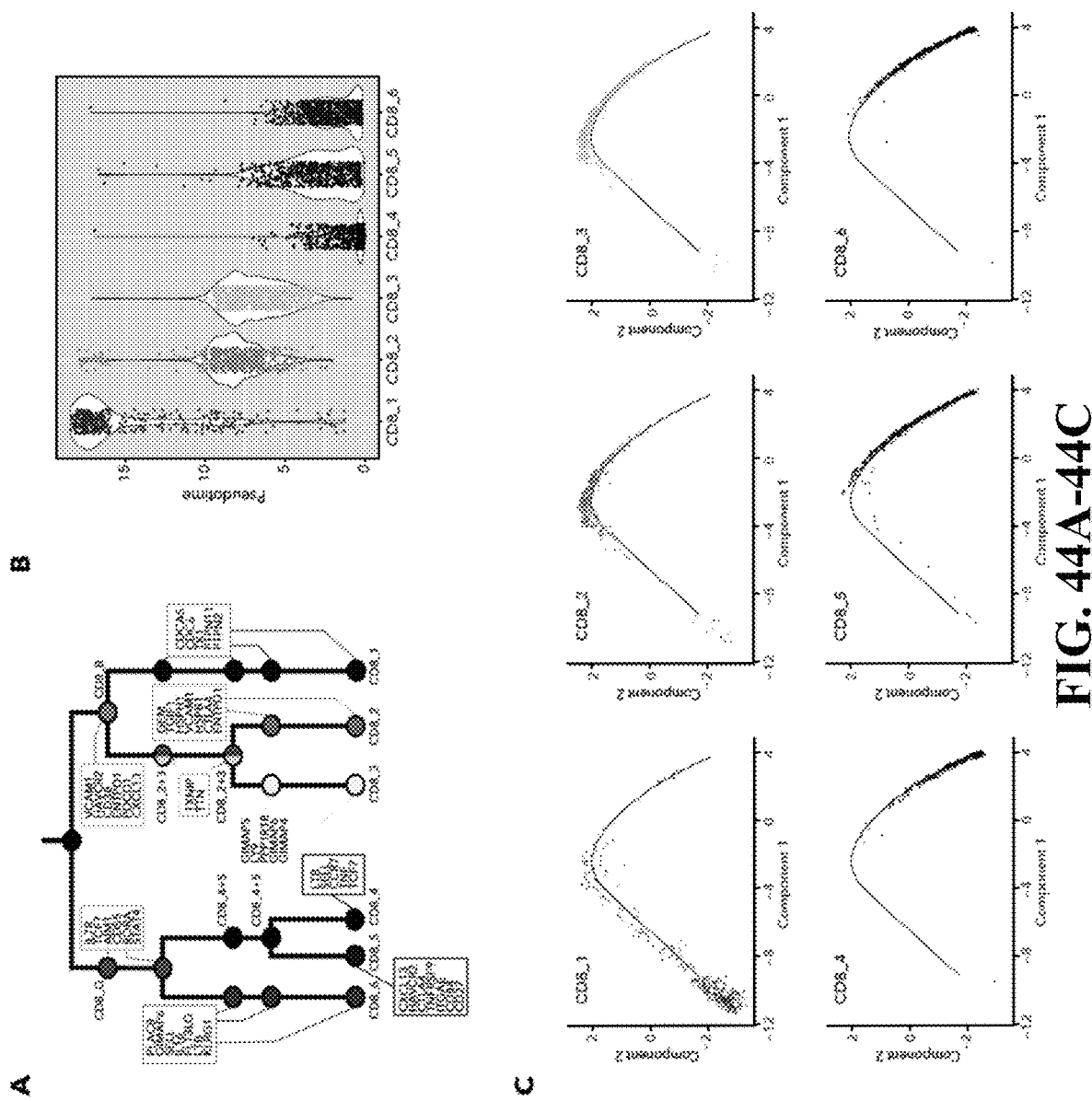
FIG. 44A. Hierarchical tree structure for the six CD8$^+$ T-cell clusters. In each split, gene markers upregulated in the corresponding cluster are identified by comparing the corresponding cells to the rest of the cells found in the last common ancestor (Methods).
FIG. 44B. Violin plots showing organization of cells corresponding to the six CD8 clusters by pseudotime as inferred by Monocle.
FIG. 44C. Cell expression profiles in a two dimensional independent space for each cluster (CD8_1 to 6) is shown. Solid black line indicates the main diameter path of the minimum spanning tree (MST) and provides the backbone of Monocle's pseudotime ordering of the cells. Each dot represent an individual cell shaded by cluster.

Example 13—Higher Resolution Analysis of CD8$^+$ T-Cells Discovers Novel Exhausted and Memory Subsets While the two CD8$^+$ T-cell clusters were able to separate responders from non-responders, Applicants wondered if a greater heterogeneity in cell states could be observed in the single cell dataset. Using k-means clustering with a correlation distance metric on all CD8$^+$ T-cells that passed quality control, and after testing for the robustness of this clustering solution (0.89; Methods) and relationships to previously known cell states, Applicants found 6 clusters, with CD8_G and CD8_B, each splitting into 3 clusters (FIG. 25A-B). To identify cluster-specific gene markers, Applicants compared the expression level of genes associated with cells within a given cluster, to that of cells outside this cluster (Methods). Applicants found that these 6 new clusters included a mixture of known and novel exhaustion and memory/effector markers and were linked to treatment outcome (FIG. 25B). CD8_1 expressed multiple markers of exhaustion (HAVCR2, ENTPD1, PDCD1 and PTPN11) and negative (CASP3, CDK2, and TP53) or positive (CDK1, CCNB1 and MKJ67) regulators of cell cycle (Table 9), similar to the pattern observed in cluster G12 when analyzing all immune cells (Table 2), and to the transcriptional phenotype of terminally exhausted CD39$^+$ (ENTPD1) CD8$^+$ T-cells, detected during chronic infection with hepatitis C virus (HCV)[32]. While CD8_2 expressed many exhaustion markers together with heat shock proteins (HAVCR2, CTLA4, TIGIT, PDCD1, HSPB1, HSPA1A and HSPA4) along with additional inhibitory receptors (ENTPD1 and KIR2DL4), CD8_3 expressed several known exhaustion markers (HAVCR2, CD38, PDCD1 and PTPN6), but lacked the expression of heat shock proteins and cell-cycle genes. In contrast, CD8_4 (CCR7, IL7R, TCF7, TNF and S100A10), and CD8_6 (SELL, TCF7, LTB, IL7R, FLT3LG, IL16) had a memory/effector like phenotype, while CD8_5 had the phenotype of early activated and more differentiated cells (IL6ST, CXCL13, IL7R and CTLA4), but was more enriched for HAVCR2 and PDCD1 when compared to CD8_4 and 6, but not CD8_1 to 3 (FIG. 43). Interestingly, GZMA, GZMB and PRF1 (coding for granzyme A, B and perforin 1), had much higher expression in the exhausted clusters CD8_1 to 3 (Table 9) and resembled exhaustion programs previously reported in melanoma[33] and in a mouse model of chronic LCMV infection[7]. Interestingly, when examining the clustering results when using fewer clusters, Applicants found that the clusters formed a hierarchy, that is, clusters split and did not mix as the number of clusters increased. To further examine the robustness and unique biological function of each of these clusters, Applicants took another approach, in which Applicants identified gene markers that are differentially expressed between the cluster and an "ancestor" cluster found in a lower-resolution cluster analysis, thus creating a functional annotation along the hierarchical branching for the identified clusters (FIG. 44A). Using this approach, similar marker genes were identified for the 6 different clusters, suggesting that these markers indeed highlight distinct biological functions (Table 10). Next, Applicants sought to associate these clusters with clinical outcome. When comparing between these 6 cell states Applicants found CD8_1 and CD8_3 to be significantly enriched in non-responder lesions (one-sided Wilcoxon P-value=0.001 for CD8_1 and P-value=0.013 for CD8_3) and CD8_5 in responder lesions (P-value=0.003; FIG. 25C); analogous to the earlier observation showing an increased exhausted phenotype in non-responders and a memory/effector phenotype in responders (FIG. 24).

Figure 25D:
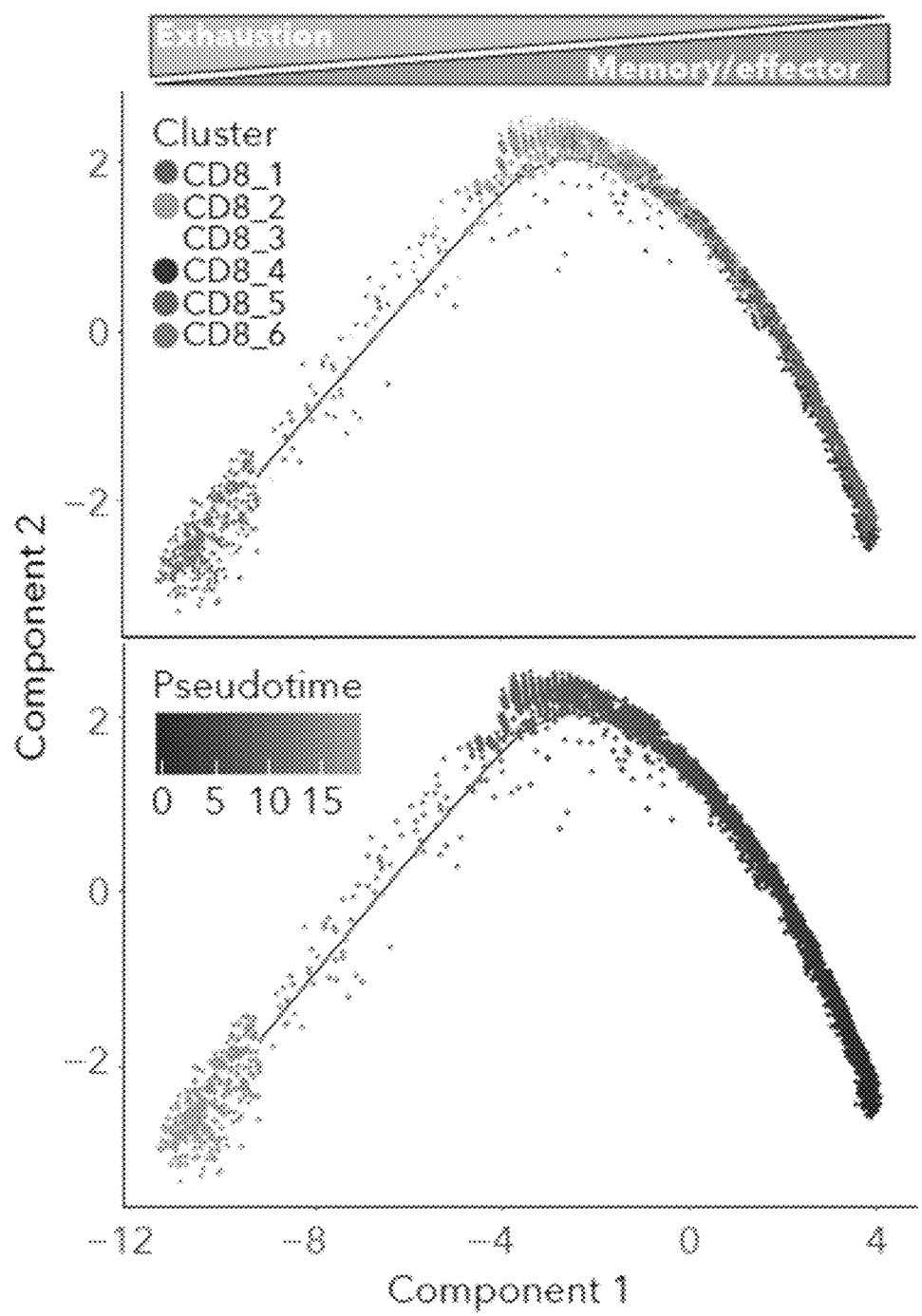
FIG. 25—$CD8^+$ T-cell state heterogeneity and its association with clinical response.

During cancer or chronic infections, T-cells in response to continuous stimuli undergo many transitions dictating cell fate, from initial activation and proliferation, to differentiation, exhaustion and in some cases reinvigoration, depending on the appropriate stimulation and state of the cells[8,30]. To determine the potential trajectories underlying transitions between the identified cell states, Applicants performed a trajectory analysis using the Monocle tool[34]. Although Applicants could not ascertain the direction of differentiation, Monocle ordered individual cells in pseudotime, placing them along a primary trajectory branch corresponding to the six clusters identified, along with 2 side branches (FIG. 25D). While some overlap between the six clusters was observed, the continuous hierarchical ordering was very clear. One end of the main branch was enriched for clusters with a memory/effector phenotype, starting with CD8_4, CD8_6 and then CD8_5, while the other end was enriched for clusters related to exhaustion, starting with CD8_1 and then moving to CD8_2 and 3, that overlapped each other and shared many transcriptional programs (FIG. 25D and FIG. 44B-C). Overall, the six states and their relationships represent novel phenotypic diversity for exhausted and memory/effector CD8+ T-cells subsets associated with clinical response, and suggest that the developmental transitions could be identified among them.

Example 14—TIM3 and ENTPD1 Segregate Exhausted from Memory Cells

Figure 26A:
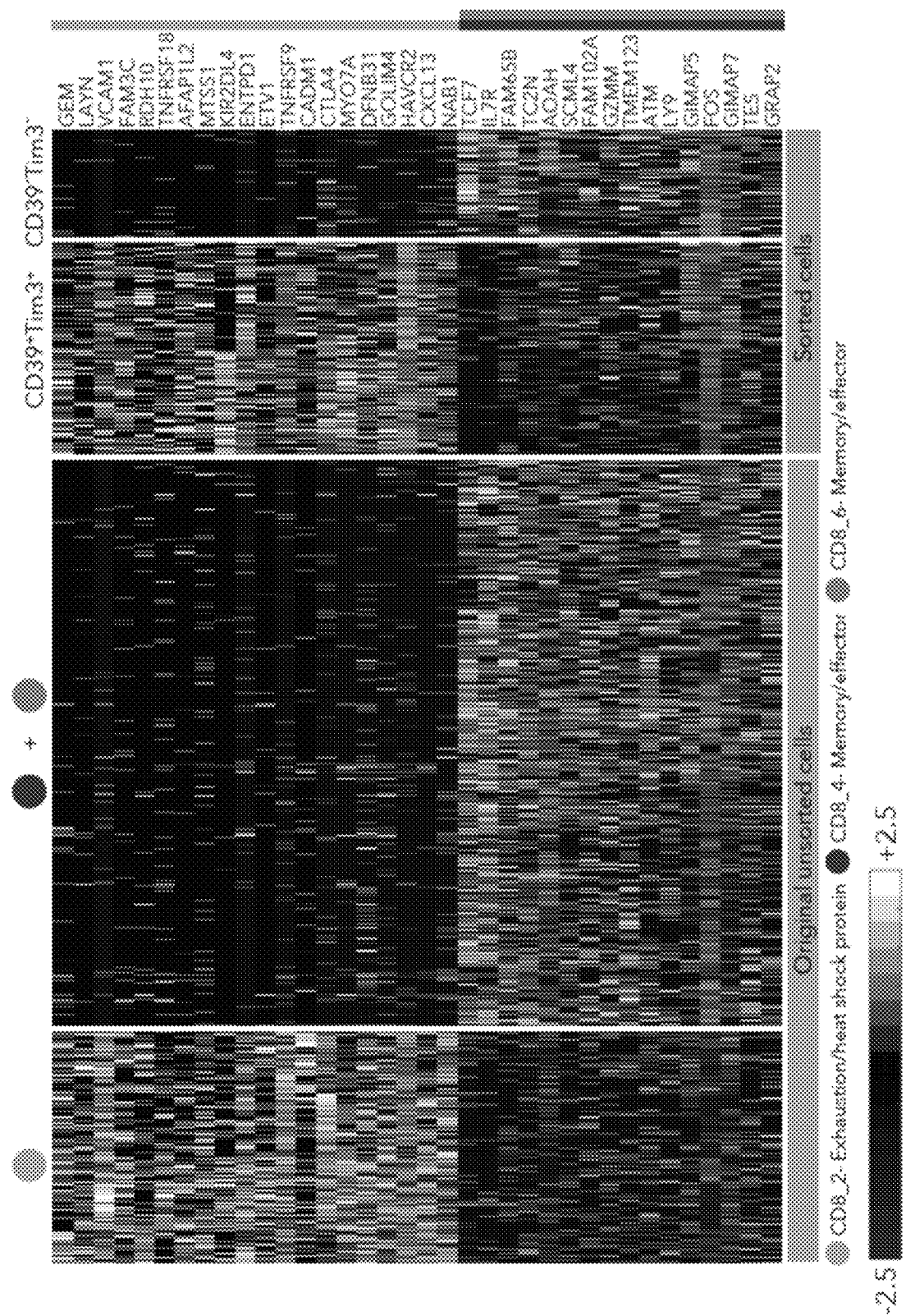
FIG. 26A. Heatmap showing scaled expression values ($\log_2(TPM+1)$) of discriminative gene sets between CD8_2 (exhaustion) and CD8_4+6 (memory/effector) with original unsorted, and sorted ($CD39^+TIM3^+$ and $CD39^-TIM3^-$) cells. A list of representative genes are shown for each cluster next to the right margin bars. Shading scheme is based on z-score distribution from −2.5 to 2.5.
Figure 26B:
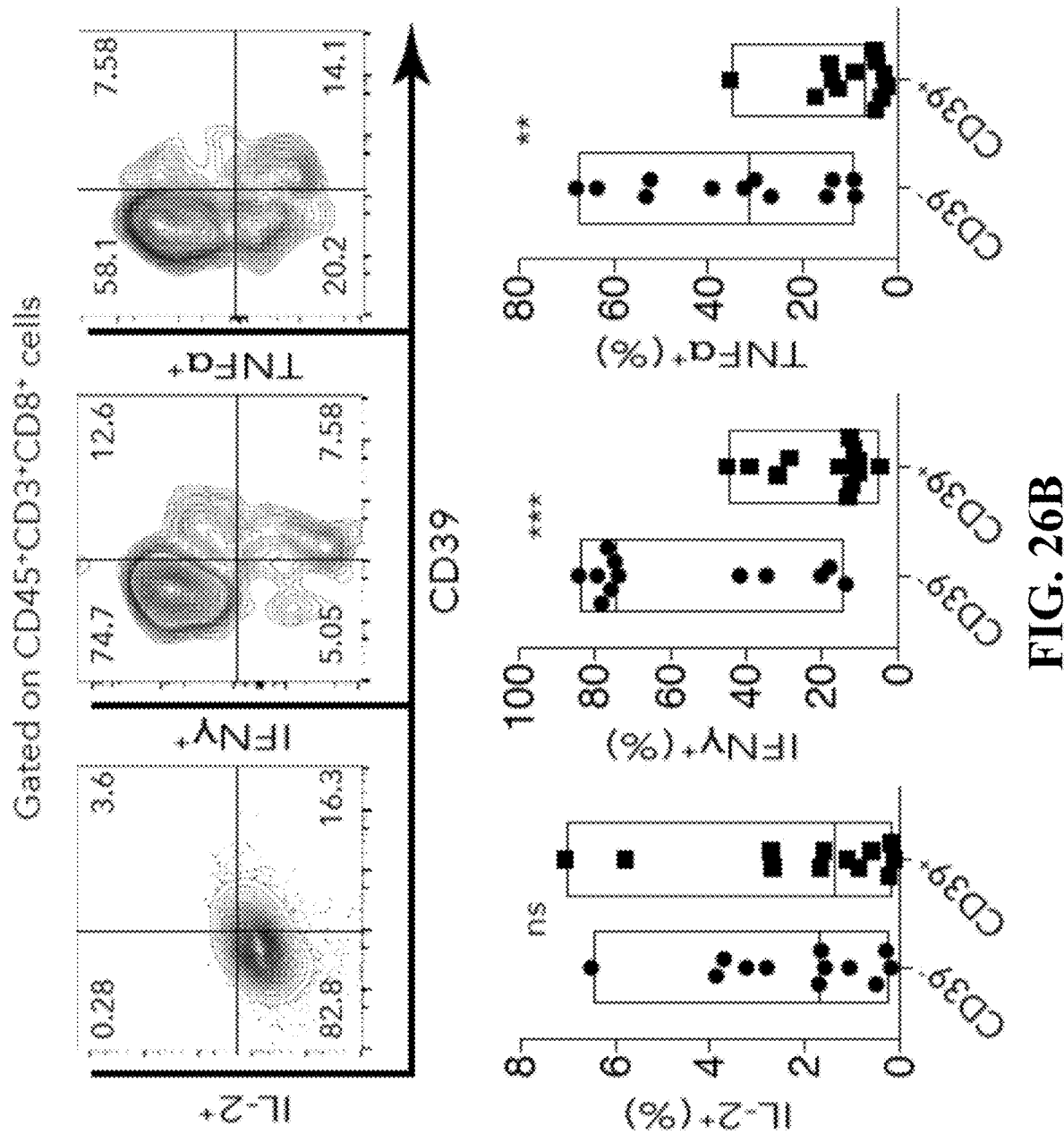
FIG. 26B. Representative flow cytometric plots (upper part) of intracellular staining for IL-2, IFNγ and TNFα in $CD39^+$ and $CD39^+$ cells (out of gated $CD45^+CD3^+CD8^+$ cells). Flow cytometry quantification of cytokine-producing cells obtained from 12 metastatic melanoma patients (lower part). Bars indicate the mean values. Data were combined from 2 replicate experiments. Unpaired-student's t-test with P-value=0.0016 and *P-value=$5\times10^{-4}$ is shown.
Figures 45A, 45B, 45C, 45D, 45E:
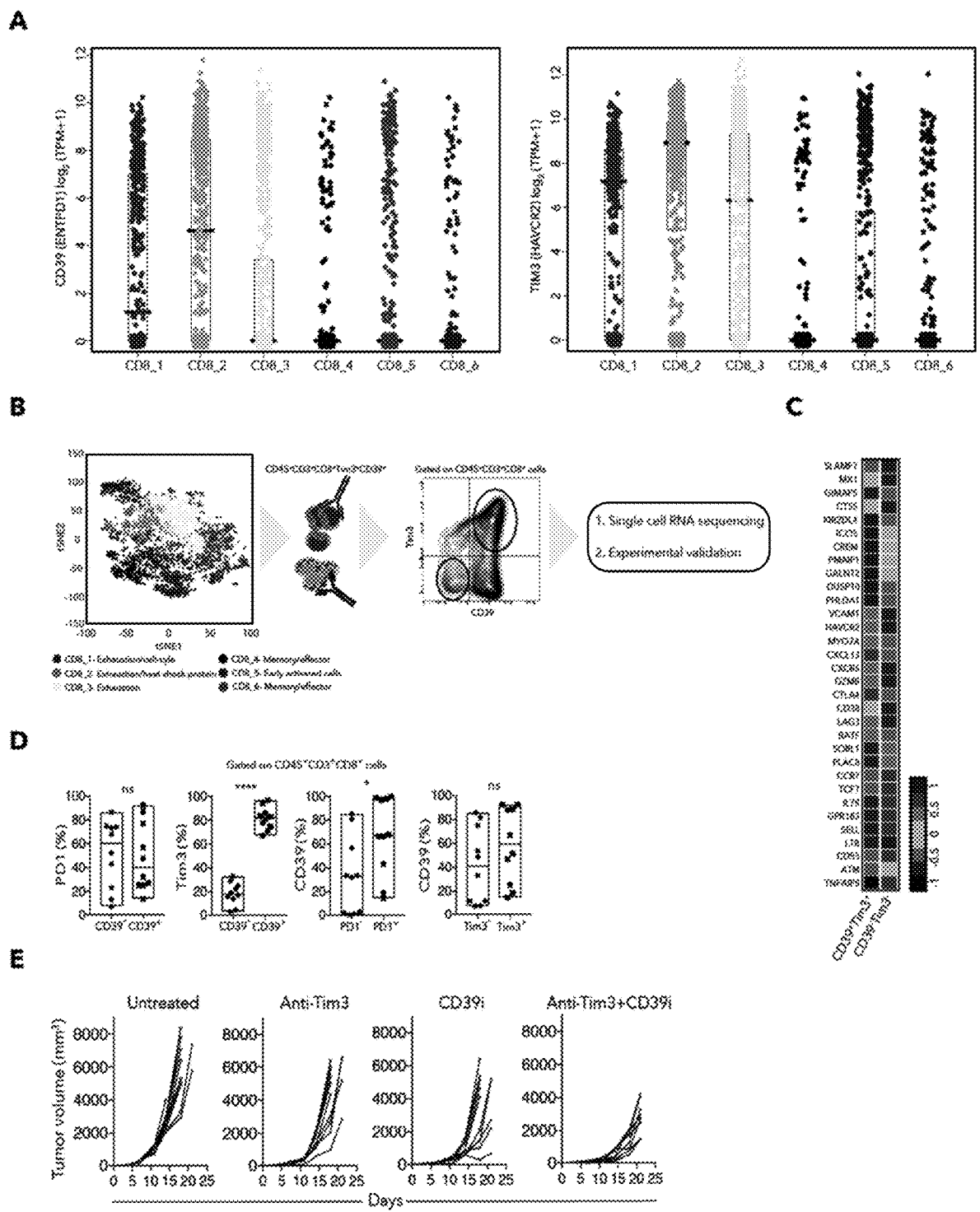
FIG. 45A. Gene expression level distribution ($\log_2$(TPM+1)) of CD39 (ENTPD1, left) and TIM3 (HAVCR2, right) in the six CD8 clusters is shown. Each dot represents an individual cell.
FIG. 45B. Gating strategy that was used to isolate CD39+ TIM$^+$ and CD39$^-$TIM3$^-$, CD8$^+$ T-cells from 4 melanoma patients.
FIG. 45C. Heatmap of scaled expression values ($\log_2$(TPM+1)) of discriminative gene sets between sorted CD39$^+$TIM3$^+$ and CD39$^-$TIM3$^-$, CD8$^+$ T-cells. A list of representative genes are shown for each cell population. Shading scheme is based on z-score distribution from −1 to 1.
FIG. 45D. Flow-cytometry quantification of PD1 and TIM3 in CD39$^+$, CD39$^-$ (CD8$^+$ T-cells), and CD39 expression in PD1$^+$, PD1$^-$, TIM3$^+$ and TIM3$^-$ (CD8$^+$ T-cells) from 10 metastatic melanomas from 10 patients is shown. Bar indicate the mean values. Data were combined from 2 replicate experiments. unpaired-student's t-test *P-value=0.03,****P-value<0.0001, ns—not significant.
FIG. 45E. Individual tumor volumes of intradermal B16-F10 implants in the untreated (control), anti-TIM3, CD39 inhibitor (CD39i), and anti-TIM3 in combination with CD39i groups is shown. Data shown represents one out of two independent experiments, n=10 for each group per experiment.

Since a significant enrichment for TCF7+ cells with a memory/effector phenotype was found in responder patients, Applicants asked if the single cell data could be used to find markers that discriminate memory/effector from exhausted clusters, and could aid in defining new surface markers of CD8+ T-cell exhaustion in melanoma. One of the targetable proteins, CD39 (ENTPD1), found on some of the exhausted subsets was significantly enriched in clusters associated with non-responding tumors. CD39 is an ectonucleotidase that plays an important role in the adenosine pathway, which in turn modulates the tumor microenvironment by reducing cytotoxicity function of effector (T and NK) cells and by increasing the abundance of suppressive cells (e.g. M2 macrophages, myeloid derived suppressor cells and regulatory T-cells)[35]. Since TIM3 was co-expressed with CD39, with both having the highest expression level in CD8_2 (Table 9 and FIG. 45A) and minimal expression in CD8_4 and CD8_6 (~3% of cells, FIG. 43) when compared to other exhaustion markers (LAG3, TIGIT, PDCD1), Applicants wanted to test if these markers could be used to isolate and validate the identity of cells corresponding to specific clusters. Applicants used scRNA-seq to profile expression of sorted CD39+TIM3+ (DP—double positive) and CD39− TIM3− (DN—double negative) CD8+ T-cells from 4 melanoma patients (FIG. 45B) and found that the profiles recapitulated the original unsorted clusters (FIG. 26A and FIG. 45C). DN shared many attributes with memory cells (CD8_4 and 6), and DP cells appeared similar to CD8_2 exhausted cells. CD39 has been shown to be a marker for terminally exhausted CD8+ T-cells in patients with chronic HCV and HIV infections[32]. However, unlike PD1, CTLA4 and TIM3, CD39 in the context of CD8+ T-cell exhaustion in cancer is not well studied. While CD39+ and CD39− cells had equal expression of PD1, CD39 turned out to be a key marker that separates all TIM3+ from TIM3− cells (FIG. 45D), the latter being reported as a marker of T-cell dysfunction in cancer and chronic infections[36]. To determine the functional properties of CD39+ and CD39− CD8+ T-cells, Applicants prepared single cell suspensions from 12 metastatic melanoma tumors and assessed their ability to produce cytokines in response to TCR stimulation. While CD39− and CD39+ cells contained equivalent percentages of IL-2 producing cells, CD39+ cells had a significant reduction in both TNFα (unpaired-student's t-test P-value=0.0016) and IFNγ-producing cells (P-value=5×10$^{-4}$; FIG. 26B). Thus, CD39 delimits a population of exhausted CD8+ T-cells in melanoma, and in conjunction with TIM3 can be used to discriminate exhausted from memory/effector cells.

Figure 26C:
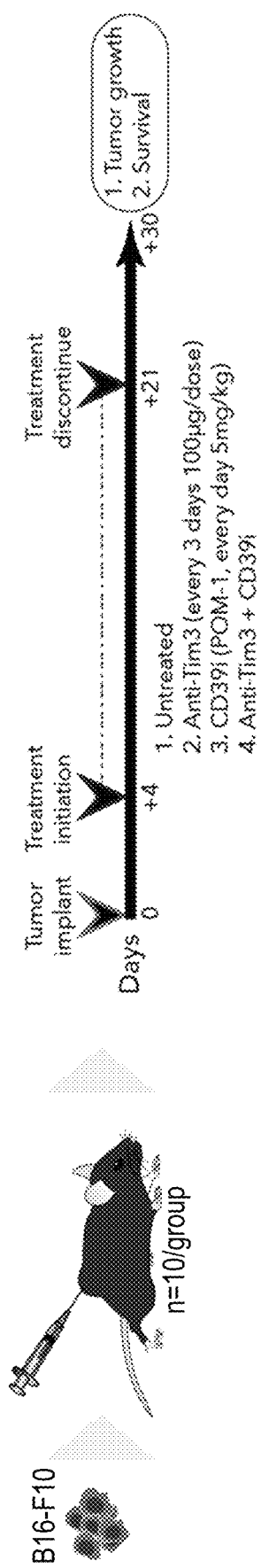
FIG. 26C. A schematic summary of the therapy regimen used in the transplantable B16-F10 mouse model (described in Methods). Mice were divided into four groups (n=10 per group): untreated (vehicle control), anti-TIM3, CD39 inhibitor (CD39i, using POM-1 small molecule) and anti-TIM3 in combination with CD39i.
Figures 26D, 26E, 26F:
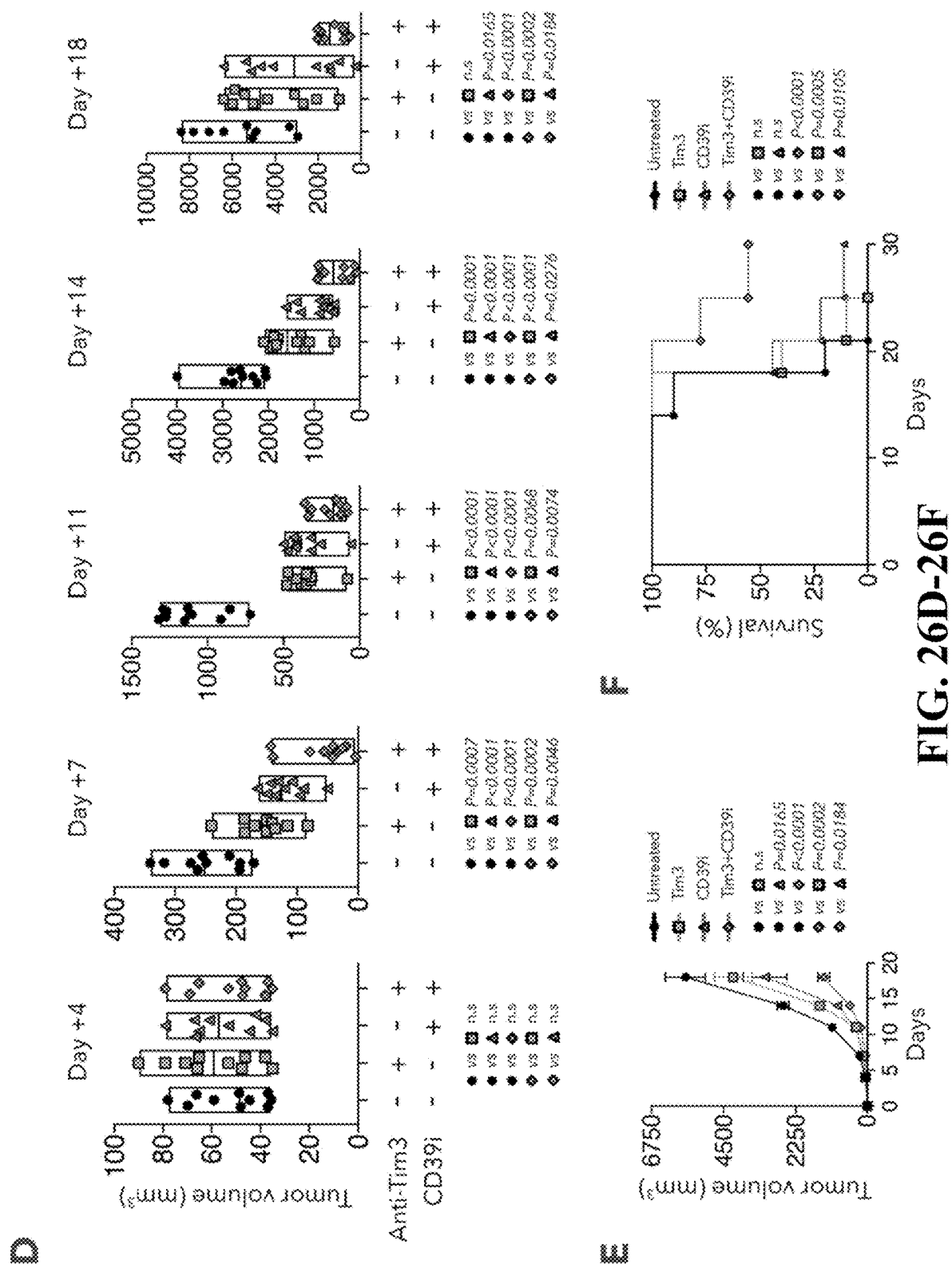
FIG. 26D. Box plots showing the kinetics of tumor growth between the different groups of mice on days +4, +7, +11, +14 and +18 post tumor transplantation. Data in box plots are means±SEM. P-value was determined by unpaired-student's t-test.
FIG. 26E. Mean tumor volumes for all 4 groups are shown, means±SEM.
FIG. 26F. Survival at day 30 of B16-F10 tumor-bearing mice for all 4 groups. Log-rank P-value is shown. Data shown for C-F represents one out of two independent experiments, n=10 for each group per experiment. ns—not significant.
Figures 46A, 46B, 46C:
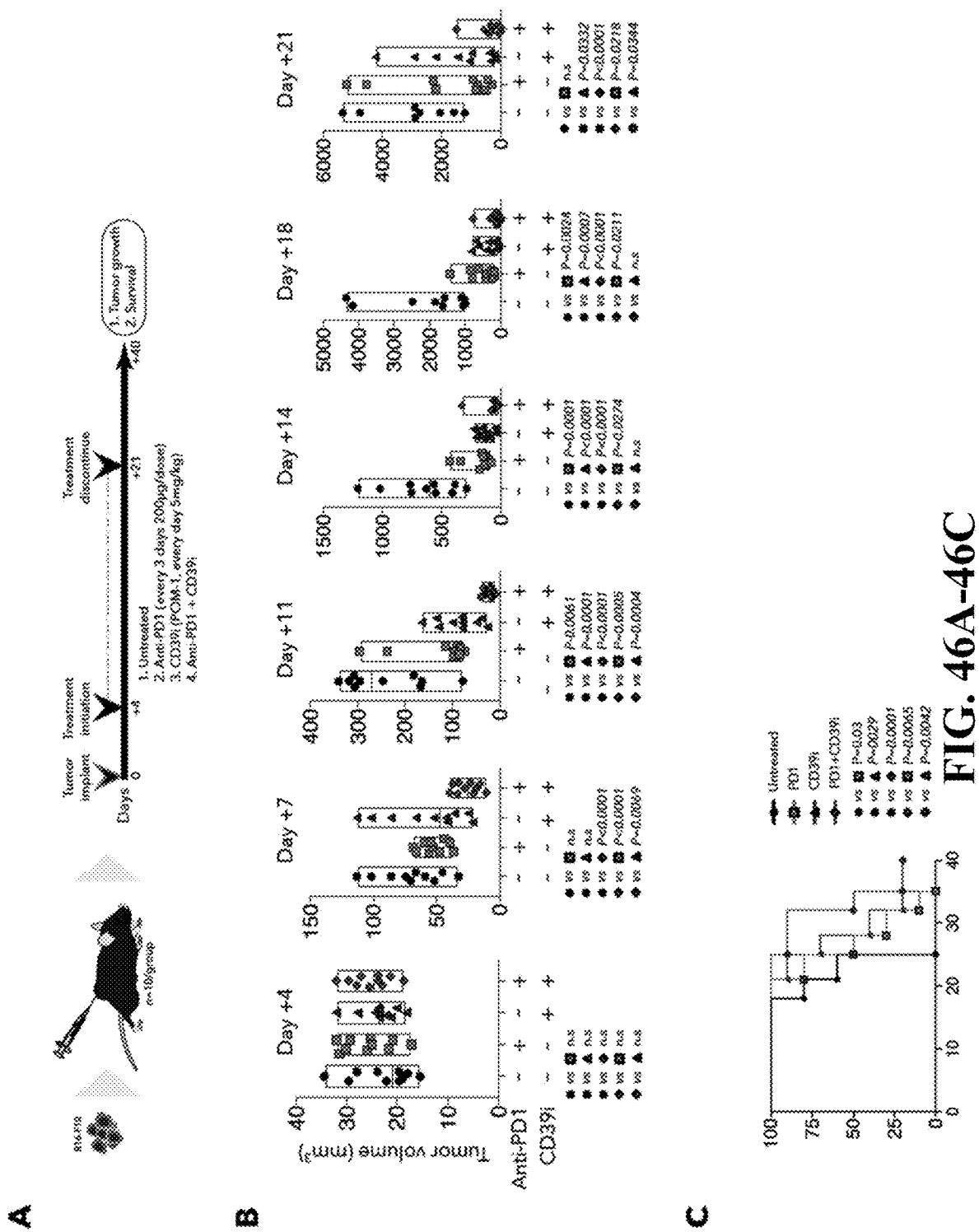
FIG. 46A. A schematic summary of the therapy regimen used in the transplantable B16-F10 mouse model (described in Methods). Mice were divided into four groups (n=10 per group): untreated (vehicle control), anti-PD1, CD39 inhibitor (CD39i, using POM-1 small molecule) and anti-PD1 in combination with CD39i.
FIG. 46B. Box plots showing the kinetics of tumor growth between the different groups of mice on days +4, +7, +11, +14, +18 and +21 post tumor transplantation. Data in box plots are means±SEM. P-value was determined by unpaired-student's t-test.
FIG. 46C. Survival at day 40 of B16-F10 tumor-bearing mice for all 4 groups. Log-rank P-value is shown. Data shown for A-C represents one out of two independent experiments, n=10 for each group per experiment. ns—not significant.

Example 15—Dual Inhibition of TIM3 and CD39 Synergistically Reduces Tumor Growth and Improves Survival Although it has been demonstrated that inhibition of the adenosine pathway through targeting of CD73, in combination with checkpoint therapy using anti-PD1 and CTLA4 antibodies, can enhance anti-tumor immunity and reduce tumor growth[37], inhibition of CD39 in combination with co-inhibitors has not been evaluated. The identification of CD39 and TIM3 as highly expressed genes in exhausted clusters associated with non-responding lesions, led us to examine the combined effect of CD39 and TIM3 blockade. To that end Applicants used the aggressive B16-F10 melanoma mouse model. Mice were treated with the small molecule POM-1 to block CD39 activity[38], alone or in combination with anti-TIM3 blocking antibodies (FIG. 26C). While monotherapy with either POM-1 or anti-TIM3 transiently reduced tumor growth until day 14 (with CD39 inhibition having a stronger effect), combination of both caused a dramatic reduction in tumor size, and more importantly, significantly increased survival (50% survival vs. 10% for CD39 inhibition or 0% for anti-TIM3 and the untreated group) on day 30 (FIG. 26D-F and FIG. 45E). Since anti-PD1 treatment is currently the standard of care in metastatic melanoma patients, and since PD1 similarly to TIM3 was one of the top markers associated with lack of response, Applicants asked whether dual inhibition of PD1 and CD39 will increase response and improve survival. Similar to the observations when targeting both CD39 and TIM3 (although to a lesser extent), dual inhibition of CD39 and PD1 significantly reduced tumor burden on day 21 post transplantation, and improved survival when compared to untreated and mono therapy treated mice (FIG. 46). Hence, through the single cell analysis of human melanoma tumors, Applicants identified new putative immunotherapeutic targets and combinations to enhance immunity.

Figure 27A:
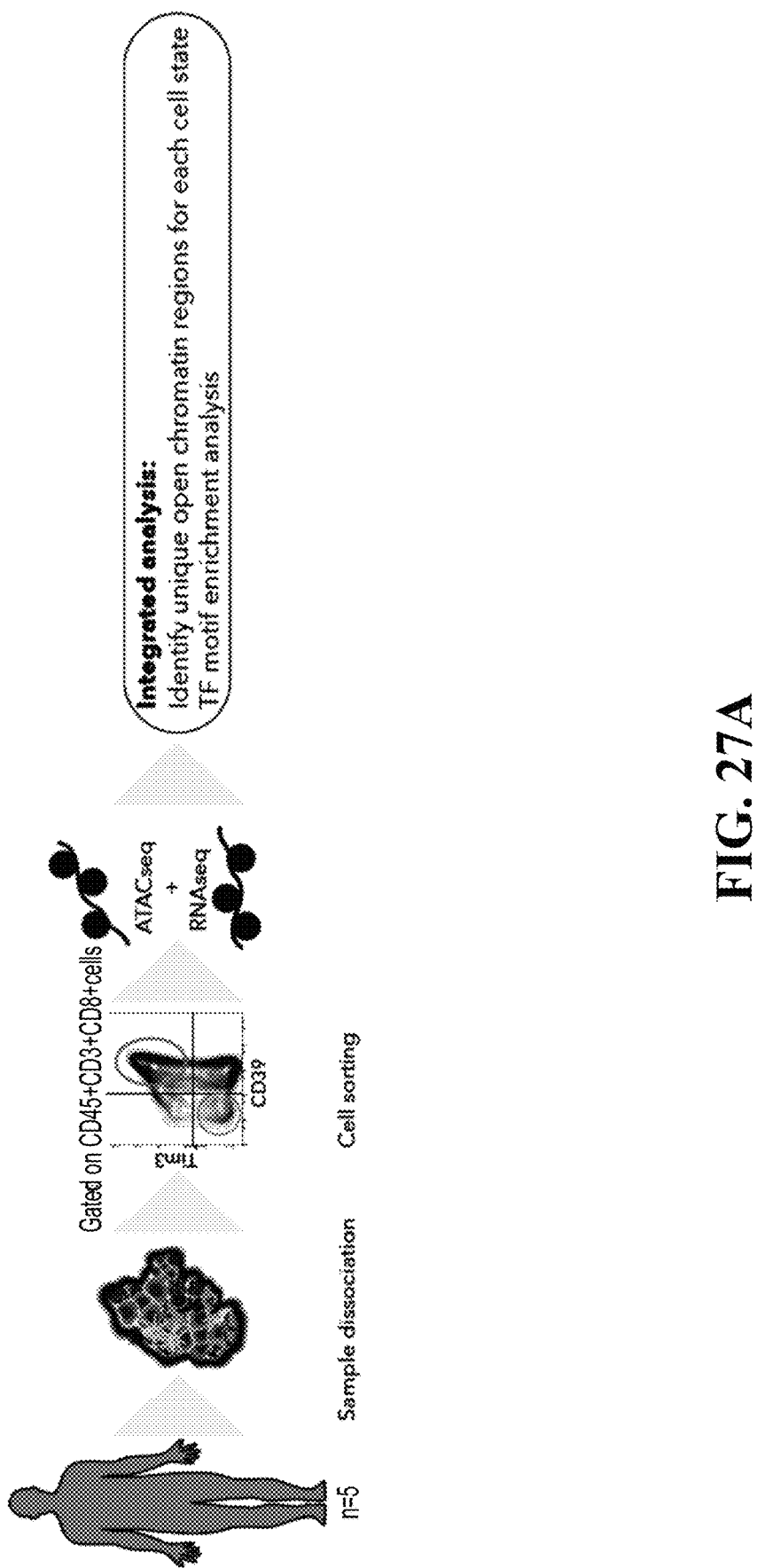
FIG. 27A. Schematic of ATAC-seq analysis performed on sorted $CD39^+TIM3^+$ and $CD39^-TIM3^-$ cells from 5 melanoma patients.
Figure 27B:
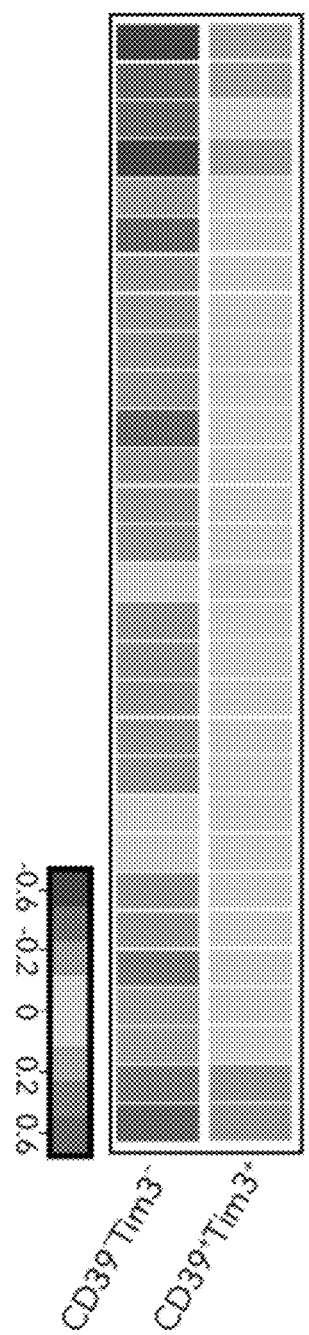
FIG. 27B. Heatmap describing averaged scaled expression values (log 2(TPM+1)) of differentially expressed transcription factors for sorted $CD39^+TIM3^+$ and $CD39^-TIM3^-$ cells (from n=5 patients). Shading scheme is based on z-score distribution from −0.6 to 0.6.
Figure 27C:
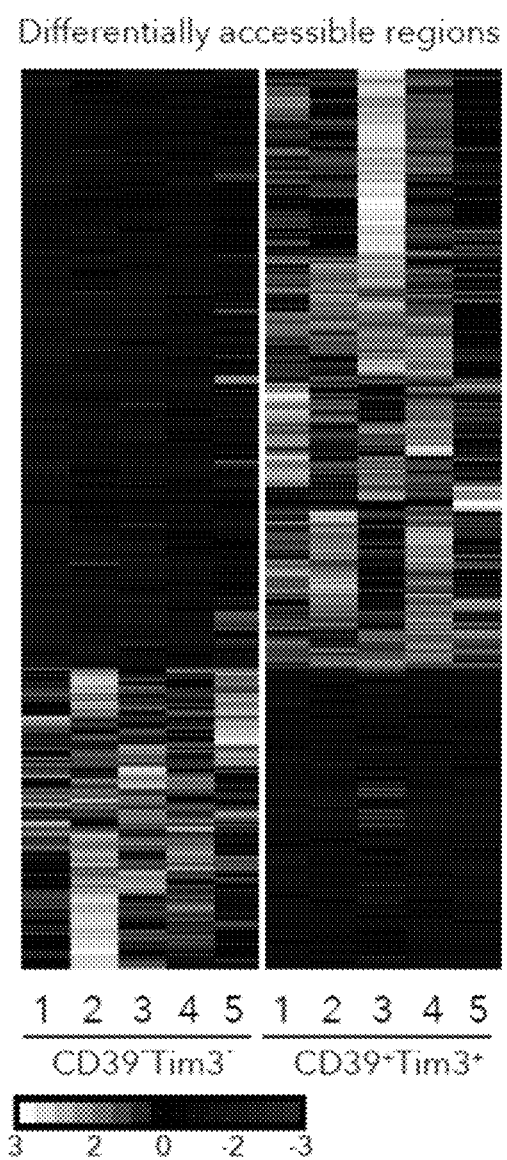
FIG. 27C. Heatmap describing patient specific (n=5) differentially accessible regions (FDR<0.01) in $CD39^+TIM3^+$ and $CD39^-TIM3^-$ sorted populations. Shading scheme is based on z-score distribution from −3 to 3.
Figure 27D:
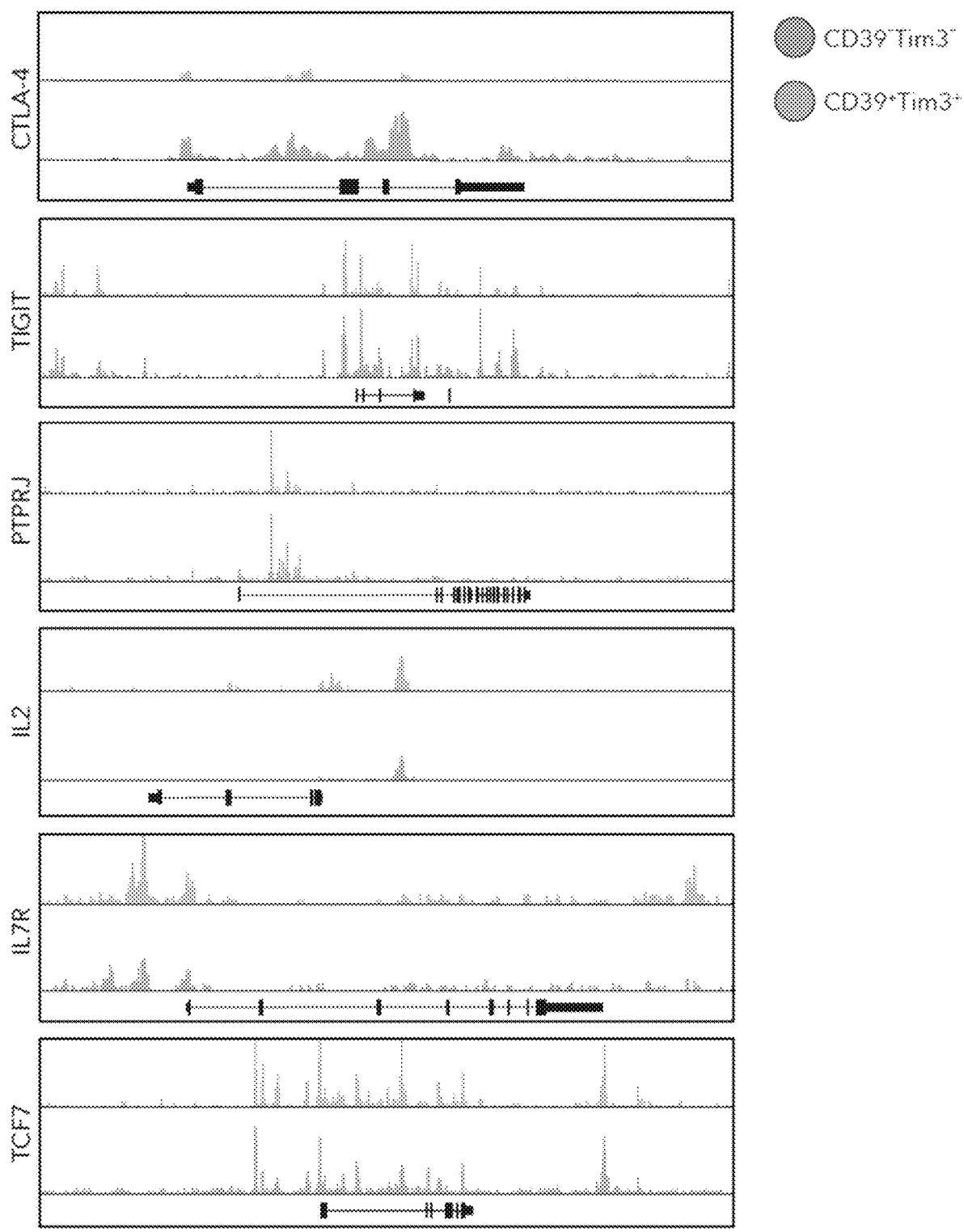
FIG. 27D. ATAC-seq traces for open chromatin regions near selected genes in $CD39^+TIM3^+$ and $CD39^-TIM3^-$ is shown.
Figure 27E:
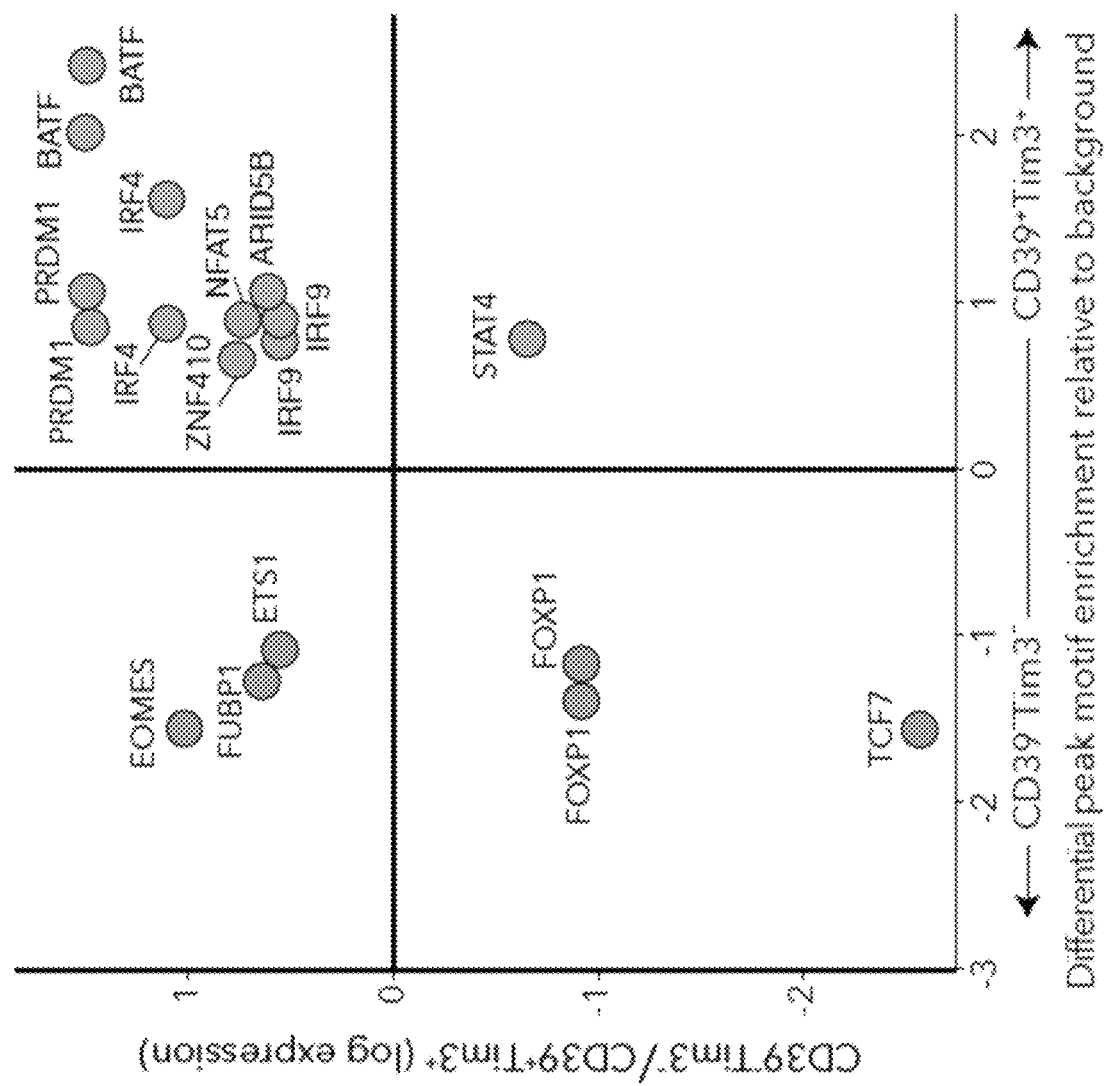
FIG. 27E. Graph depicting enrichment of TF motifs in open chromatin specific to $CD39^-TIM3^-$ and $CD39^+TIM3^+$ cells is on the x-axis, and differential expression of TF on the y-axis.
Figure 27F:
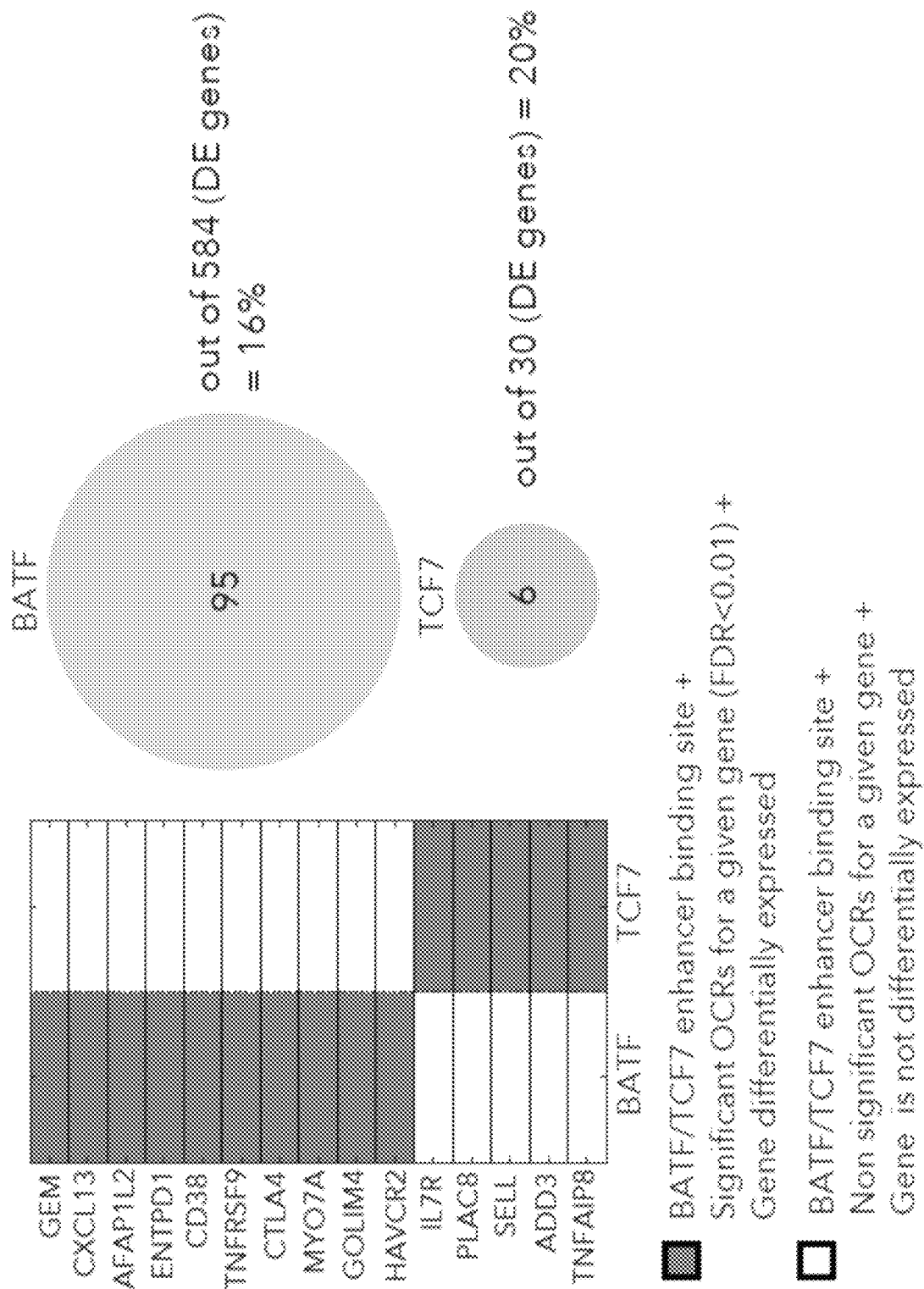
FIG. 27F. Left, enhancer binding sites near the listed genes for BATF and TCF7. Significant genes associated with these sites are marked and non-significant genes are white. The corresponding genes are also differentially expressed between $CD39^+TIM3^+$ cells (enriched with BATF) and $CD39^-TIM3^-$ cells (enriched with TCF7). Right, the number of genes that are differentially expressed with a corresponding differential peak containing BATF or TCF7 is shown.
Figures 47A, 47B, 47C, 47D:
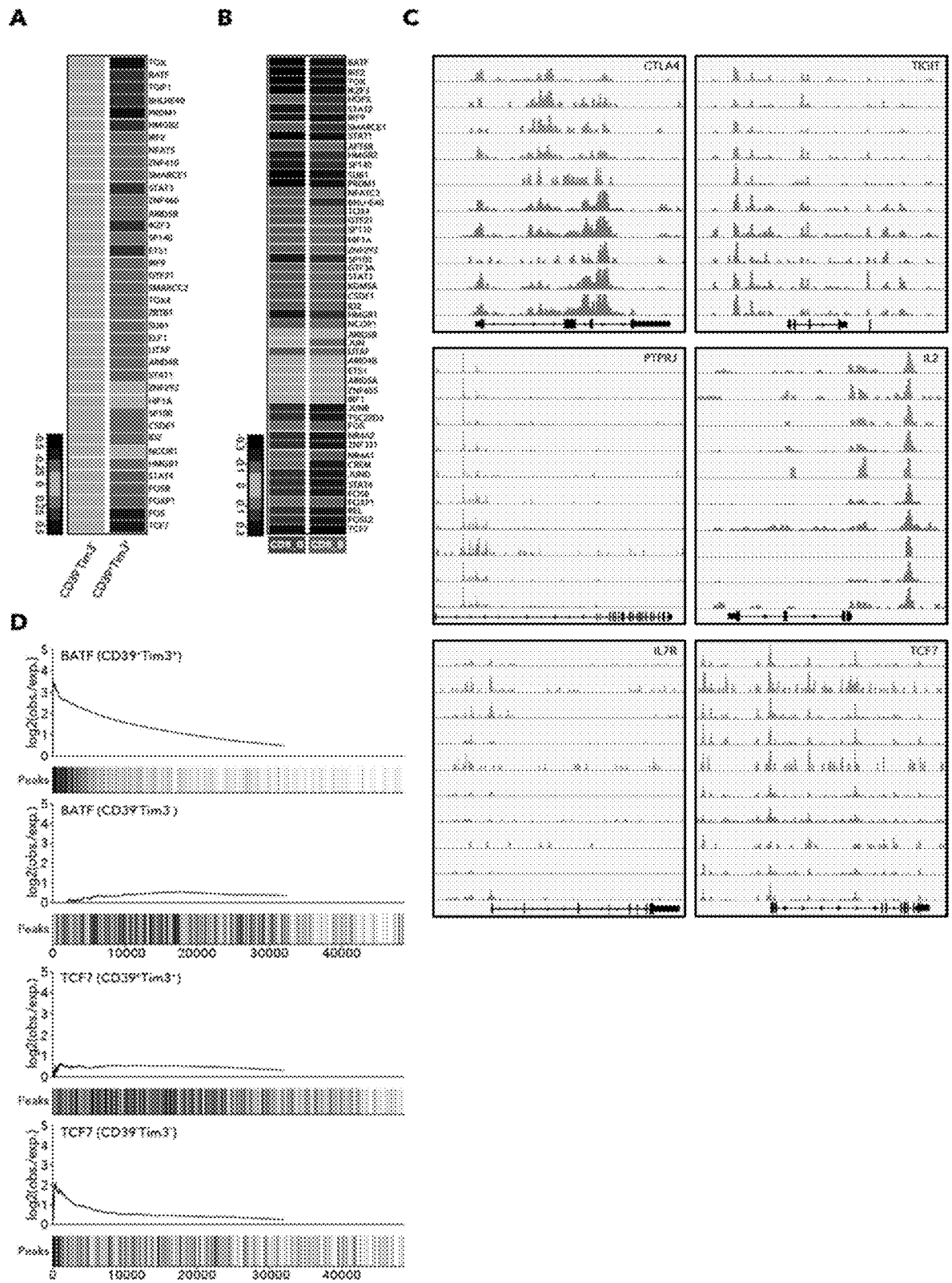
FIG. 47A. Heatmap of averaged scaled expression values ($\log_2$(TPM+1)) of discriminative transcription factors for non-sorted CD39$^+$TIM3$^+$ and CD39$^-$TIM3$^-$ cells as deified by single cell RNA expression. Shading scheme is based on z-score distribution from −0.5 to 0.5.
FIG. 47B. Heatmap of averaged scaled expression values ($\log_2$(TPM+1)) of discriminative transcription factors for CD8_B and CD8_G cells as in FIG. 24. Shading scheme is based on z-score distribution from −0.3 to 0.3.
FIG. 47C. ATAC-seq traces for open chromatin regions near selected genes in CD39⁻TIM3⁻ cells and CD39⁺TIM3⁺ cells in all 5 patients is shown.
FIG. 47D. Transcription factor (TF) enrichment graphs for BATF and TCF7 in CD39⁺TIM3⁺ and CD39⁻TIM3⁻ sorted cells are shown. Each graph shows the enrichment peaks relative to background (x-axis). Black bars indicate CD39⁺TIM3⁺ (top) or CD39⁻TIM3⁻ (bottom) peaks, while white bars indicate background peaks. Motif enrichment was calculated using the minimum hypergeometric (minHG) test (Methods).

Example 16—Chromatin Accessibility of Melanoma-Associated Exhausted and Memory Cells Since prospectively isolated CD39+TIM3+ (DP) and CD39−TIM3− (DN) cells recapitulated phenotypes of cells within the previously unrecognized CD8_2 and CD8_4+6 clusters respectively, Applicants asked what are the epigenetic programs that govern these distinctive cell states. To dissect differential regions of open chromatin that corresponded to differences in gene expression, Applicants isolated DP and DN cells from 5 metastatic melanoma patients treated with the checkpoint inhibitor PD-1 and performed assays for transposase-accessible chromatin with next generation sequencing (ATAC-seq) and scRNA-seq[39] (FIG. 27A). scRNA-seq analysis identified exclusive patterns of transcription factor (TF) expression for each of the sorted populations. Applicants found that DN cells had higher expression for several TFs, including TCF7, STAT4, FOXP1 and FOSB, previously shown to be enriched in stem-cell memory CD8+ T-cells[26], while DP cells were enriched for BATF, PRDM1, TOX, HMGB2 and IRF2, as previously described in exhausted CD8+ T-cells[7,40] (FIG. 27B). Furthermore, similar patterns of TF expression were identified when compared to the original unsorted single cells separated computationally by expression of CD39 and TIM3 at the RNA level, and also in the original CD8_G and CD8_B clusters (FIG. 47A-B). Analysis of ATAC-seq profiles identified unique patterns of open chromatin regions (OCRs) between DP and DN cells (FIG. 27C); DP and DN cells sorted from all 5 patients displayed opposite patterns of increased and decreased ATAC-seq peaks openness in specific gene loci (CTLA4, TIGIT, PTPRJ, IL2, ILR7 and TCF7) related to exhaustion and memory (FIG. 27D and FIG. 47C). OCRs were unequal between the two different cell states; a smaller fraction of OCRs were detected in DN cells (425; Benjamini-Hochberg FDR<0.01) when compared to DP cells (859; Benjamini-Hochberg FDR<0.01), consistent with a previous study showing an increase in $CD8^+$ T-cell OCRs as cells differentiate in response to chronic LCMV infection[41]. Next, Applicants sought to identify enrichment for TF motifs that distinguish DP from DN cells using the GOMER approach (Methods), comparing differential expression of specific TFs that bind to these motifs. Applicants identified differential peak motif enrichment coupled with high expression for BATF, PRDM1, IRF4 and NFAT5 in the DP cells, and TCF7 and FOXP1 in the DN cells (FIG. 27E). Interestingly, Applicants found that EOMES, previously shown to be high in terminally differentiated exhausted cells[7,42], had differential peak motif enrichment in the DN cells, but higher expression in DP cells. Since BATF and TCF7 were the two TFs that had the highest peak motif enrichment and the highest expression in DP and DN respectively (FIG. 27E and FIG. 47D), and due to the strong association of TCF7 with clinical responses, Applicants sought to identify genes that could be regulated by these TFs. To that end, Applicants compared whether differentially expressed genes near significant (Benjamini-Hochberg FDR<0.01) OCRs in DP or DN cells (as defined by GREAT[43]) contain enhancers with BATF or TCF7 motifs. Applicants identified 95 genes in DP (16%; including CXCL13, ENTPD1, CD38, CTLA4 and HAVCR2) and 6 genes in DN cells (20%; including IL7R, PLAC8 and SELL), out of the total differentially expressed genes (584 for DP and 30 for DN), that meet these criteria (FIG. 27F), suggesting that both BATF and TCF7 control the expression of some of the key markers unique to each cell state. Overall, the analysis defined epigenetic programs and key TFs controlling two distinct and novel states of $CD8^+$ T-cells associated with clinical outcome in humans, which could have implications for new therapeutic strategies that could increase the chance of durable responses.

Figure 28A:
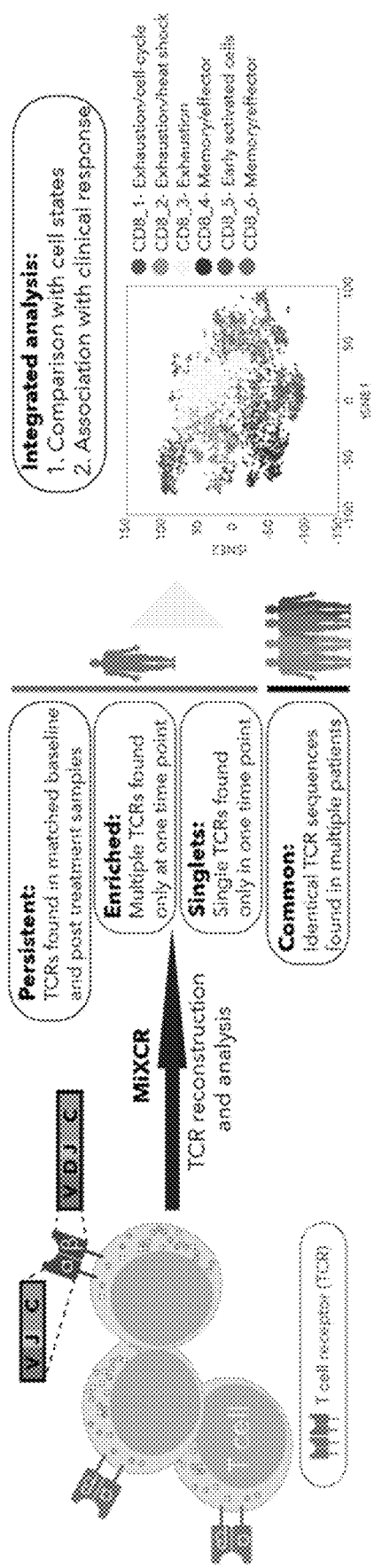
FIG. 28A. Schematic illustration of the TCR analysis pipeline. TCR reconstruction was done using the MixCR algorithm (Methods), and were classified into 4 groups: Persistent: TCRs found in matched baseline and post treatment samples; Enriched: Multiple TCRs found in a single time point of a given patient; Singlets: single TCRs that detected only once in our dataset; and Common: TCRs found in different patients.

Example 17—TCR Analysis Identifies Different Patterns of Expansion Associated with Cell States and Clinical Outcome Finally, Applicants interrogated the relationship between the clinical response, cell states and T-cell clonality. To do so, Applicants reconstructed T-cell receptor (TCR) sequences from the transcriptomic data using the MiXCR tool[44] for all identified $CD8^+$ T-cells. Applicants defined 4 patterns of TCR clonality based on the CDR3 sequence identified in both $\alpha$ and $\beta$ chains (FIG. 28A): 1. persistent—TCRs that were detected in pre- and post-therapy samples from the same patient; 2. enriched—TCRs detected in multiple T-cells at a single time point; 3. singlets—TCRs found in only one T-cell at one time point, and 4. common—TCRs that were shared across patients.

Figure 28B:
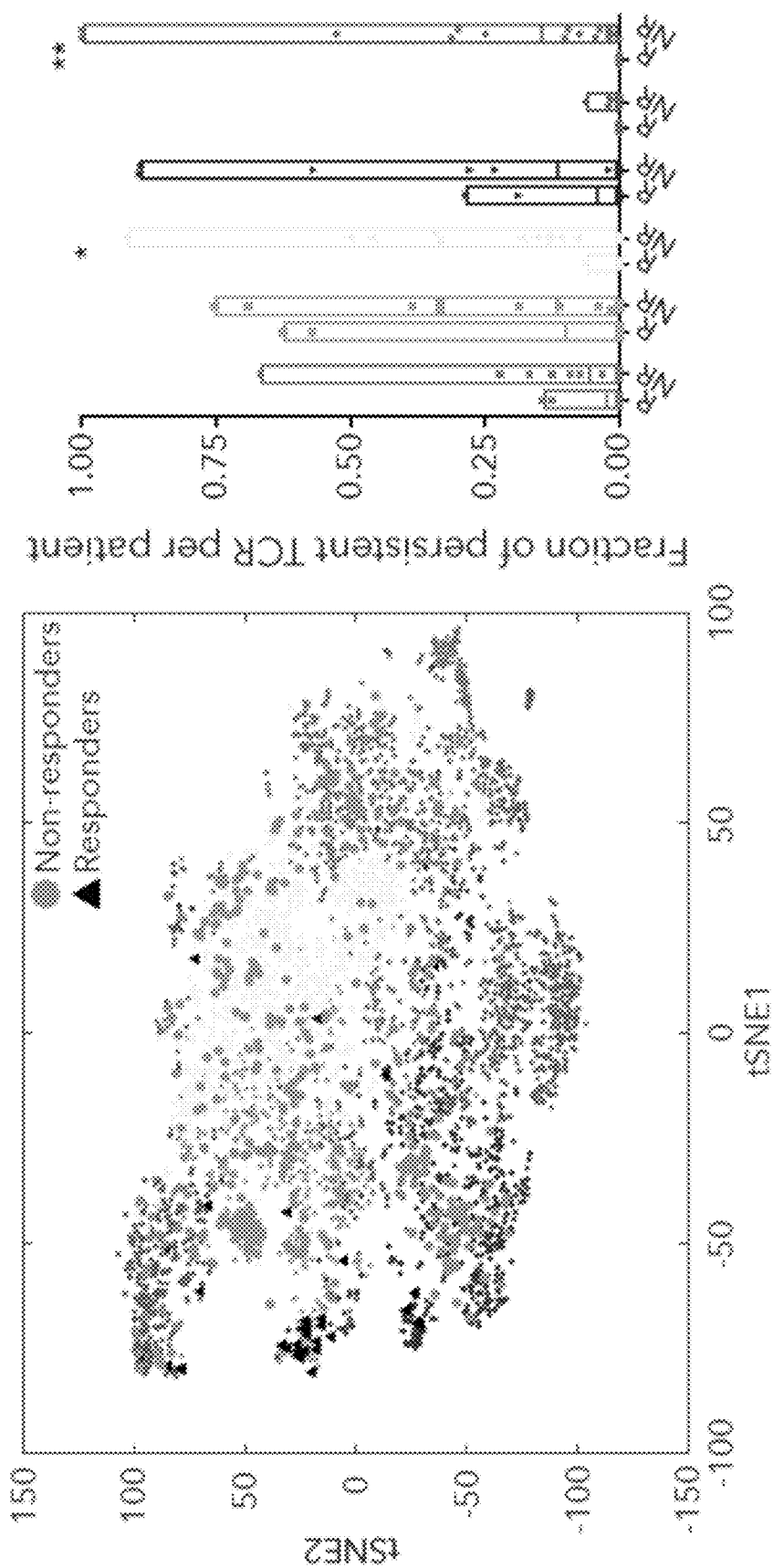
FIG. 28B. tSNE plot (left panel) delineating the six identified $CD8^+$ T-cell clusters and persistent TCRs in responder lesions (black triangles) and non-responder lesions (gray circles). Bar plot (right panel) summarizing the fraction of persistent TCRs per patient across the different clusters between responder (R) and non-responder (NR) samples. Two-sided Wilcoxon rank-sum P-value is shown *P=0.03; P=0.0085.
Figures 28C, 28D:
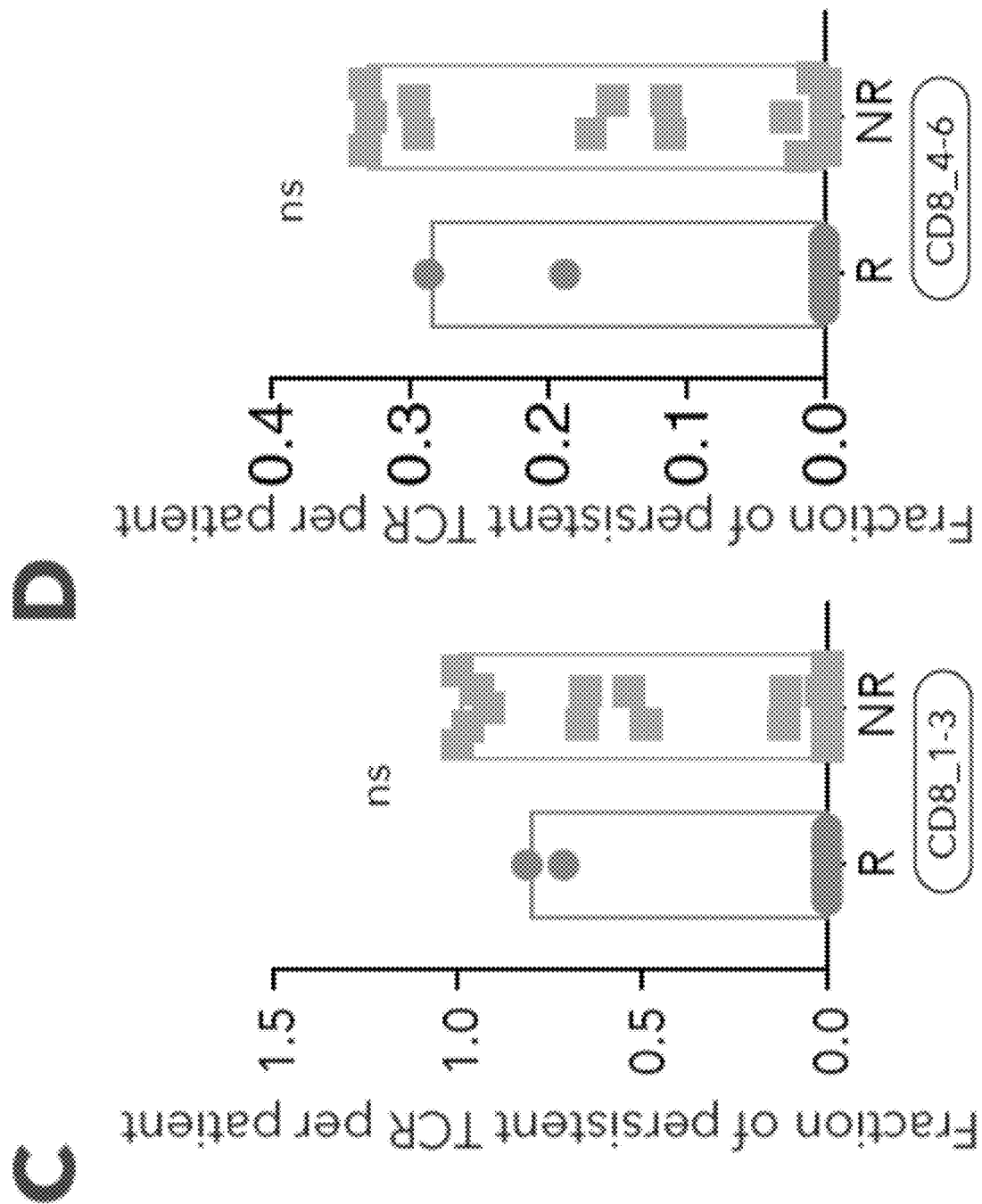
FIG. 28C-D. Fraction of persistent TCRs per patient, aggregated for CD8_1 to 3 (CD8_1-3) and CD8_4 to 6 (CD8_4-6) clusters for R and NR samples; ns—not significant.
Figure 28E:
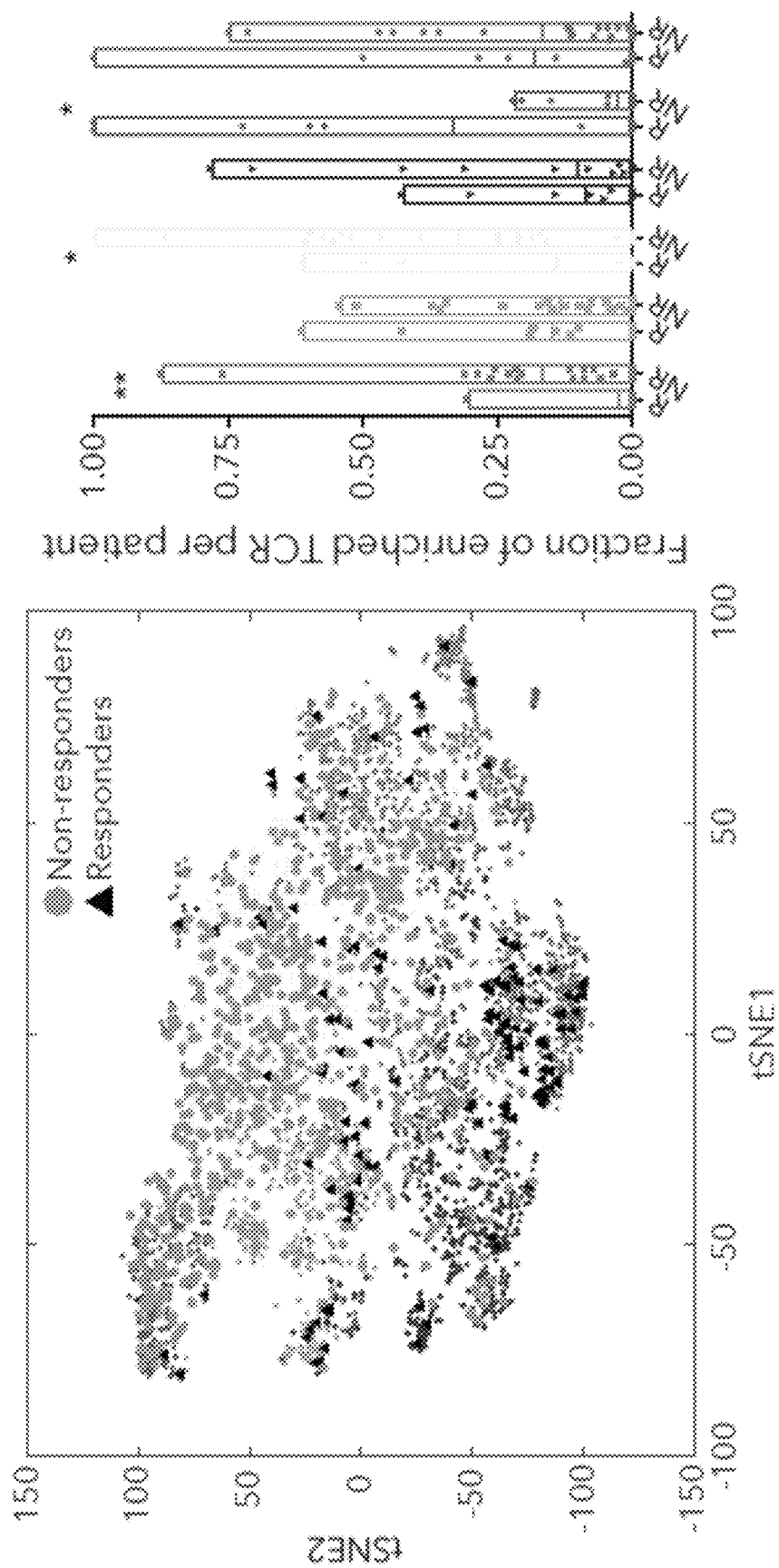
FIG. 28E. tSNE plot (left panel) delineating the six identified clusters and enriched TCRs in responders (black triangles) and non-responders (gray circles). Bar plot (right panel) summarizing the fraction of enriched TCRs per patient across the different clusters and split into R and NR samples. P=0.003.
Figures 28F, 28G:
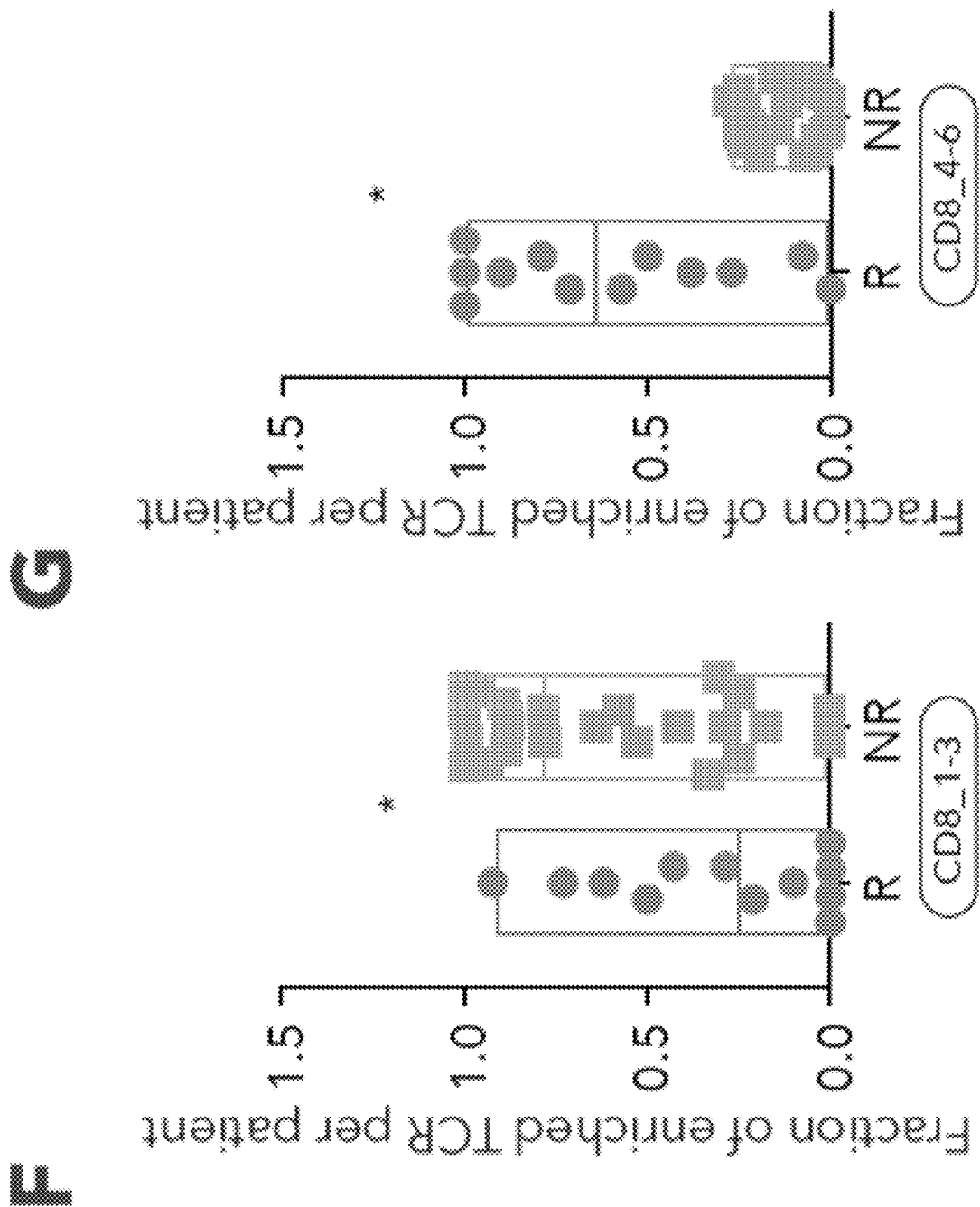
FIG. 28F-G. Fraction of enriched TCR per patient, aggregated for CD8_1 to 3 (CD8_1-3; P=0.014) and CD8_4 to 6 (CD8_4-6; P=0.019) clusters for R and NR samples.
Figure 28H:
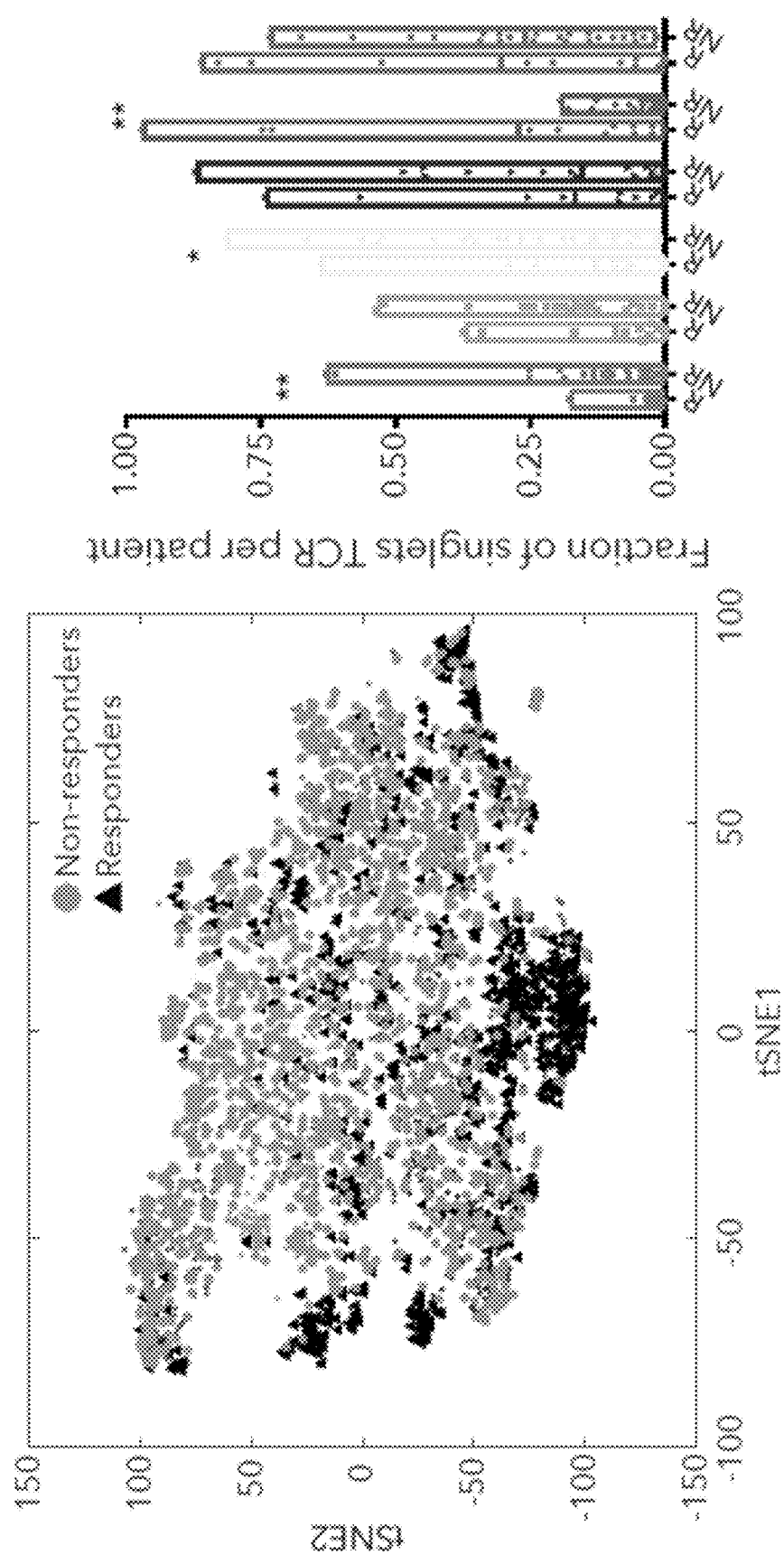
FIG. 28H. tSNE plot (left panel) delineating the six identified clusters and singlets TCRs in responders (black triangles) and non-responders (gray circles). Bar plot (right panel) summarizing the fraction of singlets TCRs per patient across the different clusters and split into R and NR samples. **P=0.009 for CD8_1; *P=0.02; **P=0.004 for CD8_5.
Figures 28I, 28J:
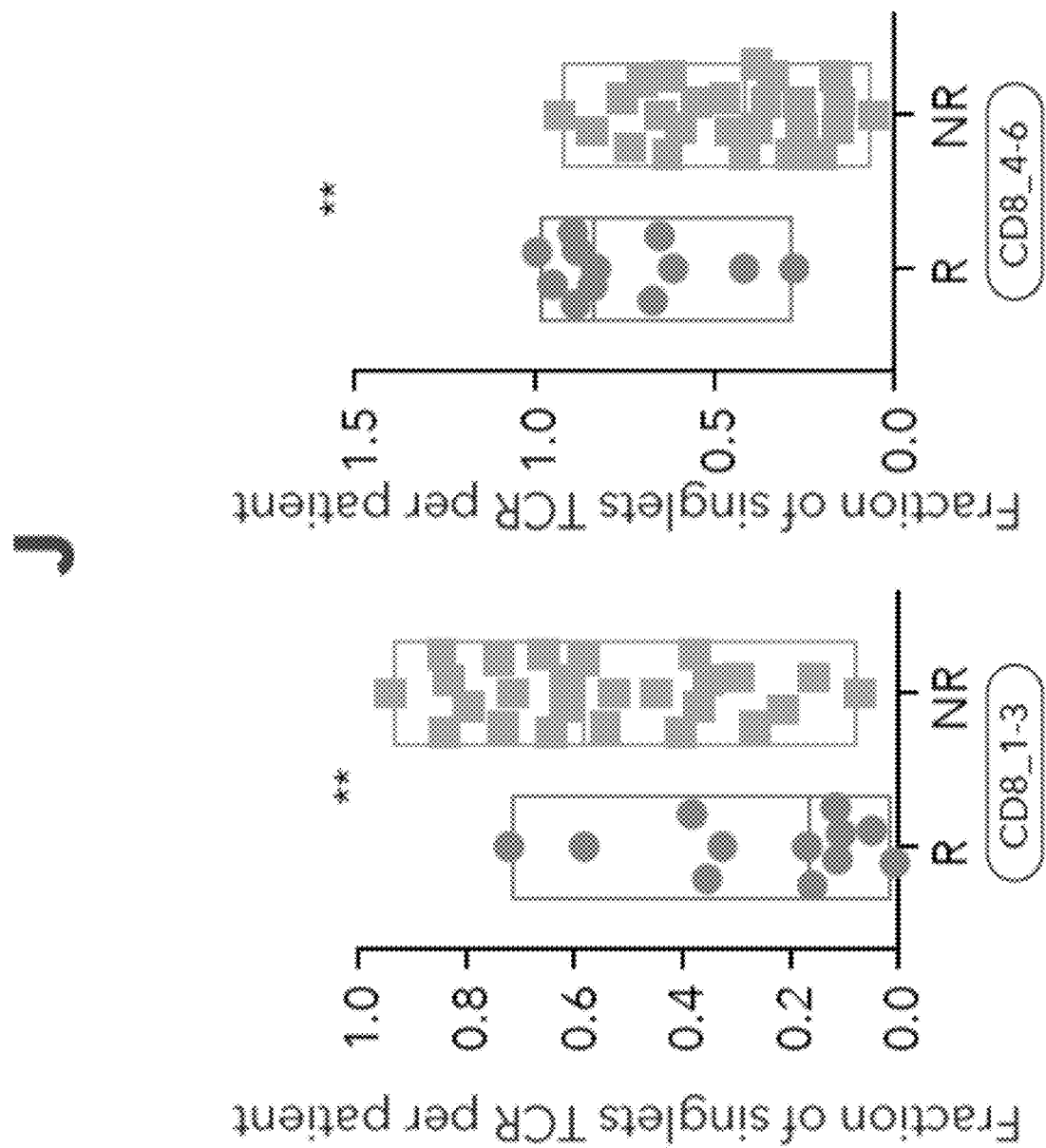
FIG. 28I-J. Fraction of singlets TCR per patient, aggregated for CD8_1 to 3 (CD8_1-3; P=0.002) and CD8_4 to 6 (CD8_4-6; P=0.002) clusters for R and NR samples.

Since the overall number of persistent TCRs was very low, especially in responders, Applicants could not make many conclusions about their relationships to clinical response. However, Applicants detected a significant enrichment for persistent TCRs in non-responders in clusters CD8_3 (two-sided Wilcoxon P-value=0.03) and CD8_6 (P-value=0.008) (FIG. 28B), but not when aggregating exhausted clusters (CD8_1-3) or memory/effector ones (CD8_4-6) (FIG. 28C-D). Interestingly, very few persistent TCRs were detected in the CD8_5 cluster (which was present predominantly in post-therapy samples) when looking at all patient $CD8^+$ cells (FIG. 48A), suggesting that these T cell clones did not exist prior to therapy.

Figures 48A, 48B, 48C, 48D, 48E, 48F, 48G:
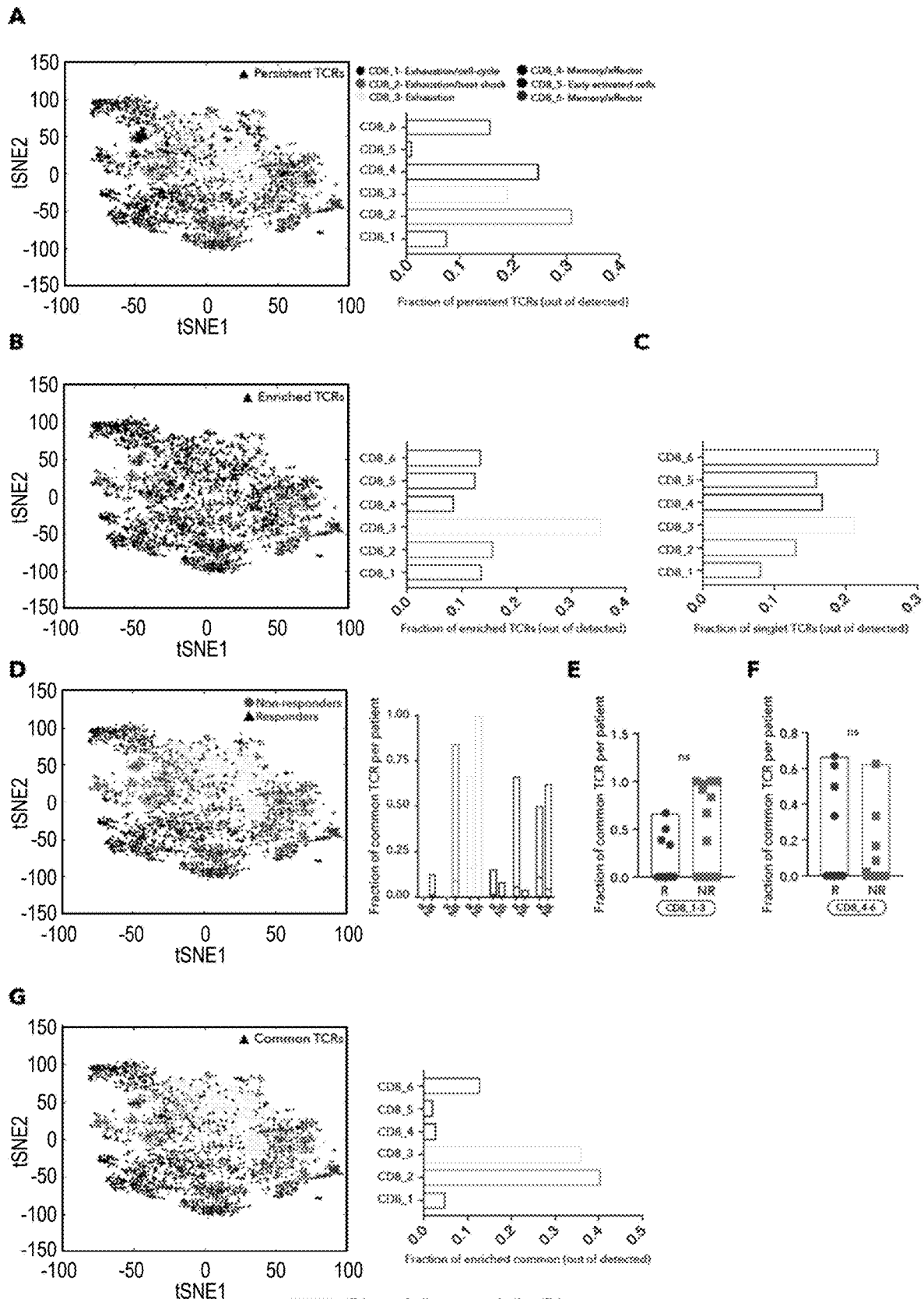
FIG. 48A. tSNE plot delineating the six clusters and persistent TCRs (black triangle). The fraction of persistent TCRs in each cluster out of total persistent TCRs is shown on the right.
FIG. 48B. tSNE plot delineating the six clusters and enriched TCRs (black triangle). The fraction of enriched TCRs in each cluster out of total enriched TCRs is shown on the right. C. The fraction of singlets TCRs in each cluster out of total singlets TCRs is presented D.tSNE plot (left panel) delineating the six identified clusters and common TCRs in responder lesions (black triangles) and non-responder lesions (gray circles). Bar plot (right panel) summarizing the fraction of common TCRs per patient across the different clusters between responder (R) and non-responder (NR) samples. ns—not significant. E-F. Fraction of common TCRs per patient, aggregated for CD8_1 to 3 (CD8_1-3) and CD8_4 to 6 (CD8_4-6) clusters for R and NR samples. G. tSNE plot delineating the six clusters and common TCRs (black triangle). The fraction of common TCRs in each cluster out of total common TCRs is shown on the right.

While enriched and singlets TCRs had different patterns of distribution across the 6 clusters (with more enriched TCRs in exhausted clusters and more singlet TCRs in effector/memory clusters, FIG. 48B-C), both were significantly enriched in the same direction for each cluster when comparing responder to non-responder lesions. Applicants detected a significant enrichment for non-responder lesions in CD8_1 (P-value=0.003 for enriched and P-value=0.009 for singlets) and CD8_3 (P-value=0.03 for enriched and P-value=0.02 for singlets), and a significant enrichment for responder lesions in CD8_5 (P-value=value=0.02 for enriched and P-value=0.004 for singlets) (FIG. 28E-J). Applicants hypothesize that enriched TCRs are likely to have been exposed to persistent stimulation, explaining their higher proportions in the exhausted than effector/memory clusters, while singlet TCRs are more likely to be newly generated T-cells with lower exhaustion properties.

Although common TCRs were predominantly present in clusters CD8_2 and 3, no significant association was found with clinical outcome (FIG. 48D-G). Collectively, this analysis allowed us to connect the transcriptional phenotype of cells and therapeutic outcomes to therapy with TCR clonality, and could aid in investigating T-cell dynamics and cell state plasticity. Indeed, when looking at the transitions of T-cell states (CD8_1-6) within a specific clone (based on identical TCR sequence) across longitudinal samples in the same patient, Applicants discovered bilateral transitions between exhausted and memory/effector states.

Example 18—Discussion

Although immune checkpoint blockade leads to durable responses in patients with metastatic melanoma, refractory disease and progression after initial response remain major causes of mortality[3,4]. While many studies have identified different components associated with clinical outcome, the principles of the immune system that underlie the success or failure to checkpoint therapy in humans remain relatively unexplored. To address this issue Applicants performed an unbiased analysis of immune cells using single-cell transcriptomics, to dissect the cellular and molecular determinants of response. Within the tumor, Applicants found specific $CD8^+$ T-cell states associated with clinical outcome in melanoma patients treated with checkpoint therapy. The association between the cellular states (as determined by gene expression or antibody staining) and treatment outcome was observed in both baseline and on-therapy samples. Applicants validated these associations in two independent cohorts: one cohort of anti-PD1 patients (n=30) using a signature of memory/effector T-cells, and a second anti-PD1 cohort (n=21) using the fraction of $TCF7^+CD8^+$ T-cells based on immunofluorescence staining. The analyses also identified novel sub-states of exhausted and memory/effector T-cells. Among the identified markers of the exhausted sub-states, CD39 (ENTPD1) emerged as a promising discriminator of exhausted $CD8^+$ T-cells in melanoma patients, and as a potential target when blocked together with TIM3 (HAVCR2) using a mouse melanoma model.

Previous studies have shown that the number of infiltrating $CD8^+$ T-cells detected in patient biopsies is significantly enriched in responders. However, some inconsistencies were found between these studies: the first showed that the number of infiltrating $CD8^+$ T-cells detected before treatment can predict clinical outcome[5], whereas the second showed that only early on-treatment, but not baseline quantification is significantly associated with patient response[6]. Despite potential spatial and temporal heterogeneity in biopsy-based studies of cancer, Applicants identified robust predictive markers in baseline and on-treatment samples, reflecting quality metrics of T-cell states (TCF7$^+$CD8$^+$), rather than the quantity of T-cells (CD8$^+$). Indeed, the number of CD8$^+$ T-cells was comparable across responders and non-responders within the cohort, consistent with the fact that the T-cell number is not a reliable predictor in pretreatment biopsies[6]. Several other studies found that the spatial distribution of the T-cells was more important in predicting survival[45-47]. Hence, further studies are needed to explore the relationship between the spatial distribution of T-cells and the cellular states Applicants identified using highly multiplexed tissue imaging systems.

One of the key markers expressed in clusters associated with response, which was found in an unbiased manner as a result of data analysis and discriminated responders from non-responders, was the transcription factor TCF7. Although, these results are in line with previous studies showing that TCF7 is required for reinvigorating CD8$^+$ T-cells in response to anti-PD1 or anti-PDL1 therapies to resolve chronic LCMV infection in mice[29,30], its association with clinical outcome in patients treated with checkpoint immunotherapy has not been previously demonstrated. More specifically, it has been shown that TCF7 is essential for the expansion of CXCR5$^+$TIM3$^-$ CD8$^+$ T-cells (but not TIM3$^+$ cells) that are important for the control of the virus[30]. Indeed, Applicants also found that TIM3$^-$ cells are TCF7$^+$ and are associated with response; however Applicants did not find CXCR5 expression associated with TCF7$^+$ cells, suggesting that this chemokine receptor may not be a critical marker for cells associated with response in the melanoma context. Additionally, a recent study suggested that decreased open chromatin regions at TCF7 sites are associated with reduced activation of non-programmable, dysfunctional PD1$^{hi}$ T-cells[48].

Furthermore, the data revealed significant heterogeneity of exhausted CD8$^+$ T-cell states, with 2 of the 3 clusters showing stronger association with non-responding lesions. While most studies have focused on PD1, TIM3, LAG3 and CTLA-4 to mark exhausted cells, Applicants identified CD39 as an additional marker for human CD8$^+$ T-cell exhaustion in melanoma, and found it to be enriched in non-responsive lesions. While not previously observed in melanoma or tested functionally, this result is consistent with recent findings, demonstrating that CD39 is a marker for terminally exhausted CD8$^+$ T-cells in HIV and HCV infected patients[32]. The results in mice support the targeting of CD39 together with TIM-3 for boosting anti-tumor immunity. Additionally, Applicants found that in all samples, regardless of whether they were collected at baseline or during treatment, there was a heterogeneous mixture of all the identified CD8$^+$ T-cell states, but that their proportions were associated with clinical outcome. Further studies will be needed to test whether other immunotherapeutic combinations or targets (e.g KIR2DL4 and CD38), which Applicants found to be enriched in clusters associated with lack of response, could be used to enhance immunity and overcome resistance.

A critical question that still remains unanswered is how the 6 CD8$^+$ T-cell states Applicants identified relate to each other. In line with previously published studies, Applicants propose that cells can transition between memory and exhausted states, and bolster this hypothesis through finding divergent memory and exhaustion phenotypes in clonal T cell populations (determined based on identical TCR sequences). Surprisingly Applicants found that CD8_5 T cells, which were predominantly found in post-therapy tumor samples, hardly share TCRs with the baseline sample, suggesting that members of the CD8_5 cluster are generated outside of the tumor and subsequently migrate to the tumor. This is consistent with observations from a recent study[49] demonstrating that lymphoid-organ derived T-cells are required for anti-PD1 potency.

Despite the identification of key components associated with response, the study has technical limitations and open biological questions that necessitate future studies to address them. First, although Applicants used an optimized version of the full length Smart-seq2 protocol, which has the highest sensitivity and lowest dropout probability compared to other methods[50], the resulting transcriptomes need to be interpreted with caution because lack of detection of a transcript in a single cell does not guarantee its absence. Applicants address this dropout challenge by relying on signatures composed of many (not single) genes in order to increase confidence in cluster definition. Second, while the approach of scRNA-seq generates relatively unbiased genome-scale transcriptome data, which is then used to identify novel immune cell states and molecular determinants of response, future studies will need to validate these signatures at the protein level (as Applicants did for TCF7) using highly multiplexed tissue imaging or mass cytometry in melanoma as well as other types of cancer. Third, although Applicants identified T cell states associated with responses, Applicants do not know which cells kill the tumors. Fourth, what are the factors that control the proportions of the identified CD8$^+$ cell states in patient samples? Is the responder-associated memory phenotype maintained post treatment? Can cells be reprogrammed from an exhausted to a memory phenotype? While the approach in this study is useful in identifying new components associated with response and useful in generating hypotheses, future mechanistic studies will be required to demonstrate these developmental process. Finally, the study focused on melanoma patients treated with checkpoint inhibitors, but Applicants need to address whether these predictive markers of response are relevant to other types of malignancies or therapies.

This study addresses the long-standing question of which immune cell states are important for the activity of checkpoint therapy in humans, and provide a powerful tool both to the medical and research communities in several ways: first, the data and analysis enables the prediction of clinical outcome in patients treated with anti-PD1 and may impact clinical trial design and execution, as well as application of this therapy as standard of care in thousands of patients across the world. Second, the identification of new targets, and the subsequent validation of two specific ones in the study, may lead to new trials focused on these targets and other combinations of targets associated with success or failure of therapy in the study (e.g. KIR2DL4 and CD38). Third, the finding that specific memory-like signatures are associated with response—together with recent studies showing that CAR T cell activity is enhanced by generating more memory-like cells using the IL-7 or IL-15 pathways, leading to better outcome in preclinical models[26,51]—suggests that manipulation of T cells prior to adoptive cell therapies by increasing the ratio of CD8_G to CD8_B (especially in patients with a low ratio) would strongly boost clinical responses when combined with checkpoint therapies.

Since an increasing number of patients are being treated with checkpoint inhibitors as a standard of care, it has become essential to fully understand the determinants of response. Utilizing the data presented in this study, one can potentially help to optimally select patients for therapy, identify new therapeutic strategies and thus increase the chance of durable responses.

Example 19—Methods

Patient samples. Metastatic melanoma patients treated with checkpoint blockade therapy at Massachusetts General Hospital (Boston, MA) and University of Texas MD Anderson Cancer Center (Houston, TX) provided written informed consent for the collection of tissue and blood samples for research and genomic profiling, as approved by the Dana-Farber/Harvard Cancer Center Institutional Review Board (DF/HCC Protocol 11-181) and UT MD Anderson Cancer Center (IRB LAB00-063 and 2012-0846). Matched tumor and normal blood samples were obtained from 23 patients at baseline and/or after checkpoint treatment.

Sample dissociation. Fresh isolated tumor samples were collected immediately after surgery and were dissociated within 1 hour using the human tumor dissociation kit (Miltenyi Biotec; 130-095-929) with the following modifications. Tissue was minced into small pieces using a scalpel and put into a 1.5 ml eppendorf tube containing 100 µl of enzyme H, 50 µl of enzyme R, 12.5 µl of enzyme A (all provided in the kit), and 837.5 µl of RPMI, followed by a 20 minute incubation in a thermomixer (Eppendorf; F1.5) at 37° C., 600 rpm. After incubation, debris were removed by filtering through a 70 µm cell strainer, followed by mincing of the remaining tissue left on the strainer with a plunger in order to increase cell yield. Dissociated cells were subsequently washed with cold 1×PBS containing 1.5% heat inactivated FCS, spun down at 1300 rpm, 4° C. for 5 minutes, resuspended, and counted for yield and viability with trypan blue using a Countess automated cell counter (Invitrogen).

Flow cytometry and cell sorting. For both flow cytometry and cell sorting, Human TruStain FcX (Biolegend, 422302) was used for blocking Fc receptors before labeling cells. To discriminate live from dead cells Applicants used Zombie violet Dye (Biolegend, 77477) for 15 min at 4° C., followed by surface labelling of cells for 30 min at 4° C., using standard protocols. The antibodies used for cell surface labelling were PE anti-human CD45 (Biolegend, 304008), APC anti-human CD3 (Biolegend, 300412), FITC anti-human HLA-A,B,C (Biolegend, 311426), APC/Cy7 anti-human CD235a (Biolegend, 349116), PE/Cy5 anti-human CD3 (Biolegend, 300309), BV421 anti-human PD1 (Biolegend, 329919), PE/Cy7 anti-human TIM3 (Biolegend, 345013), APC/Cy7 anti-human CD39 (Biolegend, 328226), AF700 anti-human CD4 (Biolegend, 317425), BV650 anti-human CD8 (biolegend, 301041). The antibodies used for intracellular staining were FITC anti-human IFNγ (Miltenyi Biotec, 130-097-936), PE anti-human IL2 (Miltenyi Biotec, 130-099-391), APC anti-human TNF (Miltenyi Biotec, 130-099-197). Sorting of cells was performed on a BD Fusion instrument using the following antibody panel: Zombie dye, CD45, CD235a and HLA-A,B,C. CD45$^+$ cells from dissociated samples were sorted into 96-well plates (Eppendorf, 951020401) containing 10 µl of lysis buffer (TCL buffer, Qiagen 1031576, supplemented with 1% β-mercaptoethanol), sealed, vortexed, spun down at 2500 rpm for 30 seconds, immediately placed on dry ice, and then stored at −80° C. until processing with the Smart-Seq2 protocol. For flow cytometry Applicants used the Beckman Coulter Cyto-FLEX instrument and analyzed the data with FlowJo v10.0.8r1 software.

Single cell RNA sequencing procedure. Libraries from single cell lysates were generated with the Smart-Seq2 protocol 52 with some modifications in the reverse transcription step as recently described 21. 96-well plates containing cell lysates were thawed on ice, spun down at 1500 rpm for 30 seconds, and mixed with Agencourt RNAClean XP SPRI beads (Beckman Coulter) for RNA purification. Purified RNA was resuspended in 4 µl of Mix-1, denatured at 72° C. for 3 min and placed immediately on ice for 1 min before 7 µl of Mix-2 was added. Reverse transcription was carried out at 50° C. for 90 min, followed by 5 min incubation at 85° C. 14 µl of Mix-3 was added in each well and the whole-transcriptome amplification step was performed at 98° C. for 3 min, followed by 21 cycles at (98° C. for 15 sec, 67° C. for 20 sec and 72° C. for 6 min), and final extension at 72° C. for 5 min. cDNA was then purified with Agencourt AMPureXP SPRI beads (Beckman Coulter) as described 21, to remove all primer dimers residues. Quality control steps were performed on samples before library construction and included the following steps: (1) concentration measurements, using the Qubit dsDNA high sensitivity assay kit on the Synergy H1 Hybrid Microplate Reader (BioTek); (2) cDNA size distribution using the High-Sensitivity Bioanalyzer Kit. Libraries were generated using the Nextera XT Library Prep kit (Illumina) with custom indexing adapters 21 in a 384-well PCR plate, followed by a cleanup step to remove residual primer dimers. Combined libraries from 384 cells were then sequenced on a NextSeq 500 sequencer (Illumina), using paired-end 38-base reads.

Immunofluorescence assay and analysis. Multiplex staining was performed on 4 µm formalin-fixed paraffin-embedded sections using the Opal multiplex IHC system (PerkinElmer; NEL800001KT) according to the manufacturer's instructions. Briefly, slides were baked for 1 hour at 65° C. followed by deparaffinization with xylene and a graded series of ethanol dilutions (100%, 95% and 70%), fixation with 10% neutral buffered formalin for 30 minutes, microwave antigen retrieval using the AR9 buffer (PerkinElmer; AR900250ML), and blocking. Primary antibodies used for staining were: CD8α (Biolegend; C8/144B; 372902; 1:100) detected with OPAL520 (1:100; Cy2); TCF7 (Cell Signaling; #2203; 1:100) detected with OPAL690 (1:100; Cy5.5). Counterstain was done using DAPI (1:1000) and subsequently mounted using Vectashield (Vectra; H-1000) fluorescence media. Slides were imaged using the Olympus IX83 confocal microscope by scanning 10 random fields on each sample at 40× magnification, and analyzed with Cell-Profiler 2.2.0$^{31}$ to detect the total number of nuclei, CD8$^+$, TCF7$^+$, and CD8$^+$TCF7$^+$ cells. Due to cellular heterogeneity between different slides/patients, in each sample the percentage of CD8$^+$TCF7$^-$ or CD8$^+$TCF7$^+$ was calculated out of the total nuclei detected. For the analysis, a new pipeline was made for detection of cells positive for CD8 and TCF7 (pipeline).

Immunohistochemistry. Procedures were done on the automated Ventana Discovery Ultra staining system, using 4 µm formalin-fixed paraffin-embedded sections. Sections were deparaffinized in xylene and graded alcohols, followed by antigen retrieval (EDTA), blocking with Discovery inhibitor (Ventana; 760-4840), incubation with primary antibodies for 16 minutes, washing and incubation with a secondary antibody conjugated with horseradish peroxidase (HRP). Sections were developed with discovery purple chromogen kit (Ventana; 760-229) and were then counterstained with hematoxylin. Primary antibodies used were: B2M (Abcam; ab27588; 1:1000); anti melanoma triple cocktail (Ventana; 790-4677; 1:100) containing antibodies against melanosome (HMB45), Mart-1/melan A (A103), tyrosinase (T311). The melanoma triple cocktail was used to separate tumor from normal cells enabling detection of B2M in the cancerous cell fraction.

Intracellular cytokine detection. For intracellular cytokine analysis of human CD8+ T-cells, 5×10$^5$ cells from dissociated samples (n=12) were cultured in the presence of soluble LEAF purified anti-CD3 (Biolegend, 317303, 2 μg/ml), anti-CD28 (Biolegend, 302913, 1 μg/ml) and GolgiPlug (BD, 555029) for 6 hours at 37° C. Intracellular cytokine labelling was performed following surface staining, fixation and permeabilization using the BD Cytofix/Cytoperm Plus kit (BD, 555028) according to the manufacturer's instructions.

Single cell RNA-seq data generation and processing. FASTQ files were aligned to the NCBI Human Reference Genome Build GRCh37 (hg19) using STAR[53]. Expression levels were quantified as Transcripts Per Million (TPM) and were computed by the RSEM tool[54]. For each cell Applicants used three quality control (QC) measures. Applicants excluded: (1) cells with a zero expression of both CD45 and CD3E; (2) cells expressing less than 1000 genes; (3) cells with an average expression of housekeeping genes, $\log_2$(TPM+1)<2.5. For downstream analysis Applicants used the set of genes with expression levels $\log_2$(TPM+1) 4.5 in at least 10 cells or genes with a particularly high expression level ($\log_2$(TPM+1)>12) in one or more cells.

A supervised classification of single cells to cell types. To classify each single cell that passed QC to a pre-defined cell type, Applicants performed a supervised analysis based on a list of known marker genes (table 3). This was done by defining a set of genes per cell type which must or must not be expressed. On average, this approach led to the unambiguous classification of 80% of the cells. The remaining cells were then annotated using a manual review process. Following this step Applicants validated that no cell had an ambiguous classification (e.g., a T-cell and a B-cell).

Figure 49:
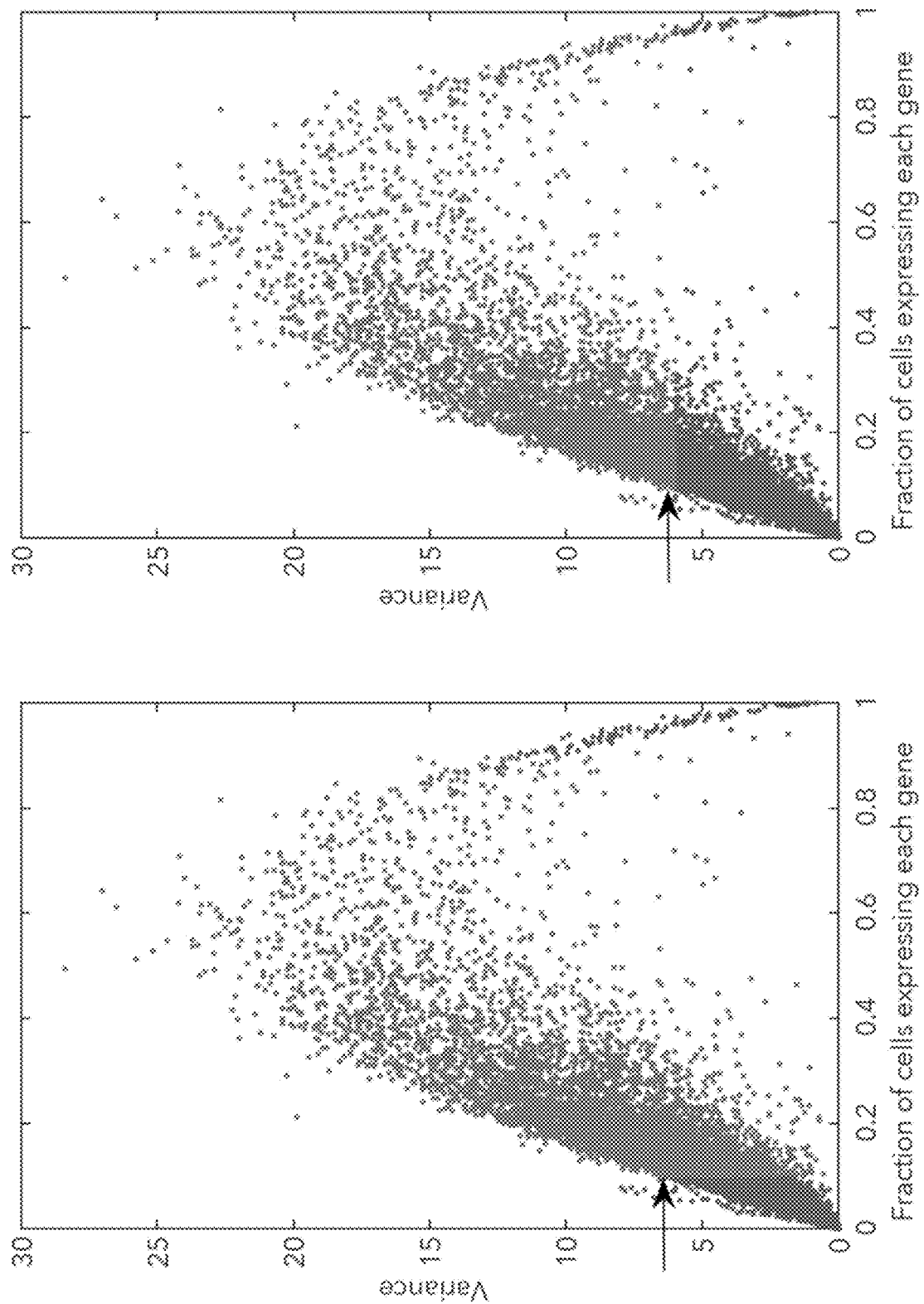
FIG. 49—Gene Variance used for the unsupervised clustering. Variance of each gene vs. the fraction of cells expressing each gene ($log_2$(TPM+1)>0). Left panel: genes expressed in more than 10% of the cells and less than 90% are shaded. Right panel: genes with variance 6 are shaded. As the set of genes expressed in less than 10% of the cells are of less interest for clustering analysis, we set as a minimal threshold the maximal variance observed in this group of genes, as indicated by the black arrow.
Figure 50:
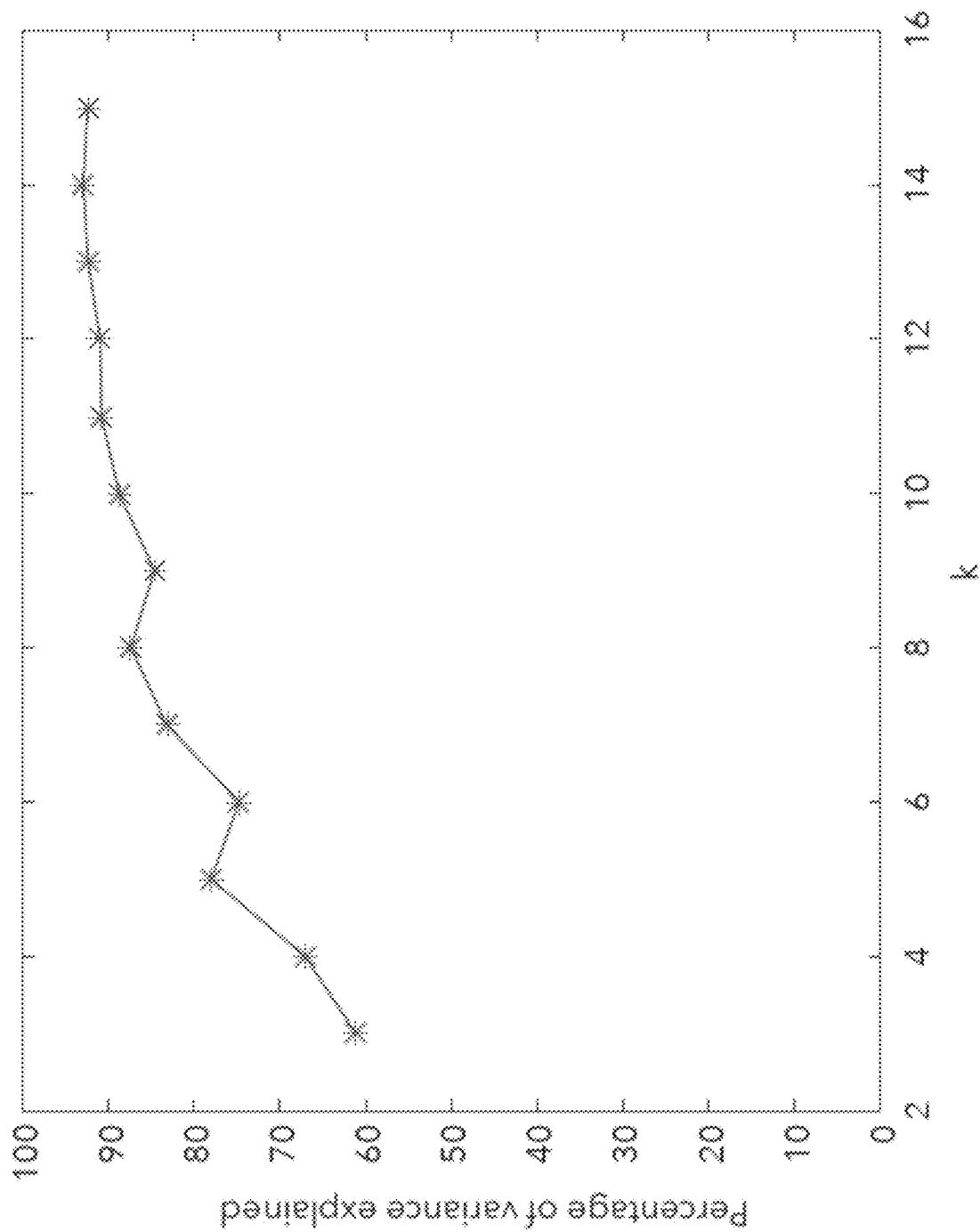
FIG. 50—Determining an optimal number of clusters for all immune cells. Variance explained by each k-means solution ranging from k=3, . . . , 15, when applied to all analyzed single-cells. Percentage of variance explained is computed as described in the Methods section.

Unsupervised clustering of immune cells. To cluster all cells that passed QC Applicants applied the k-means algorithm with a correlation distance metric, testing k=3, . . . , 15. The algorithm was applied using all genes with variance >6, yielding ~4000 genes. This value was selected based on the relation between the variance and the number of cells expressing each gene (FIG. 49). To determine the optimal number of clusters, Applicants first computed the Pearson correlation matrix R and the distance matrix D as (1+R). Applicants then computed the sum of pair-wise distances between all cells in different clusters $Dis_b = \Sigma^k_{l=1}(\Sigma_{i \in C_l, j \notin C_l} D(i,j))$ and the total distance $Dis_t = \Sigma_{i,j} D(i,j)$. The ratio between these two measures $V = Dis_b/Dis_t$ was used to estimate the variance explained by a given solution (FIG. 50). Specifically, in the extreme case where all cells are clustered together or the case where each cell is a single cluster, this ratio would be 0 and 1, respectively. Applicants then selected the optimal number of clusters, k, as the number of clusters for which there was no extreme increase in beyond it. As a few such similar solutions exist, Applicants used prior biological knowledge on distinct cell types (B-cells, myeloids and regulatory T-cells), and selected the solution in which these groups were separated into different clusters (k=11). In addition, Applicants excluded solutions in which the number of gene markers significantly increased in a given cluster is smaller than 20 genes. To determine the robustness of this clustering solution, Applicants performed 100 iterations in which Applicants randomly removed 10% of the cells, and re-ran the k-means algorithm and checked the stability of the clustering solution. Applicants quantified the agreement of a given solution with the original one as the number of pairs of cells that were either clustered together, or not clustered together, in both solutions, divided by the total number pairs shared between the runs. This process yielded a robustness measure of 0.94 for the selected.

To examine if there is a significant difference between responders and non-responders for a given cluster i, Applicants computed the fraction of cells in each lesion assigned to cluster i, and applied the Wilcoxon rank-sum test to the corresponding values of responders and non-responder lesions. P-values were corrected using the Benjamini-Hochberg False Discovery Rate (FDR) procedure and were considered significant if the FDR q-value 0.1.

Figure 51:
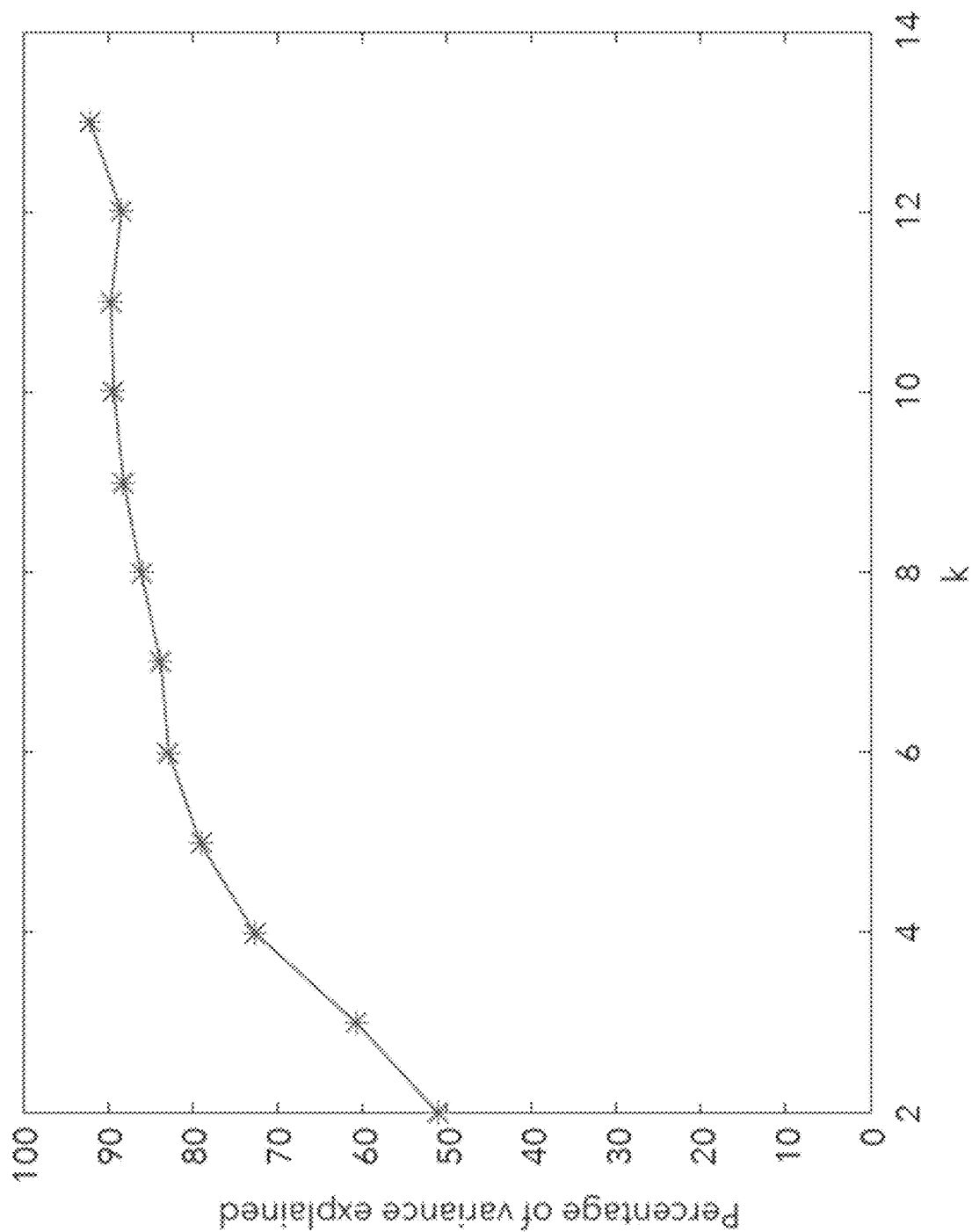
FIG. 51—Determining an optimal number of clusters for all CD8⁺ T-cells. Variance explained by each k-means solution ranging from k=2, . . . , 13, when applied to all analyzed CD8 T-cells. Percentage of variance explained is computes as described in the Methods section.
Figures 52A, 52B:
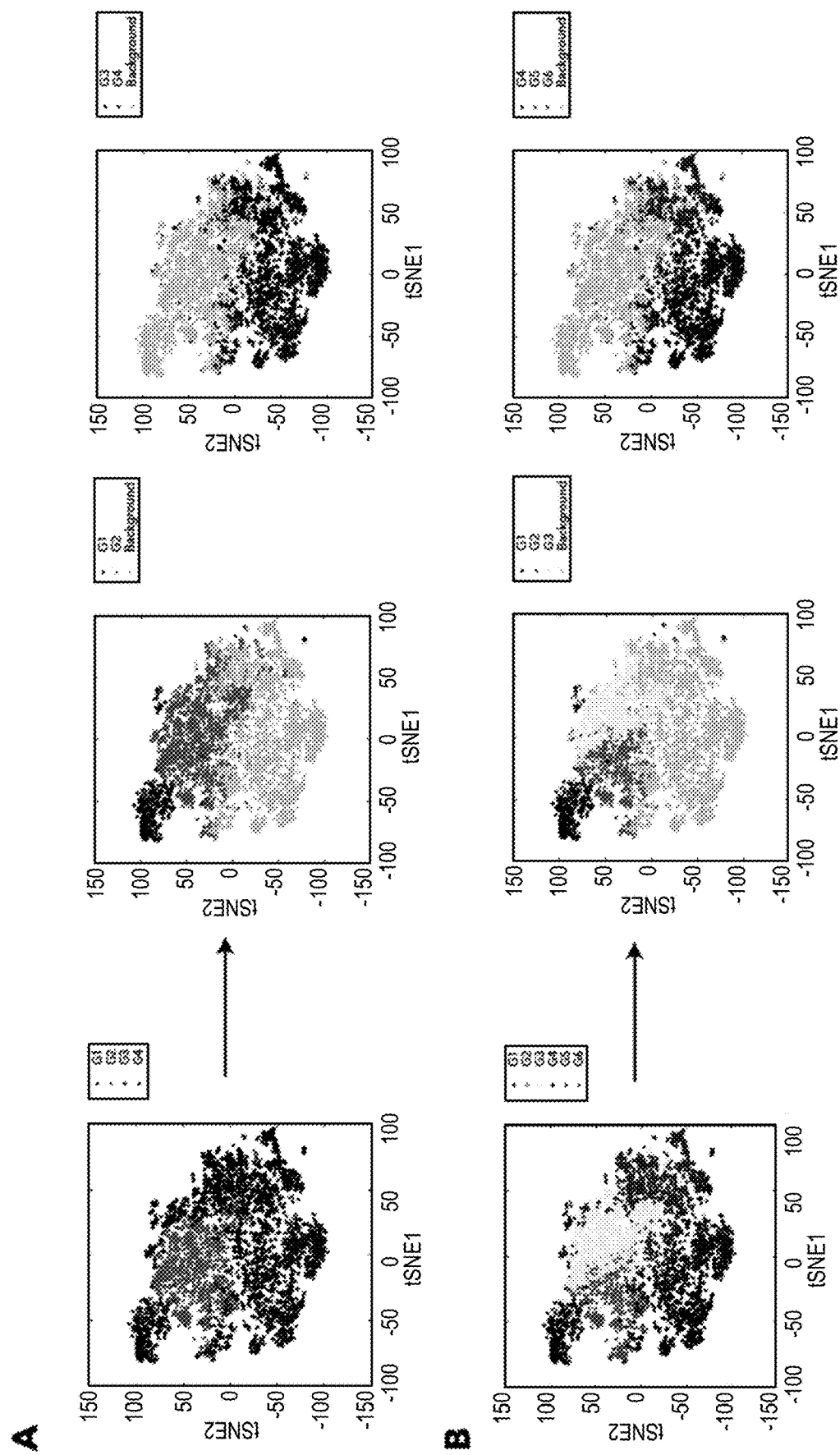
FIG. 52A. Hierarchical structure is shown where CD8_B is split into 2 or 3 clusters, which correspond to the k=4 and k=6 solutions, respectively.
FIG. 52B. Hierarchical structure is shown where CD8_G is split into 2 and 3 clusters, corresponding to the k=4 and k=6 solutions, respectively.

Unsupervised clustering of CD8 T-cells. To identify different CD8 T-cell clusters Applicants first extracted all single-cells classified as CD8 in the supervised analysis. Applicants performed a similar clustering analysis as described above (FIG. 51). Applicants identified k=6 as the optimal number of clusters since: (1) no significant increase in V was observed for K>=7; (2) All splits up to k=6 followed a hierarchical pattern in which whenever Applicants increased k a single cluster split into two sub-clusters (FIG. 52). This pattern was not seen for K>=7. Performing a robustness analysis as defined above, Applicants found that this solution yields a robustness value of 0.9. Computation of significant difference between responders and non-responders for a given cluster was done as explained above.

Differential expression analysis. In all cases, differential expression analysis was applied to all genes that had an average expression level $\log_2$(TPM+1)>2 in either tested groups, $G_1$ and $G_2$. Then, for each gene i, Applicants count the number of cells in $G_1$ and $G_2$ that express it with an expression level $\log_2$(TPM+1)>2 or 2. Applicants then apply Fisher's Exact test for the corresponding 2×2 table. To identify significant differences Applicants considered genes with a Bonferroni-corrected q-value 0.05 and log 2(fold-change)>0.5.

Trajectory analysis of CD8 T-cells. To analyze the trajectory of CD8 T-cells based on single-cell RNA-seq expression data, Applicants used Monocle v. 2.5.4[55]. As input to Monocle's Reversed Graph Embedding algorithm, Applicants selected a set of 426 genes that was the union of the top 100 differentially expressed genes ordered by ascending q-value (as described above) for each of the six CD8 T-cell clusters (or all such genes for two clusters that had fewer than 100 significant genes).

T-cell Receptor (TCR) reconstruction. Applicants applied the MixCr tool for reconstructing TCRs from all identified T-cells[44]. Applicants defined persistent TCRs as TCRs having an identical CDR3 sequence in both chains and were detected in baseline (pre-therapy) and post-therapy samples from the same patient. Enriched TCRs were defined as TCRs having an identical CDR3 sequence in both chains and detected in the same patient at a single time point, or in two parallel time points (e.g., multiple biopsies collected at the same time point). Lastly, common TCRs were defined as those having an identical CDR3 sequence in both chains and detected in different patients.

Mice and tumor transplant. Female C57BL/6 mice, age of 8-9 weeks were purchased from Jackson Laboratory and were housed at Massachusetts General Hospital under SPF conditions. All experiments followed protocols approved by the Massachusetts General Hospital Institutional Animal Care and use Committee (IACUC). B16-F10 was generously provided by Mikael Pittet. B16-F10 cells (0.5×10$^6$) were intradermally injected into the right flank using a 30 g needle and tumors were measured every 4 days in two dimensions using a digital caliper. Tumor volume (mm³) was calculated using the following formula V=(L*W²)/2 (V=volume, L=tumor length, tumor width). All treatments started on day 4 post transplantation after 100% of tumors were visible. In vivo plus rat IgG2a isotype control (BioXCell; 2A3; BE0089) 100 µg/dose (for TIM3 experiments) and 200 µg/dose (for PD1 experiments), was intraperitoneally (i.p.) injected to the control (untreated) group every 3 days. In vivo plus anti-mouse TIM3 (BioXCell; RMT3-23; BE0115) 100 µg/dose was i.p. injected every 3 days. In vivo plus anti-mouse PD1 (BioXCell; 29f.1A12; BE0273) 200 µg/dose was i.p. injected every 3 days. POM-1 (polyoxometalate-1) 5 mg/kg/day (ChemCruz; sc-203205), a CD39 inhibitor, was i.p. injected on a daily basis.

ATAC-seq tagmentation. Methods for tagmentation are as previously reported[56]. Briefly, 5,000-10,000 cells were cell sorted into RPMI containing 10% FBS, 1% Pen/Strep, 1% L-Glutamine, and 1% HEPES. The cells were then centrifuged at 500×g at 4° C. for 10 minutes, the supernatant aspirated, and resuspended in tagmentation mixture (25 ul tagmentation buffer (Illumina, FC-121-1031), 2.5 ul TBE (Illumina, FC-121-1031), 0.5 ul 1% digitonin (Promega, G9441), and 22 ul H2O). The cells were then incubated at 37° C. in a thermomixer, mixing at 300 RPM for 30 min. Following tagmentation, the sample was immediately purified via minElute PCR cleanup column (QIAGEN, 28006), and eluted in 10 ul. The tagmented DNA was then PCR'ed using Nextera indexing primers with sequencing adapters for 5 cycles in a 50 ul reaction. 5 ul of the reaction was then used for qPCR to determine the remaining number of PCR cycles required (as determined by the cycle number of each sample when it reaches ⅓ the fluorescence threshold), followed by PCR of each individual sample according to this cycle number. The samples were purified using 1.5× Agencourt AMPure XP beads (A63880), followed by two 70% EtOH washes, and elution of DNA in 15 ul buffer EB (QIAGEN, 19086). Each sample was quantified by Qubit, and measured for fragment lengths on a Tape Station. The samples were pooled and sequenced on an Illumina Nextseq 500 using 75 bp PE reads to a sequencing depth of 30 million reads per sample.

ATAC-seq analysis. Sequencing reads for each sample were aligned to hg19 using Bowtie 2.2.1 [57] with a max insert size of 2000 bp. SAM files were converted to BAM files and sorted using Samtools 1.3[58]. Duplicate (as defined by _broadinstitute.github.io/picard) and mitochondrial reads were removed, and peaks were called, initially by making tag directories according to chromosome and then by finding peaks (areas with more sequencing reads than expected by chance) for each sample, using the "DNase" peak finding style ('makeTagDirectory—format sam' and 'findPeaks—style dnase', Homer version 4.9) 59 Overlapping peaks were then merged. The number of Tn5 transposition events (5' ends of reads) lying within each peak were quantified for each sample, yielding a matrix of peaks by samples containing ATAC read counts. EdgeR 3.14.0 was used to call CD39⁺TIM3⁺ (DP)/CD39⁻TIM3⁻ (DN)-specific peaks, first by grouping the samples by cell type (DP and DN) and pairing the samples from each patient, and then using EdgeR[60] to estimate the tagwise dispersion using generalized linear models (estimateGLMTagwiseDisp function). Applicants then performed a likelihood ratio test to identify differential accessibility between paired samples from each patient (glmFit, glmLRT). Applicants obtained the top differential peaks (topTags), sorting peaks by their FDR q-value. Differential peaks between DP and DN were called significant if their FDR q-value was 0.01.

Motif Analysis. To identify TF motifs that distinguish DP- and DN-specific peaks from non-specific (background) peaks, each peak was scanned with the human motifs from the CIS-BP database[61], using the GOMER approach[62], yielding a binding score for each peak for each TF motif. The minimum hypergeometric (minHG) test was then used to gauge how well motif scores enrich DP- or DN-specific peaks (FDR q<0.01) compared to background peaks, considering the top N (1 up to 3000) highest scoring peaks. Here, background peaks included those whose ATAC DP-vs-DN FDR was over 0.1 (i.e. not significantly DP- or DN-specific) and had an average counts per million (CPM) greater than the minimum CPM of DP/DN-specific peaks (i.e. enough reads that a difference could have been detected). MinHG P-values were corrected by Benjamini-Hochberg FDR, counting each minHG test as independent (resulting in more conservative FDR q-values).

Whole exome sequencing (WES). WES of DNA from tumor and matched normal blood samples was done as previously described[15]. Briefly, 250-500 ng of extracted DNA, using Qiagen AllPrep DNA/RNA Mini Kit (cat #80204), was used as input for library preparation. Sample were barcoded using unique 8 base molecular barcodes followed by a library enrichment process, and all libraries above 40 ng/µl were considered acceptable for solution-phase hybrid selection and sequencing. Libraries preparation was carried out using the SureSelect Target Enrichment System Sequencing Platform Library Prep v2 (Agilent Technologies, G3360-90000), according to manufacturer's specifications, followed by quantification and normalization using PicoGreen to ensure equal concentration. Libraries were then quantified using qPCR (KAPA Biosystems, KK4832), denatured with 0.2M NaOH and diluted to 20 pM using hybridization buffer (Illumina). Cluster amplification was performed according to the manufacturer's protocol (Illumina), HiSeq 2500 v4 cluster chemistry and flowcells, as well as Illumina's Multiplexing Sequencing Primer Kit. Libraries were sequenced using the HiSeq 2500 v4 Sequencing-by-Synthesis method (paired end 76 bp reads) followed by analysis with RTA v.1.12.4.2. The minimum depth of coverage was 150× and 80× for tumor and normal samples respectively. All procedures were done at the Genomics Platform of the Broad Institute of Harvard and MIT.

Survival analysis based on IFC data. Applicants used the TCF7⁺CD8⁺TCF7⁻ CD8⁺ ratio to split samples into two groups (ratio >1 and <1). A standard Kaplan-Meier survival analysis was then used to determine the association of these groups with survival rate. In case two or more samples for the same patient exist, Applicants selected the baseline sample for this analysis.

Mutation calling pipeline. WES BAM files were aligned to the NCBI Human Reference Genome Build GRCh37 (hg19) and were checked for contamination by DNA originating from a different individual using ContEst[63]. Somatic single nucleotide variations (sSNVs) were then detected using MuTect[64]. Following this standard procedure, Applicants filtered sSNVs by: (1) removing potential DNA oxidation artifacts[65]; (2) realigning identified sSNVs with NovoAlign (novocraft.com) and performing an additional iteration of MuTect with the newly aligned BAM files; (3) removing technology- and site-specific artifacts using a panel of ~7000 TCGA normal samples (PoN filtering). Finally, sSNVs were annotated using Oncotator[66].

Tables

TABLE 1

| # | Patinet ID | Gender (F/M) | Age | Therapy | Clinical response (RECIST; R = CR, PR; NR = SD, PD) | Baseline Biopsy (days from basline; site; lesion response) | Post I biopsy (days from baseline; site; lesion response) |
|---|---|---|---|---|---|---|---|
| 1 | P1 | M | 49 | CTLA4 (baseline); PD1 (post I and II) | Resistance | 0; right chest; regression | 48; anterior neck; regression |
| 2 | P2 | M | 75 | PD1 | NR | 0; small bowel; progression | 35; left axilla; progression |
| 3 | P3 | F | 83 | PD1 | NR | 0; right anterior lower leg; progression | 63; right distal anterior thigh; progression |
| 4 | P4 | M | 29 | CTLA4 + PD1 | R | (−2); left shoulder; progression prior to therpay | 35; left shoulder; regression |
| 5 | P5 | M | 33 | PD1 | NR (patient had mix response) | NA | 199; Post_P#5-right iliac soft tissue mass; progression. Post_P#5_2-right buttock; regression |
| 6 | P6 | F | 66 | CTLA4 (baseline); PD1 (post I) | NR | (−70); left upper back; progression | 270; right colectomy mass in cecum; progression |
| 7 | P7 | M | 74 | CTLA4 + PD1 | R | 0; left forehead; regression | 22; left forehead; regression |
| 8 | P8 | M | 49 | CTLA4 + PD1 | R | (−12); left axillary lymph node; regression | 62; left axillary lymph node; regression |
| 9 | P10 | F | 60 | PD1 | NR | NA | 760; small bowel mass; progression |
| 10 | P11 | F | 68 | PD1 | NR | NA | 118; right inguinal lymph node; progression |
| 11 | P12 | M | 68 | PD1 | NR | (−16); small bawel resection; progression | 77; left anterior shoulder; progression |
| 12 | P13 | M | 48 | CTLA4 + PD1 | NR (patient had mix response) | NA | 297; porta hepatis; progression |
| 13 | P14 | M | 70 | PD1 | NR | NA | 462; left axilla lesion; progression |
| 14 | P15 | M | 72 | PD1 | NR | 0; right back subcutaneous; progression | 73; left lower back; progression |
| 15 | P16 | M | 62 | PD1 | NR | NA | 67; right abdomen soft tissue; progression |

TABLE 1-continued

| # | | | | | | | |
|---|---|---|---|---|---|---|---|
| 16 | P17 | F | 68 | PD1 | R | NA | 61; right axillary lymph node; regression |
| 17 | P18 | M | 79 | PD1 | NR (patient had mix response) | NA | 237; right inguinal lymph node; progression |
| 18 | P19 | M | 53 | PD1 | R | NA | 21; left axillary lymph node; regression |
| 19 | P20 | F | 64 | PD1 | NR (patient had mix response) | 0; right inguinoiliac lymphadenecctomy; progression | 199; right pelvic mass; progression |
| 20 | P21 | F | 75 | PD1 | R | NA | 867; jejunum; regression |
| 21 | P22 | M | 56 | PD1 | NR | NA | 31; right supraclavicular mass; progression |
| 22 | P23 | M | 62 | PD1 | NR | NA | 403; left frontal craniotomy; progression |
| 23 | P24 | M | 73 | PD1 | R | 0; left lower back; regression | NA |
| 24 | P25 | M | 74 | PD1 | NR | 0; adrenal gland; progression | NA |
| 25 | P26 | M | 72 | CTLA4 + PD1 | R | (−56); axillary lymph node, regression | NA |
| 26 | P27 | F | 62 | PD1 | NR | (−35); upper abdomen; progression | NA |
| 27 | P28 | F | 67 | CTLA4 + PD1 | Resistance | 0; right groin; regression | 41; right groin; progression |
| 28 | P29 | M | 79 | PD1 | R | (−67); left axillary lymph node; regression | NA |
| 29 | P30 | M | 64 | PD1 | NR | NA | 573; left laparoscopic adrenalectomy; progression |
| 30 | P31 | M | 52 | PD1 | NR | (−7); right axilla; progression | NA |
| 31 | P33 | F | 65 | PD1 | R | (−66); left axillary lymph node; regression | NA |
| 32 | P35 | M | 70 | PD1 | R | (−31); right iliac lymph node; regression | NA |

| # | Post II biopsy (days from baseline; site; lesion response) | WES | Overall survival (days) | Status (Alive = 0; Dead = 1) | Mutations/ indels in known melanoma drivers | Mutations/ indels in antigen presentation and/ or interferon-gamma pathways |
|---|---|---|---|---|---|---|
| 1 | 437; anterior neck; progression | Y | 822 | 0 | ND | ND |

TABLE 1-continued

|  |  |  |  |  |  |
|---|---|---|---|---|---|
| 2 | NA | Y | 347 | 1 | ND | ND |
| 3 | 161; right anterior knee; progression | Y | 521 | 1 | NRAS, TPTE | ERAP1, HLA-CRFX5, B2M, IRF6 |
| 4 | NA | Y | 539 | 0 | TPTE | ND |
| 5 | NA | Y | 369 | 1 | TP53 | ND |
| 6 | NA | Y | 777 | 0 | NRAS, TPTE | ND |
| 7 | NA | Y | 339 | 0 | TPTE | IFNGR1, TPP2, ADAR |
| 8 | NA | N | 388 | 0 | NA | NA |
| 9 | NA | Y | 1197 | 0 | TP53 | IFNGR1, PSMB9, TBX21 |
| 10 | NA | Y | 300 | 1 | NRAS, TP53 | ND |
| 11 | NA | Y | 101 | 1 | NRAS | TPP2 |
| 12 | NA | Y | 507 | 0 | MAP2K1, TP53, TPTE | ND |
| 13 | NA | Y | 588 | 1 | CTNNB1, NRAS, TPTE | PSMB9 |
| 14 | NA | Y | 163 | 1 | TPTE | JAK1, STAT1, CD45-cells lack HLA-I expression |
| 15 | NA | N | 476 | 1 | NA | NA |
| 16 | NA | N | 361 | 0 | NA | NA |
| 17 | NA | Y | 746 | 0 | ND | ND |
| 18 | NA | N | 570 | 0 | NA | NA |
| 19 | NA | Y | 413 | 0 | ND | ND |
| 20 | NA | Y | 1340 | 0 | ND | ND |
| 21 | NA | N | 64 | 1 | NA | NA |
| 22 | 622; left neck mass; progression | Y | 674 | 0 | TP53 | IL3RA, IRF6 |
| 23 | NA | N | 54 | 0 | NA | NA |
| 24 | NA | Y | 676 | 0 | ND | CD45− cells lack HLA-I expression |
| 25 | NA | N | 517 | 0 | NA | NA |
| 26 | NA | N | 73 | 0 | NA | NA |
| 27 | 89; right groin; progression | Y | 61 | 0 | ND | ND |
| 28 | NA | N | 417 | 0 | NA | NA |
| 29 | NA | N | 580 | 0 | NA | NA |
| 30 | NA | N | 126 | 0 | NA | NA |
| 31 | NA | N | 130 | 0 | NA | NA |
| 32 | NA | Y | 511 | 0 | ND | ND |

F—female;
M—male;
NR—nonresponder;
R—responder;
NA—not available;
ND—not detected;
DOD—dead of disease;
AWD—alive with disease

TABLE 2A

| | G1- B cells | | | | G2- Plasma cells | | | |
|---|---|---|---|---|---|---|---|---|
| Gene Name | P-value | Mean expression G1 | Mean expression non-G1 | | GeneName | P-value | Mean expression G2 | Mean expression non-G2 | |
| IGHD | <1e-300 | 5.377108613 | 0.024126888 | adjusted P-value = 2.4e-5 | SDC1 | <1e-300 | 4.233860833 | 0.008624746 | adjusted P-value = 2.4e-5 |
| PAX5 | <1e-300 | 4.830784038 | 0.023214384 | | IGLV6-57 | 9.81E-130 | 2.402558175 | 0.026153709 | |
| FCRL1 | <1e-300 | 5.758715472 | 0.033840633 | | IGHV3OR16-9 | 3.35E-147 | 2.229910869 | 0.02923494 | |
| CR2 | <1e-300 | 3.177964545 | 0.026060567 | | TNFRSF17 | 4.73E-257 | 3.814521814 | 0.060427652 | |
| VPREB3 | <1e-300 | 3.779631599 | 0.031216078 | | IGLV3-1 | 6.62E-229 | 4.11629317 | 0.067925619 | |
| FCER2 | <1e-300 | 5.175642662 | 0.04801409 | | HID1 | 1.13E-207 | 2.530148775 | 0.041918971 | |
| CD19 | <1e-300 | 6.879495185 | 0.067404363 | | IGHG4 | 3.21E-239 | 7.435463173 | 0.14692745 | |
| EBF1 | <1e-300 | 2.578367556 | 0.025833821 | | IGHV3-48 | 1.50E-135 | 2.640490419 | 0.060235217 | |
| CD22 | <1e-300 | 6.81743677 | 0.068541106 | | IGHA2 | 2.18E-131 | 4.015662376 | 0.093785671 | |
| BANK1 | <1e-300 | 6.739130158 | 0.070328664 | | IGHV3-7 | 5.17E-127 | 3.148975371 | 0.07603257 | |
| CLEC17A | <1e-300 | 3.053371072 | 0.038423373 | | IGKV3OR2-268 | 5.87E-151 | 2.660244692 | 0.069676661 | |
| FCRLA | <1e-300 | 3.62133246 | 0.056407837 | | IGHV3-11 | 6.43E-108 | 2.138997825 | 0.057035625 | |
| FCRL2 | <1e-300 | 2.350303618 | 0.036669806 | | IGHG2 | 1.87E-225 | 8.704980223 | 0.253948458 | |
| MS4A1 | <1e-300 | 9.428714865 | 0.153577919 | | IGHA1 | 2.97E-249 | 7.081368071 | 0.212315823 | |
| BLK | <1e-300 | 3.434999629 | 0.090733356 | | IGHG3 | 6.04E-223 | 8.936777049 | 0.280586437 | |
| RALGPS2 | <1e-300 | 3.757215267 | 0.104227862 | | DERL3 | <1e-300 | 7.472148401 | 0.24163785 | |
| TCL1A | <1e-300 | 4.653788476 | 0.147762744 | | IGLC1 | <1e-300 | 7.390641029 | 0.242357044 | |
| TLR10 | <1e-300 | 2.033374459 | 0.07030556 | | IGKV4-1 | 2.60E-105 | 2.766940507 | 0.091570966 | |
| FAM129C | <1e-300 | 3.325876484 | 0.130620555 | | IGKV3D-15 | 4.23E-97 | 2.64422194 | 0.08987916 | |
| CNR2 | <1e-300 | 2.230733439 | 0.087696655 | | IGLC7 | 8.72E-116 | 2.714916412 | 0.092714532 | |
| ARHGAP24 | <1e-300 | 3.986638322 | 0.163948666 | | IGLL5 | 3.08E-262 | 5.798552799 | 0.205363121 | |
| KIAA0125 | 9.02E-271 | 2.10332511 | 0.086673688 | | IGHV3-21 | 2.09E-117 | 2.703922207 | 0.096513211 | |
| HLA-DOB | <1e-300 | 3.811154047 | 0.165247649 | | IGKV3-11 | 1.40E-80 | 2.771174104 | 0.10253285 | |
| IGHM | <1e-300 | 9.327205093 | 0.407454987 | | IGHV1-69 | 1.36E-88 | 2.232666627 | 0.08526387 | |
| KIAA0226L | <1e-300 | 4.829878293 | 0.211327169 | | IGJ | 6.117000000000e-321 | 11.1054625 | 0.471095338 | |
| CD79A | <1e-300 | 8.339533791 | 0.370179647 | | IGHG1 | 2.80E-181 | 11.94464557 | 0.506833765 | |
| BCL11A | <1e-300 | 7.410500824 | 0.383614866 | | IGHV3-23 | 8.56E-108 | 3.576414272 | 0.159436939 | |
| STAP1 | <1e-300 | 3.624637562 | 0.198703365 | | TXNDC5 | 1.929097979953000e-312 | 5.759891381 | 0.260517213 | |
| IGLC3 | 8.54E-270 | 3.373050502 | 0.189793118 | | PYCR1 | 8.08E-123 | 2.068461438 | 0.098437479 | |
| PKIG | 5.82E-295 | 2.768394643 | 0.15679259 | | FCRL5 | 4.593063058974000e-312 | 5.03661425 | 0.24157025 | |
| FCRL5 | 1.17E-285 | 2.323712941 | 0.135946821 | | SPAG4 | 3.46E-165 | 3.615011752 | 0.202717913 | |
| AFF3 | 2.61E-171 | 3.170363803 | 0.200729943 | | IGKV1D-39 | 1.94E-62 | 2.299093053 | 0.134066083 | |
| COBLL1 | 4.92E-254 | 2.147172935 | 0.137193521 | | IGKV3-20 | 2.66E-79 | 2.804450155 | 0.165306404 | |
| SPIB | <1e-300 | 3.830769152 | 0.253087514 | | IGLC2 | 1.01E-104 | 5.11244812 | 0.334682063 | |
| SWAP70 | <1e-300 | 4.012414059 | 0.285717767 | | TRAM2 | 1.38E-156 | 2.156503484 | 0.150284157 | |
| IGLL5 | 9.41E-205 | 2.001834923 | 0.144164441 | | CPNE5 | 1.27E-199 | 2.916728494 | 0.203621287 | |
| ADAM28 | <1e-300 | 5.951416093 | 0.442839331 | | MZB1 | 1.21E-302 | 9.579460842 | 0.710624973 | |
| BLNK | <1e-300 | 4.28327775 | 0.340112469 | | PNOC | 8.98E-103 | 2.04343337 | 0.156697013 | |
| IGLC2 | <1e-300 | 2.621852591 | 0.208595889 | | GAB1 | 2.78E-127 | 2.382125352 | 0.187613703 | |
| IGKC | <1e-300 | 8.193025668 | 0.770440206 | | IGHV3-30 | 1.77E-62 | 2.187170865 | 0.179419799 | |
| IGHG3 | <1e-300 | 2.503660902 | 0.240519357 | | IGLC3 | 3.42E-89 | 4.720577362 | 0.393080388 | |
| WDFY4 | <1e-300 | 4.143602665 | 0.405023263 | | P2RX1 | 1.03E-145 | 2.736623227 | 0.229694535 | |
| MEF2C | <1e-300 | 4.682828475 | 0.463960473 | | COBLL1 | 6.99E-133 | 3.015099792 | 0.265413578 | |
| IGHG2 | <1e-300 | 2.282314694 | 0.228759176 | | IGKC | 1.10E-152 | 13.29958429 | 1.207440763 | |

TABLE 2A-continued

| Gene Name | G1- B cells | | | G2- Plasma cells | | |
|---|---|---|---|---|---|---|
| | P-value | Mean expression G1 | Mean expression non-G1 | GeneName | P-value | Mean expression G2 | Mean expression non-G2 |
| CCR6 | 2.39E−258 | 2.496953086 | 0.256016858 | HIST1H2BG | 1.52E−74 | 2.059760008 | 0.200125902 |
| IGLC1 | 5.30E−148 | 2.037641102 | 0.213244636 | SPATS2 | 9.27E−117 | 2.423859773 | 0.25377366 |
| SMIM14 | <1e−300 | 4.462150724 | 0.48399052 | CHPF | 6.71E−113 | 2.117267881 | 0.239375705 |
| POU2AF1 | <1e−300 | 3.39360039 | 0.390712295 | POU2AF1 | 1.59E−250 | 4.887791344 | 0.578225937 |
| CD79B | <1e−300 | 7.438894085 | 0.858467685 | PRDX4 | 3.92E−231 | 7.42691519 | 0.887516118 |
| CD40 | <1e−300 | 4.111891401 | 0.475205856 | SLC17A9 | 2.59E−160 | 3.878504064 | 0.492421351 |
| HVCN1 | <1e−300 | 4.327940992 | 0.509002105 | FKBP11 | 7.61E−229 | 8.19043275 | 1.201521743 |
| TCF4 | <1e−300 | 4.192103272 | 0.511131499 | MANEA | 2.20E−108 | 2.450440304 | 0.360454056 |
| BTK | 5.19E−251 | 3.326309241 | 0.412136272 | EAF2 | 3.97E−118 | 3.545709894 | 0.537546263 |
| RASGRP3 | 1.78E−215 | 2.512060772 | 0.312310541 | TRIB1 | 1.88E−86 | 2.598882797 | 0.410545151 |
| CXCR5 | <1e−300 | 4.061637292 | 0.528282688 | CLIC4 | 7.16E−112 | 2.511312479 | 0.39781662 |
| IGHG1 | <1e−300 | 3.399534255 | 0.458279801 | CD79A | 1.94E−231 | 6.021162152 | 0.987711276 |
| PDLIM1 | 3.20E−181 | 2.47109014 | 0.338514788 | GSTM2 | 4.02E−72 | 2.421741855 | 0.42956167 |
| PHACTR1 | 3.69E−186 | 2.395853064 | 0.354865342 | PDK1 | 4.75E−153 | 4.074910642 | 0.728483504 |
| NCF1 | <1e−300 | 5.740093848 | 0.872822397 | XBP1 | 3.60E−191 | 7.401773339 | 1.32811729 |
| FGD2 | <1e−300 | 5.508336292 | 0.849101304 | CRELD2 | 1.16E−140 | 4.52391813 | 0.819588579 |
| SIGLEC14 | 1.44E−214 | 2.335732816 | 0.369987142 | ANKRD28 | 3.29E−135 | 4.417906249 | 0.814181537 |
| HLA-DOA | 2.66E−288 | 3.892220522 | 0.621438779 | BLNK | 4.26E−128 | 3.446210992 | 0.639746238 |
| MICAL3 | 1.17E−232 | 2.527611832 | 0.408644416 | HIST1H2BC | 1.11E−51 | 2.177080138 | 0.405949212 |
| RABEP2 | 7.54E−268 | 2.981950951 | 0.485507243 | SELM | 2.26E−125 | 3.959116683 | 0.74975693 |
| LY86 | 1.38E−164 | 2.745566733 | 0.451303045 | MCEE | 5.97E−74 | 2.496366648 | 0.504433145 |
| IRF8 | <1e−300 | 8.225357104 | 1.352488687 | MANF | 6.46E−96 | 3.227529568 | 0.65488149 |
| EAF2 | 3.46E−136 | 2.451137436 | 0.411718193 | ITM2C | 1.38E−183 | 6.31322858 | 1.322986931 |
| CD72 | 7.59E−238 | 4.06312041 | 0.689670182 | RRBP1 | 3.02E−126 | 3.532988187 | 0.74580555 |
| SYK | 2.89E−234 | 3.31828298 | 0.587095072 | RAB30 | 7.00E−146 | 5.621466413 | 1.205874153 |
| MGAT5 | 8.23E−167 | 2.04701606 | 0.371143655 | MEI1 | 1.10E−120 | 4.937509634 | 1.062273968 |
| CD83 | <1e−300 | 7.068368438 | 1.282591945 | CASP10 | 1.65E−93 | 2.770726658 | 0.596765049 |
| PLCG2 | 1.68E−241 | 3.407886851 | 0.661639428 | CLPTM1L | 2.55E−91 | 2.880334185 | 0.621907925 |
| ALOX5 | 7.96E−240 | 3.135377986 | 0.613499663 | GMPPB | 3.08E−80 | 2.899835697 | 0.635163646 |
| DOK3 | 7.02E−109 | 2.028396862 | 0.398397555 | FKBP2 | 2.68E−176 | 6.80017278 | 1.507612655 |
| CIITA | <1e−300 | 6.04980438 | 1.209362996 | SLC38A5 | 2.20E−65 | 2.490288197 | 0.55858077 |
| CDCA7L | 1.11E−120 | 2.367895382 | 0.499983981 | PPAPDC1B | 1.74E−145 | 5.6849268 | 1.278357421 |
| PIK3C2B | 2.30E−170 | 2.52773813 | 0.560696916 | SDF2L1 | 6.09E−154 | 5.674643955 | 1.278720552 |
| LAT2 | 3.01E−206 | 4.194127729 | 0.937336471 | ST6GALNAC4 | 4.64E−111 | 3.6721054 | 0.830250346 |
| TPD52 | 1.87E−186 | 3.503124066 | 0.821008158 | TXNDC11 | 7.00E−110 | 3.955778344 | 0.901054997 |
| P2RX5 | 3.54E−134 | 2.740295041 | 0.657282119 | FNDC3B | 7.02E−109 | 3.100795596 | 0.707343753 |
| AKAP2 | 5.13E−239 | 3.473462021 | 0.838093411 | C11orf24 | 5.47E−87 | 2.848858532 | 0.656030539 |
| CYBB | 1.25E−268 | 3.04247863 | 0.73699243 | SIL1 | 3.34E−106 | 3.652935199 | 0.845427704 |
| SNX29 | 2.02E−175 | 3.507232908 | 0.859516634 | BSCL2 | 4.43E−73 | 3.196693824 | 0.745021812 |
| RAB30 | 3.89E−210 | 4.033664535 | 1.019322564 | TPD52 | 1.73E−130 | 4.24205515 | 0.999855857 |
| STX7 | 1.64E−193 | 3.525618377 | 0.897980358 | FBXO18 | 6.84E−47 | 2.068627834 | 0.499330665 |
| POU2F2 | 8.69E−172 | 2.919670122 | 0.745181045 | SEC24D | 4.01E−59 | 2.015829651 | 0.510166371 |
| FCGR2B | 3.63E−89 | 2.113935514 | 0.542486852 | MAGED1 | 1.05E−84 | 3.041532373 | 0.786868185 |
| HLA-DMB | 3.98E−286 | 5.966490531 | 1.546487113 | PLCG2 | 1.90E−101 | 3.311049605 | 0.861046403 |
| LY9 | <1e−300 | 6.585792811 | 1.755403625 | HSPA13 | 1.67E−79 | 2.574156037 | 0.67114269 |
| GPR18 | 7.19E−94 | 2.33193865 | 0.626069943 | HIST1H2BD | 9.55E−47 | 2.284581551 | 0.603170583 |
| HLA-DQB2 | <1e−300 | 4.274391103 | 1.199160804 | SYVN1 | 5.03E−138 | 5.21016555 | 1.378349192 |

TABLE 2A-continued

| | G1- B cells | | | | G2- Plasma cells | | |
|---|---|---|---|---|---|---|---|
| Gene Name | P-value | Mean expression G1 | Mean expression non-G1 | GeneName | P-value | Mean expression G2 | Mean expression non-G2 |
| ORAI2 | 8.21E-115 | 2.567092806 | 0.729277493 | SEC11C | 3.25E-149 | 8.092917461 | 2.170757456 |
| CHD7 | 1.20E-143 | 2.520432437 | 0.725486005 | CPEB4 | 4.40E-72 | 2.335940654 | 0.629106798 |
| CYB561A3 | 3.67E-149 | 4.388984401 | 1.270691671 | SEC24A | 1.82E-74 | 2.192828201 | 0.594959324 |
| IFT57 | 4.23E-78 | 2.235931078 | 0.651735412 | UBE2J1 | 2.81E-110 | 3.939811569 | 1.084448086 |
| HLA-DQA2 | <1e-300 | 4.527010185 | 1.334782947 | EIF2AK4 | 9.96E-63 | 2.203870035 | 0.610994331 |
| CTSH | 1.00E-148 | 4.144742288 | 1.224775771 | TMEM214 | 4.99E-69 | 2.395960083 | 0.670597627 |
| FCHSD2 | 3.28E-110 | 2.587265755 | 0.770414808 | TCF4 | 4.60E-70 | 2.850904964 | 0.80152203 |
| PIK3AP1 | 1.49E-96 | 2.608459362 | 0.778564919 | SEL1L | 4.43E-117 | 4.084917784 | 1.153660969 |
| PLEKHF2 | 3.19E-75 | 2.138249498 | 0.639260572 | WIPI1 | 1.29E-46 | 2.286958047 | 0.662780865 |

TABLE 2B

| | G3- Monocytes/Macrophages | | | | | G4- Dendritic cells | | | |
|---|---|---|---|---|---|---|---|---|---|
| Gene Name | P-value | Mean expression G3 | Mean expression non-G3 | | Gene Name | P-value | Mean expression G4 | Mean expression non-G4 | |
| MARCO | <1e-300 | 4.494608221 | 0.006001435 | adjusted P-value = 1.4e-5 | PTCRA | 5.81E-271 | 4.317581126 | 0.006904934 | adjusted P-value = 1.6e-5 |
| FPR3 | <1e-300 | 3.511914039 | 0.006271509 | | CLEC4C | <1e-300 | 5.311198887 | 0.009184315 | |
| CLEC5A | <1e-300 | 3.27509833 | 0.007399723 | | KRT5 | 6.93E-200 | 3.049996364 | 0.006357704 | |
| AQP9 | <1e-300 | 2.84885691 | 0.006991484 | | LAMP5 | 4.991724600000e-316 | 4.340020264 | 0.017556374 | |
| CLEC10A | <1e-300 | 2.633205508 | 0.007192837 | | PLEKHD1 | 2.31E-139 | 2.023539158 | 0.009645317 | |
| HNMT | <1e-300 | 3.678171429 | 0.010075893 | | EPHB1 | 7.32E-291 | 4.366254154 | 0.022027954 | |
| OLR1 | <1e-300 | 4.375271771 | 0.012256769 | | PLVAP | 4.48E-162 | 2.53171133 | 0.013197905 | |
| CD300E | <1e-300 | 3.573524067 | 0.010515607 | | LILRA4 | <1e-300 | 9.922277008 | 0.071632434 | |
| ARHGEF10L | <1e-300 | 2.487677425 | 0.007498458 | | SLC12A3 | 4.03E-213 | 3.286912261 | 0.02510332 | |
| HK3 | <1e-300 | 4.684706729 | 0.014382697 | | SCAMP5 | 6.06E-249 | 3.424387356 | 0.028139895 | |
| ANPEP | <1e-300 | 4.488331773 | 0.013850118 | | SCN9A | 3.88E-167 | 2.061117264 | 0.018780406 | |
| LGALS2 | <1e-300 | 2.728279883 | 0.009296675 | | SMIM5 | 9.00E-168 | 3.10144295 | 0.031183255 | |
| FCN1 | <1e-300 | 5.978258881 | 0.021182951 | | DNASE1L3 | 7.43E-302 | 5.728799087 | 0.058258115 | |
| GPR84 | <1e-300 | 2.923544451 | 0.010617089 | | PPM1J | 1.37E-128 | 2.406583245 | 0.026936668 | |
| CCL2 | <1e-300 | 3.193396857 | 0.011675144 | | PTGDS | 1.70E-190 | 5.983425364 | 0.074921091 | |
| CLEC4E | <1e-300 | 2.681180318 | 0.010350464 | | MAP1A | 1.99E-277 | 3.572955854 | 0.045249564 | |
| CSTA | <1e-300 | 3.250092154 | 0.012863282 | | PTPRS | <1e-300 | 7.06104686 | 0.093646469 | |
| TREM1 | <1e-300 | 5.585114796 | 0.022911938 | | TPM2 | 3.80E-212 | 4.525342399 | 0.068376039 | |
| FCGR1B | <1e-300 | 3.376233092 | 0.014487789 | | PACSIN1 | 2.19E-231 | 3.348128574 | 0.056410238 | |
| TMEM176B | <1e-300 | 4.323443109 | 0.019148981 | | IL3RA | <1e-300 | 7.843037623 | 0.164531576 | |
| C19orf59 | <1e-300 | 2.136761361 | 0.009551562 | | TNFRSF21 | 2.69E-272 | 4.91471469 | 0.108152266 | |
| OSCAR | <1e-300 | 2.772173946 | 0.013255969 | | SERPINF1 | <1e-300 | 10.173773596 | 0.229645401 | |
| CYP2S1 | <1e-300 | 2.304491572 | 0.011100612 | | PLD4 | 2.19E-231 | 9.433614852 | 0.214274098 | |
| STAB1 | <1e-300 | 4.099488588 | 0.020052129 | | C1orf186 | <1e-300 | 5.001323806 | 0.1207404 | |
| VCAN | <1e-300 | 4.596165361 | 0.022515064 | | EGLN3 | 7.11E-284 | 6.296744488 | 0.156199475 | |
| FPR1 | <1e-300 | 5.164549195 | 0.026620686 | | SMPD3 | 4.28E-296 | 6.807852594 | 0.177311825 | |
| SERPINA1 | <1e-300 | 8.372708628 | 0.043244148 | | TLR9 | 7.19E-246 | 4.49016234 | 0.121049661 | |
| TLR2 | <1e-300 | 4.625461525 | 0.023946353 | | PFKFB2 | 3.90E-242 | 4.824971934 | 0.153731269 | |
| VSIG4 | <1e-300 | 4.446590487 | 0.023094787 | | AC023590.1 | 1.88E-129 | 3.039520505 | 0.096914264 | |
| TMEM176A | <1e-300 | 3.02647851 | 0.015882793 | | SUSD1 | 5.71E-152 | 4.004070308 | 0.131104383 | |
| VMO1 | <1e-300 | 2.035487396 | 0.010703715 | | NOTCH4 | 3.28E-155 | 3.472532172 | 0.119969313 | |
| MAFB | <1e-300 | 2.992861675 | 0.015811575 | | P2RY14 | 1.35E-203 | 4.40711416 | 0.1535015 | |
| FCGR1A | <1e-300 | 4.851999426 | 0.026156116 | | PALD1 | 5.89E-126 | 2.692397799 | 0.095958683 | |
| SLC37A2 | <1e-300 | 2.914308616 | 0.015812681 | | TSPAN13 | 6.59E-301 | 7.69605524 | 0.283339689 | |
| CD14 | <1e-300 | 8.00212632 | 0.043956193 | | TLR7 | 3.18E-164 | 3.380898545 | 0.126456752 | |
| TLR4 | <1e-300 | 2.37411393 | 0.013300338 | | IGJ | 7.085376000000e-316 | 11.54519518 | 0.473094778 | |
| CD300LF | <1e-300 | 2.517276173 | 0.014931206 | | P2RY6 | 4.04E-174 | 4.325475794 | 0.181862467 | |
| CXCL3 | <1e-300 | 3.029444375 | 0.018142863 | | MYBL2 | 4.90E-168 | 3.990858601 | 0.16860412 | |
| CD33 | <1e-300 | 3.79312088 | 0.02326843 | | GAS6 | 1.64E-173 | 4.161840858 | 0.184720295 | |
| GPNMB | <1e-300 | 4.159603964 | 0.026249315 | | CBFA2T3 | 5.41E-152 | 2.787338158 | 0.123981343 | |
| FOLR2 | <1e-300 | 2.013989441 | 0.012770956 | | DERL3 | 1.09E-238 | 6.112138088 | 0.273064677 | |
| LILRA3 | <1e-300 | 2.507417195 | 0.016065897 | | ZFAT | 9.03E-243 | 6.345444588 | 0.29792319 | |
| LPCAT2 | <1e-300 | 2.968649423 | 0.019073429 | | FAM213A | 2.86E-129 | 3.396934172 | 0.16353134 | |
| TREM2 | <1e-300 | 2.455259775 | 0.016066822 | | GAB1 | 1.49E-134 | 3.453497927 | 0.170253515 | |

TABLE 2B-continued

| | G3- Monocytes/Macrophages | | | | G4- Dendritic cells | | |
|---|---|---|---|---|---|---|---|
| Gene Name | P-value | Mean expression G3 | Mean expression non-G3 | Gene Name | P-value | Mean expression G4 | Mean expression non-G4 |
| PLXDC2 | <1e-300 | 5.436866399 | 0.035654355 | GAPT | 1.23E-145 | 4.339649259 | 0.215757525 |
| CD163 | <1e-300 | 5.530894972 | 0.037030431 | SPIB | 7.71E-297 | 8.501964216 | 0.428911059 |
| RIN2 | <1e-300 | 3.637341557 | 0.02440608 | NREP | 4.93E-123 | 3.3251 6002 | 0.168844447 |
| NFAM1 | <1e-300 | 2.874852744 | 0.020133036 | ST3GAL4 | 6.64E-112 | 3.159816053 | 0.169957579 |
| CD300C | <1e-300 | 3.214495459 | 0.023083907 | CD36 | 4.11E-138 | 4.373873327 | 0.255742007 |
| IL1B | <1e-300 | 5.296217701 | 0.038055675 | NRP1 | 7.44E-205 | 5.521942083 | 0.233117957 |
| MSR1 | <1e-300 | 3.736847475 | 0.026936993 | CHAF1A | 1.37E-167 | 4.070254234 | 0.238661802 |
| LILRA6 | <1e-300 | 5.175885668 | 0.038924775 | RASD1 | 1.27E-122 | 3.779505697 | 0.221965192 |
| ALDH3B1 | <1e-300 | 2.635070801 | 0.02038212 | PHEX | 1.39E-110 | 2.47988803 | 0.149720997 |
| CXCL2 | <1e-300 | 3.977853347 | 0.031323706 | PPP1R14B | 6.60E-152 | 4.313890559 | 0.266111523 |
| C5AR1 | <1e-300 | 4.205853003 | 0.034953849 | CSF2RB | 6.36E-222 | 5.975287171 | 0.373497351 |
| ADAP2 | <1e-300 | 3.171273605 | 0.027014433 | NEK8 | 4.00E-131 | 2.981624891 | 0.186443087 |
| IL8 | <1e-300 | 5.012010115 | 0.042849971 | APP | 1.83E-209 | 5.891583787 | 0.369494378 |
| C15orf48 | <1e-300 | 5.178113429 | 0.044304113 | SOX4 | 5.16E-180 | 5.550440052 | 0.362248494 |
| MRC1L1 | <1e-300 | 2.829781152 | 0.024428465 | FAM129C | 4.25E-203 | 5.046004504 | 0.332085215 |
| BST1 | <1e-300 | 2.404742609 | 0.020785466 | ENPP2 | 5.26E-94 | 2.94381292 | 0.194393078 |
| PLAU | <1e-300 | 3.040096205 | 0.026456826 | P2RX1 | 8.11E-111 | 3.248597113 | 0.222765687 |
| SIGLEC9 | <1e-300 | 3.860344807 | 0.03384819 | LILRB4 | 1.49E-266 | 7.778257907 | 0.533816599 |
| MS4A4A | <1e-300 | 3.817932751 | 0.033895953 | MPEG1 | 6.52E-247 | 7.877899988 | 0.555668797 |
| SIRPA | <1e-300 | 3.191856425 | 0.028409212 | AC010441.1 | 6.42E-120 | 4.136618047 | 0.301243358 |
| RNASE1 | <1e-300 | 2.746377201 | 0.024449745 | ADC | 6.29E-72 | 2.410586552 | 0.175729336 |
| CPVL | <1e-300 | 6.012778317 | 0.055310537 | SRC | 3.66E-110 | 3.265493869 | 0.240164554 |
| PLBD1 | <1e-300 | 3.959869683 | 0.036493191 | TMIGD2 | 1.29E-74 | 2.198715646 | 0.164006857 |
| LILRA2 | <1e-300 | 2.841630417 | 0.026715789 | TCL1A | 4.00E-130 | 6.010216357 | 0.451253519 |
| SLC11A1 | <1e-300 | 5.314962294 | 0.050314006 | TCF4 | 4.86E-264 | 8.931979674 | 0.693230615 |
| PYGL | <1e-300 | 2.468900405 | 0.023422496 | SLC15A4 | 1.81E-219 | 6.153827806 | 0.483410870 |
| HCK | <1e-300 | 6.780378585 | 0.064583888 | SEMA7A | 4.55E-127 | 3.687309211 | 0.291190115 |
| LRP1 | <1e-300 | 4.630471418 | 0.044479138 | THBD | 1.47E-103 | 3.510802043 | 0.284711606 |
| C1QC | <1e-300 | 4.179029693 | 0.040417513 | TEX2 | 6.20E-97 | 2.805901092 | 0.228630174 |
| LYZ | <1e-300 | 10.46734162 | 0.1023447l | CMKLR1 | 3.84E-67 | 2.176123602 | 0.183074451 |
| LRRC25 | <1e-300 | 4.871266178 | 0.048319185 | RNASE6 | 2.13E-210 | 7.81860705 | 0.665833 |
| ADM | <1e-300 | 3.003396935 | 0.030070209 | ABHD15 | 1.49E-83 | 2.429881182 | 0.207279178 |
| C1QA | <1e-300 | 4.714482708 | 0.047416804 | LGMN | 1.55E-166 | 5.888963237 | 0.508285977 |
| APOBEC3A | <1e-300 | 2.564355886 | 0.027152185 | GNG7 | 1.56E-116 | 2.933468353 | 0.259987053 |
| ZNF385A | <1e-300 | 3.798441961 | 0.041277352 | TTYH2 | 1.70E-70 | 2.003525661 | 0.1786112 |
| TGM2 | <1e-300 | 2.796249949 | 0.031313461 | BCL11A | 1.32E-264 | 9.410676983 | 0.858977097 |
| TNFAIP2 | <1e-300 | 5.458961946 | 0.061582086 | GRASP | 4.07E-119 | 3.379102098 | 0.310016663 |
| CSF3R | <1e-300 | 4.994713267 | 0.05686716 | SERPING1 | 3.19E-95 | 3.123223076 | 0.289184775 |
| SLCO2B1 | <1e-300 | 2.987397171 | 0.034015469 | TRAF4 | 6.79E-170 | 4.184526526 | 0.392893634 |
| LILRB2 | <1e-300 | 5.595739866 | 0.064663485 | MGLL | 2.58E-63 | 2.0758400l | 0.196630971 |
| SIGLEC7 | <1e-300 | 2.773193853 | 0.032173181 | CTNS | 2.97E-97 | 3.531255122 | 0.343834585 |
| TNS1 | <1e-300 | 2.817236045 | 0.032767759 | AMIGO3 | 1.45E-98 | 3.083913502 | 0.301714405 |
| S100A9 | <1e-300 | 6.877247071 | 0.08156152 | PMEPA1 | 2.00E-82 | 2.586408561 | 0.254602597 |
| RAB20 | <1e-300 | 4.078191731 | 0.048534589 | CSF2RA | 1.47E-136 | 4.020982498 | 0.399443425 |
| EPB41L3 | <1e-300 | 2.699229824 | 0.032284735 | SULF2 | 1.02E-138 | 4.5072736 | 0.452889575 |
| C1QB | <1e-300 | 4.60628383 | 0.055422362 | VEGFB | 6.87E-78 | 2.800767518 | 0.281769742 |
| PTAFR | <1e-300 | 4.450110065 | 0.055337388 | CLIC3 | 2.24E-207 | 8.195072195 | 0.845830106 |

TABLE 2B-continued

| | G3- Monocytes/Macrophages | | | | G4- Dendritic cells | | |
|---|---|---|---|---|---|---|---|
| Gene Name | P-value | Mean expression G3 | Mean expression non-G3 | Gene Name | P-value | Mean expression G4 | Mean expression non-G4 |
| CD93 | <1e-300 | 2.131982401 | 0.026659193 | TXNDC5 | 3.00E-85 | 3.046115535 | 0.314856668 |
| PRAM1 | <1e-300 | 2.170457104 | 0.027443247 | COBLL1 | 5.85E-82 | 2.645605534 | 0.274687913 |
| ST3GAL6 | <1e-300 | 2.440783237 | 0.030918923 | TGFBI | 1.25E-241 | 8.500508306 | 0.885183081 |
| S100A8 | <1e-300 | 4.973172907 | 0.063309664 | MGST2 | 2.59E-97 | 3.92391662 | 0.409905018 |
| IL1RN | <1e-300 | 5.075038688 | 0.064728296 | UNC93B1 | 2.91E-61 | 2.050273765 | 0.214828122 |
| SLC8A1 | <1e-300 | 3.047463965 | 0.039628064 | BLNK | 5.13E-156 | 5.703055301 | 0.601474387 |
| FBP1 | <1e-300 | 5.831414128 | 0.077908026 | MAP2K6 | 5.06E-65 | 3.06537999 | 0.329634877 |
| LILRA1 | <1e-300 | 2.601209861 | 0.034799015 | WDFY4 | 5.11E-178 | 5.925229947 | 0.644931587 |
| ANKRD22 | <1e-300 | 2.343552843 | 0.031797091 | TNFSF13 | 1.05E-124 | 4.721003469 | 0.51561044 |

TABLE 2C

| | G5- Lymphocytes | | | | G6- Exhausted CD8 T cells | | |
|---|---|---|---|---|---|---|---|
| Gene Name | P-value | Mean expression G5 | Mean expression non-G5 | Gene Name | P-value | Mean expression G6 | Mean expression non-G6 |
| LMNA | 3.33E-178 | 4.483257461 | 1.61215679 adjusted P-value = 2.5e-5 | FASLG | 5.63E-200 | 2.950972365 | 0.744562663 adjusted P-value = 2.4e-5 |
| ELL2 | 3.35E-130 | 2.852770209 | 1.054356773 | VCAM1 | 1.53E-160 | 2.751568005 | 0.87739373 |
| NR4A3 | 8.45E-167 | 3.508565431 | 1.336581126 | CCL3 | 1.01E-265 | 5.364703548 | 1.712536222 |
| RALGAPA1 | 6.58E-104 | 2.594476701 | 1.030588483 | LAG3 | 9.39E-239 | 3.687225431 | 1.222011504 |
| IL7R | 1.75E-214 | 5.54590785 | 2.245179471 | CXCR6 | 1.10E-251 | 4.996923501 | 1.659284933 |
| FAM177A1 | 6.62E-154 | 4.946194804 | 2.099983146 | IFNG | 1.75E-264 | 5.026771581 | 1.710214715 |
| RNF125 | 2.33E-82 | 2.329936369 | 0.995233018 | KLRC4 | 1.10E-179 | 2.978076091 | 1.026292822 |
| PIK3R1 | 1.74E-99 | 3.679929588 | 1.573737097 | PDCD1 | <1e-300 | 5.943191237 | 2.065076325 |
| TIPARP | 4.97E-63 | 2.159130756 | 0.97265346 | KLRD1 | 1.49E-214 | 4.799651908 | 1.732473246 |
| RGCC | 2.65E-71 | 3.336392734 | 1.528185149 | HAVCR2 | 2.64E-287 | 5.869259595 | 2.141327751 |
| FOSL2 | 1.20E-185 | 4.790841716 | 2.246716335 | CD8B | 3.39E-299 | 6.029416641 | 2.230363101 |
| MPZL3 | 9.57E-59 | 2.675712537 | 1.280435677 | SIRPG | 5.70E-308 | 5.978470716 | 2.23501884 |
| SLC7A5 | 1.27E-67 | 2.85532891 | 1.375475703 | SNAP47 | 4.05E-160 | 3.88508538 | 1.491724953 |
| AIM1 | 1.20E-63 | 2.941911859 | 1.451222283 | DTHD1 | 3.87E-139 | 2.546749108 | 0.984506671 |
| TSPYL2 | 9.89E-110 | 4.926939553 | 2.440610963 | PRF1 | <1e-300 | 8.364701574 | 3.238149632 |
| KDM6B | 4.00E-100 | 2.970664279 | 1.480739369 | GZMH | 4.09E-246 | 5.952782625 | 2.305309885 |
| CREM | 6.19E-169 | 7.475308179 | 3.77645027 | F2R | 3.92E-142 | 2.905097628 | 1.126664628 |
| KIAA1683 | 4.51E-41 | 2.212206353 | 1.126839204 | CD38 | 4.38E-228 | 5.01813128 | 1.983841205 |
| DCTN6 | 2.60E-46 | 2.664359423 | 1.382766102 | GZMK | 6.92E-301 | 6.756990404 | 2.67261115 |
| MYADM | 2.11E-143 | 6.215073713 | 3.276258653 | CXCL13 | 4.42E-136 | 3.648209299 | 1.452309961 |
| GABARAPL1 | 7.59E-61 | 3.566725777 | 1.907228181 | CCR5 | 4.09E-144 | 3.693171952 | 1.475745868 |
| REL | 1.97E-84 | 4.252714659 | 2.2751205 | CCL4L2 | 9.22E-254 | 4.348908893 | 1.746026052 |
| TCF7 | 1.41E-77 | 2.9767793 | 1.60343374 | KLRC4-KLRK1 | 6.46E-227 | 3.650604791 | 1.476008806 |
| PERI | 1.09E-120 | 4.676737622 | 2.521043554 | MYO7A | 4.79E-81 | 2.052828501 | 0.836785249 |
| TUBA4A | 4.22E-108 | 6.854953736 | 3.717830757 | JAKMIP1 | 9.60E-95 | 2.309788301 | 0.943808472 |
| PRMT10 | 2.18E-29 | 2.236375613 | 1.216909552 | CD8A | <1e-300 | 8.426952697 | 3.465174357 |
| JMJD6 | 3.79E-48 | 3.643295975 | 1.998480473 | NKG7 | <1e-300 | 11.39575629 | 4.754483909 |
| PLK3 | 6.53E-27 | 2.247690517 | 1.237673831 | GZMA | <1e-300 | 8.825861863 | 3.682454312 |
| TSC22D2 | 4.49E-56 | 3.085375912 | 1.703252796 | CHST12 | 1.44E-137 | 3.731750649 | 1.568500397 |
| ANXA1 | 6.20E-102 | 7.031135799 | 3.869336672 | CCL4 | <1e-300 | 8.396879261 | 3.549577564 |
| ZC3H12A | 6.48E-47 | 3.209978166 | 1.77598105 | TOX | 2.10E-190 | 3.553160665 | 1.508607328 |
| VPS37B | 5.37E-72 | 3.169844117 | 1.756348442 | GZMB | 2.30E-207 | 6.329143352 | 2.698950167 |
| OAT | 9.98E-25 | 2.353238337 | 1.313506979 | CCL4L1 | 4.293232446824e-310 | 5.931473057 | 2.549172007 |
| S1PR1 | 1.19E-32 | 2.094125661 | 1.169873052 | GIMAP6 | 1.25E-139 | 3.402469461 | 1.470285917 |
| CCR7 | 5.86E-35 | 2.534004603 | 1.428024657 | CTSW | 1.03E-271 | 6.545072777 | 2.829444772 |
| CSRNP1 | 1.40E-53 | 3.517178416 | 2.013970694 | RAB37 | 2.33E-80 | 2.310113328 | 1.011989153 |
| YPEL5 | 6.75E-139 | 7.84367735 | 4.507122902 | TRGC2 | 7.48E-127 | 4.058468018 | 1.795837039 |
| STAT4 | 5.83E-105 | 5.897800297 | 3.397232288 | CD27 | 4.90E-252 | 6.560646754 | 2.908896232 |
| NR4A2 | 1.93E-144 | 7.989542435 | 4.687070745 | GPR56 | 2.52E-98 | 2.724713526 | 1.209145 |
| SYTL3 | 1.70E-77 | 3.694072575 | 2.168628854 | KLRK1 | <1e-300 | 8.872756723 | 3.959454854 |
| TC2N | 1.79E-42 | 3.185551327 | 1.891364802 | ABCA2 | 1.45E-78 | 2.352647033 | 1.057820435 |
| DENND4A | 1.54E-30 | 2.538329145 | 1.509037124 | TIGIT | 4.55E-252 | 6.24744708 | 2.814440919 |
| HEXIM1 | 5.04E-29 | 2.417577675 | 1.439410801 | RGS3 | 9.29E-56 | 2.106250717 | 0.950067873 |
| IFRD1 | 2.89E-58 | 5.64237889 | 3.36326887 | OASL | 2.02E-133 | 4.15868677 | 1.886711198 |

TABLE 2C-continued

| | G5- Lymphocytes | | | | G6- Exhausted CD8 T cells | | |
|---|---|---|---|---|---|---|---|
| Gene Name | P-value | Mean expression G5 | Mean expression non-G5 | Gene Name | P-value | Mean expression G6 | Mean expression non-G6 |
| SERTAD1 | 6.77E-29 | 2.995257536 | 1.796025464 | DDX60 | 1.33E-71 | 2.340528257 | 1.067558341 |
| CDKN1A | 1.61E-39 | 3.333581462 | 2.009148775 | GPR174 | 2.16E-107 | 3.210609894 | 1.468120263 |
| USP36 | 1.85E-63 | 4.550976324 | 2.757655349 | SLAMF7 | 1.18E-186 | 4.898205692 | 2.254239908 |
| ZFP36L2 | 5.72E-114 | 6.962937085 | 4.221571711 | IKZF3 | 1.32E-222 | 5.538176517 | 2.54936791 |
| SIK1 | 3.24E-38 | 2.342108178 | 1.423268667 | PVRIG | 5.60E-135 | 4.393113842 | 2.032352139 |
| ZNF331 | 3.31E-115 | 7.413997987 | 4.508218766 | SIT1 | 2.46E-133 | 4.415142002 | 2.073420107 |
| AREG | 3.06E-18 | 2.031327077 | 1.236962164 | UBASH3A | 6.64E-74 | 2.344569155 | 1.106470693 |
| PFKFB3 | 9.91E-39 | 3.299646621 | 2.012609218 | S100PBP | 1.45E-96 | 2.875155648 | 1.360138834 |
| CDK17 | 1.17E-25 | 2.308283241 | 1.411191671 | TNFRSF9 | 9.34E-86 | 2.815043399 | 1.332115915 |
| SLC38A2 | 2.14E-64 | 5.253235466 | 3.226172013 | ZBP1 | 6.45E-71 | 2.384897231 | 1.137656242 |
| TMEM2 | 1.28E-74 | 5.513583796 | 3.387405094 | THEMIS | 8.28E-93 | 2.710468761 | 1.296225702 |
| SKIL | 2.04E-55 | 4.281754002 | 2.657730029 | GPR171 | 1.32E-99 | 3.334383609 | 1.598490188 |
| NEU1 | 2.41E-18 | 2.648053286 | 1.653251826 | SLAMF6 | 1.32E-77 | 2.67117169 | 1.28672022 |
| HSPH1 | 5.58E-32 | 4.088457458 | 2.556352483 | FCRL3 | 4.72E-90 | 3.399030391 | 1.681186377 |
| SELK | 2.51E-53 | 5.658562928 | 3.548092381 | TRGC1 | 2.01E-79 | 2.086590409 | 1.035235899 |
| CRTAM | 1.19E-19 | 2.502167797 | 1.569776846 | ADORA2A | 1.11E-54 | 2.199697871 | 1.092217814 |
| RUNX3 | 1.27E-40 | 3.294067063 | 2.071626058 | GIMAP4 | 4.02E-182 | 6.169730717 | 3.069270893 |
| RORA | 7.47E-28 | 2.469932444 | 1.558178799 | GBP5 | 1.03E-213 | 5.91738467 | 2.949760732 |
| PTGER4 | 7.14E-39 | 4.1532374 | 2.64018825 | CCL5 | <1e-300 | 11.82207205 | 5.912713485 |
| CD55 | 8.13E-48 | 5.021173792 | 3.198932122 | BCAS4 | 1.09E-50 | 2.150881021 | 1.079645464 |
| RANBP2 | 1.48E-63 | 4.289819867 | 2.738383746 | ITGAE | 1.41E-97 | 4.005436436 | 2.013638465 |
| JUND | 4.43E-96 | 3.594413474 | 2.299738852 | FUT8 | 1.76E-64 | 2.325736723 | 1.169220628 |
| GZMM | 1.08E-20 | 2.44365394 | 1.564558264 | SLFN12L | 1.24E-105 | 3.065501062 | 1.54217004 |
| TUBB4B | 2.91E-38 | 4.729050216 | 3.053912363 | MCTP2 | 5.08E-72 | 2.376061196 | 1.202772368 |
| POLR3E | 3.40E-28 | 3.548142007 | 2.292755371 | TRAFD1 | 2.66E-63 | 2.977064102 | 1.507174063 |
| SCML4 | 3.02E-29 | 2.654116239 | 1.720545954 | ITGB7 | 4.22E-53 | 2.578948422 | 1.312803444 |
| CNOT6L | 6.42E-50 | 3.924901873 | 2.548661221 | RAB27A | 5.11E-125 | 4.326980503 | 2.226815906 |
| RGPD6 | 5.54E-27 | 2.406447677 | 1.564306238 | GIMAP5 | 1.13E-120 | 4.710296903 | 2.436961134 |
| CHD1 | 3.17E-41 | 4.07112052 | 2.653545764 | INP4B | 1.04E-146 | 4.578329196 | 2.375307719 |
| DUSP2 | 2.87E-112 | 8.75641225 | 5.738855078 | PYHIN1 | 6.81E-148 | 4.920133887 | 2.554327371 |
| TNFAIP3 | 1.90E-143 | 10.82668431 | 7.147865185 | GIMAP7 | 1.71E-153 | 5.592000459 | 2.909624761 |
| RGPD5 | 3.67E-48 | 5.294378789 | 3.507206484 | C5orf56 | 1.80E-73 | 3.249692625 | 1.69486526 |
| PDE4B | 9.74E-39 | 5.050844507 | 3.358452739 | LYST | 2.20E-240 | 6.542607446 | 3.416273912 |
| ID1 | 5.31E-24 | 3.882658642 | 2.586954705 | CST7 | <1e-300 | 8.973604137 | 4.695878907 |
| CCNH | 2.81E-23 | 4.607847925 | 3.070532419 | APOBEC3G | 6.76E-230 | 7.338873602 | 3.846833696 |
| FAM46C | 8.53E-61 | 4.978980987 | 3.332095051 | CXCR3 | 2.43E-99 | 4.179792199 | 2.199446151 |
| ATXN7 | 1.17E-30 | 2.59087926 | 1.741425098 | CD84 | 3.21E-108 | 4.221550544 | 2.223035064 |
| FYN | 9.57E-117 | 7.265854176 | 4.888805828 | CLSTN3 | 4.45E-60 | 2.050256979 | 1.081603794 |
| ATP1B3 | 1.18E-40 | 4.872050781 | 3.285414683 | ABI3 | 1.47E-63 | 3.028860386 | 1.598221831 |
| NFE2L2 | 5.11E-21 | 3.701298389 | 2.498795494 | IL2RB | 1.74E-224 | 6.254758404 | 3.301967305 |
| IVNS1ABP | 4.12E-47 | 4.676243709 | 3.183118599 | RARRES3 | 8.68E-193 | 7.257121826 | 3.867006375 |
| POLR2A | 2.20E-19 | 5.318645797 | 3.62575721 | APOBEC3D | 8.50E-121 | 3.350424048 | 1.798179903 |
| CAMK4 | 8.02E-18 | 2.328200369 | 1.589207478 | SLFN5 | 1.14E-125 | 3.908713159 | 2.098640434 |
| CHMP1B | 2.73E-19 | 2.869027966 | 1.958603621 | HAPLN3 | 1.57E-34 | 2.026954915 | 1.091698363 |
| NR4A1 | 1.30E-12 | 2.469330742 | 1.708454721 | PAM | 1.25E-77 | 2.976557681 | 1.607617497 |
| GSPT1 | 2.73E-19 | 3.845282537 | 2.656376795 | PCED1B | 3.69E-86 | 3.108828284 | 1.679076643 |
| SLC2A3 | 4.58E-63 | 7.865793495 | 5.4474217 | ITM2A | 3.98E-153 | 6.160927476 | 3.332344533 |

TABLE 2C-continued

| | G5- Lymphocytes | | | | G6- Exhausted CD8 T cells | | |
|---|---|---|---|---|---|---|---|
| Gene Name | P-value | Mean expression G5 | Mean expression non-G5 | Gene Name | P-value | Mean expression G6 | Mean expression non-G6 |
| IQGAP2 | 1.05E-15 | 2.461380266 | 1.709898404 | GBP1 | 2.78E-76 | 3.677614884 | 2.002535044 |
| GPR65 | 1.75E-08 | 2.327724667 | 1.624386821 | GOLIM4 | 1.18E-57 | 2.15886957 | 1.176344532 |
| HBP1 | 6.96E-08 | 2.668181406 | 1.865144355 | SH2D1A | 4.72E-127 | 4.881604751 | 2.670995027 |
| PAF1 | 3.43E-11 | 2.605795132 | 1.822622722 | MPHOSPH9 | 5.36E-46 | 2.538907974 | 1.402397418 |
| AMD1 | 1.34E-17 | 3.60134088 | 2.518994593 | GIMAP2 | 1.96E-35 | 2.366009331 | 1.312623963 |
| SORL1 | 5.21E-13 | 2.110970313 | 1.479529912 | TTN | 4.68E-69 | 2.264214031 | 1.256504449 |
| KLRK1 | 8.05E-54 | 6.24371431 | 4.382216785 | IFI44L | 3.63E-37 | 2.351912334 | 1.306690547 |
| GZMK | 3.71E-34 | 4.340448931 | 3.059459649 | DENND2D | 6.62E-132 | 5.923080979 | 3.313248223 |
| AKIRIN1 | 6.70E-12 | 2.705308028 | 1.90930518 | GYG1 | 1.15E-29 | 2.205350584 | 1.237052039 |

TABLE 2D

| | G7- Regulatory T cells | | | | G8- Cytotoxicity (Lymphocytes) | | |
|---|---|---|---|---|---|---|---|
| Gene Name | P-value | Mean expression G7 | Mean expression non-G7 | Gene Name | P-value | Mean expression G8 | Mean expression non-G8 |
| FOXP3 | <1e-300 | 2.908413727 | 0.090556475 adjusted P-value = 2.4e-5 | FGFBP2 | 1.00E-235 | 2.172215304 | 0.173170381 adjusted P-value = 2.6e-5 |
| CCR8 | 2.700000000000e-322 | 2.188164106 | 0.075687229 | FCRL6 | 1.00E-116 | 2.231608938 | 0.590102161 |
| TNFRSF4 | <1e-300 | 4.518400142 | 0.477269932 | TGFBR3 | 6.11E-151 | 2.039858898 | 0.553300244 |
| ICA1 | 1.79E-242 | 2.365514485 | 0.259492653 | GNLY | 1.75E-191 | 4.851250665 | 1.372456654 |
| FBLN7 | 4.85E-210 | 2.080857066 | 0.259247645 | SPON2 | 5.07E-69 | 2.138176842 | 0.746447667 |
| RTKN2 | 6.92E-238 | 2.128287792 | 0.272269648 | SAMD3 | 1.59E-198 | 4.375327362 | 1.55410411 |
| IL2RA | 3.03E-227 | 2.781628919 | 0.385409782 | TRDC | 7.32E-67 | 2.093949676 | 0.751546817 |
| TNFRSF18 | <1e-300 | 5.716135523 | 0.96786451 | KLRG1 | 1.38E-150 | 3.980879733 | 1.474460126 |
| MAGEH1 | 3.53E-159 | 2.664286329 | 0.531885504 | GZMH | 6.95E-173 | 5.687185553 | 2.360734181 |
| MAF | <1e-300 | 3.973452844 | 0.968129857 | TRGC1 | 2.65E-97 | 2.324162958 | 1.003067036 |
| ETV7 | 1.94E-114 | 2.028848135 | 0.511507871 | A2M | 2.25E-111 | 2.392790902 | 1.047033015 |
| CD4 | <1e-300 | 6.534390719 | 1.678805026 | FCGR3A | 1.47E-48 | 2.099859168 | 0.93181407 |
| TBC1D4 | 4.78E-223 | 3.600266105 | 0.956829353 | GZMM | 2.05E-82 | 3.193919768 | 1.449569907 |
| IKZF2 | 8.60E-133 | 2.160436096 | 0.585303833 | AOAH | 1.07E-148 | 4.950608016 | 2.349685852 |
| DUSP16 | 1.83E-103 | 2.256612297 | 0.664144261 | GZMA | 1.01E-257 | 7.95355369 | 3.836901532 |
| ICOS | 2.18E-270 | 5.300859072 | 1.572669758 | HOPX | 4.28E-51 | 2.62189692 | 1.276417898 |
| ZC3H12D | 2.26E-192 | 3.449779047 | 1.093100253 | KLRB1 | 4.28E-38 | 2.111991664 | 1.040188137 |
| STAM | 3.50E-126 | 2.852969928 | 0.904163289 | NKG7 | <1e-300 | 10.0124194 | 4.993297224 |
| HS3ST3B1 | 1.99E-116 | 2.519111822 | 0.799545175 | GRAP2 | 7.15E-52 | 2.373628219 | 1.209239579 |
| CTLA4 | 2.58E-306 | 6.09545911 | 1.962910377 | PXN | 4.30E-52 | 2.512300525 | 1.282253401 |
| TIAM1 | 2.80E-116 | 2.345060693 | 0.779900258 | KLRD1 | 8.89E-79 | 3.730768127 | 1.908670512 |
| TNFRSF25 | 1.25E-156 | 3.546426116 | 1.183587732 | PTPN4 | 3.07E-45 | 2.310987345 | 1.219806765 |
| GK | 9.70E-136 | 3.00550063 | 1.011438666 | TRGC2 | 2.82E-74 | 3.558418163 | 1.881606394 |
| BTLA | 7.44E-82 | 2.228277556 | 0.763674526 | CTSW | 4.15E-126 | 5.596471131 | 2.989823745 |
| BATF | 7.65E-238 | 5.503757911 | 1.90427697 | S1PR1 | 1.53E-42 | 2.163144537 | 1.159294979 |
| CORO1B | 7.06E-123 | 3.414658702 | 1.250470601 | PRF1 | 1.08E-142 | 6.336202569 | 3.569730675 |
| SDC4 | 1.89E-82 | 2.260794544 | 0.829654367 | CCL5 | <1e-300 | 10.78069907 | 6.096162864 |
| CD28 | 8.86E-200 | 4.50500395 | 1.658919166 | TC2N | 2.27E-54 | 3.273978948 | 1.877812076 |
| THADA | 1.95E-94 | 2.759335886 | 1.022705012 | C12orf75 | 5.50E-27 | 2.355791556 | 1.376957789 |
| PHTF2 | 3.08E-137 | 3.709548069 | 1.400635409 | PLAC8 | 6.48E-41 | 2.947281272 | 1.723352085 |
| TMEM173 | 2.94E-209 | 5.733396466 | 2.183616303 | ITM2C | 4.45E-27 | 2.206481328 | 1.295325762 |
| KLRB1 | 2.92E-84 | 2.611462059 | 1.011766586 | CCL4 | 1.89E-97 | 6.540425791 | 3.853663502 |
| MICAL2 | 1.83E-66 | 2.17127008 | 0.848952074 | CCL4L2 | 5.77E-73 | 3.256404037 | 1.923970079 |
| SLAMF1 | 4.59E-86 | 2.864161442 | 1.132013256 | TSEN54 | 7.10E-29 | 2.922789362 | 1.735034013 |
| SPOCK2 | <1e-300 | 7.380493892 | 2.971304765 | GZMB | 1.27E-69 | 4.926331719 | 2.928398206 |
| PBX4 | 1.39E-65 | 2.062711125 | 0.841335307 | KLRK1 | 4.41E-140 | 7.079267839 | 4.254156938 |
| PHACTR2 | 9.50E-114 | 2.594100334 | 1.063992414 | CST7 | 1.27E-142 | 7.897793801 | 4.878022605 |
| MBOAT1 | 6.49E-104 | 3.357711823 | 1.432443676 | CCL4L1 | 5.63E-70 | 4.4551144 | 2.789091846 |
| FAS | 5.43E-90 | 3.241082365 | 1.384655322 | C20orf112 | 3.45E-31 | 2.528053672 | 1.588078455 |
| RORA | 3.74E-114 | 3.425689533 | 1.470520079 | MYO1F | 2.09E-44 | 4.149589738 | 2.633861547 |
| PELI1 | 6.50E-100 | 3.533559977 | 1.524060798 | GIMAP7 | 5.03E-51 | 4.774372323 | 3.045760988 |
| TNIK | 3.34E-75 | 2.269702332 | 0.983370734 | NLRC3 | 9.30E-25 | 2.046443327 | 1.315260556 |
| LTB | 4.24E-138 | 5.062700704 | 2.20604619 | SORL1 | 7.21E-26 | 2.261301801 | 1.456489584 |
| GEM | 4.56E-42 | 2.021164159 | 0.882068113 | ZAP70 | 9.08E-91 | 6.09438547 | 3.928736743 |

TABLE 2D-continued

| | G7- Regulatory T cells | | | | G8- Cytotoxicity (Lymphocytes) | | |
|---|---|---|---|---|---|---|---|
| Gene Name | P-value | Mean expression G7 | Mean expression non-G7 | Gene Name | P-value | Mean expression G8 | Mean expression non-G8 |
| TIGIT | 7.46E−212 | 6.512435729 | 2.896471619 | C5orf56 | 1.82E−23 | 2.75171808 | 1.774760478 |
| DNPH1 | 2.19E−88 | 4.037523686 | 1.796331637 | SYNE1 | 3.87E−52 | 4.151130292 | 2.682600875 |
| UXS1 | 1.95E−45 | 2.019941213 | 0.904382548 | RORA | 8.81E−29 | 2.422308797 | 1.565477765 |
| PBXIP1 | 4.17E−189 | 5.56603595 | 2.594328128 | PYHIN1 | 1.21E−46 | 4.140225825 | 2.683405094 |
| NCF4 | 7.94E−46 | 2.218815509 | 1.040444721 | SCML4 | 1.40E−44 | 2.645322865 | 1.721895658 |
| HTATIP2 | 4.81E−37 | 2.084547089 | 0.979359507 | SLFN12L | 4.14E−30 | 2.505906524 | 1.634082262 |
| CD5 | 3.64E−116 | 4.263954583 | 2.025795414 | GPR56 | 2.80E−17 | 2.012071998 | 1.325049617 |
| ARID5B | 1.55E−214 | 6.100579262 | 2.907675605 | SLAMF7 | 9.72E−42 | 3.702881103 | 2.44810822 |
| TRAF3 | 4.82E−47 | 2.170805054 | 1.051843069 | KLRC4-KLRK1 | 3.18E−35 | 2.498775416 | 1.66131693 |
| RAB11FIP1 | 1.64E−75 | 3.190402351 | 1.561024115 | CD8A | 1.68E−69 | 5.819732955 | 3.884787277 |
| RHBDD2 | 2.73E−86 | 4.29901896 | 2.148754716 | STOM | 1.81E−40 | 4.244554774 | 2.836417195 |
| LY75 | 2.47E−53 | 2.291695435 | 1.146266509 | PIM1 | 6.06E−26 | 3.664389971 | 2.451385595 |
| SUSD3 | 1.39E−42 | 2.387510318 | 1.197390982 | SYTL1 | 3.57E−18 | 2.268683715 | 1.52264347 |
| P2RY10 | 2.41E−54 | 2.878243163 | 1.465873443 | BIN2 | 2.89E−28 | 4.352836441 | 2.939740624 |
| CNST | 1.06E−49 | 2.266553702 | 1.161711281 | MGAT4A | 7.87E−19 | 2.255204447 | 1.528885156 |
| DUSP4 | 1.09E−170 | 5.657830636 | 2.900523194 | PATL2 | 1.17E−09 | 2.122838793 | 1.441287402 |
| IL6ST | 7.78E−84 | 3.866712442 | 1.98752116 | SLC9A3R1 | 1.12E−32 | 4.23472345 | 2.884820027 |
| LIMS1 | 1.15E−66 | 3.35731492 | 1.737804209 | TNF | 8.77E−11 | 2.04312757 | 1.392053653 |
| TP53INP1 | 2.08E−66 | 2.872463091 | 1.503327014 | GLIPR2 | 3.52E−19 | 2.792178589 | 1.912894809 |
| MSI2 | 2.54E−57 | 2.690857101 | 1.423990667 | TBCD | 4.13E−18 | 3.154578983 | 2.165678834 |
| ZC3H7A | 2.93E−68 | 3.594705683 | 1.908123109 | TPST2 | 6.75E−14 | 2.620114952 | 1.802195474 |
| SIRPG | 1.06E−92 | 4.695837611 | 2.512396711 | THEMIS | 8.20E−17 | 2.031311202 | 1.406022387 |
| NR3C1 | 1.35E−55 | 4.086923476 | 2.195774422 | GZMK | 1.11E−34 | 4.400942168 | 3.050188245 |
| HNRNPLL | 2.22E−102 | 4.428322116 | 2.403323959 | ANXA1 | 6.75E−63 | 5.860312523 | 4.066378128 |
| CARD16 | 1.59E−43 | 3.571715315 | 1.947131057 | SLFN5 | 2.72E−26 | 3.185458187 | 2.216792859 |
| OTUD5 | 4.05E−28 | 2.018170252 | 1.115322696 | GIMAP5 | 6.39E−28 | 3.727718299 | 2.596727721 |
| PHLDA1 | 9.62E−80 | 3.060849244 | 1.693115558 | STAT4 | 1.21E−40 | 5.014115574 | 3.532668889 |
| CD82 | 1.44E−78 | 4.96823571 | 2.757717194 | RASAL3 | 3.30E−21 | 2.270047677 | 1.601342177 |
| GOLGA8B | 1.39E−58 | 3.115314677 | 1.732030277 | | | | |
| EPSTI1 | 1.40E−65 | 3.554496423 | 1.993749084 | | | | |
| UGP2 | 5.96E−43 | 3.432784906 | 1.940519106 | | | | |
| KIAA0319L | 1.16E−35 | 2.653182368 | 1.512545427 | | | | |
| TLK1 | 9.92E−99 | 4.788506453 | 2.734997166 | | | | |
| SYT11 | 9.75E−30 | 2.05800629 | 1.193397514 | | | | |
| TRAF1 | 1.30E−38 | 2.820144104 | 1.637534766 | | | | |
| CNIH1 | 1.24E−33 | 2.97915351 | 1.731344333 | | | | |
| ARNTL | 8.59E−27 | 2.054714299 | 1.19965166 | | | | |
| PIK3IP1 | 2.09E−82 | 5.420278643 | 3.165901718 | | | | |
| PIM2 | 8O8E−117 | 7.314116909 | 4.310127865 | | | | |
| NAB P1 | 4.51E−51 | 4.209302201 | 2.483672766 | | | | |
| LAT | 1.85E−79 | 5.398628399 | 3.19395051 | | | | |
| PCED1B | 7.85E−45 | 2.94661458 | 1.745834401 | | | | |
| GOLGA8A | 8.62E−42 | 2.262774727 | 1.346343169 | | | | |
| ITM2A | 4.94E−82 | 5.819308201 | 3.46689161 | | | | |
| IFNAR2 | 3.36E−29 | 2.565700043 | 1.535927592 | | | | |
| BTG3 | 6.37E−35 | 3.208218446 | 1.924165026 | | | | |
| GATA3 | 4.11E−33 | 2.158470698 | 1.304861133 | | | | |

TABLE 2D-continued

| | G7- Regulatory T cells | | | G8- Cytotoxicity (Lymphocytes) | | |
|---|---|---|---|---|---|---|
| Gene Name | P-value | Mean expression G7 | Mean expression non-G7 | Gene Name | P-value | Mean expression G8 | Mean expression non-G8 |
| DDHD1 | 6.85E-33 | 2.572603976 | 1.555313671 | | | | |
| CD247 | 5.64E-80 | 5.163778536 | 3.122026701 | | | | |
| SKAP1 | 5.90E-71 | 4.824473117 | 2.918432343 | | | | |
| TULP4 | 1.66E-31 | 2.170530054 | 1.319962353 | | | | |
| TRIM59 | 2.00E-33 | 2.667413582 | 1.628028112 | | | | |
| GRSF1 | 1.65E-26 | 2.857782 | 1.74443896 | | | | |
| PMAIP1 | 2.15E-35 | 3.615505376 | 2.207346783 | | | | |
| CD2 | 1.17E-183 | 8.677727572 | 5.331415144 | | | | |
| NDFIP1 | 7.69E-49 | 3.257647115 | 2.005866319 | | | | |

TABLE 2E

| | G9- Exhausted/HS CD8 T cells | | | | G10- Memory T cells | | | |
|---|---|---|---|---|---|---|---|---|
| GeneName | P-value | Mean expression G9 | Mean expression non-G9 | | Gene Name | P-value | Mean expression G10 | Mean expression non-G10 |
| VCAM1 | <1e−300 | 4.50867448 | 0.751053745 | adjusted P-value = 2.5e−5 | LEF1 | 5.45E−211 | 2.944448948 | 0.579553106 adjusted P-value = 2.6e−5 |
| KIR2DL4 | 9.85E−114 | 2.08866823 | 0.441388636 | | TCF7 | <1e−300 | 5.159375317 | 1.373967472 |
| TNFRSF9 | 1.61E−258 | 4.536989531 | 1.194621837 | | SERINC5 | 1.71E−96 | 2.168705964 | 0.679370498 |
| GEM | 1.93E−106 | 2.792306702 | 0.801348743 | | IL7R | <1e−300 | 6.773511229 | 2.184382166 |
| CXCL13 | 3.69E−209 | 4.853343918 | 1.400869995 | | CCR7 | 8.82E−149 | 3.860128514 | 1.295935281 |
| NAB1 | 4.21E−244 | 4.589709321 | 1.33732745 | | TNFRSF25 | 6.66E−122 | 3.396721145 | 1.196499513 |
| DFNB31 | 6.82E−154 | 2.703078202 | 0.833537198 | | S1PR1 | 1.30E−100 | 2.851763681 | 1.102302782 |
| CADM1 | 3.67E−87 | 2.398272064 | 0.746128607 | | PASK | 9.70E−61 | 2.066582032 | 0.81085611 |
| CRTAM | 4.53E−176 | 4.44118351 | 1.382798846 | | FLT3LG | 9.78E−81 | 2.652330145 | 1.071446837 |
| GPR56 | 1.03E−162 | 3.628686329 | 1.166018599 | | CAMK4 | 8.70E−102 | 3.475917911 | 1.468996844 |
| CTLA4 | 1.58E−239 | 5.850418868 | 2.014356959 | | SORL1 | 2.09E−106 | 3.152976621 | 1.369325162 |
| MYO7A | 1.57E−94 | 2.379161407 | 0.846889327 | | DHRS3 | 5.84E−43 | 2.059416625 | 0.985173246 |
| DUSP4 | <1e−300 | 7.439730171 | 2.714721226 | | TMEM63A | 3.90E−39 | 2.09396385 | 1.011937545 |
| HAVCR2 | 6.71E−225 | 6.04311353 | 2.265831154 | | MGAT4A | 3.97E−62 | 2.986391764 | 1.459200768 |
| TNFSF9 | 6.17E−97 | 2.608254296 | 0.984891442 | | LTB | 4.87E−98 | 4.554250313 | 2.261647026 |
| METRNL | 8.21E−71 | 2.597942207 | 0.991089694 | | RCAN3 | 1.45E−41 | 2.048866485 | 1.032986603 |
| DTHD1 | 3.04E−110 | 2.66124002 | 1.031970441 | | ABLIM1 | 5.04E−59 | 3.397358534 | 1.765303513 |
| CXCR6 | 6.08E−123 | 4.589581596 | 1.834458258 | | PLAC8 | 1.05E−77 | 3.289999003 | 1.714545204 |
| CCDC64 | 1.82E−97 | 2.782961987 | 1.134034007 | | DGKA | 3.29E−115 | 6.073166546 | 3.188214222 |
| PHLDA1 | 3.41E−155 | 3.924538328 | 1.603236536 | | TC2N | 5.40E−74 | 3.543926551 | 1.882542777 |
| PDE3B | 9.09E−95 | 2.625208934 | 1.075625687 | | SELL | 7.14E−71 | 4.334559003 | 2.33094736 |
| GZMB | 9.87E−196 | 6.765753335 | 2.789941845 | | KLRB1 | 4.46E−27 | 2.006850083 | 1.081968203 |
| LAG3 | 4.95E−107 | 3.257212374 | 1.366009638 | | C20orf112 | 1.02E−58 | 2.905723371 | 1.56733606 |
| SLC7A5 | 2.71E−95 | 3.262823167 | 1.380835101 | | TESPA1 | 6.96E−54 | 2.955438838 | 1.599015236 |
| KLRC4 | 1.74E−82 | 2.673091474 | 1.136286936 | | CCDC109B | 1.51E−28 | 2.255245599 | 1.229294002 |
| PDCD1 | 5.07E−161 | 5.327688232 | 2.284706391 | | GIMAP5 | 4.85E−81 | 4.581462166 | 2.52300272 |
| NELL2 | 1.60E−90 | 3.166174948 | 1.388173452 | | OXNAD1 | 5.15E−54 | 3.510188968 | 1.942033 |
| SNAP47 | 8.05E−79 | 3.652134497 | 1.610645941 | | FAM102A | 5.89E−53 | 3.086751212 | 1.726293832 |
| ENTPD1 | 3.31E−87 | 3.691424823 | 1.642028119 | | SATB1 | 1.34E−34 | 2.404858778 | 1.394529769 |
| CD8A | 2.18E−247 | 8.234590895 | 3.678834602 | | NOSIP | 2.09E−24 | 2.802038272 | 1.626423851 |
| TTN | 4.66E−103 | 2.745272688 | 1.241043601 | | FAM65B | 1.67E−62 | 3.887119772 | 2.26804134 |
| PRF1 | 4.91E−257 | 7.710344562 | 3.510458727 | | ICAM2 | 2.92E−27 | 2.182702003 | 1.284960731 |
| CD8B | 1.38E−140 | 5.372818259 | 2.451585597 | | ATM | 1.39E−37 | 3.278332283 | 1.964122784 |
| MCTP2 | 3.72E−61 | 2.659735058 | 1.21604996 | | SCML4 | 2.13E−38 | 2.814055406 | 1.726222746 |
| TOX | 2.58E−103 | 3.470079834 | 1.597080102 | | CD5 | 1.27E−41 | 3.440492134 | 2.121272729 |
| AHI1 | 1.84E−71 | 3.330642486 | 1.537543074 | | PIK3IP1 | 3.86E−55 | 5.071334068 | 3.203392026 |
| GZMH | 6.34E−125 | 5.417740356 | 2.506915595 | | FOXP1 | 3.30E−51 | 4.073458505 | 2.575606277 |
| SYTL3 | 8.59E−127 | 4.553187043 | 2.124468616 | | EPB41 | 7.62E−25 | 2.443182261 | 1.55896682 |
| GOLIM4 | 4.27E−58 | 2.487274603 | 1.177182963 | | CD28 | 1.79E−32 | 2.897220815 | 1.848799225 |
| PAM | 3.00E−72 | 3.387465766 | 1.614064805 | | GOLGA8A | 4.09E−24 | 2.128758246 | 1.360626747 |
| KLRC4-KLRK1 | 1.16E−86 | 3.326071101 | 1.596832114 | | GIMAP7 | 4.27E−42 | 4.798528736 | 3.089485076 |
| LYST | 2.04E−225 | 7.03566326 | 3.481392078 | | CHMP7 | 5.22E−17 | 2.444730066 | 1.600860764 |
| SLA2 | 1.09E−87 | 3.767583348 | 1.868466871 | | NELL2 | 1.15E−16 | 2.256279845 | 1.484964873 |
| NKG7 | 2.74E−283 | 10.33018118 | 5.131904651 | | DENND2D | 2.69E−51 | 5.196769448 | 3.482663105 |
| RAB27A | 5.95E−96 | 4.575299269 | 2.279940422 | | GOLGA8B | 8.87E−18 | 2.62515418 | 1.788746503 |
| ASXL2 | 5.43E−57 | 2.592934851 | 1.309028158 | | GIMAP2 | 5.90E−09 | 2.015721649 | 1.387980767 |
| HNRNPLL | 1.24E−118 | 4.71681452 | 2.382302874 | | TMEM123 | 3.74E−17 | 3.708346744 | 2.577253683 |
| ITPRIP | 6.46E−37 | 2.17084183 | 1.096513915 | | GPR183 | 1.15E−24 | 3.724598349 | 2.59332694 |
| TGIF1 | 3.21E−54 | 3.468428125 | 1.767563879 | | TTC39C | 1.03E−20 | 3.188729308 | 2.221132449 |
| BANP | 1.85E−38 | 2.528865195 | 1.291785586 | | KIAA0922 | 7.98E−12 | 2.190475571 | 1.529233079 |
| CREM | 4.86E−145 | 7.603154717 | 3.890628938 | | RAPGEF6 | 1.49E−15 | 2.751225375 | 1.924237613 |
| PON2 | 8.34E−30 | 2.33099109 | 1.201677945 | | AAK1 | 1.98E−27 | 3.901532667 | 2.757927038 |
| CCL4L1 | 9.15E−129 | 5.282412068 | 2.753423964 | | | | | |
| CCL4L2 | 5.19E−88 | 3.663629445 | 1.924232711 | | | | | |
| PDE4D | 5.60E−97 | 4.113450286 | 2.173825861 | | | | | |
| CCL4 | 1.95E−138 | 7.264325996 | 3.865196352 | | | | | |
| VPS37B | 4.16E−83 | 3.350443176 | 1.785074504 | | | | | |
| ATXN1 | 1.40E−111 | 5.10213774 | 2.731878905 | | | | | |
| CTSW | 3.37E−105 | 5.721089538 | 3.066381 | | | | | |
| KLRK1 | 6.50E−187 | 7.929933059 | 4.256157611 | | | | | |
| GABARAPL1 | 8.57E−61 | 3.638069233 | 1.956872151 | | | | | |
| CCL5 | <1e−300 | 11.48718424 | 6.179148138 | | | | | |
| F2R | 2.04E−40 | 2.33943884 | 1.259450691 | | | | | |
| JMJD6 | 4.98E−47 | 3.787826021 | 2.039332494 | | | | | |
| KLRD1 | 1.87E−56 | 3.659421822 | 1.980115484 | | | | | |
| BTG3 | 4.44E−49 | 3.498669111 | 1.898669583 | | | | | |
| DCTN6 | 3.63E−36 | 2.635997809 | 1.430548865 | | | | | |
| SAMSN1 | 8.49E−105 | 6.054534574 | 3.289197393 | | | | | |
| TIGIT | 6.76E−103 | 5.553259472 | 3.025760097 | | | | | |
| PRDM1 | 2.59E−182 | 6.735756715 | 3.672503705 | | | | | |
| ZBTB1 | 2.15E−43 | 3.176302531 | 1.735354528 | | | | | |
| CBLB | 1.93E−171 | 7.262762379 | 3.980358924 | | | | | |

TABLE 2E-continued

| | G9- Exhausted/HS CD8 T cells | | | | G10- Memory T cells | | |
|---|---|---|---|---|---|---|---|
| GeneName | P-value | Mean expression G9 | Mean expression non-G9 | Gene Name | P-value | Mean expression G10 | Mean expression non-G10 |
| DNAJA4 | 1.58E−25 | 2.054160495 | 1.128412534 | | | | |
| CST7 | 3.88E−200 | 8.862770969 | 4.873858559 | | | | |
| STAT5B | 3.00E−38 | 2.501011728 | 1.393403362 | | | | |
| CD27 | 2.14E−99 | 5.650416042 | 3.15312123 | | | | |
| CHST12 | 3.04E−41 | 3.089016389 | 1.724890392 | | | | |
| FUT8 | 2.63E−30 | 2.193337869 | 1.228929587 | | | | |
| TP53INP1 | 3.39E−46 | 2.726317568 | 1.52772226 | | | | |
| TMEM2 | 1.94E−113 | 6.048276939 | 3.400850472 | | | | |
| GSPT1 | 1.05E−39 | 2.979323847 | 1.67721026 | | | | |
| GATA3 | 2.46E−37 | 2.286279429 | 1.295298574 | | | | |
| PMAIP1 | 5.81E−45 | 3.856316071 | 2.188180593 | | | | |
| HSPH1 | 6.26E−49 | 4.501398137 | 2.562912897 | | | | |
| PFKFB3 | 5.94E−58 | 3.560264202 | 2.027882148 | | | | |
| CNOT6L | 4.58E−88 | 4.427305674 | 2.539677675 | | | | |
| IFNG | 7.99E−43 | 3.482145524 | 2.013260286 | | | | |
| GZMK | 5.47E−67 | 5.195654548 | 3.00724257 | | | | |
| ATHL1 | 1.23E−42 | 2.822416869 | 1.633708809 | | | | |
| TSPYL2 | 1.37E−56 | 4.455501087 | 2.580429436 | | | | |
| SH2D2A | 1.35E−104 | 5.210112369 | 3.023296269 | | | | |
| FCRL3 | 8.86E−38 | 3.072531215 | 1.784567474 | | | | |
| IPCEF1 | 8.03E−35 | 2.665238382 | 1.54872764 | | | | |
| LRMP | 1.47E−45 | 3.183886478 | 1.853455577 | | | | |
| TRAT1 | 7.67E−40 | 3.404751184 | 1.984115363 | | | | |
| OASL | 6.35E−39 | 3.507938729 | 2.048212867 | | | | |
| STAT5A | 6.91E−26 | 2.258358433 | 1.330095834 | | | | |
| IRF4 | 6.00E−35 | 2.865149234 | 1.69212468 | | | | |
| ETS1 | 1.64E−74 | 4.411402193 | 2.613554596 | | | | |
| PTPN22 | 5.49E−75 | 4.782315091 | 2.833610963 | | | | |

TABLE 2F

| G11- Lymphocytes exhausted/cell-cycle | | | | |
|---|---|---|---|---|
| GeneName | P-value | Mean expression G11 | Mean expression non-G11 | |
| SPC25 | <1e−300 | 2.55158841 | 0.044683954 | adjusted P-value = 1.3e−5 |
| CDCA5 | <1e−300 | 3.655492107 | 0.067760256 | |
| KIF15 | <1e−300 | 2.174404427 | 0.045021031 | |
| CDC45 | <1e−300 | 2.74204077 | 0.060438937 | |
| DLGAP5 | <1e−300 | 2.677773732 | 0.060271292 | |
| HIST1H3G | <1e−300 | 2.048930929 | 0.048216741 | |
| KIF18B | <1e−300 | 2.299645768 | 0.054267922 | |
| RRM2 | <1e−300 | 5.979473049 | 0.144311828 | |
| UBE2C | <1e−300 | 4.605312013 | 0.11221674 | |
| HJURP | <1e−300 | 2.440545198 | 0.059740348 | |
| ESCO2 | <1e−300 | 2.281039379 | 0.056143688 | |
| SPC24 | <1e−300 | 3.790205449 | 0.099149221 | |
| BIRC5 | <1e−300 | 4.160162746 | 0.110489205 | |
| CDC6 | <1e−300 | 2.129610899 | 0.061460209 | |
| CDCA8 | <1e−300 | 2.917928579 | 0.085707394 | |
| AURKB | <1e−300 | 3.938514949 | 0.118029222 | |
| ZWINT | <1e−300 | 4.880944943 | 0.146815449 | |
| CDCA2 | 3.00000000000000e−323 | 2.154636598 | 0.064819609 | |
| GTSE1 | <1e−300 | 2.237362094 | 0.067415946 | |
| DTL | <1e−300 | 3.01936579 | 0.091448243 | |
| RAD51 | <1e−300 | 3.006106426 | 0.091861703 | |
| CDCA3 | <1e−300 | 2.843509088 | 0.089148695 | |
| MELK | <1e−300 | 3.045934257 | 0.096305647 | |
| CKAP2L | <1e−300 | 2.484127304 | 0.087002675 | |
| ANLN | <1e−300 | 2.32543532 | 0.082123655 | |
| ASF1B | <1e−300 | 4.341703889 | 0.156818226 | |
| TYMS | <1e−300 | 6.623959258 | 0.242937564 | |
| NCAPG | <1e−300 | 2.760840243 | 0.102509553 | |
| TK1 | <1e−300 | 5.275512434 | 0.196568648 | |
| PKMYT1 | <1e−300 | 4.173006819 | 0.155507194 | |
| KIFC1 | <1e−300 | 2.986890319 | 0.112381109 | |
| KIAA0101 | <1e−300 | 6.132531375 | 0.231188565 | |
| CCNB2 | <1e−300 | 3.346553414 | 0.127119045 | |
| DEPDC1B | 2.35E−295 | 2.120095818 | 0.081054515 | |
| CDC20 | <1e−300 | 2.99029734 | 0.11496007 | |
| TROAP | <1e−300 | 2.730634101 | 0.108622291 | |

TABLE 2F-continued

| G11- Lymphocytes exhausted/cell-cycle | | | |
|---|---|---|---|
| GeneName | P-value | Mean expression G11 | Mean expression non-G11 |
| CLSPN | <1e-300 | 2.412512241 | 0.097904245 |
| ASPM | <1e-300 | 2.524410973 | 0.102914917 |
| GINS2 | <1e-300 | 2.591389266 | 0.105848356 |
| KIF23 | <1e-300 | 2.899077376 | 0.120677081 |
| KIF2C | <1e-300 | 2.919485764 | 0.124529204 |
| RAD51AP1 | <1e-300 | 2.831802232 | 0.12281219 |
| NUF2 | <1e-300 | 2.855727508 | 0.125977392 |
| SHCBP1 | 4.53593553773400e-312 | 2.325559651 | 0.103508687 |
| TOP2A | <1e-300 | 4.491338648 | 0.202597836 |
| CDK1 | <1e-300 | 4.802007428 | 0.2176185 |
| MKI67 | <1e-300 | 4.119201621 | 0.187968014 |
| MLF1IP | <1e-300 | 3.974550094 | 0.185022883 |
| PLK1 | 3.37E-284 | 2.527243378 | 0.121149365 |
| DHFR | <1e-300 | 3.408690236 | 0.163807152 |
| KIF11 | <1e-300 | 3.028640082 | 0.15488364 |
| CENPW | <1e-300 | 3.230577206 | 0.16790494 |
| TPX2 | <1e-300 | 3.581022453 | 0.188783365 |
| CASC5 | <1e-300 | 3.000396744 | 0.163541724 |
| CDKN3 | <1e-300 | 3.713849904 | 0.211251442 |
| CCNA2 | <1e-300 | 4.048129904 | 0.235156885 |
| BUB1B | <1e-300 | 2.778128153 | 0.163793368 |
| MCM2 | <1e-300 | 4.087032817 | 0.247259574 |
| UBE2T | <1e-300 | 4.557859797 | 0.280427572 |
| BRCA1 | 6.91E-280 | 2.22729081 | 0.137544941 |
| MCM4 | <1e-300 | 4.751741111 | 0.313942117 |
| GGH | 5.68E-276 | 2.771416642 | 0.184573495 |
| TCF19 | <1e-300 | 3.548525036 | 0.238036736 |
| BUB1 | <1e-300 | 3.051032141 | 0.208116055 |
| HMGB3 | 8.20E-265 | 2.387864303 | 0.167993506 |
| ECT2 | 2.03E-245 | 2.001276411 | 0.141510846 |
| FEN1 | <1e-300 | 4.493377252 | 0.318417899 |
| WDR34 | <1e-300 | 3.08337534 | 0.221409972 |
| NCAPG2 | <1e-300 | 3.252214597 | 0.234183609 |
| CCNB1 | 2.26E-241 | 2.726825158 | 0.198010971 |
| ORC6 | 2.16E-269 | 2.345457084 | 0.172056348 |
| CHEK1 | 5.54E-300 | 2.730370116 | 0.201519298 |
| SGOL1 | 1.48E-238 | 2.263546757 | 0.169551266 |
| CENPH | 3.54E-266 | 2.439082667 | 0.183665985 |
| CENPF | <1e-300 | 3.371903982 | 0.254122052 |
| MAD2L1 | <1e-300 | 4.377747502 | 0.333811558 |
| SPAG5 | 6.22E-282 | 2.864969673 | 0.222602813 |
| NCAPH | <1e-300 | 3.187949506 | 0.253944902 |
| CCNF | 1.34170272600000e-315 | 2.479216797 | 0.197966267 |
| CENPE | 1.50E-280 | 2.332072352 | 0.186533873 |
| RFC3 | 2.62E-245 | 2.14291466 | 0.171840946 |
| FANCI | <1e-300 | 4.024540198 | 0.324976352 |
| CENPM | <1e-300 | 4.983236941 | 0.435256782 |
| CDCA7 | <1e-300 | 4.084697463 | 0.359021698 |
| TIMELESS | 3.68E-304 | 2.602007914 | 0.232190616 |
| FBXO5 | 7.81E-263 | 2.533158157 | 0.229785725 |
| PRC1 | 3.87E-284 | 3.176132843 | 0.291974824 |
| RNASEH2A | <1e-300 | 3.454471068 | 0.333041016 |
| SMC2 | <1e-300 | 3.925122486 | 0.380064933 |
| STMN1 | <1e-300 | 8.387592123 | 0.818322649 |
| AURKA | 1.86E-208 | 2.246869717 | 0.220381455 |
| RACGAP1 | 8.14E-261 | 2.852109531 | 0.289040451 |
| HIST1H2AM | 4.23E-223 | 2.14309683 | 0.218864764 |
| APOBEC3B | 1.83E-204 | 2.520044219 | 0.259552616 |
| BRCA2 | 1.81E-235 | 2.324802474 | 0.241846519 |
| ATAD5 | 8.59426392276280e-310 | 2.356822748 | 0.246544856 |
| CENPN | 2.52E-269 | 3.366971033 | 0.352640995 |
| HIRIP3 | 5.74E-307 | 3.07915335 | 0.323115763 |
| CKS1B | <1e-300 | 5.284506046 | 0.574726378 |
| NDC80 | 2.18175000000000e-318 | 3.410466555 | 0.383395396 |

TABLE 3

| T cells | CD4 T cell | CD8 T cells | Regulatory T cells | Regulatory CD4 T cells | Regulatory CD8 T cells |
|---|---|---|---|---|---|
| CD3E | CD4 | CD8A; CD8B | FOXP3 | FOXP3 | FOXP3 |
| CD2 | CD3E | (−)NCR1 | CD3E | CD3E | CD3E |
| (−)NCR1 | (−)NCR1 | (−)NCAM1 | CTLA4; IL2RA | CD4 | CD8A; CD8B |
| (−)NCAM1 | (−)NCAM1 | (−)FOXP3 | CD4 | CTLA4; IL2RA | CTLA4; IL2RA |
| (−)FOXP3 | (−)FOXP3 |  | CD8A | (−)CD8A | (−)CD4 |
|  |  |  | CD8B | (−)CD8B |  |

| Regulatory CD4\CD8 T cells | NKT cells | NK cells | B cells | Activated T cells | Exhausted T cells |
|---|---|---|---|---|---|
| FOXP3 | CD3E | FCGR3A | CD19; MS4A1 | CD3E | CD3E |
| CD3E | NCR1; NCAM1 | NCR1; NCAM1 | (−)CD3E | CD2 | CD2 |
| CD4 | (−)FOXP3 | (−)CD3E | (−)FOXP3 | CD28 | PDCD1; CTLA4; BTLA; KIR3DL1; LAG3; HAVCR2; ADORA2A; HAVCR1 |
| CD8A; CD8B |  | (−)FOXP3 |  | IL2RA; CD69; ICOS; TNFRSF4; TNFRSF9; CD27 |  |
| CTLA4; IL2RA |  |  |  | IL2; TNF; IFNG | CD8A; CD8B; CD4 |
|  |  |  |  | CD8A; CD8B; CD4 | (−)NCR1 |
|  |  |  |  | (−)NCR1 | (−)NCAM1 |
|  |  |  |  | (−)NCAM1 |  |

| Memory T cells | Memory CD4 T cells | Memory CD8 T cells | Memory CD4\CD8 T cells | Macrophage immature | Macrophage mature |
|---|---|---|---|---|---|
| CD3E | CD3E | CD3E | CD3E | CD163 | CD163 |
| SELL | SELL | SELL | SELL | ITGAM | ITGAM |
| CCR7 | CCR7 | CCR7 | CCR7 | CD4 | CD4 |
| CD28 | CD28 | CD28 | CD28 | (−)CD3E | HLA-DRA |
| (−)FOXP3 | CD4 | CD8A; CD8B | CD4 | (−)HLA-DRA | (−)CD3E |
| (−)CD4 | (−)FOXP3 | (−)FOXP3 | CD8A; CD8B |  |  |
| (−)CD8A | (−)CD4 | (−)CD4 | (−)FOXP3 |  |  |
| (−)CD8B | (−)CD8B |  |  |  |  |

| Monocyte immature | Monocyte mature | cDCs dendritic cells | pDCs | Myeloid cells general immature | Myeloid cells general mature |
|---|---|---|---|---|---|
| CD14 | CD14 | MHCII | IL3RA | CD33 | CD33 |
| FCGR1A | FCGR1A | CD4 | CLE4C | (−)CD3E | MHCII |
| (−)HLA-DRA | HLA-DRA | ITGAX; THBD | NRP1 | (−)MHCII | (−)CD3E |
|  | (−)CD3E | (−)CD3E | LILRA4 |  |  |
|  |  |  | MHCII |  |  |
|  |  |  | (−)CD3E |  |  |

Immune cell classification based on know markers. Essential markers are bolded; non-bolded refers to markers where only one in each cell is essential;
(−) marker should be absecnt;

TABLE 4

| Responder | | | | | | | |
|---|---|---|---|---|---|---|---|
| G1- B cells Gene Name | P-value | % exp in R | % exp in NR | G10- Memory T cells Gene Name | P-value | % exp in R | % exp in NR |
| IGHD | 8.44E−72 | 0.110958904 | 0.035034347 | LEF1 | 1.13E−35 | 0.145009785 | 0.078999019 |
| PAX5 | 4.56E−85 | 0.118199609 | 0.034249264 | TCF7 | 8.03E−50 | 0.332876712 | 0.220215898 |
| FCRL1 | 1.86E−91 | 0.12446184 | 0.035426889 | CCR7 | 8.92E−148 | 0.297064579 | 0.121982336 |
| FCER2 | 1.14E−58 | 0.103913894 | 0.036408243 | S1PR1 | 1.20E−34 | 0.223679061 | 0.143179588 |
| CD19 | 4.54E−107 | 0.150097847 | 0.044357213 | LTB | 4.66E−41 | 0.354794521 | 0.249852797 |
| CD22 | 1.17E−92 | 0.147945205 | 0.048675172 | PLAC8 | 3.41E−37 | 0.281017613 | 0.189303238 |
| BANK1 | 1.97E−95 | 0.154403131 | 0.051422964 |  |  |  |  |
| MS4A1 | 1.66E−140 | 0.193542074 | 0.05750736 |  |  |  |  |
| BLK | 1.04E−59 | 0.101956947 | 0.034739941 |  |  |  |  |
| RALGPS2 | 8.21E−66 | 0.112133072 | 0.038272816 |  |  |  |  |
| FAM129C | 7.47E−43 | 0.101956947 | 0.043081452 |  |  |  |  |

TABLE 4-continued

| Non-responder | | | | | | | |
|---|---|---|---|---|---|---|---|
| G6- Exhausted CD8 T cells Gene Name | P-value | % exp in R | % exp in NR | G7- Regulatory T cells Gene Name | P-value | % exp in R | % exp in NR |
| FASLG | 1.64E−41 | 0.073972603 | 0.14720314 | TNFRSF4 | 1.21E−15 | 0.08630137 | 0.129244357 |
| VCAM1 | 3.43E−80 | 0.066927593 | 0.173307164 | TNFRSF18 | 9.19E−26 | 0.134637965 | 0.202453386 |
| CCL3 | 5.62E−158 | 0.111741683 | 0.297742885 | MAF | 2.31E−31 | 0.176320939 | 0.259273798 |
| LAG3 | 2.58E−59 | 0.14109589 | 0.252502453 | ETV7 | 2.05E−56 | 0.042661448 | 0.116584887 |
| CXCR6 | 2.69E−64 | 0.150684932 | 0.269774289 | CD4 | 6.77E−51 | 0.207827789 | 0.3218842 |
| IFNG | 1.26E−66 | 0.160861057 | 0.284592738 | CTLA4 | 7.61E−52 | 0.213111546 | 0.329146222 |
| PDCD1 | 7.40E−87 | 0.200587084 | 0.35279686 | | | | |
| KLRD1 | 8.31E−43 | 0.170450098 | 0.268302257 | | | | |
| HAVCR2 | 5.12E−168 | 0.175146771 | 0.388910697 | | | | |
| SIRPG | 1.65E−40 | 0.245596869 | 0.350539745 | | | | |
| SNAP47 | 9.99E−83 | 0.145009785 | 0.281059863 | | | | |
| DTHD1 | 8.10E−25 | 0.139334638 | 0.206575074 | | | | |
| PRF1 | 1.05E−135 | 0.292563601 | 0.500588813 | | | | |
| GZMH | 2.44E−103 | 0.17964775 | 0.342983317 | | | | |
| F2R | 1.94E−31 | 0.139334638 | 0.216290481 | | | | |
| CD38 | 7.97E−172 | 0.160469667 | 0.373012758 | | | | |
| CXCL13 | 5.60E−28 | 0.135225049 | 0.206476938 | | | | |
| G8- Cytotoxicity (Lymphocytes) Gene Name | P-value | % exp in R | % exp in NR | G9- Exhausted/HS CD8 T cells Gene Name | P-value | % exp in R | % exp in NR |
| FCRL6 | 3.00E−23 | 0.063209393 | 0.111776251 | TNFRSF9 | 9.64E−39 | 0.143052838 | 0.230716389 |
| SPON2 | 1.26E−18 | 0.099412916 | 0.149656526 | GEM | 3.04E−24 | 0.084735812 | 0.14033366 |
| KLRG1 | 9.23E−25 | 0.155381605 | 0.225024534 | NAB1 | 7.05E−43 | 0.17260274 | 0.270951914 |
| TRGC1 | 3.26E−32 | 0.134050881 | 0.211187439 | DFNB31 | 5.84E−28 | 0.132876712 | 0.203729146 |
| A2M | 2.03E−27 | 0.143835616 | 0.215799804 | CADM1 | 2.66E−58 | 0.063405088 | 0.149067713 |
| FCGR3A | 2.92E−106 | 0.048923679 | 0.165358194 | CRTAM | 1.97E−28 | 0.157142857 | 0.232777233 |
| GZMA | 5.83E−97 | 0.314285714 | 0.490088322 | GPR56 | 4.55E−50 | 0.129158513 | 0.22747792 |
| HOPX | 1.22E−23 | 0.121722114 | 0.184003925 | MYO7A | 8.82E−51 | 0.0962818 | 0.186555447 |
| NKG7 | 7.00E−120 | 0.373581213 | 0.572423945 | DUSP4 | 1.33E−78 | 0.334637965 | 0.493228656 |
| PXN | 1.24E−27 | 0.183170254 | 0.261236506 | METRNL | 5.92E−60 | 0.093542074 | 0.192345437 |
| | | | | PHLDA1 | 4.81E−50 | 0.242465753 | 0.359960746 |

TABLE 5

| GeneName | P-value | mean exp in R | mean exp in NR | % in R | % in NR | log2(R/NR) | GeneName | P-value | mean exp in R | mean exp in NR | % in R | % in NR | log2(R/NR) |
|---|---|---|---|---|---|---|---|---|---|---|---|---|---|
| CCL3 | 5.62E-158 | 0.939589005 | 2.803907774 | 0.111741683 | 0.297742885 | -1.5773 | LAMTOR1 | 1.18E-51 | 1.471970188 | 2.265803825 | 0.182778865 | 0.293915604 | -0.6223 |
| LGALS1 | 1.62E-171 | 1.434364197 | 3.469757471 | 0.166731898 | 0.380863592 | -1.2744 | UQCRFS1 | 3.66E-73 | 1.956621767 | 3.010646999 | 0.244227006 | 0.389008832 | -0.6217 |
| CD38 | 7.97E-172 | 1.224144242 | 2.896771762 | 0.160469667 | 0.373012758 | -1.2427 | NDUFB4 | 1.04E-65 | 1.821027265 | 2.801058774 | 0.218199609 | 0.351226693 | -0.6212 |
| EPSTI1 | 1.35E-164 | 1.169193654 | 2.669176018 | 0.165949119 | 0.374877331 | -1.1909 | CAPZA2 | 1.06E-68 | 2.025194021 | 3.114300151 | 0.249315068 | 0.389892051 | -0.6208 |
| WARS | 7.87E-151 | 1.506308103 | 3.324907134 | 0.190998043 | 0.395878312 | -1.1423 | BRK1 | 1.76E-105 | 2.767872611 | 4.253696156 | 0.319596472 | 0.503631011 | -0.6199 |
| PLEK | 8.00E-104 | 0.98374674 | 2.139448522 | 0.126027397 | 0.275466143 | -1.1209 | ADRM1 | 2.18E-73 | 1.978008478 | 3.037711057 | 0.243444227 | 0.38842002 | -0.6189 |
| HAVCR2 | 5.12E-168 | 1.466442103 | 3.177078253 | 0.175146771 | 0.388910697 | -1.1154 | NDUFB2 | 7.93E-63 | 1.979068619 | 3.037540066 | 0.232681018 | 0.364474975 | -0.6181 |
| LGALS3 | 1.82E-103 | 1.151931789 | 2.473107353 | 0.139921722 | 0.293326791 | -1.1023 | ETFA | 2.81E-49 | 1.548497909 | 2.376481383 | 0.195499022 | 0.30578999 | -0.6180 |
| FABP5 | 8.12E-116 | 1.227485851 | 2.634565658 | 0.160078278 | 0.329583763 | -1.1019 | VDAC3 | 2.29E-54 | 1.561910567 | 2.396264404 | 0.178669276 | 0.292247301 | -0.6175 |
| MT2A | 5.36E-180 | 1.857507939 | 3.984219391 | 0.216634051 | 0.448086359 | -1.1009 | NUDT5 | 2.48E-42 | 1.347260422 | 2.064886871 | 0.169863014 | 0.267026497 | -0.6160 |
| GBP1 | 1.20E-133 | 1.272533906 | 2.683489122 | 0.216653041 | 0.350539745 | -1.0764 | IFITM3 | 1.02E-53 | 1.844810093 | 2.82616754 | 0.33111546 | 0.460745829 | -0.6154 |
| PLSCR1 | 1.58E-103 | 1.084594548 | 2.284260645 | 0.141878669 | 0.295878312 | -1.0746 | BANF1 | 5.74E-64 | 1.870524604 | 2.861604859 | 0.238747554 | 0.372620216 | -0.6134 |
| CCR5 | 1.30E-113 | 1.032817583 | 2.140534911 | 0.131508649 | 0.290873405 | -1.0514 | ZNHIT1 | 4.43E-57 | 1.472004662 | 2.251268529 | 0.198630137 | 0.318842002 | -0.6130 |
| GSTO1 | 2.42E-110 | 1.299902209 | 2.667379622 | 0.157925636 | 0.322178606 | -1.0370 | CAPG | 3.71E-29 | 1.341358738 | 2.051292507 | 0.150880626 | 0.226394701 | -0.6128 |
| ANXA5 | 6.77E-203 | 2.167251976 | 4.429830147 | 0.258317025 | 0.511678116 | -1.0314 | NHP2 | 4.49E-48 | 1.495319661 | 2.286599938 | 0.176125245 | 0.281648675 | -0.6128 |
| GLUL | 7.02E-65 | 1.022070976 | 2.080857014 | 0.125244618 | 0.238469087 | -1.0257 | LASP1 | 1.11E-110 | 2.355484849 | 3.59954771 | 0.331506849 | 0.521000981 | -0.6118 |
| PYCARD | 6.66E-113 | 1.270979866 | 2.579921887 | 0.154207436 | 0.319725221 | -1.0214 | TOMM5 | 2.02E-42 | 1.407280385 | 2.150544244 | 0.174559687 | 0.272620216 | -0.6118 |
| TYMP | 1.16E-93 | 1.061001216 | 2.150678099 | 0.153816047 | 0.30235525 | -1.0194 | MVP | 3.84E-89 | 2.345602701 | 3.583600734 | 0.301565558 | 0.468792934 | -0.6115 |
| IFI6 | 6.30E-205 | 2.087718034 | 4.226932063 | 0.298238748 | 0.556722277 | -1.0177 | CTSW | 1.29E-74 | 2.430435004 | 3.712773088 | 0.26555773 | 0.41442598 | -0.6113 |
| VAMP5 | 1.49E-98 | 1.118835892 | 2.256616205 | 0.132485323 | 0.27595682 | -1.0122 | AURKAIP1 | 8.70E-55 | 1.644344099 | 2.509162353 | 0.20254403 | 0.32060844 | -0.6097 |
| OASL | 7.77E-109 | 1.325351664 | 2.64185416 | 0.161056751 | 0.324926398 | -0.9952 | RARRES3 | 4.54E-103 | 3.161469824 | 4.818914617 | 0.344227006 | 0.527379784 | -0.6081 |
| GZMB | 2.85E-111 | 1.920523217 | 3.756160821 | 0.191976517 | 0.364965653 | -0.9678 | PSMB10 | 2.47E-117 | 3.228693957 | 4.920713633 | 0.382778865 | 0.579587831 | -0.6079 |
| TXN | 9.43E-126 | 1.442051697 | 2.819578423 | 0.198825832 | 0.385475957 | -0.9674 | TMEM173 | 7.92E-68 | 1.947127742 | 2.964367654 | 0.231311155 | 0.368596663 | -0.6064 |
| SQRDL | 6.00E-107 | 1.286360337 | 2.514026773 | 0.160078278 | 0.321982316 | -0.9667 | SLX1A | 1.27E-67 | 1.815061258 | 2.763275323 | 0.252446184 | 0.392149166 | -0.6064 |
| RHOC | 6.20E-100 | 1.197562723 | 2.337664796 | 0.145792564 | 0.297742885 | -0.9650 | APOBEC3G | 2.10E-121 | 3.182934444 | 4.844374311 | 0.391976517 | 0.592149166 | -0.6060 |
| AP2S1 | 6.73E-108 | 1.359865175 | 2.64898374 | 0.165949119 | 0.330225711 | -0.9620 | GIMAP4 | 1.75E-92 | 2.535711152 | 3.859270313 | 0.282387476 | 0.451226693 | -0.6059 |
| GZMH | 2.44E-103 | 1.720062884 | 3.310968047 | 0.17964775 | 0.342983317 | -0.9448 | EIF4E | 3.03E-57 | 1.541477254 | 2.345722172 | 0.224853229 | 0.349067713 | -0.6057 |
| CCL4L2 | 1.76E-25 | 1.300409591 | 2.501472567 | 0.190606654 | 0.375368008 | -0.9438 | CTLA4 | 7.61E-52 | 1.752266075 | 2.752286075 | 0.213111546 | 0.329146222 | -0.6050 |
| SNAP47 | 9.99E-83 | 1.131528965 | 2.168431025 | 0.145009785 | 0.281059863 | -0.9384 | NDUFS8 | 1.61E-57 | 1.791709494 | 2.725048714 | 0.213307241 | 0.336211973 | -0.6049 |
| LAP3 | 3.15E-113 | 1.581703196 | 2.999918423 | 0.206262231 | 0.383807655 | -0.9234 | CYB5B | 2.74E-48 | 1.325618886 | 2.014882042 | 0.165166341 | 0.26908341 | -0.6040 |
| ATP6V1B2 | 6.58E-78 | 1.100783295 | 2.0846786 | 0.14481409 | 0.276251227 | -0.9213 | PIK3R5 | 1.45E-60 | 1.520046536 | 2.309809103 | 0.214677104 | 0.341441315 | -0.6037 |
| CCL4L1 | 1.11E-52 | 1.289643174 | 3.57048576 | 0.240900196 | 0.460058881 | -0.9128 | HEXB | 1.02E-40 | 1.490847043 | 2.265288375 | 0.190998043 | 0.289401374 | -0.6036 |
| LAMP2 | 1.34E-88 | 1.221584191 | 2.269052813 | 0.173776908 | 0.322374877 | -0.8933 | STXBP2 | 2.86E-67 | 1.805792862 | 2.743767549 | 0.24148728 | 0.379489696 | -0.6035 |
| PSMA4 | 1.58E-114 | 1.807421158 | 3.329267726 | 0.216438356 | 0.396859666 | -0.8813 | PSMD8 | 6.12E-93 | 2.570250329 | 3.904976297 | 0.310176125 | 0.481844946 | -0.6034 |
| SERPINB1 | 1.65E-121 | 1.702627875 | 3.131701617 | 0.218003914 | 0.4047105 | -0.8792 | SEC61B | 1.03E-78 | 2.41618832 | 3.670398637 | 0.275146771 | 0.429440628 | -0.6032 |
| HIGD1A | 1.04E-72 | 1.128748894 | 2.145632456 | 0.143639922 | 0.269676153 | -0.8781 | RGS10 | 4.15E-64 | 1.846836084 | 2.805173428 | 0.226614481 | 0.359077527 | -0.6030 |
| UBE2F | 1.72E-75 | 1.218952843 | 2.239347122 | 0.150880626 | 0.281452404 | -0.8774 | PHB | 2.15E-43 | 1.411430831 | 2.142091307 | 0.172015656 | 0.270951914 | -0.6019 |
| TALDO1 | 8.74E-108 | 1.711232093 | 3.132560282 | 0.204696673 | 0.377134446 | -0.8714 | ATP5C1 | 2.39E-80 | 2.623165221 | 3.979471194 | 0.304892368 | 0.463493621 | -0.6013 |
| CD63 | 2.60E-115 | 2.011292797 | 3.677347979 | 0.22778865 | 0.410749897 | -0.8705 | ARF5 | 1.37E-88 | 2.403208596 | 3.642911336 | 0.286692759 | 0.452109912 | -0.6001 |
| CLTA | 8.43E-98 | 1.534408413 | 2.804221471 | 0.184148728 | 0.34357213 | -0.8702 | SUMO3 | 1.36E-63 | 1.400328503 | 2.121950405 | 0.194520548 | 0.415799804 | -0.5996 |
| S100A11 | 2.39E-176 | 2.801020271 | 5.114902404 | 0.317702544 | 0.557311089 | -0.8688 | PRDX6 | 2.09E-73 | 2.211850307 | 3.350323911 | 0.268688845 | 0.416584887 | -0.5990 |
| PHPT1 | 1.48E-75 | 1.126133531 | 2.053528146 | 0.141291585 | 0.269479882 | -0.8665 | RNH1 | 3.54E-55 | 1.853690158 | 2.806035738 | 0.226418787 | 0.348380765 | -0.5981 |
| GBP4 | 9.39E-96 | 1.230451552 | 2.233802382 | 0.173972603 | 0.329244357 | -0.8603 | ATP5F1 | 8.18E-70 | 2.42465532 | 3.669077749 | 0.227045793 | 0.414818449 | -0.5976 |
| PRDX3 | 6.15E-96 | 1.547521806 | 2.800244619 | 0.192759295 | 0.352109912 | -0.8556 | UQCRC1 | 3.69E-66 | 2.229226819 | 3.373248627 | 0.250293542 | 0.388125613 | -0.5976 |
| PSMB2 | 1.00E-101 | 1.313159604 | 2.375816286 | 0.190410959 | 0.354661433 | -0.8554 | SARNP | 4.90E-50 | 1.516981551 | 2.295316086 | 0.191976517 | 0.302649657 | -0.5975 |
| BST2 | 8.95E-134 | 2.01844398 | 3.644775299 | 0.240117417 | 0.440529931 | -0.8526 | PLIN2 | 2.05E-50 | 1.760981343 | 2.664348434 | 0.205870841 | 0.319038273 | -0.5974 |
| GBP5 | 4.82E-157 | 2.197103227 | 3.961369397 | 0.298825832 | 0.523945044 | -0.8504 | PIN1 | 1.17E-52 | 1.587253316 | 2.400754615 | 0.198434442 | 0.313346418 | -0.5970 |
| CTSC | 2.10E-135 | 2.21390491 | 3.983042751 | 0.264187867 | 0.469087341 | -0.8473 | SDHC | 5.29E-45 | 1.331960257 | 2.014370399 | 0.167318982 | 0.267517174 | -0.5968 |

TABLE 5-continued

| GeneName | P-value | mean exp in R | mean exp in NR | % in R | % in NR | log2(R/NR) | GeneName | P-value | mean exp in R | mean exp in NR | % in R | % in NR | log2(R/NR) |
|---|---|---|---|---|---|---|---|---|---|---|---|---|---|
| NDUFB3 | 9.09E-88 | 1.460319121 | 2.625550575 | 0.187866928 | 0.338567223 | -0.8463 | SF3B14 | 1.21E-43 | 1.435949883 | 2.170264173 | 0.176320939 | 0.276349362 | -0.5959 |
| NPC2 | 9.68E-52 | 1.307475575 | 2.33618263 | 0.155777994 | 0.261923454 | -0.8374 | CAPRIN1 | 2.58E-56 | 1.518882097 | 2.2948595 | 0.204892368 | 0.325220805 | -0.5954 |
| GALM | 9.43E-107 | 1.623922917 | 2.899863377 | 0.21702544 | 0.39077527 | -0.8365 | POLR2G | 2.00E-52 | 1.65885776 | 2.505725428 | 0.191585127 | 0.305103042 | -0.5950 |
| GLIPR2 | 1.11E-79 | 1.33485477 | 2.372761882 | 0.174951679 | 0.315112856 | -0.8299 | COX7B | 4.10E-48 | 1.440945898 | 2.176132912 | 0.205088063 | 0.315309127 | -0.5948 |
| CCL4 | 5.54E-142 | 2.782056346 | 4.943412677 | 0.273972603 | 0.485181551 | -0.8294 | UQCR10 | 3.43E-61 | 1.88073704 | 2.837097221 | 0.23776908 | 0.368302257 | -0.5931 |
| PRF1 | 1.05E-135 | 2.557475532 | 4.540641973 | 0.292563601 | 0.500588813 | -0.8282 | FBXO7 | 5.26E-66 | 1.875581829 | 2.828712552 | 0.233855186 | 0.369479882 | -0.5928 |
| IFNG | 1.26E-66 | 1.411525111 | 2.505996296 | 0.160861057 | 0.284592738 | -0.8281 | NDUFB6 | 1.27E-45 | 1.342660733 | 2.024857299 | 0.187866928 | 0.292247301 | -0.5927 |
| IFI30 | 5.39E-74 | 1.36514752 | 2.423596814 | 0.163403088 | 0.252404318 | -0.8281 | S100A4 | 1.41E-139 | 4.03810423 | 6.086103579 | 0.427201566 | 0.641020608 | -0.5918 |
| CHST12 | 4.22E-74 | 1.219682077 | 2.163199105 | 0.159295499 | 0.290382728 | -0.8267 | PRELID1 | 2.55E-93 | 2.730074843 | 4.113289161 | 0.316829746 | 0.489303238 | -0.5914 |
| ISG15 | 4.17E-139 | 2.564714971 | 4.527295115 | 0.282778865 | 0.492639843 | -0.8199 | TRPV2 | 7.31E-43 | 1.344893411 | 2.025797438 | 0.164774951 | 0.261727184 | -0.5910 |
| MYD88 | 1.94E-85 | 1.438388303 | 2.538402632 | 0.175342466 | 0.321197252 | -0.8195 | SF3B5 | 3.37E-48 | 1.583358893 | 2.383041204 | 0.189041096 | 0.296957802 | -0.5898 |
| IDH2 | 2.70E-110 | 1.858739363 | 3.278953963 | 0.233659491 | 0.413150147 | -0.8189 | MYO1F | 1.62E-87 | 2.123671457 | 3.196173021 | 0.276712329 | 0.44013739 | -0.5898 |
| MTHFD2 | 2.44E-103 | 1.77639693 | 3.130009901 | 0.22035225 | 0.391560353 | -0.8172 | SCAMP2 | 1.09E-73 | 2.089782589 | 3.144716309 | 0.278473581 | 0.42767419 | -0.5896 |
| CHMP2A | 3.80E-89 | 1.56388008I | 2.755448958 | 0.186888454 | 0.338763494 | -0.8172 | RNF7 | 1.33E-56 | 1.872613569 | 2.814730661 | 0.226418787 | 0.350049068 | -0.5879 |
| NDUFA9 | 1.51E-72 | 1.172458056 | 2.065110912 | 0.150684932 | 0.278131207I | -0.8167 | CXCL13 | 5.60E-28 | 1.355394178 | 2.03675881 | 0.135225049 | 0.206476938 | -0.5876 |
| CHMP5 | 3.92E-72 | 1.159352377 | 2.040732289 | 0.143052838 | 0.268302257 | -0.8158 | RAB1B | 4.25E-94 | 2.254107483 | 3.386558547 | 0.325636008 | 0.499411187 | -0.5873 |
| CALM3 | 2.20E-141 | 2.312998993 | 4.067470725 | 0.350684932 | 0.566437684 | -0.8144 | SHKBP1 | 1.53E-67 | 1.99504865 | 2.993560471 | 0.242661448 | 0.381157998 | -0.5854 |
| ANXA2 | 5.54E-149 | 2.787619438 | 4.90138768 | 0.316634051 | 0.536800785 | -0.8142 | PET100 | 3.31E-44 | 1.618195769 | 2.424294819 | 0.18962818 | 0.292443572 | -0.5832 |
| PPT1 | 9.83E-74 | 1.381166982 | 2.42723641 | 0.169667319 | 0.302649657 | -0.8134 | HM13 | 1.55E-73 | 2.246515104 | 3.364901018 | 0.293542074 | 0.443866536 | -0.5829 |
| GTF3C6 | 1.12E-67 | 1.166012318 | 2.048744147 | 0.14109589 | 0.261334642 | -0.8132 | VTT1B | 4.71E-38 | 1.417555277 | 2.121390686 | 0.170645793 | 0.262315996 | -0.5816 |
| NDUFAB1 | 2.01E-62 | 1.183824812 | 2.079273503 | 0.144031311 | 0.259470069 | -0.8126 | S100A6 | 1.63E-119 | 3.667553424 | 5.48402226 | 0.444227006 | 0.641707556 | -0.5804 |
| CXCR6 | 2.69E-64 | 1.397926045 | 2.453401323 | 0.150684932 | 0.269774289 | -0.8115 | ARPC5 | 2.05E-103 | 3.108838615 | 4.645710167 | 0.377651634 | 0.5609421 | -0.5795 |
| RNF181 | 5.41E-71 | 1.292797959 | 2.267134394 | 0.152054795 | 0.271884236 | -0.8104 | FDPS | 2.19E-37 | 1.355738541 | 2.025078052 | 0.160078278 | 0.249067713 | -0.5789 |
| LGALS9 | 5.23E-76 | 1.376255246 | 2.412242552 | 0.168688845 | 0.321491658 | -0.8096 | MINOS1 | 3.77E-52 | 1.860788513 | 2.777752049 | 0.222700587 | 0.340431796 | -0.5780 |
| COX5A | 6.53E-112 | 2.228146708 | 3.899933819 | 0.2481409 | 0.431207066 | -0.8076 | RAB10 | 5.59E-63 | 1.824034863 | 2.722031122 | 0.239921722 | 0.372914622 | -0.5776 |
| OAS2 | 1.57E-78 | 1.279076885 | 2.237347045 | 0.174951076 | 0.313935231 | -0.8067 | NEDD8 | 8.71E-65 | 2.262455911 | 3.375193597 | 0.266144814 | 0.404121688 | -0.5771 |
| PDCD1 | 7.40E-87 | 1.72553088 | 3.006058479 | 0.200587084 | 0.35279686 | -0.8008 | BATF | 7.23E-49 | 1.719255022 | 2.564562221 | 0.209784736 | 0.321687929 | -0.5769 |
| SNRPC | 2.07E-65 | 1.262935824 | 2.19795701 | 0.157338552 | 0.278999019 | -0.7994 | PHB2 | 5.57E-57 | 1.910245349 | 2.848484087 | 0.234833659 | 0.360058881 | -0.5764 |
| BHLHE40 | 4.33E-125 | 1.886628502 | 3.280099866 | 0.244031311 | 0.437782139 | -0.7979 | ERH | 2.86E-51 | 1.543608861 | 2.301596185 | 0.2032698I | 0.3171737 | -0.5763 |
| TWF2 | 7.99E-102 | 1.747953739 | 3.036385443 | 0.214409002 | 0.3828263 | -0.7967 | NCOA4 | 4.84E-56 | 1.632947176 | 2.430018799 | 0.212524462 | 0.333660451 | -0.5735 |
| SLAMF7 | 3.21E-96 | 1.692220807 | 2.935333665 | 0.223091977 | 0.388125613 | -0.7946 | PDIA4 | 2.94E-49 | 1.427636408 | 2.123710781 | 0.19667319 | 0.307065751 | -0.5730 |
| TXN2 | 1.36E-61 | 1.186270608 | 2.056399429 | 0.144227006 | 0.258881256 | -0.7937 | PSMB9 | 2.69E-128 | 3.934441248 | 5.851809853 | 0.435812133 | 0.640628067 | -0.5727 |
| CARD16 | 2.47E-75 | 1.433124633 | 2.482720883 | 0.168688845 | 0.303140334 | -0.7928 | C11orf48 | 1.88E-43 | 1.460064176 | 2.17086077 | 0.175146771 | 0.27468106 | -0.5722 |
| ANAPC11 | 8.37E-81 | 1.561081884 | 2.701533754 | 0.180430528 | 0.322865554 | -0.7912 | TMEM50A | 1.39E-73 | 2.467019534 | 3.667439907 | 0.306066536 | 0.45750736 | -0.5720 |
| MRPL51 | 1.83E-68 | 1.210862163 | 2.091417197 | 0.150880626 | 0.274288518 | -0.7884 | TIGIT | 5.12E-64 | 2.438067948 | 3.620872319 | 0.281604697 | 0.420215898 | -0.5706 |
| LIMS1 | 7.33E-76 | 1.286470469 | 2.217421383 | 0.178669276 | 0.315799804 | -0.7852 | NDUFA11 | 5.56E-71 | 2.375016961 | 3.524391232 | 0.284540117 | 0.431305201 | -0.5694 |
| NDUFA12 | 2.11E-60 | 1.286434658 | 2.174997628 | 0.149236709 | 0.263395486 | -0.7837 | NELFE | 4.36E-44 | 1.420641666 | 2.120745346 | 0.171819961 | 0.271638862 | -0.5692 |
| RANBP1 | 3.77E-56 | 1.259401961 | 2.164646512 | 0.162818004 | 0.275466143 | -0.7814 | COX6C | 3.71E-75 | 2.586526218 | 3.835648953 | 0.291585127 | 0.44357213 | -0.5685 |
| GBP2 | 6.09E-162 | 2.603023181 | 4.465274352 | 0.319569472 | 0.549656526 | -0.7786 | SLA2 | 2.46E-45 | 1.547448994 | 2.294393139 | 0.211741683 | 0.319234544 | -0.5682 |
| PSMC1 | 4.42E-81 | 1.458760563 | 2.498696001 | 0.188454012 | 0.332677233 | -0.7764 | PSMB8 | 4.58E-123 | 3.904298913 | 5.787019096 | 0.43444227 | 0.635132483 | -0.5678 |
| ACTR1A | 3.34E-81 | 1.31908617 | 2.257989861 | 0.176712329 | 0.314720314 | -0.7754 | NDUFS7 | 1.09E-39 | 2.099654751 | 3.111976232 | 0.25890411 | 0.390186457 | -0.5677 |
| CD2BP2 | 3.00E-96 | 1.585053094 | 2.708127397 | 0.210176125 | 0.373110893 | -0.7728 | RER1 | 3.06E-68 | 2.157501382 | 3.196893772 | 0.27925636 | 0.422473013 | -0.5673 |
| VDAC1 | 1.37E-92 | 1.847728212 | 3.156525139 | 0.231506849 | 0.394308145 | -0.7726 | RAB8A | 6.50E-68 | 2.013079781 | 2.982013093 | 0.273385519 | 0.415701668 | -0.5669 |
| EMC7 | 6.48E-79 | 1.466560189 | 2.505247554 | 0.175146771 | 0.314524043 | -0.7725 | CAPN1 | 2.11E-58 | 1.668661948 | 2.47180585 | 0.213111546 | 0.337095191 | -0.5669 |
| MX1 | 8.91E-67 | 1.388221908 | 2.371076341 | 0.180821918 | 0.302257115 | -0.7723 | MRPL20 | 3.48E-41 | 1.423481808 | 2.108426878 | 0.17964775 | 0.276938175 | -0.5667 |
| GPS1 | 3.97E-67 | 1.250743634 | 2.134548325 | 0.153424658 | 0.276054956 | -0.7711 | COX5B | 3.22E-80 | 2.674923407 | 3.960917174 | 0.322896282 | 0.482531894 | -0.5663 |
| ATP5J2 | 3.41E-77 | 1.61494568 | 2.754509372 | 0.191193738 | 0.331992149 | -0.7703 | SEC13 | 1.97E-49 | 1.661936815 | 2.460236952 | 0.207632094 | 0.319921492 | -0.5659 |
| USMG5 | 2.84E-71 | 1.608306053 | 2.735270252 | 0.182778865 | 0.315897939 | -0.7661 | FKBP1A | 2.84E-102 | 3.227146057 | 4.776115368 | 0.40567514 | 0.589205103 | -0.5656 |
| SHFM1 | 3.31E-105 | 1.785971953 | 3.036315693 | 0.235420744 | 0.410598626 | -0.7656 | PRDM1 | 2.60E-131 | 3.046145461 | 4.507065657 | 0.418590998 | 0.62639843 | -0.5652 |
| ATP5I | 1.29E-81 | 1.721852691 | 2.923087609 | 0.199804305 | 0.346712463 | -0.7639 | RAB1A | 2.49E-51 | 1.876437975 | 2.775713516 | 0.240508806 | 0.359371933 | -0.5649 |

TABLE 5-continued

| GeneName | P-value | mean exp in R | mean exp in NR | % in R | % in NR | log2(R/NR) | GeneName | P-value | mean exp in R | mean exp in NR | % in R | % in NR | log2(R/NR) |
|---|---|---|---|---|---|---|---|---|---|---|---|---|---|
| FAM96A | 2.22E-63 | 1.324287431 | 2.244513476 | 0.159686888 | 0.279784102 | -0.7612 | RHOG | 3.38E-59 | 2.053046663 | 3.036746717 | 0.242074364 | 0.370853778 | -0.5648 |
| CASP1 | 7.11E-64 | 1.308373595 | 2.21492596 | 0.157729941 | 0.277919529 | -0.7595 | CYB5R3 | 1.63E-47 | 1.446224765 | 2.13866327 | 0.201174168 | 0.310107949 | -0.5644 |
| PARP9 | 1.11E-107 | 1.795226866 | 3.037818661 | 0.238356164 | 0.416192345 | -0.7589 | AIP | 1.01E-60 | 2.12403644 | 3.134573272 | 0.253620352 | 0.385475957 | -0.5615 |
| NOP10 | 2.84E-75 | 1.63929391 | 2.772952269 | 0.190215264 | 0.328949951 | -0.7583 | ABRACL | 1.72E-49 | 1.744334987 | 2.573380049 | 0.209917652 | 0.321687929 | -0.5610 |
| GNG5 | 5.67E-119 | 2.390555919 | 4.034456049 | 0.294911937 | 0.489205103 | -0.7550 | PSMB7 | 1.21E-54 | 1.980973893 | 2.921961937 | 0.245009785 | 0.368596663 | -0.5607 |
| CYC1 | 8.29E-69 | 1.455931537 | 2.456880997 | 0.175733855 | 0.304906771 | -0.7549 | COX6B1 | 4.58E-72 | 2.518588738 | 3.714566384 | 0.298043053 | 0.44720314 | -0.5606 |
| RAB11A | 6.28E-65 | 1.332712868 | 2.247199181 | 0.162818004 | 0.285181551 | -0.7538 | PSMD7 | 1.24E-49 | 1.697017469 | 2.502129473 | 0.22035225 | 0.334641806 | -0.5602 |
| PGAM1 | 1.84E-160 | 3.071876283 | 5.171280083 | 0.357338552 | 0.587536801 | -0.7514 | PPA1 | 6.56E-47 | 1.853357745 | 2.731471398 | 0.217221135 | 0.327576055 | -0.5595 |
| ENTPD1 | 6.80E-69 | 1.30471792 | 2.195552574 | 0.180821918 | 0.311089303 | -0.7508 | PCMT1 | 2.80E-45 | 1.681901695 | 2.476437115 | 0.207827789 | 0.314818449 | -0.5582 |
| PDIA6 | 1.21E-106 | 2.00003005 | 3.363028434 | 0.254011742 | 0.433071639 | -0.7495 | SURF4 | 2.48E-86 | 2.528509913 | 3.722968195 | 0.326614481 | 0.493236114 | -0.5582 |
| PSMC3 | 8.49E-69 | 1.450948554 | 2.434003358 | 0.182191781 | 0.312565135 | -0.7463 | TCEB2 | 1.25E-38 | 1.459667728 | 2.148906709 | 0.173972603 | 0.266928361 | -0.5580 |
| TMBIM1 | 2.67E-65 | 1.251255656 | 2.097797696 | 0.172015656 | 0.296663395 | -0.7455 | MAP2K3 | 1.30E-90 | 2.777168278 | 4.087032238 | 0.336986301 | 0.50794897 | -0.5574 |
| UBE2L6 | 2.82E-152 | 2.878188643 | 4.823160748 | 0.336007828 | 0.55966634 | -0.7448 | AL353354.2 | 8.12E-58 | 1.79395053 | 2.639840991 | 0.237377691 | 0.363886163 | -0.5573 |
| PSMA6 | 3.17E-113 | 2.509379715 | 4.199085666 | 0.289041096 | 0.477821394 | -0.7423 | AKIRIN2 | 5.26E-46 | 1.492252115 | 2.19587082 | 0.186497065 | 0.291167812 | -0.5573 |
| EIF6 | 7.35E-64 | 1.349574531 | 2.251925349 | 0.163600783 | 0.28498528 | -0.7387 | GRSF1 | 3.13E-54 | 1.524437545 | 2.242176513 | 0.208414873 | 0.326692836 | -0.5566 |
| DCTN3 | 2.49E-62 | 1.351524897 | 2.255156721 | 0.156751468 | 0.274745466 | -0.7386 | MAPRE1 | 1.87E-55 | 1.826482539 | 2.685956009 | 0.249315068 | 0.374386654 | -0.5564 |
| SEC11A | 7.16E-84 | 1.812063627 | 3.021150592 | 0.223287671 | 0.376349362 | -0.7375 | DUSP4 | 8.08E-45 | 1.411233741 | 2.074697268 | 0.187084149 | 0.290284593 | -0.5559 |
| CSTB | 3.85E-86 | 1.577670456 | 2.630013147 | 0.234637965 | 0.391658489 | -0.7373 | ATG3 | 1.33E-78 | 2.469354055 | 3.629927464 | 0.334637965 | 0.493228656 | -0.5558 |
| ETFB | 1.71E-63 | 1.227911717 | 2.046717841 | 0.152054795 | 0.270559372 | -0.7371 | SRGAP2 | 9.38E-41 | 1.596787331 | 2.346793545 | 0.210567515 | 0.311776251 | -0.5555 |
| DBI | 2.28E-87 | 1.996634143 | 3.326448161 | 0.232876712 | 0.39077527 | -0.7364 | ATP6V0D1 | 7.74E-61 | 1.597686376 | 2.344584438 | 0.253816047 | 0.385868499 | -0.5533 |
| GRN | 4.21E-45 | 1.514007222 | 2.520805477 | 0.175342466 | 0.277037 | -0.7355 | NELFCD | 1.67E-40 | 1.835699294 | 2.692707218 | 0.247162427 | 0.352306183 | -0.5527 |
| ELOVL1 | 9.44E-65 | 1.348117619 | 2.240895808 | 0.168297456 | 0.291658489 | -0.7331 | LRPAP1 | 2.43E-52 | 1.636927805 | 2.400236419 | 0.201174168 | 0.31609421 | -0.5522 |
| UBE2L3 | 1.26E-101 | 1.811664405 | 3.010482133 | 0.238551859 | 0.410991168 | -0.7327 | SLC25A39 | 3.45E-50 | 1.708756063 | 2.503393901 | 0.225244618 | 0.340824338 | -0.5509 |
| PSMB3 | 6.98E-122 | 2.537374428 | 4.216304944 | 0.288258317 | 0.484396467 | -0.7326 | C14orf166 | 4.22E-58 | 1.488180264 | 2.175633856 | 0.180039139 | 0.279489696 | -0.5509 |
| NDUFB7 | 1.06E-63 | 1.467364858 | 2.428996827 | 0.176125245 | 0.299901865 | -0.7271 | SNRPB2 | 6.19E-79 | 2.661937112 | 3.211077368 | 0.261252446 | 0.393228656 | -0.5505 |
| DOK2 | 3.48E-102 | 2.075998091 | 3.434995984 | 0.250097847 | 0.424253857 | -0.7265 | CHMP4A | 7.94E-60 | 1.779593427 | 2.606084075 | 0.235420744 | 0.364084434 | -0.5503 |
| SEC61G | 1.15E-66 | 1.558491233 | 2.544376225 | 0.187279843 | 0.316388616 | -0.7258 | SFT2D1 | 1.17E-54 | 2.0263014 | 2.967112119 | 0.246183953 | 0.369872424 | -0.5502 |
| IGFLR1 | 7.15E-86 | 1.927914089 | 3.187751194 | 0.226614481 | 0.382139352 | -0.7255 | CASP4 | 2.94E-47 | 1.697558219 | 2.484717431 | 0.21702544 | 0.327772326 | -0.5496 |
| ATP5H | 9.49E-72 | 1.716160763 | 2.826487301 | 0.205283757 | 0.342983317 | -0.7198 | NME1-NME2 | 4.68E-71 | 2.66902848 | 3.906028248 | 0.321722114 | 0.471442591 | -0.5494 |
| COPZ1 | 3.01E-85 | 1.855234152 | 3.051188527 | 0.218590998 | 0.37232581 | -0.7178 | FAM96B | 7.28E-69 | 2.595755028 | 3.798697123 | 0.292795295 | 0.437880275 | -0.5494 |
| ATP6V1F | 3.87E-70 | 1.792661754 | 2.947324786 | 0.210176125 | 0.346908734 | -0.7173 | FDFT1 | 8.90E-59 | 2.135260187 | 3.124325994 | 0.252250489 | 0.381648675 | -0.5491 |
| BNIP3L | 4.41E-56 | 1.253003626 | 2.05842955 | 0.164774951 | 0.277723258 | -0.7162 | SLC25A39 | 1.94E-53 | 1.751753286 | 2.561679345 | 0.216829746 | 0.335328754 | -0.5483 |
| NUTF2 | 5.21E-68 | 1.418983233 | 2.320652089 | 0.178864971 | 0.307850834 | -0.7097 | LMAN2 | 9.11E-43 | 1.488180264 | 2.175633856 | 0.180039139 | 0.279489696 | -0.5479 |
| AKR1A1 | 8.17E-49 | 1.294003494 | 2.113973959 | 0.15146771 | 0.253287537 | -0.7081 | MDH1 | 1.49E-56 | 2.159071577 | 3.155077466 | 0.248923679 | 0.375368008 | -0.5473 |
| MDH2 | 2.62E-89 | 1.881179422 | 3.062693449 | 0.240900196 | 0.401864573 | -0.7032 | RHBDD2 | 4.59E-48 | 1.83720283 | 2.684039216 | 0.234050881 | 0.347988224 | -0.5469 |
| VAMP8 | 2.31E-93 | 2.227780803 | 3.622727675 | 0.25890411 | 0.426202159 | -0.7015 | ARPC5L | 1.85E-40 | 1.410830582 | 2.058636406 | 0.195694716 | 0.294406281 | -0.5457 |
| ROMO1 | 1.27E-62 | 1.261924135 | 2.051824935 | 0.152641584 | 0.259175662 | -0.7013 | TBCA | 6.19E-39 | 1.424502166 | 2.079241489 | 0.177886497 | 0.271933268 | -0.5456 |
| CXCR3 | 4.85E-69 | 1.735693895 | 2.818283904 | 0.209393346 | 0.344749755 | -0.6993 | EBP | 1.03E-35 | 1.455331933 | 2.1216066 | 0.171232877 | 0.259764475 | -0.5438 |
| SAMHD1 | 2.91E-72 | 1.626140311 | 2.639789163 | 0.230528376 | 0.37252208 | -0.6990 | SEC14L1 | 7.87E-45 | 1.414991413 | 2.061812909 | 0.191976517 | 0.295976447 | -0.5431 |
| NUCB1 | 3.94E-113 | 2.007036656 | 3.256525129 | 0.270254403 | 0.457016683 | -0.6983 | EIF2S2 | 1.74E-57 | 1.575000588 | 2.294852147 | 0.253424658 | 0.381452404 | -0.5430 |
| ACTN4 | 4.27E-112 | 2.003257236 | 3.249359968 | 0.281017613 | 0.468007851 | -0.6978 | CST7 | 5.56E-104 | 4.008575403 | 5.839681355 | 0.418395303 | 0.603336605 | -0.5428 |
| ZYX | 4.38E-89 | 1.593372605 | 2.583501132 | 0.240313112 | 0.400981354 | -0.6972 | STARD7 | 2.56E-66 | 1.818963736 | 2.6485082 | 0.272407045 | 0.412757605 | -0.5421 |
| FLOT1 | 6.28E-54 | 1.290240197 | 2.091419648 | 0.167514677 | 0.278606477 | -0.6968 | SOD2 | 3.98E-28 | 1.601534898 | 2.331465365 | 0.205870841 | 0.287536801 | -0.5418 |
| BLOC1S1 | 2.55E-66 | 1.611287393 | 2.609882868 | 0.193933464 | 0.323748773 | -0.6958 | SPN | 3.25E-48 | 1.664731987 | 2.423090079 | 0.232289628 | 0.346221786 | -0.5416 |
| STAT1 | 4.08E-175 | 3.219146712 | 5.213467124 | 0.417221135 | 0.656624141 | -0.6952 | FAM32A | 1.12E-41 | 1.526685029 | 2.221696075 | 0.185518591 | 0.287046124 | -0.5413 |
| VIMP | 6.60E-60 | 1.370615426 | 2.215374882 | 0.170058708 | 0.28842002 | -0.6932 | SEC11C | 6.61E-42 | 1.738577909 | 2.528897637 | 0.2037182 | 0.305593719 | -0.5406 |
| PAM | 1.67E-57 | 1.28291235 | 2.073551864 | 0.171624266 | 0.287536801 | -0.6927 | TNFRSF1B | 8.77E-101 | 2.773295292 | 4.032776047 | 0.362426614 | 0.544160942 | -0.5402 |
| NUDT21 | 1.95E-66 | 1.534853476 | 2.480580337 | 0.191389432 | 0.320902846 | -0.6926 | POLR2E | 1.30E-62 | 2.210020053 | 3.213015133 | 0.28590998 | 0.423258096 | -0.5399 |
| MYO1G | 2.54E-73 | 1.624594799 | 2.621995609 | 0.233072407 | 0.376643768 | -0.6906 | NDUFA13 | 6.43E-87 | 3.080454379 | 4.478465372 | 0.357338552 | 0.525515211 | -0.5399 |
| C17orf49 | 2.06E-88 | 2.1470615 | 3.465120284 | 0.245988258 | 0.406771344 | -0.6905 | OSTC | 2.09E-41 | 1.636289987 | 2.378072269 | 0.201174168 | 0.301962709 | -0.5394 |

TABLE 5-continued

| GeneName | P-value | mean exp in R | mean exp in NR | % in R | % in NR | log2(R/NR) | GeneName | P-value | mean exp in R | mean exp in NR | % in R | % in NR | log2(R/NR) |
|---|---|---|---|---|---|---|---|---|---|---|---|---|---|
| GTF2A2 | 8.51E-46 | 1.291329708 | 2.083248968 | 0.147358121 | 0.244651619 | -0.6900 | UFC1 | 3.40E-53 | 1.900381493 | 2.761257513 | 0.225048924 | 0.344357213 | -0.5390 |
| HIST2H2AA4 | 3.42E-65 | 1.62102739 | 2.615123423 | 0.192759295 | 0.321197252 | -0.6900 | C18orf32 | 3.69E-41 | 1.470983154 | 2.136809024 | 0.175146771 | 0.271736997 | -0.5387 |
| C19orf10 | 2.19E-65 | 1.55602868 | 2.510211785 | 0.200587084 | 0.330520118 | -0.6899 | SRP19 | 1.37E-33 | 1.381728576 | 2.006858213 | 0.174363992 | 0.260353288 | -0.5385 |
| ABI3 | 3.02E-51 | 1.273931631 | 2.052517581 | 0.17260274 | 0.281354269 | -0.6881 | C14orf2 | 1.86E-49 | 1.849955881 | 2.686458384 | 0.222113503 | 0.336310108 | -0.5382 |
| TRAPPC5 | 2.57E-50 | 1.248130735 | 2.010460463 | 0.151076321 | 0.254563297 | -0.6878 | UQCR11 | 1.00E-77 | 2.450119094 | 3.55671787 | 0.319765166 | 0.476545633 | -0.5377 |
| PSMC4 | 4.15E-53 | 1.266475368 | 2.036536064 | 0.156360078 | 0.264180569 | -0.6853 | PDCD6 | 1.40E-40 | 1.752876152 | 2.544398287 | 0.2174168 | 0.319234544 | -0.5376 |
| NDUFC2 | 8.86E-78 | 1.934442192 | 3.109172729 | 0.226614481 | 0.373895976 | -0.6846 | AP2M1 | 5.67E-70 | 2.243646429 | 3.254494646 | 0.28590998 | 0.431697743 | -0.5366 |
| HN1 | 3.36E-68 | 1.742967474 | 2.801062863 | 0.203913894 | 0.337487733 | -0.6844 | PPP1CA | 2.61E-110 | 3.542087134 | 5.137175959 | 0.411285714 | 0.604906771 | -0.5364 |
| SNRPD3 | 4.95E-66 | 1.551930033 | 2.490946015 | 0.207436399 | 0.339254171 | -0.6826 | ATP6AP2 | 1.28E-57 | 2.076934622 | 3.010873662 | 0.260665362 | 0.389597645 | -0.5357 |
| CMC1 | 2.20E-42 | 1.24635241 | 2.000456217 | 0.146379648 | 0.239352306 | -0.6826 | SSR3 | 3.23E-60 | 2.38146269 | 3.449707614 | 0.330332681 | 0.46807851 | -0.5346 |
| RAB27A | 3.63E-64 | 1.75223614 | 2.811528835 | 0.235616438 | 0.369381747 | -0.6822 | UNC13D | 2.12E-43 | 1.399377817 | 2.027070952 | 0.197260274 | 0.300196271 | -0.5346 |
| NDUFA6 | 9.95E-83 | 1.9121482 | 3.064326825 | 0.236594912 | 0.390382728 | -0.6804 | FERMT3 | 4.68E-65 | 2.416923975 | 3.497174375 | 0.292367906 | 0.433071639 | -0.5333 |
| POMP | 1.22E-105 | 2.183841496 | 3.499591321 | 0.335029354 | 0.520215898 | -0.6803 | ARHGAP1 | 1.35E-56 | 1.438764431 | 2.082036838 | 0.238943249 | 0.364180569 | -0.5332 |
| PFKP | 1.25E-65 | 1.462573605 | 2.342123701 | 0.198825832 | 0.32875368 | -0.6794 | EIF3I | 5.12E-55 | 2.031993341 | 2.940346899 | 0.247553816 | 0.371932268 | -0.5331 |
| ATP5G3 | 1.46E-102 | 2.557809892 | 4.094370323 | 0.292759295 | 0.472129539 | -0.6787 | CECR1 | 7.73E-46 | 1.522110632 | 2.200790839 | 0.198043053 | 0.304317959 | -0.5319 |
| TMEM179B | 3.61E-55 | 1.490689438 | 2.384152284 | 0.179060565 | 0.293719333 | -0.6775 | MRPS6 | 2.15E-49 | 2.118526879 | 3.058838249 | 0.258317025 | 0.376643768 | -0.5299 |
| APOL2 | 2.52E-49 | 1.309469004 | 2.093070449 | 0.15890411 | 0.262806673 | -0.6766 | DNPH1 | 2.35E-37 | 1.554209892 | 2.244003976 | 0.180039139 | 0.272227674 | -0.5299 |
| IRF7 | 1.14E-56 | 1.52817564 | 2.441759251 | 0.204892368 | 0.325151211 | -0.6761 | DCXR | 5.17E-47 | 1.963483091 | 2.834656427 | 0.233463796 | 0.346025515 | -0.5298 |
| CNIH1 | 1.07E-51 | 1.322861705 | 2.106205977 | 0.161448141 | 0.268694799 | -0.6710 | PSMF1 | 7.85E-63 | 2.414674743 | 3.485419989 | 0.2962818 | 0.434739941 | -0.5295 |
| DYNLRB1 | 5.77E-68 | 1.696766307 | 2.701256569 | 0.207632094 | 0.341609421 | -0.6708 | SNRPG | 1.13E-43 | 1.896120791 | 2.734222101 | 0.234833659 | 0.343081452 | -0.5281 |
| APOL2 | 9.23E-106 | 1.921882275 | 3.056362968 | 0.292759295 | 0.475171737 | -0.6693 | CNDP2 | 5.21E-46 | 1.741016257 | 2.509372113 | 0.216242661 | 0.32531894 | -0.5274 |
| TKT | 2.09E-58 | 1.569007016 | 2.494917602 | 0.197847358 | 0.319430815 | -0.6691 | ANXA11 | 6.36E-65 | 2.142825583 | 3.087794303 | 0.284735812 | 0.424631992 | -0.5271 |
| DCTN2 | 1.05E-54 | 1.435568143 | 2.280425351 | 0.184148728 | 0.299116781 | -0.6677 | SLMO2 | 1.45E-65 | 2.008723235 | 2.894532759 | 0.282778865 | 0.423258096 | -0.5271 |
| GSDMD | 2.47E-62 | 1.702681197 | 2.704585935 | 0.201369863 | 0.328066732 | -0.6676 | C16orf13 | 3.60E-37 | 1.485867071 | 2.141105903 | 0.181800391 | 0.273895976 | -0.5271 |
| STOM | 7.50E-99 | 2.17069933 | 3.444828508 | 0.270841487 | 0.444651619 | -0.6663 | CAPN2 | 7.67E-64 | 2.09445037 | 3.01783551 | 0.284148728 | 0.422767419 | -0.5269 |
| CTSD | 4.88E-137 | 3.168315764 | 5.027399787 | 0.378473581 | 0.591265947 | -0.6661 | BSG | 1.31E-87 | 2.521876439 | 3.633393792 | 0.359686888 | 0.528655545 | -0.5268 |
| KDELR2 | 6.57E-69 | 1.53396517 | 2.430293933 | 0.21037182 | 0.345731109 | -0.6639 | LAMTOR5 | 4.68E-44 | 1.860021706 | 2.67880693 | 0.21037182 | 0.315996075 | -0.5263 |
| ATP5J | 4.43E-62 | 1.679760337 | 2.660460094 | 0.204305284 | 0.331207066 | -0.6635 | SIVA1 | 1.56E-35 | 1.673539324 | 2.409660697 | 0.220935421 | 0.295682041 | -0.5259 |
| RPS27L | 2.94E-55 | 1.436418283 | 2.27488032 | 0.182778865 | 0.298233562 | -0.6633 | TRAPPC1 | 2.21E-52 | 1.984435075 | 2.857244851 | 0.295303327 | 0.442296369 | -0.5259 |
| PSME2 | 1.92E-179 | 4.102563548 | 6.493552507 | 0.459099804 | 0.698429833 | -0.6625 | TMCO1 | 1.06E-47 | 1.896479686 | 2.729765327 | 0.227984344 | 0.340726202 | -0.5255 |
| NDUFB10 | 1.28E-100 | 1.808373011 | 2.859634497 | 0.263992172 | 0.438665358 | -0.6612 | PSMD13 | 2.76E-54 | 2.145791417 | 3.087878157 | 0.261252446 | 0.386162905 | -0.5251 |
| DRAP1 | 5.21E-52 | 1.486080704 | 2.350113406 | 0.182778865 | 0.294308145 | -0.6612 | PSMB1 | 1.02E-79 | 3.196722383 | 4.600145411 | 0.374755382 | 0.536113837 | -0.5251 |
| DECR1 | 3.67E-54 | 1.517312102 | 2.396356093 | 0.188258317 | 0.303336605 | -0.6593 | RSU1 | 7.79E-38 | 1.423286225 | 2.04791592 | 0.186497065 | 0.280274779 | -0.5249 |
| GSTP1 | 1.93E-93 | 2.673973655 | 4.222755796 | 0.297651663 | 0.46889107 | -0.6592 | NDUFA1 | 1.04E-58 | 2.269708231 | 3.265619634 | 0.290019569 | 0.423061825 | -0.5248 |
| TMED9 | 3.37E-56 | 1.442778538 | 2.277470639 | 0.182191781 | 0.298626104 | -0.6586 | TUBB | 1.75E-56 | 2.738605268 | 3.938452238 | 0.331506849 | 0.464671246 | -0.5242 |
| MGAT1 | 3.10E-72 | 1.878926707 | 2.963338636 | 0.2481409 | 0.392443572 | -0.6573 | DCTN1 | 5.26E-43 | 1.423097309 | 2.046352846 | 0.188649706 | 0.289793916 | -0.5240 |
| HSPB1 | 2.41E-55 | 1.436418283 | 2.971508844 | 0.240313112 | 0.386047988 | -0.6558 | SH3GLB1 | 7.29E-68 | 1.612674149 | 2.318132022 | 0.215459883 | 0.3242393945 | -0.5235 |
| COX8A | 8.81E-101 | 2.80361128 | 4.414109291 | 0.318590998 | 0.698429833 | -0.6548 | BCAP31 | 2.84E-71 | 2.5215066 | 3.623322968 | 0.306849315 | 0.455740922 | -0.5230 |
| ZEB2 | 3.94E-81 | 1.884659712 | 2.96613652 | 0.249510763 | 0.40343474 | -0.6543 | RITFDC1 | 7.09E-54 | 1.967014513 | 2.825917922 | 0.241682975 | 0.363886163 | -0.5227 |
| ILK | 4.10E-60 | 1.521718289 | 2.392781394 | 0.191585127 | 0.314131501 | -0.6530 | UFD1L | 5.86E-37 | 1.546084188 | 2.221033209 | 0.206066536 | 0.301373896 | -0.5226 |
| PSMB6 | 6.77E-91 | 2.407560648 | 3.782346578 | 0.283573739 | 0.451226693 | -0.6517 | GPI | 1.03E-94 | 3.491315947 | 5.014416983 | 0.419178082 | 0.595682041 | -0.5223 |
| HK1 | 1.33E-60 | 1.370965451 | 2.153318838 | 0.18630137 | 0.308537782 | -0.6514 | DNAJB11 | 1.90E-61 | 2.135479381 | 3.065145007 | 0.277495108 | 0.41265947 | -0.5214 |
| CD58 | 1.37E-60 | 1.571247332 | 2.467144979 | 0.194520548 | 0.318056919 | -0.6509 | SNX17 | 1.17E-59 | 2.133057713 | 3.060370451 | 0.254794521 | 0.385574092 | -0.5208 |
| TMX1 | 8.53E-76 | 1.553871494 | 2.439657333 | 0.216438356 | 0.360157017 | -0.6508 | SH2D2A | 1.81E-70 | 2.521237731 | 3.615695164 | 0.363405088 | 0.514425908 | -0.5201 |
| GZMA | 5.83E-97 | 3.123928747 | 4.903783134 | 0.314285714 | 0.490088322 | -0.6505 | C1orf43 | 1.97E-52 | 2.009510356 | 2.879724690 | 0.250880626 | 0.372423945 | -0.5192 |
| SRI | 3.66E-75 | 2.030856836 | 3.186998687 | 0.232289628 | 0.377625123 | -0.6501 | BUD31 | 3.75E-51 | 2.148078561 | 3.078494775 | 0.249706458 | 0.369381747 | -0.5192 |
| PSMG2 | 8.91E-53 | 1.451638916 | 2.276884041 | 0.177103718 | 0.28861629 | -0.6494 | PSTPIP1 | 9.64E-64 | 2.458658944 | 3.523003726 | 0.285714286 | 0.424435721 | -0.5189 |
| ARL8B | 5.95E-62 | 1.560122287 | 2.443613081 | 0.204305284 | 0.333101079 | -0.6491 | CTSA | 2.54E-46 | 1.808691027 | 2.591473043 | 0.216438356 | 0.325907753 | -0.5188 |
| NKG7 | 7.00E-120 | 4.043880904 | 6.338719747 | 0.373581213 | 0.572423945 | -0.6485 | TPST2 | 8.97E-38 | 1.452481743 | 2.080885706 | 0.181996086 | 0.275073602 | -0.5187 |
| GPX1 | 8.45E-53 | 1.899690952 | 2.975925978 | 0.234246575 | 0.354268891 | -0.6476 | MPV17 | 1.43E-33 | 1.407045512 | 2.015361459 | 0.164774951 | 0.249165849 | -0.5184 |

TABLE 5-continued

| GeneName | P-value | mean exp in R | mean exp in NR | % in R | % in NR | log2(R/NR) | GeneName | P-value | mean exp in R | mean exp in NR | % in R | % in NR | log2(R/NR) |
|---|---|---|---|---|---|---|---|---|---|---|---|---|---|
| ACP5 | 3.77E-49 | 1.491576414 | 2.334407608 | 0.177690802 | 0.284887144 | -0.6462 | APMAP | 3.57E-60 | 2.128059425 | 3.045031346 | 0.263405088 | 0.395682041 | -0.5169 |
| CHP1 | 7.06E-113 | 2.3919615 | 3.742953177 | 0.330528376 | 0.5218842 | -0.6460 | CMC2 | 2.65E-43 | 1.810994236 | 2.591294145 | 0.230136986 | 0.337291462 | -0.5169 |
| GPR171 | 2.57E-45 | 1.323280611 | 2.070529179 | 0.155968689 | 0.254465162 | -0.6459 | UQCRQ | 6.75E-65 | 2.618936974 | 3.746375317 | 0.306066536 | 0.447693817 | -0.5165 |
| ATP6V0B | 1.39E-68 | 2.061834134 | 3.226016379 | 0.238747554 | 0.377821394 | -0.6458 | TBCB | 1.49E-60 | 2.337399793 | 3.329902089 | 0.264774951 | 0.39764475 | -0.5106 |
| KLRD1 | 8.31E-43 | 1.5267059 | 2.387683815 | 0.170450098 | 0.268302257 | -0.6452 | C9orf16 | 1.57E-53 | 2.114784651 | 3.010928672 | 0.266927593 | 0.391462218 | -0.5097 |
| H2AFY | 2.44E-71 | 1.511543386 | 2.363938013 | 0.224853229 | 0.365161923 | -0.6452 | PARK7 | 4.28E-93 | 3.752065549 | 5.335504103 | 0.423874755 | 0.598724239 | -0.5079 |
| PPM1G | 4.40E-71 | 1.69538119 | 2.648519241 | 0.217221135 | 0.356035329 | -0.6436 | ATP5EP2 | 9.45E-66 | 1.51807885 | 2.158163562 | 0.30665362 | 0.44936212 | -0.5076 |
| PRDX5 | 5.89E-87 | 2.306233565 | 3.602074692 | 0.272994129 | 0.435426889 | -0.6433 | SHISA5 | 2.68E-84 | 3.079208531 | 4.376634686 | 0.37553816 | 0.541609421 | -0.5073 |
| PSMA5 | 2.63E-88 | 2.48220867 | 3.876414887 | 0.305675147 | 0.472423945 | -0.6431 | SMC4 | 1.21E-33 | 1.520154547 | 2.160502593 | 0.188454012 | 0.276447498 | -0.5071 |
| FBXW5 | 1.51E-54 | 1.284173207 | 2.005393232 | 0.173189824 | 0.286064769 | -0.6430 | TAP1 | 5.12E-120 | 3.8947457 | 5.535072219 | 0.481017613 | 0.676741904 | -0.5071 |
| ATP6AP1 | 1.94E-54 | 1.573179959 | 2.454735169 | 0.200391389 | 0.317664377 | -0.6419 | SCAND1 | 3.08E-49 | 1.914437731 | 2.720567597 | 0.242661448 | 0.359077527 | -0.5070 |
| CD4 | 6.77E-51 | 1.672169838 | 2.608131586 | 0.207827789 | 0.3218842 | -0.6413 | SIRPG | 1.65E-40 | 2.062993141 | 2.93125778 | 0.245596869 | 0.350539745 | -0.5068 |
| SNRPD1 | 3.30E-53 | 1.482262224 | 2.310551165 | 0.18630137 | 0.299803729 | -0.6404 | HDLBP | 1.59E-44 | 1.741505379 | 2.473899587 | 0.244618395 | 0.355053974 | -0.5065 |
| XAF1 | 9.54E-78 | 1.97726183 | 3.07900945 | 0.287671233 | 0.442100098 | -0.6390 | EMC4 | 9.20E-42 | 1.886672282 | 2.682920388 | 0.229745597 | 0.334739941 | -0.5064 |
| LY6E | 1.02E-148 | 3.020888118 | 4.700243222 | 0.402739726 | 0.624141315 | -0.6378 | FIS1 | 1.12E-38 | 1.645813657 | 2.337546143 | 0.198043053 | 0.294602552 | -0.5062 |
| DYNLT1 | 5.75E-58 | 1.784406761 | 2.775984229 | 0.204305284 | 0.32639843 | -0.6376 | TPI1 | 1.02E-112 | 4.674884748 | 6.639388334 | 0.508414873 | 0.696172718 | -0.5061 |
| AK2 | 2.00E-63 | 1.565549988 | 2.435278628 | 0.2037182 | 0.331992149 | -0.6374 | GOLGA7 | 3.63E-41 | 1.531938507 | 2.17560387 | 0.191780822 | 0.290873405 | -0.5061 |
| PSMA2 | 1.94E-104 | 2.554746633 | 3.973163344 | 0.328571429 | 0.512266928 | -0.6371 | POLR2J | 1.24E-31 | 1.558193147 | 2.212194482 | 0.2037182 | 0.290677134 | -0.5056 |
| YIPF3 | 1.27E-49 | 1.31822827 | 2.048333555 | 0.15851272 | 0.262708538 | -0.6359 | EIF2S1 | 3.71E-33 | 1.422118051 | 2.018862818 | 0.18630137 | 0.273307164 | -0.5055 |
| S100A10 | 9.45E-92 | 3.032387325 | 4.710687854 | 0.33111546 | 0.502944063 | -0.6355 | UBA3 | 8.86E-37 | 1.504187953 | 2.134484549 | 0.195499022 | 0.289106968 | -0.5049 |
| SCP2 | 3.67E-69 | 1.928608468 | 2.992636411 | 0.228767123 | 0.367222767 | -0.6339 | P4HB | 8.31E-73 | 2.868636442 | 4.070049518 | 0.340900196 | 0.493621197 | -0.5047 |
| MRPS34 | 3.99E-54 | 1.501805867 | 2.330021521 | 0.180430528 | 0.294111874 | -0.6336 | UQCRH | 1.94E-54 | 2.506405902 | 3.554712654 | 0.286692759 | 0.414131501 | -0.5041 |
| PSMD4 | 3.86E-72 | 2.041963977 | 3.167998122 | 0.236399217 | 0.379097154 | -0.6336 | CSNK2B | 8.75E-67 | 2.778875986 | 3.939584604 | 0.327592955 | 0.472816487 | -0.5035 |
| CDC123 | 1.47E-42 | 1.308443983 | 2.029550379 | 0.164579256 | 0.261133521 | -0.6333 | SZRD1 | 2.12E-48 | 1.458534537 | 2.134484549 | 0.22035225 | 0.334249264 | -0.5035 |
| BTG3 | 4.41E-58 | 1.520410061 | 2.358217916 | 0.198434442 | 0.319725221 | -0.6332 | NDUFA3 | 7.18E-46 | 2.038760759 | 2.888862094 | 0.251076321 | 0.363984298 | -0.5028 |
| TMEM258 | 2.01E-66 | 1.806607231 | 2.799756052 | 0.216634051 | 0.350343474 | -0.6320 | ATP5O | 6.26E-52 | 2.349668535 | 3.329290024 | 0.27553816 | 0.398822375 | -0.5028 |
| TSPO | 1.19E-91 | 2.726917293 | 4.224532226 | 0.306457926 | 0.476545633 | -0.6315 | DERL2 | 7.82E-31 | 1.455107797 | 2.060834358 | 0.176908023 | 0.259175662 | -0.5021 |
| SDHB | 6.97E-48 | 1.548778418 | 2.398980945 | 0.186888454 | 0.294013739 | -0.6313 | COPS6 | 8.06E-48 | 2.011484576 | 2.847711369 | 0.229158513 | 0.342198234 | -0.5015 |
| TCEB1 | 1.80E-53 | 1.34856019 | 2.088595179 | 0.177299413 | 0.289597645 | -0.6311 | COPE | 5.72E-100 | 3.36006141 | 4.756847292 | 0.421917808 | 0.603283469 | -0.5015 |
| WDR83OS | 6.81E-69 | 2.070996695 | 3.206339664 | 0.245988258 | 0.386359176 | -0.6306 | SNX6 | 1.75E-50 | 2.029351246 | 2.87267879 | 0.260273973 | 0.380274779 | -0.5014 |
| HCST | 6.09E-128 | 3.21655223 | 4.970230951 | 0.353620352 | 0.558684985 | -0.6278 | FLI1 | 8.24E-65 | 2.558165841 | 3.620738307 | 0.329158513 | 0.472129539 | -0.5012 |
| NAA10 | 9.16E-48 | 1.337517816 | 2.065225491 | 0.160665362 | 0.263002944 | -0.6267 | ERGIC3 | 1.33E-51 | 2.125059351 | 3.006479234 | 0.251272016 | 0.371736997 | -0.5006 |
| CTSB | 1.29E-75 | 3.031906699 | 4.68108984 | 0.3555772999 | 0.511972522 | -0.6266 | PLAC8 | 3.41E-37 | 2.356427964 | 1.649322516 | 0.281017613 | 0.189303238 | 0.5147 |
| YARS | 5.53E-56 | 1.507782384 | 2.326179183 | 0.197651663 | 0.316388616 | -0.6255 | LTB | 4.66E-41 | 3.101733281 | 2.130158423 | 0.354794521 | 0.249852797 | 0.5421 |
| GLRX | 7.33E-47 | 1.392144717 | 2.14726283 | 0.173972603 | 0.277625123 | -0.6252 | LY9 | 5.25E-35 | 2.813385319 | 1.822304404 | 0.333268102 | 0.238272816 | 0.6265 |
| RBCK1 | 2.05E-73 | 1.995075124 | 3.076310905 | 0.253816047 | 0.400098135 | -0.6248 | SELL | 9.52E-60 | 3.368380986 | 2.130479166 | 0.38258317 | 0.253581943 | 0.6609 |
| RBX1 | 8.52E-72 | 1.80373095 | 2.779282141 | 0.252641879 | 0.397055937 | -0.6237 | TCF7 | 8.03E-50 | 2.282517828 | 1.421882044 | 0.332876712 | 0.220215898 | 0.6828 |
|  |  |  |  |  |  |  | IGKC | 1.96E-44 | 2.076937956 | 1.105789635 | 0.211741683 | 0.123650638 | 0.9094 |
|  |  |  |  |  |  |  | CCR7 | 8.92E-148 | 2.670754564 | 1.040310568 | 0.297064579 | 0.121982336 | 1.3602 |

TABLE 6

| CD8_B | | | | CD8_G | | | |
|---|---|---|---|---|---|---|---|
| GeneName | P-value | Mean expression G1 | Mean expression G2 | GeneName | P-value | Mean expression G2 | Mean expression G1 |
| CD38 | 2.45E-297 | 4.503877948 | 1.067546812 | IL7R | 4.45E-217 | 4.032099183 | 0.82470727 |
| CCL3 | 1.08E-189 | 4.490273548 | 1.162498 | GPR183 | 6.53E-64 | 2.140831891 | 0.640823245 |
| STMN1 | 1.02E-82 | 2.306672782 | 0.627967181 | LMNA | 4.70E-72 | 2.280851687 | 0.746486735 |
| MYO7A | 7.55E-130 | 2.150132553 | 0.587955869 | NR4A3 | 5.45E-80 | 2.171854112 | 0.71446374 |
| GOLIM4 | 1.39E-193 | 2.474678345 | 0.724612237 | TCF7 | 1.22E-99 | 2.67922891 | 0.945088234 |
| VCAM1 | 9.48E-152 | 3.278485922 | 0.967664744 | MGAT4A | 2.63E-40 | 2.074649553 | 0.972061001 |
| WARS | 1.67E-151 | 3.549322801 | 1.056419085 | CD55 | 2.02E-62 | 3.611008837 | 1.731567098 |
| HAVCR2 | 6.33E-277 | 5.240416049 | 1.561981086 | AIM1 | 3.33E-31 | 2.221582511 | 1.204797635 |
| LGALS9 | 2.21E-92 | 2.00800184 | 0.600009745 | PER1 | 3.81E-46 | 3.370857406 | 1.90500073 |
| ID3 | 5.82E-87 | 2.012380498 | 0.605569109 | FOSL2 | 1.90E-50 | 3.389389476 | 1.995926462 |
| PRDX3 | 9.43E-156 | 3.321987666 | 1.007631697 | EGR1 | 1.99E-19 | 2.316122377 | 1.399420975 |
| MCM5 | 3.21E-101 | 2.526148252 | 0.776346958 | TSPYL2 | 6.35E-28 | 3.842494104 | 2.327893495 |
| LSM2 | 4.50E-120 | 2.664535289 | 0.823047531 | YPEL5 | 2.28E-41 | 5.890086333 | 3.80231451 |
| MTHFD1 | 3.37E-97 | 2.230218039 | 0.690497842 | CSRNP1 | 6.49E-15 | 2.359107803 | 1.542059683 |
| FASLG | 1.88E-117 | 2.741295656 | 0.866626195 | REL | 5.86E-20 | 2.71949729 | 1.780867484 |
| SNAP47 | 1.65E-174 | 3.769141235 | 1.224212618 | SKIL | 2.61E-22 | 3.266384049 | 2.155358757 |
| IFI35 | 1.13E-91 | 2.43525005 | 0.805054574 | PIK3R1 | 1.90E-15 | 2.952741142 | 1.959612009 |
| SKA2 | 1.45E-115 | 2.515678821 | 0.858582012 | FOXP1 | 3.94E-22 | 2.845200237 | 1.888462587 |
| NDUFB3 | 8.58E-120 | 3.068411059 | 1.059675286 | RGCC | 1.17E-09 | 2.18586806 | 1.463110207 |
| FABP5 | 1.35E-141 | 3.902150107 | 1.354881465 | PFKFB3 | 1.89E-12 | 2.51054407 | 1.694388984 |
| IFI27L2 | 3.19E-96 | 2.43103298 | 0.853275802 | MYADM | 1.01E-22 | 4.463153142 | 3.02595635 |
| PTTG1 | 3.55E-83 | 2.427179679 | 0.854702167 | ZFP36L2 | 2.53E-54 | 6.249733989 | 4.243453221 |
| ENTPD1 | 6.50E-121 | 2.869960348 | 1.0117944 | USP36 | 8.56E-19 | 3.423887672 | 2.344467909 |
| EPSTI1 | 6.66E-116 | 2.925729029 | 1.035540741 | TC2N | 3.05E-18 | 3.14886233 | 2.158806238 |
| PDCD1 | 6.84E-240 | 5.448490436 | 1.93012534 | FAM177A1 | 1.53E-12 | 3.136884147 | 2.165526181 |
| TRAFD1 | 1.33E-101 | 2.669610001 | 0.947092587 | BTG2 | 1.52E-23 | 4.610064959 | 3.185196999 |
| SIRPG | 1.10E-217 | 5.174793521 | 1.87397397 | TSC22D2 | 5.99E-11 | 2.133916347 | 1.47500329 |
| RGS3 | 7.93E-73 | 2.125645365 | 0.775453366 | FAM65B | 2.02E-11 | 2.291796896 | 1.584523044 |
| UBE2F | 3.45E-95 | 2.883976138 | 1.0539014 | STAT4 | 2.55E-28 | 5.177656351 | 3.582523427 |
| SNRPD1 | 1.71E-99 | 2.8909447 | 1.059663948 | RGPD5 | 2.42E-18 | 4.36502224 | 3.037824875 |
| FIBP | 1.93E-83 | 2.429236471 | 0.892221704 | NEU1 | 2.95E-08 | 2.147711506 | 1.497547611 |
| CLTA | 2.60E-105 | 3.039002863 | 1.122896472 | IFRD1 | 1.90E-14 | 4.199147598 | 2.932395951 |
| CXCL13 | 3.64E-120 | 3.951890716 | 1.460527346 | PDE4B | 1.51E-16 | 3.806892143 | 2.664211096 |
| NMI | 1.29E-82 | 2.176688391 | 0.805571318 | NR4A1 | 3.97E-09 | 2.611477311 | 1.842902699 |
| DNPH1 | 3.84E-79 | 2.381720722 | 0.883250405 | | | | |
| PCNA | 1.06E-61 | 2.182262811 | 0.810186297 | | | | |
| ACP5 | 1.17E-98 | 2.885465491 | 1.073573821 | | | | |
| MRPL28 | 1.51E-71 | 2.024609025 | 0.754615011 | | | | |
| FARSA | 2.49E-73 | 2.001442588 | 0.747150763 | | | | |
| COX5A | 5.98E-157 | 4.676954848 | 1.761865508 | | | | |
| MRPL51 | 7.34E-85 | 2.457427972 | 0.925772862 | | | | |
| SNRPE | 2.44E-75 | 2.404227446 | 0.907001261 | | | | |
| RANBP1 | 2.33E-84 | 2.670265445 | 1.016696907 | | | | |
| NOP10 | 2.34E-97 | 2.939269738 | 1.121937984 | | | | |
| PYCARD | 1.41E-95 | 2.752462272 | 1.051076801 | | | | |
| GTF3C6 | 2.43E-79 | 2.330310059 | 0.898953967 | | | | |
| CCR5 | 9.54E-127 | 3.32856227 | 1.28734614 | | | | |
| GSTO1 | 2.89E-88 | 2.653561322 | 1.027965346 | | | | |
| OAS3 | 1.17E-87 | 2.267550807 | 0.879138328 | | | | |
| IGFLR1 | 1.44E-118 | 3.636915037 | 1.41015425 | | | | |
| HLA-DMA | 2.98E-144 | 4.115547348 | 1.607931363 | | | | |
| STRA13 | 1.95E-63 | 2.095400445 | 0.820913992 | | | | |
| HSD17B10 | 6.03E-69 | 2.108135203 | 0.828597124 | | | | |
| VAMP5 | 1.36E-87 | 2.727461347 | 1.081471049 | | | | |
| NDUFAB1 | 1.62E-72 | 2.286416107 | 0.907988058 | | | | |
| BATF | 1.20E-106 | 3.284547348 | 1.305467896 | | | | |
| NDUFS2 | 2.46E-68 | 2.191532071 | 0.873496229 | | | | |
| C17orf49 | 8.32E-134 | 4.085892692 | 1.629745209 | | | | |
| GNG5 | 1.61E-151 | 4.397466903 | 1.757469193 | | | | |
| PSMB2 | 3.17E-117 | 2.884465746 | 1.155182139 | | | | |
| PDIA6 | 1.40E-148 | 3.943893622 | 1.579997884 | | | | |
| COMMD3 | 6.05E-60 | 2.035170674 | 0.8192485 | | | | |
| CD63 | 4.08E-144 | 4.568304134 | 1.847290214 | | | | |
| PSMA4 | 3.50E-118 | 3.826465017 | 1.551917638 | | | | |
| SAE1 | 2.67E-71 | 2.324560064 | 0.943978493 | | | | |
| ATP5J | 1.44E-104 | 3.193882543 | 1.29742985 | | | | |
| MEA1 | 1.79E-73 | 2.330314867 | 0.949658623 | | | | |
| EXOSC9 | 3.63E-69 | 2.020491198 | 0.824607562 | | | | |
| ARPC5L | 1.04E-111 | 3.068312322 | 1.253247292 | | | | |
| BLOC1S1 | 5.50E-102 | 3.225259843 | 1.318190273 | | | | |
| HELLS | 4.58E-76 | 2.130695664 | 0.871697169 | | | | |
| CXCR6 | 5.36E-126 | 4.305209437 | 1.774354247 | | | | |
| BCAS4 | 6.50E-65 | 2.098722766 | 0.865111332 | | | | |
| ETFB | 6.78E-81 | 2.418481829 | 0.997801189 | | | | |
| TXN2 | 1.99E-66 | 2.306400284 | 0.953598266 | | | | |

TABLE 6-continued

| | CD8_B | | | CD8_G | | | |
|---|---|---|---|---|---|---|---|
| GeneName | P-value | Mean expression G1 | Mean expression G2 | GeneName | P-value | Mean expression G2 | Mean expression G1 |
| PTPN6 | 3.30E−156 | 5.015528117 | 2.077075152 | | | | |
| SIT1 | 1.00E−144 | 4.332124739 | 1.796590741 | | | | |
| FKBP1A | 1.29E−227 | 5.929887981 | 2.462211689 | | | | |
| COPZ1 | 1.12E−107 | 3.528959222 | 1.466159688 | | | | |
| HLA-DRA | 1.57E−195 | 6.430869882 | 2.672266924 | | | | |
| CDC123 | 8.06E−66 | 2.391351443 | 0.996238928 | | | | |
| AP2S1 | 3.62E−82 | 2.615042085 | 1.089662717 | | | | |
| FUT8 | 7.70E−88 | 2.38753102 | 0.995229203 | | | | |
| BST2 | 3.80E−138 | 4.205209714 | 1.757935193 | | | | |
| ATP6V1E1 | 7.69E−66 | 2.184741648 | 0.916464286 | | | | |
| CD2BP2 | 2.25E−131 | 3.693163626 | 1.549681009 | | | | |
| HLA-DQA1 | 6.24E−104 | 3.237470161 | 1.360566264 | | | | |
| ZCRB1 | 1.20E−61 | 2.010211694 | 0.845742982 | | | | |
| MX1 | 1.00E−75 | 2.837779179 | 1.194997598 | | | | |
| TNFRSF9 | 9.68E−106 | 3.467676923 | 1.462547382 | | | | |
| SQRDL | 6.22E−79 | 2.622852717 | 1.106783424 | | | | |
| SERPINB1 | 2.57E−110 | 3.515777369 | 1.483727648 | | | | |
| PHPT1 | 1.48E−65 | 2.194049577 | 0.926881074 | | | | |
| CALM3 | 3.56E−192 | 5.170473018 | 2.185344461 | | | | |
| TOX | 9.95E−158 | 3.545285595 | 1.49868579 | | | | |
| SNRPC | 1.47E−70 | 2.474584608 | 1.046413984 | | | | |
| MRPS34 | 4.95E−84 | 2.768976948 | 1.175826428 | | | | |
| NUTF2 | 2.74E−82 | 2.608754415 | 1.108160937 | | | | |
| NDUFS6 | 2.85E−72 | 2.035602108 | 0.864947239 | | | | |
| PSMB3 | 1.75E−158 | 4.904107876 | 2.08491137 | | | | |
| CHMP2A | 4.84E−81 | 2.857076253 | 1.222009155 | | | | |
| SLC25A11 | 6.27E−61 | 2.027829326 | 0.867613358 | | | | |
| SHFM1 | 9.64E−130 | 3.777245159 | 1.616846165 | | | | |
| TMEM179B | 2.42E−76 | 2.767358685 | 1.18524941 | | | | |
| EIF6 | 2.20E−72 | 2.502067278 | 1.074616725 | | | | |
| ANXA5 | 5.84E−162 | 5.223830407 | 2.244806053 | | | | |
| JAKMIP1 | 1.03E−71 | 2.312789337 | 0.994466875 | | | | |
| TALDO1 | 9.37E−89 | 3.134857922 | 1.349123107 | | | | |
| GLRX3 | 6.48E−57 | 2.089535894 | 0.90076918 | | | | |
| ANAPC11 | 1.04E−80 | 2.8896458 | 1.252200712 | | | | |
| DUT | 4.99E−53 | 2.104622655 | 0.913261117 | | | | |
| PDCD5 | 9.09E−55 | 2.041601583 | 0.885963761 | | | | |
| ATP5G3 | 1.69E−143 | 4.749757651 | 2.062994434 | | | | |
| CHMP5 | 1.42E−65 | 2.186115189 | 0.950427238 | | | | |
| TWF2 | 1.86E−107 | 3.526082815 | 1.536184109 | | | | |
| IDH2 | 4.64E−133 | 4.501434308 | 1.965274937 | | | | |
| MPG | 5.23E−65 | 2.276372945 | 0.994200645 | | | | |
| SNRPF | 7.80E−88 | 2.269196926 | 0.991701642 | | | | |
| NDUFC1 | 2.30E−53 | 2.074849616 | 0.907011779 | | | | |
| GBP1 | 2.07E−117 | 3.524455833 | 1.542528045 | | | | |
| DCTN3 | 1.76E−68 | 2.617143149 | 1.145880627 | | | | |
| ERH | 2.08E−80 | 2.64205175 | 1.161491201 | | | | |
| NDUFA12 | 7.16E−61 | 2.312758316 | 1.017291863 | | | | |
| LIMS1 | 1.13E−64 | 2.066400504 | 0.909789851 | | | | |
| BANF1 | 5.56E−92 | 3.26276779 | 1.436691138 | | | | |
| NDUFC2 | 8.04E−97 | 3.456390807 | 1.527036232 | | | | |
| PSMC3 | 1.79E−73 | 2.746119429 | 1.213266782 | | | | |
| PON2 | 2.47E−62 | 2.403166306 | 1.062325344 | | | | |
| PRDX5 | 1.39E−125 | 4.231392267 | 1.870991009 | | | | |
| TMX1 | 1.34E−101 | 2.956400489 | 1.312311214 | | | | |
| STOML2 | 5.02E−61 | 2.169463241 | 0.963097654 | | | | |
| RPS6KA1 | 5.43E−62 | 2.231976177 | 0.991943879 | | | | |
| PAM | 1.41E−102 | 3.194179878 | 1.420230794 | | | | |
| ATP5J2 | 3.01E−77 | 2.948363375 | 1.311670832 | | | | |
| GIMAP6 | 2.57E−98 | 2.930366838 | 1.304224929 | | | | |
| NDUFB7 | 7.85E−70 | 2.601941528 | 1.158242834 | | | | |
| DBI | 2.97E−96 | 3.575932852 | 1.592327842 | | | | |
| IFI6 | 3.38E−154 | 5.201445339 | 2.318825526 | | | | |
| TSTA3 | 5.78E−63 | 2.319464423 | 1.036532055 | | | | |
| SSNA1 | 7.93E−62 | 2.042647073 | 0.913112139 | | | | |
| ADORA2A | 2.25E−55 | 2.080169228 | 0.930560714 | | | | |
| FDPS | 2.83E−62 | 2.425943892 | 1.086244465 | | | | |
| CYC1 | 1.72E−66 | 2.539964355 | 1.137807765 | | | | |
| PSMD4 | 3.20E−104 | 3.668547931 | 1.646002485 | | | | |
| FAM96A | 1.89E−56 | 2.081417771 | 0.934343428 | | | | |
| OAS2 | 5.39E−90 | 2.878625307 | 1.292503506 | | | | |
| ERCC1 | 1.64E−49 | 2.085642591 | 0.938003773 | | | | |
| PDHB | 2.18E−52 | 2.055225667 | 0.926591496 | | | | |
| CD27 | 3.60E−194 | 6.136699677 | 2.773576115 | | | | |
| SNRPA | 6.25E−61 | 2.067275057 | 0.935086166 | | | | |

TABLE 6-continued

| | CD8_B | | | CD8_G | | | |
|---|---|---|---|---|---|---|---|
| GeneName | P-value | Mean expression G1 | Mean expression G2 | GeneName | P-value | Mean expression G2 | Mean expression G1 |
| UBE2L3 | 9.31E−115 | 3.592859999 | 1.625412091 | | | | |
| MDH1 | 9.43E−99 | 3.721279971 | 1.683801365 | | | | |
| SDHC | 2.76E−63 | 2.347811248 | 1.064694838 | | | | |
| PSMG2 | 2.76E−64 | 2.555665014 | 1.159473162 | | | | |
| C11orf48 | 2.63E−76 | 2.890040778 | 1.313040137 | | | | |
| PSMA2 | 2.43E−158 | 4.802864375 | 2.188108226 | | | | |
| C7orf73 | 2.09E−62 | 2.160459497 | 0.984637314 | | | | |
| MRPS16 | 9.40E−56 | 2.076926967 | 0.948382985 | | | | |
| MCM7 | 2.41E−42 | 2.11796775 | 0.969278006 | | | | |
| SNX20 | 2.36E−59 | 2.087926298 | 0.957095188 | | | | |
| AK2 | 1.15E−75 | 2.611969942 | 1.197612803 | | | | |
| RBBP7 | 1.21E−69 | 2.818309884 | 1.293003788 | | | | |
| TIGIT | 3.77E−190 | 5.930720988 | 2.725798008 | | | | |
| TMPO | 3.11E−79 | 2.779105016 | 1.27759614 | | | | |
| CTSB | 1.01E−83 | 3.306011196 | 1.520579095 | | | | |
| PARP1 | 1.79E−87 | 2.902379776 | 1.33623695 | | | | |
| USB1 | 4.00E−56 | 2.178707226 | 1.003328766 | | | | |
| MRPS7 | 1.90E−51 | 2.0636019 | 0.951959238 | | | | |
| NHP2 | 2.37E−60 | 2.464790149 | 1.137484098 | | | | |
| ATP5I | 2.14E−81 | 3.169807005 | 1.463809999 | | | | |
| PSMC1 | 6.43E−77 | 2.849473341 | 1.317477763 | | | | |
| VDAC1 | 6.12E−86 | 3.404397887 | 1.574958304 | | | | |
| CARD16 | 3.28E−65 | 2.589653803 | 1.198332561 | | | | |
| RNF181 | 2.38E−55 | 2.235233402 | 1.035620008 | | | | |
| PGAM1 | 1.06E−178 | 6.143413578 | 2.855010843 | | | | |
| NT5C | 6.96E−49 | 2.010909629 | 0.935299453 | | | | |
| IRF2 | 9.60E−101 | 3.388234685 | 1.577120507 | | | | |
| NUDT22 | 1.82E−54 | 2.244019782 | 1.045018606 | | | | |
| NDUFA9 | 5.79E−62 | 2.3334169 | 1.08808713 | | | | |
| SRI | 1.91E−100 | 4.000315311 | 1.870272516 | | | | |
| GBP4 | 8.65E−92 | 2.833516253 | 1.325233526 | | | | |
| NDUFS8 | 2.74E−75 | 3.092642125 | 1.446840419 | | | | |
| PSMC2 | 7.23E−49 | 2.012346972 | 0.941902901 | | | | |
| FPGS | 3.10E−62 | 2.264011843 | 1.060107164 | | | | |
| PLSCR1 | 4.91E−51 | 2.23546722 | 1.048506785 | | | | |
| POLR2G | 2.80E−73 | 3.048974111 | 1.430789702 | | | | |
| COX8A | 6.54E−123 | 4.967137562 | 2.331202931 | | | | |
| SLX1B | 5.75E−73 | 2.245393336 | 1.054066173 | | | | |
| TRAPPC1 | 2.17E−124 | 3.492707062 | 1.643504305 | | | | |
| ABI3 | 7.78E−79 | 3.099603274 | 1.461146971 | | | | |
| CBX5 | 7.46E−89 | 2.590646216 | 1.221380459 | | | | |
| PSMD14 | 2.33E−56 | 2.112233684 | 0.999656109 | | | | |
| UBE2L6 | 1.55E−175 | 5.968070327 | 2.832430432 | | | | |
| IFNG | 1.81E−123 | 4.707056597 | 2.234490186 | | | | |
| DECR1 | 4.66E−62 | 2.629425264 | 1.248765457 | | | | |
| ITGB1BP1 | 3.53E−56 | 2.406344071 | 1.143163002 | | | | |
| AKR1B1 | 4.64E−62 | 2.540626941 | 1.209149866 | | | | |
| PSMA5 | 8.29E−125 | 4.746837028 | 2.25955883 | | | | |
| NUDT21 | 2.99E−80 | 3.06028903 | 1.457121678 | | | | |
| NDUFAF3 | 8.88E−55 | 2.383919436 | 1.137322319 | | | | |
| MITD1 | 3.07E−47 | 2.009722381 | 0.960963898 | | | | |
| NUDT5 | 1.88E−56 | 2.434893144 | 1.165636277 | | | | |
| SNRPD3 | 6.21E−74 | 2.92881676 | 1.403249077 | | | | |
| TMEM258 | 3.10E−72 | 2.970486925 | 1.424616179 | | | | |
| UQCRC1 | 7.64E−82 | 3.645888901 | 1.749594365 | | | | |
| TRIM59 | 8.92E−82 | 2.643379535 | 1.268587986 | | | | |
| DTX3L | 1.69E−79 | 2.33543546 | 1.121027282 | | | | |
| PHB | 2.03E−54 | 2.272531231 | 1.092024482 | | | | |
| VOPP1 | 6.19E−77 | 2.780981344 | 1.336514767 | | | | |
| GTF2A2 | 6.39E−48 | 2.25475435 | 1.085682726 | | | | |
| PSMB10 | 1.16E−171 | 6.030269925 | 2.906188687 | | | | |
| WDR83OS | 3.57E−86 | 3.557054354 | 1.715109338 | | | | |
| NDUFB10 | 1.43E−59 | 2.688975493 | 1.296723088 | | | | |
| YARS | 4.21E−92 | 3.297927977 | 1.591534117 | | | | |
| AIP | 1.21E−102 | 4.122714607 | 1.990604407 | | | | |
| CHST12 | 5.59E−99 | 3.595802492 | 1.736806178 | | | | |
| DCTN2 | 1.59E−60 | 2.576256487 | 1.244453561 | | | | |
| ATP5F1 | 5.24E−84 | 3.962567401 | 1.921573174 | | | | |
| SMC3 | 5.84E−72 | 2.682357487 | 1.302035445 | | | | |
| CTSC | 2.24E−115 | 4.560963578 | 2.216349374 | | | | |
| SAMD9L | 3.25E−66 | 2.495152105 | 1.213261926 | | | | |
| PEF1 | 2.74E−44 | 2.106208751 | 1.024666417 | | | | |
| H2AFY | 4.36E−67 | 2.366480968 | 1.151785138 | | | | |
| C9orf16 | 2.77E−97 | 3.649773462 | 1.776991219 | | | | |
| SEC11A | 2.43E−74 | 3.183121169 | 1.550593035 | | | | |

TABLE 6-continued

| | CD8_B | | | | CD8_G | | |
|---|---|---|---|---|---|---|---|
| GeneName | P-value | Mean expression G1 | Mean expression G2 | GeneName | P-value | Mean expression G2 | Mean expression G1 |
| SF3B14 | 2.53E−56 | 2.470585546 | 1.203633519 | | | | |
| SNX17 | 8.57E−81 | 3.340407842 | 1.630944085 | | | | |
| SLX1A | 9.65E−94 | 3.397692612 | 1.659810557 | | | | |
| CNP | 3.38E−51 | 2.010494426 | 0.98281337 | | | | |
| PIN1 | 9.51E−75 | 3.030442803 | 1.48319666 | | | | |
| CNIH1 | 6.20E−48 | 2.222542426 | 1.090375464 | | | | |
| AL353354.2 | 9.98E−63 | 2.618432506 | 1.286402608 | | | | |
| TOMM5 | 3.00E−55 | 2.536152718 | 1.246669896 | | | | |
| RAB27A | 2.13E−123 | 4.687421809 | 2.304364209 | | | | |
| PSMD8 | 9.26E−117 | 4.575753315 | 2.256456493 | | | | |
| NDUFS7 | 1.21E−86 | 3.590142368 | 1.771365198 | | | | |
| GSDMD | 1.89E−75 | 3.363352126 | 1.660918068 | | | | |
| SEC61G | 5.37E−55 | 2.522814855 | 1.246782876 | | | | |
| ETFA | 2.63E−56 | 2.651933137 | 1.311401693 | | | | |
| APOBEC3D | 5.34E−130 | 3.380245529 | 1.671679024 | | | | |
| GSTP1 | 5.11E−113 | 4.912488909 | 2.430082491 | | | | |
| FDFT1 | 5.14E−62 | 2.704718169 | 1.338918193 | | | | |
| LAMTOR1 | 3.10E−49 | 2.16882921 | 1.075600567 | | | | |
| LGALS1 | 5.85E−64 | 3.357009584 | 1.664933266 | | | | |
| LAG3 | 7.60E−111 | 3.541064229 | 1.757280767 | | | | |
| ACTR1A | 3.40E−65 | 2.510683291 | 1.245955297 | | | | |
| DYNLRB1 | 1.92E−65 | 2.957742724 | 1.468856794 | | | | |
| PPP1CC | 3.64E−52 | 2.203796011 | 1.094519379 | | | | |
| GYG1 | 5.40E−45 | 2.230119979 | 1.108318616 | | | | |
| BRK1 | 2.28E−116 | 4.649300583 | 2.312956199 | | | | |
| PHB2 | 1.97E−71 | 3.202588722 | 1.594157768 | | | | |
| SFT2D1 | 3.01E−51 | 2.34543133 | 1.167512921 | | | | |
| PLEKHJ1 | 9.84E−52 | 2.354150689 | 1.174696649 | | | | |
| PUF60 | 4.55E−85 | 3.561505558 | 1.777203021 | | | | |
| FCRL3 | 1.64E−73 | 3.174160935 | 1.586070711 | | | | |
| SARNP | 5.01E−61 | 2.731949001 | 1.365444301 | | | | |
| HK1 | 1.84E−62 | 2.457208967 | 1.228174703 | | | | |
| CTLA4 | 2.91E−99 | 3.690690102 | 1.845201044 | | | | |
| MDH2 | 1.86E−88 | 3.481165243 | 1.741079456 | | | | |
| ATP5H | 1.41E−62 | 2.92556102 | 1.463512768 | | | | |
| BAK1 | 1.44E−57 | 2.406565266 | 1.20447788 | | | | |
| PCMT1 | 1.83E−66 | 2.945615435 | 1.474281001 | | | | |
| TRIM69 | 2.32E−49 | 2.077449634 | 1.040347476 | | | | |
| GORASP2 | 1.20E−48 | 2.164740148 | 1.085770361 | | | | |
| PPM1M | 1.08E−59 | 2.236488966 | 1.122173655 | | | | |
| RAB8A | 1.66E−82 | 3.273781635 | 1.643043985 | | | | |
| AURKAIP1 | 5.64E−65 | 2.88947544 | 1.450645103 | | | | |
| ATP5C1 | 1.41E−106 | 4.552287027 | 2.285753391 | | | | |
| TXN | 2.64E−69 | 2.769173937 | 1.392219502 | | | | |
| SNRNP40 | 3.25E−47 | 2.257709257 | 1.135424061 | | | | |
| M6PR | 1.07E−103 | 4.274687856 | 2.150113046 | | | | |
| C12orf75 | 3.38E−60 | 2.676137792 | 1.346789383 | | | | |
| RAB11A | 4.43E−51 | 2.302870226 | 1.160980005 | | | | |
| TMCO1 | 5.19E−70 | 3.2016094 | 1.615421544 | | | | |
| NME1-NME2 | 1.16E−84 | 3.973214185 | 2.005844343 | | | | |
| OSTC | 3.86E−51 | 2.420274514 | 1.222245854 | | | | |
| PARP9 | 1.54E−91 | 3.484009902 | 1.761121297 | | | | |
| ELOVL1 | 4.25E−50 | 2.330492905 | 1.179464783 | | | | |
| NEDD8 | 1.07E−85 | 3.862897554 | 1.956859328 | | | | |
| MT2A | 6.11E−105 | 4.731740516 | 2.397041493 | | | | |
| TKT | 2.12E−52 | 2.34031621 | 1.185718352 | | | | |
| CDK2AP2 | 2.99E−106 | 4.37439044 | 2.217013994 | | | | |
| HLA-DQB1 | 6.95E−81 | 3.631009793 | 1.842553206 | | | | |
| TXLNA | 4.84E−76 | 2.517656577 | 1.277762337 | | | | |
| PPP1R7 | 2.80E−41 | 2.08959601 | 1.060776221 | | | | |
| PPM1G | 3.17E−74 | 3.137917906 | 1.593139835 | | | | |
| GBP5 | 2.61E−152 | 5.386152272 | 2.735263811 | | | | |
| ARPC5 | 7.91E−140 | 5.353269289 | 2.718813537 | | | | |
| SDHB | 1.15E−45 | 2.398175813 | 1.219644736 | | | | |
| EIF2S1 | 7.82E−45 | 2.351574855 | 1.196180759 | | | | |
| KDELR2 | 6.33E−62 | 2.459379931 | 1.251223349 | | | | |
| NDUFA2 | 2.96E−47 | 2.074992277 | 1.056426235 | | | | |
| FIS1 | 2.87E−55 | 2.583194526 | 1.315724451 | | | | |
| HIGD1A | 1.00E−40 | 2.019928924 | 1.030208517 | | | | |
| TAF9 | 1.62E−48 | 2.322383485 | 1.184774779 | | | | |
| CHMP4A | 4.27E−77 | 3.474750511 | 1.77335484 | | | | |
| PFKP | 3.56E−66 | 2.753096572 | 1.405205921 | | | | |
| YIPF3 | 6.39E−47 | 2.248718147 | 1.148418285 | | | | |
| CSK | 2.52E−81 | 3.250034273 | 1.660326862 | | | | |
| COPS6 | 1.99E−68 | 3.276262524 | 1.674127159 | | | | |

TABLE 6-continued

| | CD8_B | | | CD8_G | | | |
|---|---|---|---|---|---|---|---|
| GeneName | P-value | Mean expression G1 | Mean expression G2 | GeneName | P-value | Mean expression G2 | Mean expression G1 |
| NELFCD | 1.10E−71 | 3.08944576 | 1.579246323 | | | | |
| TMED9 | 1.32E−44 | 2.196556187 | 1.12350714 | | | | |
| PDAP1 | 3.32E−78 | 2.481359623 | 1.269843284 | | | | |
| CXCR3 | 5.78E−90 | 3.985402999 | 2.039885776 | | | | |
| SIVA1 | 1.54E−48 | 2.687595565 | 1.375766449 | | | | |
| TMEM140 | 4.32E−50 | 2.069594409 | 1.062932531 | | | | |
| THYN1 | 1.05E−42 | 2.105211154 | 1.081406696 | | | | |
| RBX1 | 3.36E−76 | 3.036093563 | 1.562362913 | | | | |
| C14orf2 | 1.12E−61 | 2.912725644 | 1.499001063 | | | | |
| TEX264 | 1.45E−41 | 2.101028148 | 1.081949894 | | | | |
| C14orf166 | 4.93E−78 | 3.620612979 | 1.864921756 | | | | |
| EZH2 | 1.13E−57 | 2.403595203 | 1.239474049 | | | | |
| CLNS1A | 1.57E−58 | 3.025513649 | 1.560188965 | | | | |
| UQCR10 | 3.47E−71 | 3.075630459 | 1.587072528 | | | | |
| PSMD9 | 3.70E−47 | 2.351284854 | 1.213670213 | | | | |
| EIF4E | 8.17E−66 | 2.775116394 | 1.43287626 | | | | |
| TUBB | 4.49E−76 | 4.440002507 | 2.294311683 | | | | |
| RPA2 | 7.46E−47 | 2.296714526 | 1.187201726 | | | | |
| ATP5O | 5.10E−71 | 3.55987787 | 1.841606686 | | | | |
| PSMA6 | 2.01E−91 | 4.545432082 | 2.35375124 | | | | |
| HLA-DRB5 | 3.29E−172 | 5.320296581 | 2.756910928 | | | | |
| EID1 | 2.82E−133 | 5.106215408 | 2.647522052 | | | | |
| HMGN3 | 1.15E−53 | 2.782395503 | 1.442863787 | | | | |
| LBR | 5.99E−73 | 3.041586205 | 1.577781934 | | | | |
| GZMB | 1.78E−115 | 6.601718045 | 3.42740232 | | | | |
| ROMO1 | 5.21E−42 | 2.177555494 | 1.132261022 | | | | |
| MPV17 | 2.40E−40 | 2.173491046 | 1.132459063 | | | | |
| HSPB11 | 1.01E−44 | 2.009504626 | 1.047387698 | | | | |
| PSMD13 | 4.20E−67 | 3.529735619 | 1.842882774 | | | | |
| C11orf31 | 2.81E−63 | 3.060043836 | 1.598063589 | | | | |
| BOLA2B | 1.17E−45 | 2.106214295 | 1.099994061 | | | | |
| LASP1 | 6.79E−133 | 4.465323537 | 2.332109448 | | | | |
| PPP2R1A | 1.46E−85 | 3.785812027 | 1.97977335 | | | | |
| DCAF7 | 4.35E−60 | 2.338428225 | 1.223321312 | | | | |
| MDM2 | 4.08E−75 | 3.184582499 | 1.667095595 | | | | |
| DGUOK | 7.98E−56 | 2.808834118 | 1.471314642 | | | | |
| SF3B5 | 1.37E−52 | 2.630323364 | 1.377975865 | | | | |
| S100PBP | 3.52E−60 | 2.455692833 | 1.286831295 | | | | |
| COX6B1 | 1.82E−90 | 4.154064004 | 2.177319719 | | | | |
| GALM | 5.53E−88 | 3.780473588 | 1.981554833 | | | | |
| POMP | 1.31E−106 | 3.792006612 | 1.988048302 | | | | |
| LAMTOR5 | 7.17E−54 | 2.805109982 | 1.470782799 | | | | |
| CYB5B | 3.67E−49 | 2.222962355 | 1.166862154 | | | | |
| USMG5 | 1.27E−49 | 2.818179477 | 1.481020226 | | | | |
| PMF1 | 2.53E−54 | 2.979208475 | 1.567302781 | | | | |
| UBE2N | 2.77E−71 | 3.458312581 | 1.819652579 | | | | |
| TSG101 | 6.93E−35 | 2.008441993 | 1.056868043 | | | | |
| COX6C | 2.47E−90 | 4.297502135 | 2.261527732 | | | | |
| MMADHC | 5.25E−54 | 2.546849333 | 1.340626269 | | | | |
| PDCD6 | 1.39E−56 | 2.867232793 | 1.509515224 | | | | |
| PRMT1 | 7.16E−51 | 2.292687821 | 1.207942454 | | | | |
| LAMP2 | 1.32E−43 | 2.060477022 | 1.085928068 | | | | |
| PPA1 | 1.00E−55 | 2.837052137 | 1.495534417 | | | | |
| RPS27L | 2.25E−45 | 2.229881524 | 1.175627681 | | | | |
| CASP3 | 4.24E−48 | 2.186665748 | 1.153377383 | | | | |
| ABRACL | 4.19E−61 | 2.984389399 | 1.574402165 | | | | |
| MRPL20 | 6.59E−46 | 2.360837079 | 1.245620918 | | | | |
| SCP2 | 1.21E−66 | 3.275205948 | 1.728686685 | | | | |
| PSMB9 | 5.99E−195 | 7.561703783 | 3.992218943 | | | | |
| IKZF3 | 1.93E−141 | 5.1333572 | 2.717179773 | | | | |
| GPAA1 | 4.28E−44 | 2.145220765 | 1.13554062 | | | | |
| PSMB7 | 2.11E−60 | 3.085829834 | 1.635268266 | | | | |
| NDUFB9 | 3.00E−53 | 2.86716967 | 1.519616379 | | | | |
| DCAF11 | 4.32E−44 | 2.09743389 | 1.111780514 | | | | |
| VAMP8 | 8.17E−71 | 3.617767006 | 1.918122959 | | | | |
| SRSF4 | 5.57E−63 | 2.855488067 | 1.515999785 | | | | |
| SDHD | 5.47E−55 | 2.573395818 | 1.368524673 | | | | |
| CAPRIN1 | 1.42E−57 | 2.578084513 | 1.372114847 | | | | |
| PSMC4 | 1.52E−43 | 2.18285663 | 1.16256485 | | | | |
| TRAF5 | 2.43E−93 | 3.831282066 | 2.040560405 | | | | |
| DRAP1 | 2.69E−98 | 3.548162957 | 1.891345203 | | | | |
| SMARCE1 | 7.62E−61 | 2.922024113 | 1.560821455 | | | | |
| ATP5A1 | 4.80E−118 | 5.270852224 | 2.816853507 | | | | |
| SRP9 | 5.99E−93 | 4.658812631 | 2.490284429 | | | | |
| TSTD1 | 4.01E−49 | 2.745580493 | 1.468068825 | | | | |

TABLE 6-continued

| | CD8_B | | | CD8_G | | | |
|---|---|---|---|---|---|---|---|
| GeneName | P-value | Mean expression G1 | Mean expression G2 | GeneName | P-value | Mean expression G2 | Mean expression G1 |
| GPS1 | 9.28E−44 | 2.323324562 | 1.242993963 | | | | |
| LAP3 | 7.20E−51 | 2.803015323 | 1.500994577 | | | | |
| PSME2 | 1.96E−193 | 7.712640895 | 4.131300065 | | | | |
| FAM195B | 1.40E−49 | 2.331982837 | 1.249248514 | | | | |
| GBP2 | 1.42E−129 | 5.627221555 | 3.015042873 | | | | |
| CCT8 | 2.17E−74 | 3.71843876 | 1.992518788 | | | | |
| PSMB8 | 5.15E−170 | 7.132616946 | 3.82284933 | | | | |
| RAB1B | 3.30E−110 | 4.215409902 | 2.259559985 | | | | |
| MPC2 | 2.79E−43 | 2.161625503 | 1.159002392 | | | | |
| NDUFS3 | 8.34E−37 | 2.142760678 | 1.149303577 | | | | |
| DAXX | 2.90E−46 | 2.244036601 | 1.204997514 | | | | |
| ITGAE | 1.43E−77 | 3.917097291 | 2.104574161 | | | | |
| NAA38 | 1.39E−50 | 2.377261287 | 1.279778449 | | | | |
| ARF5 | 1.85E−87 | 4.060602326 | 2.186438939 | | | | |
| OSBPL3 | 5.81E−63 | 2.73529629 | 1.474000296 | | | | |
| TIMM17B | 5.43E−43 | 2.079702541 | 1.12088566 | | | | |
| MUS81 | 8.91E−52 | 2.134593232 | 1.150493376 | | | | |
| TBCA | 3.48E−41 | 2.124444985 | 1.145265082 | | | | |
| ANP32A | 5.13E−71 | 2.136382557 | 1.151790944 | | | | |
| CAPZA2 | 1.87E−61 | 3.152541287 | 1.700959916 | | | | |
| CLPP | 3.38E−39 | 2.245357913 | 1.212130221 | | | | |
| PPP1CA | 2.73E−146 | 6.212183494 | 3.35851502 | | | | |
| NDUFB6 | 9.53E−42 | 2.125216074 | 1.15197839 | | | | |
| DENR | 1.29E−48 | 2.143850554 | 1.162452736 | | | | |
| NDUFA11 | 6.66E−76 | 3.815650312 | 2.070588162 | | | | |
| PSMB6 | 2.46E−79 | 4.124762054 | 2.239163153 | | | | |
| POLR2J | 4.27E−44 | 2.406944153 | 1.306660817 | | | | |
| CSNK2B | 8.94E−91 | 4.43712145 | 2.409240456 | | | | |
| PDCD10 | 4.11E−38 | 2.169152245 | 1.178244394 | | | | |
| COPS3 | 6.67E−35 | 2.044398957 | 1.110864996 | | | | |
| CASP1 | 9.07E−41 | 2.17195558 | 1.180502204 | | | | |
| RER1 | 3.75E−76 | 3.593428378 | 1.95333784 | | | | |
| ATXN10 | 3.21E−42 | 2.148757117 | 1.169066474 | | | | |
| HNRNPF | 3.88E−123 | 5.428744397 | 2.953899961 | | | | |
| SASH3 | 2.69E−112 | 4.801901906 | 2.613223269 | | | | |
| HNRNPD | 6.81E−106 | 3.831133687 | 2.085635183 | | | | |
| RBCK1 | 4.42E−80 | 3.890691947 | 2.118157521 | | | | |
| ADRM1 | 1.70E−66 | 3.369979655 | 1.834832786 | | | | |
| GPR174 | 7.12E−62 | 2.909857314 | 1.584737538 | | | | |
| SZRD1 | 5.51E−60 | 2.387023453 | 1.300070432 | | | | |
| UQCRFS1 | 2.63E−71 | 3.398175193 | 1.85184326 | | | | |
| NDUFV2 | 6.02E−76 | 4.018898441 | 2.19071813 | | | | |
| PRELID1 | 9.33E−94 | 4.54782629 | 2.479670957 | | | | |
| SRGAP2 | 2.38E−64 | 2.393103187 | 1.305643597 | | | | |
| PRF1 | 8.71E−221 | 8.148002222 | 4.447049496 | | | | |
| ZNHIT1 | 3.87E−48 | 2.358081672 | 1.287827441 | | | | |
| DNAJC8 | 1.08E−68 | 3.507921737 | 1.916118334 | | | | |
| ECH1 | 5.91E−95 | 4.513875901 | 2.465864659 | | | | |
| AP1M1 | 3.92E−51 | 2.606686949 | 1.424541654 | | | | |
| ST8SIA4 | 5.44E−52 | 2.13008172 | 1.164971994 | | | | |
| ATP6V1F | 3.74E−46 | 2.778310201 | 1.520163309 | | | | |
| DBNL | 1.26E−51 | 3.119955701 | 1.707484627 | | | | |
| SDHAF2 | 2.55E−42 | 2.231651492 | 1.221549855 | | | | |
| SNX5 | 3.71E−63 | 3.272448498 | 1.791443438 | | | | |
| RHOC | 1.52E−43 | 2.351991862 | 1.287709659 | | | | |
| TCEB1 | 8.92E−44 | 2.176761792 | 1.191861997 | | | | |
| PCED1B | 1.30E−67 | 2.944884906 | 1.613053079 | | | | |
| DCP2 | 4.12E−54 | 2.574367761 | 1.411556472 | | | | |
| POLR2E | 2.34E−66 | 3.389657353 | 1.859132157 | | | | |
| PPT1 | 2.18E−40 | 2.226713439 | 1.221724453 | | | | |
| CD82 | 1.87E−58 | 3.550286691 | 1.949856093 | | | | |
| SUMO3 | 2.22E−48 | 2.192537316 | 1.204675279 | | | | |
| PDIA4 | 1.37E−45 | 2.060217384 | 1.13206285 | | | | |
| OASL | 6.62E−77 | 4.080162676 | 2.242370091 | | | | |
| SF3B3 | 5.14E−53 | 2.718364208 | 1.494574908 | | | | |
| GARS | 5.03E−43 | 2.095421762 | 1.152341989 | | | | |
| HLA-DPA1 | 9.63E−171 | 7.690356053 | 4.231368311 | | | | |
| UQCRH | 5.60E−65 | 3.748982903 | 2.063606297 | | | | |
| SMC4 | 4.74E−49 | 2.877003225 | 1.584007396 | | | | |
| CCT5 | 3.05E−50 | 3.07573076 | 1.693789585 | | | | |
| TSPO | 9.94E−87 | 4.503418544 | 2.480531605 | | | | |
| GDI2 | 5.63E−91 | 4.137894871 | 2.279348624 | | | | |
| AAMP | 7.66E−41 | 2.476207502 | 1.364373891 | | | | |
| UBASH3A | 3.96E−41 | 2.172861948 | 1.198199292 | | | | |
| HDAC1 | 1.77E−73 | 3.679902245 | 2.030395951 | | | | |

TABLE 6-continued

| | CD8_B | | | CD8_G | | | |
|---|---|---|---|---|---|---|---|
| GeneName | P-value | Mean expression G1 | Mean expression G2 | GeneName | P-value | Mean expression G2 | Mean expression G1 |
| GPR56 | 4.78E−55 | 2.845762606 | 1.570335058 | | | | |
| COX6A1 | 9.74E−85 | 4.597021905 | 2.538102143 | | | | |
| CKLF | 8.31E−70 | 3.533151041 | 1.950775788 | | | | |
| SNX1 | 1.80E−59 | 2.947913118 | 1.628494353 | | | | |
| TINF2 | 3.49E−38 | 2.47000819 | 1.365517115 | | | | |
| MPHOSPH9 | 1.62E−47 | 2.462069474 | 1.361302101 | | | | |
| HNRNPR | 8.30E−81 | 3.944593996 | 2.181355015 | | | | |
| ATPIF1 | 9.94E−64 | 3.827276198 | 2.117266119 | | | | |
| DPF2 | 1.50E−45 | 2.283166496 | 1.264710228 | | | | |
| CAPN1 | 1.81E−49 | 2.676883079 | 1.483514192 | | | | |
| ANP32B | 1.77E−73 | 3.75028518 | 2.080260257 | | | | |
| NELFE | 2.43E−40 | 2.304716716 | 1.279213279 | | | | |
| RTFDC1 | 2.78E−56 | 3.009168631 | 1.672110798 | | | | |
| SEC11C | 3.55E−40 | 2.49896405 | 1.389247286 | | | | |
| S100A11 | 2.27E−92 | 4.795138112 | 2.666628822 | | | | |
| C16orf13 | 2.92E−43 | 2.413956514 | 1.342681762 | | | | |
| SUPT16H | 2.51E−52 | 2.486538637 | 1.383065963 | | | | |
| RFC1 | 8.03E−47 | 2.081093915 | 1.15756462 | | | | |
| AATF | 8.09E−43 | 2.24825377 | 1.250722686 | | | | |
| STT3A | 9.31E−59 | 2.831860143 | 1.575388056 | | | | |
| SYNGR2 | 1.92E−77 | 4.083210069 | 2.272278003 | | | | |
| MFF | 6.65E−41 | 2.265772763 | 1.261193134 | | | | |
| UBE2V2 | 8.14E−38 | 2.058332586 | 1.146110328 | | | | |
| SF3A3 | 5.66E−37 | 2.130428547 | 1.186285181 | | | | |
| MCTP2 | 3.35E−49 | 2.348089564 | 1.3081431 | | | | |
| PARK7 | 4.34E−131 | 6.514285459 | 3.629195583 | | | | |
| CYB5R3 | 5.56E−40 | 2.149492284 | 1.197739754 | | | | |
| SCAMP2 | 5.22E−73 | 3.533358638 | 1.969288978 | | | | |
| ZNF706 | 8.40E−68 | 3.758731285 | 2.094961179 | | | | |
| LYPLA2 | 4.77E−38 | 2.111783157 | 1.17720598 | | | | |
| NCOA4 | 1.11E−46 | 2.42508573 | 1.352964533 | | | | |
| PA2G4 | 1.78E−65 | 3.542495188 | 1.977145652 | | | | |
| NDUFB4 | 1.05E−52 | 2.869072844 | 1.60149626 | | | | |
| COX5B | 2.60E−82 | 4.197187824 | 2.347363182 | | | | |
| PTPN7 | 7.32E−100 | 4.962296328 | 2.775731868 | | | | |
| SEC13 | 3.27E−40 | 2.387478681 | 1.335942068 | | | | |
| EMC7 | 7.94E−47 | 2.683004028 | 1.501941678 | | | | |
| ILK | 6.62E−44 | 2.434167629 | 1.362800687 | | | | |
| DAD1 | 8.74E−69 | 3.736519899 | 2.091949725 | | | | |
| TMBIM4 | 7.46E−80 | 3.638319372 | 2.037367883 | | | | |
| SRP19 | 9.00E−40 | 2.275428772 | 1.274995319 | | | | |
| ITM2A | 3.24E−117 | 6.150854246 | 3.448522261 | | | | |
| C19orf53 | 4.47E−62 | 3.439266377 | 1.9285571 | | | | |
| XRCC5 | 3.62E−88 | 4.320788579 | 2.42472928 | | | | |
| EIF3I | 9.57E−54 | 3.119987352 | 1.750940226 | | | | |
| VDAC3 | 1.94E−44 | 2.625250731 | 1.474648028 | | | | |
| UBE2K | 7.02E−38 | 2.257519674 | 1.268418919 | | | | |
| MRPS21 | 3.15E−46 | 2.32412113 | 1.306502385 | | | | |
| GIMAP4 | 1.94E−104 | 5.335535476 | 3.003143476 | | | | |
| MEAF6 | 7.14E−52 | 2.66748427 | 1.502330936 | | | | |
| PET100 | 1.02E−42 | 2.511283089 | 1.414738891 | | | | |
| TCEB2 | 1.08E−95 | 4.602014608 | 2.593134304 | | | | |
| NAA10 | 6.03E−37 | 2.273235998 | 1.281421157 | | | | |
| NDUFB11 | 3.32E−57 | 2.853365581 | 1.608439899 | | | | |
| SNRPB | 3.41E−96 | 5.128555101 | 2.891284185 | | | | |
| C21orf33 | 3.50E−50 | 2.512882177 | 1.416695681 | | | | |
| SF3B4 | 1.60E−48 | 2.225339306 | 1.254652104 | | | | |
| LSM7 | 2.19E−43 | 2.597846536 | 1.464910635 | | | | |
| CCT3 | 7.14E−62 | 3.702446152 | 2.088709284 | | | | |
| C12orf57 | 3.83E−60 | 3.323240918 | 1.874858495 | | | | |
| DYNLL1 | 5.81E−60 | 3.684041564 | 2.07877425 | | | | |
| ESYT1 | 4.54E−60 | 3.285822163 | 1.856171524 | | | | |
| F2R | 1.65E−52 | 2.625227856 | 1.483165607 | | | | |
| FIP1L1 | 4.06E−43 | 2.372173615 | 1.340613928 | | | | |
| CASP2 | 2.95E−69 | 3.030701507 | 1.713160684 | | | | |
| STAT2 | 1.61E−59 | 2.8142147 | 1.591185386 | | | | |
| PVRIG | 1.23E−65 | 3.861993979 | 2.183660575 | | | | |
| SNW1 | 1.90E−40 | 2.240520696 | 1.266900748 | | | | |
| PSMB1 | 1.73E−86 | 5.074311692 | 2.870398857 | | | | |
| LY6E | 7.30E−165 | 6.009189042 | 3.400342445 | | | | |
| KIF22 | 5.72E−32 | 2.041998279 | 1.155711967 | | | | |
| ISG15 | 1.81E−90 | 5.278851896 | 2.98841662 | | | | |
| FERMT3 | 2.77E−70 | 3.763681847 | 2.131397907 | | | | |
| CDK6 | 8.58E−51 | 2.443856705 | 1.384757455 | | | | |
| ZC3H7A | 2.93E−52 | 2.456371941 | 1.393177961 | | | | |

TABLE 6-continued

| | CD8_B | | | CD8_G | | | |
|---|---|---|---|---|---|---|---|
| GeneName | P-value | Mean expression G1 | Mean expression G2 | GeneName | P-value | Mean expression G2 | Mean expression G1 |
| C19orf24 | 7.11E−38 | 2.038582649 | 1.156930025 | | | | |
| PSMD11 | 5.81E−62 | 3.193231368 | 1.812524189 | | | | |
| ACTR3 | 2.62E−133 | 6.151550845 | 3.491770598 | | | | |
| ARHGAP1 | 3.02E−58 | 2.283923702 | 1.296543845 | | | | |
| NDUFB2 | 9.88E−47 | 2.955264647 | 1.683076084 | | | | |
| SMIM7 | 2.36E−32 | 2.045495605 | 1.166469824 | | | | |
| VTI1B | 5.38E−32 | 2.271012962 | 1.296326986 | | | | |
| CCT7 | 3.73E−65 | 3.781517822 | 2.159130382 | | | | |
| COX7A2 | 3.52E−75 | 4.547667793 | 2.599484015 | | | | |
| TUFM | 1.06E−59 | 3.423716784 | 1.960362498 | | | | |
| EIF2S2 | 8.96E−54 | 2.413538809 | 1.383047818 | | | | |
| UBE2A | 2.16E−43 | 2.493342543 | 1.429235196 | | | | |
| LSM4 | 4.05E−40 | 2.447377251 | 1.40315026 | | | | |
| PKM | 1.33E−153 | 6.179521227 | 3.54300505 | | | | |
| PFKL | 3.57E−47 | 2.406279403 | 1.38002417 | | | | |
| HADHA | 2.29E−49 | 2.810865774 | 1.612627924 | | | | |
| MYO1G | 1.68E−59 | 3.240016542 | 1.859070572 | | | | |
| SPCS2 | 7.25E−68 | 3.811066908 | 2.189851049 | | | | |
| HLA-DRB1 | 3.77E−165 | 6.967266382 | 4.00442777 | | | | |
| CNOT8 | 1.50E−40 | 2.432739323 | 1.398761456 | | | | |
| EIF3CL | 1.23E−55 | 2.748844976 | 1.580784317 | | | | |
| GRSF1 | 8.36E−37 | 2.143522011 | 1.233334784 | | | | |
| CHFR | 1.69E−37 | 2.114229595 | 1.216750772 | | | | |
| DDOST | 9.62E−90 | 4.673164159 | 2.69003846 | | | | |
| SCAMP3 | 1.09E−33 | 2.173346259 | 1.251186304 | | | | |
| ACTR2 | 4.15E−68 | 3.191222066 | 1.837780259 | | | | |
| SLBP | 4.37E−33 | 2.034977143 | 1.172823601 | | | | |
| RAB10 | 1.59E−50 | 2.696983817 | 1.554789953 | | | | |
| PRDX6 | 1.03E−64 | 3.885077785 | 2.241772484 | | | | |
| NDUFA13 | 3.66E−90 | 4.998517507 | 2.885087091 | | | | |
| SNRPG | 2.61E−45 | 2.976214081 | 1.718308873 | | | | |
| ACLY | 1.15E−44 | 2.379660011 | 1.374353644 | | | | |
| NDUFA1 | 1.68E−55 | 3.37702517 | 1.950682295 | | | | |
| ACP1 | 2.45E−47 | 2.81906422 | 1.628461461 | | | | |
| ZBP1 | 1.12E−33 | 2.006786173 | 1.159547377 | | | | |
| ATP6V0E2 | 1.44E−34 | 2.168896362 | 1.253228804 | | | | |
| MED4 | 4.61E−41 | 2.454344233 | 1.418229547 | | | | |
| SEC61B | 1.54E−60 | 3.6693737 | 2.122504368 | | | | |
| CNDP2 | 4.03E−42 | 2.433574726 | 1.408888708 | | | | |
| MTHFD2 | 2.25E−52 | 3.216472819 | 1.864006829 | | | | |
| DERL2 | 7.68E−35 | 2.317280583 | 1.342915 | | | | |
| CLTC | 5.54E−48 | 2.286040953 | 1.325431599 | | | | |
| APOBEC3G | 4.39E−169 | 7.387496204 | 4.285227047 | | | | |
| HNRNPH2 | 2.12E−35 | 2.105987544 | 1.221991416 | | | | |
| ATF6B | 2.04E−51 | 2.730617224 | 1.58502401 | | | | |
| SHKBP1 | 1.40E−55 | 3.246521987 | 1.88515449 | | | | |
| CBX3 | 1.41E−86 | 4.370196565 | 2.5392877 | | | | |
| STAT1 | 3.35E−119 | 5.871721173 | 3.414712047 | | | | |
| AP2M1 | 7.28E−62 | 3.364224985 | 1.958107331 | | | | |
| PSMD7 | 2.90E−39 | 2.584577846 | 1.505225089 | | | | |
| CNPY2 | 1.42E−34 | 2.22220602 | 1.294765954 | | | | |
| PSMF1 | 4.73E−62 | 3.856697471 | 2.247402371 | | | | |
| RPA1 | 7.21E−40 | 2.028592351 | 1.182269083 | | | | |
| DEK | 4.13E−68 | 3.835775009 | 2.237733473 | | | | |
| GMFG | 3.75E−77 | 4.617705133 | 2.694975168 | | | | |
| ARPP19 | 4.12E−54 | 3.13275547 | 1.829847012 | | | | |
| CMTM6 | 3.83E−57 | 2.719332241 | 1.588656201 | | | | |
| HN1 | 9.22E−51 | 3.164230388 | 1.849404684 | | | | |
| POLR1D | 4.80E−46 | 2.837670349 | 1.659097961 | | | | |
| CCDC12 | 1.68E−39 | 2.703333781 | 1.580761946 | | | | |
| NUCB1 | 5.75E−68 | 3.349321427 | 1.959011308 | | | | |
| POLD4 | 2.03E−64 | 3.413085521 | 1.998190932 | | | | |
| ARPC1B | 1.78E−160 | 7.440338777 | 4.356042726 | | | | |
| CNPY3 | 2.19E−48 | 2.906730404 | 1.702201148 | | | | |
| WDR1 | 5.44E−123 | 5.301253851 | 3.104574596 | | | | |
| DLD | 8.96E−38 | 2.173121961 | 1.273371189 | | | | |
| NCKAP1L | 1.83E−41 | 2.177225621 | 1.275859341 | | | | |
| SPN | 2.05E−59 | 3.268888822 | 1.917193626 | | | | |
| UBA3 | 2.40E−42 | 2.346926931 | 1.37756974 | | | | |
| OTUB1 | 5.06E−72 | 4.001172429 | 2.348997366 | | | | |
| RALY | 1.34E−51 | 3.238547541 | 1.902042773 | | | | |
| C19orf10 | 5.77E−39 | 2.194410859 | 1.28894004 | | | | |
| CTSS | 1.07E−48 | 3.238021065 | 1.902534072 | | | | |
| PIH1D1 | 7.18E−33 | 2.156620901 | 1.268662345 | | | | |
| MYD88 | 1.11E−35 | 2.296118284 | 1.350893587 | | | | |

TABLE 6-continued

| | CD8_B | | | CD8_G | | | |
|---|---|---|---|---|---|---|---|
| GeneName | P-value | Mean expression G1 | Mean expression G2 | GeneName | P-value | Mean expression G2 | Mean expression G1 |
| ARHGAP30 | 8.37E−73 | 3.643988384 | 2.144212036 | | | | |
| SP140 | 1.95E−61 | 3.581496238 | 2.107700389 | | | | |
| TOMM6 | 9.35E−40 | 2.636942561 | 1.551895264 | | | | |
| ATP5D | 2.80E−77 | 3.97069663 | 2.337834529 | | | | |
| MINOS1 | 1.34E−36 | 2.619683698 | 1.542628797 | | | | |
| FAM96B | 3.52E−56 | 3.495232888 | 2.060010521 | | | | |
| HOPX | 8.26E−33 | 2.671478308 | 1.575465985 | | | | |
| SNRNP27 | 1.60E−38 | 2.27848107 | 1.344322105 | | | | |
| CASP4 | 3.81E−70 | 4.500271672 | 2.655700938 | | | | |
| MAPRE1 | 2.48E−46 | 2.855612801 | 1.685446275 | | | | |
| NDUFB8 | 2.12E−81 | 4.562793927 | 2.69319591 | | | | |
| VCP | 2.63E−83 | 4.176202737 | 2.465209746 | | | | |
| ENSA | 8.65E−81 | 3.347095606 | 1.975961694 | | | | |
| UQCRQ | 3.13E−65 | 3.971405319 | 2.34596961 | | | | |
| PPCS | 4.30E−36 | 2.263033129 | 1.336883791 | | | | |
| DNMT1 | 3.30E−51 | 3.355560977 | 1.982540994 | | | | |
| TMEM109 | 1.25E−45 | 2.922630843 | 1.727400943 | | | | |
| RBBP4 | 5.39E−61 | 3.884808608 | 2.296584282 | | | | |
| UFC1 | 4.09E−47 | 2.929065197 | 1.731861768 | | | | |
| CTNNBL1 | 9.03E−34 | 2.011805059 | 1.190096386 | | | | |
| PSMA1 | 1.57E−80 | 4.470406933 | 2.646200971 | | | | |
| RAD21 | 2.47E−40 | 2.188661996 | 1.295760943 | | | | |
| KARS | 1.58E−37 | 2.482437262 | 1.472273377 | | | | |
| GTF3C1 | 1.18E−27 | 2.053035546 | 1.217688343 | | | | |
| SPCS1 | 9.85E−70 | 4.342427969 | 2.576198999 | | | | |
| LMAN2 | 1.90E−74 | 4.233762231 | 2.512699961 | | | | |
| CHMP1A | 1.07E−36 | 2.167820355 | 1.287451502 | | | | |
| SNX14 | 2.76E−39 | 2.307111802 | 1.371304965 | | | | |
| NUBP2 | 1.40E−31 | 2.060139802 | 1.225689618 | | | | |
| ACAA1 | 4.88E−30 | 2.092522101 | 1.245199394 | | | | |
| NDUFA4 | 5.69E−78 | 3.639458342 | 2.166682567 | | | | |
| CIAO1 | 8.35E−38 | 2.405011278 | 1.432469594 | | | | |
| PSMD2 | 1.42E−33 | 2.334094941 | 1.392275458 | | | | |
| DDB1 | 4.95E−42 | 2.532118824 | 1.510505688 | | | | |
| ATP6V0B | 6.96E−39 | 2.80574037 | 1.674421148 | | | | |
| ILF2 | 3.70E−51 | 3.376083165 | 2.015288469 | | | | |
| ITGB7 | 6.39E−36 | 2.472216783 | 1.476023317 | | | | |
| UBE2V1 | 4.45E−88 | 4.775893402 | 2.852785225 | | | | |
| XAF1 | 2.49E−63 | 3.621032676 | 2.163568099 | | | | |
| NUCB2 | 5.31E−41 | 3.045367444 | 1.82027719 | | | | |
| ATP6V0D1 | 1.21E−33 | 2.433517425 | 1.454761148 | | | | |
| BABAM1 | 1.11E−35 | 2.489980121 | 1.4885406 | | | | |
| SLAMF7 | 1.82E−84 | 4.403054002 | 2.633365188 | | | | |
| RGS10 | 1.64E−44 | 2.760205778 | 1.65087194 | | | | |
| SH3BGRL | 2.43E−63 | 3.673615864 | 2.198524241 | | | | |
| TMEM230 | 5.66E−44 | 2.948120907 | 1.764685206 | | | | |
| SFXN1 | 1.13E−61 | 3.425027863 | 2.050331362 | | | | |
| GOLGA7 | 1.14E−41 | 2.4748934 | 1.481793613 | | | | |
| TMEM14B | 3.30E−39 | 2.669337892 | 1.598221489 | | | | |
| OCIAD1 | 1.68E−38 | 2.550827587 | 1.527459075 | | | | |
| IAH1 | 2.56E−47 | 3.310667233 | 1.982882161 | | | | |
| C1orf43 | 4.04E−44 | 2.913590992 | 1.746072105 | | | | |
| USP39 | 6.46E−34 | 2.253191519 | 1.351529262 | | | | |
| CHTOP | 1.18E−39 | 2.455200876 | 1.472895285 | | | | |
| SNRPD2 | 1.29E−61 | 4.556391844 | 2.733660493 | | | | |
| CAP1 | 6.20E−159 | 6.587729015 | 3.953535771 | | | | |
| CKAP2 | 1.34E−32 | 2.019820487 | 1.212316639 | | | | |
| HCFC1 | 3.40E−52 | 2.405949753 | 1.445431568 | | | | |
| COX7A2L | 5.09E−51 | 3.165310074 | 1.903124683 | | | | |
| SLC25A39 | 4.30E−31 | 2.186974683 | 1.316076859 | | | | |
| IRF9 | 4.84E−82 | 4.852908536 | 2.920824885 | | | | |
| UCP2 | 2.15E−93 | 6.566217146 | 3.952308259 | | | | |
| MGAT1 | 6.60E−46 | 2.766568464 | 1.665299426 | | | | |
| CTSD | 7.99E−115 | 6.002393763 | 3.613129473 | | | | |
| SSBP1 | 1.59E−37 | 2.8742402 | 1.730879067 | | | | |
| UFD1L | 2.12E−33 | 2.450430328 | 1.475774991 | | | | |
| CNPPD1 | 7.27E−30 | 2.003207449 | 1.207019064 | | | | |
| NUP50 | 4.57E−48 | 2.427163276 | 1.462662319 | | | | |
| TMEM219 | 1.01E−33 | 2.3623323 | 1.424213697 | | | | |
| UNC13D | 4.86E−41 | 2.400866965 | 1.448024258 | | | | |
| RNASEK-C17orf49 | 4.18E−74 | 2.626613281 | 1.584930988 | | | | |
| FLII | 5.16E−62 | 3.958454833 | 2.388711356 | | | | |
| KLRD1 | 2.50E−62 | 4.785232487 | 2.88846001 | | | | |
| NMT1 | 8.68E−44 | 2.55701375 | 1.544151148 | | | | |
| SUMO2 | 1.32E−135 | 6.834840357 | 4.127950433 | | | | |

TABLE 6-continued

| | CD8_B | | | CD8_G | | | |
|---|---|---|---|---|---|---|---|
| GeneName | P-value | Mean expression G1 | Mean expression G2 | GeneName | P-value | Mean expression G2 | Mean expression G1 |
| CMTM3 | 4.20E−44 | 2.037418871 | 1.231124403 | | | | |
| GHITM | 1.88E−65 | 3.864410453 | 2.335491023 | | | | |
| ANXA6 | 2.81E−128 | 6.137607803 | 3.714349198 | | | | |
| PKN1 | 9.57E−33 | 2.091753964 | 1.266131927 | | | | |
| MIS18BP1 | 1.14E−39 | 2.266019504 | 1.372095957 | | | | |
| RPS19BP1 | 2.21E−30 | 2.045430756 | 1.238694653 | | | | |
| TOR1AIP1 | 4.60E−31 | 2.118965183 | 1.285089538 | | | | |
| UQCR11 | 6.03E−70 | 3.81499423 | 2.313899577 | | | | |
| RNPS1 | 1.04E−51 | 3.621261758 | 2.196520824 | | | | |
| PPP1R18 | 4.59E−41 | 2.407582254 | 1.46043692 | | | | |
| ATRAID | 3.97E−33 | 2.582840298 | 1.566956202 | | | | |
| SNRPB2 | 1.37E−44 | 2.76625871 | 1.678255108 | | | | |
| HADHB | 1.41E−45 | 2.864129737 | 1.738105589 | | | | |
| EIF3C | 5.87E−70 | 4.306295836 | 2.613902117 | | | | |
| TBCB | 2.00E−54 | 3.688196621 | 2.240515824 | | | | |
| SH3GLB1 | 1.14E−37 | 2.53906012 | 1.543070541 | | | | |
| HIGD2A | 4.75E−58 | 3.980579233 | 2.419574317 | | | | |
| IRF7 | 7.49E−32 | 2.380521094 | 1.447232527 | | | | |
| PITPNB | 1.34E−37 | 2.325670154 | 1.415011998 | | | | |
| TPI1 | 1.79E−121 | 7.395881465 | 4.500070553 | | | | |
| CEP57 | 1.50E−34 | 2.212695351 | 1.346684502 | | | | |
| PHF11 | 9.09E−49 | 3.158822197 | 1.922889936 | | | | |
| TRPV2 | 8.80E−32 | 2.367709838 | 1.441911108 | | | | |
| SRSF10 | 4.47E−44 | 2.980511358 | 1.815932343 | | | | |
| OSTF1 | 2.00E−42 | 2.999144375 | 1.827395893 | | | | |
| MTG1 | 1.22E−31 | 2.218643439 | 1.3521046 | | | | |
| CPSF3L | 1.63E−31 | 2.211174717 | 1.347725009 | | | | |
| PIGT | 2.80E−34 | 2.513227558 | 1.532672741 | | | | |
| ARPC4 | 1.30E−157 | 6.851827127 | 4.181712088 | | | | |
| HMOX2 | 4.77E−41 | 3.022930956 | 1.844946179 | | | | |
| C19orf66 | 1.40E−47 | 2.993548301 | 1.827579941 | | | | |
| MVP | 1.73E−60 | 3.722136708 | 2.272412176 | | | | |
| SSR3 | 1.45E−44 | 3.40424105 | 2.079401191 | | | | |
| FBXO7 | 3.01E−47 | 3.198461449 | 1.956190438 | | | | |
| EMC4 | 1.17E−35 | 2.835750302 | 1.735406425 | | | | |
| C17orf62 | 1.71E−83 | 5.33172607 | 3.263614179 | | | | |
| PSMD6 | 4.03E−38 | 2.830631129 | 1.733510045 | | | | |
| RAN | 1.37E−98 | 6.544539291 | 4.009440789 | | | | |
| NT5C3A | 1.35E−27 | 2.140812368 | 1.311837323 | | | | |
| CLIC1 | 7.42E−178 | 8.433449003 | 5.169662289 | | | | |
| ERGIC3 | 1.60E−41 | 2.995469656 | 1.837187244 | | | | |
| PYURF | 5.47E−34 | 2.348458197 | 1.440953676 | | | | |
| VPS26A | 2.11E−30 | 2.078535177 | 1.275365333 | | | | |
| GIMAP2 | 4.82E−24 | 2.035579516 | 1.249501889 | | | | |
| VPS29 | 1.08E−44 | 3.142644748 | 1.929865286 | | | | |
| NDUFA3 | 3.10E−44 | 3.176811748 | 1.951182522 | | | | |
| ARL6IP4 | 5.99E−55 | 3.819418005 | 2.346764209 | | | | |
| COPE | 4.82E−99 | 5.259363554 | 3.231909649 | | | | |
| PRKAR1A | 1.22E−76 | 4.416608671 | 2.714563501 | | | | |
| ANP32E | 4.47E−68 | 4.261755181 | 2.622919456 | | | | |
| FAS | 1.63E−30 | 2.02784923 | 1.248420175 | | | | |
| TIA1 | 1.04E−44 | 3.042713453 | 1.873605809 | | | | |
| POLR2K | 1.01E−36 | 2.458093031 | 1.51421495 | | | | |
| HSPB1 | 6.13E−48 | 2.906386041 | 1.790537005 | | | | |
| IFI16 | 5.40E−119 | 6.172864049 | 3.804689139 | | | | |
| CALCOCO2 | 5.28E−46 | 3.250633353 | 2.004822383 | | | | |
| C5orf56 | 8.27E−42 | 2.961541242 | 1.826940818 | | | | |
| BUB3 | 2.88E−77 | 5.1357333 | 3.169195142 | | | | |
| STXBP2 | 5.59E−43 | 2.690955946 | 1.661080838 | | | | |
| AP3S1 | 5.75E−35 | 2.455741841 | 1.516783649 | | | | |
| TPM4 | 3.79E−70 | 4.197012241 | 2.593640032 | | | | |
| GPI | 1.02E−90 | 5.719836631 | 3.534864332 | | | | |
| ANXA11 | 3.41E−52 | 3.361449258 | 2.078475622 | | | | |
| SNX6 | 9.10E−41 | 2.969658784 | 1.83647297 | | | | |
| RSU1 | 4.77E−29 | 2.181984201 | 1.349562929 | | | | |
| COX7B | 5.84E−32 | 2.110043765 | 1.305363144 | | | | |
| NDUFA10 | 5.38E−36 | 2.822888697 | 1.746415241 | | | | |
| HM13 | 3.35E−42 | 3.185304677 | 1.970775858 | | | | |
| ACSL5 | 3.69E−31 | 2.131074781 | 1.318955199 | | | | |
| MAP2K3 | 2.09E−36 | 2.818078082 | 1.744193579 | | | | |
| GABARAP | 1.06E−107 | 6.463268119 | 4.002597503 | | | | |
| RAD23A | 3.28E−52 | 2.939828452 | 1.820626087 | | | | |
| FBXW5 | 1.12E−31 | 2.166893027 | 1.342509072 | | | | |
| ATP5L | 4.72E−85 | 5.902632358 | 3.660315242 | | | | |
| NDUFV1 | 1.13E−46 | 3.654319147 | 2.266213741 | | | | |

TABLE 6-continued

| | CD8_B | | | CD8_G | | | |
|---|---|---|---|---|---|---|---|
| GeneName | P-value | Mean expression G1 | Mean expression G2 | GeneName | P-value | Mean expression G2 | Mean expression G1 |
| RNF7 | 3.21E−35 | 2.966729911 | 1.841285164 | | | | |
| CPSF6 | 5.24E−28 | 2.188809842 | 1.358854684 | | | | |
| FAM32A | 6.74E−27 | 2.26521548 | 1.406355453 | | | | |
| RWDD1 | 1.75E−33 | 2.328616423 | 1.445913612 | | | | |
| TLN1 | 2.13E−55 | 2.83477322 | 1.760609391 | | | | |
| REEP5 | 7.21E−56 | 4.012890333 | 2.493302187 | | | | |
| NAB1 | 2.51E−43 | 2.583117048 | 1.605329927 | | | | |
| SUB1 | 5.51E−119 | 6.926868887 | 4.305358205 | | | | |
| RNF167 | 2.14E−59 | 3.251788854 | 2.021327615 | | | | |
| ACTN4 | 2.54E−65 | 4.017527807 | 2.497511726 | | | | |
| CD164 | 3.44E−84 | 4.798223656 | 2.984003276 | | | | |
| RBPJ | 1.08E−72 | 4.599572129 | 2.860650726 | | | | |
| SYNCRIP | 1.43E−29 | 2.075675416 | 1.291195927 | | | | |
| SF3B2 | 8.25E−74 | 3.749571466 | 2.333567052 | | | | |
| MAP4 | 3.98E−61 | 3.519160811 | 2.190424566 | | | | |
| HLA-DPB1 | 5.57E−130 | 7.298193735 | 4.54313944 | | | | |
| DNAJB11 | 3.95E−52 | 3.215496625 | 2.003386312 | | | | |
| EIF4G1 | 3.68E−46 | 3.023582729 | 1.884145293 | | | | |
| ATP5EP2 | 5.57E−59 | 2.336498104 | 1.456041078 | | | | |
| BCAP31 | 7.14E−57 | 3.681222571 | 2.294156976 | | | | |
| SPATA13 | 3.34E−58 | 3.308985653 | 2.062711146 | | | | |
| NOL7 | 1.59E−30 | 2.079211994 | 1.296612709 | | | | |
| TMEM173 | 5.44E−34 | 2.610443626 | 1.628024411 | | | | |
| C1QBP | 4.96E−33 | 2.536382203 | 1.582148766 | | | | |
| ZBTB38 | 3.52E−36 | 2.27467782 | 1.419366096 | | | | |
| RCSD1 | 2.10E−30 | 2.100879039 | 1.310998204 | | | | |
| RASSF1 | 1.82E−41 | 3.140334137 | 1.96011208 | | | | |
| TROVE2 | 1.64E−57 | 3.282108424 | 2.049797753 | | | | |
| OS9 | 1.70E−41 | 2.880583433 | 1.799945872 | | | | |
| HPS1 | 1.50E−37 | 2.564393391 | 1.602542015 | | | | |
| DCXR | 5.94E−35 | 2.961817246 | 1.851052392 | | | | |
| APOL2 | 3.23E−74 | 3.629181003 | 2.268673089 | | | | |
| MAT2B | 8.08E−87 | 4.937590513 | 3.086767073 | | | | |
| C4orf3 | 1.61E−61 | 3.01178837 | 1.88408595 | | | | |
| PSTPIP1 | 3.60E−73 | 4.936433608 | 3.097994208 | | | | |
| NUCKS1 | 9.06E−67 | 2.647890735 | 1.66186903 | | | | |
| FRG1 | 7.94E−33 | 2.277768457 | 1.43174302 | | | | |
| NSD1 | 3.06E−38 | 2.088236806 | 1.313409035 | | | | |
| APOBEC3C | 5.37E−186 | 7.962933634 | 5.011603653 | | | | |
| NEDD9 | 1.02E−42 | 2.908674059 | 1.831089133 | | | | |
| NRD1 | 1.96E−50 | 3.205726873 | 2.01817484 | | | | |
| ATP6AP1 | 1.35E−26 | 2.189337028 | 1.378495297 | | | | |
| ZYX | 2.36E−44 | 2.874590561 | 1.811519884 | | | | |
| ARHGEF6 | 1.55E−37 | 2.143868022 | 1.351594141 | | | | |
| NDUFA6 | 3.29E−45 | 3.223481384 | 2.032653591 | | | | |
| SHISA5 | 6.88E−79 | 5.16156127 | 3.255939187 | | | | |
| TAP1 | 5.20E−120 | 6.827121183 | 4.3072061 | | | | |
| USP10 | 4.16E−32 | 2.594303424 | 1.637529873 | | | | |
| VDAC2 | 1.80E−40 | 3.340362467 | 2.108772919 | | | | |
| BSG | 3.75E−73 | 3.917750256 | 2.473335439 | | | | |
| SLAMF6 | 4.50E−33 | 2.312527898 | 1.46025311 | | | | |
| GIMAP7 | 1.04E−73 | 4.837423871 | 3.056014 | | | | |
| GZMA | 3.88E−133 | 8.404353185 | 5.310526823 | | | | |
| PARVG | 4.32E−59 | 3.786798932 | 2.393050277 | | | | |
| ENY2 | 2.49E−23 | 2.079785881 | 1.314895961 | | | | |
| SUMO1 | 1.48E−51 | 3.888958758 | 2.458807328 | | | | |
| CTSA | 3.31E−33 | 2.567656219 | 1.624903178 | | | | |
| YWHAE | 3.14E−82 | 4.46749523 | 2.829183738 | | | | |
| GABARAPL2 | 1.49E−42 | 3.272339636 | 2.073958931 | | | | |
| TM9SF2 | 3.12E−42 | 2.842103705 | 1.801523074 | | | | |
| TMEM9B | 1.07E−26 | 2.101387846 | 1.332514489 | | | | |
| RHOG | 1.89E−33 | 2.783782498 | 1.768194821 | | | | |
| ATP5G2 | 2.86E−113 | 7.216807229 | 4.585891172 | | | | |
| HMGN1 | 1.44E−90 | 5.907073802 | 3.756389242 | | | | |
| CCT4 | 3.99E−43 | 3.391043905 | 2.157415929 | | | | |
| DGKZ | 5.02E−34 | 2.105760861 | 1.339720442 | | | | |
| MOB3A | 2.80E−40 | 2.685889951 | 1.709771621 | | | | |
| YY1AP1 | 1.60E−29 | 2.052913444 | 1.307074888 | | | | |
| SCAND1 | 2.84E−41 | 2.970307459 | 1.891248721 | | | | |
| SURF4 | 1.44E−72 | 4.488437276 | 2.858364656 | | | | |
| KRTCAP2 | 2.30E−50 | 3.937107647 | 2.508411369 | | | | |
| DGCR6L | 7.08E−24 | 2.081946672 | 1.326516078 | | | | |
| CCL4L2 | 2.16E−64 | 3.938525142 | 2.509655941 | | | | |
| RNASEK | 2.03E−94 | 6.224449345 | 3.966543979 | | | | |
| PDHA1 | 7.17E−23 | 2.151780493 | 1.373902705 | | | | |

TABLE 6-continued

| | CD8_B | | | CD8_G | | | |
|---|---|---|---|---|---|---|---|
| GeneName | P-value | Mean expression G1 | Mean expression G2 | GeneName | P-value | Mean expression G2 | Mean expression G1 |
| EIF3M | 4.27E−44 | 3.974408381 | 2.539108444 | | | | |
| SEL1L3 | 1.98E−30 | 2.018099472 | 1.289543953 | | | | |
| HMGN4 | 1.31E−39 | 3.042008177 | 1.944082372 | | | | |
| C18orf32 | 2.47E−26 | 2.166044511 | 1.384511589 | | | | |
| GZMH | 1.30E−73 | 5.894512086 | 3.777397432 | | | | |
| DARS | 1.15E−36 | 3.084375538 | 1.977232192 | | | | |
| U2AF1L4 | 1.43E−29 | 2.17184753 | 1.39265974 | | | | |
| AC040977.1 | 1.29E−47 | 2.916354617 | 1.87128586 | | | | |
| RAB11B | 5.73E−39 | 2.050342686 | 1.31608312 | | | | |
| IDH3B | 2.35E−40 | 2.954707051 | 1.898308248 | | | | |
| STIP1 | 2.79E−44 | 3.537545486 | 2.274889059 | | | | |
| BECN1 | 8.05E−37 | 2.722915881 | 1.754051395 | | | | |
| P4HB | 8.44E−56 | 4.165336865 | 2.683632485 | | | | |
| LSP1 | 3.35E−159 | 7.616866902 | 4.912004868 | | | | |
| GPR171 | 1.11E−38 | 3.012734056 | 1.943265783 | | | | |
| ADAR | 3.26E−55 | 3.151379602 | 2.034872014 | | | | |
| TMEM50A | 4.96E−48 | 4.089997255 | 2.642051936 | | | | |
| DNAJC7 | 1.57E−34 | 2.740896263 | 1.771205422 | | | | |
| UBE2I | 8.71E−55 | 3.93333298 | 2.542167011 | | | | |
| APEH | 1.66E−26 | 2.475388449 | 1.600109311 | | | | |
| TRAF3IP3 | 1.19E−67 | 4.851180082 | 3.137389949 | | | | |
| TYK2 | 1.22E−25 | 2.394766099 | 1.549470291 | | | | |
| ATP5E | 1.22E−109 | 3.975723569 | 2.57244789 | | | | |
| DCTN1 | 4.03E−29 | 2.18443937 | 1.413688251 | | | | |
| PSMC5 | 1.04E−54 | 4.193865191 | 2.714172324 | | | | |
| EIF4EBP2 | 1.79E−41 | 2.068074222 | 1.33852577 | | | | |
| SELT | 7.76E−49 | 4.143695783 | 2.682014846 | | | | |
| ATP6V0E1 | 5.68E−58 | 4.56706923 | 2.956505851 | | | | |
| HMGB2 | 1.22E−44 | 4.506775593 | 2.919106762 | | | | |
| MTF2 | 9.03E−27 | 2.197695309 | 1.424038046 | | | | |
| TRMT112 | 4.34E−60 | 4.489644923 | 2.909558402 | | | | |
| UXT | 8.23E−28 | 2.6923466 | 1.745444661 | | | | |
| KXD1 | 1.54E−30 | 2.345004629 | 1.520294147 | | | | |
| PAK2 | 1.75E−38 | 2.210017912 | 1.432838882 | | | | |
| RARRES3 | 1.62E−94 | 6.596902368 | 4.277118092 | | | | |
| AP2B1 | 2.87E−45 | 3.091383683 | 2.006271352 | | | | |
| IL2RB | 1.08E−113 | 5.921323797 | 3.843423808 | | | | |
| PSMC6 | 6.33E−33 | 2.726625769 | 1.770379729 | | | | |
| MOB1A | 1.33E−78 | 4.783929954 | 3.107595821 | | | | |
| VIMP | 7.05E−27 | 2.126371165 | 1.381467199 | | | | |
| ARPC3 | 1.47E−124 | 7.484204265 | 4.86977031 | | | | |
| ARCN1 | 5.77E−28 | 2.220026945 | 1.444717564 | | | | |
| ADD1 | 2.77E−28 | 2.103970307 | 1.369235942 | | | | |
| MAP4K1 | 8.59E−82 | 5.155918314 | 3.357699393 | | | | |
| VPS28 | 5.98E−49 | 4.09828844 | 2.668959842 | | | | |
| ZNF106 | 4.46E−30 | 2.101794045 | 1.36882088 | | | | |
| DR1 | 5.20E−67 | 3.668343403 | 2.390324384 | | | | |
| UBL5 | 2.19E−52 | 4.147431556 | 2.70273483 | | | | |
| SH2D1A | 4.70E−66 | 4.779902653 | 3.117910972 | | | | |
| TCEA1 | 3.94E−51 | 3.467395717 | 2.261883953 | | | | |
| EXOSC10 | 2.12E−31 | 2.432550976 | 1.586969488 | | | | |
| LRMP | 2.25E−39 | 2.499096302 | 1.630516899 | | | | |
| CTSW | 4.34E−105 | 6.84297274 | 4.466128898 | | | | |
| CD84 | 9.09E−45 | 3.469082844 | 2.26450223 | | | | |
| MIF | 9.58E−80 | 6.014896083 | 3.927408813 | | | | |
| SLFN5 | 1.70E−54 | 3.398082577 | 2.219132774 | | | | |
| QARS | 9.65E−26 | 2.452104416 | 1.601861754 | | | | |
| CHCHD2 | 2.90E−94 | 6.538412547 | 4.273878212 | | | | |
| IP6K2 | 1.84E−26 | 2.484193419 | 1.624111357 | | | | |
| CHP1 | 4.51E−61 | 3.739156984 | 2.444679058 | | | | |
| ADSS | 1.54E−26 | 2.178959942 | 1.425127795 | | | | |
| MED28 | 4.90E−29 | 2.067390347 | 1.352321366 | | | | |
| FAM192A | 9.47E−33 | 2.568577547 | 1.682271284 | | | | |
| CANX | 4.09E−58 | 3.870752171 | 2.536022704 | | | | |
| HBS1L | 4.44E−23 | 2.179472352 | 1.427959995 | | | | |
| TLK1 | 3.55E−56 | 3.260350119 | 2.136328049 | | | | |
| MRPS6 | 1.64E−35 | 3.200933281 | 2.098333354 | | | | |
| MARS | 5.52E−28 | 2.763540175 | 1.812189436 | | | | |
| ZC3H15 | 1.97E−29 | 2.516663689 | 1.651347011 | | | | |
| MFSD10 | 1.13E−34 | 2.918352126 | 1.916295808 | | | | |
| FBXW2 | 1.21E−28 | 2.085014048 | 1.369322522 | | | | |
| ANAPC5 | 4.23E−42 | 3.366507941 | 2.211121676 | | | | |
| LAMTOR4 | 1.30E−32 | 3.05638239 | 2.007499692 | | | | |
| ARL6IP1 | 3.79E−71 | 5.300427623 | 3.482998051 | | | | |
| DNAJC1 | 8.01E−25 | 2.003317792 | 1.316599617 | | | | |

TABLE 6-continued

| | CD8_B | | | CD8_G | | | |
|---|---|---|---|---|---|---|---|
| GeneName | P-value | Mean expression G1 | Mean expression G2 | GeneName | P-value | Mean expression G2 | Mean expression G1 |
| TOMM22 | 3.94E−24 | 2.27015687 | 1.492370255 | | | | |
| PHLDA1 | 1.07E−45 | 2.69859196 | 1.775240081 | | | | |
| RHBDD2 | 5.80E−31 | 2.777370902 | 1.827336336 | | | | |
| NFATC3 | 7.51E−34 | 2.606514375 | 1.715450148 | | | | |
| HCST | 1.89E−90 | 6.511946895 | 4.285861261 | | | | |
| EBP | 1.70E−25 | 2.55007453 | 1.678394885 | | | | |
| DYNLT1 | 5.85E−28 | 2.872671838 | 1.891727315 | | | | |
| CCT6A | 2.54E−38 | 3.321361789 | 2.187737041 | | | | |
| UBE2G1 | 2.56E−26 | 2.197962624 | 1.44790689 | | | | |
| METTL17 | 4.44E−26 | 2.563268413 | 1.688628376 | | | | |
| PEBP1 | 3.54E−38 | 3.324489184 | 2.190503711 | | | | |
| RASSF5 | 5.73E−48 | 3.619722393 | 2.385040754 | | | | |
| LDHB | 3.28E−106 | 7.217618466 | 4.755923988 | | | | |
| CYCS | 1.11E−49 | 4.056734588 | 2.673620261 | | | | |
| ARRDC1 | 3.13E−22 | 2.187529473 | 1.44210077 | | | | |
| TMED2 | 4.52E−47 | 3.759359558 | 2.478331276 | | | | |
| SERBP1 | 2.42E−52 | 4.079834454 | 2.690620905 | | | | |
| PPP6R1 | 2.24E−27 | 2.075315769 | 1.368888607 | | | | |
| SLC25A5 | 7.59E−81 | 6.146292619 | 4.05672534 | | | | |
| ASCC2 | 2.70E−26 | 2.2935164 | 1.514241414 | | | | |
| XRCC6 | 2.24E−66 | 5.33286631 | 3.521552017 | | | | |
| HINT1 | 2.00E−69 | 5.444269191 | 3.595154415 | | | | |
| COMMD6 | 1.80E−47 | 3.942989244 | 2.603894656 | | | | |
| GTF2I | 1.03E−39 | 2.605337448 | 1.720800727 | | | | |
| ARFGAP2 | 1.11E−26 | 2.162878566 | 1.428586221 | | | | |
| RPN2 | 1.63E−50 | 4.076933247 | 2.693455312 | | | | |
| CACYBP | 2.40E−40 | 3.568917103 | 2.360132739 | | | | |
| FAM49B | 2.80E−54 | 4.50407231 | 2.978784542 | | | | |
| LYST | 2.85E−111 | 6.035206783 | 3.993901492 | | | | |
| CCT2 | 4.17E−27 | 2.457412094 | 1.627710862 | | | | |
| GIMAP5 | 5.74E−43 | 3.971161226 | 2.630381797 | | | | |
| ABCA2 | 1.06E−23 | 2.039543058 | 1.351010325 | | | | |
| ARL6IP5 | 2.79E−80 | 5.55168428 | 3.677661258 | | | | |
| PJA2 | 5.00E−31 | 2.135106401 | 1.416392377 | | | | |
| PAG1 | 9.42E−44 | 2.771094813 | 1.838611606 | | | | |
| ICAM3 | 2.50E−55 | 4.184529093 | 2.77808883 | | | | |
| RABGGTB | 2.94E−24 | 2.190477192 | 1.455249049 | | | | |
| CBX6 | 1.35E−68 | 3.207576836 | 2.131129713 | | | | |
| ANAPC16 | 1.60E−60 | 4.44128641 | 2.951423548 | | | | |
| UBE2D2 | 1.54E−49 | 3.332037896 | 2.214660952 | | | | |
| CMC2 | 1.34E−32 | 3.045057414 | 2.024752334 | | | | |
| CYTH4 | 6.93E−29 | 2.419694933 | 1.609750572 | | | | |
| DHPS | 1.64E−21 | 2.141145494 | 1.424754178 | | | | |
| ARL8B | 3.82E−27 | 2.315513892 | 1.541026135 | | | | |
| SRP54 | 8.06E−25 | 2.172518355 | 1.446446899 | | | | |
| HNRNPA3 | 2.02E−51 | 4.177375906 | 2.782387515 | | | | |
| WDR33 | 1.44E−29 | 2.355311056 | 1.569538437 | | | | |
| PSD4 | 2.22E−37 | 2.687355534 | 1.791678741 | | | | |
| ARMC8 | 1.33E−28 | 2.176526092 | 1.451279875 | | | | |
| PRRC2A | 2.37E−36 | 2.172182912 | 1.450127423 | | | | |
| DERL1 | 1.07E−30 | 2.65210845 | 1.770523144 | | | | |
| U2SURP | 8.87E−38 | 3.084151355 | 2.059096389 | | | | |
| CERS5 | 9.81E−28 | 2.570971162 | 1.716920578 | | | | |
| NUDC | 2.88E−44 | 3.484075924 | 2.327423089 | | | | |
| PRDX2 | 1.75E−35 | 3.43953608 | 2.298228498 | | | | |
| AHI1 | 6.76E−31 | 2.398367212 | 1.603880689 | | | | |
| SSR1 | 4.06E−43 | 3.517697239 | 2.353620607 | | | | |
| POLR2L | 1.06E−32 | 2.491882379 | 1.667384234 | | | | |
| INPP4B | 2.00E−71 | 4.37672435 | 2.9288058 | | | | |
| ASXL2 | 3.17E−32 | 2.108317351 | 1.411605009 | | | | |
| ATG4B | 5.16E−25 | 2.225661294 | 1.492125773 | | | | |
| LSM12 | 2.66E−42 | 3.000791735 | 2.011861684 | | | | |
| PPP6C | 1.94E−25 | 2.328711003 | 1.562259411 | | | | |
| RNF4 | 9.68E−49 | 3.772541129 | 2.532500365 | | | | |
| EFCAB14 | 6.51E−36 | 2.717792101 | 1.826863823 | | | | |
| EWSR1 | 1.02E−61 | 5.27069016 | 3.543415803 | | | | |
| ATP6AP2 | 3.67E−33 | 2.87956881 | 1.938545201 | | | | |
| EIF3H | 7.42E−66 | 5.23594245 | 3.525377653 | | | | |
| TCIRG1 | 2.95E−47 | 4.148180031 | 2.793223022 | | | | |
| CMC1 | 3.18E−25 | 2.600570046 | 1.752536789 | | | | |
| SEPW1 | 7.17E−38 | 3.616324667 | 2.437144725 | | | | |
| BTG3 | 5.87E−33 | 2.661145175 | 1.793626458 | | | | |
| HSPA4 | 8.41E−27 | 2.044235635 | 1.378377771 | | | | |
| BUD31 | 1.89E−30 | 3.232431906 | 2.180395611 | | | | |
| MLF2 | 6.07E−37 | 3.252881601 | 2.194581786 | | | | |

TABLE 6-continued

| | CD8_B | | | CD8_G | | | |
|---|---|---|---|---|---|---|---|
| GeneName | P-value | Mean expression G1 | Mean expression G2 | GeneName | P-value | Mean expression G2 | Mean expression G1 |
| BRD8 | 1.89E−23 | 2.094298243 | 1.413056636 | | | | |
| ARHGEF3 | 3.03E−30 | 2.707102202 | 1.82704047 | | | | |
| ZFR | 5.21E−29 | 2.405365423 | 1.623894417 | | | | |
| RNH1 | 2.16E−24 | 2.394140938 | 1.616911589 | | | | |
| RQCD1 | 2.16E−68 | 4.384180221 | 2.960957559 | | | | |
| RHOA | 6.46E−133 | 7.902922231 | 5.338622161 | | | | |
| IRF3 | 1.57E−25 | 2.452275937 | 1.656606717 | | | | |
| ERAP1 | 1.11E−29 | 2.384571644 | 1.611020213 | | | | |
| EDF1 | 3.39E−76 | 5.942447836 | 4.016529304 | | | | |
| CCNDBP1 | 8.39E−51 | 4.382605668 | 2.962971368 | | | | |
| ATG3 | 1.21E−20 | 2.021986514 | 1.367075446 | | | | |
| C7orf55-LUC7L2 | 9.40E−37 | 2.3808909 | 1.609954217 | | | | |
| ST6GALNAC6 | 4.05E−28 | 2.719470888 | 1.839496906 | | | | |
| OST4 | 4.22E−67 | 5.471192314 | 3.700928585 | | | | |
| TPR | 1.13E−38 | 3.246980918 | 2.197245647 | | | | |
| CCL4L1 | 3.04E−82 | 5.49689949 | 3.723660885 | | | | |
| RALGDS | 6.97E−33 | 3.030525765 | 2.053538761 | | | | |
| LARP4B | 6.35E−38 | 2.326104909 | 1.577917765 | | | | |
| CNTRL | 6.04E−29 | 2.35429884 | 1.597295692 | | | | |
| TESPA1 | 1.97E−25 | 2.168661239 | 1.472198248 | | | | |
| RBM17 | 2.30E−33 | 3.037559551 | 2.062735027 | | | | |
| PARP14 | 1.15E−48 | 3.051280657 | 2.073373049 | | | | |
| IRF4 | 1.26E−26 | 2.303676426 | 1.565454138 | | | | |
| OGDH | 1.69E−28 | 2.241572448 | 1.523431079 | | | | |
| DOK2 | 5.38E−38 | 3.74488755 | 2.545605284 | | | | |
| JTB | 2.32E−21 | 2.104395367 | 1.430642404 | | | | |
| CNOT7 | 1.06E−31 | 2.801609526 | 1.904721688 | | | | |
| SRP14 | 2.15E−103 | 7.49178249 | 5.093426717 | | | | |
| ELMO1 | 1.01E−37 | 3.216027022 | 2.186654238 | | | | |
| SDHA | 2.92E−33 | 3.468793636 | 2.359065802 | | | | |
| CAPZB | 1.29E−97 | 6.388918429 | 4.345279637 | | | | |
| EIF4H | 5.60E−55 | 4.6389405 | 3.157794688 | | | | |
| METTL23 | 1.50E−19 | 2.124483219 | 1.446921131 | | | | |
| PRDX1 | 1.44E−44 | 4.396664763 | 2.995606468 | | | | |
| ISCU | 2.06E−44 | 3.938433077 | 2.683637768 | | | | |
| ERP29 | 9.87E−40 | 3.419556374 | 2.331961517 | | | | |
| TMED10 | 9.34E−41 | 3.511693538 | 2.395543973 | | | | |
| MRFAP1L1 | 4.11E−23 | 2.229358073 | 1.520923709 | | | | |
| TOX4 | 5.77E−30 | 2.797710276 | 1.909218279 | | | | |
| PCBP1 | 6.62E−58 | 4.102823361 | 2.800690533 | | | | |
| DENND2D | 5.62E−57 | 5.158701613 | 3.522687205 | | | | |
| SARS | 4.60E−31 | 2.986622641 | 2.039576497 | | | | |
| RPN1 | 3.79E−55 | 4.36650348 | 2.983135575 | | | | |
| PSMA3 | 8.73E−37 | 4.340402057 | 2.965569046 | | | | |
| NECAP2 | 3.29E−28 | 2.409938585 | 1.646810367 | | | | |
| GLIPR2 | 1.15E−20 | 2.331104148 | 1.592954483 | | | | |
| ETNK1 | 2.37E−84 | 4.798208956 | 3.278870917 | | | | |
| YWHAQ | 9.21E−42 | 4.104026719 | 2.804935287 | | | | |
| SPCS3 | 1.58E−34 | 3.127057817 | 2.13767614 | | | | |
| BROX | 2.77E−43 | 2.996718284 | 2.051504294 | | | | |
| MRPL10 | 1.51E−20 | 2.354203605 | 1.613160182 | | | | |
| GIT2 | 3.73E−30 | 2.698452322 | 1.849510866 | | | | |
| COX7C | 1.32E−55 | 5.381874146 | 3.690008942 | | | | |
| PSMA7 | 1.17E−96 | 7.078722592 | 4.855421638 | | | | |
| SOD1 | 1.35E−72 | 6.411638789 | 4.399025983 | | | | |
| USP4 | 1.68E−24 | 2.307293925 | 1.58314858 | | | | |
| GPS2 | 1.21E−26 | 2.906658924 | 1.994953297 | | | | |
| NHP2L1 | 7.82E−43 | 3.977571773 | 2.733500307 | | | | |
| HDLBP | 1.43E−26 | 2.457331413 | 1.689720212 | | | | |
| CCL4 | 7.70E−87 | 7.808356716 | 5.372671392 | | | | |
| RAPGEF1 | 3.42E−27 | 2.063916233 | 1.420260587 | | | | |
| LCP2 | 1.00E−86 | 5.663713418 | 3.901307532 | | | | |
| MYL12B | 7.68E−99 | 7.213916034 | 4.970445418 | | | | |
| PRR13 | 1.24E−62 | 5.322610825 | 3.667346792 | | | | |
| SS18L2 | 4.25E−19 | 2.106912803 | 1.452105718 | | | | |
| TNFRSF1B | 2.25E−53 | 4.644268949 | 3.201693272 | | | | |
| PTBP1 | 1.45E−45 | 3.794388964 | 2.616270243 | | | | |
| CCND2 | 1.44E−51 | 4.061882522 | 2.800977741 | | | | |
| RNF114 | 3.71E−26 | 2.173974866 | 1.501754604 | | | | |
| PPIB | 1.91E−82 | 6.548210729 | 4.523737308 | | | | |
| PRPF40A | 1.84E−26 | 2.648378951 | 1.831100989 | | | | |
| C11orf58 | 3.73E−62 | 5.222474652 | 3.611557859 | | | | |
| APOL6 | 6.90E−35 | 2.198346714 | 1.520484108 | | | | |
| PNRC2 | 2.01E−47 | 4.010840361 | 2.774926298 | | | | |
| PSMB4 | 5.20E−48 | 4.66978486 | 3.232451809 | | | | |

TABLE 6-continued

| | CD8_B | | | | CD8_G | | |
|---|---|---|---|---|---|---|---|
| GeneName | P-value | Mean expression G1 | Mean expression G2 | GeneName | P-value | Mean expression G2 | Mean expression G1 |
| ANKRD10 | 4.38E−99 | 6.007181504 | 4.160622794 | | | | |
| ATP5B | 4.73E−65 | 6.115050004 | 4.235792502 | | | | |
| DDX39A | 4.84E−30 | 3.712509471 | 2.572770358 | | | | |
| SLFN12L | 2.12E−39 | 2.927231643 | 2.028795903 | | | | |
| SSR4 | 6.53E−49 | 4.995265015 | 3.462286143 | | | | |
| PCIF1 | 4.10E−22 | 2.301368176 | 1.595419291 | | | | |
| NFAT5 | 1.31E−25 | 2.204989861 | 1.528663709 | | | | |
| GPRIN3 | 2.50E−40 | 2.567966118 | 1.780423811 | | | | |
| LRBA | 1.57E−31 | 2.339541687 | 1.622592678 | | | | |
| RAP1GDS1 | 1.48E−29 | 2.557433928 | 1.774580173 | | | | |
| TCERG1 | 3.09E−32 | 2.785889889 | 1.933391533 | | | | |
| DEGS1 | 4.72E−20 | 2.016088116 | 1.399270935 | | | | |
| HMGN2 | 2.02E−71 | 7.681448766 | 5.331525844 | | | | |
| RAC2 | 7.60E−141 | 8.860802821 | 6.150823213 | | | | |
| BIN1 | 2.66E−29 | 2.83383341 | 1.97085633 | | | | |
| CASC4 | 9.33E−24 | 2.159554092 | 1.501983373 | | | | |
| TARDBP | 1.41E−32 | 2.739400892 | 1.90547687 | | | | |
| TANK | 2.86E−44 | 4.063031988 | 2.827364459 | | | | |
| RAB7L1 | 3.07E−24 | 2.459221023 | 1.71154895 | | | | |
| EXOC7 | 4.89E−22 | 2.105264834 | 1.465731362 | | | | |
| SSU72 | 2.09E−18 | 2.027775189 | 1.412453934 | | | | |
| SEC24C | 5.05E−28 | 2.414842903 | 1.682107238 | | | | |
| ANXA2 | 3.71E−40 | 4.612027355 | 3.215640818 | | | | |
| FYTTD1 | 3.22E−22 | 2.049003575 | 1.428906094 | | | | |
| NDUFA5 | 1.84E−25 | 2.468249327 | 1.722233131 | | | | |
| TPST2 | 2.41E−23 | 2.472095316 | 1.725695558 | | | | |
| H2AFV | 1.13E−16 | 2.238773457 | 1.56333869 | | | | |
| RABAC1 | 2.88E−40 | 4.222925453 | 2.949687442 | | | | |
| CRKL | 1.06E−24 | 2.120279667 | 1.481085685 | | | | |
| PIM1 | 1.57E−29 | 3.223902327 | 2.252243029 | | | | |
| SH3KBP1 | 2.17E−59 | 4.755111806 | 3.32353741 | | | | |
| PTBP3 | 1.51E−31 | 2.530875076 | 1.768986375 | | | | |
| UBXN1 | 2.34E−47 | 4.586560378 | 3.207664016 | | | | |
| GRB2 | 5.84E−48 | 3.973754698 | 2.779366956 | | | | |
| U2AF1 | 5.42E−48 | 4.509899275 | 3.15466215 | | | | |
| PPIE | 2.77E−26 | 2.616046102 | 1.830196288 | | | | |
| ZNF410 | 2.91E−18 | 2.218616014 | 1.552580564 | | | | |
| NONO | 1.36E−73 | 5.933940446 | 4.153338329 | | | | |
| DNAJA2 | 2.06E−26 | 2.432867867 | 1.703382509 | | | | |
| KIF2A | 3.43E−24 | 2.134265978 | 1.494728594 | | | | |
| NKG7 | 1.05E−169 | 11.35967924 | 7.957885544 | | | | |
| NPEPPS | 8.93E−47 | 3.173894128 | 2.22416716 | | | | |
| VAPA | 1.70E−33 | 3.681594647 | 2.58107836 | | | | |
| ADIPOR1 | 1.65E−22 | 2.367477939 | 1.662704735 | | | | |
| DAP3 | 5.05E−25 | 2.657307061 | 1.866391882 | | | | |
| LRPAP1 | 1.04E−20 | 2.290634382 | 1.608865841 | | | | |
| LCK | 3.46E−101 | 7.533473442 | 5.292448282 | | | | |
| SYNRG | 2.86E−27 | 2.450990742 | 1.722655895 | | | | |
| ANXA7 | 4.56E−26 | 3.011478691 | 2.117222328 | | | | |
| NAPA | 8.82E−36 | 3.548349886 | 2.494764913 | | | | |
| ERP44 | 3.07E−27 | 2.191002041 | 1.54054131 | | | | |
| LAT | 1.42E−43 | 4.725957504 | 3.324566062 | | | | |
| S100A4 | 1.04E−62 | 6.339108393 | 4.461573784 | | | | |
| STARD7 | 1.18E−39 | 2.890297078 | 2.034417983 | | | | |
| UBAP2L | 6.25E−25 | 2.621606628 | 1.846663437 | | | | |
| CLK3 | 2.07E−22 | 2.558200789 | 1.802038652 | | | | |
| PCNP | 1.74E−31 | 3.078049292 | 2.168410705 | | | | |
| PRDM1 | 2.33E−84 | 5.477404345 | 3.860395533 | | | | |
| C2orf68 | 4.24E−41 | 2.77814339 | 1.958678758 | | | | |
| HP1BP3 | 1.16E−37 | 3.260553477 | 2.300180925 | | | | |
| USP22 | 2.33E−29 | 2.161033427 | 1.526466989 | | | | |
| SS18 | 6.42E−21 | 2.168153993 | 1.532124355 | | | | |
| PYHIN1 | 4.65E−50 | 4.441494759 | 3.139252438 | | | | |
| COTL1 | 2.43E−91 | 7.728695226 | 5.463550006 | | | | |

TABLE 7

| Gene Name | P-value | % exp in R | % exp in NR |
|---|---|---|---|
| Significant in Non-responder | | | |
| CD38 | 1.97E−112 | 0.1522694 | 0.427109974 |
| EPSTI1 | 4.28E−56 | 0.141532455 | 0.321553127 |
| GOLIM4 | 1.38E−49 | 0.162030259 | 0.335038363 |
| WARS | 2.44E−49 | 0.155197657 | 0.3257382 |
| PDCD1 | 8.07E−47 | 0.292337726 | 0.48058591 |
| CCL3 | 1.45E−45 | 0.187408492 | 0.357823762 |
| SNAP47 | 2.24E−43 | 0.192288921 | 0.358986282 |
| VCAM1 | 8.75E−43 | 0.145436798 | 0.299697745 |
| SKA2 | 3.86E−38 | 0.133235725 | 0.273889793 |
| HAVCR2 | 2.66E−37 | 0.273792094 | 0.438502674 |
| LGALS9 | 8.18E−32 | 0.096632504 | 0.211578703 |
| PRDX3 | 1.15E−31 | 0.169350903 | 0.303882818 |
| FASLG | 2.46E−29 | 0.133235725 | 0.253429435 |
| ENTPD1 | 3.76E−29 | 0.167886774 | 0.29597768 |
| FABP5 | 2.54E−28 | 0.221571498 | 0.356893746 |
| SIRPG | 3.49E−28 | 0.310395315 | 0.454545455 |
| LSM2 | 2.20E−27 | 0.133235725 | 0.24854685 |
| NDUFB3 | 5.28E−27 | 0.167886774 | 0.290165078 |
| TRAFD1 | 2.07E−25 | 0.153733529 | 0.268774704 |
| UBE2F | 4.24E−25 | 0.152757443 | 0.266914671 |
| NMI | 4.08E−24 | 0.123474866 | 0.227853987 |
| IFI35 | 1.58E−22 | 0.128355295 | 0.229946524 |
| CLTA | 3.50E−22 | 0.170326989 | 0.279702395 |
| MTHFD1 | 5.40E−21 | 0.12249878 | 0.218321321 |
| MYO7A | 1.36E−20 | 0.132259639 | 0.229249012 |
| IFI27L2 | 1.46E−16 | 0.138604197 | 0.224831435 |
| MCM5 | 6.19E−16 | 0.142020498 | 0.227156475 |
| STMN1 | 2.12E−15 | 0.110297706 | 0.186933271 |
| ID3 | 1.31E−14 | 0.108833577 | 0.182515694 |
| RGS3 | 1.65E−14 | 0.131283553 | 0.209486166 |
| SNRPD1 | 1.66E−14 | 0.179599805 | 0.266217159 |
| PTTG1 | 2.02E−14 | 0.134699854 | 0.213206231 |
| FIBP | 1.72E−13 | 0.142996584 | 0.219948849 |
| Significant in Responder | | | |
| IL7R | 9.60E−48 | 0.41727672 | 0.236921646 |
| TCF7 | 3.02E−20 | 0.354807223 | 0.24226924 |
| GPR183 | 1.54E−16 | 0.21522694 | 0.132527319 |
| MGAT4A | 1.28E−12 | 0.263543192 | 0.184840735 |

TABLE 8A

| # | Patinet ID | Gender (F/M) | Age | Therapy | Clinical response (RECIST; R = CR, PR; NR = SD, PD) | Baseline Biopsy (days from basline; site; lesion response) | Post I biopsy (days from baseline; site; lesion response) | Post II biopsy (days from baseline; site; lesion response) | Overall survival (days) | Status (Alive = 0; Dead = 1) |
|---|---|---|---|---|---|---|---|---|---|---|
| 1 | P36 | F | 80 | PD1 | R | NA | 42; right upper arm; regression | NA | 823 | 0 |
| 2 | P37 | M | 67 | PD1 | NR | | 42; left prosterior; progression | NA | 144 | 1 |
| 3 | P38 | F | 62 | PD1 | R | (−1); adreanl gland (left biopsy); regression | NA | NA | 1496 | 0 |
| 4 | P39 | M | 71 | PD1 | Resistance | 0; upper back lession; regression | 21; upper back lession; regression | 207; adrenalectomy; progression | 490 | 0 |
| 5 | P40 | M | 81 | PD1 | NR | (−55); lung wedge biopsy (left lobe); progression | NA | NA | 175 | 1 |
| 6 | P41 | M | 86 | PD1 | R | NA | 341; left lower leg; regression | NA | 642 | 0 |
| 7 | P42 | M | 77 | PD1 | R | (−30); Skin left flank; regression | NA | NA | 597 | 1 |
| 8 | P43 | F | 45 | PD1 | R | (−86); lymph node right axillary; regression | NA | NA | 383 | 0 |
| 9 | P44 | M | 52 | PD1 | NR | NA | 9; small bowel resection; progression | NA | 558 | 0 |
| 10 | P45 | F | 77 | PD1 | NR | (−192); left iliac lymph node; progression | 30; left retroperitoneal lymph node; progression | 290; brian right temporal; progression | 371 | 1 |
| 11 | P46 | M | 81 | PD1 | NR (patient had mix response) | (−22); brain lession; regression | 97; right chest wall; progression | NA | 558 | 1 |
| 12 | P47 | M | 85 | PD1 | R | (−112); left forehead; regression | NA | NA | 642 | 0 |
| 13 | P49 | M | 70 | PD1 | NR | (−15); liver; progression | 141; left parotid gland mass; progression | NA | 345 | 1 |
| 14 | P50 | M | 64 | PD1 | NR | (−132); proximal jejunum; progression | NA | NA | 328 | 0 |
| 15 | P51 | M | 72 | PD1 | NR | 0; right neck (skin); progression | 142; right neck (skin); progression | NA | 241 | 1 |
| 16 | P52 | F | 67 | PD1 | Resistance | (−195); left leg (skin); regression | 342; left arm; progression | | 1943 | 0 |

TABLE 8A-continued

| # | Patient ID | Gender (F/M) | Age | Therapy | Clinical response (RECIST; R = CR, PR; NR = SD, PD) | Baseline Biopsy (days from basline; site; lesion response) | Post I biopsy (days from baseline; site; lesion response) | Post II biopsy (days from baseline; site; lesion response) | Overall survival (days) | Status (Alive = 0; Dead = 1) |
|---|---|---|---|---|---|---|---|---|---|---|
| 17 | P53 | M | 61 | PD1 | Resistance | NA | 113; left groin; progression | NA | 492 | 1 |
| 18 | P54 | M | 82 | PD1 | Resistance | 0; lower left abdomen; regression | 209; left groin; progression | NA | 420 | 1 |
| 19 | P55 | M | 75 | PD1 | NR (patient had mix response) | 0; left neck; progression | NA | NA | 504 | 0 |
| 20 | P56 | M | 66 | PD1 | R | 0; left upper arm; regression | NA | NA | 658 | 0 |
| 21 | P57 | F | 56 | PD1 | R | 0; left upper arm; regression | NA | NA | 612 | 0 |
| 22 | P58 | M | 78 | PD1 | R | (−2); left chest; regression | NA | NA | 605 | 0 |
| 23 | P59 | F | 65 | PD1 | R | (−66); left axillary lymph node; regression | NA | NA | 413 | 0 |
| 24 | P60 | M | 76 | PD1 | R | (−1); right lateral calf (leg); regression | NA | NA | 438 | 0 |
| 25 | P61 | F | 67 | PD1 + CTLA4 | NR | | 23; lung; progression | NA | 27 | 1 |
| 26 | P62 | M | 60 | PD1 | R | NA | 126; skin back; regression | NA | 1895 | 0 |
| 27 | P63 | M | 72 | PD1 | NR | (−105); gastric tumor; progression | NA | NA | 954 | 1 |
| 28 | P64 | M | 63 | PD1 | NR | NA | 39; left frontal brain; progression | NA | 1295 | 0 |
| 29 | P65 | F | 40 | PD1 | R | (−17); right temple inferior lower; regression | 146; right cheek (skin); regression | NA | 1138 | 0 |
| 30 | P66 | M | 75 | PD1 | NR | (−174); axillary lymph node; progression | NA | NA | 963 | 0 |
| 31 | P67 | F | 71 | PD1 | NR | (−20); lung wedge lower left lobe; progression | NA | NA | 929 | 0 |
| 32 | P68 | M | 63 | PD1 | NR | NA | 244; right lower lobe- lung biopsy; progression | NA | 756 | 1 |
| 33 | P69 | M | 65 | PD1 | R | (−21); left upper arm; regression | NA | NA | 406 | 0 |
| Samples from the scRNAseq cohort | | | | | | | | | | |
| 34 | P1 | M | 49 | CTLA4 (baseline); PD1 (post I and II) | Resistance | NA | 48; anterior neck; regression | 437; anterior neck; progression | 822 | 0 |
| 35 | P2 | M | 75 | PD1 | NR | 0; small bowel; progression | 35; left axilla; progression | NA | 347 | 1 |
| 36 | P4 | M | 29 | CTLA4 + PD1 | R | (−2); left shoulder; progression prior to therpay | 35; left shoulder; regression | NA | 539 | 0 |
| 37 | P24 | M | 73 | PD1 | R | 0; left lower back; regression | NA | NA | 54 | 0 |

F—female;
M—male;
NR—nonresponder;
R—responder;
NA—not available;
DOD—dead of disease;
AWD—alive with disease

TABLE 8B

| Patinet | Sample name | Lesion Response status; R-responder, NR-non-responders | CD8% of nuceli | CD8+ TCF7+/CD8+ TCF7− ratio |
|---|---|---|---|---|
| P36 | Post_P36 | R | 23.02 | 2.103 |
| P37 | Post_P37 | NR | 6.06 | 0.849 |
| P38 | Pre_P38 | R | 5.65 | 1.36 |
| P39 | Pre_P39 | R | 6.65 | 1.93 |
| P39 | Post_P39 | R | 32.4 | 2.07 |
| P39 | Post_P39_2 | NR | 8.34 | 0.77 |
| P40 | Pre_P40 | NR | 5.35 | 0.926 |
| P41 | Post_P41 | R | 12.7 | 4.17 |
| P42 | Pre_P42 | R | 12.67 | 0.81 |
| P43 | Pre_P43 | R | 17.96 | 1.33 |
| P44 | Post_P44 | NR | 19.65 | 0.852 |
| P45 | Pre_45 | NR | 18.62 | 0.882 |
| P45 | Post_P45 | NR | 16.67 | 1.049 |
| P45 | Post_P45_2 | NR | 3.32 | 0.655 |
| P46 | Pre_P46 | R | 3.94 | 1.718 |
| P46 | Post_P46 | NR | 3.23 | 0.946 |
| P47 | Pre_P47 | R | 23.51 | 1.599 |
| P49 | Pre_P49 | NR | 3.988 | 0.792 |
| P49 | Post_P49 | NR | 8.85 | 1.29 |
| P50 | Pre_P50 | NR | 12.2 | 0.533 |
| P51 | Pre_P51 | NR | 14.62 | 0.413 |
| P51 | Post_P51 | NR | 18.72 | 0.174 |
| P52 | Pre_P52 | R | 16.74 | 2.73 |
| P52 | Post_P52 | NR | 33.6 | 0.534 |
| P53 | Post_P53 | NR | 8.7 | 1.12 |
| P54 | Pre_P54 | R | 4.919 | 0.57 |
| P54 | Post_P54 | NR | 12.5 | 0.471 |
| P55 | Pre_P55 | NR | 27.7 | 0.36 |
| P56 | Pre_P56 | R | 36.52 | 1.189 |
| P57 | Pre_P57 | R | 20.45 | 1.2 |
| P58 | Pre_P58 | R | 3.877 | 0.86 |
| P59 | Pre_P59 | R | 22.2 | 1.202 |
| P60 | Pre_P60 | R | 66.36 | 0.961 |
| P61 | Post_P61 | NR | 29.73 | 0.243 |
| P62 | Post_P62 | R | 9.242 | 1.272 |
| P63 | Pre_P63 | NR | 16.68 | 1.22 |
| P64 | Post_P64 | NR | 4.3 | 0.238 |
| P65 | Pre_P65 | R | 2.2 | 1.657 |
| P65 | Post_P65 | R | 11.12 | 1.885 |
| P66 | Pre_P66 | NR | 12.88 | 0.27 |
| P67 | Pre_P67 | NR | 8.357 | 0.82 |
| P68 | Post_P68 | NR | 7.723 | 0.634 |
| P69 | Pre_P69 | R | 1.53 | 3.416 |
| Samples from the scRNAseq cohort ||||||
| P1 | Post_P1 | R | 50.7 | 1.01 |
| P1 | Post_P1_2 | NR | 17.57 | 0.576 |
| P2 | Pre_P2 | NR | 3.8 | 0.395 |
| P2 | Post_P2 | NR | 12.04 | 0.858 |
| P4 | Pre_P4 | NR | 25.39 | 0.209 |
| P4 | Post_P4 | R | 9.48 | 3.44 |
| P24 | Pre_P24 | R | 7.366 | 1.457 |

TABLE 9

CD8_1

| GeneName | P-value | Mean expression G1 | Mean expression non-G1 | |
|---|---|---|---|---|
| SPC25 | 7.29E-183 | 2.152793671 | 0.022709593 | adjusted P-value = 1.4e-5 |
| CDCA5 | 9.61E-249 | 3.283968204 | 0.048568291 | |
| ESCO2 | 2.05E-173 | 2.107874319 | 0.031717053 | |
| CDC45 | 2.77E-199 | 2.662546645 | 0.041064042 | |
| ZWINT | <1E-300 | 4.54154968 | 0.078683491 | |
| SHCBP1 | 5.45E-176 | 2.166191529 | 0.038651757 | |
| DLGAP5 | 1.19E-173 | 2.297602153 | 0.044316935 | |
| RAD51 | 1.01E-197 | 2.792017792 | 0.056664368 | |
| KIF18B | 5.15E-197 | 2.197946499 | 0.044829274 | |
| RRM2 | <1E-300 | 5.545835323 | 0.113463575 | |
| BIRC5 | 2.61E-284 | 3.649241861 | x | |
| TK1 | <1E-300 | 5.010059873 | 0.107424617 | |
| HJURP | 1.34E-173 | 2.210552183 | 0.048501849 | |
| UBE2C | 2.82E-231 | 3.899002096 | 0.085658551 | |
| CCNB2 | 5.21E-194 | 2.890822394 | 0.065006324 | |
| CENPW | 1.08E-193 | 2.850658243 | 0.068347806 | |
| GINS2 | 3.56E-212 | 2.566792107 | 0.061865207 | |
| RAD51AP1 | 9.10E-206 | 2.754092108 | 0.066994063 | |
| DTL | 2.77E-246 | 3.010444717 | 0.075483325 | |
| SPC24 | 9.51E-257 | 3.284411816 | 0.086262498 | |
| CDCA3 | 1.26E-148 | 2.310214642 | 0.062926119 | |
| PKMYT1 | 2.46E-274 | 3.912074882 | 0.111843438 | |
| MELK | 1.37E-206 | 2.827927308 | 0.083703387 | |
| ANLN | 9.63E-163 | 2.167852433 | 0.064238576 | |
| CDCA8 | 3.22E-188 | 2.516171112 | 0.076333804 | |
| KIAA0101 | <1E-300 | 6.014545588 | 0.184748739 | |
| GGH | 3.61E-165 | 2.628317969 | 0.082894389 | |
| AURKB | 1.19E-202 | 3.417845343 | 0.109220569 | |
| ASF1B | 7.64E-275 | 3.989642884 | 0.131899853 | |
| CDC20 | 9.13E-155 | 2.571097633 | 0.090072626 | |
| NCAPG | 1.48E-186 | 2.466952224 | 0.086576421 | |
| DHFR | 2.55E-243 | 3.380729828 | 0.119371977 | |
| KIFC1 | 9.14E-172 | 2.507275778 | 0.090625638 | |
| TYMS | <1E-300 | 6.372852514 | 0.234303573 | |
| CKAP2L | 4.81E-154 | 2.219315268 | 0.085362763 | |
| CLSPN | 2.56E-223 | 2.431790608 | 0.095589012 | |
| MLF1IP | 5.73E-257 | 3.889404448 | 0.159321142 | |
| TROAP | 4.14E-159 | 2.472509996 | 0.102008367 | |

TABLE 9-continued

| GeneName | P-value | Mean expression G2 | Mean expression non-G2 | |
|---|---|---|---|---|
| KIF2C | 7.79E−181 | 2.510278759 | 0.1044348 | |
| WDR34 | 1.19E−195 | 3.019929166 | 0.126847555 | |
| CDK1 | 1.80E−244 | 4.306984329 | 0.183943699 | |
| KIF23 | 9.39E−172 | 2.617700489 | 0.1120404 | |
| PLK1 | 2.33E−120 | 2.080904536 | 0.089427249 | |
| TOP2A | 1.43E−254 | 3.95379396 | 0.176154169 | |
| NUF2 | 8.11E−150 | 2.292506517 | 0.108500218 | |
| HMGB3 | 2.22E−129 | 2.007443518 | 0.095277255 | |
| ASPM | 5.98E−192 | 2.24647022 | 0.107948753 | |
| MCM2 | 1.89E−266 | 4.24019511 | 0.206950214 | |
| ORC6 | 1.54E−134 | 2.019910216 | 0.099102929 | |
| CASC5 | 5.68E−191 | 2.758978817 | 0.136299446 | |
| CENPH | 1.89E−152 | 2.446495791 | 0.123996713 | |
| FEN1 | 1.26E−255 | 4.146844098 | 0.210752282 | |
| BRCA1 | 4.31E−149 | 2.194349072 | 0.11261379 | |
| MCM4 | 5.26E−298 | 4.748202624 | 0.248402619 | |
| TIMELESS | 1.17E−175 | 2.504879494 | 0.131966386 | |
| MKI67 | 7.00E−281 | 3.779424913 | 0.215975467 | |
| CDKN3 | 1.16E−168 | 3.42287434 | 0.19826645 | |
| APOBEC3B | 4.05E−113 | 2.356293552 | 0.14094421 | |
| CCNB1 | 1.25E−112 | 2.286673065 | 0.14388862 | |
| TPX2 | 6.61E−197 | 3.249133415 | 0.205462527 | |
| NCAPG2 | 3.85E−212 | 2.933777691 | 0.187046063 | |
| KIF11 | 6.72E−186 | 2.706508395 | 0.173099323 | |
| TCF19 | 1.24E−205 | 3.19100032 | 0.212179404 | |
| UBE2T | 2.92E−220 | 4.231471082 | 0.291429352 | |
| SPAG5 | 1.11E−132 | 2.566249104 | 0.178360671 | |
| BRCA2 | 5.99E−146 | 2.351130485 | 0.171149721 | |
| CCNA2 | 4.68E−179 | 3.743000261 | 0.280210068 | |
| BUB1B | 2.51E−143 | 2.660515065 | 0.199743709 | |
| CHEK1 | 2.16E−147 | 2.688171153 | 0.207169333 | |
| BUB1 | 1.33E−157 | 2.793982614 | 0.216484658 | |
| FANCI | 1.35E−220 | 3.866443915 | 0.324877844 | |
| CENPM | 1.85E−215 | 4.506968995 | 0.380463346 | |
| RNASEH2A | 3.04E−175 | 3.344405757 | 0.285050354 | |
| HIRIP3 | 1.27E−169 | 3.013656013 | 0.2597295 | |
| MAD2L1 | 1.82E−195 | 3.956829854 | 0.342664735 | |
| CCNF | 3.32E−137 | 2.207423429 | 0.194829078 | |
| STMN1 | <1E−300 | 8.059433725 | 0.733797002 | |
| SMC2 | 2.09E−234 | 3.743958836 | 0.341639173 | |
| CKS1B | 9.89E−243 | 4.8473316 | 0.44974339 | |
| PAICS | 1.14E−174 | 3.383508732 | 0.317117771 | |
| NCAPH | 1.03E−138 | 2.80566619 | 0.26310969 | |
| ATAD5 | 6.59E−164 | 2.381247448 | 0.226256736 | |
| PRC1 | 2.25E−118 | 2.741020483 | 0.274952715 | |
| RFC5 | 1.64E−107 | 2.354298256 | 0.23995904 | |
| CENPF | 7.52E−171 | 3.067207453 | 0.312810158 | |
| CENPN | 2.26E−126 | 3.141653788 | 0.320472248 | |
| CDCA7 | 5.48E−208 | 4.143105633 | 0.425232965 | |
| CHTF18 | 6.60E−111 | 2.294463343 | 0.237158675 | |
| CENPE | 1.22E−106 | 2.009763256 | 0.214883208 | |
| WDR76 | 1.13E−191 | 3.226942728 | 0.362578907 | |
| FBXO5 | 4.35E−110 | 2.317128112 | 0.260966949 | |
| CDCA7L | 2.06E−93 | 2.054712356 | 0.232381135 | |
| RFC4 | 1.49E−151 | 3.563842214 | 0.409382908 | |
| POLD1 | 1.29E−130 | 2.936785803 | 0.3384978 | |
| LRR1 | 1.21E−100 | 2.259551767 | 0.263080986 | |
| RACGAP1 | 1.13E−108 | 2.46958953 | 0.287645547 | |
| SNRNP25 | 9.20E−144 | 3.439113101 | 0.417194751 | |
| KNTC1 | 5.06E−202 | 4.078080883 | 0.495378126 | |
| NUDT1 | 1.06E−160 | 3.833035974 | 0.474433354 | |
| ACOT7 | 2.66E−132 | 3.145357502 | 0.400520512 | |

CD8_2

| GeneName | P-value | Mean expression G2 | Mean expression non-G2 | |
|---|---|---|---|---|
| GEM | 3.01E−97 | 3.212921547 | 0.626392714 | adjusted P-value = 2.5e−5 |
| LAYN | 1.71E−57 | 2.341179483 | 0.605117134 | |
| VCAM1 | 9.49E−153 | 5.745571447 | 1.494735054 | |
| RDH10 | 1.81E−55 | 2.085194324 | 0.574960204 | |
| FAM3C | 4.62E−68 | 2.699856838 | 0.758692255 | |
| KIR2DL4 | 1.25E−55 | 2.743079022 | 0.78306608 | |
| TNFRSF18 | 1.80E−47 | 2.222603508 | 0.666522377 | |
| MTSS1 | 3.59E−51 | 2.379706089 | 0.729873791 | |
| CADM1 | 5.38E−46 | 2.394829138 | 0.744721504 | |
| ENTPD1 | 7.16E−101 | 4.438595811 | 1.500307988 | |
| ETV1 | 1.38E−41 | 2.042430288 | 0.712259261 | |
| AFAP1L2 | 2.42E−40 | 2.174279724 | 0.762835224 | |
| TNFRSF9 | 3.53E−113 | 5.512980442 | 1.93475996 | |

TABLE 9-continued

| | | | |
|---|---|---|---|
| NAB1 | 1.73E−99 | 4.684753101 | 1.663550573 |
| PELI1 | 5.89E−58 | 3.121591718 | 1.127848712 |
| DFNB31 | 1.97E−75 | 3.091277624 | 1.143209508 |
| CTLA4 | 2.28E−106 | 5.903760001 | 2.228307516 |
| HSPB1 | 2.48E−81 | 5.018019213 | 1.901655837 |
| FKBP4 | 2.07E−32 | 2.357262179 | 0.900943487 |
| NAMPTL | 3.70E−55 | 2.828322525 | 1.082805125 |
| MYO7A | 2.70E−55 | 2.851829292 | 1.094796871 |
| CXCL13 | 3.20E−76 | 5.537703257 | 2.196116878 |
| GOLIM4 | 1.70E−71 | 3.257832778 | 1.292870894 |
| PHLDA1 | 5.37E−105 | 4.61451026 | 1.840925822 |
| DNAJA4 | 7.45E−35 | 2.466346883 | 0.987327141 |
| TGIF1 | 5.04E−52 | 3.707163014 | 1.49388894 |
| HAVCR2 | 1.70E−125 | 6.721208897 | 2.782150341 |
| APLP2 | 8.51E−37 | 2.829096569 | 1.193574792 |
| GPR56 | 3.81E−67 | 4.305002658 | 1.84604347 |
| BPGM | 3.55E−24 | 2.112090785 | 0.912324729 |
| SEC14L1 | 6.30E−45 | 3.165973951 | 1.368216333 |
| TNIP3 | 1.08E−28 | 2.29389018 | 1.02796927 |
| METRNL | 9.31E−31 | 2.530023686 | 1.139591291 |
| HSPH1 | 5.06E−59 | 5.204278335 | 2.347337913 |
| KLRC2 | 1.86E−16 | 2.029681849 | 0.941238889 |
| PMAIP1 | 4.13E−48 | 4.357067179 | 2.021451401 |
| DUSP4 | 2.68E−131 | 7.476213847 | 3.48564483 |
| IGFLR1 | 3.22E−50 | 4.574899349 | 2.14231225 |
| HSPA1A | 5.69E−59 | 6.348691619 | 2.974468662 |
| ZFAND2A | 2.19E−20 | 2.186631309 | 1.027281707 |
| NDFIP2 | 1.27E−21 | 2.2106574 | 1.050155852 |
| PAM | 6.49E−47 | 4.145597678 | 1.971693122 |
| TP53INP1 | 5.31E−38 | 2.693198774 | 1.296099613 |
| AHI1 | 6.99E−39 | 3.595532505 | 1.730724301 |
| UBE2F | 4.76E−34 | 3.487548578 | 1.681697896 |
| HSPA4 | 9.10E−29 | 3.032981266 | 1.486959447 |
| ICOS | 1.30E−31 | 3.618907106 | 1.775485924 |
| CHORDC1 | 2.26E−43 | 4.649213815 | 2.289473394 |
| TRPS1 | 5.81E−26 | 2.212680953 | 1.094915301 |
| TBC1D4 | 9.10E−24 | 2.108456723 | 1.04372663 |
| RALA | 2.93E−25 | 2.579740721 | 1.286294041 |
| CD82 | 5.25E−46 | 4.774476431 | 2.390377878 |
| SEMA4A | 3.03E−18 | 2.121371796 | 1.063602252 |
| PON2 | 3.54E−24 | 2.966853817 | 1.503367546 |
| ACP5 | 7.77E−29 | 3.375622269 | 1.711869243 |
| CCDC64 | 1.08E−36 | 3.054795949 | 1.549817138 |
| BHLHE40 | 1.33E−52 | 4.938329191 | 2.513266968 |
| NAMPT | 4.65E−42 | 4.558315 | 2.3391288 |
| AHSA1 | 3.43E−40 | 4.846807326 | 2.496974426 |
| BANP | 1.49E−24 | 2.471967382 | 1.28050943 |
| RHBDD2 | 4.79E−33 | 3.890107086 | 2.028687397 |
| CREM | 2.62E−71 | 7.56604644 | 3.946265062 |
| SLC7A5 | 4.60E−35 | 3.268624015 | 1.705861583 |
| CACYBP | 6.31E−38 | 5.00305574 | 2.613466019 |
| NUSAP1 | 2.82E−20 | 2.072815795 | 1.092495033 |
| STIP1 | 1.99E−39 | 4.832561502 | 2.571147298 |
| LRMP | 2.71E−33 | 3.424957531 | 1.828855879 |
| PDE3B | 6.25E−33 | 2.710816144 | 1.451470982 |
| RGS2 | 1.06E−73 | 8.050777843 | 4.323433952 |
| CCDC141 | 1.64E−22 | 2.035200121 | 1.096683788 |
| SNAP47 | 7.17E−31 | 4.052440361 | 2.183869746 |
| DEDD2 | 1.76E−27 | 3.450491584 | 1.861237221 |
| BTG3 | 7.47E−32 | 3.662598245 | 1.979769384 |
| ITPRIP | 8.91E−19 | 2.207231209 | 1.193183727 |
| HSPA1B | 5.19E−37 | 5.352638687 | 2.904830246 |
| GALNT2 | 5.41E−22 | 2.233759079 | 1.218402379 |
| TNFSF9 | 5.15E−22 | 2.70962443 | 1.478562319 |
| RANGAP1 | 1.28E−17 | 2.368495249 | 1.296540042 |
| PDCD1 | 2.71E−54 | 5.925199432 | 3.243600815 |
| DDX3Y | 6.08E−26 | 3.145532035 | 1.722551562 |
| ARID5B | 7.16E−48 | 4.680313383 | 2.564657935 |
| DUSP10 | 9.99E−28 | 3.510076713 | 1.933146697 |
| ZBTB1 | 2.12E−28 | 3.436305385 | 1.899592732 |
| SAMSN1 | 3.73E−58 | 6.360674706 | 3.525389463 |
| IRF4 | 4.39E−25 | 3.082040237 | 1.735357355 |
| CD2BP2 | 2.22E−32 | 4.111559791 | 2.329946702 |
| SYNGR2 | 5.84E−38 | 5.013596264 | 2.841604396 |
| CDK6 | 1.25E−22 | 3.020199495 | 1.71270042 |
| MCTP2 | 7.30E−21 | 2.876967415 | 1.635926964 |
| RAB27A | 4.01E−45 | 5.459190278 | 3.124067888 |
| HSPD1 | 8.82E−39 | 6.077649059 | 3.480454567 |
| NFAT5 | 9.99E−28 | 2.931103048 | 1.682294193 |
| BATF | 4.37E−23 | 3.555787596 | 2.043815825 |

TABLE 9-continued

| | | | |
|---|---|---|---|
| GZMB | 1.30E−56 | 7.758277758 | 4.499249256 |
| NEU1 | 6.93E−16 | 2.886639105 | 1.67483792 |
| SYT11 | 1.08E−18 | 2.440568325 | 1.419244954 |
| CXCR6 | 2.58E−28 | 4.655644289 | 2.718000218 |
| CNIH1 | 1.12E−16 | 2.541655109 | 1.487216627 |
| FCRL3 | 1.67E−22 | 3.65262676 | 2.137913589 |
| CRTAM | 7.97E−24 | 4.445338565 | 2.601965542 |

CD8_3

| GeneName | P-value | Mean expression G3 | Mean expression non-G3 | |
|---|---|---|---|---|
| CCL3 | 8.51E−117 | 5.015059335 | 1.887855906 | adjusted P-value = 2.6e−5 |
| EPSTI1 | 4.29E−74 | 3.295223458 | 1.420359201 | |
| CD38 | 5.20E−113 | 4.545668162 | 2.005928356 | |
| FASLG | 8.75E−56 | 2.94645835 | 1.309504723 | |
| IFI44L | 1.37E−32 | 2.11646469 | 0.964395941 | |
| GIMAP6 | 2.43E−79 | 3.400092837 | 1.577918668 | |
| TRAFD1 | 1.91E−50 | 2.885862016 | 1.343522517 | |
| LGALS9 | 1.11E−34 | 2.070086127 | 0.967475419 | |
| CXCR6 | 4.56E−86 | 4.846134919 | 2.272311204 | |
| RAB37 | 4.19E−43 | 2.28535694 | 1.079728993 | |
| CCR5 | 9.42E−62 | 3.552480197 | 1.769370144 | |
| ZBP1 | 1.16E−40 | 2.427047475 | 1.235683441 | |
| SAMD9L | 4.66E−45 | 2.823461812 | 1.44490878 | |
| SIRPG | 8.13E−91 | 5.329178021 | 2.732094169 | |
| MX1 | 1.41E−42 | 3.056292666 | 1.568430104 | |
| HAVCR2 | 1.09E−86 | 5.110139367 | 2.63274115 | |
| ACP5 | 3.56E−41 | 2.975743001 | 1.542519863 | |
| DDX60 | 9.04E−33 | 2.158055201 | 1.118673932 | |
| PDCD1 | 8.20E−93 | 5.522853643 | 2.878952853 | |
| SH2D3C | 5.22E−29 | 2.006760405 | 1.056157919 | |
| GPR174 | 4.10E−50 | 3.358551212 | 1.782806586 | |
| RPS6KA1 | 3.08E−30 | 2.377415894 | 1.281208847 | |
| GBP5 | 1.68E−118 | 5.978542127 | 3.247065468 | |
| GBP1 | 1.48E−48 | 3.697213452 | 2.02745995 | |
| PTPN6 | 1.37E−68 | 5.151317565 | 2.841613699 | |
| S100PBP | 3.82E−43 | 2.721960992 | 1.510583409 | |
| IFI35 | 9.67E−20 | 2.326512656 | 1.298901302 | |
| OAS3 | 8.08E−27 | 2.26072679 | 1.267258312 | |
| SNAP47 | 1.68E−44 | 3.566898004 | 2.007468349 | |
| GIMAP4 | 8.46E−86 | 5.999604075 | 3.399364434 | |
| PARP9 | 4.36E−50 | 3.752100501 | 2.138026317 | |
| IFNG | 2.98E−64 | 4.95583907 | 2.826877465 | |
| SIT1 | 9.26E−52 | 4.360720044 | 2.489833852 | |
| PYCARD | 3.34E−27 | 2.698145533 | 1.544086008 | |
| RGS3 | 5.80E−22 | 2.053497623 | 1.177694189 | |
| XAF1 | 5.14E−59 | 4.120833869 | 2.379035731 | |
| OAS2 | 6.39E−35 | 2.946307406 | 1.707312929 | |
| C5orf56 | 3.50E−36 | 3.398169743 | 1.976674608 | |
| GIMAP5 | 1.37E−52 | 4.670269131 | 2.737983339 | |
| ABI3 | 3.58E−34 | 3.200470446 | 1.877923624 | |
| SNX20 | 6.74E−23 | 2.133950473 | 1.253679389 | |
| VAMP5 | 1.76E−24 | 2.66021222 | 1.563994728 | |
| IRF2 | 3.28E−40 | 3.479010551 | 2.045661958 | |
| UBASH3A | 6.78E−27 | 2.370123324 | 1.394154502 | |
| PARP10 | 3.51E−22 | 2.17349071 | 1.281779284 | |
| GIMAP7 | 6.26E−74 | 5.557729331 | 3.2779442 | |
| GBP4 | 2.47E−35 | 2.907061262 | 1.716208583 | |
| PVRIG | 8.46E−45 | 4.243408789 | 2.50528476 | |
| CYTH4 | 9.69E−31 | 2.833281744 | 1.678057875 | |
| DTX3L | 9.21E−31 | 2.40929227 | 1.430280817 | |
| RHOC | 1.54E−25 | 2.535523964 | 1.513748945 | |
| SASH3 | 2.61E−66 | 5.164050448 | 3.083855688 | |
| CCL4L2 | 7.05E−76 | 4.503046587 | 2.692677718 | |
| IFI6 | 5.35E−56 | 5.206051374 | 3.117531087 | |
| BCAS4 | 4.27E−18 | 2.046159933 | 1.22756435 | |
| IKZF3 | 1.73E−70 | 5.425905348 | 3.277337602 | |
| GIMAP2 | 2.10E−17 | 2.26933074 | 1.379274176 | |
| ADORA2A | 1.42E−19 | 2.063948349 | 1.255927302 | |
| ARPC5L | 3.07E−29 | 2.95597189 | 1.799793078 | |
| GYG1 | 1.64E−16 | 2.292308191 | 1.39627513 | |
| SLFN5 | 9.32E−56 | 3.873564682 | 2.366470161 | |
| CHST12 | 1.76E−35 | 3.652602619 | 2.231508059 | |
| APOBEC3D | 6.61E−56 | 3.436403521 | 2.124852498 | |
| WARS | 3.41E−22 | 3.099554913 | 1.918950359 | |
| UBE2L6 | 7.28E−62 | 5.964259648 | 3.704581811 | |
| TMEM140 | 2.16E−23 | 2.123334107 | 1.322115881 | |
| CSK | 1.37E−30 | 3.318055645 | 2.076003481 | |
| F2R | 4.40E−27 | 2.78115134 | 1.741256588 | |

TABLE 9-continued

| GeneName | P-value | Mean expression G4 | Mean expression non-G4 | |
|---|---|---|---|---|
| CTSS | 6.45E−30 | 3.476249917 | 2.183171663 | |
| SLAMF7 | 5.65E−56 | 4.759575299 | 2.989782655 | |
| CXCR3 | 1.24E−33 | 4.057073582 | 2.552982396 | |
| CD27 | 5.49E−58 | 5.978865328 | 3.767214443 | |
| PPP1R18 | 4.38E−35 | 2.60976111 | 1.646889148 | |
| TOX | 3.27E−43 | 3.37345819 | 2.132048391 | |
| CTSC | 6.15E−40 | 4.545762838 | 2.873160416 | |
| SLAMF6 | 5.36E−23 | 2.544432842 | 1.609106178 | |
| STAT1 | 9.53E−67 | 6.247628281 | 3.954645325 | |
| FUT8 | 7.21E−21 | 2.25709318 | 1.431233895 | |
| IDH2 | 4.98E−38 | 4.318082043 | 2.738942801 | |
| PCED1B | 1.94E−30 | 3.054548165 | 1.941355334 | |
| BST2 | 1.07E−31 | 3.973119153 | 2.525375499 | |
| PSMB10 | 9.15E−59 | 5.964359202 | 3.79864379 | |
| STAT2 | 6.52E−26 | 2.950115892 | 1.879340578 | |
| RNASET2 | 9.81E−18 | 2.305998235 | 1.472168555 | |
| RBCK1 | 8.05E−34 | 4.012686146 | 2.564165695 | |
| SEL1L3 | 2.35E−21 | 2.215650861 | 1.417050007 | |
| C14orf159 | 1.59E−20 | 2.24808124 | 1.438035499 | |
| HLA-DRA | 1.20E−53 | 6.027667429 | 3.868627815 | |
| GZMA | 5.05E−109 | 9.15450386 | 5.885590032 | |
| CD63 | 3.56E−29 | 4.240658328 | 2.726923538 | |
| DENND2D | 8.25E−55 | 5.799247975 | 3.734443517 | |
| HLA-DQB1 | 4.75E−28 | 3.624285685 | 2.341720123 | |
| PRF1 | 1.76E−111 | 8.352915718 | 5.397147064 | |
| CD84 | 1.10E−33 | 3.816408078 | 2.467481691 | |
| TIGIT | 2.54E−52 | 5.710777486 | 3.699023791 | |
| CCL4L1 | 4.81E−83 | 6.131891763 | 3.975624769 | |
| PLSCR1 | 7.18E−14 | 2.165168213 | 1.404721258 | |
| LAG3 | 1.85E−36 | 3.496287471 | 2.269558169 | |
| DAXX | 1.73E−15 | 2.274292791 | 1.482063123 | |
| PHF11 | 3.85E−27 | 3.360321274 | 2.189790278 | |

CD8_4

| GeneName | P-value | Mean expression G4 | Mean expression non-G4 | |
|---|---|---|---|---|
| LMNA | 7.56E−209 | 5.130250252 | 0.897090823 | adjusted P-value = 2.6e−5 |
| NR4A3 | 1.42E−148 | 3.975385123 | 1.022291452 | |
| GPR183 | 2.24E−90 | 3.818257547 | 0.990291243 | |
| CDKN1A | 2.22E−101 | 3.549498599 | 0.94656863 | |
| CCR7 | 2.63E−70 | 2.960438007 | 0.803254077 | |
| S1PR1 | 7.18E−60 | 2.603870566 | 0.834184323 | |
| KDM6B | 2.71E−93 | 3.094151685 | 1.107145291 | |
| ELL2 | 7.77E−64 | 2.644214961 | 0.95895337 | |
| TIPARP | 9.18E−46 | 2.385312133 | 0.926764373 | |
| SC5D | 2.88E−26 | 2.070300226 | 0.836568015 | |
| PLK3 | 4.51E−36 | 2.416236716 | 0.979321478 | |
| CD55 | 2.46E−88 | 5.44915903 | 2.217537782 | |
| NR4A1 | 1.31E−65 | 4.503772288 | 1.833479149 | |
| REL | 1.05E−92 | 4.557582437 | 1.855660913 | |
| PBX4 | 4.34E−34 | 2.027854951 | 0.829354777 | |
| TNF | 3.29E−32 | 2.403875852 | 0.983417335 | |
| IL7R | 2.09E−90 | 4.963852356 | 2.056482076 | |
| RGCC | 4.18E−52 | 3.641583354 | 1.513335849 | |
| FOSL2 | 8.27E−136 | 5.364391103 | 2.244521639 | |
| SIK1 | 5.06E−53 | 2.40027799 | 1.007615991 | |
| CSRNP1 | 2.21E−67 | 3.840776722 | 1.628759198 | |
| GPR132 | 3.72E−30 | 2.031526995 | 0.862615998 | |
| GLUL | 3.47E−28 | 2.233099233 | 0.955295655 | |
| KIAA1683 | 2.40E−34 | 2.26575626 | 0.983533953 | |
| RALGAPA1 | 1.31E−46 | 2.72402864 | 1.193898593 | |
| PRNP | 3.55E−55 | 3.899739622 | 1.716398012 | |
| PRMT10 | 4.41E−28 | 2.203831344 | 0.9761392 | |
| SORL1 | 1.27E−35 | 2.260898386 | 1.01695799 | |
| FAM177A1 | 9.55E−69 | 4.913747872 | 2.265796329 | |
| CHMP1B | 1.35E−36 | 3.133082345 | 1.445099161 | |
| ZC3H12A | 3.57E−48 | 3.561182965 | 1.642960962 | |
| TSC22D2 | 2.88E−49 | 3.320356189 | 1.546466586 | |
| P2RY8 | 3.38E−31 | 2.188617927 | 1.02961924 | |
| NEU1 | 3.84E−33 | 3.292790536 | 1.572735173 | |
| TCF7 | 4.31E−55 | 3.308469276 | 1.588174381 | |
| ZNF683 | 2.11E−24 | 2.138956815 | 1.033050095 | |
| MYADM | 1.01E−96 | 6.675116754 | 3.250421254 | |
| ATP2B1 | 1.23E−26 | 2.195986914 | 1.083249042 | |
| CREM | 4.66E−88 | 7.694627082 | 3.839214426 | |
| OAT | 1.25E−23 | 2.672595049 | 1.339019187 | |
| NFE2L2 | 1.79E−38 | 3.919369557 | 1.968883709 | |
| DNAJB9 | 5.60E−24 | 2.504239718 | 1.2672753 | |
| SKIL | 7.06E−62 | 4.655206906 | 2.387487241 | |

TABLE 9-continued

| | | | | |
|---|---|---|---|---|
| DENND4A | 1.27E−26 | 2.594070684 | 1.331951845 | |
| SERTAD1 | 2.13E−28 | 3.212803971 | 1.651394441 | |
| YPEL5 | 8.59E−102 | 8.312255233 | 4.272756772 | |
| BCL6 | 6.10E−18 | 2.009622059 | 1.043811958 | |
| EGR1 | 3.08E−28 | 3.166562297 | 1.644871081 | |
| PDE4B | 2.21E−52 | 5.475796637 | 2.859061378 | |
| ANXA1 | 1.08E−75 | 8.252186176 | 4.309847652 | |
| SOD2 | 1.87E−17 | 2.085073676 | 1.092164253 | |
| RNF125 | 1.38E−28 | 2.565902115 | 1.351957248 | |
| GADD45B | 6.41E−24 | 3.364530673 | 1.776721079 | |
| SELK | 9.61E−57 | 6.050397655 | 3.235516633 | |
| RORA | 2.42E−28 | 2.748664848 | 1.472234075 | |
| SELL | 6.32E−15 | 2.192817714 | 1.182804004 | |
| MXD1 | 3.38E−16 | 2.033120542 | 1.110371579 | |
| IFRD1 | 1.88E−47 | 5.818877601 | 3.190446363 | |
| PIK3R1 | 2.58E−28 | 4.007311792 | 2.201212537 | |
| TUBB4B | 3.55E−43 | 5.045470043 | 2.789748361 | |
| HECA | 9.74E−18 | 2.036137426 | 1.129865662 | |
| MPZL3 | 1.98E−20 | 2.797447121 | 1.5528395 | |
| USP36 | 2.46E−43 | 4.655958467 | 2.591389474 | |
| INSIG1 | 2.08E−16 | 2.55250692 | 1.439353343 | |
| LTB | 3.90E−14 | 2.089285828 | 1.198337274 | |
| NR4A2 | 5.10E−90 | 8.670934348 | 4.978803937 | |
| SLC2A3 | 4.55E−74 | 8.37521012 | 4.823150952 | |
| PER1 | 9.92E−49 | 4.141906157 | 2.404951911 | |
| S100A10 | 1.27E−33 | 5.772765577 | 3.365144408 | |
| AIM1 | 5.94E−21 | 2.682598663 | 1.565058021 | |
| MGAT4A | 4.11E−15 | 2.392257396 | 1.395993896 | |
| CDC42EP3 | 3.37E−13 | 2.06843029 | 1.208080475 | |
| NDEL1 | 5.54E−19 | 3.040275733 | 1.785412472 | |
| IDI1 | 3.48E−25 | 4.042451327 | 2.384296543 | |
| EIF4A3 | 1.37E−22 | 3.948449863 | 2.330234315 | |
| BIRC3 | 9.01E−53 | 6.903173588 | 4.08020683 | |
| TSPYL2 | 2.84E−30 | 4.732493188 | 2.827440707 | |
| DCTN6 | 8.75E−15 | 2.536182616 | 1.520922064 | |
| HSPH1 | 7.87E−20 | 4.125500345 | 2.478239555 | |
| CDK17 | 2.15E−16 | 2.666535913 | 1.601978123 | |
| DDX21 | 8.00E−15 | 2.162987449 | 1.305638568 | |
| PPP1R15B | 1.89E−16 | 2.648701678 | 1.606445949 | |
| ZNF331 | 1.66E−60 | 7.593874475 | 4.608366594 | |
| BTG2 | 2.63E−40 | 5.882677141 | 3.575700754 | |
| AMD1 | 1.48E−21 | 3.941359871 | 2.397415885 | |
| SLC7A5 | 3.33E−20 | 2.859871351 | 1.744370906 | |
| POLR3E | 4.71E−22 | 3.753752835 | 2.299589379 | |
| JMJD6 | 5.78E−24 | 4.169181055 | 2.554897493 | |
| CHD1 | 3.93E−29 | 4.143608426 | 2.545256433 | |
| TAF13 | 4.69E−10 | 2.0291608 | 1.246698643 | |
| VPS37B | 2.86E−27 | 3.178217463 | 1.954695663 | |
| GTF2B | 4.95E−16 | 3.257013677 | 2.004816899 | |
| PAF1 | 5.69E−16 | 2.842525353 | 1.760833823 | |
| BCAS2 | 7.19E−13 | 2.897021121 | 1.799772551 | |
| RGPD6 | 1.68E−18 | 2.421350288 | 1.514084212 | |
| TUBA4A | 3.95E−39 | 7.524898698 | 4.709933457 | |
| RASA3 | 1.26E−12 | 2.006153535 | 1.259197185 | |
| GPCPD1 | 3.23E−16 | 3.349453356 | 2.103388505 | |
| RASGEF1B | 1.62E−28 | 4.382473959 | 2.754447436 | |
| DNAJA1 | 6.40E−61 | 8.74019538 | 5.494176996 | |

CD8_5

| GeneName | P-value | Mean expression G5 | Mean expression non-G5 | |
|---|---|---|---|---|
| ELL2 | 1.31E−22 | 2.258396304 | 1.067507406 | adjusted P-value = 2.7e−5 |
| PFKFB3 | 1.33E−42 | 3.870436405 | 1.867088669 | |
| DTHD1 | 9.22E−25 | 3.016910937 | 1.591313865 | |
| SMAP2 | 6.22E−27 | 3.463112365 | 1.843131344 | |
| FKBP5 | 9.70E−34 | 4.64587865 | 2.499918859 | |
| AIM1 | 3.33E−22 | 2.886082577 | 1.570074619 | |
| TMEM39A | 7.32E−14 | 2.40024324 | 1.311120526 | |
| NR4A3 | 7.59E−19 | 2.437574361 | 1.338149122 | |
| PER1 | 1.35E−33 | 4.400570708 | 2.421147359 | |
| TSPYL2 | 8.32E−32 | 5.136559275 | 2.827654281 | |
| TTN | 8.07E−33 | 3.006134786 | 1.70228753 | |
| TMEM2 | 3.91E−43 | 6.796935223 | 3.983607915 | |
| IL6ST | 1.46E−13 | 3.235083521 | 1.945757496 | |
| NAB1 | 3.92E−16 | 3.143292963 | 1.914455934 | |
| IQGAP2 | 4.61E−14 | 3.047102441 | 1.905282765 | |
| SLC7A5 | 9.88E−11 | 2.838234759 | 1.782145797 | |
| IPCEF1 | 1.26E−11 | 3.07776164 | 1.953653511 | |
| DCTN6 | 1.59E−10 | 2.457942502 | 1.563838489 | |

TABLE 9-continued

| | | | |
|---|---|---|---|
| DUSP4 | 1.00E−35 | 5.832137839 | 3.75990696 |
| RANBP2 | 1.32E−19 | 4.321354137 | 2.822142334 |
| FAM177A1 | 3.84E−11 | 3.807664523 | 2.509239673 |
| GABARAPL1 | 2.32E−14 | 4.077268197 | 2.709526568 |
| RGPD6 | 4.36E−11 | 2.329022986 | 1.555702802 |
| CTLA4 | 1.67E−09 | 3.774779483 | 2.570537393 |
| CREM | 5.70E−23 | 6.131408184 | 4.18678062 |
| ETS1 | 2.79E−18 | 4.60707062 | 3.157814837 |
| PNRC1 | 5.84E−09 | 2.786248611 | 1.92252723 |
| ZFP36L2 | 4.30E−29 | 7.252180572 | 5.009213671 |
| RGPD5 | 1.69E−12 | 5.1040558 | 3.533326688 |
| ZNF331 | 1.18E−26 | 6.910385854 | 4.800673733 |
| CNOT6L | 8.52E−15 | 4.421764785 | 3.084404685 |
| TGIF1 | 6.44E−07 | 2.428224881 | 1.699522135 |
| CXCL13 | 8.39E−09 | 3.576063687 | 2.511057499 |
| PDE4D | 1.37E−11 | 3.884342535 | 2.727585217 |
| RNF19A | 8.14E−31 | 7.769482372 | 5.488817066 |

CD8_6

| GeneName | P-value | Mean expression G6 | Mean expression non-G6 | |
|---|---|---|---|---|
| PLAC8 | 1.34E−120 | 2.721051972 | 0.566040001 | adjusted P-value = 2.7e−5 |
| S1PR1 | 1.02E−90 | 2.557930913 | 0.711569251 | |
| SORL1 | 1.03E−98 | 2.652430432 | 0.815150733 | |
| SELL | 1.27E−59 | 2.718867008 | 0.962164936 | |
| TCF7 | 1.24E−103 | 3.604480319 | 1.376047023 | |
| CCR7 | 6.60E−44 | 2.205452096 | 0.844474512 | |
| IL7R | 2.15E−106 | 4.655784091 | 1.918493067 | |
| MGAT4A | 2.63E−54 | 2.764843807 | 1.218269602 | |
| FAM65B | 1.44E−68 | 3.448613271 | 1.547656599 | |
| LTB | 2.50E−36 | 2.351713108 | 1.058707102 | |
| FLT3LG | 1.14E−23 | 2.056693579 | 1.041080521 | |
| PXN | 1.99E−26 | 2.16526495 | 1.148703348 | |
| A2M | 6.51E−27 | 2.121310831 | 1.167318427 | |
| ATM | 2.94E−35 | 3.170115623 | 1.8197708 | |
| C20orf112 | 6.25E−23 | 2.417727967 | 1.428535109 | |
| GPR183 | 6.76E−16 | 2.058556979 | 1.254371682 | |
| EPB41 | 3.94E−16 | 2.376064591 | 1.550241763 | |
| ADD3 | 1.04E−13 | 2.343780842 | 1.535037596 | |
| GRAP2 | 1.25E−14 | 2.670324792 | 1.768772329 | |
| KLRG1 | 4.62E−16 | 3.474387291 | 2.30863397 | |
| GIMAP5 | 6.58E−26 | 4.430095626 | 2.951842148 | |
| TC2N | 1.04E−20 | 3.566506845 | 2.434887756 | |
| TXNIP | 3.24E−37 | 7.185732762 | 4.9742525 | |
| GIMAP2 | 1.21E−06 | 2.132831683 | 1.484839796 | |
| TNFAIP8 | 1.81E−11 | 2.489851327 | 1.738181279 | |
| IL16 | 1.41E−14 | 3.41919275 | 2.398557056 | |

TABLE 10

| First split | | Second split | | Third split | | Fourth split | | Fifth split | |
|---|---|---|---|---|---|---|---|---|---|
| | | CD8_2 + | | CD8_4 + | | | | | |
| CD8_B | CD8_G | CD8_1 | 3 | CD8_6 | 5 | CD8_2 | CD8_3 | CD8_4 | CD8_5 |
| VCAM1 | IL7R | SPC25 | TXNIP | PLAC8 | CXCL13 | GEM | GIMAP5 | S1PR1 | CXCL13 |
| CCL3 | TCF7 | CDCA5 | TTN | GIMAP6 | ELL2 | APLP2 | AOAH | LTB | HAVCR2 |
| HAVCR2 | GPR183 | ESCO2 | | GIMAP2 | SLC7A5 | GIMAP7 | GIMAP7 | GPR183 | CTLA4 |
| MYO7A | LMNA | CDC6 | | GIMAP5 | NR4A3 | TGIF1 | SCML4 | ZNF683 | TOX |
| GOLIM4 | NR4A3 | SHCBP1 | | GIMAP4 | LMNA | RDH10 | LY9 | SELL | TNFRSF9 |
| CD38 | MGAT4A | CDC45 | | GIMAP7 | DUSP4 | FKBP4 | GIMAP6 | CCR7 | DTHD1 |
| ENTPD1 | AIM1 | RRM2 | | GNLY | CREM | HSPH1 | TC2N | P2RY8 | NAB1 |
| NDFIP2 | CD55 | DLGAP5 | | SELL | CDKN1A | NAMPTL | GIMAP2 | LMNA | TTN |
| MCM5 | FAM65B | ZWINT | | DENND2D | KPNA2 | TNFRSF18 | GBP1 | TNF | PDCD1 |
| FASLG | RORA | RAD51 | | PTPN6 | CCDC64 | DCTN6 | GIMAP4 | CDKN1A | IPCEF1 |
| ACP5 | TC2N | DTL | | TRPV2 | PHLDA1 | MTSS1 | SAMD9L | S100A10 | ITGAE |
| SNAP47 | PER1 | KIF18B | | IL16 | CKS2 | TNFRSF9 | PPP1R18 | PRNP | FKBP5 |
| STMN1 | FAM102A | TK1 | | FLT3LG | ATP1B3 | PFKFB3 | GYG1 | SORL1 | SIRPG |
| PDCD1 | FAM177A1 | CCNB2 | | S1PR1 | TIPARP | PELI1 | SAMD3 | FAM65B | FCRL3 |
| CXCL13 | ATM | SPC24 | | FAM65B | PFKFB3 | DNAJA4 | STOM | TMEM123 | CD84 |
| WARS | REL | BIRC5 | | LTB | SAMSN1 | RANGAP1 | CYTH4 | TES | PAM |
| CXCR6 | FOSL2 | UBE2C | | TNFAIP8 | AHI1 | CREM | GZMM | PIM1 | CXCR6 |
| PRDX3 | STAT4 | CDC20 | | TRAF3IP3 | DCTN6 | FAM3C | GLIPR2 | EMP3 | ETS1 |
| LSM2 | FOXP1 | CENPW | | PARP9 | FAM177A1 | SEC14L1 | RAB37 | GLIPR2 | ATHL1 |
| IGFLR1 | EGR1 | CDCA3 | | A2M | KDM6B | CKS2 | TBC1D10C | TPM4 | CD27 |

TABLE 10-continued

|  |  |  | Second split |  | Third split |  |  |  | Fifth split |  |
|---|---|---|---|---|---|---|---|---|---|---|
| First split |  |  | CD8_2 + |  | CD8_4 + |  | Fourth split |  |  |  |
| CD8_B | CD8_G | CD8_1 | 3 | CD8_6 | 5 | CD8_2 | CD8_3 | CD8_4 | CD8_5 |  |
| MTHFD1 | PIK3R1 | HJURP | SAMD3 | GABARAPL1 | DFNB31 | MYO1F | OASL | PYHIN1 |  |  |
| FABP5 | TSPYL2 | MELK | GRAP2 | INSIG1 | VCAM1 | GPR174 | GLUL | IL6ST |  |  |
| DNPH1 |  | RAD51AP1 | PXN | TNFSF9 | RGCC | C5orf56 | RORA | SMAP2 |  |  |
| SIRPG |  | DHFR | KLRG1 | GTF2B | AHI1 | GRAP2 | NR4A1 | LYST |  |  |
| PTTG1 |  | GINS2 | SASH3 | TSPYL2 | KPNA2 | SLFN5 | CXCR3 | ERAP2 |  |  |
| IFI35 |  | PKMYT1 | SSBP1 | NAMPT | NR4A1 | FAM102A | ANXA1 | KLRC4 |  |  |
| CCR5 |  | ANLN | SAMHD1 | RALGAPA1 | TSPYL2 | PATL2 | ANXA2 | LRMP |  |  |
| TNFRSF9 |  | CENPH | SORL1 | JMJD6 | ZFAND2A | PVRIG | GPR132 | CCL4L2 |  |  |
| SKA2 |  | ASF1B | ADD3 | RGCC | LAYN | AGTRAP | LYAR | PRDM1 |  |  |
| UBE2F |  | CLSPN | DBNL | MTHFD2 | NAB1 | ARHGAP25 | GADD45B | AHI1 |  |  |
| SAE1 |  | CDCA8 | MGAT4A | TSC22D2 | RALA | PARP9 | HSPA1A | PLCB2 |  |  |
| TRAFD1 |  | GGH | GIT2 | REL | HSPB1 | C14orf159 | S100A11 | EVL |  |  |
| HLA-DQA1 |  | KIFC1 | PRMT2 | PLK3 | PDE3B | RPS6KA1 | TMBIM1 | LPIN1 |  |  |
| EPSTI1 |  | TYMS | C19orf66 | VPS37B | ITPRIP | PKN1 | DNAJB9 | PDE4D |  |  |
| CTLA4 |  | FEN1 | COX7A2L | SELK | PHLDA1 | CSK | MTRNR2L1 | RBPJ |  |  |
| GTF3C6 |  | KIF2C | RGS10 | HSPH1 | ETV1 | TBCD | PBX4 | TCIRG1 |  |  |
| IFI27L2 |  | KIAA0101 | DAD1 | SLC38A2 | HSPD1 | HMOX2 | TCF7 | OXNAD1 |  |  |
| HLA-DMA |  | PLK1 | PTPN4 | OAT | ZEB2 | EPSTI1 | MGAT4A | CBLB |  |  |
| PDIA6 |  | SPAG5 | XAF1 | RASGEF1B | METRNL | CCND3 | SOD2 | HNRNPLL |  |  |
| CD2BP2 |  | ORC6 | PVRIG | YPEL5 | CTLA4 | KLRG1 | CSRNP1 | DUSP4 |  |  |
| BATF |  | WDR34 | SLC44A2 | SERTAD1 | FOSL2 | TES | BIRC2 | NAP1L4 |  |  |
| RANBP1 |  | KIF23 | PIM1 | ZNF331 | TNFSF9 | SASH3 | CDC42EP3 | TXNIP |  |  |
| MRPL51 |  | TOP2A | TMBIM4 | GSPT1 | CADM1 | IDH2 | CD55 | RGS1 |  |  |
| OAS3 |  | RFC3 | CMC1 | HNRNPLL | AHSA1 | RP4-583P15.14 | MT2A | CCL4L1 |  |  |
| CDC123 |  | TIMELESS | TXNIP | CRTAM | ZBTB1 | SELPLG | VIM | RAP1GDS1 |  |  |
| PCNA |  | AURKB | ATM | TGIF1 | BPGM | SLAMF7 | XCL2 | TIGIT |  |  |
| HSD17B10 |  | NUF2 | PHB2 | EIF4A3 | CACYBP | RCSD1 | ZC3H12A | PARK7 |  |  |
| CLTA |  | NCAPG | COA1 | ICOS | GSPT1 | MX1 | HSPA1B | CCL4 |  |  |
| VAMP5 |  | MLF1IP | SIT1 | MPZL3 | REL | CD52 | STIP1 | IKZF3 |  |  |
| FKBP1A |  | BRCA1 | HERC3 | BTG3 | ICOS | SP110 | TUBA1C | SH2D1A |  |  |
| NDUFB3 |  | SGOL1 | PSD4 | HBP1 | ENTPD1 | ARHGEF3 | IL21R | ATXN1 |  |  |
| NOP10 |  | CKAP2L | AES | TMEM2 | HBP1 | SLAMF6 | TTC39C | ITK |  |  |
| SHFM1 |  | CDK1 | POLD4 | NR4A2 | TBC1D4 | LIME1 | EIF4A3 |  |  |  |
| COX5A |  | MCM4 | C20orf112 | NASP | NEU1 | CXCR3 | LGALS1 |  |  |  |
| TIGIT |  | TROAP | C2orf68 | NFE2L2 | CCDC64 | RNF166 | PPP3CA |  |  |  |
| BLOC1S1 |  | ASPM | GMFG | FAM46C | PMAIP1 | OAS2 | MOB4 |  |  |  |
| ANXA5 |  | HMGB3 | OXNAD1 | FOSL2 | AMD1 | TPST2 | DOK2 |  |  |  |
| PAM |  | MCM2 | GPSM3 | ETF1 | RASGEF1B | IL16 | IFNG |  |  |  |
| JAKMIP1 |  | NCAPG2 | ESYT1 | HSPD1 | GTF2B | CD48 | CCT2 |  |  |  |
| HLA-DRA |  | CDKN3 | TBC1D10C | ZEB2 | SERTAD1 | DENND2D | RILPL2 |  |  |  |
| SNRPD1 |  | CASC5 | IRF9 | AMD1 | NAMPT | PIM1 | C14orf166 |  |  |  |
| GZMB |  | TCF19 | ERP29 | SDCBP | CHORDC1 |  | CAST |  |  |  |
| COPZ1 |  | KIF11 | TMEM230 | MYADM | NFE2L2 |  | YWHAQ |  |  |  |
| CD63 |  | HIRIP3 | ARHGAP25 | TUBB4B | DDX3Y |  | PPP2R3C |  |  |  |
| CARD16 |  | BRCA2 | DEF6 | PAF1 | MORF4L2 |  | CHMP1B |  |  |  |
| FIBP |  | CCNB1 | GNG5 | FAM129A | BIRC3 |  | RGCC |  |  |  |
| ATP5J |  | APOBEC3B | TTC39C | IFRD1 | BTG3 |  | REL |  |  |  |
| GSTO1 |  | MKI67 | BIN2 | BIRC3 | PER1 |  | STOM |  |  |  |
| TOX |  | TPX2 | MFNG | GTPBP1 | CRTAM |  | KPNA2 |  |  |  |
| TXN2 |  | CCNF | SRP9 | HEXIM1 | AFAP1L2 |  | PTP4A1 |  |  |  |
| C17orf49 |  | NCAPH | PTEN | NEU1 | EIF4A3 |  | RAB8B |  |  |  |
| ADORA2A |  | ECT2 | SYTL1 | SYAP1 | RHBDD2 |  | SC5D |  |  |  |
| CHST12 |  | ATAD5 | PRKACB | ZC3H12A | HSPE1 |  | BCAS2 |  |  |  |
| TRIM59 |  | STMN1 | C5orf56 | IL21R | JMJD6 |  | CDK17 |  |  |  |
| TMPO |  | UBE2T | MYO1F | RGPD6 | DEDD2 |  | INSIG1 |  |  |  |
| PSMB2 |  | FANCI | HMOX2 | IDI1 | IFRD1 |  | NEU1 |  |  |  |
| HELLS |  | PRC1 | NUCB2 | NR4A1 | CXCL13 |  | ABLIM1 |  |  |  |
| SNRPE |  | RNASEH2A | NME1-NME2 | TUBA4A | B3GNT2 |  | PPP2CA |  |  |  |
| NDUFAB1 |  | BUB1B | UBE2L6 | RNF19A | IL21R |  | SDCBP |  |  |  |
| SQRDL |  | CKS1B | VPS29 | NR3C1 | HSPA4 |  | CHP1 |  |  |  |
| SERPINB1 |  | CENPM | SNX17 | IL6ST | BHLHE40 |  | CACYBP |  |  |  |
| MX1 |  | SMC2 | ST6GAL1 | RGS2 | SDCBP |  | SAMD3 |  |  |  |
| MEA1 |  | CCNA2 | CSK | ZBTB1 | ATP1B3 |  | MAP1LC3B2 |  |  |  |
| GPR56 |  | BUB1 | RBL2 | RANBP2 | CHD1 |  | FOS |  |  |  |
| NUTF2 |  | CENPN | PPIE | MAT2A | BANP |  | SLFN11 |  |  |  |
| BST2 |  | AURKA | STX16 | CHMP1B | ZC3H12A |  | TAGLN2 |  |  |  |
| FUT8 |  | MAD2L1 | PILRB | DNTTIP2 | EIF5 |  | DDX21 |  |  |  |
| DUT |  | CDCA7 | LENG8 | BCAS2 | LRMP |  | TMEM50A |  |  |  |
| GNG5 |  | CHTF18 | C11orf31 | SKIL | CD55 |  | SLMO2 |  |  |  |
| ATP6V1E1 |  | CHEK1 | ABRACL | TNFRSF1B | ZNF331 |  | CD5 |  |  |  |
| AP2S1 |  | CENPF | ANP32B | POLR3E | POLR3E |  | SCP2 |  |  |  |
| CALM3 |  | LIG1 | TPST2 | CSRNP1 | TUBB4B |  | CD28 |  |  |  |
| MRPS34 |  | KNTC1 | ATP5A1 | LYST | SLC38A2 |  | RAB7L1 |  |  |  |
| CD27 |  | RPL39L | NFATC3 | GOLGB1 | DUSP4 |  | ATP2B1 |  |  |  |

TABLE 10-continued

| First split | | Second split | | Third split | | Fourth split | | Fifth split | |
| --- | --- | --- | --- | --- | --- | --- | --- | --- | --- |
| | | CD8_2 + | | CD8_4 + | | | | | |
| CD8_B | CD8_G | CD8_1 | 3 | CD8_6 | 5 | CD8_2 | CD8_3 | CD8_4 | CD8_5 |
| TMEM179B | | POLE | | ARHGEF3 | EIF5 | CNIH1 | | CD52 | |
| SRI | | POLD1 | | GLIPR2 | PDE4B | TMPO | | CAMLG | |
| PSMB3 | | RFC5 | | CKLF | JUND | STIP1 | | PLP2 | |
| IFI6 | | MXD3 | | OSTF1 | PER1 | RGS2 | | TOR1AIP2 | |
| SIT1 | | RFC4 | | SNX6 | DNAJA1 | GLS | | MAP2K3 | |
| PON2 | | RACGAP1 | | LAMTOR4 | TFRC | CCT2 | | CAMK4 | |

Pipeline for Detection of Cells Positive for CD8 and TCF7

CellProfiler Pipeline: www.cellprofiler.org
Version:3
DateRevision:20160418141927
GitHash:9969f42
ModuleCount:16
HasImagePlaneDetails:False
Images:[module_num:1|svn_version:\'Unknown\'|variable_revision_number:2
|show_window:False|notes:\x5B\'To begin creating your project, use the
Images module to compile a list of files and/or folders that you want
to analyze. You can also specify a set of rules to include only the
desired files in your selected
folders.\'\x5D|batch_state:array(\x5B\x5D,
dtype=uint8)|enabled:True|wants_pause:False]
    :
    Filter images?:Images only
    Select the rule criteria:and (extension does isimage) (directory
doesnot containregexp "\x5B\\\\\\\\\\\\\\\/\x5D\\\\\\\.")
Metadata:[module_num:2|svn_version:\'Unknown\'|variable_revision_number
:4|show_window:False|notes:\x5B\'The Metadata module optionally allows
you to extract information describing your images (i.e, metadata) which
will be stored along with your measurements. This information can be
contained in the file name and/or location, or in an external
file.\'\x5D|batch_state:array(\x5B\x5D,
dtype=uint8)|enabled:True|wants_pause:False]
    Extract metadata?:No
    Metadata data type:Text
    Metadata types:{ }
    Extraction method count:1
    Metadata extraction method:Extract from file/folder names
    Metadata source:File name
    Regular expression:^(?P<Plate>.*)_(?P<Well>\x5BA-P\x5D\x5B0-
9\x5D{2})_s(?P<Site>\x5B0-9\x5D)_w(?P<ChannelNumber>\x5B0-9\x5D)
    Regular expression:(?P<Date>\x5B0-9\x5D{4}_\x5B0-9\x5D{2}_\x5B0-
9\x5D{2})$
    Extract metadata from:All images
    Select the filtering criteria:and (file does contain "")
    Metadata file location:
    Match file and image metadata:\x5B\x5D
    Use case insensitive matching?:No
NamesAndTypes:[module_num:3|svn_version:\'Unknown\'|variable_revision_n
umber:6|show_window:False|notes:\x5B\'The NamesAndTypes module allows
you to assign a meaningful name to each image by which other modules
will refer to it.\'\x5D|batch_state:array(\x5B\x5D,
dtype=uint8)|enabled:True|wants_pause:False]
    Assign a name to:All images
    Select the image type:Color image
    Name to assign these images:ColorImage
    Match metadata:\x5B\x5D
    Image set matching method:Order
    Set intensity range from:Image metadata
    Assignments count:1
    Single images count:0
    Maximum intensity:255.0
    Select the rule criteria:and (file does contain "")
    Name to assign these images:DNA
    Name to assign these objects:Cell
    Select the image type:Grayscale image
    Set intensity range from:Image metadata
    Retain outlines of loaded objects?:No
    Name the outline image:LoadedOutlines
    Maximum intensity:255.0

-continued

```
Groups:[module_num:4|svn_version:\'Unknown\'|variable_revision_number:2
|show_window:False|notes:\x5B\'The Groups module optionally allows you
to split your list of images into image subsets (groups) which will be
processed independently of each other. Examples of groupings include
screening batches, microtiter plates, time-lapse movies,
etc.\'\x5D|batch_state:array(\x5B\x5D,
dtype=uint8)|enabled:True|wants_pause:False]
    Do you want to group your images?:No
    grouping metadata count:1
    Metadata category:None
ColorToGray:[module_num:5|svn_version:\'Unknown\'|variable_revision_num
ber:3|show_window:False|notes:\x5B\x5D|batch_state:array(\x5B\x5D,
dtype=uint8)|enabled:True|wants_pause:False]
    Select the input image:ColorImage
    Conversion method:Split
    Image type:Channels
    Name the output image:OrigGray
    Relative weight of the red channel:1.0
    Relative weight of the green channel:1.0
    Relative weight of the blue channel:1.0
    Convert red to gray?:Yes
    Name the output image:OrigRed
    Convert green to gray?:Yes
    Name the output image:OrigGreen
    Convert blue to gray?:Yes
    Name the output image:OrigBlue
    Convert hue to gray?:Yes
    Name the output image:OrigHue
    Convert saturation to gray?:Yes
    Name the output image:OrigSaturation
    Convert value to gray?:Yes
    Name the output image:OrigValue
    Channel count:3
    Channel number:Red\x3A 1
    Relative weight of the channel:1.0
    Image name:TCF7
    Channel number:Green\x3A 2
    Relative weight of the channel:1.0
    Image name:CD8
    Channel number:Blue\x3A 3
    Relative weight of the channel:1.0
    Image name:DAPI
EnhanceOrSuppressFeatures:[module_num:6|svn_version:\'Unknown\'|variabl
e_revision_number:5|show_window:False|notes:\x5B\x5D|batch_state:array(
\x5B\x5D, dtype=uint8)|enabled:True|wants_pause:False]
    Select the input image:DAPI
    Name the output image:FilteredDAPI
    Select the operation:Enhance
    Feature size:20
    Feature type:Speckles
    Range of hole sizes:1,10
    Smoothing scale:2.0
    Shear angle:0.0
    Decay:0.95
    Enhancement method:Tubeness
    Speed and accuracy:Fast / hexagonal
IdentifyPrimaryObjects:[module_num:7|svn_version:\'Unknown\'|variable_r
evision_number:10|show_window:False|notes:\x5B\x5D|batch_state:array(\x
5B\x5D, dtype=uint8)|enabled:True|wants_pause:False]
    Select the input image:FilteredDAPI
    Name the primary objects to be identified:Nuclei
    Typical diameter of objects, in pixel units (Min,Max):15,50
    Discard objects outside the diameter range?:Yes
    Try to merge too small objects with nearby larger objects?:No
    Discard objects touching the border of the image?:Yes
    Method to distinguish clumped objects:Shape
    Method to draw dividing lines between clumped objects:Propagate
    Size of smoothing filter:10
    Suppress local maxima that are closer than this minimum allowed
distance:7.0
    Speed up by using lower-resolution image to find local maxima?:Yes
    Name the outline image:PrimaryOutlines
    Fill holes in identified objects?:After both thresholding and
declumping
    Automatically calculate size of smoothing filter for
declumping?:Yes
    Automatically calculate minimum allowed distance between local
maxima?:Yes
    Retain outlines of the identified objects?:No
```

Automatically calculate the threshold using the Otsu method?:Yes
    Enter Laplacian of Gaussian threshold:0.5
    Automatically calculate the size of objects for the Laplacian of
Gaussian filter?:Yes
    Enter LoG filter diameter:5.0
    Handling of objects if excessive number of objects
identified:Continue
    Maximum number of objects:500
    Threshold setting version:2
    Threshold strategy:Adaptive
    Thresholding method:Otsu
    Select the smoothing method for thresholding:Automatic
    Threshold smoothing scale:1.0
    Threshold correction factor:1.0
    Lower and upper bounds on threshold:0.0,1.0
    Approximate fraction of image covered by objects?:0.01
    Manual threshold:0.0
    Select the measurement to threshold with:None
    Select binary image:None
    Masking objects:None
    Two-class or three-class thresholding?:Two classes
    Minimize the weighted variance or the entropy?:Weighted variance
    Assign pixels in the middle intensity class to the foreground or
the background?:Foreground
    Method to calculate adaptive window size:Image size
    Size of adaptive window:10
    Use default parameters?:Default
    Lower outlier fraction:0.05
    Upper outlier fraction:0.05
    Averaging method:Mean
    Variance method:Standard deviation
    # of deviations:2.0
RescaleIntensity:[module_num:8|svn_version:\'Unknown\'|variable_revisio
n_number:2|show_window:False|notes:\x5B\x5D|batch_state:array(\x5B\x5D,
dtype=uint8)|enabled:True|wants_pause:False]
    Select the input image:CD8
    Name the output image:RescaledCD8
    Rescaling method:Stretch each image to use the full intensity range
    Method to calculate the minimum intensity:Custom
    Method to calculate the maximum intensity:Custom
    Lower intensity limit for the input image:0.0
    Upper intensity limit for the input image:1.0
    Intensity range for the input image:0.0,1.0
    Intensity range for the output image:0.0,1.0
    Method to rescale pixels below the lower limit:Mask pixels
    Custom value for pixels below lower limit:0.0
    Method to rescale pixels above the upper limit:Mask pixels
    Custom value for pixels above upper limit:0.0
    Select image to match in maximum intensity:None
    Divisor value:1.0
    Divisor measurement:None
MeasureObjectIntensity:[module_num:9|svn_version:\'Unknown\'|variable_r
evision_number:3|show_window:False|notes:\x5B\x5D|batch_state:array(\x5
B\x5D, dtype=uint8)|enabled:True|wants_pause:False]
    Hidden:1
    Select an image to measure:RescaledCD8
    Select objects to measure:Nuclei
FilterObjects:[module_num:10|svn_version:\'Unknown\'|variable_revision_
number:7|show_window:False|notes:\x5B\x5D|batch_state:array(\x5B\x5D,
dtype=uint8)|enabled:True|wants_pause:False]
    Name the output objects:CD8PosNuclei
    Select the object to filter:Nuclei
    Select the filtering mode:Measurements
    Select the filtering method:Limits
    Select the objects that contain the filtered objects:None
    Retain outlines of the identified objects?:No
    Name the outline image:FilteredObjects
    Rules file location:Elsewhere...\x7C
    Rules file name:rules.txt
    Class number:1
    Measurement count:1
    Additional object count:0
    Assign overlapping child to:Both parents
    Select the measurement to filter
by:Intensity_MeanIntensityEdge_RescaledCD8
    Filter using a minimum measurement value?:Yes
    Minimum value:0.1
    Filter using a maximum measurement value?:No
    Maximum value:1.0

-continued

IdentifyPrimaryObjects:[module_num:11|svn_version:\'Unknown\'|variable_revision_number:10|show_window:False|notes:\x5B\x5D|batch_state:array(\x5B\x5D, dtype=uint8)|enabled:True|wants_pause:False]
    Select the input image:TCF7
    Name the primary objects to be identified:TCF7Nuclei
    Typical diameter of objects, in pixel units (Min,Max):10,40
    Discard objects outside the diameter range?:Yes
    Try to merge too small objects with nearby larger objects?:No
    Discard objects touching the border of the image?:Yes
    Method to distinguish clumped objects:Intensity
    Method to draw dividing lines between clumped objects:Intensity
    Size of smoothing filter:10
    Suppress local maxima that are closer than this minimum allowed distance:7.0
    Speed up by using lower-resolution image to find local maxima?:Yes
    Name the outline image:PrimaryOutlines
    Fill holes in identified objects?:After both thresholding and declumping
    Automatically calculate size of smoothing filter for declumping?:Yes
    Automatically calculate minimum allowed distance between local maxima?:Yes
    Retain outlines of the identified objects?:No
    Automatically calculate the threshold using the Otsu method?:Yes
    Enter Laplacian of Gaussian threshold:0.5
    Automatically calculate the size of objects for the Laplacian of Gaussian filter?:Yes
    Enter LoG filter diameter:5.0
    Handling of objects if excessive number of objects identified:Continue
    Maximum number of objects:500
    Threshold setting version:2
    Threshold strategy:Automatic
    Thresholding method:Otsu
    Select the smoothing method for thresholding:Automatic
    Threshold smoothing scale:1.0
    Threshold correction factor:1.0
    Lower and upper bounds on threshold:0.0,1.0
    Approximate fraction of image covered by objects?:0.01
    Manual threshold:0.0
    Select the measurement to threshold with:None
    Select binary image:None
    Masking objects:None
    Two-class or three-class thresholding?:Two classes
    Minimize the weighted variance or the entropy?:Weighted variance
    Assign pixels in the middle intensity class to the foreground or the background?:Foreground
    Method to calculate adaptive window size:Image size
    Size of adaptive window:10
    Use default parameters?:Default
    Lower outlier fraction:0.05
    Upper outlier fraction:0.05
    Averaging method:Mean
    Variance method:Standard deviation
    # of deviations:2.0
Maskobjects:[module_num:12|svn_version:\'Unknown\'|variable_revision_number:2|show_window:False|notes:\x5B\x5D|batch_state:array(\x5B\x5D, dtype=uint8)|enabled:True|wants_pause:False]
    Select objects to be masked:CD8PosNuclei
    Name the masked objects:TCF7PosCD8PosNuclei
    Mask using a region defined by other objects or by binary image?:Objects
    Select the masking object:TCF7Nuclei
    Select the masking image:None
    Handling of objects that are partially masked:Remove depending on overlap
    Fraction of object that must overlap:0.3
    Numbering of resulting objects:Renumber
    Retain outlines of the resulting objects?:No
    Name the outline image:MaskedOutlines
    Invert the mask?:No
CalculateMath:[module_num:13|svn_version:\'Unknown\'|variable_revision_number:2|show_window:False|notes:\x5B\x5D|batch_state:array(\x5B\x5D, dtype=uint8)|enabled:True|wants_pause:False]
    Name the output measurement:Count_CD8Pos_TCFNeg
    Operation:Subtract
    Select the minuend measurement type:Image
    Select the minuend objects:None
    Select the minuend measurement:Count_CD8PosNuclei Multiply the above operand by:1.0
Raise the power of above operand by:1.0
Select the subtrahend measurement type:Image
Select the subtrahend objects:None
Select the subtrahend measurement:Count_TCF7PosCD8PosNuclei
Multiply the above operand by:1.0
Raise the power of above operand by:1.0
Take log10 of result?:No
Multiply the result by:1.0
Raise the power of result by:1.0
Add to the result:0.0
Constrain the result to a lower bound?:No
Enter the lower bound:0.0
Constrain the result to an upper bound?:No
Enter the upper bound:1.0
OverlayOutlines:[module_num:14|svn_version:\'Unknown\'|variable_revision_number:3|show_window:False|notes:\x5B\x5D|batch_state:array(\x5B\x5D, dtype=uint8)|enabled:True|wants_pause:False]
    Display outlines on a blank image?:No
    Select image on which to display outlines:ColorImage
    Name the output image:OrigOverlay
    Outline display mode:Color
    Select method to determine brightness of outlines:Max of image
    Width of outlines:1
    Select outlines to display:None
    Select outline color:#F8FF2D
    Load outlines from an image or objects?:Objects
    Select objects to display:CD8PosNuclei
    Select outlines to display:None
    Select outline color:#F1F7F7
    Load outlines from an image or objects?:Objects
    Select objects to display:TCF7PosCD8PosNuclei
SaveImages:[module_num:15|svn_version:\'Unknown\'|variable_revision_number:11|show_window:False|notes:\x5B\x5D|batch_state:array(\x5B\x5D, dtype=uint8)|enabled:True|wants_pause:True]
    Select the type of image to save:Image
    Select the image to save:OrigOverlay
    Select the objects to save:None
    Select the module display window to save:None
    Select method for constructing file names:From image filename
    Select image name for file prefix:ColorImage
    Enter single file name:OrigBlue
    Number of digits:4
    Append a suffix to the image file name?:Yes
    Text to append to the image name:_Overlay
    Saved file format:tif
    Output file location:Default Output Folder\x7C
    Image bit depth:8-bit integer
    Overwrite existing files without warning?:No
    When to save:Every cycle
    Rescale the images? :Yes
    Save as grayscale or color image?:Grayscale
    Select colormap:gray
    Record the file and path information to the saved image?:No
    Create subfolders in the output folder?:No
    Base image folder:Elsewhere ...\x7C
    Saved movie format:avi
ExportToSpreadsheet:[module_num:16|svn_version:\'Unknown\'|variable_revision_number:11|show_window:False|notes:\x5B\x5D|batch_state:array(\x5B\x5D, dtype=uint8)|enabled:True|wants_pause:False]
    Select the column delimiter:Comma (",")
    Add image metadata columns to your object data file?:No
    Limit output to a size that is allowed in Excel?:No
    Select the measurements to export:Yes
    Calculate the per-image mean values for object measurements?:No
    Calculate the per-image median values for object measurements?:No
    Calculate the per-image standard deviation values for object measurements?:No
    Output file location:Default Output Folder\x7C
    Create a GenePattern GCT file?:No
    Select source of sample row name:Metadata
    Select the image to use as the identifier:None
    Select the metadata to use as the identifier:None
    Export all measurement types?:No
:Image\x7CCount_TCF7Nuclei,Image\x7CCount_Nuclei,Image\x7CCount_CD8PosNuclei,Image\x7CCount_TCF7PosCD8PosNuclei,Image\x7CMath_Count_CD8Pos_TCFNeg
    Representation of Nan/Inf:NaN
    Add a prefix to file names?:No Filename prefix:MyExpt_
Overwrite existing files without warning?:No
Data to export:Image
Combine these object measurements with those of the previous object?:No
File name:DATA.csv
Use the object name for the file name?:Yes

REFERENCES

1. Callahan, M. K., Postow, M. A. & Wolchok, J. D. Targeting T Cell Co-receptors for Cancer Therapy. *Immunity* 44, 1069-1078, doi:10.1016/j.immuni.2016.04.023 (2016).
2. Iwai, Y., Hamanishi, J., Chamoto, K. & Honjo, T. Cancer immunotherapies targeting the PD-1 signaling pathway. *J Biomed Sci* 24, 26, doi:10.1186/s12929-017-0329-9 (2017).
3. Robert, C. et al. Pembrolizumab versus Ipilimumab in Advanced Melanoma. *N Engl J Med* 372, 2521-2532, doi:10.1056/NEJMoa1503093 (2015).
4. Larkin, J. et al. Combined Nivolumab and Ipilimumab or Monotherapy in Untreated Melanoma. *N Engl J Med* 373, 23-34, doi:10.1056/NEJMoa1504030 (2015).
5. Tumeh, P. C. et al. PD-1 blockade induces responses by inhibiting adaptive immune resistance. *Nature* 515, 568-571, doi:10.1038/nature13954 (2014).
6. Chen, P. L. et al. Analysis of Immune Signatures in Longitudinal Tumor Samples Yields Insight into Biomarkers of Response and Mechanisms of Resistance to Immune Checkpoint Blockade. *Cancer Discov* 6, 827-837, doi:10.1158/2159-8290.CD-15-1545 (2016).
7. Wherry, E. J. et al. Molecular signature of CD8+ T cell exhaustion during chronic viral infection. *Immunity* 27, 670-684, doi:10.1016/j.immuni.2007.09.006 (2007).
8. Speiser, D. E., Ho, P. C. & Verdeil, G. Regulatory circuits of T cell function in cancer. *Nat Rev Immunol* 16, 599-611, doi:10.1038/nri.2016.80 (2016).
9. Schumacher, T. N. & Schreiber, R. D. Neoantigens in cancer immunotherapy. *Science* 348, 69-74, doi:10.1126/science.aaa4971 (2015).
10. Hulpke, S. & Tampe, R. The MHC I loading complex: a multitasking machinery in adaptive immunity. *Trends Biochem Sci* 38, 412-420, doi:10.1016/j.tibs.2013.06.003 (2013).
11. Garon, E. B. et al. Pembrolizumab for the treatment of non-small-cell lung cancer. *N Engl J Med* 372, 2018-2028, doi:10.1056/NEJMoa1501824 (2015).
12. Van Allen, E. M. et al. Genomic correlates of response to CTLA-4 blockade in metastatic melanoma. *Science* 350, 207-211, doi:10.1126/science.aad0095 (2015).
13. Gao, J. et al. Loss of IFN-gamma Pathway Genes in Tumor Cells as a Mechanism of Resistance to Anti-CTLA-4 Therapy. *Cell* 167, 397-404 e399, doi:10.1016/j.cell.2016.08.069 (2016).
14. Zaretsky, J. M. et al. Mutations Associated with Acquired Resistance to PD-1 Blockade in Melanoma. *N Engl J Med* 375, 819-829, doi:10.1056/NEJMoa1604958 (2016).
15. Sade-Feldman, M. et al. Resistance to checkpoint blockade therapy through inactivation of antigen presentation. *Nat Commun* 8, 1136, doi:10.1038/s41467-017-01062-w (2017).
16. McGranahan, N. et al. Allele-Specific HLA Loss and Immune Escape in Lung Cancer Evolution. *Cell*, doi:10.1016/j.cell.2017.10.001 (2017).
17. Daud, A. I. et al. Tumor immune profiling predicts response to anti-PD-1 therapy in human melanoma. *J Clin Invest* 126, 3447-3452, doi:10.1172/JCI87324 (2016).
18. Sade-Feldman, M. et al. Clinical Significance of Circulating CD33+CD11b+HLA-DR-Myeloid Cells in Patients with Stage IV Melanoma Treated with Ipilimumab. *Clin Cancer Res* 22, 5661-5672, doi:10.1158/1078-0432.CCR-15-3104 (2016).
19. Huang, A. C. et al. T-cell invigoration to tumour burden ratio associated with anti-PD-1 response. *Nature* 545, 60-65, doi:10.1038/nature22079 (2017).
20. Eisenhauer, E. A. et al. New response evaluation criteria in solid tumours: revised RECIST guideline (version 1.1). *Eur J Cancer* 45, 228-247, doi:10.1016/j.ejca.2008.10.026 (2009).
21. Villani, A. C. et al. Single-cell RNA-seq reveals new types of human blood dendritic cells, monocytes, and progenitors. *Science* 356, doi:10.1126/science.aah4573 (2017).
22. Fuertes Marraco, S. A., Neubert, N. J., Verdeil, G. & Speiser, D. E. Inhibitory Receptors Beyond T Cell Exhaustion. *Front Immunol* 6, 310, doi:10.3389/fimmu.2015.00310 (2015).
23. Cohen, N. R. et al. Shared and distinct transcriptional programs underlie the hybrid nature of iNKT cells. *Nat Immunol* 14, 90-99, doi:10.1038/ni.2490 (2013).
24. Hidalgo, L. G., Einecke, G., Allanach, K. & Halloran, P. F. The transcriptome of human cytotoxic T cells: similarities and disparities among allostimulated CD4(+) CTL, CD8(+) CTL and NK cells. *Am J Transplant* 8, 627-636, doi:10.1111/j.1600-6143.2007.02128.x (2008).
25. Pardoll, D. M. The blockade of immune checkpoints in cancer immunotherapy. *Nat Rev Cancer* 12, 252-264, doi:10.1038/nrc3239 (2012).
26. Hurton, L. V. et al. Tethered IL-15 augments antitumor activity and promotes a stem-cell memory subset in tumor-specific T cells. *Proc Natl Acad Sci USA* 113, E7788-E7797, doi:10.1073/pnas.1610544113 (2016).
27. Gattinoni, L., Ji, Y. & Restifo, N. P. Wnt/beta-catenin signaling in T-cell immunity and cancer immunotherapy. *Clin Cancer Res* 16, 4695-4701, doi:10.1158/1078-0432.CCR-10-0356 (2010).
28. Zhou, X. et al. Differentiation and persistence of memory CD8(+) T cells depend on T cell factor 1. *Immunity* 33, 229-240, doi:10.1016/j.immuni.2010.08.002 (2010).
29. Utzschneider, D. T. et al. T Cell Factor 1-Expressing Memory-like CD8(+) T Cells Sustain the Immune Response to Chronic Viral Infections. *Immunity* 45, 415-427, doi:10.1016/j.immuni.2016.07.021 (2016).
30. Im, S. J. et al. Defining CD8+ T cells that provide the proliferative burst after PD-1 therapy. *Nature* 537, 417-421, doi:10.1038/nature19330 (2016).
31. Carpenter, A. E. et al. CellProfiler: image analysis software for identifying and quantifying cell phenotypes. *Genome Biol* 7, R100, doi:10.1186/gb-2006-7-10-r100 (2006).

32. Gupta, P. K. et al. CD39 Expression Identifies Terminally Exhausted CD8+ T Cells. *PLoS Pathog* 11, e1005177, doi:10.1371/journal.ppat.1005177 (2015).
33. Tirosh, I. et al. Dissecting the multicellular ecosystem of metastatic melanoma by single-cell RNA-seq. *Science* 352, 189-196, doi:10.1126/science.aad0501 (2016).
34. Trapnell, C. et al. The dynamics and regulators of cell fate decisions are revealed by pseudotemporal ordering of single cells. *Nat Biotechnol* 32, 381-386, doi:10.1038/nbt.2859 (2014).
35. Young, A., Mittal, D., Stagg, J. & Smyth, M. J. Targeting cancer-derived adenosine: new therapeutic approaches. *Cancer Discov* 4, 879-888, doi:10.1158/2159-8290.CD-14-0341 (2014).
36. Anderson, A. C., Joller, N. & Kuchroo, V. K. Lag-3, Tim-3, and TIGIT: Co-inhibitory Receptors with Specialized Functions in Immune Regulation. *Immunity* 44, 989-1004, doi:10.1016/j.immuni.2016.05.001 (2016).
37. Allard, B., Pommey, S., Smyth, M. J. & Stagg, J. Targeting CD73 enhances the antitumor activity of anti-PD-1 and anti-CTLA-4 mAbs. *Clin Cancer Res* 19, 5626-5635, doi:10.1158/1078-0432.CCR-13-0545 (2013).
38. Sun, X. et al. CD39/ENTPD1 expression by CD4+ Foxp3+ regulatory T cells promotes hepatic metastatic tumor growth in mice. *Gastroenterology* 139, 1030-1040, doi:10.1053/j.gastro.2010.05.007 (2010).
39. Buenrostro, J. D., Giresi, P. G., Zaba, L. C., Chang, H. Y. & Greenleaf, W. J. Transposition of native chromatin for fast and sensitive epigenomic profiling of open chromatin, DNA-binding proteins and nucleosome position. *Nat Methods* 10, 1213-1218, doi:10.1038/nmeth.2688 (2013).
Waugh, K. A. et al. Molecular Profile of Tumor-Specific CD8+ T Cell Hypofunction in a Transplantable Murine Cancer Model. *J Immunol* 197, 1477-1488, doi:10.4049/jimmunol.1600589 (2016).
41. Sen, D. R. et al. The epigenetic landscape of T cell exhaustion. *Science* 354, 1165-1169, doi:10.1126/science.aae0491 (2016).
42. Paley, M. A. et al. Progenitor and terminal subsets of CD8+ T cells cooperate to contain chronic viral infection. *Science* 338, 1220-1225, doi:10.1126/science.1229620 (2012).
43. McLean, C. Y. et al. GREAT improves functional interpretation of cis-regulatory regions. *Nat Biotechnol* 28, 495-501, doi:10.1038/nbt.1630 (2010).
44. Bolotin, D. A. et al. MiXCR: software for comprehensive adaptive immunity profiling. *Nat Methods* 12, 380-381, doi:10.1038/nmeth.3364 (2015).
Galon, J. et al. Type, density, and location of immune cells within human colorectal tumors predict clinical outcome. *Science* 313, 1960-1964, doi:10.1126/science.1129139 (2006).
46. Sharma, P. et al. CD8 tumor-infiltrating lymphocytes are predictive of survival in muscle-invasive urothelial carcinoma. *Proc Natl Acad Sci USA* 104, 3967-3972, doi:10.1073/pnas.0611618104 (2007).
47. Mahmoud, S. M. et al. Tumor-infiltrating CD8+ lymphocytes predict clinical outcome in breast cancer. *J Clin Oncol* 29, 1949-1955, doi:10.1200/JCO.2010.30.5037 (2011).
48. Philip, M. et al. Chromatin states define tumour-specific T cell dysfunction and reprogramming. *Nature* 545, 452-456, doi:10.1038/nature22367 (2017).
49. Spitzer, M. H. et al. Systemic Immunity Is Required for Effective Cancer Immunotherapy. *Cell* 168, 487-502 e415, doi:10.1016/j.cell.2016.12.022 (2017).
50. Ziegenhain, C. et al. Comparative Analysis of Single-Cell RNA Sequencing Methods. *Mol Cell* 65, 631-643 e634, doi:10.1016/j.molcel.2017.01.023 (2017).
51. Shum, T. et al. Constitutive Signaling from an Engineered IL7 Receptor Promotes Durable Tumor Elimination by Tumor-Redirected T Cells. *Cancer Discov* 7, 1238-1247, doi:10.1158/2159-8290.CD-17-0538 (2017).
52. Picelli, S. et al. Smart-seq2 for sensitive full-length transcriptome profiling in single cells. *Nat Methods* 10, 1096-1098, doi:10.1038/nmeth.2639 (2013).
53. Dobin, A. et al. STAR: ultrafast universal RNA-seq aligner. *Bioinformatics* 29, 15-21, doi:10.1093/bioinformatics/bts635 (2013).
54. Li, B. & Dewey, C. N. RSEM: accurate transcript quantification from RNA-Seq data with or without a reference genome. *BMC Bioinformatics* 12, 323, doi:10.1186/1471-2105-12-323 (2011).
55. Qiu, X. et al. Reversed graph embedding resolves complex single-cell trajectories. *Nat Methods* 14, 979-982, doi:10.1038/nmeth.4402 (2017).
56. Corces, M. R. et al. Lineage-specific and single-cell chromatin accessibility charts human hematopoiesis and leukemia evolution. *Nat Genet* 48, 1193-1203, doi:10.1038/ng.3646 (2016).
57. Langmead, B. & Salzberg, S. L. Fast gapped-read alignment with Bowtie 2. *Nat Methods* 9, 357-359, doi:10.1038/nmeth.1923 (2012).
58. Li, H. et al. The Sequence Alignment/Map format and SAMtools. *Bioinformatics* 25, 2078-2079, doi:10.1093/bioinformatics/btp352 (2009).
59. Heinz, S. et al. Simple combinations of lineage-determining transcription factors prime cis-regulatory elements required for macrophage and B cell identities. *Mol Cell* 38, 576-589, doi:10.1016/j.molcel.2010.05.004 (2010).
60. Robinson, M. D., McCarthy, D. J. & Smyth, G. K. edgeR: a Bioconductor package for differential expression analysis of digital gene expression data. *Bioinformatics* 26, 139-140, doi:10.1093/bioinformatics/btp616 (2010).
61. Weirauch, M. T. et al. Determination and inference of eukaryotic transcription factor sequence specificity. *Cell* 158, 1431-1443, doi:10.1016/j.cell.2014.08.009 (2014).
62. Granek, J. A. & Clarke, N. D. Explicit equilibrium modeling of transcription-factor binding and gene regulation. *Genome Biol* 6, R87, doi:10.1186/gb-2005-6-10-r87 (2005).
63. Cibulskis, K. et al. ContEst: estimating cross-contamination of human samples in next-generation sequencing data. *Bioinformatics* 27, 2601-2602, doi:10.1093/bioinformatics/btr446 (2011).
64. Cibulskis, K. et al. Sensitive detection of somatic point mutations in impure and heterogeneous cancer samples. *Nat Biotechnol* 31, 213-219, doi:10.1038/nbt.2514 (2013).
65. Costello, M. et al. Discovery and characterization of artifactual mutations in deep coverage targeted capture sequencing data due to oxidative DNA damage during sample preparation. *Nucleic Acids Res* 41, e67, doi:10.1093/nar/gks1443 (2013).
66. Ramos, A. H. et al. Oncotator: cancer variant annotation tool. *Hum Mutat* 36, E2423-2429, doi:10.1002/humu.22771 (2015).

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method of treating melanoma in a checkpoint blockade (CPB) therapy non-responder subject in need thereof comprising administering polyoxometalate-1 (POM-1) and an anti-T-cell immunoglobulin and mucin-domain containing-3 (TIM3) monoclonal antibody to the subject, wherein the subject expresses a checkpoint blockade (CPB) therapy non-responder gene signature in CD8$^+$ tumor infiltrating lymphocytes (TILs), said CPB therapy non-responder gene signature comprising ENTPD1 (CD39) and HAVCR2 (TIM3), wherein the TIM3 monoclonal antibody is an inhibitor of TIM3 activity, and wherein the response is synergistic.

2. The method of claim 1, wherein the checkpoint blockade comprises anti-PD1.

3. The method of claim 1, further comprising detecting in single CD8+ T cells obtained from the subject ENTPD1 (CD39) and HAVCR2 (TIM3), and treating the subject if ENTPD1 (CD39) and HAVCR2 (TIM3) are detected in the single CD8+ T cells.

4. The method of claim 3, wherein CD39 and TIM3 are detected by immunofluorescence.

5. The method of claim 1, wherein said CPB therapy non-responder gene signature further comprises one or more genes selected from the group consisting of CCL3, CD38, PDCD1, SNAP47, VCAM1, FASLG, SIRPG, MYO7A, FABP5, NDUFB3, UBE2F, SNRPD1, LAG3, CXCR6, CXCL13, TNFRSF18, CTLA4, TNFRSF9, GEM, NAB1, DFNB31, CADM1, LAYN, RDH10, FAM3C, AFAP1L2, KIR2DL4, MTSS1, ETV1, GOLIM4, LGALS1, EPSTI1, WARS, PLEK, LGALS3, MT2A, GBP1, PLSCR1, CCR5, GSTO1, ANXA5, GLUL, PYCARD, TYMP, IFI6, VAMP5, PRDX3, LGALS9, BATF, PTTG1, TRAFD1, PTPN6, SKA2, LSM2, NMI, IFI35, MTHFD1, IFI27L2, MCM5, STMN1, ID3, RGS3, and FIBP.

\* \* \* \* \*